(12) United States Patent
Kawaguchi et al.

(10) Patent No.: US 8,822,503 B2
(45) Date of Patent: Sep. 2, 2014

(54) 2-PYRIDONE COMPOUNDS

(75) Inventors: Takanori Kawaguchi, Tokyo (JP); Kengo Watatani, Tokyo (JP); Keiko Fusegi, Tokyo (JP); Masahiro Bohno, Tokyo (JP); Hajime Asanuma, Tokyo (JP); Shoichi Kuroda, Tokyo (JP); Yudai Imai, Tokyo (JP); Tomomichi Chonan, Tokyo (JP); Nagaaki Sato, Tokyo (JP); Shigeru Tokita, Tokyo (JP); Shigetada Sasako, Funabashi (JP); Takumi Okada, Funabashi (JP); Keishi Hayashi, Funabashi (JP); Shin Itoh, Funabashi (JP); Noriko Saito, Funabashi (JP); Rui Jibiki, Funabashi (JP); Seishi Ishiyama, Funabashi (JP); Hirofumi Ota, Funabashi (JP)

(73) Assignees: Taisho Pharmaceutical Co., Ltd, Tokyo (JP); Nissan Chemical Industries, Ltd., Tokyo (JP)

(*) Notice: Subject to any disclaimer, the term of this patent is extended or adjusted under 35 U.S.C. 154(b) by 308 days.

(21) Appl. No.: 13/081,201

(22) Filed: Apr. 6, 2011

(65) Prior Publication Data
US 2011/0237791 A1    Sep. 29, 2011

Related U.S. Application Data

(63) Continuation of application No. PCT/JP2010/071709, filed on Dec. 3, 2010.

(30) Foreign Application Priority Data

Dec. 4, 2009  (JP) ................. 2009-277048
Apr. 28, 2010  (JP) ................. 2010-104615

(51) Int. Cl.
*A61K 31/4439*    (2006.01)
*C07D 401/06*    (2006.01)

(52) U.S. Cl.
USPC ................................. 514/343; 546/278.4

(58) Field of Classification Search
USPC ................................. 546/278.4; 514/343
See application file for complete search history.

(56) References Cited

U.S. PATENT DOCUMENTS

| 4,275,069 | A | 6/1981 | Youngdale |
| 7,629,362 | B2 | 12/2009 | Mitsuya et al. |
| 2010/0087360 | A1 | 4/2010 | Ogino et al. |

FOREIGN PATENT DOCUMENTS

| JP | 63-166855 A | 7/1988 |
| JP | 2002-508355 A | 3/2002 |
| JP | 2009-532379 A | 9/2009 |
| WO | 99/31061 A1 | 6/1999 |
| WO | 00/58293 A2 | 10/2000 |
| WO | 01/44216 A1 | 6/2001 |
| WO | 01/85707 A1 | 11/2001 |
| WO | 2004/081001 A1 | 9/2004 |
| WO | 2005/044801 A1 | 5/2005 |
| WO | 2007/007910 A1 | 1/2007 |
| WO | 2007/115058 A2 | 10/2007 |
| WO | 2008/079787 A2 | 7/2008 |
| WO | 2009/040288 A1 | 4/2009 |
| WO | 2010/013161 A1 | 2/2010 |

OTHER PUBLICATIONS

Guillory (in Brittain ed.), "Polymorphism, etc.," NY: Marcel Dekker, Inc., 1999, 1-2, 125-181, 183-226.*
Yu et al., "Physical characterization of, etc.," PSTT, vl. 1(3), 118-127 (1998).*
Vippagunta et a;. "Crystalline Solid" Advanced Drug Delivery Reviews 48 (2001) 3-26.*

(Continued)

*Primary Examiner* — Patricia L Morris
(74) *Attorney, Agent, or Firm* — Sughrue Mion, PLLC

(57) ABSTRACT

A 2-pyridone compound represented by the formula [1]:

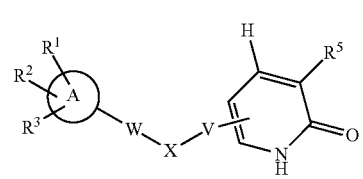

{wherein in the formula [1],
the ring represented by A represents a benzene ring or a pyridine ring,
X represents any of the structures represented by the formulas [3] shown below:

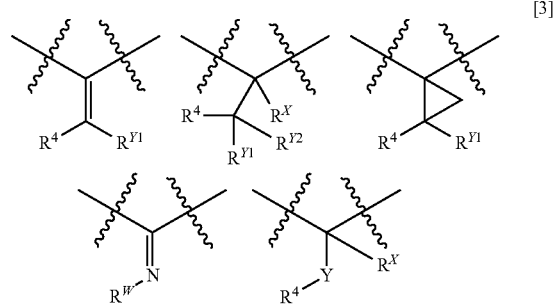

V represents a single bond or a lower alkylene group, and W represents a single bond, an ether bond or a lower alkylene group (wherein the lower alkylene group may contain an ether bond)},
a tautomer or stereoisomer of the compound, a pharmaceutically acceptable salt thereof, or a solvate thereof is a compound that has an excellent GK activating effect and is useful as a pharmaceutical.

23 Claims, No Drawings

(56) References Cited

OTHER PUBLICATIONS

Susanne Berglund, et al., "Optimization of 2-piperidin-4-yl-acetamides as melanin-concentrating hormone receptor 1 (MCH-R1) antagonists: Designing out hERG inhibition", Bioorganic & Medicinal Chemistry Letters, 2009, pp. 4268-4273, vol. 19.

Winton D. Jones, et al., "A Convenient Synthesis of 5-Acyl-6-substituted 3-Cyano-2(1H)-pyridinones", Merrell Dow Research Institute, 1990, pp. 511-518, vol. 27.

A. Corsaro, et al., "Cycloadducts of Benzonitrile Oxide to Pyridine. A Case of Two-Step Cycloaddition", Tetrahedron Letters, 1986, pp. 1517-1520, vol. 27, No. 13.

Latif Rateb, et al., "Reactions of Hydroxymethylene Ketones. Part III. Synthesis of 1,2-Dihydro-2-oxopyridine Polycarboxylic Acids", Journal of the Chemical Society (C) Organic, 1968, pp. 2140-2144, vol. 17.

F. M. Matschinsky, et al., "Glucokinase and Glycemic Disease From Basics to Novel Therapeutics", Frontiers in Diabetes, 2004, pp. 1-15, 34-35, vol. 16.

Andrew Grupe, et al., "Transgenic Knockouts Reveal a Critical Requirement for Pancreatic β Cell Glucokinase in Maintaining Glucose Homeostasis", Cell, Oct. 6, 1995, pp. 69-78, vol. 83.

Tura Ferre, et al., "Correction of Diabetic Alterations by Glucokinase", Proceedings of the National Academy of Sciences of the United States of America, Jul. 9, 1996, pp. 7225-7230, vol. 93, No. 14.

N. Vionnet, et al., "Nonsense Mutation in the Glucokinase Gene Causes Early-Onset Non-Insulin-Dependent Diabetes Mellitus", Nature; International Weekly Journal of Science, Apr. 23, 1992, pp. 721-722, vol. 356, No. 6371.

Benjamin Glaser, M.D., et al., "Familial Hyperinsulinism Caused by an Activating Glucokinase Mutation", The New England Journal of Medicine, Jan. 22, 1998, pp. 226-230, vol. 338, No. 4.

Ling Kang, et al., "Glucokinase Is a Critical Regulator of Ventromedial Hypothalamic Neuronal Glucosensing", Diabetes, Feb. 2006, pp. 412-420, vol. 55, No. 2.

\* cited by examiner

2-PYRIDONE COMPOUNDS

CROSS REFERENCE TO RELATED APPLICATIONS

This application is a Continuation of International Application No. PCT/JP2010/071709 filed Dec. 3, 2010, which claims priority from Japanese Patent Application No. 2009-277048 filed Dec. 4, 2009 and Japanese Patent Application No. 2010-104615 filed Apr. 28, 2010, the contents of all of which are incorporated herein by reference in their entirety.

TECHNICAL FIELD

The present invention relates to novel 2-pyridone compounds having a glucokinase activating effect and to a medicine comprising the compounds as an active ingredient.

BACKGROUND ART

Glucokinase (hereinafter described as GK) belongs to the hexokinase family and catalyzes phosphorylation of glucose incorporated in cells such as pancreatic beta cells or hepatocytes. GK in the liver and GK in pancreatic beta cells differ from each other in terms of the sequence of N-terminal 15 amino acids due to the difference in splicing but are enzymatically identical. GK has a high affinity to glucose $S_{0.5}$ of about 10 mM and is not inhibited by the product, glucose 6-phosphate. Therefore, its reaction rate sensitively responds to physiological changes of blood glucose levels. GK in pancreatic beta cells modulates glucose-dependent insulin secretion, while GK in the liver modulates the glycolytic pathway or glycogenesis, so that blood glucose levels are maintained and controlled. Therefore, GK is assumed to function as a glucose sensor to maintain homeostasis of blood glucose levels (see Non-Patent Document 1).

Genetically engineered mice and gene mutations discovered in humans support a hypothesis that GK functions as an in vivo glucose sensor. GK homozygous mice have been died of hyperglycemia immediately after birth, and heterozygous mice have been observed to have hyperglycemia and impaired glucose tolerance (see Non-Patent Document 2). In contrast, GK overexpressed mice have been confirmed to have hypoglycemia (see Non-Patent Document 3). Moreover, in human MODY2 (maturity onset diabetes of the young), in which GK gene mutation is observed, diabetes develops from his youth (see Non-Patent Document 4). These gene mutations have been confirmed to reduce GK activity. In contrast, families have been reported having gene mutations to enhance GK activity (see Non-Patent Document 5). These gene mutations have been observed to enhance affinity of GK to glucose and cause symptoms of fasting hypoglycemia associated with elevated blood insulin concentrations.

In this way, GK has been shown to function as a glucose sensor in mammals including humans.

Substances to increase GK activity (hereinafter described as GK activating substances) may improve hyperglycemia by increasing glucose metabolism and glycogenesis in the liver and/or glucose-induced insulin secretion from pancreatic beta cells. It can also expected that improvement of hyperglycemia leads to treatment and prevention of chronic diabetic complications such as retinopathy, nephropathy, neurosis, ischemic heart disease and arteriosclerosis and to treatment and prevention of diabetes-related diseases such as obesity, hyperlipidemia, hypertension and metabolic syndrome. Therefore, compounds to increase the function of GK are expected to be effective therapeutic agents for diabetes.

On the other hand, GK has been reported to be expressed not only in the pancreas and liver but also in the feeding center and to have an important function in the antifeeding effect by glucose (see Non-Patent Document 6). Accordingly, GK activating substances may act on the feeding center and have an antifeeding effect and can be expected not only as therapeutic agents for diabetes but also as therapeutic agents for obesity.

Certain propionamide compounds, picolinamide compounds, benzamide compounds and benzimidazole compounds have conventionally been reported as GK activating substances, but the compounds of the present invention have not been disclosed (see Patent Document 1, 2, 3 and 4). 2-Pyridone compounds structurally similar to the compounds of the present invention have also been reported, but the compounds of the present invention have not been disclosed; such compounds differ from the compounds of the present invention in that they are not described for pharmaceutical applications and are intended to provide a process for synthesizing 2-pyridone compounds (see Non-Patent Document 7). Moreover, 2-pyridone compounds have been reported as therapeutic agents for diabetes, but they differ from the compounds of the present invention in terms of the structure, for example, the substituent at the 3-position of pyridone (see Patent Document 5). Further, certain acylurea compounds that can have a pseudocyclic structure have been reported as GK activating substances, but they are noncyclic compounds and differ from the compounds of the present invention (see Patent Document 6).

PRIOR ART DOCUMENT

Non-Patent Document

[Non-Patent Document 1] Matschinsky F. M. and Magnuson M. A., Frontiers in Diabetes, 16, 2004
[Non-Patent Document 2] Grupe A. et al. Cell, 83, 1, 69-78, 1995
[Non-Patent Document 3] Ferre T. et al. Proc. Natl. Acad. Sci., 93, 14, 7225-7230, 1996
[Non-Patent Document 4] Vionnet N. et al. Nature, 356, 6371, 721-722, 1992
[Non-Patent Document 5] Glaser B. et al. N. Engl. J. Med. 338, 4, 226-230, 1998
[Non-Patent Document 6] Kang L. et al, Diabetes, 55, 2, 412-420, 2006
[Non-Patent Document 7] Latif R. et al. J. Chem. Soc. C. Organic, 17, 2140-2144, 1968

Patent Document

[Patent Document 1] WO 01/085707
[Patent Document 2] WO 04/081001
[Patent Document 3] WO 05/044801
[Patent Document 4] WO 07/007,910
[Patent Document 5] U.S. Pat. No. 4,275,069
[Patent Document 6] WO 01/44216

SUMMARY OF INVENTION

Problem to be Solved by the Invention

An object of the present invention is to provide compounds that have an excellent GK activating effect and are useful as pharmaceuticals.

Means for Solving the Problem

As a result of extensive studies to find compounds having a GK activating effect, the present inventors have found that the object can be achieved by 2-pyridone compounds represented by the general formula [1] or pharmaceutically acceptable salts thereof. This finding has led to the completion of the present invention.

Specifically, the present invention provides:
(I) A 2-pyridone compound represented by the formula [1]:

[Ka 1]

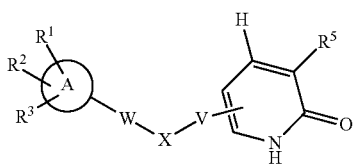

[1]

{wherein in the formula [1],
the ring represented by A represents a benzene ring or a pyridine ring,
$R^1$ represents $R^A—Z^A—$,
wherein $—Z^A—$ represents a single bond or represents any of the following formulas [2]:

[Ka 2]

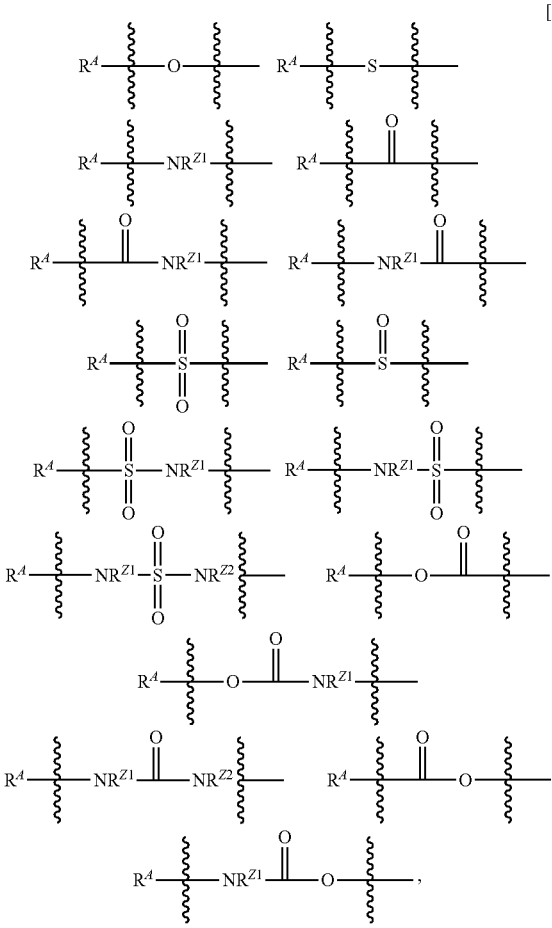

[2]

when $—Z^A—$ represents any of the formulas [2],
$R^A$ represents a lower alkyl group, a lower cycloalkyl group, a lower alkenyl group, a lower alkynyl group, an aryl group or a heterocyclyl group (wherein the lower alkyl group, lower cycloalkyl group, lower alkenyl group, lower alkynyl group, aryl group or heterocyclyl group is unsubstituted or substituted with 1 to 3 groups which may be the same or different and selected from the following Substituent Group A1); or when $—Z^A—$ represents a single bond,
$R^A$ represents a lower alkyl group, a lower cycloalkyl group, a lower alkenyl group, a lower alkynyl group, an aryl group, a heterocyclyl group (wherein the lower alkyl group, lower cycloalkyl group, lower alkenyl group, lower alkynyl group, aryl group or heterocyclyl group is unsubstituted or substituted with 1 to 3 groups which may be the same or different and selected from the following Substituent Group A1), a hydrogen atom, a cyano group, a halogen atom, a nitro group, a formyl group, a hydroxy group, an amino group, a carbamoyl group, a formylamino group, a sulfamoyl group or a ureido group;

X represents any of the structures represented by the formulas [3] shown below:

[Ka 3]

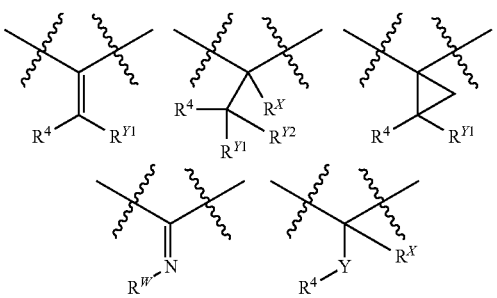

[3]

$R^X$ represents a hydrogen atom, a lower alkyl group, a lower cycloalkyl group, $OR^{Z3}$, $SR^{Z3}$ or $NR^{Z3}R^{Z4}$,
$R^{Z1}$, $R^{Z2}$, $R^{Z3}$ and $R^{Z4}$ are the same or different and each represent a hydrogen atom or a lower alkyl group,
$R^{Y1}$ and $R^{Y2}$ are the same or different and each represent a hydrogen atom, a halogen atom, a lower alkyl group, a lower cycloalkyl group or a hydroxy group,
Y represents $—O—$, $—S—$ or $—NR^{Z5}—$,
$R^{Z5}$ represents a hydrogen atom or a lower alkyl group,
$R^4$ together with $R^{Y1}$ form a saturated or unsaturated 3- to 8-membered ring which is formed together with the carbon atom to which the substituents are bonded and which may contain one or more nitrogen, oxygen or sulfur atoms (wherein the ring is unsubstituted or substituted with 1 to 3 groups which may be the same or different and selected from the following Substituent Group A1),
or $R^4$ together with $R^{Z5}$ form a saturated or unsaturated 3- to 8-membered ring which is formed together with the nitrogen atom to which the substituents are bonded and which may contain one or more nitrogen, oxygen or sulfur atoms (wherein the ring is unsubstituted or substituted with 1 to 3 groups which may be the same or different and selected from the following Substituent Group A1),
or $R^4$ represents $R^B—Z^B—$,
wherein $—Z^B—$ represents a single bond or represents any of the following formulas [4]:

[Ka 4]

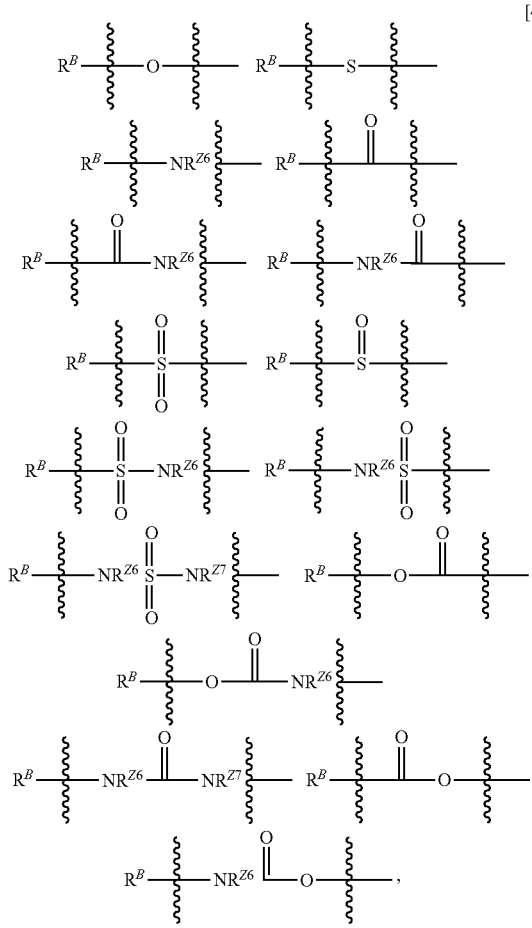

when —$Z^B$— represents any of the formulas [4],
$R^B$ represents a lower alkyl group, a lower cycloalkyl group, a lower alkenyl group, a lower alkynyl group, an aryl group or a heterocyclyl group (wherein the lower alkyl group, lower cycloalkyl group, lower alkenyl group, lower alkynyl group, aryl group or heterocyclyl group is unsubstituted or substituted with 1 to 3 groups which may be the same or different and selected from the following Substituent Group A1); or
when —$Z^B$— represents a single bond,
$R^B$ represents a lower alkyl group, a lower cycloalkyl group, a lower alkenyl group, a lower alkynyl group, an aryl group, a heterocyclyl group (wherein the lower alkyl group, lower cycloalkyl group, lower alkenyl group, lower alkynyl group, aryl group or heterocyclyl group is unsubstituted or substituted with 1 to 3 groups which may be the same or different and selected from the following Substituent Group A1), a hydrogen atom, a cyano group, a halogen atom, a nitro group, a formyl group, a hydroxy group, an amino group, a carbamoyl group, a formylamino group, a sulfamoyl group or a ureido group;
$R^{Z6}$ and $R^{Z7}$ are the same or different and each represent a hydrogen atom or a lower alkyl group,
$R^W$ represents $OR^C$ or $NR^C R^{Z8}$,
$R^C$ represents a lower alkyl group, a lower cycloalkyl group, a lower alkenyl group, a lower alkynyl group, an aryl group or a heterocyclyl group (wherein the lower alkyl group, lower cycloalkyl group, lower alkenyl group, lower alkynyl group, aryl group or heterocyclyl group is unsubstituted or substituted with 1 to 3 groups which may be the same or different and selected from the following Substituent Group A1),
$R^{Z8}$ represents a hydrogen atom or a lower alkyl group,
or $R^{Z8}$ together with $R^C$ may form a saturated or unsaturated 3- to 8-membered ring which is formed together with the nitrogen atom to which the substituents are bonded and which may contain one or more nitrogen, oxygen or sulfur atoms (wherein the ring is unsubstituted or substituted with 1 to 3 groups which may be the same or different and selected from the following Substituent Group A1),
Substituent Group A1 represents a halogen atom, a nitro group, a cyano group, a lower alkyl group (wherein the lower alkyl group is unsubstituted or substituted with 1 to 3 groups which may be the same or different and selected from the group consisting of a halogen atom, a nitro group, a cyano group, a lower cycloalkyl group, an aryl group (wherein the aryl group is unsubstituted or substituted with 1 to 3 halogen atoms), a heterocyclyl group, a hydroxy group, a lower alkoxy group (wherein the lower alkoxy group is unsubstituted or substituted with 1 to 3 halogen atoms), a lower cycloalkoxy group, an aryloxy group, an aryl-lower alkoxy group, a heterocyclyloxy group, a heterocyclyl-lower alkoxy group, a lower alkylthio group, an amino group, a mono-lower alkylamino group, a mono-lower cycloalkylamino group, a di-lower alkylamino group, a lower alkanoyl group, a lower alkylsulfonyl group, a lower alkoxycarbonyl group, a lower alkanoylamino group and an oxo group), a lower cycloalkyl group, an aryl group, a heterocyclyl group (wherein the lower cycloalkyl group, aryl group or heterocyclyl group is unsubstituted or substituted with 1 to 2 groups which may be the same or different and selected from the following Substituent Group A2), a hydroxy group, a lower alkoxy group (wherein the lower alkoxy group is unsubstituted or substituted with 1 to 3 halogen atoms), a lower cycloalkoxy group, an aryloxy group, an aryl-lower alkoxy group, a heterocyclyloxy group, a heterocyclyl-lower alkoxy group, a lower alkylthio group, an amino group, a mono-lower alkylamino group, a mono-lower cycloalkylamino group, a di-lower alkylamino group, a lower alkanoyl group, a lower cycloalkylcarbonyl group, a heterocyclylcarbonyl group, a lower alkylsulfonyl group, a lower alkoxycarbonyl group, a lower alkanoylamino group or an oxo group,
Substituent Group A2 represents a lower alkyl group, a lower alkoxy group, a lower alkylthio group, a mono-lower alkylamino group, a di-lower alkylamino group, a lower alkanoyl group, a lower alkylsulfonyl group, a lower alkoxycarbonyl group, a lower alkanoylamino group, a hydroxy group, a halogen atom, an oxo group or an amino group,
$R^2$ and $R^3$ are the same or different and each represent a hydrogen atom, a halogen atom, a cyano group, a carbamoyl group, a lower alkyl group, a lower alkylsulfonyl group, a lower cycloalkyl group, a lower alkoxy group, a lower cycloalkoxy group (wherein the lower alkyl group, lower alkylsulfonyl group, lower cycloalkyl group, lower alkoxy group or lower cycloalkoxy group is unsubstituted or substituted with 1 to 3 groups which may be the same or different and selected from the group consisting of a halogen atom and a hydroxy group) or a hydroxy group,
or the adjacent $R^1$ and $R^2$ together form a $C_9$-$C_{12}$ fused bicyclic hydrocarbon ring or a $C_6$-$C_{11}$ fused bicyclic heteroring together with the benzene ring or pyridine ring to which the substituents are bonded (wherein the $C_9$-$C_{12}$ fused bicyclic hydrocarbon ring or $C_6$-$C_{11}$ fused bicyclic heteroring is unsubstituted or substituted with 1 to 3 groups which may be the same or different and selected from the following Substituent Group A4), R⁵ and Substituent Group A4 are the same or different and each represent a halogen atom, a carbamoyl group, a lower alkanoyl group, an amino group, a di-lower alkylamino group, a lower alkyl group, a lower cycloalkyl group, a lower alkoxy group, a lower cycloalkoxy group, an aryl group, a heteroaryl group, an aryloxy group or a heterocyclyl group (wherein the lower alkyl group, lower cycloalkyl group, lower alkoxy group, lower cycloalkoxy group, aryl group, heteroaryl group, aryloxy group or heterocyclyl group is unsubstituted or substituted with 1 to 3 groups which may be the same or different and selected from the following Substituent Group A3), Substituent Group A3 represents a halogen atom, a nitro group, a cyano group, a hydroxy group, a lower alkyl group (wherein the lower alkyl group is unsubstituted or substituted with 1 to 3 groups which may be the same or different and selected from the group consisting of a halogen atom, a nitro group, a cyano group, a hydroxy group, a lower cycloalkyl group, an aryl group, a heterocyclyl group, a lower alkoxy group (wherein the lower alkoxy group is unsubstituted or substituted with 1 to 3 halogen atoms), a lower cycloalkoxy group, an aryloxy group, an aryl-lower alkoxy group, a heterocyclyloxy group, a heterocyclyl-lower alkoxy group, an amino group, a mono-lower alkylamino group, a mono-lower cycloalkylamino group and a di-lower alkylamino group), a lower cycloalkyl group, an aryl group, a heterocyclyl group, a lower alkoxy group (wherein the lower alkoxy group is unsubstituted or substituted with 1 to 3 halogen atoms), a lower cycloalkoxy group, an aryloxy group, an aryl-lower alkoxy group, a heterocyclyloxy group, a heterocyclyl-lower alkoxy group, an amino group, a mono-lower alkylamino group, a mono-lower cycloalkylamino group, a di-lower alkylamino group, a lower alkoxycarbonyl group or a carbamoyl group, V represents a single bond or a lower alkylene group, and W represents a single bond, an ether bond or a lower alkylene group (wherein the lower alkylene group may contain an ether bond)}, a tautomer or stereoisomer of the compound, a pharmaceutically acceptable salt thereof, or a solvate thereof (II) Another embodiment of the present invention provides:

The 2-pyridone compound according to (I) represented by the formula [1]:

[Ka 5]

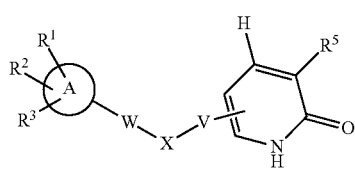

[1]

{wherein in the formula [1], the ring represented by A represents a benzene ring or a pyridine ring, $R^1$ represents $R^A$—$Z^A$—, wherein —$Z^A$— represents a single bond or represents any of the following formulas [2]:

[Ka 6]

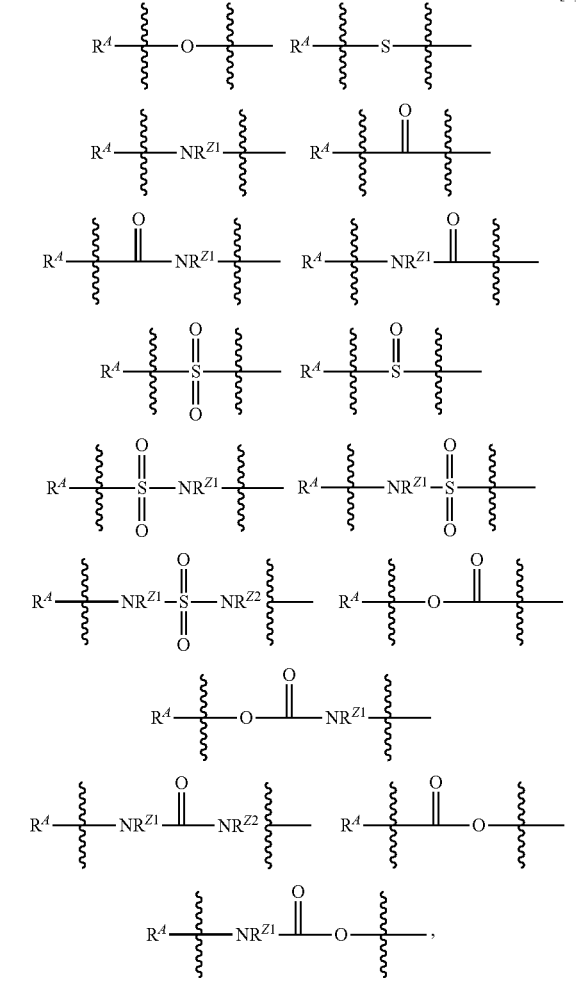

[2]

when —$Z^A$— represents any of the formulas [2], $R^A$ represents a lower alkyl group, a lower cycloalkyl group, a lower alkenyl group, a lower alkynyl group, an aryl group or a heterocyclyl group (wherein the lower alkyl group, lower cycloalkyl group, lower alkenyl group, lower alkynyl group, aryl group or heterocyclyl group is unsubstituted or substituted with 1 to 3 groups which may be the same or different and selected from the following Substituent Group A1); or when —$Z^A$— represents a single bond, $R^A$ represents a lower alkyl group, a lower cycloalkyl group, a lower alkenyl group, a lower alkynyl group, an aryl group, a heterocyclyl group (wherein the lower alkyl group, lower cycloalkyl group, lower alkenyl group, lower alkynyl group, aryl group or heterocyclyl group is unsubstituted or substituted with 1 to 3 groups which may be the same or different and selected from the following Substituent Group A1), a hydrogen atom, a cyano group, a halogen atom, a nitro group, a formyl group, a hydroxy group, an amino group, a carbamoyl group, a formylamino group, a sulfamoyl group or a ureido group;

X represents any of the structures represented by the formulas [3] shown below:

[Ka 7]

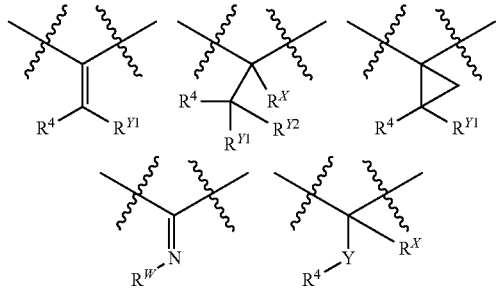

[3]

$R^X$ represents a hydrogen atom, a lower alkyl group, a lower cycloalkyl group, $OR^{Z3}$, $SR^{Z3}$ or $NR^{Z3}R^{Z4}$, $R^{Z1}$, $R^{Z2}$, $R^{Z3}$ and $R^{Z4}$ are the same or different and each represent a hydrogen atom or a lower alkyl group, $R^{Y1}$ and $R^{Y2}$ are the same or different and each represent a hydrogen atom, a halogen atom, a lower alkyl group, a lower cycloalkyl group or a hydroxy group, Y represents —O—, —S— or —$NR^{Z5}$—, $R^{Z5}$ represents a hydrogen atom or a lower alkyl group, $R^4$ together with $R^{Y1}$ form a saturated or unsaturated 3- to 8-membered ring which is formed together with the carbon atom to which the substituents are bonded and which may contain one or more nitrogen, oxygen or sulfur atoms (wherein the ring is unsubstituted or substituted with 1 to 3 groups which may be the same or different and selected from the following Substituent Group A1), or $R^4$ together with $R^{Z5}$ form a saturated or unsaturated 3- to 8-membered ring which is formed together with the nitrogen atom to which the substituents are bonded and which may contain one or more nitrogen, oxygen or sulfur atoms (wherein the ring is unsubstituted or substituted with 1 to 3 groups which may be the same or different and selected from the following Substituent Group A1), or $R^4$ represents $R^B$—$Z^B$—, wherein —$Z^B$— represents a single bond or represents any of the following formulas [4]:

[Ka 8]

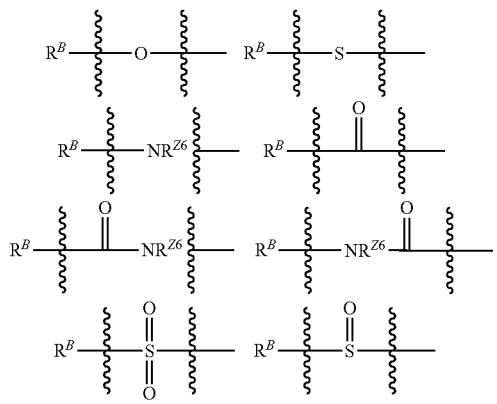

[4]

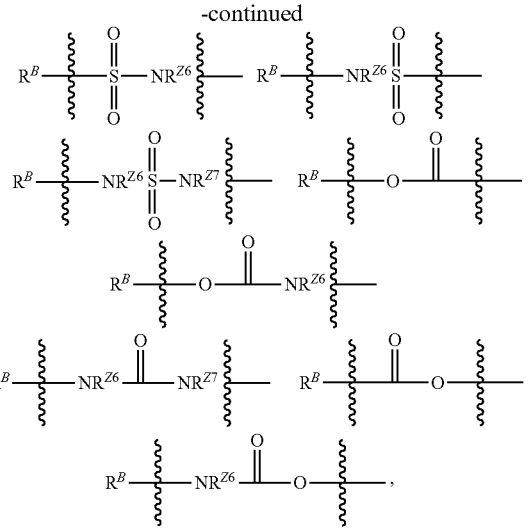

when —$Z^B$— represents any of the formulas [4], $R^B$ represents a lower alkyl group, a lower cycloalkyl group, a lower alkenyl group, a lower alkynyl group, an aryl group or a heterocyclyl group (wherein the lower alkyl group, lower cycloalkyl group, lower alkenyl group, lower alkynyl group, aryl group or heterocyclyl group is unsubstituted or substituted with 1 to 3 groups which may be the same or different and selected from the following Substituent Group A1); or when —$Z^B$— represents a single bond, $R^B$ represents a lower alkyl group, a lower cycloalkyl group, a lower alkenyl group, a lower alkynyl group, an aryl group, a heterocyclyl group (wherein the lower alkyl group, lower cycloalkyl group, lower alkenyl group, lower alkynyl group, aryl group or heterocyclyl group is unsubstituted or substituted with 1 to 3 groups which may be the same or different and selected from the following Substituent Group A1), a hydrogen atom, a cyano group, a halogen atom, a nitro group, a formyl group, a hydroxy group, an amino group, a carbamoyl group, a formylamino group, a sulfamoyl group or a ureido group;

$R^{Z6}$ and $R^{Z7}$ are the same or different and each represent a hydrogen atom or a lower alkyl group, $R^W$ represents $OR^C$ or $NR^CR^{Z8}$, $R^C$ represents a lower alkyl group, a lower cycloalkyl group, a lower alkenyl group, a lower alkynyl group, an aryl group or a heterocyclyl group (wherein the lower alkyl group, lower cycloalkyl group, lower alkenyl group, lower alkynyl group, aryl group or heterocyclyl group is unsubstituted or substituted with 1 to 3 groups which may be the same or different and selected from the following Substituent Group A1), $R^{Z8}$ represents a hydrogen atom or a lower alkyl group, or $R^{Z8}$ together with $R^C$ may form a saturated or unsaturated 3- to 8-membered ring which is formed together with the nitrogen atom to which the substituents are bonded and which may contain one or more nitrogen, oxygen or sulfur atoms (wherein the ring is unsubstituted or substituted with 1 to 3 groups which may be the same or different and selected from the following Substituent Group A1), Substituent Group A1 represents a halogen atom, a nitro group, a cyano group, a lower alkyl group (wherein the lower alkyl group is unsubstituted or substituted with 1 to 3 groups which may be the same or different and selected from the group consisting of a halogen atom, a nitro group, a cyano group, a lower cycloalkyl group, an aryl group, a heterocyclyl group, a hydroxy group, a lower alkoxy group (wherein the lower alkoxy group is unsubstituted or substituted with 1 to 3 halogen atoms), a lower cycloalkoxy group, an aryloxy group, an aryl-lower alkoxy group, a heterocyclyloxy group, a heterocyclyl-lower alkoxy group, a lower alkylthio group, an amino group, a mono-lower alkylamino group, a mono-lower cycloalkylamino group, a di-lower alkylamino group, a lower alkanoyl group, a lower alkylsulfonyl group, a lower alkoxycarbonyl group, a lower alkanoylamino group and an oxo group), a lower cycloalkyl group, an aryl group, a heterocyclyl group (wherein the lower cycloalkyl group, aryl group or heterocyclyl group is unsubstituted or substituted with 1 to 2 groups which may be the same or different and selected from the following Substituent Group A2), a hydroxy group, a lower alkoxy group (wherein the lower alkoxy group is unsubstituted or substituted with 1 to 3 halogen atoms), a lower cycloalkoxy group, an aryloxy group, an aryl-lower alkoxy group, a heterocyclyloxy group, a heterocyclyl-lower alkoxy group, a lower alkylthio group, an amino group, a mono-lower alkylamino group, a mono-lower cycloalkylamino group, a di-lower alkylamino group, a lower alkanoyl group, a lower alkylsulfonyl group, a lower alkoxycarbonyl group, a lower alkanoylamino group or an oxo group, Substituent Group A2 represents a lower alkyl group, a lower alkoxy group, a lower alkylthio group, a mono-lower alkylamino group, a di-lower alkylamino group, a lower alkanoyl group, a lower alkylsulfonyl group, a lower alkoxycarbonyl group, a lower alkanoylamino group, a hydroxy group, a halogen atom, an oxo group or an amino group, $R^2$ and $R^3$ are the same or different and each represent a hydrogen atom, a halogen atom, a lower alkyl group, a lower cycloalkyl group, a lower alkoxy group or a lower cycloalkoxy group (wherein the lower alkyl group, lower cycloalkyl group, lower alkoxy group or lower cycloalkoxy group is unsubstituted or substituted with 1 to 3 halogen atoms), or the adjacent $R^1$ and $R^2$ together form a $C_9$-$C_{12}$ fused bicyclic hydrocarbon ring or a $C_6$-$C_{11}$ fused bicyclic heteroring together with the benzene ring or pyridine ring to which the substituents are bonded (wherein the $C_9$-$C_{12}$ fused bicyclic hydrocarbon ring or $C_6$-$C_{11}$ fused bicyclic heteroring is unsubstituted or substituted with 1 to 3 groups which may be the same or different and selected from the following Substituent Group A4), $R^5$ and Substituent Group A4 are the same or different and each represent a halogen atom, a lower alkyl group, a lower cycloalkyl group, a lower alkoxy group, a lower cycloalkoxy group, an aryl group, a heteroaryl group or a heterocyclyl group (wherein the lower alkyl group, lower cycloalkyl group, lower alkoxy group, lower cycloalkoxy group, aryl group, heteroaryl group or heterocyclyl group is unsubstituted or substituted with 1 to 3 groups which may be the same or different and selected from the following Substituent Group A3), Substituent Group A3 represents a halogen atom, a nitro group, a cyano group, a hydroxy group, a lower alkyl group (wherein the lower alkyl group is unsubstituted or substituted with 1 to 3 groups which may be the same or different and selected from the group consisting of a halogen atom, a nitro group, a cyano group, a hydroxy group, a lower cycloalkyl group, an aryl group, a heterocyclyl group, a lower alkoxy group (wherein the lower alkoxy group is unsubstituted or substituted with 1 to 3 halogen atoms), a lower cycloalkoxy group, an aryloxy group, an aryl-lower alkoxy group, a heterocyclyloxy group, a heterocyclyl-lower alkoxy group, an amino group, a mono-lower alkylamino group, a mono-lower cycloalkylamino group and a di-lower alkylamino group), a lower cycloalkyl group, an aryl group, a heterocyclyl group, a lower alkoxy group (wherein the lower alkoxy group is unsubstituted or substituted with 1 to 3 halogen atoms), a lower cycloalkoxy group, an aryloxy group, an aryl-lower alkoxy group, a heterocyclyloxy group, a heterocyclyl-lower alkoxy group, an amino group, a mono-lower alkylamino group, a mono-lower cycloalkylamino group, a di-lower alkylamino group or a lower alkoxycarbonyl group, V represents a single bond or a lower alkylene group, and W represents a single bond, an ether bond or a lower alkylene group (wherein the lower alkylene group may contain an ether bond)}, a tautomer or stereoisomer of the compound, a pharmaceutically acceptable salt thereof, or a solvate thereof (III) Another embodiment of the present invention provides:
The 2-pyridone compound according to (I) or (II) represented by the formula [5]:

[Ka 9]

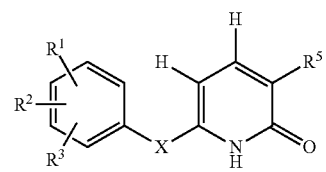

[5]

a tautomer or stereoisomer of the compound, a pharmaceutically acceptable salt thereof, or a solvate thereof (IV) Another embodiment of the present invention provides:
The 2-pyridone compound according to (III) represented by the formula [6]:

[Ka 10]

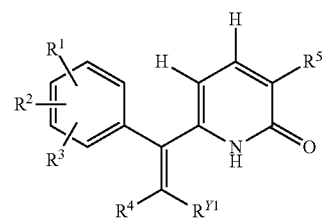

[6]

a tautomer or stereoisomer of the compound, a pharmaceutically acceptable salt thereof, or a solvate thereof (V) Another embodiment of the present invention provides:
The 2-pyridone compound according to (IV) represented by the formula [7]:

[Ka 11]

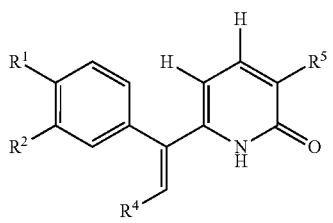

[7]

{wherein in the formula [7],
$R^4$ represents $R^B$—$Z^B$—,
wherein —$Z^B$— represents a single bond or represents any of the following formulas [8]:

[Ka 12]

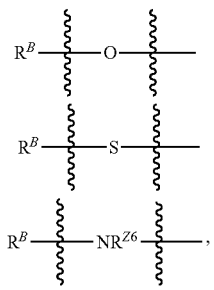

[8]

when —$Z^B$— represents any of the formulas [8],
$R^B$ represents a lower alkyl group (wherein the lower alkyl group is unsubstituted or substituted with 1 to 2 groups which may be the same or different and selected from the following Substituent Group A1); or
when —$Z^B$— represents a single bond,
$R^B$ represents a lower alkyl group, a lower cycloalkyl group, an aryl group or a heterocyclyl group (wherein the lower alkyl group, lower cycloalkyl group, aryl group or heterocyclyl group is unsubstituted or substituted with 1 to 2 groups which may be the same or different and selected from the following Substituent Group A1);
Substituent Group A1 represents a halogen atom, a lower alkyl group, a lower cycloalkyl group, an aryl group, a heterocyclyl group (wherein the lower cycloalkyl group, aryl group or heterocyclyl group is unsubstituted or substituted with 1 to 2 groups which may be the same or different and selected from the following Substituent Group A2), a hydroxy group, a lower alkoxy group (wherein the lower alkoxy group is unsubstituted or substituted with 1 to 3 halogen atoms), a lower alkylthio group, an amino group, a mono-lower alkylamino group, a di-lower alkylamino group, a lower alkanoyl group, a lower alkylsulfonyl group, a lower alkoxycarbonyl group, a lower alkanoylamino group or an oxo group, and
Substituent Group A2 represents a lower alkyl group, a lower alkoxy group, a lower alkylthio group, a mono-lower alkylamino group, a di-lower alkylamino group, a lower alkanoyl group, a lower alkylsulfonyl group, a lower alkoxycarbonyl group, a lower alkanoylamino group, a hydroxy group, a halogen atom, an oxo group or an amino group},
a tautomer or stereoisomer of the compound, a pharmaceutically acceptable salt thereof, or a solvate thereof
(VI) Another embodiment of the present invention provides:
The 2-pyridone compound according to (V), wherein
$R^1$ represents $R^A$—$Z^A$—,
wherein —$Z^A$— represents a single bond or represents any of the following formulas [9]:

[Ka 13]

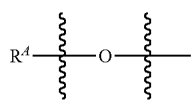

[9]

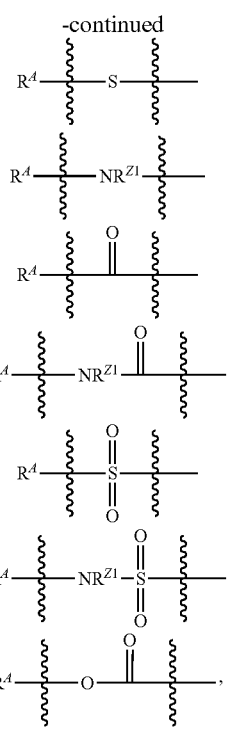

when —$Z^A$— represents any of the formulas [9],
$R^A$ represents a lower alkyl group (wherein the lower alkyl group is unsubstituted or substituted with 1 to 3 groups which may be the same or different and selected from the group consisting of a halogen atom, a hydroxy group, a heterocyclyl group, a mono-lower alkylamino group and a di-lower alkylamino group), a lower cycloalkyl group or a heterocyclyl group (wherein the heterocyclyl group is unsubstituted or substituted with one lower alkyl group); or
when —$Z^A$— represents a single bond,
$R^A$ represents a hydrogen atom or a lower alkyl group (wherein the lower alkyl group is unsubstituted or substituted with 1 to 3 groups which may be the same or different and selected from the group consisting of a halogen atom, a hydroxy group, a heterocyclyl group, a lower alkoxy group and a di-lower alkylamino group);
$R^2$ represents a hydrogen atom, a halogen atom, a lower alkyl group (wherein the lower alkyl group is unsubstituted or substituted with 1 to 3 halogen atoms) or a lower alkoxy group,
$R^4$ represents $R^B$—$Z^B$—,
wherein —$Z^B$— represents a single bond and
$R^B$ represents a lower alkyl group (wherein the lower alkyl group is unsubstituted or substituted with one group selected from the group consisting of a lower cycloalkyl group, a heterocyclyl group, a hydroxy group and a lower alkanoylamino group), a lower cycloalkyl group (wherein the lower cycloalkyl group is unsubstituted or substituted with one group selected from the group consisting of a lower alkyl group (wherein the lower alkyl group is unsubstituted or substituted with one hydroxy group), a hydroxy group and an oxo group) or a heterocyclyl group (wherein the heterocyclyl group is unsubstituted or substituted with 1 to 2 groups which may be the same or different and selected from the group consisting of a lower alkyl group, a hydroxy group, a lower alkanoyl group and an oxo group), and
$R^5$ represents a halogen atom, a lower alkyl group (wherein the lower alkyl group is unsubstituted or substituted with 1 to 3 groups which may be the same or different and selected from the group consisting of a halogen atom and a hydroxy group), a lower cycloalkyl group or an aryl group, a tautomer or stereoisomer of the compound, a pharmaceutically acceptable salt thereof, or a solvate thereof (VII) Another embodiment of the present invention provides:
The 2-pyridone compound according to (IV) represented by the formula [10]:

[Ka 14]

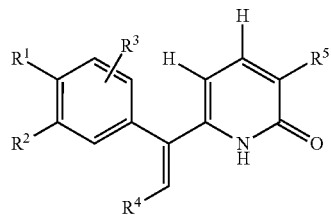

[10]

{wherein in the formula [10],
$R^4$ represents $R^B$—$Z^B$—,
wherein —$Z^B$— represents a single bond or represents any of the following formulas [8]:

[Ka 15]

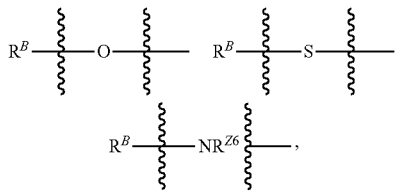

[8]

when —$Z^B$— represents any of the formulas [8],
$R^B$ represents a lower alkyl group (wherein the lower alkyl group is unsubstituted or substituted with 1 to 2 groups which may be the same or different and selected from the following Substituent Group A1); or
when —$Z^B$— represents a single bond,
$R^B$ represents a lower alkyl group, a lower cycloalkyl group, an aryl group or a heterocyclyl group (wherein the lower alkyl group, lower cycloalkyl group, aryl group or heterocyclyl group is unsubstituted or substituted with 1 to 2 groups which may be the same or different and selected from the following Substituent Group A1);
Substituent Group A1 represents a halogen atom, a lower alkyl group, a lower cycloalkyl group, an aryl group, a heterocyclyl group (wherein the lower cycloalkyl group, aryl group or heterocyclyl group is unsubstituted or substituted with 1 to 2 groups which may be the same or different and selected from the following Substituent Group A2), a hydroxy group, a lower alkoxy group (wherein the lower alkoxy group is unsubstituted or substituted with 1 to 3 halogen atoms), a lower alkylthio group, an amino group, a mono-lower alkylamino group, a di-lower alkylamino group, a lower alkanoyl group, a lower alkylsulfonyl group, a lower alkoxycarbonyl group, a lower alkanoylamino group or an oxo group, and
Substituent Group A2 represents a lower alkyl group, a lower alkoxy group, a lower alkylthio group, a mono-lower alkylamino group, a di-lower alkylamino group, a lower alkanoyl group, a lower alkylsulfonyl group, a lower alkoxycarbonyl group, a lower alkanoylamino group, a hydroxy group, a halogen atom, an oxo group or an amino group}, a tautomer or stereoisomer of the compound, a pharmaceutically acceptable salt thereof, or a solvate thereof.

(VIII) Another embodiment of the present invention provides:
The 2-pyridone compound according to (VII), wherein
$R^1$ represents $R^A$—$Z^A$—,
wherein —$Z^A$— represents a single bond or represents any of the following formulas [9]:

[Ka 16]

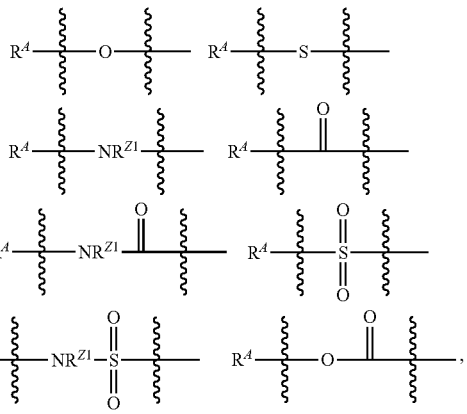

[9]

when —$Z^A$— represents any of the formulas [9],
$R^A$ represents a lower alkyl group (wherein the lower alkyl group is unsubstituted or substituted with 1 to 3 groups which may be the same or different and selected from the group consisting of a halogen atom, a hydroxy group, a heterocyclyl group, a mono-lower alkylamino group and a di-lower alkylamino group), a lower cycloalkyl group or a heterocyclyl group (wherein the heterocyclyl group is unsubstituted or substituted with one lower alkyl group); or
when —$Z^A$— represents a single bond,
$R^A$ represents a hydrogen atom, a halogen atom, a lower alkyl group (wherein the lower alkyl group is unsubstituted or substituted with 1 to 3 groups which may be the same or different and selected from the group consisting of a halogen atom, a hydroxy group, a heterocyclyl group, a lower alkoxy group and a di-lower alkylamino group), a lower cycloalkyl group, an aryl group or a heterocyclyl group;
$R^2$ represents a hydrogen atom, a halogen atom, a carbamoyl group, a lower alkyl group (wherein the lower alkyl group is unsubstituted or substituted with 1 to 3 groups which may be the same or different and selected from the group consisting of a halogen atom and a hydroxy group) or a lower alkoxy group (wherein the lower alkoxy group is unsubstituted or substituted with 1 to 3 halogen atoms),
$R^3$ represents a hydrogen atom, a halogen atom, a lower alkyl group (wherein the lower alkyl group is unsubstituted or substituted with 1 to 3 halogen atoms), a lower alkoxy group or a hydroxy group,
$R^4$ represents $R^B$—$Z^B$—,
wherein —$Z^B$— represents a single bond and
$R^B$ represents a lower alkyl group (wherein the lower alkyl group is unsubstituted or substituted with one group selected from the group consisting of a lower cycloalkyl group, an aryl group, a heterocyclyl group (wherein the heterocyclyl group is unsubstituted or substituted with 1 to 3 groups which may be the same or different and selected from the group consisting of a lower alkyl group and an oxo group), a hydroxy group and a lower alkanoylamino group), a lower cycloalkyl group (wherein the lower cycloalkyl group is unsubstituted or substituted with one group selected from the group consisting of a lower alkyl group (wherein the lower alkyl group is unsubstituted or substituted with one hydroxy group), a hydroxy group and an oxo group) or a heterocyclyl group (wherein the heterocyclyl group is unsubstituted or substituted with 1 to 2 groups which may be the same or different and selected from the group consisting of a lower alkyl group, a hydroxy group, a lower alkanoyl group, a lower cycloalkylcarbonyl group, a heterocyclylcarbonyl group, a lower alkylsulfonyl group and an oxo group), and $R^5$ represents a halogen atom, a carbamoyl group, a lower alkanoyl group, an amino group, a di-lower alkylamino group, a lower alkyl group (wherein the lower alkyl group is unsubstituted or substituted with 1 to 3 groups which may be the same or different and selected from the group consisting of a halogen atom and a hydroxy group), a lower cycloalkyl group (wherein the lower cycloalkyl group is unsubstituted or substituted with one hydroxy group), a lower alkoxy group (wherein the lower alkoxy group is unsubstituted or substituted with 1 to 3 halogen atoms), an aryl group, a heteroaryl group or an aryloxy group (wherein the aryloxy group is unsubstituted or substituted with one group selected from the group consisting of a halogen atom and a lower alkyl group), a tautomer or stereoisomer of the compound, a pharmaceutically acceptable salt thereof, or a solvate thereof (IX) Another embodiment of the present invention provides: The 2-pyridone compound according to (VIII), wherein $R^1$ represents $R^A$—$Z^A$—,
wherein —$Z^A$— represents a single bond or represents any of the following formulas [11]:

[Ka 17]

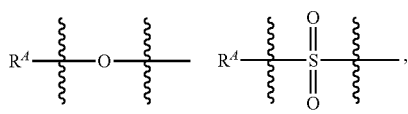
[11]

when —$Z^A$— represents any of the formulas [11],
$R^A$ represents a lower alkyl group (wherein the lower alkyl group is unsubstituted or substituted with 1 to 3 halogen atoms), a lower cycloalkyl group or a heterocyclyl group; or when —$Z^A$— represents a single bond,
$R^A$ represents a lower alkyl group (wherein the lower alkyl group is unsubstituted or substituted with 1 to 3 halogen atoms) or a halogen atom;
$R^2$ represents a hydrogen atom, a lower alkyl group (wherein the lower alkyl group is unsubstituted or substituted with 1 to 3 halogen atoms), a halogen atom or a lower alkoxy group,
$R^3$ represents a hydrogen atom or a halogen atom, and
$R^5$ represents a chlorine atom or a cyclopropyl group,
a tautomer or stereoisomer of the compound, a pharmaceutically acceptable salt thereof, or a solvate thereof (X) Another embodiment of the present invention provides: The 2-pyridone compound according to (VI) or (IX), wherein $R^B$ is a pyrrolidinyl group (wherein the pyrrolidinyl group is substituted with one oxo group or lower alkanoyl group), a tautomer or stereoisomer of the compound, a pharmaceutically acceptable salt thereof, or a solvate thereof (XI) Another embodiment of the present invention provides: The 2-pyridone compound according to (X), wherein $R^B$ is a group represented by the formula [12]:

[Ka 18]

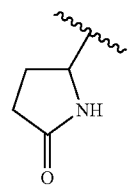
[12]

a tautomer or stereoisomer of the compound, a pharmaceutically acceptable salt thereof, or a solvate thereof (XII) Another embodiment of the present invention provides: Any of 2-pyridone compounds shown below:
6-{(E)-1-(3-chloro-4-ethoxyphenyl)-2-[(2R)-5-oxopyrrolidin-2-yl]ethenyl}-3-cyclopropylpyridin-2(1H)-one,
6-{(E)-1-(4-chlorophenyl)-2-[(2R)-5-oxopyrrolidin-2-yl]ethenyl}-3-cyclopropylpyridin-2(1H)-one,
6-{(E)-1-[3-chloro-4-(trifluoromethyl)phenyl]-2-[(2R)-5-oxopyrrolidin-2-yl]ethenyl}-3-cyclopropylpyridin-2(1H)-one,
6-{(E)-1-(4-chloro-3-methylphenyl)-2-[(2R)-5-oxopyrrolidin-2-yl]ethenyl}-3-cyclopropylpyridin-2(1H)-one,
6-{(E)-1-(4-chloro-3-fluorophenyl)-2-[(2R)-5-oxopyrrolidin-2-yl]ethenyl}-3-cyclopropylpyridin-2(1H)-one,
3-cyclopropyl-6-{(E)-1-(4-fluoro-3-methylphenyl)-2-[(2R)-5-oxopyrrolidin-2-yl]ethenyl}pyridin-2(1H)-one,
3-cyclopropyl-6-{(E)-1-[3-fluoro-4-(trifluoromethyl)phenyl]-2-[(2R)-5-oxopyrrolidin-2-yl]ethenyl}pyridin-2(1H)-one,
3-cyclopropyl-6-{(E)-1-[4-fluoro-3-(trifluoromethyl)phenyl]-2-[(2R)-5-oxopyrrolidin-2-yl]ethenyl}pyridin-2(1H)-one,
6-{(E)-1-(4-chloro-3-methoxyphenyl)-2-[(2R)-5-oxopyrrolidin-2-yl]ethenyl}-3-cyclopropylpyridin-2(1H)-one,
3-cyclopropyl-6-{(E)-1-[4-(difluoromethyl)-3-fluorophenyl]-2-[(2R)-5-oxopyrrolidin-2-yl]ethenyl}pyridin-2(1H)-one,
3-cyclopropyl-6-{(E)-1-[4-methoxy-3-(trifluoromethyl)phenyl]-2-[(2R)-5-oxopyrrolidin-2-yl]ethenyl}pyridin-2(1H)-one,
3-cyclopropyl-6-{(E)-1-[3-methyl-4-(trifluoromethyl)phenyl]-2-[(2R)-5-oxopyrrolidin-2-yl]ethenyl}pyridin-2(1H)-one,
6-{(E)-1-(4-chloro-2-fluorophenyl)-2-[(2R)-5-oxopyrrolidin-2-yl]ethenyl}-3-cyclopropylpyridin-2(1H)-one,
3-cyclopropyl-6-{(E)-1-[2-fluoro-4-(trifluoromethyl)phenyl]-2-[(2R)-5-oxopyrrolidin-2-yl]ethenyl}pyridin-2(1H)-one,
6-{(E)-1-[3-chloro-4-(cyclopropyloxy)phenyl]-2-[(2R)-5-oxopyrrolidin-2-yl]ethenyl}-3-cyclopropylpyridin-2(1H)-one,
6-{(E)-1-[3-chloro-4-(2,2,2-trifluoroethoxy)phenyl]-2-[(2R)-5-oxopyrrolidin-2-yl]ethenyl}-3-cyclopropylpyridin-2(1H)-one,
6-{(E)-1-(5-chloro-2-fluoro-4-methoxyphenyl)-2-[(2R)-5-oxopyrrolidin-2-yl]ethenyl}-3-cyclopropylpyridin-2(1H)-one,
6-{(E)-1-[3-chloro-4-(difluoromethoxy)phenyl]-2-[(2R)-5-oxopyrrolidin-2-yl]ethenyl}-3-cyclopropylpyridin-2(1H)-one, 3-cyclopropyl-6-{(E)-1-(4-ethoxy-2,3-difluorophenyl)-2-[(2R)-5-oxopyrrolidin-2-yl]ethenyl}pyridin-2(1H)-one,
3-cyclopropyl-6-{(E)-1-[4-(cyclopropylsulfonyl)phenyl]-2-[(2R)-5-oxopyrrolidin-2-yl]ethenyl}pyridin-2(1H)-one,
6-{(E)-1-(2-chloro-4-ethoxyphenyl)-2-[(2R)-5-oxopyrrolidin-2-yl]ethenyl}-3-cyclopropylpyridin-2(1H)-one,
3-cyclopropyl-6-[(E)-2-[(2R)-5-oxopyrrolidin-2-yl]-1-{4-[(trifluoromethyl)sulfonyl]phenyl}ethenyl]pyridin-2(1H)-one,
3-chloro-6-{(E)-1-[4-(cyclopropylsulfonyl)phenyl]-2-[(2R)-5-oxopyrrolidin-2-yl]ethenyl}pyridin-2(1H)-one,
3-chloro-6-{(E)-1-[3-chloro-4-(ethylsulfonyl)phenyl]-2-[(2R)-5-oxopyrrolidin-2-yl]ethenyl}pyridin-2(1H)-one,
3-chloro-6-{(E)-1-[4-(cyclopentylsulfonyl)phenyl]-2-[(2R)-5-oxopyrrolidin-2-yl]ethenyl}pyridin-2(1H)-one,
3-cyclopropyl-6-{(E)-1-[4-(methylsulfonyl)phenyl]-2-[(2R)-5-oxopyrrolidin-2-yl]ethenyl}pyridin-2(1H)-one,
6-{(E)-1-[3-chloro-4-(cyclopropylsulfonyl)phenyl]-2-[(2R)-5-oxopyrrolidin-2-yl]ethenyl}-3-cyclopropylpyridin-2(1H)-one,
3-cyclopropyl-6-{(E)-1-[4-(cyclopropylsulfonyl)-3-methylphenyl]-2-[(2R)-5-oxopyrrolidin-2-yl]ethenyl}pyridin-2(1H)-one,
3-chloro-6-{(E)-1-[4-(cyclopropylsulfonyl)-3-methylphenyl]-2-[(2R)-5-oxopyrrolidin-2-yl]ethenyl}pyridin-2(1H)-one and
3-chloro-6-{(E)-1-[3-chloro-4-(cyclopropylsulfonyl)phenyl]-2-[(2R)-5-oxopyrrolidin-2-yl]ethenyl}pyridin-2(1H)-one,
a tautomer or stereoisomer of the compound, a pharmaceutically acceptable salt thereof, or a solvate thereof (XIII) Another embodiment of the present invention provides:

The 2-pyridone compound according to (III) represented by the formula [13]:

[Ka 19]

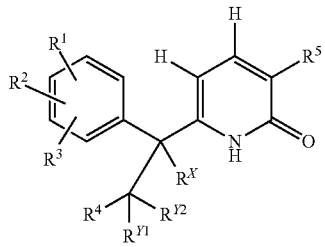

[13]

a tautomer or stereoisomer of the compound, a pharmaceutically acceptable salt thereof, or a solvate thereof (XIV) Another embodiment of the present invention provides:

The 2-pyridone compound according to (XIII) represented by the formula [14]:

[Ka 20]

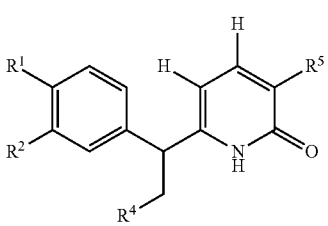

[14]

{wherein in the formula [14],
$R^4$ represents $R^B$—$Z^B$—,
wherein —$Z^B$— represents a single bond or represents any of the following formulas [8]:

[Ka 21]

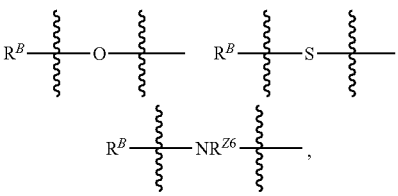

[8]

when —$Z^B$— represents any of the formulas [8],
$R^B$ represents a lower alkyl group, a lower cycloalkyl group or a heterocyclyl group (wherein the lower alkyl group, lower cycloalkyl group or heterocyclyl group is unsubstituted or substituted with 1 to 2 groups which may be the same or different and selected from the following Substituent Group A1); or when —$Z^B$— represents a single bond,
$R^B$ represents a lower alkyl group, a lower cycloalkyl group, an aryl group or a heterocyclyl group (wherein the lower alkyl group, lower cycloalkyl group, aryl group or heterocyclyl group is unsubstituted or substituted with 1 to 2 groups which may be the same or different and selected from the following Substituent Group A1);

Substituent Group A1 represents a halogen atom, a lower alkyl group, a lower cycloalkyl group, an aryl group, a heterocyclyl group (wherein the lower cycloalkyl group, aryl group or heterocyclyl group is unsubstituted or substituted with 1 to 2 groups which may be the same or different and selected from the following Substituent Group A2), a lower alkoxy group (wherein the lower alkoxy group is unsubstituted or substituted with 1 to 3 halogen atoms), a lower alkylthio group, an amino group, a mono-lower alkylamino group, a di-lower alkylamino group, a lower alkanoyl group, a lower alkylsulfonyl group, a lower alkoxycarbonyl group, a lower alkanoylamino group or an oxo group, and Substituent Group A2 represents a lower alkyl group, a lower alkoxy group, a lower alkylthio group, a mono-lower alkylamino group, a di-lower alkylamino group, a lower alkanoyl group, a lower alkylsulfonyl group, a lower alkoxycarbonyl group, a lower alkanoylamino group, a hydroxy group, a halogen atom, an oxo group or an amino group}, a tautomer or stereoisomer of the compound, a pharmaceutically acceptable salt thereof, or a solvate thereof (XV) Another embodiment of the present invention provides:

The 2-pyridone compound according to (XIV), wherein
$R^1$ represents $R^A$—$Z^A$—,
wherein —$Z^A$— represents a single bond or represents any of the following formulas [9]:

[Ka 22]

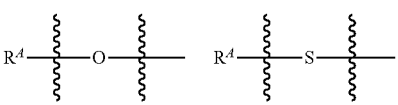

[9]

-continued

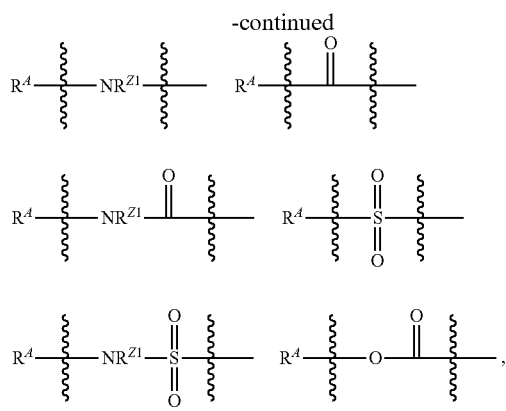

when —$Z^A$— represents any of the formulas [9],
$R^A$ represents a lower alkyl group (wherein the lower alkyl group is unsubstituted or substituted with 1 to 3 groups which may be the same or different and selected from the group consisting of a halogen atom, a hydroxy group, a heterocyclyl group, a mono-lower alkylamino group and a di-lower alkylamino group), a lower cycloalkyl group or a heterocyclyl group (wherein the heterocyclyl group is unsubstituted or substituted with one lower alkyl group); or when —$Z^A$— represents a single bond, $R^A$ represents a hydrogen atom or a lower alkyl group (wherein the lower alkyl group is unsubstituted or substituted with 1 to 3 groups which may be the same or different and selected from the group consisting of a halogen atom, a hydroxy group, a heterocyclyl group, a lower alkoxy group and a di-lower alkylamino group);

$R^2$ represents a hydrogen atom, a halogen atom, a lower alkyl group (wherein the lower alkyl group is unsubstituted or substituted with 1 to 3 halogen atoms) or a lower alkoxy group, $R^4$ represents $R^B$—$Z^B$—,
wherein —$Z^B$— represents a single bond and
$R^B$ represents a lower alkyl group (wherein the lower alkyl group is unsubstituted or substituted with one group selected from the group consisting of a lower cycloalkyl group, a heterocyclyl group, a hydroxy group and a lower alkanoylamino group), a lower cycloalkyl group (wherein the lower cycloalkyl group is unsubstituted or substituted with one group selected from the group consisting of a lower alkyl group (wherein the lower alkyl group is unsubstituted or substituted with one hydroxy group), a hydroxy group and an oxo group) or a heterocyclyl group (wherein the heterocyclyl group is unsubstituted or substituted with 1 to 2 groups which may be the same or different and selected from the group consisting of a lower alkyl group, a hydroxy group, a lower alkanoyl group and an oxo group), and $R^5$ represents a halogen atom, a lower alkyl group (wherein the lower alkyl group is unsubstituted or substituted with 1 to 3 groups which may be the same or different and selected from the group consisting of a halogen atom and a hydroxy group), a lower cycloalkyl group or an aryl group, a tautomer or stereoisomer of the compound, a pharmaceutically acceptable salt thereof, or a solvate thereof.

(XVI) Another embodiment of the present invention provides:

The 2-pyridone compound according to (XIII) represented by the formula [15]:

[Ka 23]

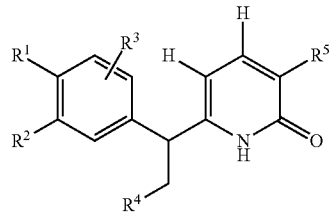

[15]

{wherein in the formula [15],
$R^4$ represents $R^B$—$Z^B$—,
wherein —$Z^B$— represents a single bond or represents any of the following formulas [8]:

[Ka 24]

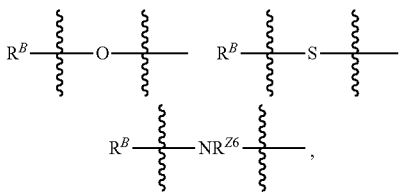

[8]

when —$Z^B$— represents any of the formulas [8],
$R^B$ represents a lower alkyl group (wherein the lower alkyl group is unsubstituted or substituted with 1 to 2 groups which may be the same or different and selected from the following Substituent Group A1); or when —$Z^B$— represents a single bond,
$R^B$ represents a lower alkyl group, a lower cycloalkyl group, an aryl group or a heterocyclyl group (wherein the lower alkyl group, lower cycloalkyl group, aryl group or heterocyclyl group is unsubstituted or substituted with 1 to 2 groups which may be the same or different and selected from the following Substituent Group A1);

Substituent Group A1 represents a halogen atom, a lower alkyl group, a lower cycloalkyl group, an aryl group, a heterocyclyl group (wherein the lower cycloalkyl group, aryl group or heterocyclyl group is unsubstituted or substituted with 1 to 2 groups which may be the same or different and selected from the following Substituent Group A2), a hydroxy group, a lower alkoxy group (wherein the lower alkoxy group is unsubstituted or substituted with 1 to 3 halogen atoms), a lower alkylthio group, an amino group, a mono-lower alkylamino group, a di-lower alkylamino group, a lower alkanoyl group, a lower alkylsulfonyl group, a lower alkoxycarbonyl group, a lower alkanoylamino group or an oxo group, and Substituent Group A2 represents a lower alkyl group, a lower alkoxy group, a lower alkylthio group, a mono-lower alkylamino group, a di-lower alkylamino group, a lower alkanoyl group, a lower alkylsulfonyl group, a lower alkoxycarbonyl group, a lower alkanoylamino group, a hydroxy group, a halogen atom, an oxo group or an amino group}, a tautomer or stereoisomer of the compound, a pharmaceutically acceptable salt thereof, or a solvate thereof.

(XVII) Another embodiment of the present invention provides:
The 2-pyridone compound according to (XVI), wherein $R^1$ represents $R^A$—$Z^A$—,
wherein —$Z^A$— represents a single bond or represents any of the following formulas [9]:

[Ka 25]

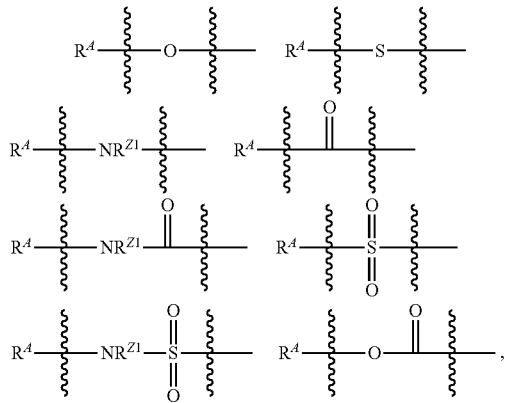

[9]

when —$Z^A$— represents any of the formulas [9],
$R^A$ represents a lower alkyl group (wherein the lower alkyl group is unsubstituted or substituted with 1 to 3 groups which may be the same or different and selected from the group consisting of a halogen atom, a hydroxy group, a heterocyclyl group, a mono-lower alkylamino group and a di-lower alkylamino group), a lower cycloalkyl group or a heterocyclyl group (wherein the heterocyclyl group is unsubstituted or substituted with one lower alkyl group); or
when —$Z^A$— represents a single bond,
$R^A$ represents a hydrogen atom, a halogen atom, a lower alkyl group (wherein the lower alkyl group is unsubstituted or substituted with 1 to 3 groups which may be the same or different and selected from the group consisting of a halogen atom, a hydroxy group, a heterocyclyl group, a lower alkoxy group and a di-lower alkylamino group), a lower cycloalkyl group, an aryl group or a heterocyclyl group;
$R^2$ represents a hydrogen atom, a halogen atom, a carbamoyl group, a lower alkyl group (wherein the lower alkyl group is unsubstituted or substituted with 1 to 3 groups which may be the same or different and selected from the group consisting of a halogen atom and a hydroxy group) or a lower alkoxy group (wherein the lower alkoxy group is unsubstituted or substituted with 1 to 3 halogen atoms),
$R^3$ represents a hydrogen atom, a halogen atom, a lower alkyl group (wherein the lower alkyl group is unsubstituted or substituted with 1 to 3 halogen atoms), a lower alkoxy group or a hydroxy group,
$R^4$ represents $R^B$—$Z^B$—,
wherein —$Z^B$— represents a single bond and
$R^B$ represents a lower alkyl group (wherein the lower alkyl group is unsubstituted or substituted with one group selected from the group consisting of a lower cycloalkyl group, an aryl group, a heterocyclyl group (wherein the heterocyclyl group is unsubstituted or substituted with 1 to 3 groups which may be the same or different and selected from the group consisting of a lower alkyl group and an oxo group), a hydroxy group and a lower alkanoylamino group), a lower cycloalkyl group (wherein the lower cycloalkyl group is unsubstituted or substituted with one group selected from the group consisting of a lower alkyl group (wherein the lower alkyl group is unsubstituted or substituted with one hydroxy group), a hydroxy group and an oxo group) or a heterocyclyl group (wherein the heterocyclyl group is unsubstituted or substituted with 1 to 2 groups which may be the same or different and selected from the group consisting of a lower alkyl group, a hydroxy group, a lower alkanoyl group, a lower cycloalkylcarbonyl group, a heterocyclylcarbonyl group, a lower alkylsulfonyl group and an oxo group), and
$R^5$ represents a halogen atom, a carbamoyl group, a lower alkanoyl group, an amino group, a di-lower alkylamino group, a lower alkyl group (wherein the lower alkyl group is unsubstituted or substituted with 1 to 3 groups which may be the same or different and selected from the group consisting of a halogen atom and a hydroxy group), a lower cycloalkyl group (wherein the lower cycloalkyl group is unsubstituted or substituted with one hydroxy group), a lower alkoxy group (wherein the lower alkoxy group is unsubstituted or substituted with 1 to 3 halogen atoms), an aryl group, a heteroaryl group or an aryloxy group (wherein the aryloxy group is unsubstituted or substituted with one group selected from the group consisting of a halogen atom and a lower alkyl group),
a tautomer or stereoisomer of the compound, a pharmaceutically acceptable salt thereof, or a solvate thereof
(XVIII) Another embodiment of the present invention provides:
The 2-pyridone compound according to (XVII), wherein $R^1$ represents $R^A$—$Z^A$—,
wherein —$Z^A$— represents a single bond or represents any of the following formulas [11]:

[Ka 26]

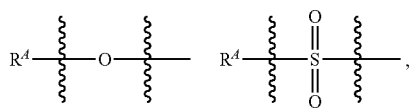

[11]

when —$Z^A$— represents any of the formulas [11],
$R^A$ represents a lower alkyl group (wherein the lower alkyl group is unsubstituted or substituted with 1 to 3 halogen atoms), a lower cycloalkyl group or a heterocyclyl group; or
when —$Z^A$— represents a single bond,
$R^A$ represents a lower alkyl group (wherein the lower alkyl group is unsubstituted or substituted with 1 to 3 halogen atoms) or a halogen atom;
$R^2$ represents a hydrogen atom, a lower alkyl group (wherein the lower alkyl group is unsubstituted or substituted with 1 to 3 halogen atoms), a halogen atom or a lower alkoxy group,
$R^3$ represents a hydrogen atom or a halogen atom, and
$R^5$ represents a chlorine atom or a cyclopropyl group,
a tautomer or stereoisomer of the compound, a pharmaceutically acceptable salt thereof, or a solvate thereof
(XIX) Another embodiment of the present invention provides:
The 2-pyridone compound according to (XV) or (XVIII), wherein $R^B$ is a pyrrolidinyl group (wherein the pyrrolidinyl group is substituted with one oxo group or lower alkanoyl group), a tautomer or stereoisomer of the compound, a pharmaceutically acceptable salt thereof, or a solvate thereof
(XX) Another embodiment of the present invention provides:
The 2-pyridone compound according to (XIX), wherein $R^B$ is a group represented by the formula [12]:

[Ka 27]

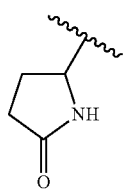

[12]

a tautomer or stereoisomer of the compound, a pharmaceutically acceptable salt thereof, or a solvate thereof.

(XXI) Another embodiment of the present invention provides:

Any of 2-pyridone compounds shown below:
6-{1-(4-chloro-3-methylphenyl)-2-[(2R)-5-oxopyrrolidin-2-yl]ethyl}-3-cyclopropylpyridin-2(1H)-one,
6-{1-[4-chloro-3-(trifluoromethyl)phenyl]-2-[(2R)-5-oxopyrrolidin-2-yl]ethyl}-3-cyclopropylpyridin-2(1H)-one,
3-cyclopropyl-6-{1-[4-(difluoromethyl)-3-methylphenyl]-2-[(2R)-5-oxopyrrolidin-2-yl]ethyl}pyridin-2(1H)-one,
3-cyclopropyl-6-{1-[4-(difluoromethyl)-3-fluorophenyl]-2-[(2R)-5-oxopyrrolidin-2-yl]ethyl}pyridin-2(1H)-one,
6-{1-[3-chloro-4-(trifluoromethyl)phenyl]-2-[(2R)-5-oxopyrrolidin-2-yl]ethyl}-3-cyclopropylpyridin-2(1H)-one,
6-{1-[3-chloro-4-(propan-2-yloxy)phenyl]-2-[(2R)-5-oxopyrrolidin-2-yl]ethyl}-3-cyclopropylpyridin-2(1H)-one,
3-cyclopropyl-6-{1-[3-methyl-4-(trifluoromethyl)phenyl]-2-[(2R)-5-oxopyrrolidin-2-yl]ethyl}pyridin-2(1H)-one,
6-{1-[3-chloro-4-(cyclopropyloxy)phenyl]-2-[(2R)-5-oxopyrrolidin-2-yl]ethyl}-3-cyclopropylpyridin-2(1H)-one,
6-{1-(5-chloro-2-fluoro-4-methoxyphenyl)-2-[(2R)-5-oxopyrrolidin-2-yl]ethyl}-3-cyclopropylpyridin-2(1H)-one,
6-{1-[3-chloro-4-(difluoromethoxy)phenyl]-2-[(2R)-5-oxopyrrolidin-2-yl]ethyl}-3-cyclopropylpyridin-2(1H)-one,
3-cyclopropyl-6-{1-[4-(cyclopropylsulfonyl)-3-methylphenyl]-2-[(2R)-5-oxopyrrolidin-2-yl]ethyl}pyridin-2(1H)-one,
3-chloro-6-{1-[3-chloro-4-(cyclopropylsulfonyl)phenyl]-2-[(2R)-5-oxopyrrolidin-2-yl]ethyl}pyridin-2(1H)-one and
6-{1-[3-chloro-4-(cyclopropylsulfonyl)phenyl]-2-[(2R)-5-oxopyrrolidin-2-yl]ethyl}-3-cyclopropylpyridin-2(1H)-one,
a tautomer or stereoisomer of the compound, a pharmaceutically acceptable salt thereof, or a solvate thereof (XXII) Another embodiment of the present invention provides:

The 2-pyridone compound according to (III) represented by the formula [16]:

[Ka 28]

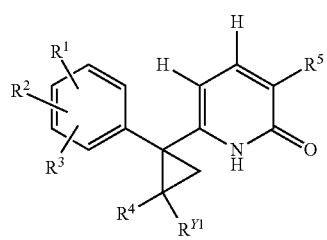

[16]

a tautomer or stereoisomer of the compound, a pharmaceutically acceptable salt thereof, or a solvate thereof (XXIII) Another embodiment of the present invention provides:

The 2-pyridone compound according to (III) represented by the formula [17]:

[Ka 29]

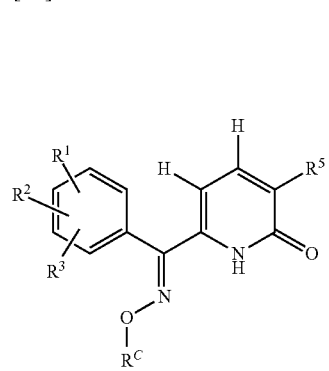

[17]

a tautomer or stereoisomer of the compound, a pharmaceutically acceptable salt thereof, or a solvate thereof.

(XXIV) Another embodiment of the present invention provides:

The 2-pyridone compound according to (III) represented by the formula [18]:

[Ka 30]

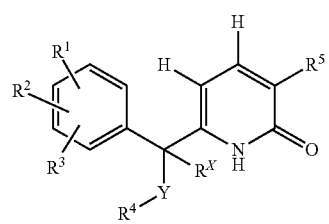

[18]

a tautomer or stereoisomer of the compound, a pharmaceutically acceptable salt thereof, or a solvate thereof (XXV) Another embodiment of the present invention provides:

A medicine comprising, as an active ingredient, the 2-pyridone compound according to any of (I) to (XXIV), a tautomer or stereoisomer of the compound, a pharmaceutically acceptable salt thereof, or a solvate thereof.

(XXVI) Another embodiment of the present invention provides:

The medicine according to (XXV), wherein the medicine is used for preventing or treating a disease or condition that can be improved by a glucokinase activating effect.

(XXVII) Another embodiment of the present invention provides:

The medicine according to (XXV), wherein the medicine is a prophylactic or therapeutic agent for diabetes or obesity.

Advantages of the Invention

The present invention can provide compounds having an excellent GK activating effect.

MODE FOR CARRYING OUT THE INVENTION

The present invention will be described in detail below, but is not particularly limited to the exemplified embodiments.

In the present invention, "n" refers to normal, "i" refers to iso, "s" refers to secondary, "t" and "tert" refers to tertiary, "c" refers to cyclo, "o" refers to ortho, "m" refers to meta and "p" refers to para.

The "halogen atom" refers to a fluorine atom, a chlorine atom, a bromine atom and an iodine atom.

The "lower alkyl group" refers to a linear or branched alkyl group having 1 to 6 carbon atoms. Examples of the group include a methyl group, an ethyl group, an n-propyl group, an i-propyl group, an n-butyl group, an i-butyl group, an s-butyl group, a t-butyl group, an n-pentyl group, an i-pentyl group, a neopentyl group, an n-hexyl group and an i-hexyl group.

The "lower cycloalkyl group" refers to a cyclic alkyl group having 3 to 8 carbon atoms. Examples of the group include a c-propyl group, a c-butyl group, a c-pentyl group, a c-hexyl group, a c-heptyl group and a c-octyl group.

The "4- to 6-membered lower cycloalkyl group" refers to a cyclic alkyl group having 4 to 6 carbon atoms. Examples of the group include a c-butyl group, a c-pentyl group and a c-hexyl group.

The "aryl group" refers to a monocyclic hydrocarbon aromatic ring group or fused polycyclic aromatic hydrocarbon ring group having 6 to 14 carbon atoms. Examples of the group include a phenyl group, a naphthyl group and an anthryl group.

The "heteroaryl group" refers to a 5- to 7-membered monocyclic aromatic heterocyclic group or a fused polycyclic aromatic heterocyclic group constituted by 10 to 14 atoms, each of which is composed of one or more same or different atoms selected from the group consisting of an oxygen atom, a sulfur atom and a nitrogen atom and 1 to 9 carbon atoms. Examples of the group include an imidazolyl group, a pyrazolyl group, an thiazolyl group, a thiadiazolyl group, an oxazolyl group, an isoxazolyl group, a pyrrolyl group, a triazolyl group, a pyridyl group, a pyrimidinyl group, a pyrazinyl group, an indolyl group, a quinolyl group, a pyridazinyl group and a tetrazolyl group.

The "heterocyclyl group" refers to a 4- to 7-membered monocyclic saturated heterocyclic group, a 4- to 7-membered partially saturated monocyclic heterocyclic group, or a fused polycyclic heterocyclic group constituted by 10 to 14 atoms, each of which is composed of one or more same or different atoms selected from the group consisting of an oxygen atom, a sulfur atom and a nitrogen atom and 1 to 9 carbon atoms. Examples of the group include an azetidinyl group, a pyrrolidinyl group, a piperidinyl group, a piperazinyl group, a morpholinyl group, a tetrahydropyranyl group, a tetrahydrofuryl group, a tetrahydrofuranyl group, a dihydrofuranyl group, a tetrahydropyranyl group, a tetrahydrothiophenyl group, a tetrahydrothiopyranyl group, a dihydrothiopyranyl group, a tetrahydropyridinyl group, a dihydropyridinyl group, a thiomorpholinyl group, a dioxanyl group, an imidazolinyl group, a thiazolinyl group, an isothiazolidinyl group, a thiazinanyl group, a diazepanyl group, a dioxolanyl group, an imidazolidinyl group, a thiazolidinyl group, a 1,3-oxazolidinyl group, a 1,4,5,6-tetrahydropyridazinyl group, a 1,2,3,4-tetrahydropyrimidinyl group, a pyrazolidinyl group, an oxabicyclo[2,2,1]heptyl group, a tetrahydro-2H-thiopyranyl group and a 1,1-dihydropyridazinyl group.

The "4- to 6-membered heterocyclyl group" refers to a 4- to 6-membered monocyclic saturated heterocyclic group or a 4- to 6-membered partially saturated monocyclic heterocyclic group, each of which is composed of one or more same or different atoms selected from the group consisting of an oxygen atom, a sulfur atom and a nitrogen atom and 1 to 5 carbon atoms. Examples of the group include an azetidinyl group, a pyrrolidinyl group, a piperidinyl group, a tetrahydrofuranyl group, a tetrahydropyranyl group, a 1,1-dihydropyridazinyl group and a morpholinyl group.

The "$C_9$-$C_{12}$ fused bicyclic hydrocarbon ring" refers to an aromatic or partially saturated fused bicyclic hydrocarbon ring which is composed of 9 to 12 carbon atoms and which contains a benzene ring in the structure. Examples of the ring include an indan ring and a naphthalene ring.

The "$C_6$-$C_{11}$ fused bicyclic heterering" refers to an aromatic or partially saturated fused bicylic heterocycle which is composed of one or more same or different atoms selected from the group consisting of an oxygen atom, a nitrogen atom and a sulfur atom and 6 to 11 carbon atoms and which contains a benzene ring or a pyridine ring in the structure. Examples of the heterocycle include a chroman ring, a chromene ring, a 3,4-dihydro-2H-benzo[b][1,4]oxazine ring, a benzofuran ring, a quinoline ring, a 1,3-dihydroisobenzofuran ring, an isoindoline ring, a 2,3-dihydrobenzo[b][1,4]oxathiin ring and a 2,3-dihydrobenzo[d]isothiazoline ring.

The "saturated or unsaturated 3- to 8-membered ring which is formed together with the carbon atom to which the substituents are bonded and which may contain one or more nitrogen, oxygen or sulfur atoms" refers to a 3- to 8-membered ring which may contain one or more same or different atoms selected from the group consisting of an oxygen atom, a sulfur atom, and a nitrogen atom and which is composed of 1 to 8 carbon atoms, wherein the ring may be partially unsaturated. Examples of the ring include a cyclohexane ring, a pyrrolidine ring, a piperidine ring, a piperazine ring, a morpholine ring, a thiomorpholine ring, a 1,2,3,6-tetrahydropyridine ring, an isothiazolidine ring, a 1,3-oxazolidine ring and a 1,1-dihydropyridazine ring.

The "saturated or unsaturated 3- to 8-membered ring which is formed together with the nitrogen atom to which the substituents are bonded and which may contain one or more nitrogen, oxygen or sulfur atoms" refers to a 3- to 8-membered heterocycle composed of one or more same or different atoms selected from the group consisting of an oxygen atom, a sulfur atom, and a nitrogen atom and 1 to 7 carbon atoms, wherein the heterocycle may be partially unsaturated. Examples of the ring include a pyrrolidine ring, a piperidine ring, a piperazine ring, a morpholine ring, a thiomorpholine ring, a 1,2,3,6-tetrahydropyridine ring, an isothiazolidine ring, a 1,3-oxazolidine ring and a 1,1-dihydropyridazine ring.

The "lower alkenyl group" refers to a linear or branched alkenyl group having 2 to 6 carbon atoms. Examples of the group include an (E)-ethenyl group, a (Z)-ethenyl group, a (1E)-propenyl group, a (2E)-propenyl group, a (1E)-butenyl group, a (1E)-pentenyl group, a (1E)-hexenyl group, an i-propenyl group, an i-butenyl group, an s-butenyl group, an i-pentenyl group, a neopentenyl group and a t-pentenyl group.

The "lower alkynyl group" refers to a linear or branched alkynyl group having 2 to 6 carbon atoms. Examples of the group include an ethynyl group, an n-propynyl group, an n-butynyl group, an n-pentynyl group and an n-hexynyl group.

The "lower alkoxy group" refers to a linear or branched alkoxy group having 1 to 6 carbon atoms. Examples of the group include a methoxy group, an ethoxy group, an n-propoxy group, an i-propoxy group, an n-butoxy group, an i-butoxy group, an s-butoxy group, a t-butoxy group, an n-pentyloxy group, an i-pentyloxy group and an n-hexyloxy group.

The "lower cycloalkoxy group" refers to a group in which the aforementioned "lower cycloalkyl group" is connected to an oxy group. Examples of the group include a c-propoxy group, a c-butoxy group, a c-pentyloxy group and a c-hexyloxy group.

The "aryloxy group" refers to a group in which the aforementioned "aryl group" is connected to an oxy group. Examples of the group include a phenoxy group and a naphthyloxy group.

The "heterocyclyloxy group" refers to a group in which the aforementioned "heterocyclyl group" is connected to an oxy group. Examples of the group include a pyranyloxy group and a piperidinyloxy group.

The "aryl-lower alkoxy group" refers to a "lower alkoxy group" having the aforementioned "aryl group" as a substituent.

The "heterocyclyl-lower alkoxy group" refers to a "lower alkoxy group" having the aforementioned "heterocyclyl group" as a substituent.

The "lower alkylthio group" refers to a linear or branched alkylthio group having 1 to 6 carbon atoms. Examples of the group include a methylthio group, an ethylthio group, an n-propylthio group, an i-propylthio group, an n-butylthio group, an i-butylthio group, an s-butylthio group and a t-butylthio group.

The "mono-lower alkylamino group" refers to an amino group having the one aforementioned "lower alkyl group" as a substituent. Examples of the group include a methylamino group, an ethylamino group, an n-propylamino group, an i-propylamino group and an n-butylamino group.

The "mono-lower cycloalkylamino group" refers to an amino group having the one aforementioned "lower cycloalkyl group" as a substituent. Examples of the group include a c-propylamino group, a c-butylamino group, a c-pentylamino group, a c-hexylamino group, a c-heptylamino group and a c-octylamino group.

The "di-lower alkylamino group" refers to an amino group having the two same or different aforementioned "lower alkyl groups" as substituents. Examples of the group include a dimethylamino group, a di(n-propyl)amino group, a di(i-propyl)amino group, an ethylmethylamino group and a methyl(n-propyl)amino group.

The "lower alkanoyl group" refers to a carbonyl group having 2 to 7 carbon atoms and having a linear or branched alkyl group. Examples of the group include an acetyl group, a propionyl group, an n-butyryl group, an i-butyryl group, an n-valeryl group, an i-valeryl group and a pivaloyl group.

The "lower cycloalkylcarbonyl group" refers to a carbonyl group having the aforementioned "lower cycloalkyl group" as a substituent. Examples of the group include a cyclopropanecarbonyl group.

The "heterocyclylcarbonyl group" refers to a carbonyl group having the aforementioned "heterocyclyl group" as a substituent. Examples of the group include a tetrahydro-2H-pyran-4-carbonyl group.

The "lower alkylsulfonyl group" refers to a group in which a linear or branched alkyl group having 1 to 6 carbon atoms is bonded to a sulfonyl group. Examples of the group include a methylsulfonyl group, an n-propylsulfonyl group, an i-butylsulfonyl group and an n-hexylsulfonyl group.

The "lower alkoxycarbonyl group" refers to a group in which the aforementioned "lower alkoxy group" is bonded to a carbonyl group. Examples of the group include a methoxycarbonyl group and an ethoxycarbonyl group.

The "lower alkanoylamino group" refers to a group in which the aforementioned "lower alkanoyl group" is bonded to an amino group. Examples of the group include an acetylamino group.

The "lower alkylene group" refers to a divalent hydrocarbon group having 1 to 3 carbon atoms. Examples of the group include a methylene group, an ethylene group and a propylene group. The "lower alkylene group which may contain an ether bond" refers to a group in which 1 or 2 ether bonds are inserted into any location of the aforementioned "lower alkylene group".

The "oxo group" refers to a substituent (=O) in which an oxygen atom substitutes through a double bond. Accordingly, an oxo group that substitutes a carbon atom forms a carbonyl group together with the carbon atom, one oxo group that substitutes a sulfur atom forms a sulfinyl group together with the sulfur atom, and two oxo groups that substitute a sulfur atom form a sulfonyl group together with the sulfur atom. Specific examples of the oxo group-substituted heterocyclyl group in which an oxo group substitutes a heterocyclyl group in the present invention include a 2-oxopyrrolidinyl group, a 2-oxopiperidinyl group, a 1-oxidotetrahydro-2H-thiopyranyl group, a 1,1-dioxidotetrahydro-2H-thiopyranyl group, a 1,1-dioxidoisothiazolidinyl group, a 2-oxo-1,3-oxazolidinyl group and a 6-oxo-1,1-dihydropyridazinyl group.

A preferred embodiment of the compound of the present invention is as follows.

Specifically,
the preferred ring represented by A is a benzene ring,
preferred $R^1$ is $R^A—Z^A—$,
one preferred $—Z^A—$ in $R^1$ is any of the following formulas [9]:

[Ka 31]

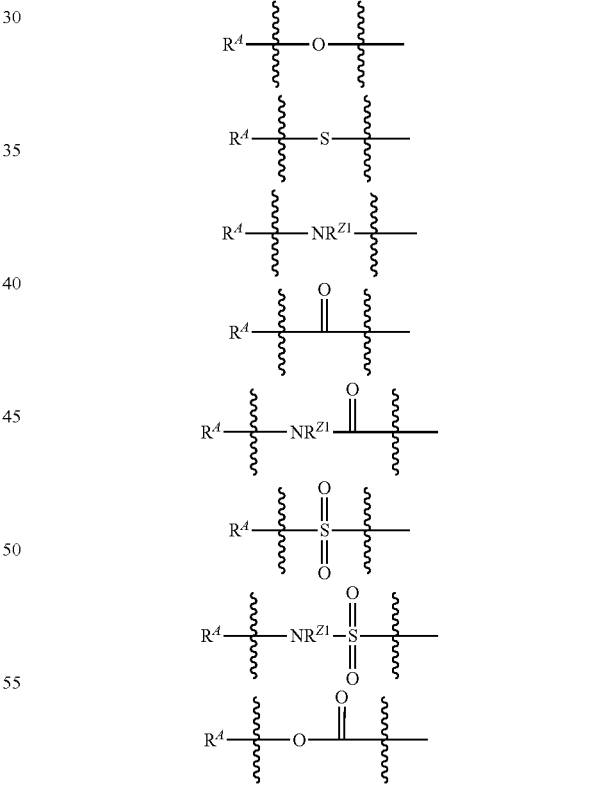

[9]

preferred $R^{Z1}$ here is a hydrogen atom or a lower alkyl group,
preferred $R^A$ here is a lower alkyl group (wherein the lower alkyl group is unsubstituted or substituted with 1 to 3 groups which may be the same or different and selected from the group consisting of a halogen atom, a hydroxy group, a heterocyclyl group, a mono-lower alkylamino group and a di-lower alkylamino group), a lower cycloalkyl group or a heterocyclyl group (wherein the heterocyclyl group is unsubstituted or substituted with one lower alkyl group), more preferred —$Z^A$— is the following formula [19]:

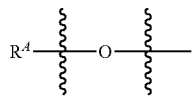

[19]

more preferred $R^A$ here is a lower alkyl group or a lower cycloalkyl group,
another preferred —$Z^A$— is a single bond,
preferred $R^A$ here is a hydrogen atom or a lower alkyl group (wherein the lower alkyl group is unsubstituted or substituted with 1 to 3 groups which may be the same or different and selected from the group consisting of a halogen atom, a hydroxy group, a heterocyclyl group, a lower alkoxy group and a di-lower alkylamino group),
more preferred $R^A$ is a lower alkyl group (wherein the lower alkyl group is unsubstituted or substituted with 1 to 3 halogen atoms),
preferred $R^X$ is a hydrogen atom,
preferred $R^{Y1}$ and $R^{Y2}$ are each a hydrogen atom,
preferred $R^4$ is $R^B$—$Z^B$—,
preferred —$Z^B$— is a single bond,
preferred $R^B$ is a lower alkyl group (wherein the lower alkyl group is unsubstituted or substituted with one group selected from the group consisting of a lower cycloalkyl group, a heterocyclyl group, a hydroxy group and a lower alkanoylamino group), a lower cycloalkyl group (wherein the lower cycloalkyl group is unsubstituted or substituted with one group selected from the group consisting of a lower alkyl group (wherein the lower alkyl group is unsubstituted or substituted with one hydroxy group), a hydroxy group and an oxo group) or a heterocyclyl group (wherein the heterocyclyl group is unsubstituted or substituted with 1 to 2 groups which may be the same or different and selected from the group consisting of a lower alkyl group, a hydroxy group, a lower alkanoyl group and an oxo group),
more preferred $R^B$ is a lower cycloalkyl group (wherein the lower cycloalkyl group is unsubstituted or substituted with one group selected from the group consisting of a lower alkyl group (wherein the lower alkyl group is unsubstituted or substituted with one hydroxy group), a hydroxy group and an oxo group) or a heterocyclyl group (wherein the heterocyclyl group is unsubstituted or substituted with 1 to 2 groups which may be the same or different and selected from the group consisting of a lower alkyl group, a hydroxy group, a lower alkanoyl group and an oxo group),
particularly preferred $R^B$ is a 4- to 6-membered lower cycloalkyl group (wherein the lower cycloalkyl group is unsubstituted or substituted with one group selected from the group consisting of a lower alkyl group (wherein the lower alkyl group is unsubstituted or substituted with one hydroxy group), a hydroxy group and an oxo group) or a 4- to 6-membered heterocyclyl group (wherein the heterocyclyl group is unsubstituted or substituted with 1 to 2 groups which may be the same or different and selected from the group consisting of a lower alkyl group, a hydroxy group, a lower alkanoyl group and an oxo group),
preferred $R^W$ is $OR^C$,
preferred $R^C$ is a lower cycloalkyl group, preferred $R^2$ is a hydrogen atom, a halogen atom, a lower alkyl group (wherein the lower alkyl group is unsubstituted or substituted with 1 to 3 halogen atoms) or a lower alkoxy group,
more preferred $R^2$ is a hydrogen atom, a halogen atom or a lower alkyl group (wherein the lower alkyl group is unsubstituted or substituted with 1 to 3 halogen atoms),
preferred $R^3$ is a hydrogen atom,
preferred $R^5$ is a halogen atom, a lower alkyl group (wherein the lower alkyl group is unsubstituted or substituted with 1 to 3 groups selected from the group consisting of a halogen atom and a hydroxy group), a lower cycloalkyl group or an aryl group,
more preferred $R^5$ is a halogen atom, a lower alkyl group (wherein the lower alkyl group is unsubstituted or substituted with 1 to 3 halogen atoms) or a lower cycloalkyl group,
preferred V is a single bond, and
preferred W is a single bond.

Another preferred embodiment is as follows.
The preferred ring represented by A is a benzene ring,
preferred $R^1$ is $R^A$—$Z^A$—,
one preferred —$Z^A$— in $R^1$ is any of the following formulas [9]:

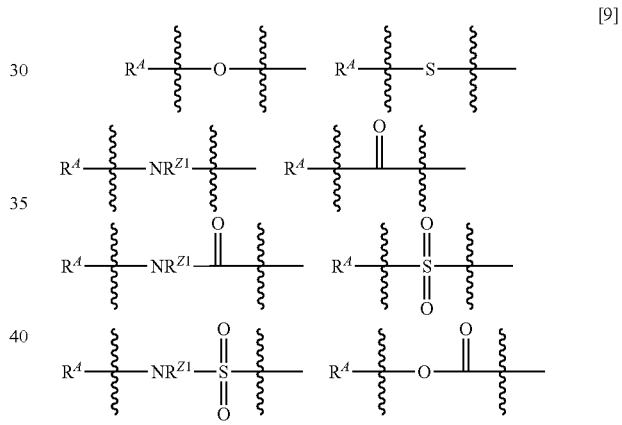

[9]

preferred $R^{Z1}$ here is a hydrogen atom or a lower alkyl group,
preferred $R^A$ here is a lower alkyl group (wherein the lower alkyl group is unsubstituted or substituted with 1 to 3 groups which may be the same or different and selected from the group consisting of a halogen atom, a hydroxy group, a heterocyclyl group, a mono-lower alkylamino group and a di-lower alkylamino group), a lower cycloalkyl group or a heterocyclyl group (wherein the heterocyclyl group is unsubstituted or substituted with one lower alkyl group),
more preferred —$Z^A$— is the following formula [11]:

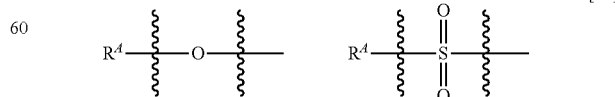

[11]

more preferred $R^A$ here is a lower alkyl group (wherein the lower alkyl group is unsubstituted or substituted with 1 to 3 halogen atoms) or a lower cycloalkyl group, another preferred —$Z^A$— is a single bond,
preferred $R^A$ here is a hydrogen atom, a halogen atom or a lower alkyl group (wherein the lower alkyl group is unsubstituted or substituted with 1 to 3 groups which may be the same or different and selected from the group consisting of a halogen atom, a hydroxy group, a heterocyclyl group, a lower alkoxy group and a di-lower alkylamino group),
more preferred $R^A$ is a lower alkyl group (wherein the lower alkyl group is unsubstituted or substituted with 1 to 3 halogen atoms) or a halogen atom,
preferred $R^X$ is a hydrogen atom,
preferred $R^{Y1}$ and $R^{Y2}$ are each a hydrogen atom,
preferred $R^4$ is $R^B$—$Z^B$—,
preferred —$Z^B$— is a single bond,
preferred $R^B$ is a lower alkyl group (wherein the lower alkyl group is unsubstituted or substituted with one group selected from the group consisting of a lower cycloalkyl group, an aryl group, a heterocyclyl group (wherein the heterocyclyl group is unsubstituted or substituted with 1 to 3 groups which may be the same or different and selected from the group consisting of a lower alkyl group and an oxo group), a hydroxy group and a lower alkanoylamino group), a lower cycloalkyl group (wherein the lower cycloalkyl group is unsubstituted or substituted with one group selected from the group consisting of a lower alkyl group (wherein the lower alkyl group is unsubstituted or substituted with one hydroxy group), a hydroxy group and an oxo group) or a heterocyclyl group (wherein the heterocyclyl group is unsubstituted or substituted with 1 to 2 groups which may be the same or different and selected from the group consisting of a lower alkyl group, a hydroxy group, a lower alkanoyl group, a lower cycloalkylcarbonyl group, a heterocyclylcarbonyl group, a lower alkylsulfonyl group and an oxo group),
more preferred $R^B$ is a lower cycloalkyl group (wherein the lower cycloalkyl group is unsubstituted or substituted with one group selected from the group consisting of a lower alkyl group (wherein the lower alkyl group is unsubstituted or substituted with one hydroxy group), a hydroxy group and an oxo group) or a heterocyclyl group (wherein the heterocyclyl group is unsubstituted or substituted with 1 to 2 groups which may be the same or different and selected from the group consisting of a lower alkyl group, a hydroxy group, a lower alkanoyl group, a lower alkylsulfonyl group and an oxo group),
particularly preferred $R^B$ is a 4- to 6-membered lower cycloalkyl group (wherein the lower cycloalkyl group is unsubstituted or substituted with one group selected from the group consisting of a lower alkyl group (wherein the lower alkyl group is unsubstituted or substituted with one hydroxy group), a hydroxy group and an oxo group) or a 4- to 6-membered heterocyclyl group (wherein the heterocyclyl group is unsubstituted or substituted with 1 to 2 groups which may be the same or different and selected from the group consisting of a lower alkyl group, a hydroxy group, a lower alkanoyl group, a lower alkylsulfonyl group and an oxo group),
preferred $R^W$ is $OR^C$,
preferred $R^C$ is a lower cycloalkyl group,
preferred $R^2$ is a hydrogen atom, a halogen atom, a carbamoyl group, a lower alkyl group (wherein the lower alkyl group is unsubstituted or substituted with 1 to 3 groups which may be the same or different and selected from the group consisting of a halogen atom and a hydroxy group) or a lower alkoxy group (wherein the lower alkoxy group is unsubstituted or substituted with 1 to 3 halogen atoms),
more preferred $R^2$ is a hydrogen atom, a halogen atom, a lower alkyl group (wherein the lower alkyl group is unsubstituted or substituted with 1 to 3 halogen atoms) or a lower alkoxy group,
preferred $R^3$ is a hydrogen atom, a halogen atom, a lower alkyl group, a lower alkoxy group (wherein the lower alkyl group or lower alkoxy group is unsubstituted or substituted with 1 to 3 halogen atoms) or a hydroxy group,
more preferred $R^3$ is a hydrogen atom or a halogen atom,
preferred $R^5$ is a halogen atom, a carbamoyl group, a lower alkanoyl group, an amino group, a di-lower alkylamino group, a lower alkyl group (wherein the lower alkyl group is unsubstituted or substituted with 1 to 3 groups which may be the same or different and selected from the group consisting of a halogen atom and a hydroxy group), a lower cycloalkyl group (wherein the lower cycloalkyl group is unsubstituted or substituted with one hydroxy group), a lower alkoxy group (wherein the lower alkoxy group is unsubstituted or substituted with 1 to 3 halogen atoms), an aryl group, a heteroaryl group or an aryloxy group (wherein the aryloxy group is unsubstituted or substituted with one group selected from the group consisting of a halogen atom and a lower alkyl group),
more preferred $R^5$ is a halogen atom, a lower alkyl group (wherein the lower alkyl group is unsubstituted or substituted with 1 to 3 halogen atoms) or a lower cycloalkyl group,
particularly preferred $R^5$ is a chlorine atom or a cyclopropyl group,
preferred V is a single bond, and
preferred W is a single bond.
One preferred embodiment is a structure represented by the formula [7]:

[Ka 35]

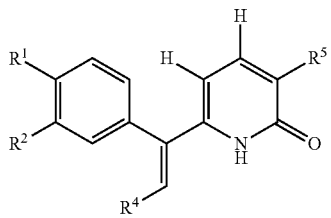

(wherein in the formula [7],
preferred $R^1$ is $R^A$—$Z^A$—,
one preferred —$Z^A$— in $R^1$ is the following formula [19]:

[Ka 36]

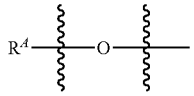

preferred $R^A$ here is a lower alkyl group or a lower cycloalkyl group,
another preferred —$Z^A$— is a single bond,
preferred $R^A$ here is a lower alkyl group (wherein the lower alkyl group is unsubstituted or substituted with 1 to 3 halogen atoms),
preferred $R^2$ is a hydrogen atom, a halogen atom or a lower alkyl group (wherein the lower alkyl group is unsubstituted or substituted with 1 to 3 halogen atoms), preferred $R^4$ is $R^B$—$Z^B$—, preferred —$Z^B$— is a single bond,
preferred $R^B$ is a lower cycloalkyl group (wherein the lower cycloalkyl group is unsubstituted or substituted with one group selected from the group consisting of a lower alkyl group (wherein the lower alkyl group is unsubstituted or substituted with one hydroxy group), a hydroxy group and an oxo group) or a heterocyclyl group (wherein the heterocyclyl group is unsubstituted or substituted with 1 to 2 groups which may be the same or different and selected from the group consisting of a lower alkyl group, a hydroxy group, a lower alkanoyl group and an oxo group), more preferred $R^B$ is a 4- to 6-membered lower cycloalkyl group (wherein the lower cycloalkyl group is unsubstituted or substituted with one group selected from the group consisting of a lower alkyl group (wherein the lower alkyl group is unsubstituted or substituted with one hydroxy group), a hydroxy group and an oxo group) or a 4- to 6-membered heterocyclyl group (wherein the heterocyclyl group is unsubstituted or substituted with 1 to 2 groups which may be the same or different and selected from the group consisting of a lower alkyl group, a hydroxy group, a lower alkanoyl group and an oxo group), and preferred $R^5$ is a halogen atom, a lower alkyl group (wherein the lower alkyl group is unsubstituted or substituted with 1 to 3 halogen atoms) or a lower cycloalkyl group).

Another preferred embodiment is a structure represented by the formula [10]:

[Ka 37]

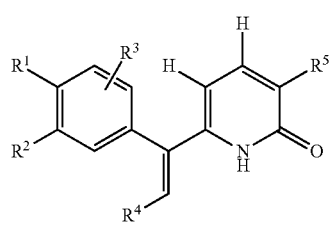

[10]

(wherein in the formula [10],
preferred $R^1$ is $R^A$—$Z^A$—,
one preferred —$Z^A$— in $R^1$ is the following formula [11]:

[Ka 38]

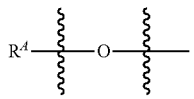

[11]

preferred $R^A$ here is a lower alkyl group (wherein the lower alkyl group is unsubstituted or substituted with 1 to 3 halogen atoms) or a lower cycloalkyl group,
another preferred —$Z^A$— is a single bond,
preferred $R^A$ here is a lower alkyl group (wherein the lower alkyl group is unsubstituted or substituted with 1 to 3 halogen atoms) or a halogen atom,
preferred $R^2$ is a hydrogen atom, a lower alkyl group (wherein the lower alkyl group is unsubstituted or substituted with 1 to 3 halogen atoms), a halogen atom or a lower alkoxy group,
preferred $R^3$ is a hydrogen atom or a halogen atom,
preferred $R^4$ is $R^B$—$Z^B$—, preferred —$Z^B$— is a single bond, preferred $R^B$ is a lower cycloalkyl group (wherein the lower cycloalkyl group is unsubstituted or substituted with one group selected from the group consisting of a lower alkyl group (wherein the lower alkyl group is unsubstituted or substituted with one hydroxy group), a hydroxy group and an oxo group) or a heterocyclyl group (wherein the heterocyclyl group is unsubstituted or substituted with 1 to 2 groups which may be the same or different and selected from the group consisting of a lower alkyl group, a hydroxy group, a lower alkanoyl group, a lower alkylsulfonyl group and an oxo group), more preferred $R^B$ is a 4- to 6-membered lower cycloalkyl group (wherein the lower cycloalkyl group is unsubstituted or substituted with one group selected from the group consisting of a lower alkyl group (wherein the lower alkyl group is unsubstituted or substituted with one hydroxy group), a hydroxy group and an oxo group) or a 4- to 6-membered heterocyclyl group (wherein the heterocyclyl group is unsubstituted or substituted with 1 to 2 groups which may be the same or different and selected from the group consisting of a lower alkyl group, a hydroxy group, a lower alkanoyl group, a lower alkylsulfonyl group and an oxo group), preferred $R^5$ is a halogen atom, a lower alkyl group (wherein the lower alkyl group is unsubstituted or substituted with 1 to 3 halogen atoms) or a lower cycloalkyl group, and more preferred $R^5$ is a chlorine atom or a cyclopropyl group).

Another preferred embodiment is a structure represented by the formula [14]:

[Ka 39]

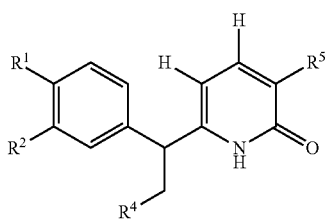

[14]

(wherein in the formula [14],
preferred $R^1$ is $R^A$—$Z^A$—,
one preferred —$Z^A$— in $R^1$ is the following formula [19]:

[Ka 40]

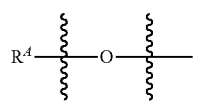

[19]

preferred $R^A$ here is a lower alkyl group or a lower cycloalkyl group,
another preferred —$Z^A$— is a single bond,
preferred $R^A$ here is a lower alkyl group (wherein the lower alkyl group is unsubstituted or substituted with 1 to 3 halogen atoms),
preferred $R^2$ is a hydrogen atom, a halogen atom or a lower alkyl group (wherein the lower alkyl group is unsubstituted or substituted with 1 to 3 halogen atoms),
preferred $R^4$ is $R^B$—$Z^B$—,
preferred —$Z^B$— is a single bond,
preferred $R^B$ is a lower cycloalkyl group (wherein the lower cycloalkyl group is unsubstituted or substituted with one group selected from the group consisting of a lower alkyl group (wherein the lower alkyl group is unsubstituted or substituted with one hydroxy group), a hydroxy group and an oxo group) or a heterocyclyl group (wherein the heterocyclyl group is unsubstituted or substituted with 1 to 2 groups which may be the same or different and selected from the group consisting of a lower alkyl group, a hydroxy group, a lower alkanoyl group and an oxo group), more preferred $R^B$ is a 4- to 6-membered lower cycloalkyl group (wherein the lower cycloalkyl group is unsubstituted or substituted with one group selected from the group consisting of a lower alkyl group (wherein the lower alkyl group is unsubstituted or substituted with one hydroxy group), a hydroxy group and an oxo group) or a 4- to 6-membered heterocyclyl group (wherein the heterocyclyl group is unsubstituted or substituted with 1 to 2 groups which may be the same or different and selected from the group consisting of a lower alkyl group, a hydroxy group, a lower alkanoyl group and an oxo group), and preferred $R^5$ is a halogen atom, a lower alkyl group (wherein the lower alkyl group is unsubstituted or substituted with 1 to 3 halogen atoms) or a lower cycloalkyl group).

Another preferred embodiment is a structure represented by the formula [15]:

[Ka 41]

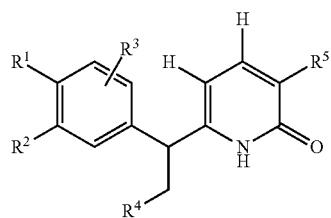

[15]

(wherein in the formula [15],
preferred $R^1$ is $R^A$—$Z^A$—,
one preferred —$Z^A$— in $R^1$ is the following formula [11]:

[Ka 42]

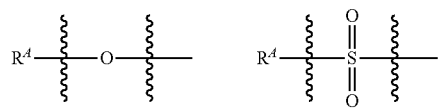

[11]

preferred $R^A$ here is a lower alkyl group (wherein the lower alkyl group is unsubstituted or substituted with 1 to 3 halogen atoms) or a lower cycloalkyl group,
another preferred —$Z^A$— is a single bond,
preferred $R^A$ here is a lower alkyl group (wherein the lower alkyl group is unsubstituted or substituted with 1 to 3 halogen atoms) or a halogen atom,
preferred $R^2$ is a hydrogen atom, a lower alkyl group (wherein the lower alkyl group is unsubstituted or substituted with 1 to 3 halogen atoms), a halogen atom or a lower alkoxy group,
preferred $R^3$ is a hydrogen atom or a halogen atom,
preferred $R^4$ is $R^B$—$Z^B$—, preferred —$Z^B$— is a single bond,
preferred $R^B$ is a lower cycloalkyl group (wherein the lower cycloalkyl group is unsubstituted or substituted with one group selected from the group consisting of a lower alkyl group (wherein the lower alkyl group is unsubstituted or substituted with one hydroxy group), a hydroxy group and an oxo group) or a heterocyclyl group (wherein the heterocyclyl group is unsubstituted or substituted with 1 to 2 groups which may be the same or different and selected from the group consisting of a lower alkyl group, a hydroxy group, a lower alkanoyl group, a lower alkylsulfonyl group and an oxo group), more preferred $R^B$ is a 4- to 6-membered lower cycloalkyl group (wherein the lower cycloalkyl group is unsubstituted or substituted with one group selected from the group consisting of a lower alkyl group (wherein the lower alkyl group is unsubstituted or substituted with one hydroxy group), a hydroxy group and an oxo group) or a 4- to 6-membered heterocyclyl group (wherein the heterocyclyl group is unsubstituted or substituted with 1 to 2 groups which may be the same or different and selected from the group consisting of a lower alkyl group, a hydroxy group, a lower alkanoyl group, a lower alkylsulfonyl group and an oxo group), preferred $R^5$ is a halogen atom, a lower alkyl group (wherein the lower alkyl group is unsubstituted or substituted with 1 to 3 halogen atoms) or a lower cycloalkyl group, and more preferred $R^5$ is a chlorine atom or a cyclopropyl group).

Examples of the pharmaceutically acceptable salts in the present invention include mineral acid salts such as hydrochlorides, hydrobromides, hydroiodides, phosphates, sulfates and nitrates; sulfonates such as methanesulfonates, ethanesulfonates, benzenesulfonates and p-toluenesulfonates; carboxylates such as oxalates, tartrates, citrates, maleates, succinates, acetates, benzoates, mandelates, ascorbates, lactates, gluconates and malates; amino acid salts such as glycine salts, lysine salts, arginine salts, ornithine salts, glutamates and aspartates; and mineral salts such as lithium salts, sodium salts, potassium salts, calcium salts and magnesium salts, and salts with organic bases such as ammonium salts, triethylamine salts, diisopropylamine salts and cyclohexylamine salts. Preferred examples include hydrochlorides, hydrobromides, phosphates, sulfates, methanesulfonates, p-toluenesulfonates, oxalates, tartrates, citrates, acetates, lactates, glutamates, aspartates, sodium salts, potassium salts, ammonium salts and triethylamine salts.

The solvates in the present invention are pharmaceutically acceptable solvates of the compounds of the present invention or salts thereof. The compounds of the present invention and salts thereof may absorb moisture, have adsorbed water, or form hydrates by exposure to the air, recrystallization or the like. The compounds of the present invention also include such hydrates.

The compounds of the present invention may have an asymmetric center; various optical isomers exist in this case. Therefore, the compounds of the present invention may exist as (R)-isomers (single), (S)-isomers (single), racemates, or (RS)-mixtures containing both optical isomers in any proportions. Such compounds having two or more asymmetric centers have diastereomers arising from optical isomerism for each asymmetric center. The compounds of the present invention also include those containing all these forms in any proportions. For example, diastereomers can be separated by methods well known to a person skilled in the art such as fractional crystallization and optically active compounds can be obtained by organic chemistry techniques well known for this purpose. In the present specification, a symbol "*" attached to the asymmetric carbon atom of a compound in the figures relates to stereoisomerism in the asymmetric carbon atom with the symbol attached, and means a greater percentage of one enantiomer; however, it is preferable that the compound be substantially a single enantiomer. The absolute configuration of the asymmetric carbon atom may also be unclear. The compounds of the present invention may have geometric isomers such as (E)- and (Z)-isomers. The compounds of the present invention also include such isomers and those containing such isomers in any proportions.

The 2-pyridone compounds of the present invention may be pharmaceutically acceptable salts thereof, or may be solvates of the compounds or the salts. Hereinafter, the 2-pyridone compounds of the present invention, tautomers or stereoisomers of the compounds, or pharmaceutically acceptable salts thereof, or solvates of the compounds or the salts are inclusively referred to as "compounds of the present invention".

The "compounds of the present invention" also include compounds commonly called prodrugs which have a chemically or metabolically decomposable group and form the pharmacologically active compounds of the present invention by solvolysis or in vivo under physiological conditions.

The compounds of the present invention have a GK activating effect. Therefore, the compounds of the present invention can improve hyperglycemia by increasing glucose metabolism and glycogenesis in the liver and/or glucose-induced insulin secretion from pancreatic beta cells. Accordingly, the compounds can be used as novel drug therapies differing from existing therapeutic agents for diabetes in mechanism of action. Diabetes include type I diabetes, type II diabetes and other diabetes due to specific causes. The compounds of the present invention are also effective for the treatment and prevention of diabetic complications such as ketoacidosis, microangiopathy (retinopathy or nephropathy), arteriosclerosis (such as atherosclerosis, myocardial infarction, cerebral infarction or peripheral arterial occlusive disease), neuropathy (such as sensory neuropathy, motor neuropathy or autonomic neuropathy), foot gangrene and infections.

The compounds can also be used for the treatment and prevention of diabetes-related diseases such as obesity, hyperlipidemia, hypertension, metabolic syndrome, edema, hyperuricemia and gout.

The compounds of the present invention can also be used in combination with therapeutic agents for diabetes, therapeutic agents for diabetic complications, therapeutic agents for hyperlipidemia, therapeutic agents for hypertension and the like having a mechanism of action other than a GK activating effect. For the above diseases, combinations of the compounds of the present invention with other agents can be expected to have an additive effect on the effect achieved by these respective agents alone.

Examples of the therapeutic agents for diabetes and the therapeutic agents for diabetic complications usable in combination with the compounds of the present invention include insulin preparations, insulin sensitizers (such as PPARγ agonists, PPARα/γ agonists, PPARγ agonists and PPARα/γ/δ agonists) (e.g. pioglitazone, rosiglitazone, GW-501516, GW-590735, ABT-335, AZD-6610 and AVE-8133), α-glucosidase inhibitors (e.g. voglibose, acarbose and miglitol), biguanide drugs (e.g. metformin, buformin and phenformin), insulin secretion promoters (e.g. glibenclamide, glimepiride, repaglinide, nateglinide and mitiglinide), glucagon receptor antagonists, insulin receptor kinase promoters, dipeptidyl peptidase IV inhibitors (e.g. vildagliptin, alogliptin, sitagliptin, linagliptin and saxagliptin), SGLT inhibitors (e.g. sergliflozin, canagliflozin, dapagliflozin, TS-071 and ASP-1941), PTP1b inhibitors (e.g. sodium vanadate), glucose 6-phosphatase inhibitors, glycogen phosphorylase inhibitors (e.g. PSN-357 and FR-258900), FBPase inhibitors (e.g. MB-07803), PEPCK inhibitors, pyruvate dehydrogenase kinase inhibitors, D-chiro-inositol, GSK3 inhibitors, GLP-1 agonists (e.g. liraglutide and exenatide), amylin agonists (e.g. pramlintide), glucocorticoid receptor antagonists, 11βHSD1 inhibitors (e.g. AMG-221 and INCB-13739), protein kinase C inhibitors (e.g. ruboxistaurin), β3 adrenaline receptor agonists (e.g. AJ-9677), phosphatidylinositol kinase inhibitors, phosphatidylinositol phosphatase inhibitors, ACC inhibitors, GPR40 receptor agonists, GPR119 receptor agonists (e.g. APD-597), GPR120 receptor agonists, TGR5 receptor agonists, AMPK activators (e.g. DRL-16536), aldose reductase inhibitors and AGE inhibitors.

Examples of the agents for diabetes-related diseases usable in combination with the compounds of the present invention include HMG-CoA reductase inhibitors, squalene synthase inhibitors, bile acid adsorbents, IBAT inhibitors, CETP inhibitors, CPT inhibitors, fibrates, ACAT inhibitors, MGAT inhibitors, DGAT inhibitors, cholesterol absorption inhibitors, pancreatic lipase inhibitors, MTP inhibitors, nicotinic acid derivatives, LXR agonists, LDL receptor promoters, angiotensin-converting enzyme inhibitors, angiotensin II antagonists, diuretics, calcium antagonists, endothelin-converting enzyme inhibitors, endothelin receptor antagonists, appetite suppressants, uric acid production inhibitors and uricosuric agents.

The compounds of the present invention can be administered alone or with pharmaceutically or pharmacologically acceptable carriers or diluents. The compounds of the present invention used as GK activating substances or the like may be orally or parenterally administered as such. The compounds of the present invention may also be orally or parenterally administered as agents containing the compounds as active ingredients. Examples of the parenteral administration include intravenous administration, nasal administration, transdermal administration, subcutaneous administration, intramuscular administration and sublingual administration.

The dosage of the compound of the present invention varies depending on the subject of administration, the route of administration, the disease of interest, the symptom and the like, and is usually about 0.01 to 1000 mg, and preferably 0.1 to 100 mg as a single dose when orally administered to an adult patient with diabetes, for example; it is desirable to administer this dose once to three times per day.

The compounds of the present invention can be synthesized by the processes shown below. The following production processes show general examples of production processes and do not limit production processes.

The compounds of the present invention may be synthesized using a method known in the field of chemistry per se or a method through one or more processes similar to that method. Examples of such methods include methods described in Organic Functional Group Preparations, 2nd ed., Academic Press, Inc., 1989, Comprehensive Organic Transformations, VCH Publishers Inc., 1989 and Fundamentals and Experiments of Peptide Synthesis, Maruzen Co., Ltd., 1985.

Suitable methods of protection and deprotection of functional groups contained in starting materials, intermediates or the like in the synthesis of the compounds of the present invention can be performed according to methods well known to a person skilled in the art such as the methods described in Greene's Protective Groups in Organic Synthesis, John Wily and Sons, 2006.

General processes for producing the compounds of the present invention are shown in Schemes 1 to 13. The following production processes show general examples of processes for producing compounds of the majority of Examples and do not limit production processes. The compounds of the present invention can also be produced by using methods well known to a person skilled in the art, for example, by changing $R^1$, $R^2$, $R^3$ and $R^5$ within the scope of the present invention by changing the order of performing the steps; providing a protecting group for a hydroxy group or an amino group, reacting and deprotecting in the subsequent step; or adding a new step in the course of respective steps.

Scheme 1: Process for synthesizing compound (1-c) from compound (1-a)

[Ka 43]

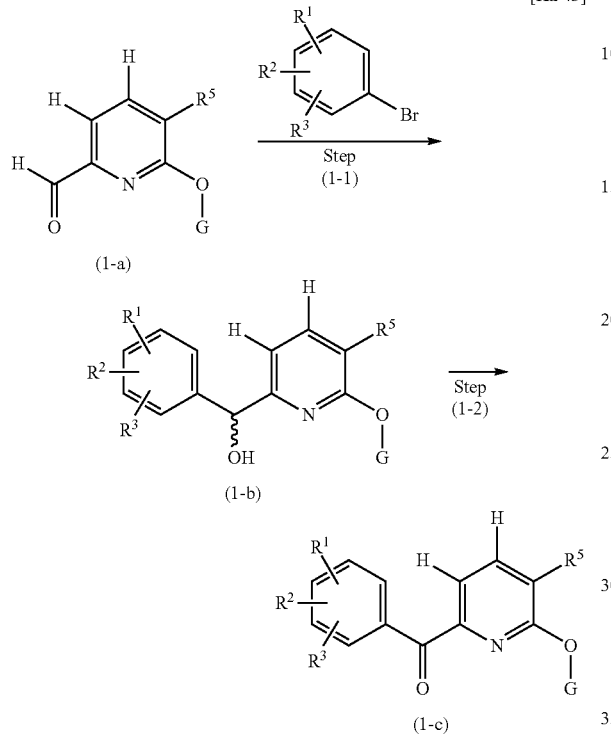

as n-butyllithium, s-butyllithium or t-butyllithium or a base such as lithium hexamethyldisilazide or potassium hexamethyldisilazide in an inert solvent at a temperature of −78° C. to 100° C. and then reacting the anion with a carbonyl compound such as a compound (1-a).

Step (1-2):

Method for producing compound (1-c): This is a method for producing a compound (1-c) by performing "oxidation reaction" of the compound (1-b) having a hydroxy group with an oxidizing agent.

Examples of the "oxidation reaction" include a method for providing a compound (1-c) by reacting the compound (1-b) with an oxidizing agent such as manganese dioxide in an inert solvent at a temperature of 0° C. to 100° C.

Scheme 2: Process for synthesizing compound (2-a) from compound (1-b)

[Ka 44]

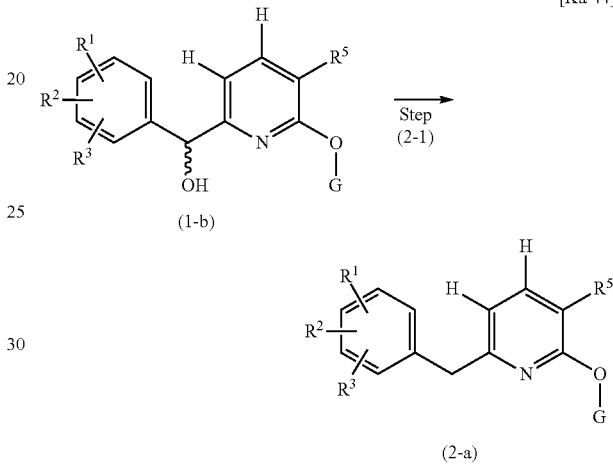

In the scheme, $R^1$, $R^2$, $R^3$ and $R^5$ are as described above and G represents a protecting group for the hydroxy group.

Step (1-1):

Method for producing compound (1-b): This is a method for producing a compound (1-b) by performing "addition reaction" using a compound (1-a) and a lithium reagent such as an aryllithium, a Grignard reagent such as an arylmagnesium bromide, or the like.

Examples of the "addition reaction" include a method for providing a compound (1-b) by generating an anion using an aryl bromide as a matrix and an organometallic reagent such In the scheme, $R^1$, $R^2$, $R^3$ and $R^5$ are as described above and G represents a protecting group for the hydroxy group.

Step (2-1):

Method for producing compound (2-a): This is a method for producing a compound (2-a) by performing "reduction reaction" of a compound (1-b) having a hydroxy group with a reducing agent.

Examples of the "reduction reaction" include a method for providing a compound (2-a) by reacting a compound (1-b) with triethylsilyl hydride and trifluoroacetic acid at a temperature of 0° C. to 100° C.

Scheme 3:
Process for synthesizing compounds (3-b), (3-d) and (3-f) from compound (1-c), or process for synthesizing compound (3-d) from compound (2-a)

[Ka 45]

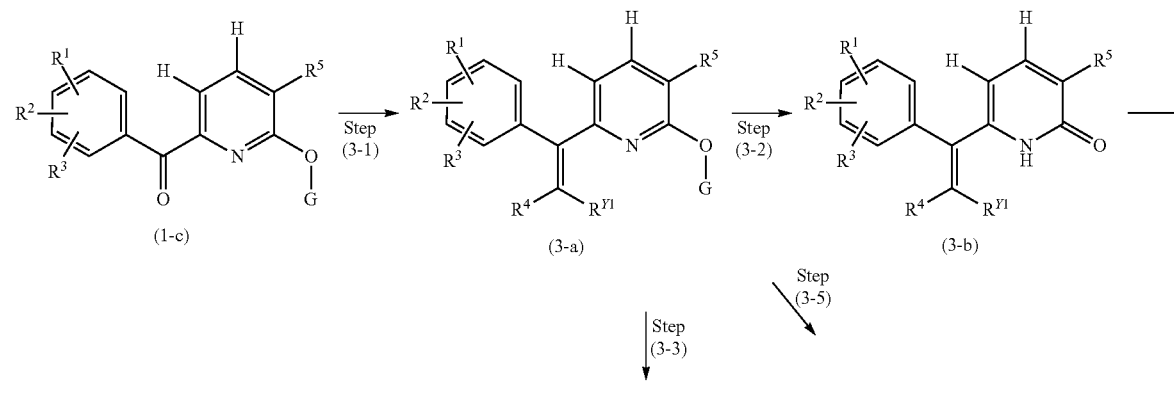

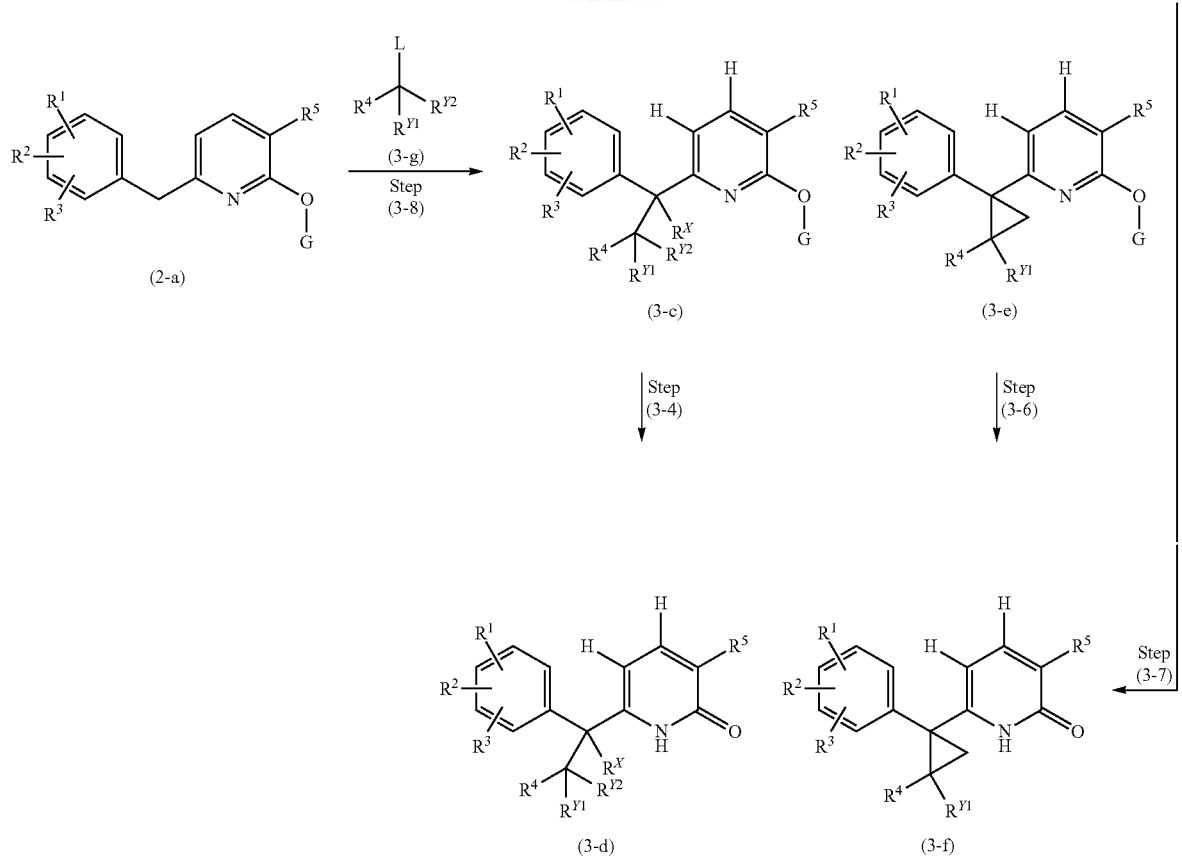

In the scheme, $R^1$, $R^2$, $R^3$, $R^4$, $R^5$, $R^X$, $R^{Y1}$ and $R^{Y2}$ are as described above, G represents a protecting group for the hydroxy group and L represents a leaving group such as a halogen atom or a mesylate, tosylate or triflate.

The Wittig reagent such as a triarylphosphonium salt, the Horner-Emmons reagent such as a phosphonate ester or the Julia reagent such as an arylalkylsulfone used in Step (3-1) is available as a commercially available compound, a known compound, or a compound synthesized from a readily available compound using various organic synthesis techniques known to a person skilled in the art.

The alkylating reagent (3-g) used in Step (3-8) is available as a commercially available compound, a known compound, or a compound synthesized from a readily available compound using various organic synthesis techniques known to a person skilled in the art.

Step (3-1):

Method for producing compound (3-a): This is a method for producing a compound (3-a) by performing "coupling reaction" using a carbonyl compound (1-c) and a Wittig reagent such as a triarylphosphonium salt, a Horner-Emmons reagent such as a phosphonate ester or a Julia reagent such as an arylalkylsulfone.

Examples of the "coupling reaction" include a method for providing an olefin compound (3-a) by generating an anion using a triarylphosphonium salt, a phosphonate ester or an arylalkylsulfone as a matrix and an organometallic reagent such as n-butyllithium, s-butyllithium or t-butyllithium or a base such as lithium hexamethyldisilazide or potassium hexamethyldisilazide in an inert solvent at a temperature of −78° C. to 100° C. and then reacting the anion with a carbonyl compound (1-c). The resulting olefin compound is generally an E/Z mixture and each isomer can be isolated using silica gel column chromatography, HPLC or the like.

Step (3-2):

Method for producing compound (3-b): A compound (3-b) can be produced by performing "deprotection reaction" of G possessed by the compound (3-a).

Examples of the "deprotection reaction" include (i) deprotection reactions where the protecting group G is an alkyl group or an allyl group, such as a method of removing the protecting group by hydrolysis reaction in an inert solvent in the presence of an acid or a strong acid at a temperature of 0° C. to 200° C., a method using trimethylsilyl iodide or the like and a method using aluminum chloride and an alkylthiol, and (ii) deprotection reactions where the protecting group G is a benzyl group, a 4-methoxybenzyl group, a 2,4-dimethoxybenzyl group, a benzyloxycarbonyl group, a benzhydryl (diphenylmethyl) group or the like, such as a method of removing the protecting group by hydrogenolysis reaction using a catalytic amount of palladium-activated carbon or rhodium-activated carbon in an inert solvent in the presence or absence of an acid at a temperature of 0° C. to 80° C. and a method using an oxidizing agent such as ammonium cerium (IV) nitrate or 2,3-dichloro-5,6-dicyano-p-benzoquinone.

Step (3-3):

Method for producing compound (3-c): This may be a method of reducing the compound (3-a) as a matrix by catalytic hydrogenation reaction using a catalytic amount of palladium-activated carbon, rhodium-activated carbon or platinum-activated carbon in an inert solvent in the presence or absence of an acid at a temperature of 0° C. to 80° C.

Step (3-4):
Method for producing compound (3-d): A compound (3-d) can be produced by performing "deprotection reaction" of G possessed by the compound (3-c).
Examples of the "deprotection reaction" include the same "deprotection reaction" as previously described in Step (3-2).
Step (3-5):
Method for producing compound (3-e): A cyclopropane compound (3-e) can be produced by performing "cyclopropanation reaction" of the olefin compound (3-a) as a matrix.
Examples of the "cyclopropanation reaction" include Simmons-Smith cyclopropanation reaction of reacting a zinc-copper alloy or dialkylzinc with a dihalomethane such as diiodomethane or chloroiodomethane in an inert solvent at a temperature of −78° C. to 100° C.
Step (3-6):
Method for producing compound (3-f): A compound (3-f) can be produced by performing "deprotection reaction" of G possessed by the compound (3-e).
Examples of the "deprotection reaction" include the same "deprotection reaction" as previously described in Step (3-2).

Step (3-7):
Another method for producing compound (3-f): A cyclopropane compound (3-f) can be produced by performing "cyclopropanation reaction" of the olefin compound (3-b) as a matrix. Examples of the "cyclopropanation reaction" include the same "cyclopropanation reaction" as previously described in Step (3-5).

Another method for producing compound (3-c): This is a method for producing a compound (3-c) by performing "alkylation reaction" using a methylene compound (2-a) and a compound (3-g).

Examples of the "alkylation reaction" include a method for providing a compound (3-c) by generating an anion using a methylene compound (2-a) as a matrix and an organometallic reagent such as n-butyllithium, s-butyllithium or t-butyl-lithium or a base such as lithium hexamethyldisilazide or potassium hexamethyldisilazide in an inert solvent at a temperature of −78° C. to 100° C. and then reacting the anion with a compound (3-g).

Scheme 4:
Process for synthesizing compounds (4-b), (4-d) and (4-g) from compound (1-c)

[Ka 46]

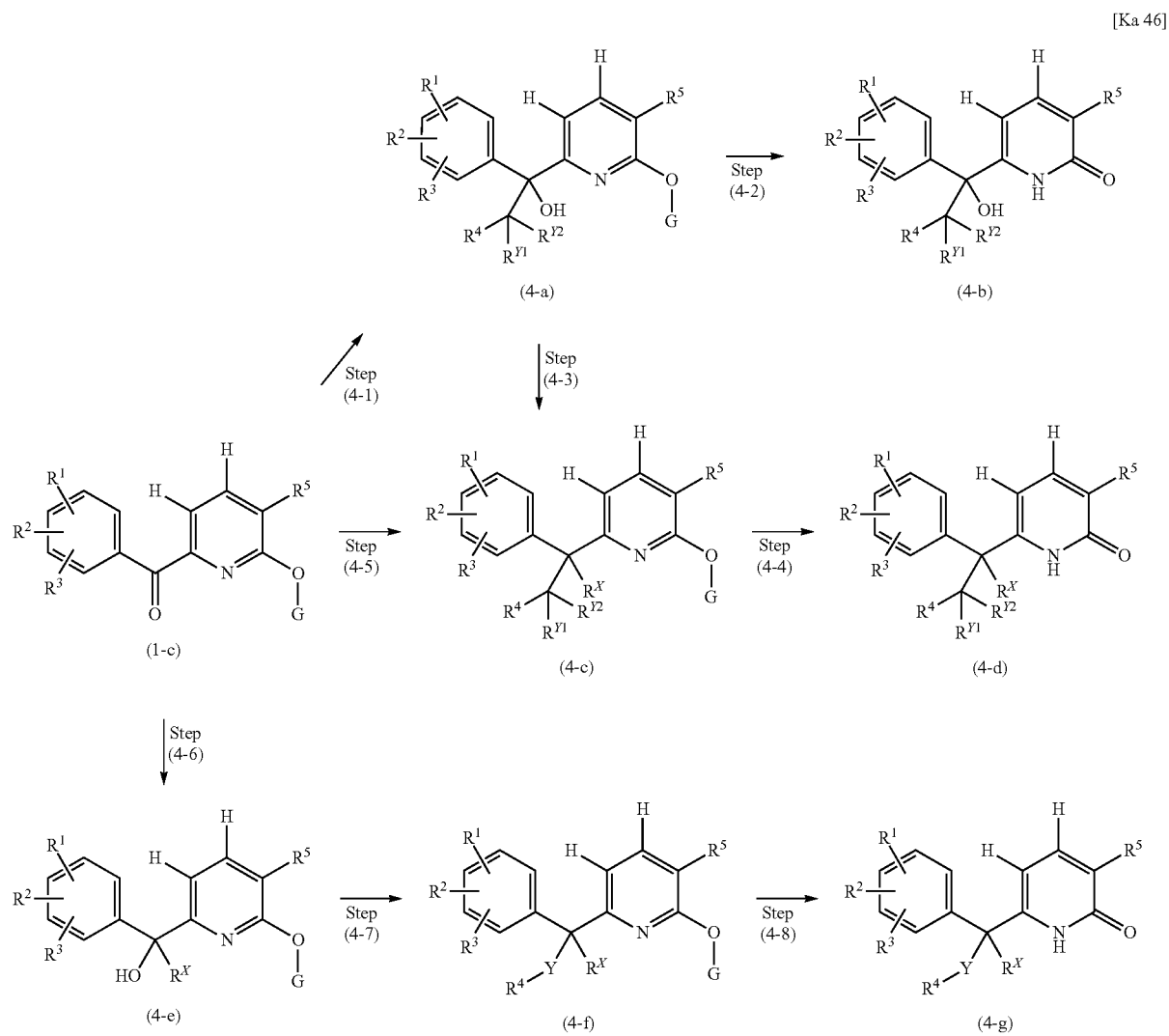

In the scheme, $R^1$, $R^2$, $R^3$, $R^4$, $R^5$, $R^X$, $R^{Y1}$, $R^{Y2}$ and Y are as described above and G represents a protecting group for the hydroxy group.

Step (4-1):

Method for producing compound (4-a): A compound (4-a) can be produced by reacting a carbonyl compound (1-c) as a matrix with a metal reagent such as an organolithium reagent, an organomagnesium reagent or an organozinc reagent in an inert solvent at a temperature of −78° C. to 100° C.

Step (4-2):

Method for producing compound (4-b): A compound (4-b) can be produced by performing "deprotection reaction" of G possessed by the compound (4-a).

Examples of the "deprotection reaction" include the same "deprotection reaction" as previously described in Step (3-2).

Step (4-3):

Method for producing compound (4-c): When $R^X$ represents $OR^{Z3}$, $SR^{Z3}$ or $NR^{Z3}R^{Z4}$, a compound (4-c) can be produced by converting the hydroxy group of the compound (4-a) to a leaving group such as a mesylate, a tosylate or a halogen atom in an inert solvent at a temperature of −78° C. to 100° C. and then reacting the compound with a corresponding lower alkyl alcohol, lower alkylthiol, mono-lower alkylamine or the like in the presence of a base.

Step (4-4):

Method for producing compound (4-d): A compound (4-d) can be produced by performing "deprotection reaction" of G possessed by the compound (4-c).

Examples of the "deprotection reaction" include the same "deprotection reaction" as previously described in Step (3-2).

Step (4-5):

Another method for producing compound (4-c): When $R^X$ represents $NR^{Z3}R^{Z4}$, a compound (4-c) can be produced by allowing a mono-lower alkylamine or the like to act on a carbonyl compound (1-c) as a matrix in an inert solvent at a temperature of −78° C. to 100° C. to yield an imine and then reacting the imine with a metal reagent such as an organolithium reagent, an organomagnesium reagent or an organozinc reagent.

Step (4-6):

Method for producing compound (4-e): When $R^X$ represents a lower alkyl group or a lower cycloalkyl group, a compound (4-e) can be produced by reacting a carbonyl compound (1-c) as a matrix with a metal reagent such as an organolithium reagent, an organomagnesium reagent or an organozinc reagent in an inert solvent at a temperature of −78° C. to 100° C.

Step (4-7):

Method for producing compound (4-f): A compound (4-f) can be produced by converting the hydroxy group of the compound (4-e) to a leaving group such as a mesylate, a tosylate or a halogen atom in an inert solvent at a temperature of −78° C. to 100° C. and then reacting the compound with a corresponding lower alkyl alcohol, lower alkylthiol, mono-lower alkylamine or the like in the presence of a base.

Step (4-8):

Method for producing compound (4-g): A compound (4-g) can be produced by performing "deprotection reaction" of G possessed by the compound (4-f).

Examples of the "deprotection reaction" include the same "deprotection reaction" as previously described in Step (3-2).

Scheme 5: Process for synthesizing compound (5-b) from compound (1-b) or (1-c)

[Ka 47]

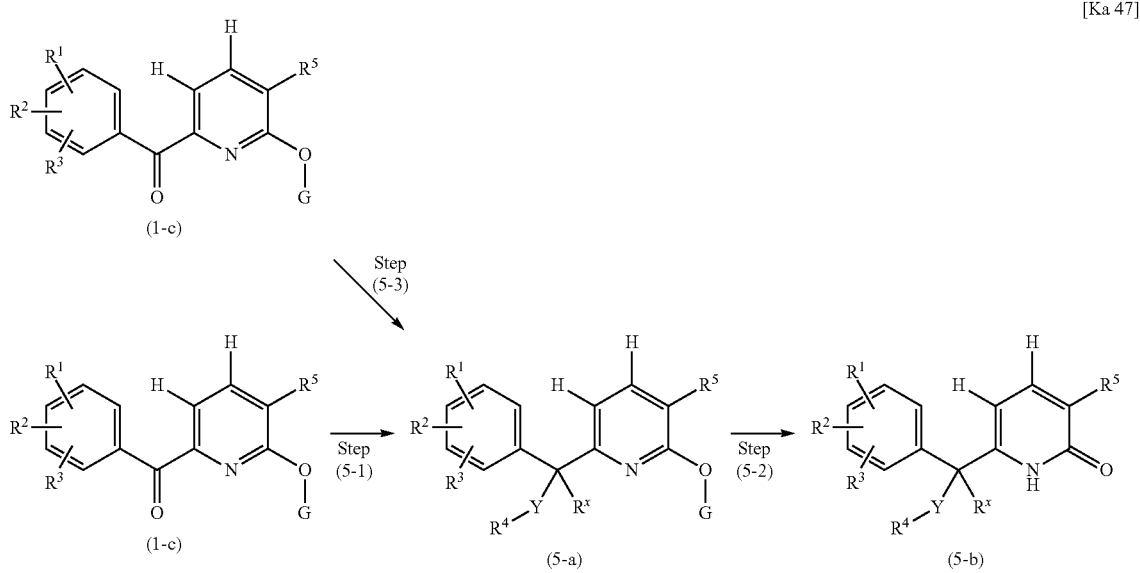

In the scheme, $R^1$, $R^2$, $R^3$, $R^4$, $R^5$, $R^X$ and Y are as described above and G represents a protecting group for the hydroxy group.

Step (5-1):

Method for producing compound (5-a): A compound (5-a) can be produced by converting the hydroxy group of a compound (1-b) to a leaving group such as a mesylate, a tosylate or a halogen atom in an inert solvent at a temperature of −78° C. to 100° C. and then allowing a corresponding lower alkyl alcohol, lower alkylthiol, mono-lower alkylamine or the like to act on the compound in the presence of a base.

Alternatively, when Y represents —O—, a compound (5-a) can be produced by allowing a lower alkyl alcohol to act on the hydroxy group of a compound (1-b) in an inert solvent in the presence of a palladium catalyst at a temperature of 0° C. to 100° C.

Alternatively, a compound (5-a) can be produced by performing nucleophilic substitution reaction of a mixture of a compound (1-b) and a phenol compound with an azo compound such as diethyl azodicarboxylate and a phosphine compound such as triphenylphosphine in an inert solvent at a temperature of room temperature to 100° C.

Step (5-2):

Method for producing compound (5-b): A compound (5-b) can be produced by performing "deprotection reaction" of G possessed by the compound (5-a).

Examples of the "deprotection reaction" include the same "deprotection reaction" as previously described in Step (3-2).

Step (5-3):

Another method for producing compound (5-a): When Y represents —$NR^{Z5}$—, a compound (5-a) can be produced by performing "reductive amination reaction" using a compound (1-c) as a matrix in an inert solvent at a temperature of −78° C. to 100° C.

Examples of the "reductive amination reaction" include reducing amination reaction of allowing a corresponding mono-lower alkylamine or the like to act on a compound (1-c) in an inert solvent at a temperature of −78° C. to 100° C. to yield an imine and then allowing a metal reducing agent such as sodium triacetoxyborohydride, sodium cyanoborohydride, sodium borohydride or lithium aluminum hydride to act on the imine.

Scheme 6: Process for synthesizing compound (6-b) from compound (1-c)

[Ka 48]

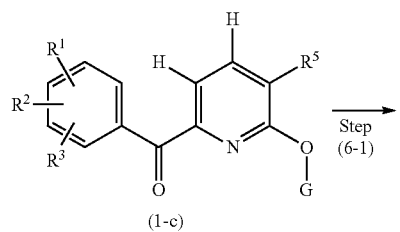

In the scheme, $R^1$, $R^2$, $R^3$, $R^5$ and $R^W$ are as described above and G represents a protecting group for the hydroxy group.

Step (6-1):

Method for producing compound (6-a): A compound (6-a) can be produced by performing "deprotection reaction" of G possessed by a compound (1-c).

Examples of the "deprotection reaction" include the same "deprotection reaction" as previously described in Step (3-2).

Step (6-2):

Method for producing compound (6-b): A compound (6-b) can be produced by allowing a lower alkylhydroxylamine, a mono-lower alkylhydrazine or the like to act on the compound (6-a) as a matrix in an inert solvent at a temperature of 0° C. to 200° C.

Scheme 7: Process for synthesizing compounds (7-d), (7-e), (7-f) and (7-h) from compound (7-a), and process for synthesizing compounds (7-k) and (7-l) from compounds (7-i)

[Ka 49]

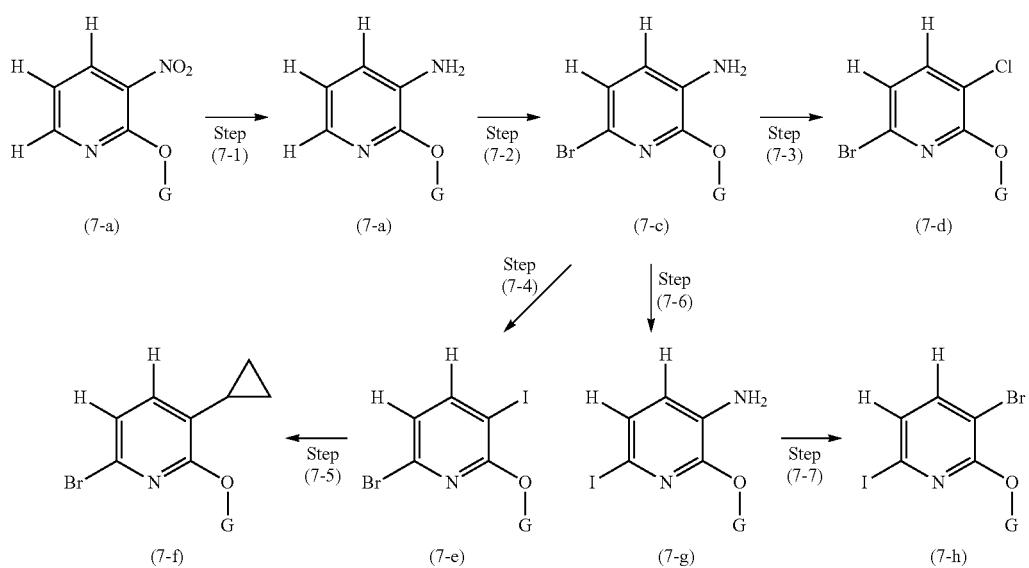

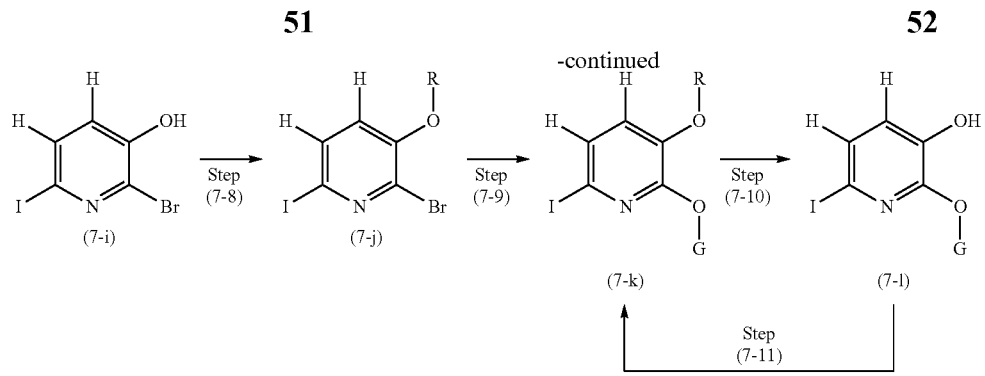

In the scheme, G represents a protecting group for the hydroxy group.

Step (7-1):

Method for producing compound (7-b): A compound (7-b) can be produced by heating under reflux a mixture of iron or tin chloride and a compound (7-a) in a solvent such as ethanol in the presence of an acid such as ammonium chloride or hydrochloric acid. Alternatively, a compound (7-b) can be produced by performing catalytic reduction reaction of a compound (7-a) as a matrix with a catalytic amount of palladium-activated carbon, rhodium-activated carbon or platinum-activated carbon in an inert solvent in the presence or absence of an acid at a temperature of 0° C. to 80° C. in a hydrogen atmosphere.

Step (7-2):

Method for producing compound (7-c): A compound (7-c) can be produced by reacting the compound (7-b) in an inert solvent such as N,N-dimethylformamide in the presence of a brominating agent such as N-bromosuccinimide or tetrabutylammonium tribromide at a temperature of –30° C. to 80° C.

Step (7-3):

Method for producing compound (7-d): A compound (7-d) can be produced by forming a diazonium salt from a mixture of the compound (7-c) and sodium nitrite or tert-butyl nitrite in concentrated hydrochloric acid or concentrated sulfuric acid as a solvent at a temperature of –30° C. to 80° C. and then allowing copper chloride to act on the diazonium salt.

Step (7-4):

Method for producing compound (7-e): A compound (7-e) can be produced by forming a diazonium salt from a mixture of the compound (7-c) and sodium nitrite or tert-butyl nitrite in concentrated hydrochloric acid or concentrated sulfuric acid as a solvent at a temperature of –30° C. to 80° C. and then allowing potassium iodide to act on the diazonium salt.

Step (7-5):

Method for producing compound (7-f): A compound (7-f) can be produced by performing coupling reaction of the compound (7-e) as a matrix with cyclopropylboronic acid in an inert solvent in the presence of a palladium catalyst at a temperature of 0° C. to 200° C.

Step (7-6):

Method for producing compound (7-g): A compound (7-g) can be produced by allowing sodium iodide to act on the compound (7-c) as a matrix in an inert solvent in the presence of copper iodide and DMEDA (N,N'-dimethylethylenediamine) at a temperature of 0° C. to 200° C.

Step (7-7):

Method for producing compound (7-h): A compound (7-h) can be produced by forming a diazonium salt from a mixture of the compound (7-g) and sodium nitrite or tert-butyl nitrite in concentrated hydrochloric acid or concentrated sulfuric acid as a solvent at a temperature of –30° C. to 80° C. and then allowing copper bromide to act on the diazonium salt.

Step (7-8):

Method for producing compound (7-j): A compound (7-j) can be produced by allowing an alkyl halide to act on a compound (7-i) as a matrix in an inert solvent in the presence of a base at a temperature of 0° C. to 200° C.

Step (7-9):

Method for producing compound (7-k): A compound (7-k) can be produced by allowing an alcohol such as methanol or 4-methoxybenzyl alcohol to act on the compound (7-j) in an inert solvent in the presence of a base at a temperature of 0° C. to 200° C.

Step (7-10):

Method for producing compound (7-l): A compound (7-l) can be produced by allowing triisopropylsilane to act on the compound (7-k) in an inert solvent in the presence of an acid such as trifluoroacetic acid at a temperature of 0° C. to 200° C. and deprotecting the 4-methoxybenzyl group.

Step (7-11):

Another method for producing compound (7-k): A compound (7-k) can be produced by allowing an alkyl halide to act on the compound (7-l) as a matrix in an inert solvent in the presence of a base at a temperature of 0° C. to 200° C.

Scheme 8: Process for synthesizing compound (8-i) from compound (8-a)
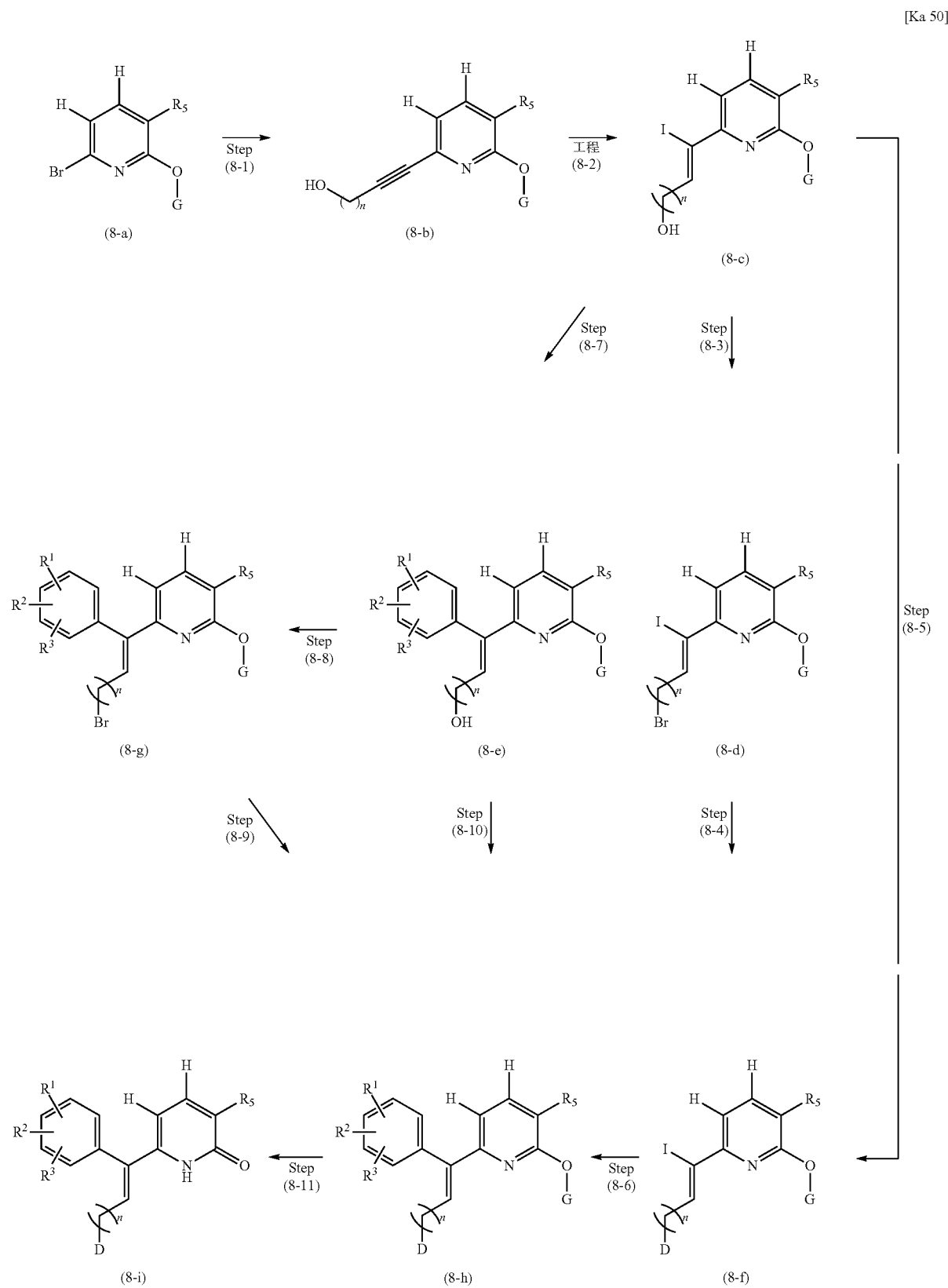

In the scheme, $R^1$, $R^2$, $R^3$ and $R^5$ are as described above, G represents a protecting group for the hydroxy group, n represents an integer of 1 to 3 and D represents a group represented by the following formula (α):

[Ka 51]

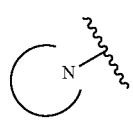

(α)

(wherein the formula (α) represents a heterocyclyl group), an aryl group or an aryloxy group.

Step (8-1):

Method for producing compound (8-b): A compound (8-b) can be produced by Pd(0)-Cu(I) coupling of a compound (8-a) and 3-butyn-1-ol or 2-propyn-1-ol with a palladium(0) catalyst such as tetrakistriphenylphosphine palladium(0) and a copper(I) halide such as copper(I) iodide in an inert solvent in the presence of a base at a temperature of 0° C. to 80° C.

Step (8-2):

Method for producing compound (8-c): A compound (8-c) can be produced by adding sodium bis(2-methoxyethoxy) aluminum hydride (Red-Al(R)) or lithium aluminum hydride to the compound (8-b) as a matrix in an inert solvent at −20° C. to room temperature and then adding an iodinating agent such as N-iodosuccinimide at −78° C. to −20° C. An olefin compound can be Z-selectively obtained if the number of carbon atoms represented by n is an integer of 1 to 2.

Step (8-3):

Method for producing compound (8-d): A compound (8-d) can be produced by allowing triphenylphosphine and carbon tetrabromide to act on the compound (8-c) as a matrix in an inert solvent at 0° C. to room temperature.

Step (8-4):

Method for producing compound (8-f): A compound (8-f) can be produced by performing nucleophilic substitution reaction of a mixture of the compound (8-d) and a compound represented by the formula D-H with a base in an inert solvent at a temperature of room temperature to 100° C.

Step (8-5):

Another method for producing compound (8-f): A compound (8-f) can be produced by performing nucleophilic substitution reaction of a mixture of the compound (8-c) and a compound represented by the formula D-H with an azo compound such as diethyl azodicarboxylate and a phosphine compound such as triphenylphosphine in an inert solvent at a temperature of room temperature to 100° C.

Step (8-6):

Method for producing compound (8-h): A compound (8-h) can be produced by performing coupling reaction of the compound (8-f) as a matrix with an arylboron compound or an aryltin compound in the presence of a palladium catalyst.

Examples of the coupling reaction include a method of reacting the compound (8-f) with an arylboron compound or an aryltin compound in an inert solvent such as 1,2-dimethoxyethane, acetonitrile, toluene, tetrahydrofuran, dimethyl sulfoxide, 1,4-dioxane or water in the presence of a palladium catalyst and a base at a temperature of 20° C. to 160° C. The reaction may be performed using microwaves.

Examples of the palladium catalyst used for the coupling reaction include palladium catalysts known to a person skilled in the art such as tetrakistriphenylphosphine palladium(0), bis(dibenzylideneacetone)palladium(0), bis(triphenylphosphine)palladium(II) dichloride, bis(triphenylphosphine)palladium(II) acetate and a [1,1'-bis(diphenylphosphino)ferrocene]palladium(II) dichloride-dichloromethane complex (1:1). It is also possible to generate a palladium(0) catalyst in the system using palladium(II) acetate or palladium-activated carbon and triphenylphosphine in the presence of a base and use the catalyst for the reaction.

Step (8-7):

Method for producing compound (8-e): A compound (8-e) can be produced by performing coupling reaction of the compound (8-c) as a matrix with an arylboron compound or an aryltin compound in the presence of a palladium catalyst.

Examples of the "coupling reaction" include the same "coupling reaction" as previously described in Step (8-6).

Step (8-8):

Method for producing compound (8-g): A compound (8-g) can be produced by allowing triphenylphosphine and carbon tetrabromide to act on the compound (8-e) as a matrix in an inert solvent at 0° C. to room temperature.

Step (8-9):

Method for producing compound (8-h):

A compound (8-h) can be produced by performing nucleophilic substitution reaction of a mixture of the compound (8-g) and a compound represented by the formula D-H with a base in an inert solvent at a temperature of room temperature to 100° C.

Alternatively, a compound (8-h) can be produced by performing coupling reaction of the compound (8-g) as a matrix with an arylboron compound or an aryltin compound in an inert solvent in the presence of a palladium catalyst.

Examples of the "coupling reaction" include the same "coupling reaction" as previously described in Step (8-6).

Step (8-10):

Another method for producing compound (8-h): A compound (8-h) can be produced by performing nucleophilic substitution reaction of a mixture of the compound (8-e) and a compound represented by the formula D-H with a dialkyl azodicarboxylate such as diethyl azodicarboxylate and triphenylphosphine in an inert solvent at a temperature of room temperature to 100° C.

Step (8-11):

Method for producing compound (8-i): A compound (8-i) can be produced by performing "deprotection reaction" of G possessed by the compound (8-h).

Examples of the "deprotection reaction" include the same "deprotection reaction" as previously described in Step (3-2).

Scheme 9: Process for synthesizing compound (9-d) from compound (8-e)

[Ka 52]

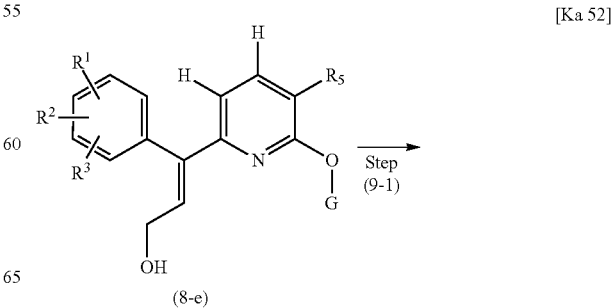

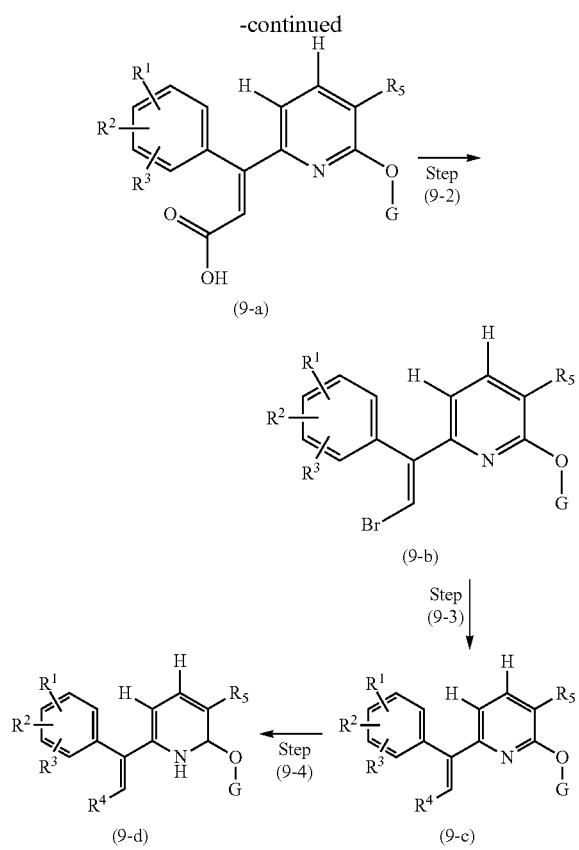

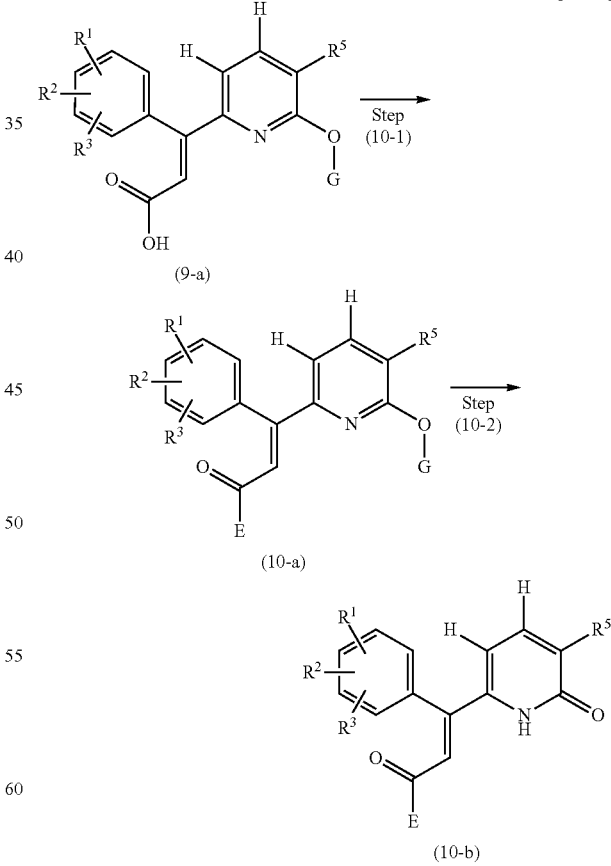

In the scheme, $R^1$, $R^2$, $R^3$, $R^4$ and $R^5$ are as described above and G represents a protecting group for the hydroxy group.

Step (9-1):

Method for producing compound (9-a): A compound (9-a) can be produced in two steps or one step by allowing various oxidizing agents to act on a compound (8-e) as a matrix. Examples of the production method in two steps include a method of oxidizing an alcohol to an aldehyde with an oxidizing agent such as a Dess-Martin reagent or manganese dioxide, or dimethyl sulfoxide, oxalyl chloride or triethylamine and oxidizing the aldehyde to a carboxylic acid with chlorous acid. Examples of the production method in one step include a method of oxidizing with potassium permanganate.

Step (9-2):

Method for producing compound (9-b): A compound (9-b) can be produced by allowing N-bromosuccinimide to act on the compound (9-a) as a matrix using triethylamine, lithium acetate, a quaternary ammonium salt or the like as a catalyst.

Step (9-3):

Method for producing compound (9-c): A compound (9-c) can be produced by performing coupling reaction of the compound (9-b) as a matrix with an arylboron compound or C—N coupling reaction of the compound (9-b) with a compound represented by the formula D'-H (wherein D' represents a heterocyclyl group represented by the above formula (a)), in the presence of a palladium catalyst.

Examples of the C—N coupling reaction include a method of reacting the compound (9-b) with a compound represented by the formula D'-H in an inert solvent such as 1,2-dimethoxyethane, acetonitrile, toluene, tetrahydrofuran, dimethyl sulfoxide or 1,4-dioxane in the presence of a palladium catalyst and a base at a temperature of 20° C. to 160° C. The reaction may be performed using microwaves. Examples of the palladium catalyst used for the C—N coupling reaction include palladium catalysts known to a person skilled in the art such as tetrakistriphenylphosphine palladium(0), bis(dibenzylideneacetone)palladium(0), bis(triphenylphosphine)palladium(II) dichloride, bis(triphenylphosphine)palladium(II) acetate, tris(dibenzylideneacetone)dipalladium(0) and a [1,1'-bis(diphenylphosphino)ferrocene]palladium(II) dichloride-dichloromethane complex (1:1). It is also possible to generate a palladium catalyst in the system using palladium (II) acetate or palladium-activated carbon and a monodentate or bidentate ligand such as triphenylphosphine, dppf ([1,1'-bis(diphenylphosphino)ferrocene]) or BINAP (2,2'-bis (diphenylphosphino)-1,1'-binaphthyl) in the presence of a base and use the catalyst for the reaction.

Examples of the method also include a method for providing a compound (9-c) by performing coupling reaction with an amide compound in the presence of a metal catalyst. Examples of the metal catalyst include copper iodide and various palladium catalysts.

Step (9-4):

Method for producing compound (9-d): A compound (9-d) can be produced by performing "deprotection reaction" of G possessed by the compound (9-c).

Examples of the "deprotection reaction" include the same "deprotection reaction" as previously described in Step (3-2).

Scheme 10: Process for synthesizing compound (10-b) from compound (9-a)

[Ka 53]

In the scheme, $R^1$, $R^2$, $R^3$ and $R^5$ are as described above, G represents a protecting group for the hydroxy group and E represents a primary aliphatic amino group such as a methylamino group or an ethylamino group, a secondary aliphatic amino group such as a dimethylamino group or a diethylamino group, a cyclic amino group such as a piperidinyl group or a morpholinyl group or an aromatic amino group such as an anilino group.

Step (10-1):

Method for producing compound (10-a): A compound (10-a) can be produced by reacting a compound (9-a) with an amine represented by the formula E-H in an inert solvent in the presence of a dehydration condensing agent such as various carbodiimides, diphenylphosphoryl azide, benzotriazol-1-yloxy-trisdimethylaminophosphonium salt or 4-(4,6-dimethoxy-1,3,5-triazin-2-yl)-4-methylmorpholine hydrochloride and in the presence or absence of a base such as triethylamine or diisopropylethylamine at a temperature of 0° C. to 80° C.

Step (10-2):

Method for producing compound (10-b): A compound (10-b) can be produced by performing "deprotection reaction" of G possessed by the compound (10-a).

Examples of the "deprotection reaction" include the same "deprotection reaction" as previously described in Step (3-2).

Scheme 11: Process for synthesizing compound (11-g) from compound (11-a)

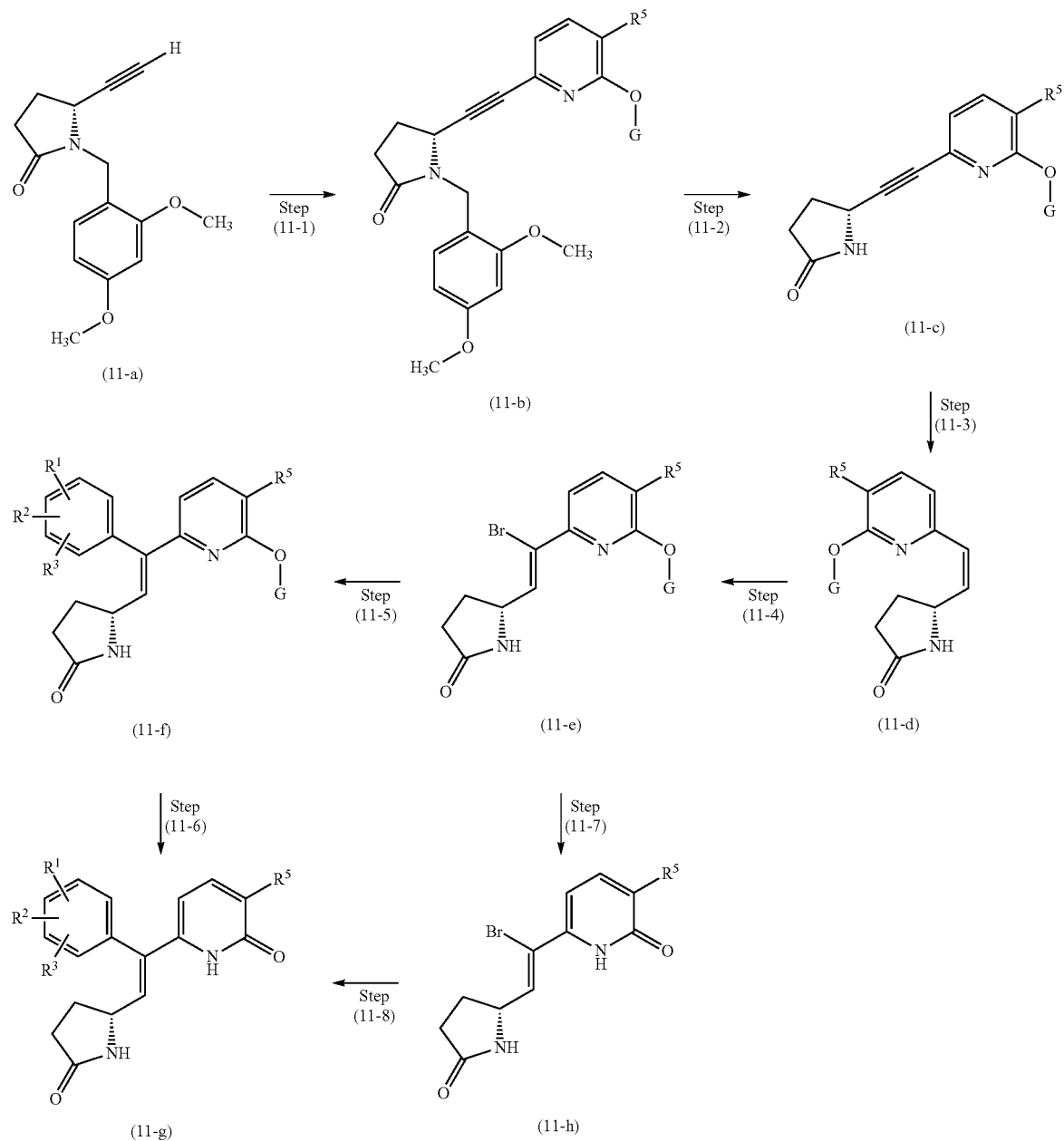

In the scheme, $R^1$, $R^2$, $R^3$ and $R^5$ are as described above and G represents a protecting group for the hydroxy group.

Step (11-1):

Method for producing compound (11-b): A compound (11-b) can be produced by Pd(0)-Cu(I) coupling of a compound (11-a) and a 2-bromopyridine or 2-iodopyridine compound with a palladium(0) catalyst such as tetrakistriphenylphosphine palladium(0) and a copper(I) halide such as copper(I) iodide in an inert solvent in the presence of a base at a temperature of room temperature to 100° C.

Step (11-2):

Method for producing compound (11-c): A compound (11-c) can be produced by performing "deprotection reaction" of the 2,4-dimethoxybenzyl group possessed by the compound (11-b) in an inert solvent at a temperature of room temperature to 100° C.

Examples of the "deprotection reaction" include a method using an acid such as trifluoroacetic acid, a method of removing the protecting group by hydrogenolysis reaction using a catalytic amount of palladium-activated carbon or rhodium-activated carbon, and a method using an oxidizing agent such as ammonium cerium(IV) nitrate or 2,3-dichloro-5,6-dicyano-p-benzoquinone.

Step (11-3):

Method for producing compound (11-d): A compound (11-d) can be produced by performing catalytic hydrogenation reaction of the compound (11-c) as a matrix with a catalytic amount of a Lindlar catalyst (palladium-calcium carbonate-lead acetate, palladium-barium carbonate, nickel-barium carbonate or platinum-barium carbonate) in an inert solvent at a temperature of room temperature to 100° C.

Step (11-4):

Method for producing compound (11-e): A compound (11-e) can be produced by brominating the compound (11-d) with bromine in an inert solvent at a temperature of room temperature to 100° C. and then allowing a base to act on the compound.

Step (11-5):

Method for producing compound (11-f): A compound (11-f) can be produced by performing coupling reaction of the compound (11-e) as a matrix with an arylboron compound or an aryltin compound in an inert solvent in the presence of a base and a palladium catalyst at a temperature of room temperature to 100° C.

Examples of the "coupling reaction" include the same "coupling reaction" as previously described in Step (8-6).

Step (11-6):

Method for producing compound (11-g): A compound (11-g) can be produced by performing "deprotection reaction" of G possessed by the compound (11-f).

Examples of the "deprotection reaction" include the same "deprotection reaction" as previously described in Step (3-2).

Step (11-7):

Method for producing compound (11-h): A compound (11-h) can be produced by performing "deprotection reaction" of G possessed by the compound (11-e).

Examples of the "deprotection reaction" include the same "deprotection reaction" as previously described in Step (3-2).

Step (11-8):

Another method for producing compound (11-g): A compound (11-g) can be produced by performing coupling reaction of the compound (11-h) as a matrix with an arylboron compound or an aryltin compound in an inert solvent in the presence of a base and a palladium catalyst at a temperature of room temperature to 100° C.

Examples of the "coupling reaction" include the same "coupling reaction" as previously described in Step (8-6).

Scheme 12: Process for synthesizing compound (12-e) from compound (11-a)

[Ka 55]

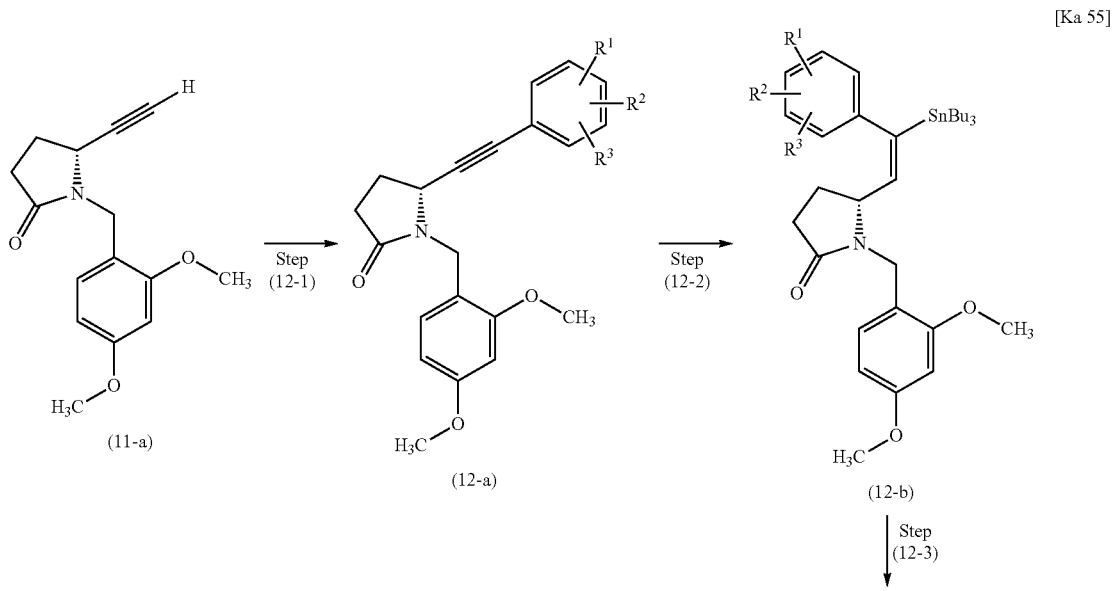

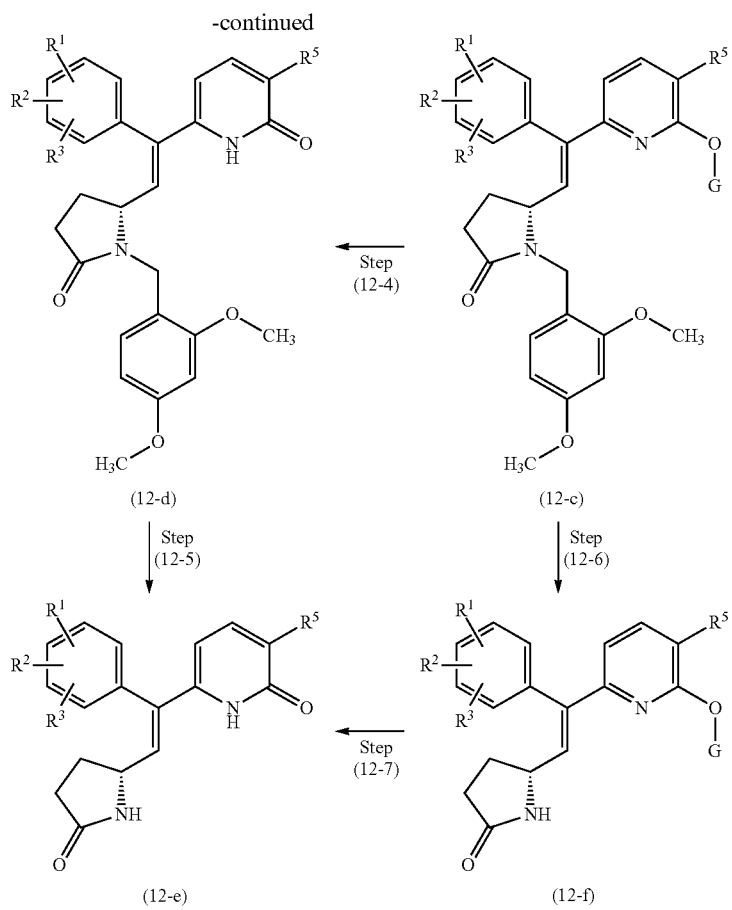

In the scheme, $R^1$, $R^2$, $R^3$ and $R^5$ are as described above and G represents a protecting group for the hydroxy group.

Step (12-1):

Method for producing compound (12-a): A compound (12-a) can be produced by Pd(0)-Cu(I) coupling of a compound (11-a) and an aryl halide or aryl triflate compound with a palladium(0) catalyst such as tetrakistriphenylphosphine palladium(0) and a copper(I) halide such as copper(I) iodide in an inert solvent in the presence of a base at a temperature of room temperature to 100° C.

Step (12-2):

Method for producing compound (12-b): A compound (12-b) can be produced by allowing a tin hydride compound such as tributyltin hydride to act on the compound (12-a) as a matrix in an inert solvent in the presence of a palladium catalyst at a temperature of 0° C. to 100° C.

Step (12-3):

Method for producing compound (12-c): A compound (12-c) can be produced by performing coupling reaction of the compound (12-b) as a matrix with a 2-bromopyridine or 2-iodopyridine compound in an inert solvent in the presence of a base and a palladium catalyst at a temperature of room temperature to 100° C.

Step (12-4):

Method for producing compound (12-d): A compound (12-d) can be produced by performing "deprotection reaction" of G possessed by the compound (12-c).

Examples of the "deprotection reaction" include the same "deprotection reaction" as previously described in Step (3-2).

Step (12-5):

Method for producing compound (12-e): A compound (12-e) can be produced by performing "deprotection reaction" of the 2,4-dimethoxybenzyl group possessed by the compound (12-d) in an inert solvent at a temperature of room temperature to 100° C.

Examples of the "deprotection reaction" include the same "deprotection reaction" as previously described in Step (11-2).

Step (12-6):

Method for producing compound (12-f): A compound (12-f) can be produced by performing "deprotection reaction" of the protecting 2,4-dimethoxybenzyl group possessed by the compound (12-c) in an inert solvent at a temperature of room temperature to 100° C.

Examples of the "deprotection reaction" include the same "deprotection reaction" as previously described in Step (11-2).

Step (12-7):

Another method for producing compound (12-e): A compound (12-e) can be produced by performing "deprotection reaction" of G possessed by the compound (12-f).

Examples of the "deprotection reaction" include the same "deprotection reaction" as previously described in Step (3-2).

Scheme 13: Process for synthesizing compound (13-e) from compound (13-a)

[Ka 56]

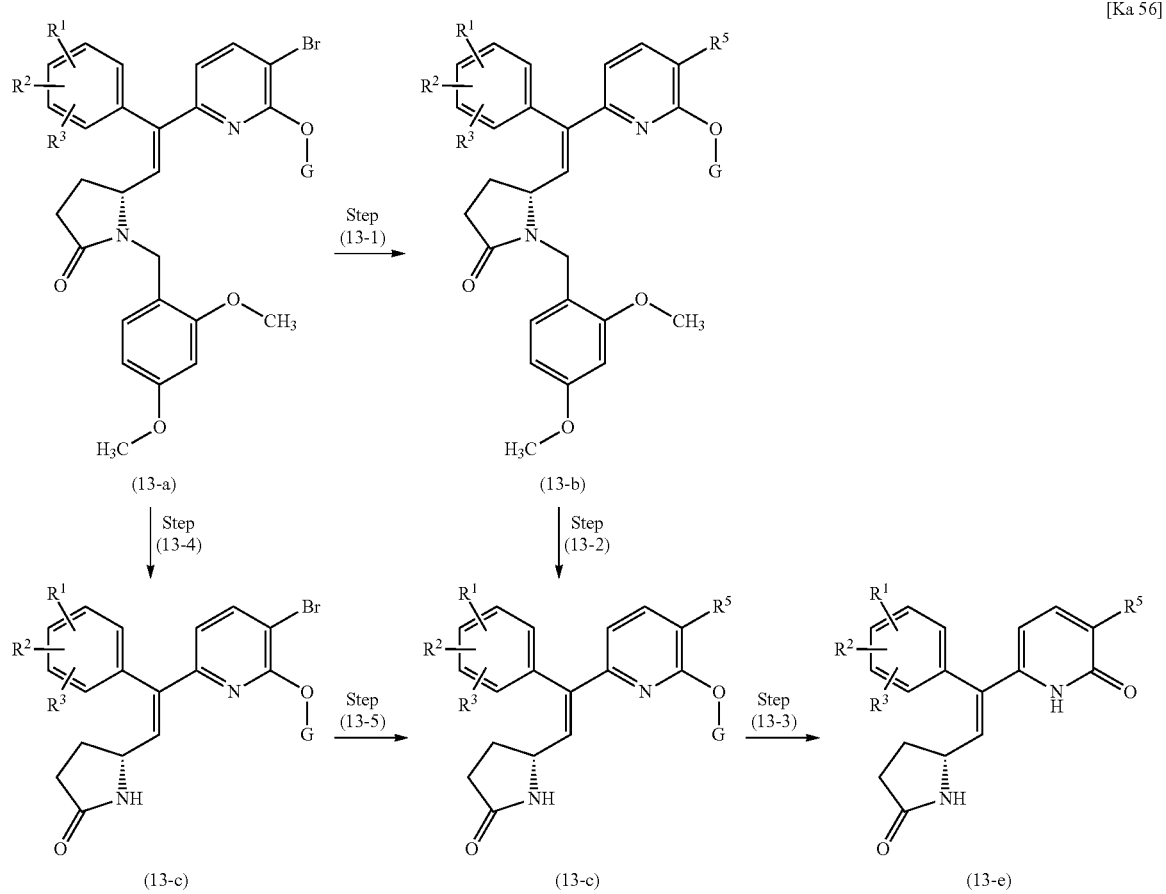

In the scheme, $R^1$, $R^2$, $R^3$ and $R^5$ are as described above and G represents a protecting group for the hydroxy group.

Step (13-1):

Method for producing compound (13-b): A compound (13-b) can be produced by performing coupling reaction of a compound (13-a) as a matrix with an arylboron or vinylboron compound, an aryltin compound, a benzylzinc compound or a phenol in an inert solvent in the presence of a palladium catalyst or a copper catalyst at a temperature of room temperature to 100° C.

Examples of the "coupling reaction" include the same "coupling reaction" as previously described in Step (8-6).

Step (13-2):

Method for producing compound (13-d): A compound (13-d) can be produced by performing "deprotection reaction" of the 2,4-dimethoxybenzyl group possessed by the compound (13-b) in an inert solvent at a temperature of room temperature to 100° C.

Examples of the "deprotection reaction" include the same "deprotection reaction" as previously described in Step (11-2).

Step (13-3):

Method for producing compound (13-e): A compound (13-e) can be produced by performing "deprotection reaction" of G possessed by the compound (13-d).

Examples of the "deprotection reaction" include the same "deprotection reaction" as previously described in Step (3-2).

Step (13-4):

Method for producing compound (13-c): This is a method for producing a compound (13-c) by performing "deprotection reaction" of the 2,4-dimethoxybenzyl group possessed by the compound (13-a) in an inert solvent at a temperature of room temperature to 100° C.

Examples of the "deprotection reaction" include the same "deprotection reaction" as previously described in Step (11-2).

Step (13-5):

Another method for producing compound (13-d): A compound (13-d) can be produced by performing coupling reaction of the compound (13-c) as a matrix with an arylboron or vinylboron compound, an aryltin compound, a benzylzinc compound or a phenol in an inert solvent in the presence of a palladium catalyst or a copper catalyst at a temperature of room temperature to 100° C.

Examples of the "coupling reaction" include the same "coupling reaction" as previously described in Step (8-6).

The reaction temperature in the general processes for producing the compounds of the present invention is −78° C. to 250° C., and preferably −20° C. to 80° C. The reaction time is 5 minutes to 3 days, and preferably 30 minutes to 18 hours. The production processes may be performed under normal pressure, under pressure or under microwave irradiation, for example.

The base, the acid and the inert solvent in the description of the general processes for producing the compounds of the present invention will be more specifically described, but are not limited to the following illustrations. The usable isolation techniques will also be specifically described, but are similarly not limited to the following illustrations.

Examples of the "base" include inorganic bases such as alkali metal or alkaline earth metal hydrides (such as lithium hydride, sodium hydride, potassium hydride and calcium hydride), alkali metal or alkaline earth metal amides (such as lithium amide, sodium amide, lithium diisopropylamide, lithium dicyclohexylamide, lithium hexamethyldisilazide and potassium hexamethyldisilazide), alkali metal or alkaline earth metal $C_1$-$C_6$ alkoxides (such as sodium methoxide, sodium ethoxide and potassium t-butoxide), alkali metal or alkaline earth metal hydroxides (such as sodium hydroxide, potassium hydroxide, lithium hydroxide and barium hydroxide), alkali metal or alkaline earth metal carbonates (such as sodium carbonate, potassium carbonate, calcium carbonate and cesium carbonate), alkali metal bicarbonates (such as sodium bicarbonate and potassium bicarbonate) and alkali metal or alkaline earth metal phosphates (such as tripotassium phosphate), amines (such as triethylamine, diisopropylethylamine and N-methylmorpholine) and basic heterocyclic compounds (such as pyridine, 4-dimethylaminopyridine, DBU (1,8-diazabicyclo[5.4.0]undec-7-ene), DBN (1,5-diazabicyclo[4.3.0]non-5-ene), imidazole and 2,6-lutidine).

Examples of the "acid" include inorganic acids (such as hydrochloric acid, hydrobromic acid, sulfuric acid, nitric acid and phosphoric acid), organic acids (such as p-toluenesulfonic acid, methanesulfonic acid, trifluoroacetic acid, formic acid, acetic acid and camphorsulfonic acid) and Lewis acids (such as boron trifluoride, boron tribromide, aluminum chloride, scandium triflate and ytterbium triflate).

Examples of the "inert solvent" include nitrile solvents, amide solvents, halocarbon solvents, ether solvents, aromatic solvents, hydrocarbon solvents, ester solvents, alcohol solvents, sulfoxide solvents and water. These solvents may be used as a mixture of two or more solvents in an appropriate proportion.

Examples of the nitrile solvents used include acetonitrile and propionitrile. Examples of the amide solvents include N,N-dimethylformamide (hereinafter sometimes abbreviated as DMF), N,N-dimethylacetamide and N-methylpyrrolidone. Examples of the halocarbon solvents include dichloromethane, chloroform, 1,2-dichloroethane and carbon tetrachloride. Examples of the ether solvents include diethyl ether (hereinafter sometimes abbreviated as "ether"), tetrahydrofuran (hereinafter sometimes abbreviated as THF), 1,4-dioxane and 1,2-dimethoxyethane. Examples of the aromatic solvents include benzene, toluene, xylene and pyridine. Examples of the hydrocarbon solvents include hexane, pentane and cyclohexane. Examples of the ester solvents include ethyl acetate and ethyl formate. Examples of the alcohol solvents include methanol, ethanol, isopropyl alcohol, t-butyl alcohol and ethylene glycol. Examples of the sulfoxide solvents include dimethyl sulfoxide (hereinafter sometimes abbreviated as DMSO).

Compounds obtained by the above production processes can be isolated and purified by known means such as solvent extraction, liquidity change, transfer, crystallization, recrystallization and various chromatography techniques.

Protecting groups that can be used by the compounds in the general processes for producing the compounds of the present invention will be described below, but are not limited to such illustrations; other protecting groups may also suitably selected.

Examples of the protecting group for the amino group include $C_1$-$C_6$ acyl groups (such as formyl, acetyl and propionyl), $C_2$-$C_{12}$ alkoxycarbonyl groups (such as methoxycarbonyl, ethoxycarbonyl, t-butoxycarbonyl, benzyloxycarbonyl and 9-fluorenylmethyleneoxycarbonyl), arylcarbonyl groups (such as benzoyl), a trityl group, a phthaloyl group, a N,N-dimethylaminomethylene group, substituted silyl groups (such as trimethylsilyl, triethylsilyl, dimethylphenylsilyl, t-butyldimethylsilyl and t-butyldiethylsilyl) and $C_2$-$C_6$ alkenyl groups (such as 1-allyl), each of which is generally used in peptide synthesis. These groups may be substituted with one or more substituents selected from halogen atoms, $C_1$-$C_6$ alkoxy groups (such as methoxy, ethoxy and propoxy) and a nitro group.

Examples of the protecting group for the carboxy group include $C_1$-$C_6$ alkyl groups (such as methyl, ethyl and t-butyl), $C_7$-$C_{20}$ aralkyl groups (such as benzyl and trityl), a phenyl group, substituted silyl groups (such as trimethylsilyl, triethylsilyl, dimethylphenylsilyl, t-butyldimethylsilyl and t-butyldiethylsilyl) and $C_2$-$C_6$ alkenyl groups (such as 1-allyl). These groups may be substituted with one or more substituents selected from halogen atoms, $C_1$-$C_6$ alkoxy groups (such as methoxy, ethoxy and propoxy) and a nitro group.

Examples of the protecting group for the hydroxy group include $C_1$-$C_6$ alkyl groups (such as methyl, ethyl and t-butyl), $C_7$-$C_{20}$ aralkyl groups (such as benzyl and trityl), a phenyl group, substituted silyl groups (such as trimethylsilyl, triethylsilyl, dimethylphenylsilyl, t-butyldimethylsilyl and t-butyldiethylsilyl), $C_2$-$C_6$ alkenyl groups (such as 1-allyl), $C_1$-$C_6$ acyl groups (such as formyl, acetyl and propionyl), $C_2$-$C_{12}$ alkoxycarbonyl groups (such as methoxycarbonyl, ethoxycarbonyl, t-butoxycarbonyl, benzyloxycarbonyl and 9-fluorenylmethyleneoxycarbonyl), arylcarbonyl groups (such as benzoyl), a 2-tetrahydropyranyl group and a 2-tetrahydrofuranyl group. These groups may be substituted with one or more substituents selected from halogen atoms, $C_1$-$C_6$ alkoxy groups (such as methoxy, ethoxy and propoxy) and a nitro group.

Examples of the protecting group for the carbonyl group include cyclic acetals (such as 1,3-dioxane and 1,3-dioxolane) and acyclic acetals (such as di-$C_1$-$C_6$ alkyl acetals (dimethyl acetal, diethyl acetal and the like)).

The present invention will be described in more detail by the following Reference Examples, Examples, Test Example and Formulation Examples. These examples do not limit the present invention and may be changed within the scope of the present invention.

NMR (nuclear magnetic resonance) spectra were measured at room temperature at 200 MHz (GEMINI 2000/200, Varian Instruments), 300 MHz (NOVA 300, Varian Instruments, JEOL JNM-ECP300, JEOL Ltd., JEOL JNM-ECX300, JEOL Ltd.), 500 MHz (JEOL ECA500, JEOL JNM-ECP500, JEOL Ltd.), 600 MHz (JEOL JNM-ECA600, JEOL Ltd.) and 700 MHz (JEOL JNM-ECA700, JEOL Ltd.). Chemical shifts in the present specification were reported in parts per million (δ) relative to internal standard (tetramethylsilane).

Mass spectra were measured by Waters micromass ZQ (ESI: electrospray ionization), micromass Platform-LC mass spectrometer (EI: electron ionization) or Shimadzu LCMS-2010EV (ESI: electrospray ionization/APCI: atmospheric pressure chemical ionization Dual).

The progress of the reaction was monitored by TLC (Silica gel 60, F254; manufactured by Merck & Co., Inc.) or reverse phase HPLC.

Merck "Silica gel 60", Fuji Silysia Chemical "Silica gel PSQ60", Kanto Chemical "Silica gel 60", "Silica gel 60N", Fuji Silysia Chemical "Chromatorex NH" or a packed column (YAMAZEN Hi-Flash™ Column or MORITEX Purif Pack or Biotage(R) SNAP Catridge KP-Sil) was used for silica gel column chromatography. Fuji Silysia Chemical "Silica gel PSQ60", Kanto Chemical "Silica gel 60N" or a packed column was used unless otherwise indicated.

Merck Silica gel 60, 1 mm or 0.5 mm, F254 or Fuji Silysia Chemical CHROMATOREX NH-PLC 05 PLATE was used when the product was purified by preparative TLC.

SunFire™ Prep C180BD™ 5 μm (I.D. 30 mm, Length 50 mm), Daicel Chemical Industries, LTD. CHIRALCEL OD-H 5 μm (I.D. 20 mm, Length 250 mm), GL Science Inc. Inertsil ODS-3 5 μm (I.D. 20 mm, Length 250 mm), Daicel Chemical Industries, LTD. CHIRALPAK IA 5 μm (I.D. 10 mm, Length 250 mm) or Daicel Chemical Industries, LTD. CHIRALPAK IB 5 μm (I.D. 20 mm, Length 250 mm) was used as a preparative HPLC column.

Initiator Sixty™ manufactured by Biotage AB was used for reactions using microwaves in the present Reference Examples and Examples.

Reference Example 1-1

(5-Chloro-6-methoxypyridin-2-yl)[4-(methylsulfanyl)phenyl]methanone

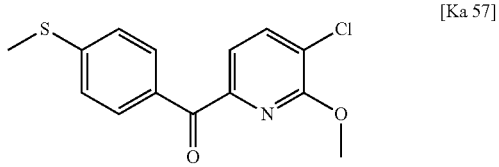 [SMILES: COc1nc(C(=O)c2ccc(SC)cc2)ccc1Cl]

[Ka 57]

(1) A solution of methylpiperazine (2.31 g) in tetrahydrofuran (20 mL) was cooled to −78° C., and n-butyllithium (2.64 M, 7.55 mL) was added dropwise in an argon gas atmosphere. After stirring at the same temperature for 15 minutes, a solution of 6-methoxypicolinaldehyde (2.5 g) in tetrahydrofuran was added and the mixture was stirred for 30 minutes. t-Butyllithium (1.59 M, 17.1 mL) was added dropwise to the reaction solution, and the mixture was stirred at the same temperature for one hour and at −40° C. for 15 minutes. The reaction solution was cooled again to −78° C. A solution of hexachloroethane (12.9 g) in tetrahydrofuran (20 mL) was slowly added dropwise, and the mixture was stirred at the same temperature for 30 minutes. The reaction solution was poured into water, followed by extraction with ethyl acetate. The organic layer was washed with brine, dried over anhydrous magnesium sulfate and filtered, after which the filtrate was concentrated under reduced pressure. The resulting residue was purified by silica gel column chromatography (hexane:ethyl acetate=20:1→10:1) to give 5-chloro-6-methoxypyridine-2-carbaldehyde as a colorless powder (1.21 g).

(2) n-Butyllithium (2.64 M, 2.9 mL) was added to a solution of 4-bromothioanisole (1.61 g) in tetrahydrofuran (20 mL) at −78° C. in a nitrogen atmosphere, and the mixture was stirred at the same temperature for 30 minutes. A solution of 5-chloro-6-methoxypyridine-2-carbaldehyde (1.14 g) in tetrahydrofuran (10 mL) was added to the reaction solution, followed by stirring for one hour. The reaction solution was poured into a saturated ammonium chloride solution, followed by extraction with ethyl acetate. The organic layer was washed with brine, dried over anhydrous magnesium sulfate and filtered, after which the filtrate was concentrated under reduced pressure. The resulting residue was purified by silica gel column chromatography (hexane:ethyl acetate=10:1→4:1) to give (5-chloro-6-methoxypyridin-2-yl)[4-(methylsulfanyl)phenyl]methanol as a pale yellow oil (1.42 g).

(3) Manganese dioxide (8.34 g) was added to a solution of (5-chloro-6-methoxypyridin-2-yl)[4-(methylsulfanyl)phenyl]methanol (1.42 g) in chloroform (40 mL), and the mixture was stirred at 65° C. for one hour. The reaction solution was filtered through celite and the filtrate was concentrated. The residue was purified by silica gel column chromatography (hexane:ethyl acetate=4:1→1:1) to give the title compound as a yellow powder (1.02 g, 71%).

$^1$H NMR (300 MHz, CDCl$_3$) δ ppm 2.55 (s, 3H), 4.02 (s, 3H), 7.29 (d, J=8.7 Hz, 2H), 7.56-7.68 (m, 1H), 7.82 (d, J=7.9 Hz, 1H), 8.09 (d, J=8.9 Hz, 2H).

MS(+): 294 [M+H]$^+$.

The following compounds (Reference Examples 1-2 to 1-29) were obtained by performing reaction by the same method as in Reference Example 1-1 using corresponding aryl bromides, respectively.

Reference Example 1-2

(5-Chloro-6-methoxypyridin-2-yl)[4-(cyclopropylsulfanyl)phenyl]methanone $^1$H NMR (300 MHz, CDCl$_3$) δ ppm 0.61-0.83 (m, 2H), 1.07-1.22 (m, 2H), 2.23 (tt, J=7.3, 4.4 Hz, 1H), 4.02 (s, 3H), 7.43 (d, J=8.7 Hz, 2H), 7.63 (d, J=7.8 Hz, 1H), 7.82 (d, J=7.9 Hz, 1H), 8.09 (d, J=8.7 Hz, 2H).

MS(+): 342 [M+Na]$^+$.

Reference Example 1-3

(5-Chloro-6-methoxypyridin-2-yl)[4-(cyclopentylsulfanyl)phenyl]methanone $^1$H NMR (300 MHz, CDCl$_3$) δ ppm 1.58-1.74 (m, 4H), 1.75-1.91 (m, 2H), 2.08-2.30 (m, 2H), 3.61-3.85 (m, 1H), 4.02 (s, 3H), 7.34 (d, J=8.7 Hz, 2H), 7.63 (d, J=7.8 Hz, 1H), 7.81 (d, J=7.8 Hz, 1H), 8.07 (d, J=8.7 Hz, 2H).

MS(+): 348 [M+H]$^+$.

Reference Example 1-4

[3-Chloro-4-(ethylsulfanyl)phenyl](5-chloro-6-methoxypyridin-2-yl)methanone $^1$H NMR (300 MHz, CDCl$_3$) δ ppm 1.45 (t, J=7.4 Hz, 3H), 3.06 (q, J=7.3 Hz, 2H), 4.04 (s, 3H), 7.27 (d, J=8.4 Hz, 1H), 7.68 (d, J=7.8 Hz, 1H), 7.83 (d, J=7.9 Hz, 1H), 8.04 (dd, J=8.4, 1.9 Hz, 1H), 8.31 (d, J=1.9 Hz, 1H).

Reference Example 1-5

(5-Chloro-6-methoxypyridin-2-yl)[3-(cyclopropylsulfanyl)phenyl]methanone $^1$H NMR (300 MHz, CDCl$_3$) δ ppm 0.68-0.75 (m, 2H), 1.06-1.14 (m, 2H), 2.17-2.27 (m, 1H), 4.01 (s, 3H), 7.35-7.43 (m, 1H), 7.56-7.61 (m, 1H), 7.65 (d, J=7.8 Hz, 1H), 7.82 (d, J=7.8 Hz, 1H), 7.86 (dt, J=7.7, 1.3 Hz, 1H), 8.10 (t, J=1.6 Hz, 1H).

MS(+): 320 [M+H]$^+$.

Reference Example 1-6

(5-Chloro-6-methoxypyridin-2-yl)[4-(cyclopropylsulfanyl)-3-methylphenyl]methanone $^1$H NMR (300 MHz, CDCl$_3$) δ ppm 0.70-0.80 (m, 2H), 1.12-1.23 (m, 2H), 2.10-2.22 (m, 1H), 2.29 (s, 3H), 4.03 (s, 3H), 7.61 (d, J=7.7 Hz, 1H), 7.62 (d, J=8.3 Hz, 1H), 7.81 (d, J=8.0 Hz, 1H), 7.92-7.95 (m, 1H), 8.00 (dd, J=8.3, 1.9 Hz, 1H).
MS(+): 334 [M+H]$^+$.

Reference Example 1-7

(4-tert-Butylphenyl)(5-chloro-6-methoxypyridin-2-yl)methanone $^1$H NMR (300 MHz, CDCl$_3$) δ ppm 1.37 (s, 9H), 4.04 (s, 3H), 7.45-7.52 (m, 2H), 7.62 (d, J=8.0 Hz, 1H), 7.80 (d, J=7.7 Hz, 1H), 8.05-8.12 (m, 2H).
MS(+): 304 [M+H]$^+$.

Reference Example 1-8

(5-Chloro-6-methoxypyridin-2-yl)[4-methyl-3-(trifluoromethyl)phenyl]methanone $^1$H NMR (300 MHz, CDCl$_3$) δ ppm 2.58 (d, J=1.5 Hz, 3H), 4.01 (s, 3H), 7.42 (d, J=7.1 Hz, 1H), 7.73 (d, J=7.7 Hz, 1H), 7.84 (d, J=8.3 Hz, 1H), 8.20 (dd, J=7.7, 1.8 Hz, 1H), 8.63 (d, J=1.2 Hz, 1H).
MS(+): 330 [M+H]$^+$.

Reference Example 1-9

(5-Chloro-6-methoxypyridin-2-yl)(4-ethylphenyl)methanone $^1$H NMR (300 MHz, CDCl$_3$) δ ppm 1.29 (t, J=7.6 Hz, 3H), 2.74 (q, J=7.6 Hz, 2H), 4.02 (s, 3H), 7.30 (d, J=8.6 Hz, 2H), 7.61 (d, J=8.3 Hz, 1H), 7.80 (d, J=7.7 Hz, 1H), 8.07 (dd, J=6.6, 1.8 Hz, 2H).
MS(+): 276 [M+H]$^+$.

Reference Example 1-10

(5-Chloro-6-methoxypyridin-2-yl){4-[(3-methylbutoxy)methyl]phenyl}methanone $^1$H NMR (300 MHz, CDCl$_3$) δ ppm 0.92 (d, J=6.6 Hz, 6H), 1.50-1.60 (m, 2H), 1.67-1.84 (m, 1H), 3.54 (t, J=6.7 Hz, 2H), 4.00 (s, 3H), 4.58 (s, 2H), 7.44 (d, J=8.3 Hz, 2H), 7.64 (d, J=7.7 Hz, 1H), 7.81 (d, J=7.7 Hz, 1H), 8.10 (d, J=8.0 Hz, 2H).
MS(+): 348 [M+H]$^+$.

Reference Example 1-11

(5-Chloro-6-methoxypyridin-2-yl)[4-(propan-2-yl)phenyl]methanone $^1$H NMR (300 MHz, CDCl$_3$) δ ppm 1.29 (s, 3H), 1.31 (s, 3H), 2.92-3.06 (m, 1H), 4.03 (s, 3H), 7.33 (d, J=8.4 Hz, 2H), 7.61 (d, J=7.8 Hz, 1H), 7.80 (d, J=7.8 Hz, 1H), 8.09 (d, J=8.7 Hz, 2H).

Reference Example 1-12

(5-Chloro-6-methoxypyridin-2-yl)[4-(methylsulfanyl)-3-(trifluoromethyl)phenyl]methanone $^1$H NMR (300 MHz, CDCl$_3$) δ ppm 2.60 (s, 3H), 4.03 (s, 3H), 7.41 (d, J=8.2 Hz, 1H), 7.74 (d, J=7.8 Hz, 1H), 7.84 (d, J=7.8 Hz, 1H), 8.28 (dd, J=8.2, 1.7 Hz, 1H), 8.71 (d, J=1.7 Hz, 1H).
MS(+): 362 [M+H]$^+$.

Reference Example 1-13

(5-Chloro-6-methoxypyridin-2-yl){4-[2-(2-methylpropoxy)ethyl]phenyl}methanone $^1$H NMR (300 MHz, CDCl$_3$) δ ppm 0.88 (d, J=6.8 Hz, 6H), 1.75-1.95 (m, 1H), 2.96 (t, J=6.8 Hz, 2H), 3.20 (d, J=6.8 Hz, 2H), 3.67 (t, J=6.8 Hz, 2H), 4.01 (s, 3H), 7.34 (d, J=8.2 Hz, 2H), 7.63 (d, J=7.8 Hz, 1H), 7.81 (d, J=7.8 Hz, 1H), 8.06 (d, J=8.2 Hz, 2H).
MS(+): 348 [M+H]$^+$.

Reference Example 1-14

(5-Chloro-6-methoxypyridin-2-yl)(3,4-dimethylphenyl)methanone $^1$H NMR (300 MHz, CDCl$_3$) δ ppm 2.33 (s, 3H), 2.35 (s, 3H), 4.01 (s, 3H), 7.23 (d, J=7.8 Hz, 1H), 7.61 (d, J=8.2 Hz, 1H), 7.81 (d, J=7.8 Hz, 1H), 7.87 (dd, J=8.0, 1.4 Hz, 1H), 7.93 (s, 1H).

Reference Example 1-15

(4-Butylphenyl)(5-chloro-6-methoxypyridin-2-yl)methanone $^1$H NMR (300 MHz, CDCl$_3$) δ ppm 0.94 (t, J=7.4 Hz, 3H), 1.30-1.45 (m, 2H), 1.57-1.71 (m, 2H), 2.69 (t, J=7.8 Hz, 2H), 4.02 (s, 3H), 7.28 (d, J=8.6 Hz, 2H), 7.62 (d, J=7.8 Hz, 1H), 7.81 (d, J=7.8 Hz, 1H), 8.07 (d, J=8.6 Hz, 2H).
MS(+): 304 [M+H]$^+$.

Reference Example 1-16

(5-Chloro-6-methoxypyridin-2-yl)(3-chloro-4-methylphenyl)methanone $^1$H NMR (300 MHz, CDCl$_3$) δ ppm 2.47 (s, 3H), 4.03 (s, 3H), 7.34 (d, J=7.8 Hz, 1H), 7.68 (d, J=8.2 Hz, 1H), 7.83 (d, J=8.2 Hz, 1H), 7.94 (dd, J=8.0, 1.8 Hz, 1H), 8.25 (d, J=1.6 Hz, 1H).
MS(+): 296 [M+H]$^+$.

Reference Example 1-17

(5-Chloro-6-methoxypyridin-2-yl)[4-(trifluoromethyl)phenyl]methanone $^1$H NMR (300 MHz, CDCl$_3$) δ ppm 3.98 (s, 3H), 7.68-7.78 (m, 3H), 7.86 (d, J=8.2 Hz, 1H), 8.22 (d, J=8.2 Hz, 2H).
MS(+): 316 [M+H]$^+$.

Reference Example 1-18

(5-Chloro-6-methoxypyridin-2-yl)(4-propylphenyl)methanone $^1$H NMR (300 MHz, CDCl$_3$) δ ppm 0.97 (t, J=7.4 Hz, 3H), 1.61-1.76 (m, 2H), 2.67 (t, J=7.8 Hz, 2H), 4.02 (s, 3H), 7.28 (d, J=8.6 Hz, 2H), 7.62 (d, J=7.8 Hz, 1H), 7.81 (d, J=7.8 Hz, 1H), 8.07 (d, J=8.2 Hz, 2H).
MS(+): 290 [M+H]$^+$.

Reference Example 1-19

(5-Chloro-6-methoxypyridin-2-yl)[4-(2-methylpropyl)phenyl]methanone $^1$H NMR (300 MHz, CDCl$_3$) δ ppm 0.92 (s, 3H), 0.94 (s, 3H), 1.84-2.00 (m, 1H), 2.56 (d, J=7.4 Hz, 2H), 4.02 (s, 3H), 7.21-7.28 (m, 2H), 7.61 (d, J=7.7 Hz, 1H), 7.80 (d, J=7.7 Hz, 1H), 8.06 (d, J=8.3 Hz, 2H).

Reference Example 1-20

(5-Chloro-6-methoxypyridin-2-yl)(2,4-dimethylphenyl)methanone $^1$H NMR (300 MHz, CDCl$_3$) δ ppm 2.37 (s, 3H), 2.39 (s, 3H), 3.89 (s, 3H), 7.02 (d, J=7.7 Hz, 1H), 7.08 (s, 1H), 7.42 (d, J=7.7 Hz, 1H), 7.59 (d, J=7.7 Hz, 1H), 7.76 (d, J=7.7 Hz, 1H).
MS(+): 276 [M+H]$^+$.

Reference Example 1-21

[4-(4-{[tert-Butyl(dimethyl)silyl]oxy}butyl)phenyl](5-chloro-6-methoxypyridin-2-yl)methanone $^1$H NMR (300 MHz, CDCl$_3$) δ ppm 0.00 (s, 6H), 0.85 (s, 9H), 1.46-1.75 (m, 4H), 2.67 (t, J=7.4 Hz, 2H), 3.59 (t, J=6.3 Hz, 2H), 3.97 (s, 3H), 7.23 (d, J=8.6 Hz, 2H), 7.57 (d, J=7.7 Hz, 1H), 7.75 (d, J=7.7 Hz, 1H), 8.01 (d, J=8.3 Hz, 2H).
MS(+): 434 [M+H]$^+$.

Reference Example 1-22

[3-Chloro-4-(cyclopropylsulfanyl)phenyl](5-chloro-6-methoxypyridin-2-yl)methanone $^1$H NMR (300 MHz, CDCl$_3$) δ ppm 0.74-0.82 (m, 2H), 1.15-1.27 (m, 2H), 2.13-2.22 (m, 1H), 4.05 (s, 3H), 7.67 (d, J=8.3 Hz, 1H), 7.68 (d, J=8.0 Hz, 1H), 7.83 (d, J=7.7 Hz, 1H), 8.07 (dd, J=8.3, 1.9 Hz, 1H), 8.28 (d, J=1.9 Hz, 1H).
MS(+): 354 [M+H]$^+$.

Reference Example 1-23 tert-Butyl 4-({4-[(5-chloro-6-methoxypyridin-2-yl)carbonyl]phenyl}sulfonyl)piperazine-1-carboxylate $^1$H NMR (300 MHz, CDCl$_3$) δ ppm 1.41 (s, 9H), 3.03 (t, J=5.1 Hz, 4H), 3.53 (t, J=5.1 Hz, 4H), 3.98 (s, 3H), 7.73-7.78 (m, 1H), 7.82-7.90 (m, 3H), 8.23-8.31 (m, 2H).
MS(+): 518 [M+Na]$^+$.

Reference Example 1-24

(3-Chloro-4-ethoxyphenyl)(5-chloro-6-methoxypyridin-2-yl)methanone $^1$H NMR (300 MHz, CDCl$_3$) δ ppm 1.42-1.61 (m, 3H), 4.05 (s, 3H), 4.22 (q, J=7.0 Hz, 2H), 6.98 (d, J=8.7 Hz, 1H), 7.65 (d, J=7.9 Hz, 1H), 7.83 (s, 1H), 8.11 (dd, J=8.7, 2.2 Hz, 1H), 8.39 (s, 1H).
MS(+): 326 [M+H]$^+$.

Reference Example 1-25

(4-{[tert-Butyl(dimethyl)silyl]oxy}-3-methylphenyl)(5-chloro-6-methoxypyridin-2-yl)methanone $^1$H NMR (300 MHz, CDCl$_3$) δ ppm 0.28 (s, 6H), 1.03 (s, 9H), 2.26 (s, 3H), 4.03 (s, 3H), 6.81 (d, J=8.4 Hz, 1H), 7.58 (d, J=7.9 Hz, 1H), 7.80 (d, J=7.9 Hz, 1H), 7.91-7.96 (m, 1H), 8.01-8.05 (m, 1H).
MS(+): 392 [M+H]$^+$.

Reference Example 1-26

(4-{[tert-Butyl(dimethyl)silyl]oxy}-3-fluorophenyl)(5-chloro-6-methoxypyridin-2-yl)methanone $^1$H NMR (300 MHz, CDCl$_3$) δ ppm 0.23-0.26 (m, 6H), 1.02 (s, 9H), 4.04 (s, 3H), 6.98 (t, J=8.4 Hz, 1H), 7.64 (d, J=7.9 Hz, 1H), 7.82 (d, J=7.9 Hz, 1H), 7.92 (ddd, J=8.5, 2.1, 1.0 Hz, 1H), 8.03 (dd, J=11.8, 2.2 Hz, 1H).
MS(+): 396 [M+H]$^+$.

Reference Example 1-27

[4-{[tert-Butyl(dimethyl)silyl]oxy}-3-(trifluoromethyl)phenyl](5-chloro-6-methoxypyridin-2-yl)methanone $^1$H NMR (300 MHz, CDCl$_3$) δ ppm 0.34 (s, 6H), 1.03 (s, 9H), 4.04 (s, 3H), 6.99 (d, J=8.4 Hz, 1H), 7.71 (d, J=7.9 Hz, 1H), 7.83 (d, J=7.8 Hz, 1H), 8.27 (dd, J=8.9, 2.1 Hz, 1H), 8.74 (d, J=2.3 Hz, 1H).
MS(+): 446 [M+H]$^+$.

Reference Example 1-28

(4-{[tert-Butyl(dimethyl)silyl]oxy}phenyl)(5-chloro-6-methoxypyridin-2-yl)methanone $^1$H NMR (300 MHz, CDCl$_3$) δ ppm 0.25 (s, 6H), 1.00 (s, 9H), 4.03 (s, 3H), 6.78-6.97 (m, 2H), 7.60 (d, J=7.9 Hz, 1H), 7.80 (d, J=7.8 Hz, 1H), 8.04-8.19 (m, 2H).
MS(+): 378 [M+H]$^+$.

Reference Example 1-29

(5-Chloro-6-methoxypyridin-2-yl)[4-(trifluoromethoxy)phenyl]methanone $^1$H NMR (300 MHz, CDCl$_3$) δ ppm 4.01 (s, 3H), 7.30 (d, J=7.8 Hz, 2H), 7.68 (d, J=7.8 Hz, 1H), 7.83 (d, J=7.8 Hz, 1H), 8.18-8.25 (m, 2H).
MS(+): 332 [M+H]$^+$.

The structures of Reference Examples 1-2 to 1-29 are shown below.

[Hyo 1-1]

Reference Example 1-2

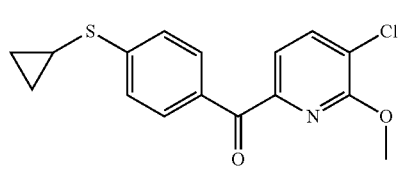

Reference Example 1-3
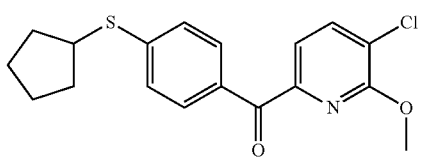
Reference Example 1-4
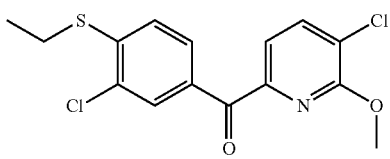
Reference Example 1-5
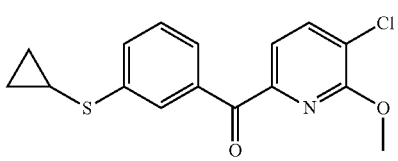
Reference Example 1-6
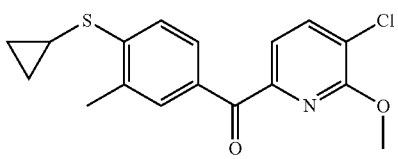
Reference Example 1-7
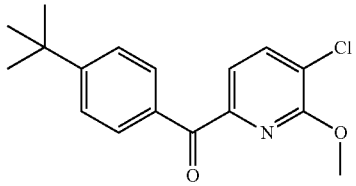
Reference Example 1-8
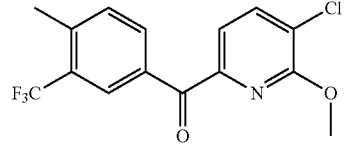
Reference Example 1-9
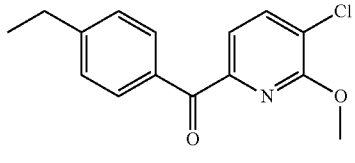
Reference Example 1-10
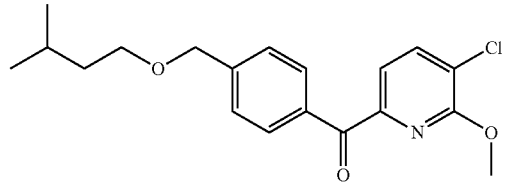
Reference Example 1-11
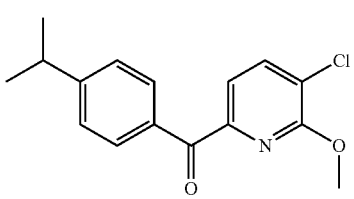
Reference Example 1-12
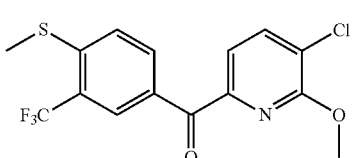
Reference Example 1-13
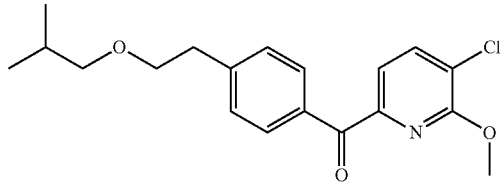
Reference Example 1-14
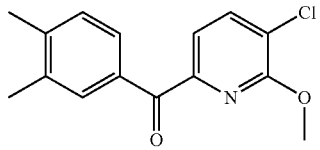
Reference Example 1-15
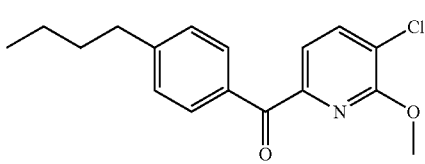
[Hyo 1-2]
Reference Example 1-16
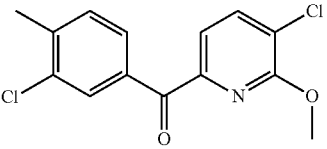
Reference Example 1-17
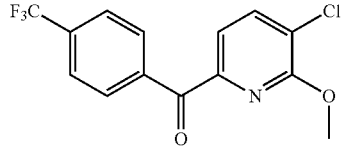
Reference Example 1-18
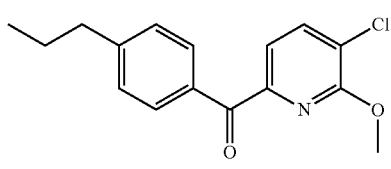

Reference Example 1-19
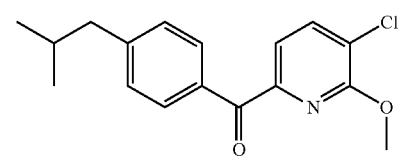

Reference Example 1-20
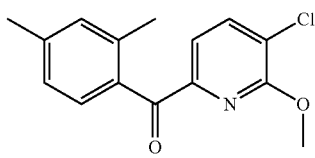

Reference Example 1-21
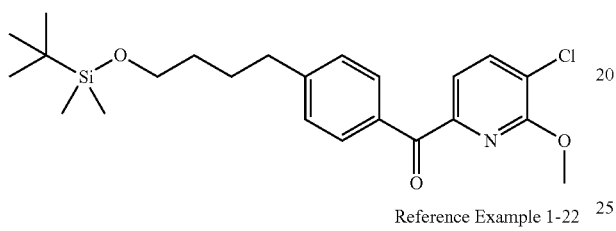

Reference Example 1-22
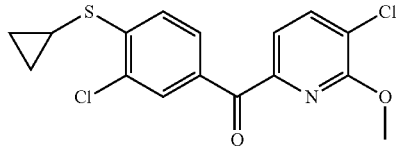

Reference Example 1-23
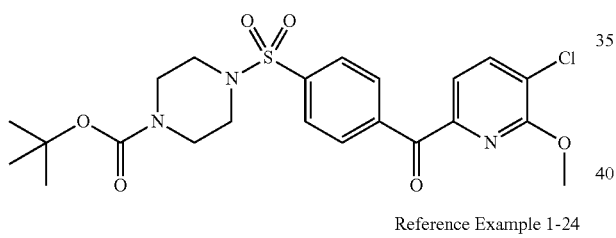

Reference Example 1-24
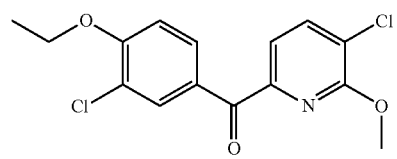

Reference Example 1-25
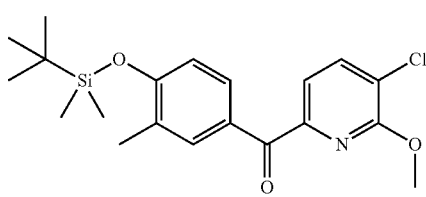

Reference Example 1-26
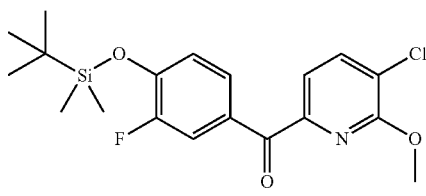

Reference Example 1-27
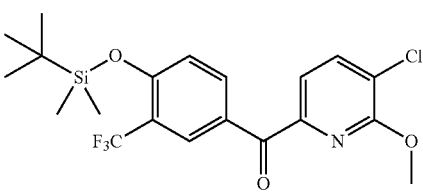

Reference Example 1-28
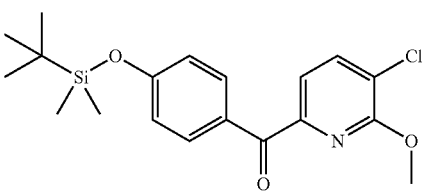

Reference Example 1-29
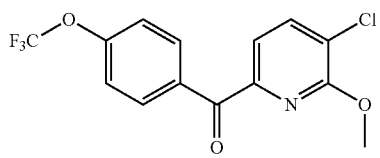

Reference Example 1-30

(5-Chloro-6-methoxypyridin-2-yl)[3-chloro-4-(propan-2-yloxy)phenyl]methanone

[Ka 58]

(1) (4-{[tert-Butyl(dimethyl)silyl]oxy}-3-chlorophenyl)(5-chloro-6-methoxypyridin-2-yl)methanone was obtained as an orange oil (3.94 g, 55% (two steps)) by performing substantially the same reaction as in Reference Example 1-1 (2)(3) except for using (4-bromo-2-chlorophenoxy)(tert-butyl)dimethylsilane.

(2) A 1 M solution of tetrabutylammonium fluoride in tetrahydrofuran (3.39 mL) was added to a solution of (4-{[tert-butyl(dimethyl)silyl]oxy}-3-chlorophenyl)(5-chloro-6-methoxypyridin-2-yl)methanone (700 mg) in tetrahydrofuran (10 mL) at room temperature, and the mixture was stirred at room temperature for two hours. Water was added to the reaction solution, followed by extraction with ethyl acetate. The organic layer was washed with brine, dried over anhydrous magnesium sulfate and filtered, after which the filtrate was concentrated under reduced pressure. The resulting residue was dissolved in N,N-dimethylformamide (10 mL), and 2-iodopropane (333 µL) and potassium carbonate (464 mg) were sequentially added at room temperature, followed by stirring at 65° C. for three hours. The reaction solution was returned to room temperature and water was added, followed by extraction with ethyl acetate. The organic layer was dried over anhydrous magnesium sulfate and filtered. The solvent was then evaporated under reduced pressure. The residue was purified by silica gel column chromatography (hexane:ethyl acetate=30:1) to give the title compound as a colorless oil (538 mg, 93%).

¹H NMR (300 MHz, CDCl₃) δ ppm 1.42 (s, 3H), 1.44 (s, 3H), 4.03 (s, 3H), 4.60-4.80 (m, 1H), 6.98 (d, J=8.6 Hz, 1H), 7.62 (d, J=7.7 Hz, 1H), 7.78 (d, J=7.7 Hz, 1H), 8.08 (dd, J=8.6, 2.1 Hz, 1H), 8.38 (d, J=2.7 Hz, 1H).

MS(+): 340 [M+H]⁺.

The following compounds (Reference Examples 1-31 to 1-33) were obtained by performing reaction by the same method as in Reference Example 1-30 using corresponding alkyl halides, respectively.

Reference Example 1-31

(5-Chloro-6-methoxypyridin-2-yl)[3-chloro-4-(3-methylbutoxy)phenyl]methanone

[Ka 59]

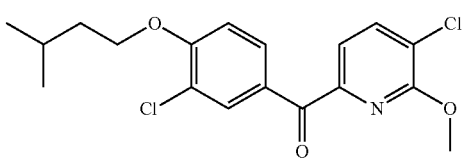

¹H NMR (300 MHz, CDCl₃) δ ppm 0.99 (s, 3H), 1.01 (s, 3H), 1.79 (td, J=6.5 Hz, 6.5 Hz, 2H), 1.82-1.98 (m, 1H), 4.05 (s, 3H), 4.16 (t, J=6.6 Hz, 2H), 6.99 (d, J=8.4 Hz, 1H), 7.65 (d, J=7.8 Hz, 1H), 7.82 (d, J=7.5 Hz, 1H), 8.11 (dd, J=8.7, 2.1 Hz, 1H), 8.38 (d, J=2.4 Hz, 1H).

Reference Example 1-32

(5-Chloro-6-methoxypyridin-2-yl)[3-chloro-4-(2-methylpropoxy)phenyl]methanone

[Ka 60]

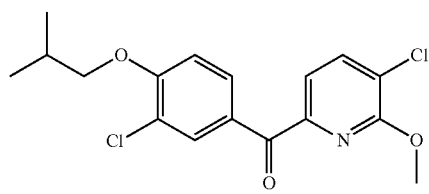

¹H NMR (300 MHz, CDCl₃) δ ppm 1.09 (d, J=6.8 Hz, 6H), 2.12-2.30 (m, 1H), 3.88 (d, J=6.8 Hz, 2H), 4.04 (s, 3H), 6.97 (d, J=8.7 Hz, 1H), 7.65 (d, J=7.8 Hz, 1H), 7.81 (d, J=7.8 Hz, 1H), 8.10 (dd, J=8.7, 2.2 Hz, 1H), 8.38 (d, J=2.2 Hz, 1H).

MS(+): 354 [M+H]⁺.

Reference Example 1-33

(5-Chloro-6-methoxypyridin-2-yl){3-chloro-4-[(4-methylpentyl)oxy]phenyl}methanone

[Ka 61]

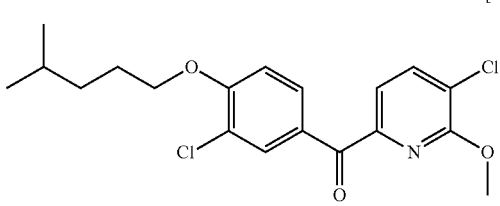

¹H NMR (300 MHz, CDCl₃) δ ppm 0.93 (d, J=6.8 Hz, 6H), 1.32-1.43 (m, 2H), 1.55-1.72 (m, 1H), 1.82-1.97 (m, 2H), 4.04 (d, J=1.7 Hz, 3H), 4.11 (t, J=6.0 Hz, 2H), 6.97 (d, J=8.7 Hz, 1H), 7.65 (d, J=7.8 Hz, 1H), 7.81 (d, J=7.8 Hz, 1H), 8.10 (dd, J=8.7, 2.2 Hz, 1H), 8.38 (d, J=2.2 Hz, 1H).

MS(+): 382 [M+H]⁺.

Reference Example 1-34

[4-(4-{[tert-Butyl(dimethyl)silyl]oxy}butoxy)-3-chlorophenyl](5-chloro-6-methoxypyridin-2-yl)methanone

[Ka 62]

(1) [3-Chloro-4-(4-hydroxybutoxy)phenyl](5-chloro-6-methoxypyridin-2-yl)methanone (759 mg, 54%) was obtained by performing substantially the same reaction as in Reference Example 1-30(2) except for using 4-bromo-1-butanol in place of 2-iodopropane.

(2) tert-Butyldimethylchlorosilane (240 mg) and imidazole (108 mg) were sequentially added to a solution of [3-chloro-4-(4-hydroxybutoxy)phenyl](5-chloro-6-methoxypyridin-2-yl)methanone (391 mg) in N,N-dimethylformamide (10 mL) under ice-cooling, and the mixture was stirred at room temperature for 4.5 hours. The reaction solution was ice-cooled and a saturated ammonium chloride solution was added, followed by extraction with ethyl acetate. The organic layer was dried over anhydrous magnesium sulfate and filtered. The filtrate was concentrated under reduced pressure. The residue was purified by silica gel column chromatography (hexane:ethyl acetate=100:0→10:1) to give the title compound (389 mg, 76%).

¹H NMR (300 MHz, CDCl₃) δ ppm 0.06 (s, 6H), 0.89 (s, 9H), 1.69-1.80 (m, 2H), 1.89-2.00 (m, 2H), 3.71 (t, J=6.1 Hz, 2H), 4.04 (s, 3H), 4.17 (t, J=6.3 Hz, 2H), 6.97 (d, J=8.9 Hz, 1H), 7.65 (d, J=7.7 Hz, 1H), 7.81 (d, J=7.7 Hz, 1H), 8.09 (dd, J=8.5, 2.2 Hz, 1H), 8.37 (d, J=2.4 Hz, 1H).

Reference Example 1-35

4-{2-Chloro-4-[(5-chloro-6-methoxypyridin-2-yl)carbonyl]phenoxy}butyl 4-methylbenzenesulfonate

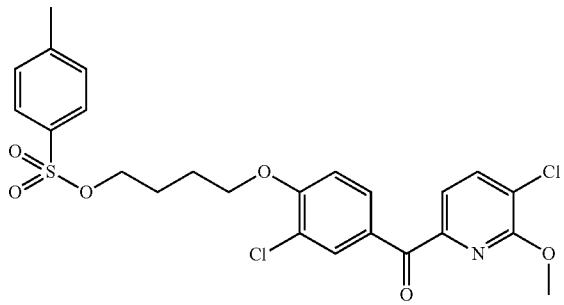

[Ka 63]

Triethylamine (830 μL), trimethylamine hydrochloride (188 mg) and 4-methylbenzenesulfonyl chloride (555 mg) were sequentially added to a solution of [3-chloro-4-(4-hydroxybutoxy)phenyl](5-chloro-6-methoxypyridin-2-yl)methanone obtained in Reference Example 1-34(1) (360 mg) in chloroform (8 mL) under ice-cooling, and the mixture was stirred at room temperature for 4.5 hours. Triethylamine (150 μL) and 4-methylbenzenesulfonyl chloride (185 mg) were sequentially added under ice-cooling, and the mixture was stirred at room temperature for further 1.5 hours. Water was added to the reaction solution, followed by extraction with chloroform. The organic layer was dried over anhydrous magnesium sulfate and filtered. The solvent was then evaporated under reduced pressure. The residue was purified by silica gel column chromatography (hexane:ethyl acetate=3:1) to give the title compound (357 mg, 70%).

$^1$H NMR (300 MHz, CDCl$_3$) δ ppm 1.90-2.00 (m, 4H), 2.44 (s, 3H), 4.04 (s, 3H), 4.06-4.22 (m, 4H), 6.93 (d, J=8.9 Hz, 1H), 7.34 (d, J=8.6 Hz, 2H), 7.66 (d, J=7.9 Hz, 1H), 7.76-7.85 (m, 3H), 8.10 (dd, J=8.8, 2.1 Hz, 1H), 8.36 (d, J=2.0 Hz, 1H).

MS(+): 524 [M+H]$^+$.

Reference Example 1-36

(6-Methoxy-5-methylpyridin-2-yl)[4-(methylsulfanyl)phenyl]methanone

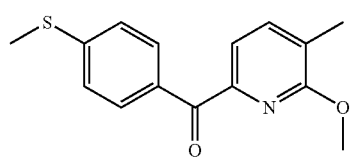

[Ka 64]

(1) 6-Methoxy-5-methylpyridine-2-carbaldehyde (14.8 g, 67%) was obtained by performing substantially the same reaction as in Reference Example 1-1(1) except for using methyl iodide.

(2) (6-Methoxy-5-methylpyridin-2-yl)[4-(methylsulfanyl)phenyl]methanol (15.0 g, 74%) was obtained by performing substantially the same reaction as in Reference Example 1-1(2) except for using 6-methoxy-5-methylpyridine-2-carbaldehyde.

(3) (6-Methoxy-5-methylpyridin-2-yl)[4-(methylsulfanyl)phenyl]methanone (400 mg, 81%) was obtained by performing substantially the same reaction as in Reference Example 1-1(3) except for using (6-methoxy-5-methylpyridin-2-yl)[4-(methylsulfanyl)phenyl]methanol.

$^1$H NMR (300 MHz, CDCl$_3$) δ ppm 2.28 (s, 3H), 2.54 (s, 3H), 3.95 (s, 3H), 7.28 (d, J=9.8 Hz, 2H), 7.49-7.66 (m, 2H), 8.14 (d, J=8.7 Hz, 2H).

The following compounds (Reference Examples 1-37 to 1-50) were obtained by performing reaction by the same method as in Reference Example 1-36 using methyl iodide or alternatively ethyl iodide and using corresponding aryl bromides, respectively.

Reference Example 1-37

[4-(Cyclopropylsulfanyl)phenyl](6-methoxy-5-methylpyridin-2-yl)methanone $^1$H NMR (300 MHz, CDCl$_3$) δ ppm 0.67-0.78 (m, 2H), 1.10-1.21 (m, 2H), 2.18-2.26 (m, 1H), 2.28 (s, 3H), 3.96 (s, 3H), 7.42 (d, J=8.9 Hz, 2H), 7.51-7.66 (m, 2H), 8.14 (d, J=8.9 Hz, 2H).

MS(+): 300 [M+H]$^+$.

Reference Example 1-38

4-[(6-Methoxy-5-methylpyridin-2-yl)carbonyl]-N,N-dimethylbenzenesulfonamide $^1$H NMR (300 MHz, CDCl$_3$) δ ppm 2.30 (s, 3H), 2.76 (s, 6H), 3.90 (s, 3H), 7.56-7.65 (m, 1H), 7.73 (d, J=7.3 Hz, 1H), 7.87 (d, J=8.7 Hz, 2H), 8.30 (d, J=8.9 Hz, 2H).

MS(+): 335 [M+H]$^+$.

Reference Example 1-39

N-(2-{[tert-Butyl(dimethyl)silyl]oxy}ethyl)-4-[(6-methoxy-5-methylpyridin-2-yl)carbonyl]-N-methylbenzenesulfonamide $^1$H NMR (300 MHz, CDCl$_3$) δ ppm 0.06 (s, 6H), 0.88 (s, 9H), 2.30 (s, 3H), 2.91 (s, 3H), 3.20 (t, J=5.8 Hz, 2H), 3.76-3.84 (m, 2H), 3.90 (s, 3H), 7.56-7.63 (m, 1H), 7.72 (d, J=7.5 Hz, 1H), 7.88 (d, J=8.7 Hz, 2H), 8.23-8.34 (m, 2H).

MS(+): 479 [M+H]$^+$.

Reference Example 1-40

[3-Chloro-4-(methylsulfanyl)phenyl](6-methoxy-5-methylpyridin-2-yl)methanone $^1$H NMR (300 MHz, CDCl$_3$) δ ppm 2.29 (s, 3H), 2.55 (s, 3H), 3.97 (s, 3H), 7.21 (d, J=8.4 Hz, 1H), 7.54-7.61 (m, 1H), 7.63-7.69 (m, 1H), 8.12 (dd, J=8.4, 1.9 Hz, 1H), 8.38 (d, J=1.9 Hz, 1H).

MS(+): 308 [M+H]$^+$.

Reference Example 1-41

{4-[(3-{[tert-Butyl(dimethyl)silyl]oxy}propyl)sulfanyl]-3-chlorophenyl}(6-methoxy-5-methylpyridin-2-yl)methanone $^1$H NMR (300 MHz, CDCl$_3$) δ ppm 0.08 (s, 6H), 0.92 (s, 9H), 1.90-2.01 (m, 2H), 2.29 (s, 3H), 3.12 (t, J=7.4 Hz, 2H), 3.77 (t, J=5.8 Hz, 2H), 3.97 (s, 3H), 7.32 (d, J=8.4 Hz, 1H), 7.54-7.60 (m, 1H), 7.63-7.68 (m, 1H), 8.08 (dd, J=8.4, 1.9 Hz, 1H), 8.38 (d, J=1.87 Hz, 1H).
MS(+): 466 [M+H]$^+$.

Reference Example 1-42 tert-Butyl 3-({4-[(6-methoxy-5-methylpyridin-2-yl)carbonyl]phenyl}sulfanyl)azetidine-1-carboxylate $^1$H NMR (300 MHz, CDCl$_3$) δ ppm 1.44 (s, 9H), 2.28 (s, 3H), 3.85-3.97 (m, 5H), 4.06-4.21 (m, 1H), 4.37-4.53 (m, 2H), 7.19 (d, J=8.9 Hz, 2H), 7.50-7.70 (m, 2H), 8.14 (d, J=8.9 Hz, 2H).
MS(+): 414 [M+H]$^+$.

Reference Example 1-43

[4-(Ethylsulfanyl)phenyl](6-methoxy-5-methylpyridin-2-yl)methanone $^1$H NMR (300 MHz, CDCl$_3$) δ ppm 1.39 (t, J=7.4 Hz, 3H), 2.28 (s, 3H), 3.05 (q, J=7.4 Hz, 2H), 3.95 (s, 3H), 7.32 (d, J=8.9 Hz, 2H), 7.51-7.66 (m, 2H), 8.13 (d, J=8.7 Hz, 2H).
MS(+): 288 [M+H]$^+$.

Reference Example 1-44

[4-(4,4-Dimethyl-4,5-dihydro-1,3-oxazol-2-yl)phenyl](6-methoxy-5-methylpyridin-2-yl)methanone $^1$H NMR (300 MHz, CDCl$_3$) δ ppm 1.41 (s, 6H), 2.28 (s, 3H), 3.90 (s, 3H), 4.15 (s, 2H), 7.51-7.61 (m, 1H), 7.64-7.71 (m, 1H), 7.98-8.07 (m, 2H), 8.13-8.23 (m, 2H).
MS(+): 325 [M+H]$^+$.

Reference Example 1-45

(6-Methoxy-5-methylpyridin-2-yl)[6-(methylsulfanyl)pyridin-3-yl]methanone $^1$H NMR (300 MHz, CDCl$_3$) δ ppm 2.29 (s, 3H), 2.63 (s, 3H), 3.97 (s, 3H), 7.18-7.37 (m, 1H), 7.49-7.63 (m, 1H), 7.65-7.74 (m, 1H), 8.24-8.41 (m, 1H), 9.29-9.41 (m, 1H).
MS(+): 275 [M+H]$^+$.

Reference Example 1-46

[3-Chloro-4-(methylsulfanyl)phenyl](5-ethyl-6-methoxypyridin-2-yl)methanone $^1$H NMR (300 MHz, CDCl$_3$) δ ppm 1.25 (t, J=7.5 Hz, 3H), 2.55 (s, 3H), 2.68 (q, J=7.7 Hz, 2H), 3.97 (s, 3H), 7.21 (d, J=8.4 Hz, 1H), 7.56-7.62 (m, 1H), 7.66-7.72 (m, 1H), 8.12 (dd, J=8.4, 1.8 Hz, 1H), 8.39 (d, J=1.7 Hz, 1H).
MS(+): 322 [M+H]$^+$.

Reference Example 1-47

{4-[(3-{[tert-Butyl(dimethyl)silyl]oxy}propyl)sulfanyl]phenyl}(5-ethyl-6-methoxypyridin-2-yl)methanone $^1$H NMR (200 MHz, CDCl$_3$) δ ppm 0.07 (s, 6H), 0.91 (s, 9H), 1.14-1.37 (m, 3H), 1.78-2.05 (m, 2H), 2.55-2.81 (m, 2H), 2.99-3.21 (m, 2H), 3.65-3.82 (m, 2H), 3.94 (s, 3H), 7.28-7.43 (m, 2H), 7.51-7.72 (m, 2H), 8.03-8.25 (m, 2H).
MS(+): 446 [M+H]$^+$.

Reference Example 1-48

{4-[(3-{[tert-Butyl(dimethyl)silyl]oxy}propyl)sulfanyl]-3-chlorophenyl}(5-ethyl-6-methoxypyridin-2-yl)methanone $^1$H NMR (300 MHz, CDCl$_3$) δ ppm 0.08 (s, 6H), 0.92 (s, 9H), 1.20-1.30 (m, 3H), 1.89-2.02 (m, 2H), 2.68 (q, J=7.7 Hz, 2H), 3.03-3.17 (m, 2H), 3.77 (t, J=5.8 Hz, 2H), 3.96 (s, 3H), 7.32 (d, J=8.4 Hz, 1H), 7.58 (d, J=6.7 Hz, 1H), 7.70 (s, 1H), 8.08 (dd, J=8.4, 1.7 Hz, 1H), 8.39 (s, 1H).
MS(+): 480 [M+H]$^+$.

Reference Example 1-49

[4-(Cyclopropylsulfanyl)phenyl](5-ethyl-6-methoxypyridin-2-yl)methanone $^1$H NMR (300 MHz, CDCl$_3$) δ ppm 0.66-0.80 (m, 2H), 1.08-1.20 (m, 2H), 1.24 (t, J=7.5 Hz, 3H), 2.16-2.30 (m, 1H), 2.68 (q, J=7.7 Hz, 2H), 3.95 (s, 3H), 7.42 (d, J=8.9 Hz, 2H), 7.53-7.60 (m, 1H), 7.61-7.66 (m, 1H), 8.15 (d, J=8.7 Hz, 2H).
MS(+): 314 [M+H]$^+$.

Reference Example 1-50

(4-{[tert-Butyl(dimethyl)silyl]oxy}-3-chlorophenyl)(5-ethyl-6-methoxypyridin-2-yl)methanone $^1$H NMR (300 MHz, CDCl$_3$) δ ppm 0.28 (s, 6H), 1.05 (s, 9H), 1.25 (t, J=7.5 Hz, 3H), 2.68 (q, J=7.7 Hz, 2H), 3.97 (s, 3H), 6.94 (d, J=8.6 Hz, 1H), 7.53-7.60 (m, 1H), 7.63-7.70 (m, 1H), 8.05 (dd, J=8.6, 2.2 Hz, 1H), 8.45 (d, J=2.2 Hz, 1H).
MS(+): 406 [M+H]$^+$.

The structures of Reference Examples 1-37 to 1-50 are shown below.

[Hyo 2]

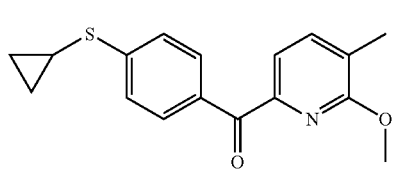

Reference Example 1-37

-continued

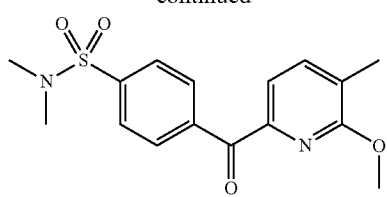

Reference Example 1-38

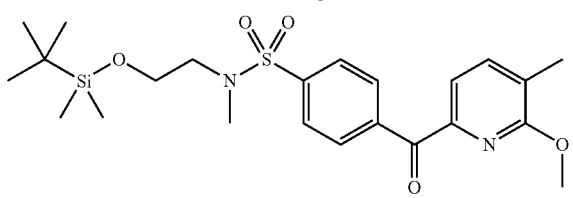

Reference Example 1-39

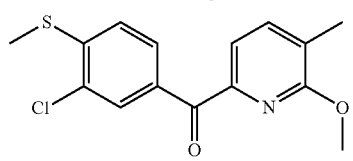

Reference Example 1-40

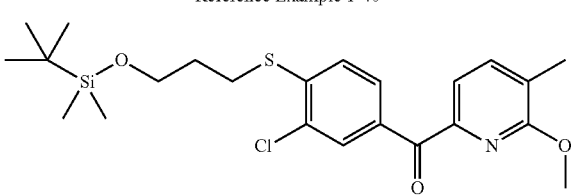

Reference Example 1-41

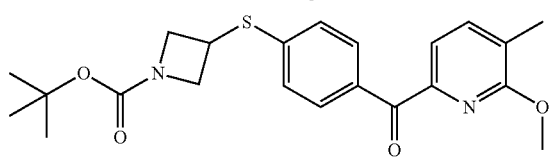

Reference Example 1-42

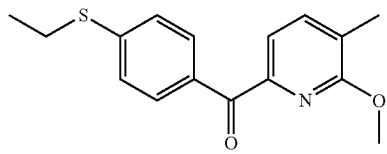

Reference Example 1-43

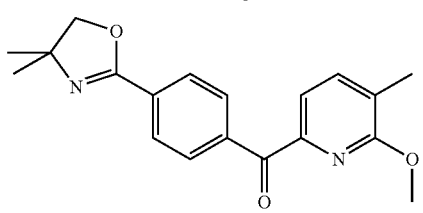

Reference Example 1-44

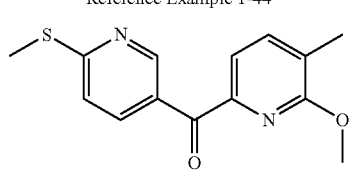

Reference Example 1-45

-continued

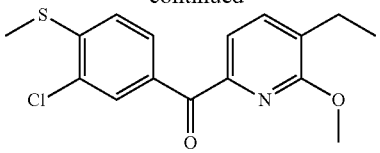

Reference Example 1-46

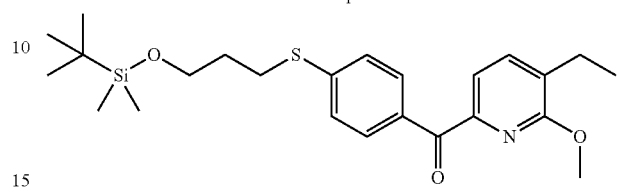

Reference Example 1-47

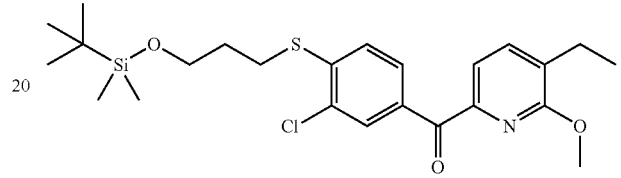

Reference Example 1-48

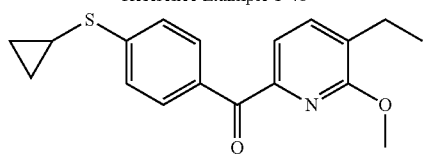

Reference Example 1-49

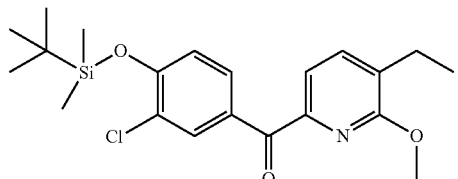

Reference Example 1-50

Reference Example 1-51

(5-Cyclopropyl-6-methoxypyridin-2-yl)[4-(methyl-sulfanyl)phenyl]methanone

[Ka 65]

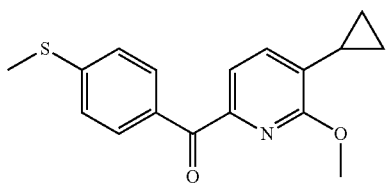

(1) A suspension of zinc chloride (27 g) in tetrahydrofuran (300 mL) was cooled to 0° C. in the presence of a nitrogen gas, and a 1 M solution of cyclopropanemagnesium bromide in tetrahydrofuran (186 mL) was added thereto, followed by stirring at room temperature for 30 minutes. The reaction solution was cooled to 0° C. Dichlorobis(triphenylphosphine)-palladium(II) (3.26 g) and a solution of ethyl 5-bromopyridine-2-carboxylate (21.4 g) in tetrahydrofuran (100 mL) were sequentially added, and the mixture was stirred at 0° C. for 30 minutes and at room temperature for one hour. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (hexane:ethyl acetate=4:1→1:1) to give ethyl 5-cyclopropylpyridine-2-carboxylate (15.5 g, 87%) as a pale brown oil.

(2) m-Chloroperbenzoic acid (55 g) was added to a solution of ethyl 5-cyclopropylpyridine-2-carboxylate (15.5 g) in chloroform (300 mL) under ice-cooling, and the mixture was stirred at room temperature for four hours. The reaction solution was poured into a mixed solvent of saturated aqueous sodium bicarbonate and a saturated sodium thiosulfate solution, and the mixture was stirred at room temperature for 30 minutes. After extraction with chloroform, the organic layer was washed with brine, dried over anhydrous magnesium sulfate and filtered. The solvent was then evaporated under reduced pressure. The residue was purified by silica gel column chromatography (chloroform:methanol=10:0→9:1) to give ethyl 5-cyclopropylpyridine-2-carboxylate 1-oxide (15.4 g) as a pale yellow oil.

(3) Trifluoroacetic anhydride (23 mL) was added to a solution of ethyl 5-cyclopropylpyridine-2-carboxylate 1-oxide (15.4 g) in N,N-dimethylformamide (45 mL), and the mixture was stirred at 50° C. for two hours. The reaction solution was poured into water, followed by extraction with ethyl acetate. The organic layer was washed with saturated aqueous sodium bicarbonate and brine, dried over anhydrous magnesium sulfate and filtered. The solvent was then evaporated under reduced pressure. The residue was purified by silica gel column chromatography (chloroform:methanol=10:0→9:1) to give ethyl 5-cyclopropyl-6-hydroxypyridine-2-carboxylate (12.4 g, 78%) as a colorless powder.

(4) Silver carbonate (70 g) and methyl iodide (11.2 mL) were added to a solution of ethyl 5-cyclopropyl-6-hydroxypyridine-2-carboxylate (12.4 g) in chloroform (250 mL), and the mixture was stirred at 60° C. for eight hours. The reaction solution was filtered through celite, and then the solvent was evaporated under reduced pressure. The residue was purified by silica gel column chromatography (hexane:ethyl acetate=9:1→4:1) to give ethyl 5-cyclopropyl-6-methoxypyridine-2-carboxylate (13.05 g, 99%) as a colorless oil.

(5) Lithium aluminum hydride (4.44 g) was added in small portions to a solution of ethyl 5-cyclopropyl-6-methoxypyridine-2-carboxylate (17.3 g) in tetrahydrofuran (300 mL) under ice-cooling, and the mixture was stirred at the same temperature for one hour. The reaction solution was poured into a saturated ammonium chloride solution, followed by extraction with ethyl acetate. The organic layer was washed with brine, dried over anhydrous magnesium sulfate and filtered, after which the filtrate was concentrated under reduced pressure to give (5-cyclopropyl-6-methoxypyridin-2-yl)methanol (14.1 g).

(6) Manganese dioxide (67 g) was added to a solution of (5-cyclopropyl-6-methoxypyridin-2-yl)methanol (14.1 g) in chloroform (200 mL), and the mixture was stirred at 65° C. for one hour. The reaction solution was filtered through celite and the filtrate was concentrated to give 5-cyclopropyl-6-methoxypyridine-2-carbaldehyde (11 g, 85%).

(7) (5-Cyclopropyl-6-methoxypyridin-2-yl)[4-(methylsulfanyl)phenyl]methanol (2.93 g, 93%) was obtained by performing substantially the same reaction as in Reference Example 1-1(2) except for using 5-cyclopropyl-6-methoxypyridine-2-carbaldehyde (1.53 g).

(8) The title compound was obtained as a pale yellow oil (2.38 g, 99%) by performing substantially the same reaction as in Reference Example 1-1(3) except for using (5-cyclopropyl-6-methoxypyridin-2-yl)[4-(methylsulfanyl)phenyl]methanol.

$^1$H NMR (300 MHz, CDCl$_3$) δ ppm 0.71-0.81 (m, 2H), 0.99-1.12 (m, 2H), 2.11-2.24 (m, 1H), 2.55 (s, 3H), 3.97 (s, 3H), 7.20-7.32 (m, 3H), 7.62 (d, J=7.6 Hz, 1H), 8.11-8.19 (m, 2H).

MS(+): 300 [M+H]$^+$.

The following compounds (Reference Examples 1-52 to 1-59) were obtained by performing reaction by the same method as in Reference Example 1-51 using corresponding aryl bromides, respectively.

Reference Example 1-52

[3-Chloro-4-(methylsulfanyl)phenyl](5-cyclopropyl-6-methoxypyridin-2-yl)methanone $^1$H NMR (300 MHz, CDCl$_3$) δ ppm 0.72-0.83 (m, 2H), 0.98-1.16 (m, 2H), 2.09-2.26 (m, 1H), 2.55 (s, 3H), 3.99 (s, 3H), 7.15-7.31 (m, 2H), 7.66 (d, J=7.6 Hz, 1H), 8.12 (dd, J=8.3, 1.8 Hz, 1H), 8.39 (d, J=1.7 Hz, 1H).

MS(+): 334 [M+H]$^+$.

Reference Example 1-53

(5-Cyclopropyl-6-methoxypyridin-2-yl)(4-ethylphenyl)methanone $^1$H NMR (300 MHz, CDCl$_3$) δ ppm 0.67-0.82 (m, 2H), 0.97-1.15 (m, 2H), 1.29 (t, J=7.6 Hz, 3H), 2.10-2.27 (m, 1H), 2.73 (q, J=7.6 Hz, 2H), 3.98 (s, 3H), 7.15-7.37 (m, 3H), 7.60 (d, J=8.1 Hz, 1H), 8.13 (d, J=8.2 Hz, 2H).

MS(+): 282 [M+H]$^+$.

Reference Example 1-54

(4-{[tert-Butyl(dimethyl)silyl]oxy}phenyl)(5-cyclopropyl-6-methoxypyridin-2-yl)methanone $^1$H NMR (300 MHz, CDCl$_3$) δ ppm 0.25 (s, 6H), 0.65-0.84 (m, 2H), 0.93-1.12 (m, 11H), 2.05-2.32 (m, 1H), 3.98 (s, 3H), 6.79-6.96 (m, 2H), 7.23 (d, J=7.6 Hz, 1H), 7.58 (d, J=7.6 Hz, 1H), 8.05-8.35 (m, 2H).

MS(+): 384 [M+H]$^+$.

Reference Example 1-55

(4-{[tert-Butyl(dimethyl)silyl]oxy}-3-chlorophenyl)(5-cyclopropyl-6-methoxypyridin-2-yl)methanone $^1$H NMR (300 MHz, CDCl$_3$) δ ppm 0.28 (s, 6H), 0.65-0.83 (m, 2H), 0.95-1.31 (m, 11H), 2.05-2.29 (m, 1H), 4.00 (s, 3H), 6.94 (d, J=8.6 Hz, 1H), 7.24 (d, J=7.6 Hz, 1H), 7.63 (d, J=8.1 Hz, 1H), 8.05 (dd, J=8.5, 2.1 Hz, 1H), 8.45 (d, J=2.2 Hz, 1H).

MS(+): 418 [M+H]$^+$.

Reference Example 1-56

[4-(3-{[tert-Butyl(dimethyl)silyl]oxy}propoxy)phenyl](5-cyclopropyl-6-methoxypyridin-2-yl)methanone $^1$H NMR (300 MHz, CDCl$_3$) δ ppm 0.00 (s, 6H), 0.66-0.75 (m, 2H), 0.84 (s, 9H), 0.94-1.03 (m, 2H), 1.89-2.03 (m, 2H), 2.06-2.18 (m, 1H), 3.76 (t, J=6.0 Hz, 2H), 3.93 (s, 3H), 4.11 (t, J=6.4 Hz, 2H), 6.86-6.92 (m, 2H), 7.17 (d, J=7.4 Hz, 1H), 7.53 (d, J=8.3 Hz, 1H), 8.13-8.20 (m, 2H).

MS(+): 442 [M+H]⁺.

Reference Example 1-57

(5-Cyclopropyl-6-methoxypyridin-2-yl)[4-(cyclopropylsulfanyl)-3-methylphenyl]methanone ¹H NMR (300 MHz, CDCl₃) δ ppm 0.70-0.80 (m, 4H), 1.00-1.09 (m, 2H), 1.13-1.22 (m, 2H), 2.12-2.22 (m, 2H), 2.29 (s, 3H), 3.99 (s, 3H), 7.23 (d, J=7.4 Hz, 1H), 7.60 (d, J=7.7 Hz, 1H), 7.61 (d, J=8.3 Hz, 1H), 7.98-8.02 (m, 1H), 8.05 (dd, J=8.3, 1.9 Hz, 1H).

MS(+): 340 [M+H]⁺.

Reference Example 1-58

(5-Cyclopropyl-6-methoxypyridin-2-yl)(4-methylphenyl)methanone

¹H NMR (300 MHz, CDCl₃) δ ppm 0.70-0.80 (m, 2H), 0.95-1.11 (m, 2H), 2.08-2.25 (m, 1H), 2.44 (s, 3H), 3.97 (s, 3H), 7.23 (d, J=7.7 Hz, 1H), 7.27 (d, J=8.0 Hz, 2H), 7.60 (d, J=7.4 Hz, 1H), 8.09 (d, J=8.3 Hz, 2H).

MS(+): 268 [M+H]⁺.

Reference Example 1-59

(5-Cyclopropyl-6-methoxypyridin-2-yl)[4-(4,4-dimethyl-4,5-dihydro-1,3-oxazol-2-yl)phenyl]methanone ¹H NMR (300 MHz, CDCl₃) δ ppm 0.71-0.80 (m, 2H), 1.00-1.09 (m, 2H), 1.41 (s, 6H), 2.10-2.22 (m, 1H), 3.92 (s, 3H), 4.15 (s, 2H), 7.24 (d, J=7.7 Hz, 1H), 7.66 (d, J=7.7 Hz, 1H), 8.02 (d, J=8.9 Hz, 2H), 8.17 (dd, J=7.1, 2.1 Hz, 2H).

MS(+): 351 [M+H]⁺.

The structures of Reference Examples 1-52 to 1-59 are shown below.

[Hyo 3]

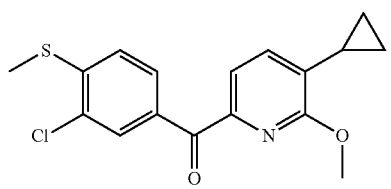

Reference Example 1-52

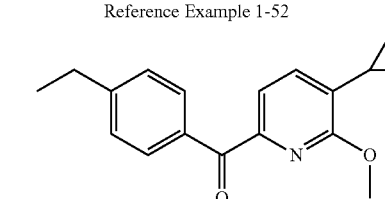

Reference Example 1-53

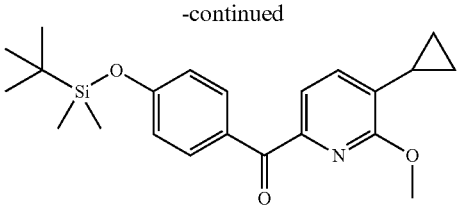

Reference Example 1-54

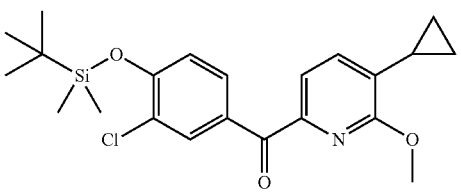

Reference Example 1-55

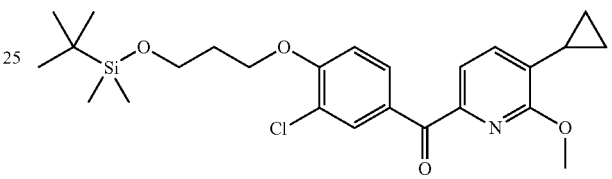

Reference Example 1-56

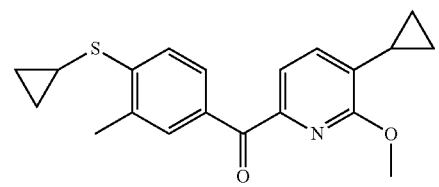

Reference Example 1-57

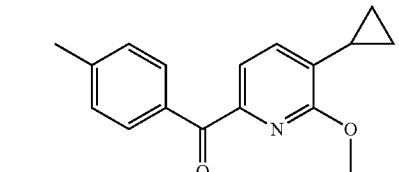

Reference Example 1-58

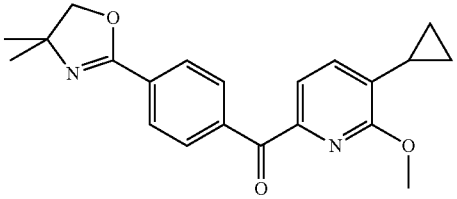

Reference Example 1-59

Reference Example 1-60

(5-Cyclopropyl-6-methoxypyridin-2-yl)(4-ethoxyphenyl)methanone

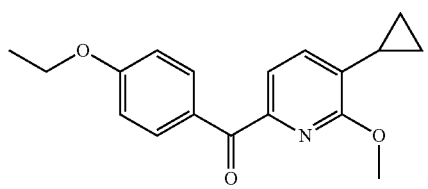

[Ka 66]

(1) A small amount of iodine was added to a suspension of 1-bromo-4-ethoxybenzene (484 µL) and magnesium (82.3 mg) in THF at room temperature in a nitrogen atmosphere, and the mixture was stirred at 50° C. for one hour. The reaction solution was returned to room temperature and a solution of 5-cyclopropyl-6-methoxypyridine-2-carbaldehyde (300 mg) in tetrahydrofuran (1 mL) was added, followed by stirring at 50° C. for one hour. Tetrahydrofuran was concentrated under reduced pressure and a saturated ammonium chloride solution was added, followed by extraction with ethyl acetate. The organic layer was filtered through diatomaceous earth, and then the solvent was concentrated under reduced pressure. The resulting residue was purified by silica gel column chromatography (hexane:ethyl acetate=50:1→9:1) to give (5-cyclopropyl-6-methoxypyridin-2-yl)(4-ethoxyphenyl)methanol as a yellow oil (438 mg, 86%).

(2) The title compound was obtained as a pale yellow oil (441 mg, 99%) by performing substantially the same reaction as in Reference Example 1-1(3) except for using (5-cyclopropyl-6-methoxypyridin-2-yl)(4-ethoxyphenyl)methanol.

$^1$H NMR (300 MHz, CDCl$_3$) δ ppm 0.71-0.79 (m, 2H), 0.99-1.08 (m, 2H), 1.45 (t, J=7.2 Hz, 3H), 2.10-2.23 (m, 1H), 3.98 (s, 3H), 4.12 (q, J=7.2 Hz, 2H), 6.94 (d, J=8.9 Hz, 2H), 7.22 (d, J=7.6 Hz, 1H), 7.58 (d, J=7.6 Hz, 1H), 8.22 (d, J=8.9 Hz, 2H).

MS(+): 298 [M+H]$^+$.

Reference Example 1-61

(5-Cyclopropyl-6-methoxypyridin-2-yl)(3-ethoxyphenyl)methanone

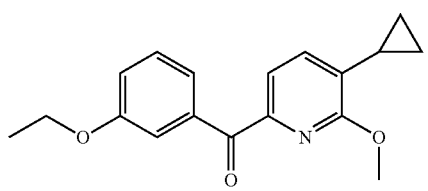

[Ka 67]

(1) (3-{[tert-Butyl(dimethyl)silyl]oxy}phenyl)(5-cyclopropyl-6-methoxypyridin-2-yl)methanone was obtained as a brown oil (1.193 g, 84% (two steps)) by performing substantially the same reaction as in Reference Example 1-51(7)(8) except for using (3-bromophenoxy)(tert-butyl)dimethylsilane.

(2) The title compound was obtained as a colorless oil (270 mg, 75%) by performing substantially the same reaction as in Reference Example 1-30(2) except for using (3-{[tert-butyl(dimethyl)silyl]oxy}phenyl)(5-cyclopropyl-6-methoxypyridin-2-yl)methanone and using ethyl iodide in place of 2-iodopropane.

$^1$H NMR (300 MHz, CDCl$_3$) δ ppm 0.71-0.82 (m, 2H), 0.99-1.11 (m, 2H), 1.43 (t, J=6.9 Hz, 3H), 2.11-2.24 (m, 1H), 3.97 (s, 3H), 4.10 (q, J=6.9 Hz, 2H), 7.07-7.16 (m, 1H), 7.23 (d, J=7.6 Hz, 1H), 7.35 (t, J=8.1 Hz, 1H), 7.60 (d, J=7.6 Hz, 1H), 7.64-7.70 (m, 1H), 7.74 (dd, J=8.1, 2.0 Hz, 1H).

MS(+): 298 [M+H]$^+$.

Reference Example 1-62

(3-Chloro-4-ethoxyphenyl)(5-cyclopropyl-6-methoxypyridin-2-yl)methanone

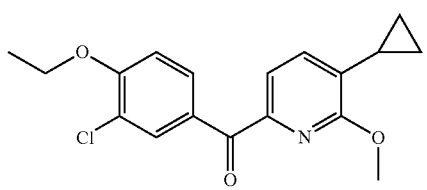

[Ka 68]

The title compound was obtained as a white solid (1.77 g, 94%) by performing substantially the same reaction as in Reference Example 1-61(2) except for using (4-{[tert-butyl(dimethyl)silyl]oxy}-3-chlorophenyl)(5-cyclopropyl-6-methoxypyridin-2-yl)methanone obtained in Reference Example 1-55.

$^1$H NMR (300 MHz, CDCl$_3$) δ ppm 0.73-0.79 (m, 2H), 1.01-1.09 (m, 2H), 1.52 (t, J=7.2 Hz, 3H), 2.12-2.22 (m, 1H), 4.00 (s, 3H), 4.21 (q, J=7.2 Hz, 2H), 6.97 (d, J=8.7 Hz, 1H), 7.23 (d, J=7.8 Hz, 1H), 7.63 (d, J=7.8 Hz, 1H), 8.15 (dd, J=8.7 Hz, 1.8 Hz, 1H), 8.46-8.49 (m, 1H).

MS(+): 332 [M+H]$^+$.

Reference Example 1-63

[3-(4-{[tert-Butyl(dimethyl)silyl]oxy}butoxy)phenyl](5-cyclopropyl-6-methoxypyridin-2-yl)methanone

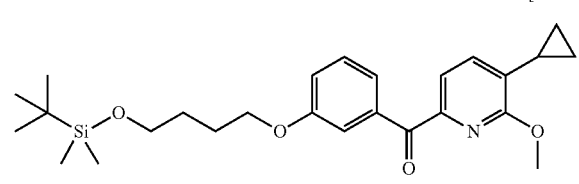

[Ka 69]

The title compound was obtained as a pale yellow oil (291 mg, 59% (two steps)) by performing substantially the same reaction as in Reference Example 1-34 except for using (3-{[tert-butyl(dimethyl)silyl]oxy}phenyl)(5-cyclopropyl-6-methoxypyridin-2-yl)methanone obtained in Reference Example 1-61(1).

$^1$H NMR (300 MHz, CDCl$_3$) δ ppm 0.06 (s, 6H), 0.73-0.80 (m, 2H), 0.90 (s, 9H), 1.00-1.11 (m, 2H), 1.64-1.75 (m, 2H), 1.80-1.92 (m, 2H), 2.11-2.23 (m, 1H), 3.69 (t, J=6.3 Hz, 2H), 3.97 (s, 3H), 4.04 (t, J=6.3 Hz, 2H), 7.11 (ddd, J=8.3, 2, 8, 1.1

Hz, 1H), 7.23 (d, J=7.7 Hz, 1H), 7.35 (t, J=8.0 Hz, 1H), 7.60 (d, J=7.4 Hz, 1H), 7.67 (dd, J=2.8, 1.7 Hz, 1H), 7.73 (dt, J=8.0, 1.1 Hz, 1H).

MS(+): 456 [M+H]⁺.

Reference Example 1-64

[3-(3-{[tert-Butyl(dimethyl)silyl]oxy}propoxy)phenyl](5-cyclopropyl-6-methoxypyridin-2-yl)methanone

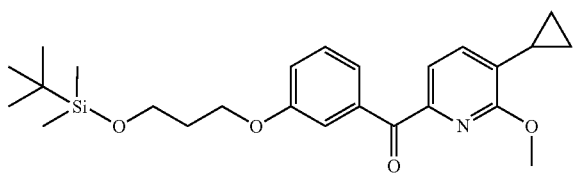

The title compound was obtained as a colorless oil (349 mg, 72% (two steps)) by performing substantially the same reaction as in Reference Example 1-63 except for using 3-bromo-1-propanol in place of 4-bromo-1-butanol.

¹H NMR (300 MHz, CDCl₃) δ ppm 0.04 (s, 6H), 0.72-0.81 (m, 2H), 0.88 (s, 9H), 1.01-1.11 (m, 2H), 1.95-2.04 (m, 2H), 2.07-2.23 (m, 1H), 3.81 (t, J=6.1 Hz, 2H), 3.97 (s, 3H), 4.12 (t, J=6.1 Hz, 2H), 7.11 (ddd, J=8.3, 2.5, 0.8 Hz, 1H), 7.23 (d, J=7.4 Hz, 1H), 7.36 (t, J=7.7 Hz, 1H), 7.60 (d, J=7.7 Hz, 1H), 7.68 (dd, J=2.8, 1.4 Hz, 1H), 7.73 (dt, J=7.7, 1.1 Hz, 1H).

MS(+): 442 [M+H]⁺.

Reference Example 1-65

4-{2-Chloro-4-[(5-cyclopropyl-6-methoxypyridin-2-yl)carbonyl]phenoxy}butyl 4-methylbenzenesulfonate

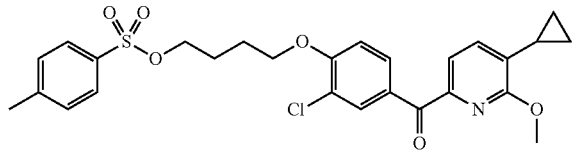

The title compound (440 mg, 52% (two steps)) was obtained by performing substantially the same reaction as in Reference Examples 1-34(1) and 1-35 sequentially except for using (4-{[tert-butyl(dimethyl)silyl]oxy}-3-chlorophenyl)(5-cyclopropyl-6-methoxypyridin-2-yl)methanone obtained in Reference Example 1-55.

¹H NMR (300 MHz, CDCl₃) δ ppm 0.68-0.81 (m, 2H), 1.00-1.10 (m, 2H), 1.83-1.98 (m, 4H), 2.10-2.23 (m, 1H), 2.44 (s, 3H), 3.99 (s, 3H), 4.01-4.20 (m, 4H), 6.91 (d, J=8.7 Hz, 1H), 7.23 (d, J=7.5 Hz, 1H), 7.33 (d, J=8.4 Hz, 2H), 7.63 (d, J=7.5 Hz, 1H), 7.79 (d, J=8.4 Hz, 2H), 8.14 (dd, J=8.7, 2.1 Hz, 1H), 8.43 (d, J=2.4 Hz, 1H)

MS(+): 530 [M+H]⁺.

Reference Example 1-66

[4-(4-{[tert-Butyl(dimethyl)silyl]oxy}butoxy)-3-chlorophenyl](5-cyclopropyl-6-methoxypyridin-2-yl)methanone

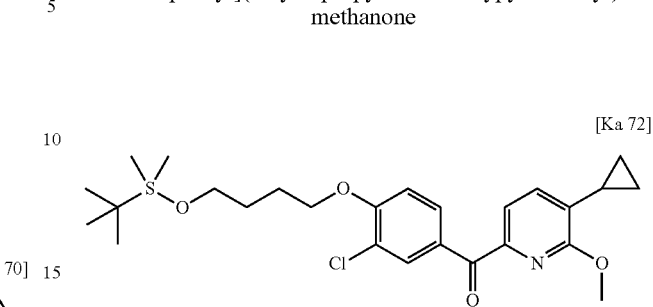

The title compound (277 mg, 57% (two steps)) was obtained by performing substantially the same reaction as in Reference Example 1-34 except for using (4-{[tert-butyl(dimethyl)silyl]oxy}-3-chlorophenyl)(5-cyclopropyl-6-methoxypyridin-2-yl)methanone obtained in Reference Example 1-55.

¹H NMR (300 MHz, CDCl₃) δ ppm 0.06 (s, 6H), 0.72-0.82 (m, 2H), 0.90 (s, 9H), 0.98-1.12 (m, 2H), 1.68-1.81 (m, 2H), 1.88-2.02 (m, 2H), 2.12-2.23 (m, 1H), 3.72 (t, J=6.1 Hz, 2H), 4.00 (s, 3H), 4.16 (t, J=6.3 Hz, 2H), 6.97 (d, J=8.6 Hz, 1H), 7.24 (d, J=7.8 Hz, 1H), 7.63 (d, J=7.8 Hz, 1H), 8.15 (dd, J=8.8, 2.3 Hz, 1H), 8.46 (d, J=2.5 Hz, 1H).

Reference Example 1-67

[6-Methoxy-5-(trifluoromethyl)pyridin-2-yl][4-(methylsulfanyl)phenyl]methanone

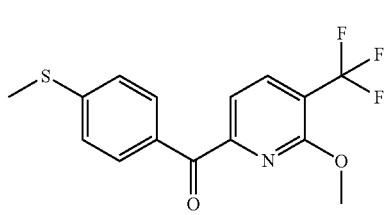

(1) Sodium borohydride (405 mg) was added to a solution of ethyl 6-methoxy-5-(trifluoromethyl)pyridine-2-carboxylate (670 mg, described in WO 2005058830) in methanol (20 mL) under ice-cooling, and the mixture was stirred at room temperature for two hours. The reaction solution was poured into water, followed by extraction with chloroform. The organic layer was washed with brine, dried over anhydrous magnesium sulfate and filtered, after which the filtrate was concentrated under reduced pressure to give [6-methoxy-5-(trifluoromethyl)pyridin-2-yl]methanol (540 mg).

(2) 6-Methoxy-5-(trifluoromethyl)pyridine-2-carbaldehyde (405 mg) was obtained by performing substantially the same reaction as in Reference Example 1-51(6) except for using [6-methoxy-5-(trifluoromethyl)pyridin-2-yl]methanol.

(3) The title compound was obtained as a colorless oil (305 mg) by performing reaction by substantially the same method as in Reference Example 1-1(2)(3) except for using 6-methoxy-5-(trifluoromethyl)pyridine-2-carbaldehyde.

¹H NMR (300 MHz, CDCl₃) δ ppm 2.55 (s, 3H), 4.04 (s, 3H), 7.30 (d, J=8.9 Hz, 2H), 7.63-7.70 (m, 1H), 8.01-8.14 (m, 3H).
MS(+): 328 [M+H]⁺.

The following compounds (Reference Examples 1-68 to 1-75) were obtained by performing reaction by the same method as in Reference Example 1-67 using corresponding aryl bromides, respectively.

Reference Example 1-68

[4-(Cyclopropylsulfanyl)phenyl][6-methoxy-5-(trifluoromethyl)pyridin-2-yl]methanone ¹H NMR (300 MHz, CDCl₃) δ ppm 0.68-0.79 (m, 2H), 1.12-1.22 (m, 2H), 2.23 (tt, J=7.4, 4.4 Hz, 1H), 4.04 (s, 3H), 7.36-7.50 (m, 2H), 7.60-7.70 (m, 1H), 7.99-8.13 (m, 3H).
MS(+): 354 [M+H]⁺.

Reference Example 1-69

(4-{[tert-Butyl(dimethyl)silyl]oxy}-3-chlorophenyl)[6-methoxy-5-(trifluoromethyl)pyridin-2-yl]methanone ¹H NMR (300 MHz, CDCl₃) δ ppm 0.29 (s, 6H), 1.05 (s, 9H), 4.06 (s, 3H), 6.96 (d, J=8.5 Hz, 1H), 7.68 (dd, J=7.7, 0.8 Hz, 1H), 8.00 (dd, J=8.5, 2.2 Hz, 1H), 8.05 (dd, J=7.7, 0.6 Hz, 1H), 8.35 (d, J=2.2 Hz, 1H).
MS(+): 446 [M+H]⁺.

Reference Example 1-70

{4-[(3-{[tert-Butyl(dimethyl)silyl]oxy}propyl)sulfanyl]-3-chlorophenyl}[6-methoxy-5-(trifluoromethyl)pyridin-2-yl]methanone ¹H NMR (300 MHz, CDCl₃) δ ppm 0.08 (s, 6H), 0.91 (s, 9H), 1.90-2.02 (m, 2H), 3.12 (t, J=7.2 Hz, 2H), 3.77 (t, J=5.4 Hz, 2H), 4.05 (s, 3H), 7.33 (d, J=8.2 Hz, 1H), 7.71 (dd, J=7.5, 0.7 Hz, 1H), 8.02 (dd, J=8.2, 1.7 Hz, 1H), 8.06 (dd, J=7.8, 0.7 Hz, 1H), 8.27 (d, J=1.7 Hz, 1H).
MS(+): 520 [M+H]⁺.

Reference Example 1-71

{4-[(3-{[tert-Butyl(dimethyl)silyl]oxy}propyl)sulfanyl]phenyl}[6-methoxy-5-(trifluoromethyl)pyridin-2-yl]methanone ¹H NMR (300 MHz, CDCl₃) δ ppm 0.07 (s, 6H), 0.91 (s, 9H), 1.85-2.00 (m, 2H), 3.05-3.18 (t, J=7.4 Hz, 2H), 3.75 (t, J=6.3 Hz, 2H), 4.03 (s, 3H), 7.34 (d, J=8.6 Hz, 2H), 7.65 (d, J=7.7 Hz, 1H), 8.00-8.10 (m, 3H).
MS(+): 486 [M+H]⁺.

Reference Example 1-72

[4-(4-{[tert-Butyl(dimethyl)silyl]oxy}butyl)phenyl][6-methoxy-5-(trifluoromethyl)pyridin-2-yl]methanone ¹H NMR (300 MHz, CDCl₃) δ ppm 0.05 (s, 6H), 0.89 (s, 9H), 1.50-1.80 (m, 4H), 2.72 (t, J=7.7 Hz, 2H), 3.64 (t, J=6.3 Hz, 2H), 4.04 (s, 3H), 7.30 (d, J=8.4 Hz, 2H), 7.64 (dd, J=7.8, 0.6 Hz, 1H), 8.00-8.10 (m, 3H)
MS(+): 468 [M+H]⁺.

Reference Example 1-73

(3-Chloro-4-methoxyphenyl)[6-methoxy-5-(trifluoromethyl)pyridin-2-yl]methanone

¹H NMR (300 MHz, CDCl₃) δ ppm 4.01 (s, 3H), 4.06 (s, 3H), 7.02 (d, J=8.5 Hz, 1H), 7.70 (dd, J=7.7, 0.8 Hz, 1H), 8.06 (dd, J=7.7, 0.6 Hz, 1H), 8.13 (dd, J=8.5, 2.2 Hz, 1H), 8.37 (d, J=2.2 Hz, 1H).

Reference Example 1-74

(4-{[tert-Butyl(dimethyl)silyl]oxy}phenyl)[6-methoxy-5-(trifluoromethyl)pyridin-2-yl]methanone ¹H NMR (300 MHz, CDCl₃) δ ppm 0.26 (s, 6H), 1.00 (s, 9H), 4.04 (s, 3H), 6.91 (d, J=9.0 Hz, 2H), 7.62 (d, J=9.0 Hz, 1H), 7.95-8.11 (m, 3H).
MS(+): 412 [M+H]⁺.

Reference Example 1-75

(4-{2-[3-(Diethylamino)propyl]-1,3-dioxolan-2-yl}phenyl)[6-methoxy-5-(trifluoromethyl)pyridin-2-yl]methanone ¹H NMR (300 MHz, CDCl₃) δ ppm 0.98 (t, J=7.1 Hz, 6H), 1.45-1.65 (m, 2H), 1.86-1.95 (m, 2H), 2.40 (t, J=7.6 Hz, 2H), 2.47 (q, J=7.0 Hz, 4H), 3.75-3.82 (m, 2H), 4.01-4.07 (m, 5H), 7.57 (d, J=8.6 Hz, 2H), 7.66 (d, J=7.7 Hz, 1H), 8.05 (d, J=7.7 Hz, 1H), 8.10 (d, J=8.6 Hz, 2H).
MS(+): 467 [M+H]⁺.

The structures of Reference Examples 1-68 to 1-75 are shown below.

[Hyo 4]

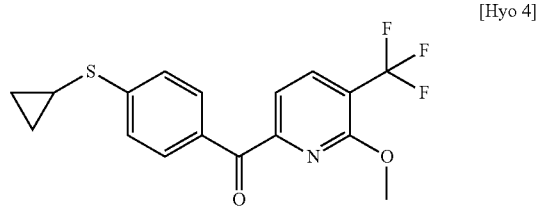

Reference Example 1-68

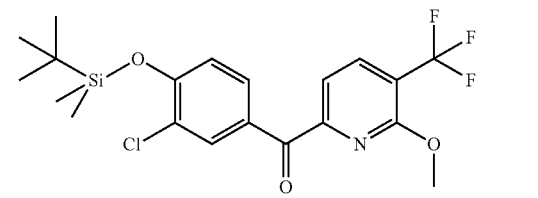

Reference Example 1-69

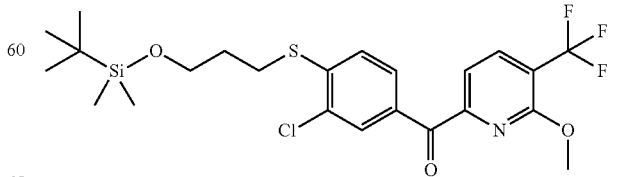

Reference Example 1-70

-continued

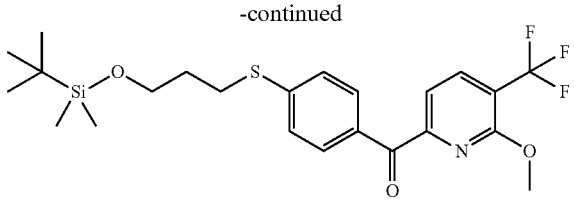

Reference Example 1-71

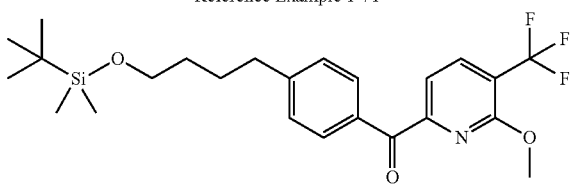

Reference Example 1-72

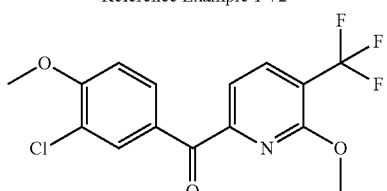

Reference Example 1-73

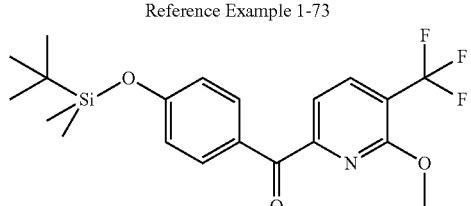

Reference Example 1-74

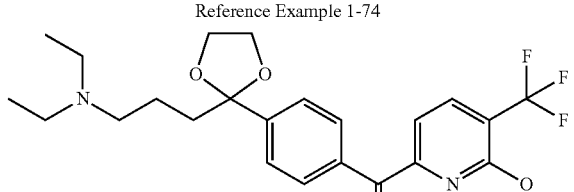

Reference Example 1-75

Reference Example 1-76

[6-Methoxy-5-(propan-2-yl)pyridin-2-yl][4-(methylsulfanyl)phenyl]methanone

[Ka 74]

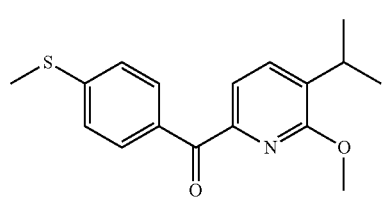

(1) Ethyl 5-(prop-1-en-2-yl)pyridine-2-carboxylate was obtained as a yellow oil (10 g, 71%) by performing substantially the same reaction as in Reference Example 1-51(1) except for using prop-1-en-2-ylmagnesium bromide.

(2) 10% palladium-activated carbon (5.8 g) was added to a solution of ethyl 5-(prop-1-en-2-yl)pyridine-2-carboxylate (10 g) in ethanol (100 mL), and the mixture was stirred in a hydrogen gas stream at room temperature overnight. The reaction solution was filtered through celite, and then the solvent was evaporated under reduced pressure. The residue was purified by silica gel column chromatography (hexane: ethyl acetate=9:1→0:1) to give ethyl 5-isopropylpyridine-2-carboxylate as a colorless oil (10 g, 95%).

(3) The title compound was obtained as a yellow oil (1.88 g) by performing reaction by substantially the same method as in Reference Example 1-51(2)-(7) except for using ethyl 5-isopropylpyridine-2-carboxylate.

$^1$H NMR (300 MHz, CDCl$_3$) δ ppm 1.26 (d, J=7.0 Hz, 6H), 2.54 (s, 3H), 3.12-3.35 (m, 1H), 3.95 (s, 3H), 7.28 (d, J=8.7 Hz, 2H), 7.52-7.75 (m, 2H), 8.16 (d, J=8.7 Hz, 2H).

MS(+): 302 [M+H]$^+$.

Reference Example 1-77

[5-({[tert-Butyl(diphenyl)silyl]oxy}methyl)-6-methoxypyridin-2-yl][4-(cyclopropylsulfanyl)phenyl]methanone

[Ka 75]

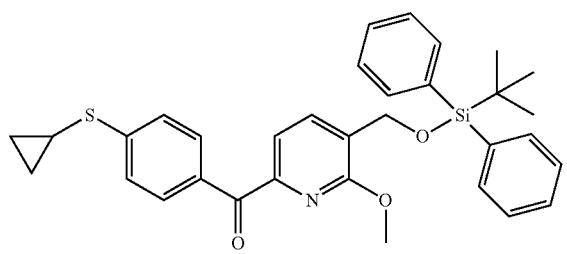

(1) 6-(Dimethoxymethyl)-2-methoxypyridine-3-carbonitrile was obtained as a pale yellow oil (4.17 g, 86%) by performing substantially the same reaction as in Reference Example 1-51(4) except for using 6-(dimethoxymethyl)-2-oxo-1,2-dihydropyridine-3-carbonitrile (4.47 g, described in J. Hetero. Chem., 1994, 31, p. 297).

(2) Water (10 mL) and sodium hydroxide (3.96 g) were added to a solution of 6-(dimethoxymethyl)-2-methoxypyridine-3-carbonitrile (4.17 g) in tetrahydrofuran-methanol (30 mL), and the mixture was stirred at 90° C. for 15 hours. The reaction solution was poured into water and made weak acidic with 1 M hydrochloric acid, followed by extraction with chloroform. The organic layer was washed with brine, dried over anhydrous magnesium sulfate and filtered, after which the solvent was evaporated under reduced pressure to give a crude product containing 6-(dimethoxymethyl)-2-methoxypyridine-3-carboxylic acid (4.1 g).

(3) Diisopropylethylamine (4.56 mL) and Bop reagent (registered trademark) (10 g) were added to a solution of 6-(dimethoxymethyl)-2-methoxypyridine-3-carboxylic acid (4.1 g) in tetrahydrofuran (40 mL) under ice-cooling, and the mixture was stirred at room temperature for 30 minutes. The reaction solution was cooled to 0° C. and sodium borohydride (2.72 g) was added, followed by stirring at room temperature overnight. The reaction solution was poured into a saturated ammonium chloride solution, followed by extraction with ethyl acetate. The organic layer was washed with brine, dried over anhydrous magnesium sulfate and filtered. The solvent was then evaporated under reduced pressure. The residue was purified by silica gel column chromatography (hexane:ethyl acetate=5:1→1:1) to give [6-(dimethoxymethyl)-2-methoxypyridin-3-yl]methanol (2.3 g, 60%) as a colorless oil.

(5) Imidazole (1.47 g) and t-butyldiphenylchlorosilane (3.54 g) was added to a solution of [6-(dimethoxymethyl)-2-methoxypyridin-3-yl]methanol (2.3 g) in N,N-dimethylformamide (23 mL), and the mixture was stirred at room temperature for two hours. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (hexane:ethyl acetate=50:1→10:1) to give 3-({[tert-butyl(diphenyl)silyl]oxy}methyl)-6-(dimethoxymethyl)-2-methoxypyridine (5.47 g, 99%) as a colorless oil.

(6) 1 M hydrochloric acid (40 mL) was added to a solution of 3-({[tert-butyl(diphenyl)silyl]oxy}methyl)-6-(dimethoxymethyl)-2-methoxypyridine (5.47 g) in tetrahydrofuran (40 mL), and the mixture was stirred at 60° C. for two hours. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (hexane:ethyl acetate=5:1→1:1) to give 5-({[tert-butyl(diphenyl)silyl]oxy}methyl)-6-methoxypyridine-2-carbaldehyde (3.2 g, 73%) as a colorless oil.

(7) The title compound was obtained as a colorless oil (2.3 g, 51%) by performing substantially the same reaction as in Reference Example 1-1(2)(3) except for using 5-({[tert-butyl(diphenyl)silyl]oxy}methyl)-6-methoxypyridine-2-carbaldehyde and using 1-bromo-4-(cyclopropylsulfanyl)benzene in place of 4-bromothioanisole.

$^1$H NMR (300 MHz, CDCl$_3$) δ ppm 0.67-0.80 (m, 2H), 1.08-1.20 (m, 11H), 2.22 (tt, J=7.4, 4.4 Hz, 1H), 3.85 (s, 3H), 4.80 (s, 2H), 7.34-7.53 (m, 8H), 7.64-7.78 (m, 5H), 8.04-8.17 (m, 3H).

MS(+): 554 [M+H]$^+$.

Reference Example 1-78

[4-(Cyclopropylsulfanyl)phenyl](6-methoxy-5-phenylpyridin-2-yl)methanone

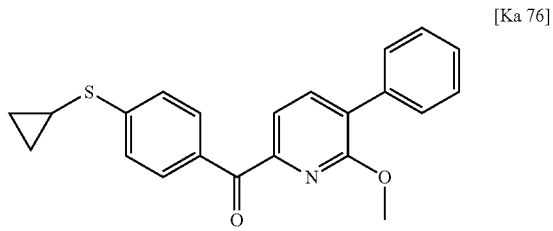 [SMILES: COc1nc(C(=O)c2ccc(SC3CC3)cc2)ccc1-c1ccccc1]

[Ka 76]

(1) 5-Bromo-6-methoxypyridine-2-carbaldehyde (754 mg, 42%) was obtained by performing substantially the same reaction as in Reference Example 1-1(1) except for using carbon tetrabromide.

(2) Tetrakistriphenylphosphine palladium (403 mg), phenylboronic acid (510 mg) and a 2 M sodium carbonate solution (3.5 mL) were sequentially added to a solution of 5-bromo-6-methoxypyridine-2-carbaldehyde (753 mg) in 1,2-dimethoxyethane (23 mL) in a nitrogen atmosphere, and the mixture was stirred at 80° C. for three hours. Water was added to the reaction solution at room temperature, followed by extraction with ethyl acetate. The organic layer was washed with brine, dried over anhydrous sodium sulfate and filtered. The solvent was then evaporated under reduced pressure. The resulting residue was purified by silica gel column chromatography (hexane:ethyl acetate=50:1→1:1) and further purified by silica gel column chromatography (hexane:ethyl acetate=50:1) to give 6-methoxy-5-phenylpyridine-2-carbaldehyde (445 mg, 60%).

(3) The title compound was obtained (360 mg, 53% (two steps)) by performing substantially the same reaction as in Reference Example 1-1(2)(3) except for using 6-methoxy-5-phenylpyridine-2-carbaldehyde and using 1-bromo-4-(cyclopropylsulfanyl)benzene in place of 4-bromothioanisole.

$^1$H NMR (300 MHz, CDCl$_3$) δ ppm 0.70-0.85 (m, 2H), 1.10-1.25 (m, 2H), 2.15-2.35 (m, 1H), 3.97 (s, 3H), 7.40-7.50 (m, 5H), 7.60-7.65 (m, 2H), 7.76 (d, J=7.8 Hz, 1H), 7.81 (d, J=7.8 Hz, 1H), 8.15-8.25 (m, 2H).

MS(+): 362 [M+H]$^+$.

Reference Example 1-79

(5-Cyclopropyl-6-methoxypyridin-2-yl)[4-(propan-2-yl)phenyl]methanone

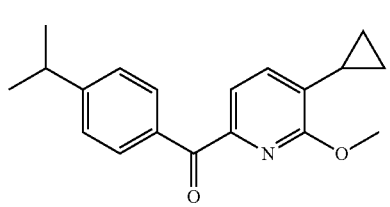

[Ka 77]

The title compound (352 mg, 76% (two steps)) was obtained by performing substantially the same reaction as in Reference Example 1-51(7)(8) sequentially except for using 1-bromo-4-(propan-2-yl)benzene.

$^1$H NMR (300 MHz, CDCl$_3$) δ ppm 0.73-0.80 (m, 2H), 1.00-1.08 (m, 2H), 1.28 (s, 3H), 1.31 (s, 3H), 2.12-2.23 (m, 1H), 2.91-3.06 (m, 1H), 3.97 (s, 3H), 7.22 (d, J=7.4 Hz, 1H), 7.31 (d, J=8.0 Hz, 2H), 7.57-7.62 (m, 1H), 8.14 (d, J=8.3 Hz, 2H).

Reference Example 1-80

(4-tert-Butyl-3-chlorophenyl)(5-chloro-6-methoxypyridin-2-yl)methanone

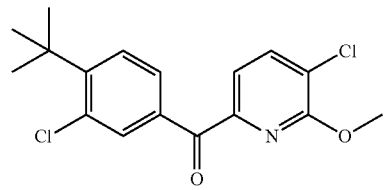

[Ka 78]

(1) A mixture of 4-bromo-1-tert-butyl-2-chlorobenzene and 4-bromo-2-chloro-1-(prop-1-en-2-yl)benzene (1:1) was obtained as a colorless oil (166 mg) by performing reaction according to the method described in WO 2006013048 using 4-bromo-2-chlorobenzoic acid (2 g).

(2) A mixture of the title compound and (5-chloro-6-methoxypyridin-2-yl)[3-chloro-4-(prop-1-en-2-yl)phenyl]methanone (1:1) was obtained by performing substantially the same reaction as in Reference Example 1-1(2)(3) sequentially except for using the mixture of 4-bromo-1-tert-butyl-2-chlorobenzene and 4-bromo-2-chloro-1-(prop-1-en-2-yl)benzene (1:1).

MS(+): 338 [M+H]$^+$.

Reference Example 1-81

(5-Chloro-6-methoxypyridin-2-yl)[4-(4-methoxybutyl)phenyl]methanone

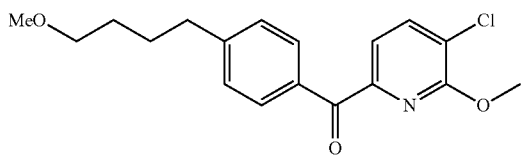

[Ka 79]

The title compound (625 mg, 66% (two steps)) was obtained by performing substantially the same reaction as in Reference Example 1-1(2)(3) sequentially except for using 1-bromo-4-(4-methoxybutyl)benzene.

$^1$H NMR (300 MHz, CDCl$_3$) δ ppm 1.55-1.81 (m, 4H), 2.72 (t, J=7.4 Hz, 2H), 3.33 (s, 3H), 3.40 (t, J=6.4 Hz, 2H), 4.01 (s, 3H), 7.28 (d, J=8.6 Hz, 2H), 7.61 (d, J=7.7 Hz, 1H), 7.80 (d, J=8.0 Hz, 1H), 8.06 (d, J=8.3 Hz, 2H).

MS(+): 334 [M+H]$^+$.

Reference Example 1-82

(4-tert-Butylphenyl) [6-methoxy-5-(trifluoromethyl)pyridin-2-yl]methanone

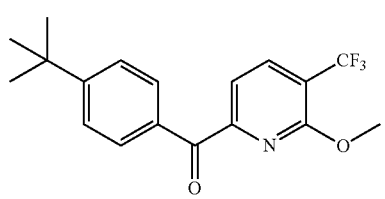

[Ka 80]

The title compound (694 mg, 54% (two steps)) was obtained by performing substantially the same reaction as in Reference Example 1-67(3) except for using 1-bromo-4-tert-butylbenzene.

$^1$H NMR (300 MHz, CDCl$_3$) δ ppm 1.37 (s, 9H), 4.06 (s, 3H), 7.51 (d, J=8.7 Hz, 2H), 7.65 (d, J=8.1 Hz, 1H), 8.05 (d, J=7.5 Hz, 1H), 8.10 (d, J=8.1 Hz, 2H).

MS(+): 338 [M+H]$^+$.

Reference Example 1-83

(5-Chloro-6-methoxypyridin-2-yl)(4-methyl-3,4-dihydro-2H-1,4-benzoxazin-7-yl)methanone

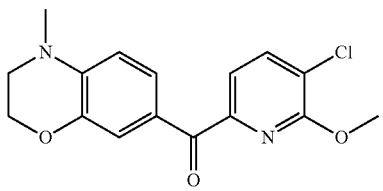

[Ka 81]

(1) (5-Chloro-6-methoxypyridin-2-yl)(4-methyl-3,4-dihydro-2H-1,4-benzoxazin-7-yl)methanol was obtained as yellow crystals (413 mg, 72%) by performing substantially the same reaction as in Reference Example 1-1(2) except for using 7-bromo-4-methyl-3,4-dihydro-2H-1,4-benzoxazine.

(2) Sodium hydride (purity: 63%, 75 mg) was added to a solution of (5-chloro-6-methoxypyridin-2-yl)(4-methyl-3,4-dihydro-2H-1,4-benzoxazin-7-yl)methanol (302 mg) in tetrahydrofuran (2 mL) under ice-cooling, and the mixture was stirred with warming to room temperature overnight. Water was added to the reaction solution, followed by extraction with ethyl acetate. The organic layer was dried over anhydrous magnesium sulfate and filtered. The solvent was then evaporated under reduced pressure. The resulting residue was purified by silica gel column chromatography (hexane:ethyl acetate=2:1→1:1) to give the title compound as a yellow solid (231 mg).

$^1$H NMR (300 MHz, CDCl$_3$) δ ppm 3.02 (s, 3H), 3.40-3.45 (m, 2H), 4.05 (s, 3H), 4.23-4.28 (m, 2H), 6.63 (d, J=8.6 Hz, 1H), 7.51 (d, J=7.7 Hz, 1H), 7.69 (d, J=2.1 Hz, 1H), 7.76 (d, J=7.7 Hz, 1H), 7.80 (dd, J=8.6, 2.1 Hz, 1H).

MS(+): 319 [M+H]$^+$.

Reference Example 1-84

[3-Chloro-4-(propan-2-yl)phenyl](5-cyclopropyl-6-methoxypyridin-2-yl)methanone

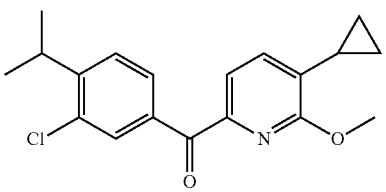

[Ka 82]

The title compound (160 mg, 54% (two steps)) was obtained by performing substantially the same reaction as in Reference Example 1-51(7)(8) sequentially except for using 4-bromo-2-chloro-1-(propan-2-yl)benzene.

$^1$H NMR (300 MHz, CDCl$_3$) δ ppm 0.68-0.81 (m, 2H), 0.98-1.10 (m, 2H), 1.28 (s, 3H), 1.31 (s, 3H), 2.08-2.26 (m, 1H), 3.41-3.53 (m, 1H), 4.00 (s, 3H), 7.20-7.29 (m, 1H), 7.40 (d, J=8.1 Hz, 1H), 7.66 (d, J=7.8 Hz, 1H), 8.07 (dd, J=8.1, 1.5 Hz, 1H), 8.35 (d, J=1.8 Hz, 1H)

MS(+): 330 [M+H]$^+$. .

Reference Example 1-85

(4-tert-Butylphenyl)(5-cyclopropyl-6-methoxypyridin-2-yl)methanone

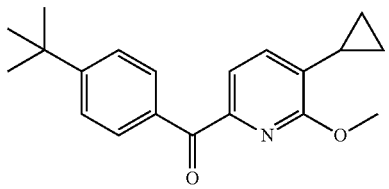

[Ka 83]

The title compound was obtained as a colorless oil (405 mg, 71% (two steps)) by performing substantially the same reaction as in Reference Example 1-51(7)(8) sequentially except for using 1-bromo-4-tert-butylbenzene.

$^1$H NMR (300 MHz, CDCl$_3$) δ ppm 0.73-0.79 (m, 2H), 1.00-1.08 (m, 2H), 1.33 (s, 9H), 2.12-2.23 (m, 1H), 4.00 (s, 3H), 7.23 (d, J=7.5 Hz, 1H), 7.48 (d, J=8.7 Hz, 2H), 7.61 (d, J=7.5 Hz, 1H), 8.17 (d, J=8.7 Hz, 2H).

Reference Example 1-86

(5-Chloro-6-methoxypyridin-2-yl)[3-chloro-4-(propan-2-yl)phenyl]methanone

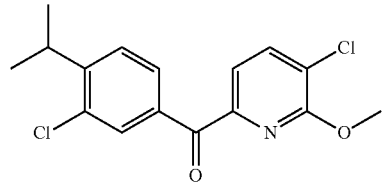

[Ka 84]

The title compound was obtained as a pale yellow oil (240 mg, 23% (two steps)) by performing substantially the same reaction as in Reference Example 1-1(2)(3) sequentially except for using 4-bromo-2-chloro-1-(propan-2-yl)benzene.

$^1$H NMR (300 MHz, CDCl$_3$) δ ppm 1.28 (s, 3H), 1.31 (s, 3H), 3.40-3.56 (m, 1H), 4.05 (s, 3H), 7.41 (d, J=8.1 Hz, 1H), 7.68 (d, J=7.5 Hz, 1H), 7.83 (d, J=7.8 Hz, 1H), 8.03 (d, J=9.8 Hz, 1H), 8.28 (s, 1H).

Reference Example 1-87

(5-Chloro-6-methoxypyridin-2-yl)(4-cyclopropylphenyl)methanone

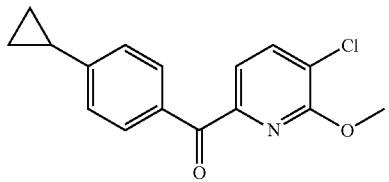

[Ka 85]

(1) A solution of bromine (0.65 mL) in acetic acid (3 mL) was added dropwise to a solution of cyclopropylbenzene (1.59 mL) and sodium acetate (1.14 g) in acetic acid (16 mL) under ice-cooling, and the mixture was stirred at room temperature overnight. Hexane and water were added to the reaction solution and a saturated sodium bisulfite solution, followed by extraction. The organic layer was washed with a saturated sodium carbonate solution, dried over anhydrous magnesium sulfate and filtered, after which the filtrate was concentrated under reduced pressure. The resulting residue was purified by silica gel column chromatography (hexane only) to give a mixture of 4-bromo-1-cyclopropylbenzene and cyclopropylbenzene as a colorless oil (851 mg).

(2) n-Butyllithium (1.65 M, 3 mL) was added dropwise to a solution of the mixture of 4-bromo-1-cyclopropylbenzene and cyclopropylbenzene (976 mg) in tetrahydrofuran (20 mL) at −78° C. in a nitrogen atmosphere, and the mixture was stirred at the same temperature for 30 minutes. A solution of 5-chloro-6-methoxypyridine-2-carbaldehyde (732 mg) in tetrahydrofuran (9 mL) was added to the reaction solution at −78° C., and the mixture was stirred at the same temperature for three hours. Water was added to the reaction solution, followed by extraction with ethyl acetate. The organic layer was washed with brine, dried over anhydrous magnesium sulfate and filtered. The solvent was then evaporated under reduced pressure. The resulting residue was purified by silica gel column chromatography (hexane:ethyl acetate=100:0→1:10) to give (5-chloro-6-methoxypyridin-2-yl)(4-cyclopropylphenyl)methanol (765 mg).

(3) The title compound (732 mg, 96%) was obtained by performing substantially the same reaction as in Reference Example 1-1(3) except for using (5-chloro-6-methoxypyridin-2-yl)(4-cyclopropylphenyl)methanol.

$^1$H NMR (300 MHz, CDCl$_3$) δ ppm 0.74-0.87 (m, 2H), 1.01-1.14 (m, 2H), 1.90-2.05 (m, 1H), 4.02 (s, 3H), 7.14 (d, J=8.4 Hz, 2H), 7.62 (d, J=7.2 Hz, 1H), 7.81 (d, J=8.1 Hz, 1H), 8.05 (d, J=8.4 Hz, 2H).

MS(+): 288 [M+H]$^+$.

Reference Example 1-88

(5-Chloro-6-methoxypyridin-2-yl)[4-(cyclopropyloxy)phenyl]methanone

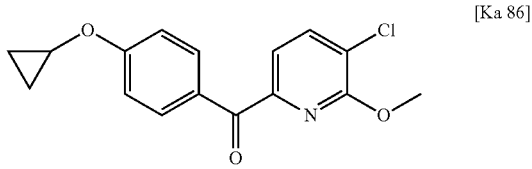 [SMILES: COc1nc(C(=O)c2ccc(OC3CC3)cc2)ccc1Cl]

[Ka 86]

The title compound (813 mg, 46% (two steps)) was obtained by performing substantially the same reaction as in Reference Example 1-1(2)(3) sequentially except for using 1-bromo-4-cyclopropyloxybenzene.

$^1$H NMR (300 MHz, CDCl$_3$) δ ppm 0.70-0.79 (m, 2H), 1.12-1.21 (m, 2H), 2.18-2.28 (m, 1H), 4.03 (s, 3H), 7.43 (d, J=8.9 Hz, 2H), 7.63 (d, J=7.8 Hz, 1H), 7.82 (d, J=7.8 Hz, 1H), 8.09 (d, J=8.9 Hz, 2H).

MS(+): 304[M+H]$^+$.

Reference Example 1-89 tert-Butyl {4-[(5-chloro-6-methoxypyridin-2-yl)carbonyl]phenyl}carbamate

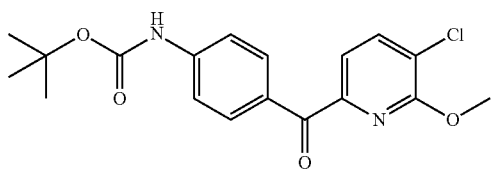

The title compound (2.15 g) was obtained by performing substantially the same reaction as in Reference Example 1-1 (2)(3) sequentially except for using tert-butyl 4-bromophenylcarbamate.

$^1$H NMR (300 MHz, CDCl$_3$) δ ppm 1.54 (s, 9H), 4.01 (s, 3H), 6.67-6.72 (brs, 1H), 7.48 (d, J=8.9 Hz, 2H), 7.63 (d, J=7.9 Hz, 1H), 7.81 (d, J=7.8 Hz, 1H), 8.16 (d, J=8.9 Hz, 2H).
MS(+): 363 [M+H]$^+$.

Reference Example 1-90

(3-Chloro-4-ethylphenyl)(5-chloro-6-methoxypyridin-2-yl)methanone

The title compound was obtained as a pale yellow oil (385 mg, 66% (two steps)) by performing substantially the same reaction as in Reference Example 1-1(2)(3) except for using 4-bromo-2-chloro-1-ethylbenzene.

$^1$H NMR (300 MHz, CDCl$_3$) δ ppm 1.28 (t, J=7.5 Hz, 3H), 2.84 (q, J=7.5 Hz, 2H), 4.04 (s, 3H), 7.35 (d, J=7.5 Hz, 1H), 7.68 (dd, J=9.2, 0.8 Hz, 1H), 7.83 (dd, J=7.8, 0.6 Hz, 1H), 7.98 (dd, J=7.5, 1.5 Hz, 1H), 8.26 (d, J=1.5 Hz, 1H).

Reference Example 1-91

(5-Chloro-6-methoxypyridin-2-yl)(4-methylphenyl)methanone

The title compound was obtained as a white amorphous (584 mg, 77% (two steps)) by performing substantially the same reaction as in Reference Example 1-1(2)(3) except for using 4-bromotoluene.

$^1$H NMR (300 MHz, CDCl$_3$) δ ppm 2.44 (s, 3H), 4.00 (s, 3H), 7.27 (d, J=7.8 Hz, 2H), 7.62 (d, J=7.8 Hz, 1H), 7.75 (d, J=7.8 Hz, 1H), 8.03 (d, J=8.2 Hz, 2H).
MS(+): 262 [M+H]$^+$.

Reference Example 1-92

[3-Chloro-4-(propan-2-yloxy)phenyl] (5-cyclopropyl-6-methoxypyridin-2-yl)methanone The title compound was obtained as a colorless amorphous (643 mg, 78% (two steps)) by performing substantially the same reaction as in Reference Example 1-30(2) except for using (4-{[tert-butyl(dimethyl)silyl]oxy}-3-chlorophenyl)(5-cyclopropyl-6-methoxypyridin-2-yl)methanone obtained in Reference Example 1-55.

$^1$H NMR (300 MHz, CDCl$_3$) δ ppm 0.72-0.80 (m, 2H), 1.00-1.10 (m, 2H), 1.43 (s, 3H), 1.45 (s, 3H), 2.10-2.25 (m, 1H), 4.00 (s, 3H), 4.60-4.80 (m, 1H), 6.98 (d, J=8.9 Hz, 1H), 7.23 (d, J=7.4 Hz, 1H), 7.62 (d, J=7.4 Hz, 1H), 8.13 (dd, J=8.3, 2.1 Hz, 1H), 8.47 (d, J=2.1 Hz, 1H).

Reference Example 1-93

[6-Methoxy-5-(trifluoromethyl)pyridin-2-yl][4-(trifluoromethyl)phenyl]methanone

The title compound was obtained as a colorless oil (201 mg, 16% (two steps)) by performing substantially the same reaction as in Reference Example 1-67(3) except for using 4-bromobenzotrifluoride.

$^1$H NMR (300 MHz, CDCl$_3$) δ ppm 4.01 (s, 3H), 7.76 (d, J=8.7 Hz, 2H), 7.77 (d, J=7.8 Hz, 1H), 8.10 (d, J=7.8 Hz, 1H), 8.23 (d, J=8.1 Hz, 2H).
MS(+): 350 [M+H]$^+$.

Reference Example 1-94

(3-Chloro-4-methoxyphenyl)(5-cyclopropyl-6-methoxypyridin-2-yl)methanone

The title compound was obtained as a colorless amorphous (772 mg, quant. (two steps)) by performing substantially the same reaction as in Reference Example 1-30(2) except for using (4-{[tert-butyl(dimethyl)silyl]oxy}-3-chlorophenyl)(5-cyclopropyl-6-methoxypyridin-2-yl)methanone obtained in Reference Example 1-55 and using methyl iodide in place of 2-iodopropane.

$^1$H NMR (300 MHz, CDCl$_3$) δ ppm 0.73-0.80 (m, 2H), 1.00-1.10 (m, 2H), 2.10-2.25 (m, 1H), 3.99 (s, 3H), 4.00 (s, 3H), 7.00 (d, J=8.6 Hz, 1H), 7.23 (d, J=7.7 Hz, 1H), 7.63 (d, J=8.3 Hz, 1H), 8.18 (dd, J=8.6, 2.1 Hz, 1H) 8.47 (d, J=2.1 Hz, 1H).

Reference Example 1-95

(4-Chlorophenyl)(5-cyclopropyl-6-methoxypyridin-2-yl)methanone

The title compound was obtained as a white solid (1.04 g, 69% (two steps)) by performing substantially the same reaction as in Reference Example 1-51(7)(8) except for using 4-bromochlorobenzene.

$^1$H NMR (300 MHz, CDCl$_3$) δ ppm 0.71-0.81 (m, 2H), 1.01-1.10 (m, 2H), 2.11-2.23 (m, 1H), 3.95 (s, 3H), 7.24 (d, J=7.6 Hz, 1H), 7.44 (d, J=8.3 Hz, 2H), 7.65 (d, J=7.6 Hz, 1H), 8.14 (d, J=8.3 Hz, 2H).

The structures of Reference Examples 1-90 to 1-95 are shown below.

Reference Example 1-90

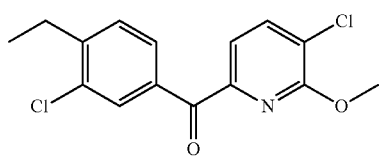

-continued

Reference Example 1-91
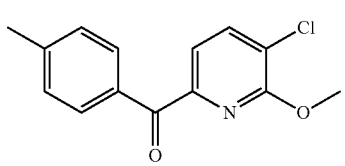

Reference Example 1-92
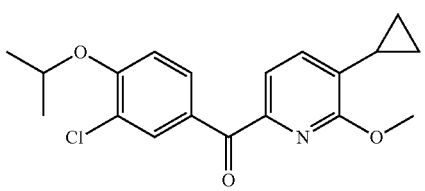

Reference Example 1-93
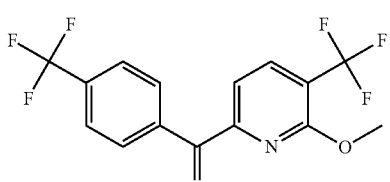

Reference Example 1-94
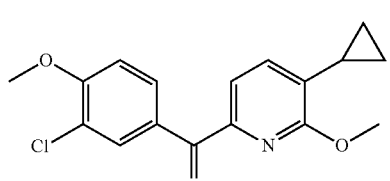

Reference Example 1-95
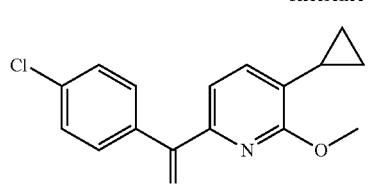

Reference Example 2-1

2-Methoxy-3-methyl-6-[4-(methylsulfanyl)benzyl]pyridine

[Ka 88]

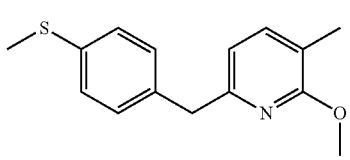

Triethylsilane (5 mL) and trifluoroacetic acid (5 mL) were sequentially added to (6-methoxy-5-methylpyridin-2-yl)[4-(methylsulfanyl)phenyl]methanol obtained in Reference Example 1-36(2) (2.13 g), and the mixture was stirred at 60° C. for four hours. The reaction solution was poured into saturated aqueous sodium bicarbonate, followed by extraction with chloroform. The organic layer was washed with brine, dried over anhydrous magnesium sulfate and filtered. The solvent was then evaporated under reduced pressure. The residue was purified by silica gel column chromatography (hexane:ethyl acetate=9:1→4:1→2:1) to give the title compound as a colorless oil (1.69 g).

$^1$H NMR (300 MHz, CDCl$_3$) δ ppm 2.13 (s, 3H), 2.46 (s, 3H), 3.93 (s, 3H), 3.95 (s, 2H), 6.55 (d, J=7.6 Hz, 1H), 7.15-7.28 (m, 5H).

MS(+): 260 [M+H]$^+$.

The compounds of Reference Examples 2-2 to 2-4 were obtained by performing substantially the same reaction as in Reference Example 2-1 except for using corresponding pyridine-2-carbaldehydes, respectively.

Reference Example 2-2

3-Ethyl-2-methoxy-6-[4-(methylsulfanyl)benzyl]pyridine

[Ka 89]

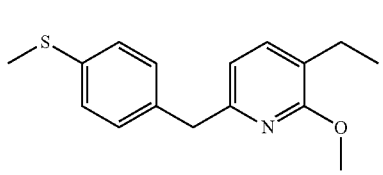

$^1$H NMR (300 MHz, CDCl$_3$) δ ppm 1.15 (t, J=7.5 Hz, 3H), 2.46 (s, 3H), 2.53 (q, J=7.4 Hz, 2H), 3.93 (s, 3H), 3.95 (s, 2H), 6.58 (d, J=7.3 Hz, 1H), 7.17-7.29 (m, 5H).

MS(+): 274 [M+H]$^+$.

Reference Example 2-3

2-Methoxy-6-[4-(methylsulfanyl)benzyl]-3-propylpyridine

[Ka 90]

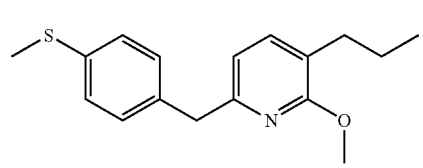

$^1$H NMR (300 MHz, CDCl$_3$) δ ppm 0.92 (t, J=7.4 Hz, 3H), 1.48-1.67 (m, 2H), 2.47 (dd, J=8.5, 6.8 Hz, 5H), 3.92 (s, 3H), 3.95 (s, 2H), 6.57 (d, J=7.3 Hz, 1H), 7.11-7.32 (m, 5H).

MS(+): 288 [M+H]$^+$.

Reference Example 2-4

6-[3-Chloro-4-(methylsulfanyl)benzyl]-2-methoxy-3-methylpyridine

[Ka 91]

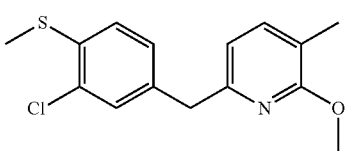

¹H NMR (300 MHz, CDCl₃) δ ppm 2.13 (s, 3H), 2.45 (s, 3H), 3.92 (s, 2H), 3.93 (s, 3H), 6.57 (d, J=7.2 Hz, 1H), 7.04-7.13 (m, 1H), 7.16-7.21 (m, 1H), 7.23-7.29 (m, 1H), 7.33 (d, J=1.7 Hz, 1H).

MS(+): 294 [M+H]⁺.

Reference Example 3-1

5-({[(2R,3R,7S)-2,3-Diphenyl-1,4-dioxaspiro[4.4]non-7-yl]methyl}sulfonyl)-1-phenyl-1H-tetrazole

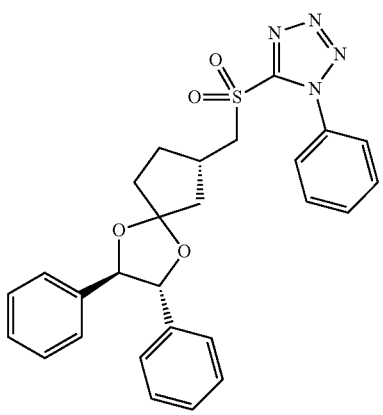

[Ka 92]

(1) 1-Phenyl-1H-tetrazole-5-thiol sodium salt (25 g) was added to a solution of (2R,3R,7S)-7-(iodomethyl)-2,3-diphenyl-1,4-dioxaspiro[4.4]nonane (48.3 g, described in WO 2003095438) in acetone (500 mL), and the mixture was stirred at 60° C. for three hours. The solvent was evaporated from the reaction solution under reduced pressure. The residue was purified by silica gel column chromatography (hexane:ethyl acetate=4:1→1:1) to give 5-({[(2R,3R,7S)-2,3-diphenyl-1,4-dioxaspiro[4.4]non-7-yl]methyl}sulfanyl)-1-phenyl-1H-tetrazole (39.5 g) as a pale yellow oil.

(2) m-Chloroperbenzoic acid was added to a solution of 5-({[(2R,3R,7S)-2,3-diphenyl-1,4-dioxaspiro[4.4]non-7-yl]methyl}sulfanyl)-1-phenyl-1H-tetrazole (39.5 g) in chloroform (395 mL) under ice-cooling, and the mixture was stirred at room temperature overnight. The reaction solution was poured into a mixed solvent of saturated aqueous sodium bicarbonate and a saturated sodium thiosulfate solution, and the mixture was stirred at room temperature for 30 minutes. After extraction with chloroform, the organic layer was washed with brine, dried over anhydrous magnesium sulfate and filtered. The solvent was then evaporated under reduced pressure. The residue was purified by silica gel column chromatography (hexane:ethyl acetate=10:1→4:1→1:1) to give 5-({[(2R,3R,7S)-2,3-diphenyl-1,4-dioxaspiro[4.4]non-7-yl]methyl}sulfonyl)-1-phenyl-1H-tetrazole (41 g) as a pale yellow oil.

¹H NMR (300 MHz, CDCl₃) δ ppm 1.69-1.86 (m, 1H), 1.99-2.37 (m, 4H), 2.46-2.59 (m, 1H), 2.83-3.05 (m, 1H), 3.82-4.02 (m, 2H), 4.70 (s, 2H), 7.15-7.24 (m, 4H), 7.28-7.36 (m, 6H), 7.56-7.65 (m, 3H), 7.66-7.73 (m, 2H).

Reference Example 3-2

(5R)-5-{[(1-Phenyl-1H-tetrazol-5-yl)sulfonyl]methyl}pyrrolidin-2-one

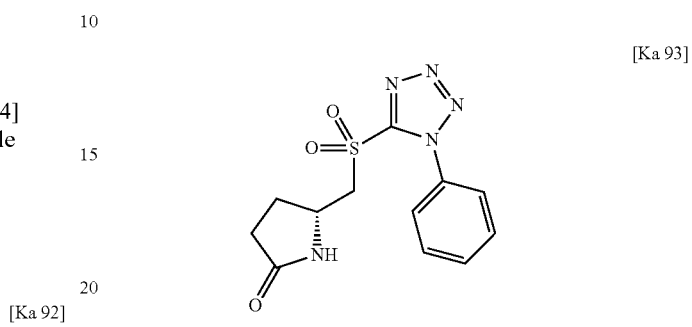

[Ka 93]

(1) 1-Phenyl-1H-tetrazole-5-thiol (9.0 g) and triphenylphosphine (13.2 g) were added to a solution of (R)-(−)-5-(hydroxymethyl)-2-pyrrolidinone (4.5 g) in tetrahydrofuran (90 mL), followed by ice-cooling. A solution of 2.2 M diethyl azodicarboxylate in toluene (23 mL) was added dropwise thereto, and the mixture was stirred at room temperature overnight. The reaction solution was poured into water, followed by extraction with ethyl acetate. The organic layer was washed with brine, dried over anhydrous magnesium sulfate and filtered. The solvent was then evaporated under reduced pressure. The residue was purified by NH silica gel column chromatography (hexane:ethyl acetate=4:1→1:1→0:1) to give (R)-5-{[(1-phenyl-1H-tetrazol-5-yl)sulfanyl]methyl}pyrrolidin-2-one (1.98 g) as a colorless oil.

(2) The title compound (5.8 g, 87%) was obtained as a colorless powder by performing substantially the same reaction as in Reference Example 3-1(2) except for using (R)-5-{[(1-phenyl-1H-tetrazol-5-yl)sulfanyl]methyl}pyrrolidin-2-one.

¹H NMR (300 MHz, CDCl₃) δ ppm 1.88-2.03 (m, 1H), 2.32-2.44 (m, 2H), 2.46-2.64 (m, 1H), 3.73-3.93 (m, 1H), 4.09-4.20 (m, 1H), 4.32-4.48 (m, 1H), 6.41-6.54 (m, 1H), 7.55-7.74 (m, 5H).

Reference Example 3-3

(5R)-1-Methyl-5-{[(1-phenyl-1H-tetrazol-5-yl)sulfonyl]methyl}pyrrolidin-2-one

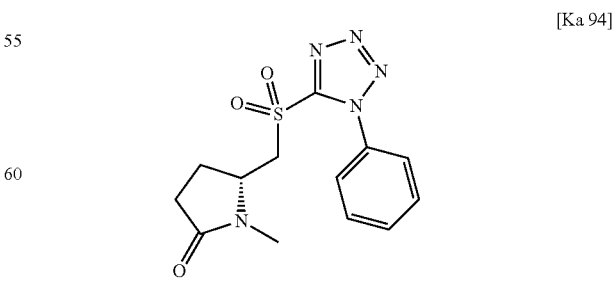

[Ka 94]

(1) Triethylamine (5.26 mL), trimethylamine hydrochloride (1.07 g) and 4-methylbenzenesulfonyl chloride (5.6 g)

were sequentially added to a solution of (R)-5-(hydroxymethyl)-1-methylpyrrolidin-2-one (2.93 g, 48.3 g, described in J. Med. Chem., 34(3), 1991, 887-900) in chloroform (40 mL) under ice-cooling, and the mixture was stirred at room temperature for one hour. The reaction solution was poured into water, followed by extraction with ethyl acetate. The organic layer was washed with brine, dried over anhydrous magnesium sulfate and filtered. The solvent was then evaporated under reduced pressure to give (R)-(1-methyl-5-oxopyrrolidin-2-yl)methyl 4-methylbenzenesulfonate as a yellow amorphous (6.6 g).

(2) (R)-1-Methyl-5-{[(1-phenyl-1H-tetrazol-5-yl)sulfanyl]methyl}pyrrolidin-2-one was obtained as a colorless powder (4.9 g) by performing substantially the same reaction as in Reference Example 3-1(1) except for using (R)-(1-methyl-5-oxopyrrolidin-2-yl)methyl 4-methylbenzenesulfonate.

(3) The title compound was obtained as a colorless powder (2.2 g) by performing substantially the same reaction as in Reference Example 3-1(2) except for using (R)-1-methyl-5-{[(1-phenyl-1H-tetrazol-5-yl)sulfanyl]methyl}pyrrolidin-2-one.

$^1$H NMR (300 MHz, CDCl$_3$) δ ppm 2.09-2.28 (m, 1H), 2.31-2.57 (m, 3H), 2.95 (s, 3H), 3.61-3.84 (m, 1H), 4.15-4.36 (m, 2H), 7.53-7.82 (m, 5H).

MS(+): 321 [M+H]$^+$.

The following compounds (Reference Examples 3-4 to 3-21) were obtained by performing reaction and purification by the same operation as in the above Reference Examples 3-1 to 3-3 using corresponding alcohols.

Reference Example 3-4

5-{[(cis-4-{[tert-Butyl(dimethyl)silyl]oxy}cyclohexyl)methyl]sulfonyl}-1-phenyl-1H-tetrazole $^1$H NMR (300 MHz, CDCl$_3$) δ ppm 0.03 (s, 6H), 0.89 (s, 9H), 1.40-1.57 (m, 2H), 1.60-1.77 (m, 6H), 2.11-2.30 (m, 1H), 3.69 (d, J=6.2 Hz, 2H), 3.87-4.05 (m, 1H), 7.55-7.65 (m, 3H), 7.66-7.74 (m, 2H).

MS(+): 437 [M+H]$^+$.

Reference Example 3-5

5-{[(trans-4-{[tert-Butyl(dimethyl)silyl]oxy}cyclohexyl)methyl]sulfonyl}-1-phenyl-1H-tetrazole $^1$H NMR (300 MHz, CDCl$_3$) δ ppm 0.05 (s, 6H), 0.87 (s, 9H), 1.10-1.44 (m, 4H), 1.79-2.06 (m, 4H), 2.07-2.23 (m, 1H), 3.44-3.60 (m, 1H), 3.69 (d, J=6.4 Hz, 2H), 7.54-7.75 (m, 5H).

MS(+): 437 [M+H]$^+$.

Reference Example 3-6

1-Phenyl-5-[(tetrahydrofuran-3-ylmethyl)sulfonyl]-1H-tetrazole $^1$H NMR (300 MHz, CDCl$_3$) δ ppm 1.74-1.94 (m, 1H), 2.21-2.38 (m, 1H), 2.81-3.07 (m, 1H), 3.65 (dd, J=9.1, 6.3 Hz, 1H), 3.73-4.06 (m, 5H), 7.56-7.66 (m, 3H), 7.66-7.74 (m, 2H).

MS(+): 295 [M+H]$^+$.

Reference Example 3-7

1-Phenyl-5-{[2-(tetrahydrofuran-2-yl)ethyl]sulfonyl}-1H-tetrazole $^1$H NMR (300 MHz, CDCl$_3$) δ ppm 1.47-1.62 (m, 1H), 1.84-1.98 (m, 2H), 2.00-2.27 (m, 3H), 3.66-4.03 (m, 5H), 7.53-7.65 (m, 3H), 7.65-7.73 (m, 2H).

MS(+): 309 [M+H]$^+$.

Reference Example 3-8

1-Phenyl-5-{[2-(tetrahydrofuran-3-yl)ethyl]sulfonyl}-1H-tetrazole $^1$H NMR (300 MHz, CDCl$_3$) δ ppm 1.48-1.74 (m, 1H), 1.92-2.22 (m, 3H), 2.30-2.50 (m, 1H), 3.45 (dd, J=8.6, 6.4 Hz, 1H), 3.66-3.84 (m, 3H), 3.84-3.99 (m, 2H), 7.52-7.66 (m, 3H), 7.67-7.75 (m, 2H).

MS(+): 309 [M+H]$^+$.

Reference Example 3-9

1-(4-{[(1-Phenyl-1H-tetrazol-5-yl)sulfonyl]methyl}piperidin-1-yl)ethanone $^1$H NMR (300 MHz, CDCl$_3$) δ ppm 1.33-1.49 (m, 2H), 1.94-2.01 (m, 1H), 2.09 (s, 3H), 2.13 (s, 1H), 2.35-2.52 (m, 1H), 2.53-2.67 (m, 1H), 3.03-3.17 (m, 1H), 3.74 (d, J=6.2 Hz, 2H), 3.78-3.88 (m, 1H), 4.58-4.69 (m, 1H), 7.54-7.73 (m, 5H).

MS(+): 372 [M+Na]$^+$.

Reference Example 3-10

1-[(3S)-3-{[(1-Phenyl-1H-tetrazol-5-yl)sulfonyl]methyl}pyrrolidin-1-yl]ethanone $^1$H NMR (300 MHz, CDCl$_3$) δ ppm 1.69-2.00 (m, 1H), 2.02 (s, 3H), 2.20-2.54 (m, 1H), 2.74-3.11 (m, 1H), 3.15-4.13 (m, 6H), 7.53-7.79 (m, 5H).

MS(+): 358 [M+Na]$^+$.

Reference Example 3-11

1-(3-{[(1-Phenyl-1H-tetrazol-5-yl)sulfonyl]methyl}azetidin-1-yl)ethanone $^1$H NMR (300 MHz, CDCl$_3$) δ ppm 1.87 (s, 3H), 3.32-3.46 (m, 1H), 3.91 (dd, J=10.6, 6.0 Hz, 1H), 4.06-4.17 (m, 3H), 4.23-4.44 (m, 2H), 7.56-7.73 (m, 5H).

MS(+): 344 [M+Na]$^+$.

Reference Example 3-12

(5R)-5-[(1,3-Benzothiazol-2-ylsulfonyl)methyl]pyrrolidin-2-one $^1$H NMR (300 MHz, CDCl$_3$) δ ppm 1.79-1.98 (m, 1H), 2.31-2.55 (m, 3H), 3.59 (dd, J=14.5, 9.9 Hz, 1H), 3.73-3.85 (m, 1H), 4.26-4.42 (m, 1H), 6.36-6.51 (brs, 1H), 7.58-7.74 (m, 2H), 7.99-8.07 (m, 1H), 8.20-8.29 (m, 1H).

MS(+): 297 [M+H]$^+$.

Reference Example 3-13

5-({[1-({[tert-Butyl(dimethyl)silyl]oxy}methyl)cyclopropyl]methyl}sulfonyl)-1-phenyl-1H-tetrazole LC-Mass retention time 5.20 min SunFire C18 3.5 μm 2.1×20 mm column temperature 40° C.

H$_2$O:CH$_3$CN (0.1% HCO$_2$H added)=
90:10 to 15:85 v/v 0.4 mL/min (0 to 3 min)
15:85 v/v 0.4 mL/min (3 to 5 min)
15:85 to 90:10 v/v 0.5 mL/min (5 to 5.5 min)
MS(+): 409 [M+H]$^+$.

Reference Example 3-14

5-{[(2R)-3-{[tert-Butyl(diphenyl)silyl]oxy}-2-methylpropyl]sulfonyl}-1-phenyl-1H-tetrazole $^1$H NMR (300 MHz, CDCl$_3$) δ ppm 1.06 (s, 9H), 1.16 (d, J=6.8 Hz, 3H), 2.41-2.60 (m, 1H), 3.45-3.65 (m, 2H), 3.67-3.80 (m, 1H), 4.05-4.20 (m, 1H), 7.30-7.49 (m, 6H), 7.52-7.73 (m, 9H).
MS(+): 543 [M+Na]$^+$.

Reference Example 3-15

5-{[(2S)-3-{[tert-Butyl(diphenyl)silyl]oxy}-2-methylpropyl]sulfonyl}-1-phenyl-1H-tetrazole $^1$H NMR (300 MHz, CDCl$_3$) δ ppm 1.08 (s, 9H), 1.17 (d, J=6.8 Hz, 3H), 2.45-2.60 (m, 1H), 3.50-3.65 (m, 2H), 3.75 (dd, J=10.4, 4.8 Hz, 1H), 4.16 (dd, J=14.6, 4.5 Hz, 1H), 7.30-7.50 (m, 6H), 7.55-7.75 (m, 9H).
MS(+): 543 [M+Na]$^+$.

Reference Example 3-16 tert-Butyl (3S)-3-[(1,3-benzothiazol-2-ylsulfonyl)methyl]pyrrolidine-1-carboxylate $^1$H NMR (300 MHz, CDCl$_3$) δ ppm 1.43 (s, 9H), 1.65-1.89 (m, 1H), 2.11-2.32 (m, 1H), 2.73-2.94 (m, 1H), 3.09 (dd, J=11.0, 8.0 Hz, 1H), 3.21-3.36 (m, 1H), 3.40-3.77 (m, 4H), 7.57-7.70 (m, 2H), 8.00-8.06 (m, 1H), 8.19-8.25 (m, 1H).

Reference Example 3-17

1-{(3S)-3-[(1,3-Benzothiazol-2-ylsulfonyl)methyl]pyrrolidin-1-yl}ethanone $^1$H NMR (300 MHz, CDCl$_3$) δ ppm 1.64-2.00 (m, 1H), 2.05 (s, 3H), 2.15-2.49 (m, 1H), 2.78-3.04 (m, 1H), 3.09-3.96 (m, 6H), 7.59-7.71 (m, 2H), 8.01-8.08 (m, 1H), 8.23 (d, J=7.5 Hz, 1H).

Reference Example 3-18 tert-Butyl (2R)-2-[(1,3-benzothiazol-2-ylsulfonyl)methyl]pyrrolidine-1-carboxylate $^1$H NMR (300 MHz, CDCl$_3$) δ ppm 1.36 (s, 9H), 1.79-1.99 (m, 2H), 2.09-2.30 (m, 2H), 3.27-3.61 (m, 3H), 3.90-4.28 (m, 1H), 4.28-4.48 (m, 1H), 7.50-7.70 (m, 2H), 8.01 (d, J=7.5 Hz, 1H), 8.22 (dd, J=7.5, 1.8 Hz, 1H).
MS(+): 405 [M+Na]$^+$.

Reference Example 3-19

1-{(3S)-3-[(1,3-Benzothiazol-2-ylsulfonyl)methyl]pyrrolidin-1-yl}propan-1-one $^1$H NMR (300 MHz, CDCl$_3$) δ ppm 1.14 (tt, J=7.4, 1.6 Hz, 3H), 1.64-1.99 (m, 1H), 2.16-2.42 (m, 3H), 2.74-3.01 (m, 1H), 3.32-3.92 (m, 6H), 7.59-7.71 (m, 2H), 8.03-8.05 (m, 1H), 8.21-8.24 (m, 1H).

Reference Example 3-20

2-({[(3S)-1-(Ethylsulfonyl)pyrrolidin-3-yl]methyl}sulfonyl)-1,3-benzothiazole $^1$H NMR (300 MHz, CDCl$_3$) δ ppm 1.37 (t, J=7.4 Hz, 3H), 1.87 (ddd, J=19.4, 10.6, 6.8 Hz, 1H), 2.27-2.37 (m, 1H), 2.91 (dd, J=15.3, 8.0 Hz, 1H), 3.02 (q, J=7.4 Hz, 2H), 3.24 (dd, J=10.0, 8.0 Hz, 1H), 3.32-3.41 (m, 1H), 3.56 (tt, J=9.0, 3.1 Hz, 1H), 3.61-3.79 (m, 3H), 7.60-7.70 (m, 2H), 8.04 (dd, J=7.0, 1.6 Hz, 1H), 8.23 (dd, J=7.6, 1.8 Hz, 1H).
MS(+): 375 [M+H]$^+$.

Reference Example 3-21

(5S)-5-[(1,3-Benzothiazol-2-ylsulfonyl)methyl]pyrrolidin-2-one $^1$H NMR (300 MHz, CDCl$_3$) δ ppm 1.80-1.99 (m, 1H), 2.30-2.52 (m, 3H), 3.50-3.68 (m, 1H), 3.74-3.87 (m, 1H), 4.26-4.42 (m, 1H), 6.32-6.54 (brs, 1H), 7.58-7.73 (m, 2H), 8.00-8.10 (m, 1H), 8.20-8.30 (m, 1H).
MS(+): 297 [M+H]$^+$.

The structures of Reference Examples 3-4 to 3-21 are shown below.

[Hyo 6-1]

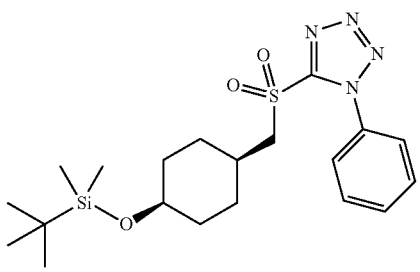

Reference Example 3-4

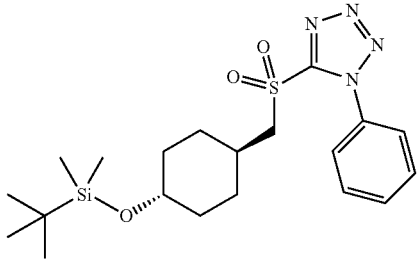

Reference Example 3-5

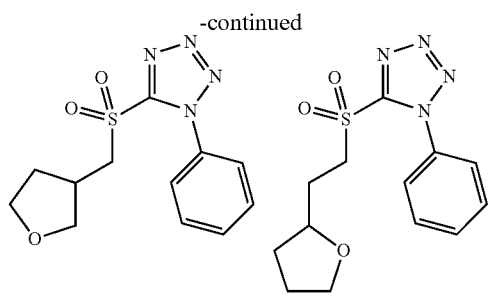
Reference Example 3-6    Reference Example 3-7
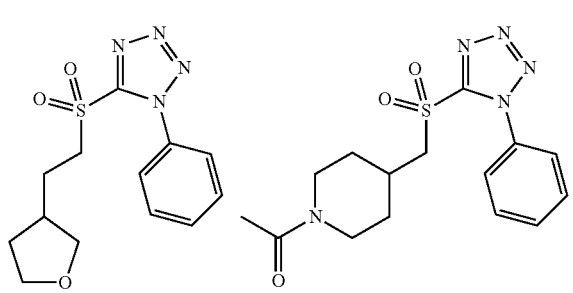
Reference Example 3-8    Reference Example 3-9
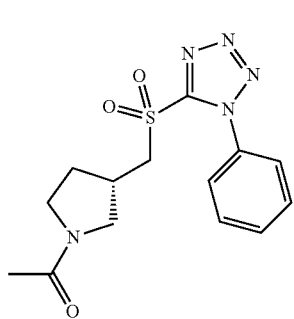
Reference Example 3-10
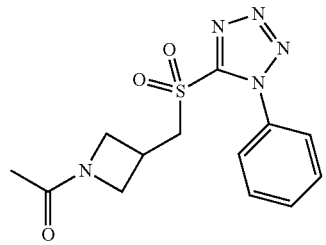
Reference Example 3-11
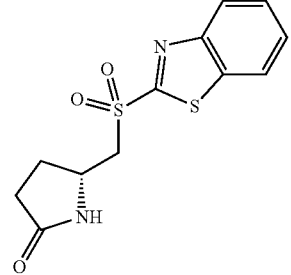
Reference Example 3-12
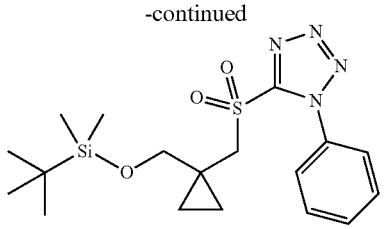
Reference Example 3-13
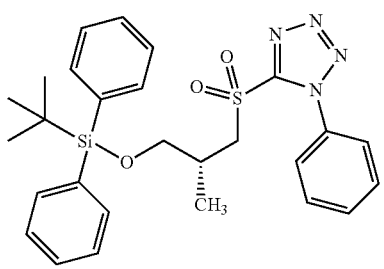
Reference Example 3-14
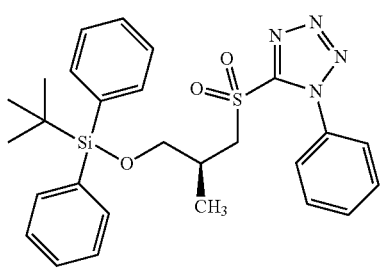
Reference Example 3-15
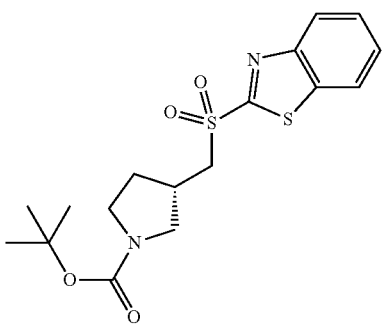
Reference Example 3-16
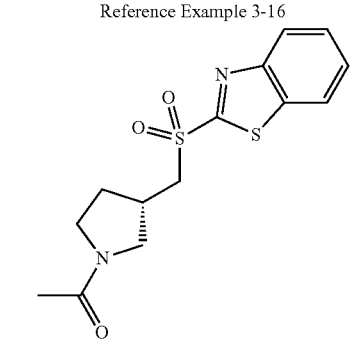
Reference Example 3-17

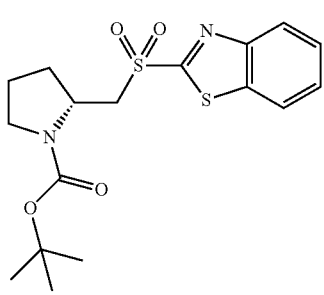

Reference Example 3-18

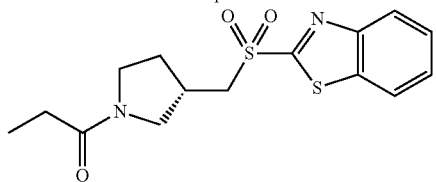

Reference Example 3-19

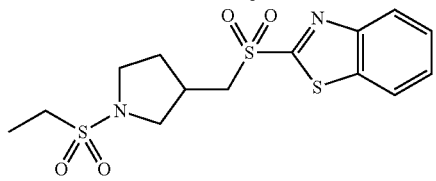

Reference Example 3-20

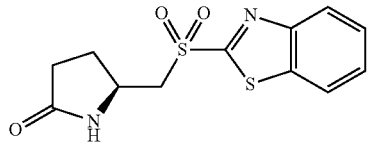

Reference Example 3-21

Reference Example 4-1

6-Bromo-3-chloro-2-methoxypyridine

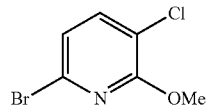

[Ka 95]

(1) 10% palladium-activated carbon (2.5 g) was added to a solution of commercially available 2-methoxy-3-nitropyridine (50.5 g) in methanol (500 mL), and the mixture was stirred for four hours in a hydrogen atmosphere. The reaction solution was filtered through celite, and then the filtrate was concentrated under reduced pressure. The resulting residue was purified by silica gel column chromatography (hexane:ethyl acetate=8:1) to give 2-methoxypyridin-3-amine as a yellow powder (37.2 g, 92%).

$^1$H NMR (300 MHz, CDCl$_3$) δ ppm 3.64-3.88 (m, 2H), 3.92-4.05 (m, 3H), 6.67-6.76 (m, 1H), 6.84-6.92 (m, 1H), 7.54-7.62 (m, 1H).

MS(+): 125 [M+H]$^+$.

(2) A solution of 2-methoxypyridin-3-amine (39.4 g) in N,N-dimethylformamide (200 mL) was cooled to −30° C., and a solution of N-bromosuccinimide (62.1 g) in N,N-dimethylformamide (100 mL) was added dropwise. After stirring for 30 minutes, the reaction solution was poured into water and extracted with chloroform. The organic layer was sequentially washed with a saturated sodium sulfite solution, water and brine and dried over sodium sulfate. After filtration, the filtrate was concentrated under reduced pressure. The residue was purified by silica gel column chromatography (hexane:ethyl acetate=9:1→4:1) to give 6-bromo-2-methoxypyridin-3-amine as a yellow powder (51.9 g, 80%).

$^1$H NMR (300 MHz, CDCl$_3$) δ ppm 3.64-3.84 (m, 2H), 3.98 (s, 3H), 6.78 (dd, J=7.9, 1.0 Hz, 1H), 6.87 (d, J=7.9 Hz, 1H).

MS(+): 203 [M+H]$^+$.

(3) A solution of sodium nitrite (7.04 g) in water (10 mL) was added dropwise to a suspension of 6-bromo-2-methoxypyridin-3-amine (10.4 g) in concentrated hydrochloric acid (35 mL) under ice-cooling. After stirring for 10 minutes, the reaction system was added dropwise to a suspension of copper chloride (12.7 g) in concentrated hydrochloric acid (15 mL) under ice-cooling, and the mixture was stirred at 65° C. for one hour and 15 minutes. The reaction solution was poured into water, followed by extraction with ethyl acetate. The organic layer was washed with brine and dried over anhydrous magnesium sulfate. After filtration, the filtrate was concentrated under reduced pressure. The residue was purified by silica gel column chromatography (hexane:ethyl acetate=9:1→7:3) to give the title compound as a yellow powder (9.69 g, 85%).

$^1$H NMR (300 MHz, CDCl$_3$) δ ppm 4.03 (s, 3H), 7.03 (d, J=7.9 Hz, 1H), 7.47 (d, J=7.9 Hz, 1H).

Reference Example 4-2

3-(5-Chloro-6-methoxypyridin-2-yl)prop-2-yn-1-ol

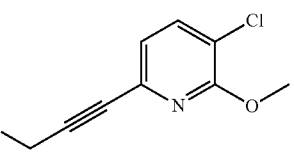

[Ka 96]

Triethylamine (70 mL) and bistriphenylphosphinepalladium(II) dichloride (756 mg) were added to 6-bromo-3-chloro-2-methoxypyridine (12.1 g), 2-propyn-1-ol (4.0 g) and copper iodide (210 mg) in a nitrogen atmosphere, and the mixture was stirred at room temperature for four hours. Water and ethyl acetate were added to the reaction solution, followed by filtration. The aqueous layer was adjusted to pH 3 or less with 1 M hydrochloric acid, followed by extraction with ethyl acetate. The organic layer was washed with brine and dried over sodium sulfate. After filtration, the solvent was evaporated under reduced pressure. The residue was purified by silica gel column chromatography (hexane:ethyl acetate=7:3→5:5) to give the title compound as a light brown powder (8.60 g, 80%).

$^1$H NMR (300 MHz, CDCl$_3$) δ ppm 4.03 (s, 3H), 4.52 (s, 2H), 7.01 (d, J=7.9 Hz, 1H), 7.58 (d, J=7.8 Hz, 1H)

MS(+): 198 [M+H]$^+$.

Reference Example 4-3

(2Z)-3-(5-Chloro-6-methoxypyridin-2-yl)-3-iodoprop-2-en-1-ol

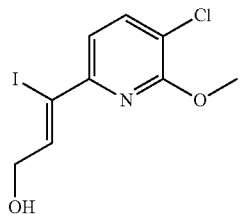
[Ka 97]

A solution of 3-(5-chloro-6-methoxypyridin-2-yl)prop-2-yn-1-ol (3.0 g) in tetrahydrofuran (50 mL) was stirred under ice-cooling in a nitrogen atmosphere, during which a solution of sodium bis(2-methoxyethoxy)aluminum hydride (Red-Al (R)) in toluene (3.6 M, 7 mL) was added dropwise thereto. The mixture was stirred at room temperature for one hour. The reaction solution was cooled to an external temperature of −78° C. A solution of N-iodosuccinimide (6.2 g) in tetrahydrofuran (30 mL) was added dropwise and then the mixture was stirred at an external temperature of −78° C. for one hour. 1 M hydrochloric acid was added to the reaction solution, followed by extraction with ethyl acetate. The organic layer was sequentially washed with a 10% sodium thiosulfate solution and brine and dried over sodium sulfate. After filtration, the solvent was evaporated under reduced pressure. The residue was purified by silica gel column chromatography (hexane:ethyl acetate=9:1→5:5) to give the title compound as a brown powder (3.79 g, 76%).

$^1$H NMR (300 MHz, CDCl$_3$) δ ppm 4.07 (s, 3H), 4.47 (t, J=5.8 Hz, 2H), 7.11 (t, J=5.6 Hz, 1H), 7.24 (d, J=7.9 Hz, 1H), 7.60 (d, J=7.9 Hz, 1H).

MS(+): 326[M+H]$^+$.

Reference Example 4-4

(2E)-3-(4-tert-Butylphenyl)-3-(5-chloro-6-methoxypyridin-2-yl)prop-2-en-1-ol

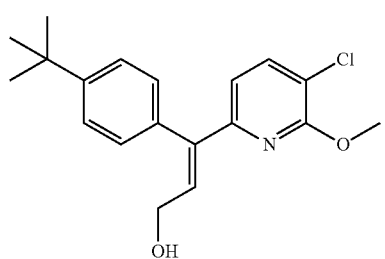
[Ka 98]

4-tert-Butylphenylboronic acid (3.5 g), tris(dibenzylideneacetone)dipalladium(0) (183 mg), tri(2-furyl)phosphine (280 mg) and cesium carbonate (1.98 g) were added to a solution of (2Z)-3-(5-chloro-6-methoxypyridin-2-yl)-3-iodoprop-2-en-1-ol (881 mg) in 1,4-dioxane (20 mL)-water (10 mL) in a nitrogen atmosphere, and the mixture was stirred at an external temperature of 65° C. for 1.5 hours. The reaction solution was left to cool, diluted with ethyl acetate and filtered. The filtrate was washed with brine and dried over sodium sulfate. After filtration, the solvent was evaporated under reduced pressure. The residue was purified by silica gel column chromatography (hexane:ethyl acetate=19:1→1:1) to give the title compound as a light yellow powder (912 mg, 91%).

$^1$H NMR (300 MHz, CDCl$_3$) δ ppm 1.36 (s, 9H), 4.09 (s, 3H), 4.18-4.24 (m, 2H), 6.42 (d, J=7.9 Hz, 1H), 7.09-7.17 (m, 3H), 7.39-7.46 (m, 3H).

MS(+): 332 [M+H]$^+$.

Reference Example 4-5

6-[(1E)-3-Bromo-1-(4-tert-butylphenyl)prop-1-en-1-yl]-3-chloro-2-methoxypyridine

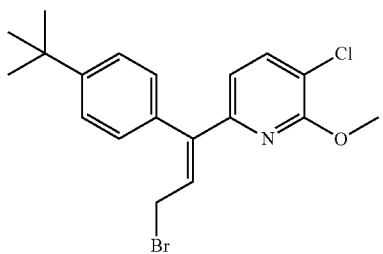
[Ka 99]

Triphenylphosphine (1.10 g) and carbon tetrabromide (1.81 g) were sequentially added to a solution of (2E)-3-(4-tert-butylphenyl)-3-(5-chloro-6-methoxypyridin-2-yl)prop-2-en-1-ol (912 mg) in tetrahydrofuran (30 mL) under ice-cooling, and the mixture was stirred under ice-cooling for 1.5 hours. Water was added to the reaction solution, followed by extraction with ethyl acetate. The organic layer was washed with brine and dried over sodium sulfate. After filtration, the solvent was evaporated under reduced pressure. The residue was purified by silica gel column chromatography (hexane:ethyl acetate=9:1) to give the title compound as a black powder (1.28 g).

$^1$H NMR (300 MHz, CDCl$_3$) δ ppm 1.38 (s, 9H), 4.03 (d, J=8.9 Hz, 2H), 4.11 (s, 3H), 6.42 (d, J=7.9 Hz, 1H), 7.17-7.24 (m, 3H), 7.42-7.50 (m, 3H).

Reference Example 4-6

(2E)-3-(4-tert-Butylphenyl)-3-(5-chloro-6-methoxypyridin-2-yl)prop-2-enoic acid

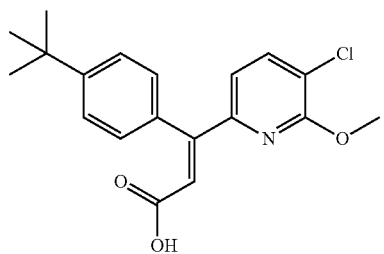
[Ka 100]

Dess-Martin reagent (770 mg) was added to a solution of (2E)-3-(4-tert-butylphenyl)-3-(5-chloro-6-methoxypyridin- 2-yl)prop-2-en-1-ol (601 mg) in chloroform (20 mL), and the mixture was stirred at room temperature for 30 minutes. A 10% sodium thiosulfate solution was added to the reaction solution, followed by extraction with chloroform. The organic layer was washed with brine and dried over sodium sulfate. After filtration, the solvent was evaporated under reduced pressure. Sodium dihydrogenphosphate (1.0 g) and chlorous acid (1.6 g) were added to a solution of the resulting residue and 2-methyl-2-butene (2.3 g) in tert-butanol (15 mL)-water (5 mL), and the mixture was stirred at room temperature for one hour. The reaction solution was ice-cooled and then adjusted to a pH of less than 2 with 1 M hydrochloric acid, followed by extraction with chloroform. The organic layer was washed with brine and dried over sodium sulfate. After filtration, the solvent was evaporated under reduced pressure. The residue was purified by silica gel column chromatography (chloroform:methanol=9:1). Thereafter, the resulting solid was washed with hexane and then dried to give the title compound as a colorless powder (434 mg, 69%).

$^1$H NMR (300 MHz, CDCl$_3$) δ ppm 1.37 (s, 9H), 4.10 (s, 3H), 6.50 (d, J=7.9 Hz, 1H), 7.13-7.19 (m, 2H), 7.22 (s, 1H), 7.43 (d, J=8.2 Hz, 2H), 7.50 (d, J=7.9 Hz, 1H).

MS(+): 368[M+Na]$^+$.

Reference Example 4-7

6-[(E)-2-Bromo-1-(4-tert-butylphenyl)ethenyl]-3-chloro-2-methoxypyridine

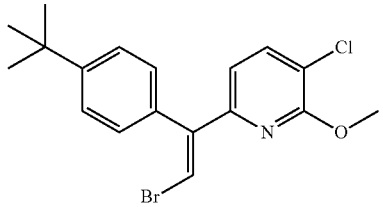

[Ka 101]

A 97% acetonitrile solution (52 mL) containing triethylamine (26 μL) was added to (2E)-3-(4-tert-butylphenyl)-3-(5-chloro-6-methoxypyridin-2-yl)prop-2-enoic acid (1.3 g). N-bromosuccinimide (806 mg) was added thereto and the mixture was stirred at room temperature for 15 minutes. The solvent was evaporated under reduced pressure from the reaction solution. The residue was purified by silica gel column chromatography (hexane:ethyl acetate=19:1) to give the title compound as a colorless powder (363 mg, 25%).

$^1$H NMR (300 MHz, CDCl$_3$) δ ppm 1.37 (s, 9H), 4.07 (s, 3H), 6.39 (d, J=7.9 Hz, 1H), 7.19 (d, J=8.2 Hz, 2H), 7.42-7.49 (m, 3H) 7.72 (s, 1H).

MS(+): 380 [M+H]$^+$.

Reference Example 4-8

4-(5-Chloro-6-methoxypyridin-2-yl)but-3-yn-1-ol

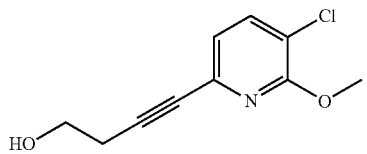

[Ka 102]

The title compound was obtained as a pale brown solid (4.10 g, 85%) by performing substantially the same reaction as in Reference Example 4-2 except for using 3-butyn-1-ol in place of 2-propyn-1-ol.

$^1$H NMR (300 MHz, CDCl$_3$) δ ppm 2.73 (t, J=6.3 Hz, 2H), 3.86 (t, J=6.3 Hz, 2H), 4.03 (s, 3H), 6.97 (d, J=7.9 Hz, 1H), 7.55 (d, J=7.8 Hz, 1H).

MS(+): 212 [M+H]$^+$.

Reference Example 4-9

(3Z)-4-(5-Chloro-6-methoxypyridin-2-yl)-4-iodobut-3-en-1-ol

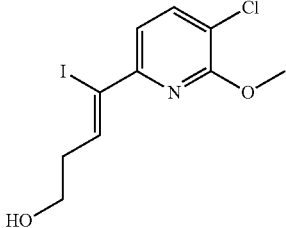

[Ka 103]

The title compound was obtained as a brown solid (2.26 g, 47%) by performing substantially the same reaction as in Reference Example 4-3 except for using 4-(5-chloro-6-methoxypyridin-2-yl)but-3-yn-1-ol in place of 3-(5-chloro-6-methoxypyridin-2-yl)prop-2-yn-1-ol.

$^1$H NMR (300 MHz, CDCl$_3$) δ ppm 2.69 (q, J=6.5 Hz, 2H), 3.87 (t, J=6.5 Hz, 2H), 4.06 (s, 3H), 6.88 (t, J=6.9 Hz, 1H), 7.22 (d, J=7.9 Hz, 1H), 7.58 (d, J=7.9 Hz, 1H).

MS(+): 340 [M+H]$^+$.

Reference Example 4-10

(3E)-4-(4-tert-Butylphenyl)-4-(5-chloro-6-methoxypyridin-2-yl)but-3-en-1-ol

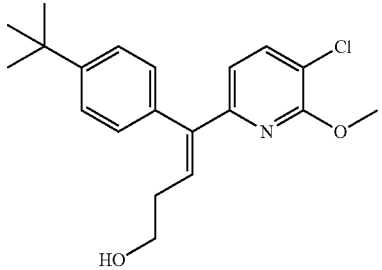

[Ka 104]

The title compound was obtained as an orange powder (2.39 g, quant.) by performing substantially the same reaction as in Reference Example 4-4 except for using (3Z)-4-(5-chloro-6-methoxypyridin-2-yl)-4-iodobut-3-en-1-ol in place of (2Z)-3-(5-chloro-6-methoxypyridin-2-yl)-3-iodoprop-2-en-1-ol.

$^1$H NMR (300 MHz, CDCl$_3$) δ ppm 1.36 (s, 9H), 2.33-2.43 (m, 2H), 3.69-3.80 (m, 2H), 4.08 (s, 3H), 6.36 (d, J=7.9 Hz, 1H), 7.04 (t, J=7.7 Hz, 1H), 7.12 (d, J=8.4 Hz, 2H), 7.41 (d, J=7.3 Hz, 3H).

MS(+): 346 [M+H]$^+$.

Reference Example 4-11

5-Chloro-6-methoxypyridine-2-carbaldehyde

[Ka 105]

(1) Concentrated sulfuric acid (4 mL) was added to a solution of 5-chloropyridine-2-carboxylic acid (25.3 g) in ethanol (500 mL) under ice-cooling, and the mixture was stirred under reflux for four hours. The reaction solution was cooled to room temperature and water was added, followed by extraction with chloroform. The organic layer was dried over anhydrous magnesium sulfate and filtered. The solvent was then evaporated under reduced pressure. The residue was purified by silica gel column chromatography (chloroform only→hexane:ethyl acetate=1:1) and the solvent was evaporated under reduced pressure from the fraction containing ethyl 5-chloropyridine-2-carboxylate. Urea peroxide (30.2 g) was added to a solution of the residue in chloroform (300 mL) under ice-cooling. A mixture of trifluoroacetic anhydride (44.7 mL) and chloroform (300 mL) was added dropwise over 30 minutes, and the mixture was stirred while gradually returning to room temperature for two hours. A saturated sodium thiosulfate solution was added dropwise to the reaction solution, followed by extraction with chloroform. The organic layer was dried over anhydrous magnesium sulfate and filtered. The solvent was then evaporated under reduced pressure. The residue was purified by silica gel column chromatography (hexane:ethyl acetate=1:1) to give ethyl 5-chloropyridine-2-carboxylate 1-oxide as a yellow oil (36.8 g, quant.).

(2) Trifluoroacetic anhydride (147 mL) was added dropwise to a solution of ethyl 5-chloropyridine-2-carboxylate 1-oxide (36.8 g) in N,N-dimethylformamide (220 mL) under ice-cooling over 20 minutes, and the mixture was stirred at 50° C. for one hour. The reaction solution was ice-cooled and water was added. Sodium bicarbonate was slowly added to effect neutralization, followed by extraction with chloroform. The organic layer was dried over anhydrous magnesium sulfate and filtered. The solvent was then evaporated under reduced pressure. The residue was suspended with ethyl acetate, stirred and then filtered. The filtrate was concentrated under reduced pressure. The same operation was further repeated twice. The resulting solids were combined and dried under reduced pressure to give ethyl 5-chloro-6-hydroxypyridine-2-carboxylate as a white solid (24.2 g, 75%). The filtrate was purified by silica gel column chromatography (hexane:ethyl acetate=1:1) to give ethyl 5-chloro-6-hydroxypyridine-2-carboxylate as a white solid (1.84 g, 6%).

(3) Silver carbonate (142.4 g) and methyl iodide (25 mL) were added to a solution of ethyl 5-chloro-6-hydroxypyridine-2-carboxylate (26.0 g) in chloroform (500 mL), and the mixture was stirred at 70° C. for seven hours. The reaction solution was filtered through celite, and then the solvent was evaporated under reduced pressure. The residue was purified by silica gel column chromatography (hexane:ethyl acetate=30:1) and purified again by silica gel column chromatography (hexane:ethyl acetate=20:1) to give ethyl 5-chloro-6-methoxypyridine-2-carboxylate as a white solid (22.3 g, 80%).

(4) Lithium aluminum hydride (2.54 g) was added in small portions to a solution of ethyl 5-chloro-6-methoxypyridine-2-carboxylate (22.3 g) in tetrahydrofuran (223 mL) under ice-cooling, and the mixture was stirred at the same temperature for 10 minutes. Water was added to the reaction solution under ice-cooling. After filtration through celite, the filtrate was concentrated under reduced pressure. Brine was added to the residue, followed by extraction with ethyl acetate. The organic layer was dried over anhydrous magnesium sulfate and filtered, after which the filtrate was concentrated under reduced pressure. Manganese dioxide (116.4 g) was added to a solution of the residue in chloroform (223 mL), and the mixture was stirred at 60° C. for one hour. The reaction solution was filtered through celite, and the filtrate was concentrated under reduced pressure. The resulting residue was suspended with hexane, stirred and then filtered. The filtrate was concentrated under reduced pressure. The same operation was further repeated three times. The resulting solids were combined and dried under reduced pressure to give the title compound as a white solid (14.7 g, 83%).

$^1$H NMR (300 MHz, CDCl$_3$) δ ppm 4.13 (s, 3H), 7.54 (d, J=7.7 Hz, 1H), 7.80 (dd, J=7.7, 0.8 Hz, 1H), 9.94 (d, J=0.8 Hz, 1H).

MS(+): 172 [M+H]$^+$.

Reference Example 4-12

6-{(1E)-3-Bromo-1-[4-(cyclopropylsulfanyl)phenyl]prop-1-en-1-yl}-3-chloro-2-methoxypyridine The title compound was obtained as a black oil (1.2 g) by performing substantially the same reaction as in Reference Examples 4-4 and 4-5 except for using [4-(cyclopropylsulfanyl)phenyl]boronic acid in place of 4-tert-butylphenylboronic acid.

$^1$H NMR (300 MHz, CDCl$_3$) δ ppm 0.70-0.81 (m, 2H) 1.07-1.18 (m, 2H) 2.16-2.29 (m, 1H) 4.01 (d, J=8.7 Hz, 2H) 4.09 (s, 3H) 6.43 (d, J=7.9 Hz, 1H) 7.17-7.25 (m, 3H) 7.44 (d, J=5.8 Hz, 2H) 7.46 (d, J=5.1 Hz, 1H).

Reference Example 4-13

(3E)-4-(4-tert-Butylphenyl)-4-(5-chloro-6-methoxypyridin-2-yl)but-3-enenitrile Sodium cyanide (137 mg) was added to a solution of 6-[(1E)-3-bromo-1-(4-tert-butylphenyl)prop-1-en-1-yl]-3-chloro-2-methoxypyridine (500 mg) in ethanol (10 mL), and the mixture was stirred at room temperature for 22 hours. Water was added to the reaction solution, followed by extraction with ethyl acetate. The organic layer was washed with a 2 M sodium hydroxide solution and brine, dried over sodium sulfate and filtered, after which the solvent was evaporated under reduced pressure. The residue was purified by silica gel column chromatography (hexane:ethyl acetate=19:1→4:1) to give the title compound as a yellow oil (230 mg, 53%).

$^1$H NMR (300 MHz, CDCl$_3$) δ ppm 1.37 (s, 9H), 3.11 (d, J=7.5 Hz, 2H), 4.10 (s, 3H), 6.38 (d, J=7.9 Hz, 1H), 6.96 (t, J=7.5 Hz, 1H), 7.12 (d, J=8.4 Hz, 2H), 7.43-7.50 (m, 3H).

MS(+): 341 [M+H]$^+$.

Reference Example 4-14

6-Methoxy-5-propylpyridine-2-carbaldehyde

The title compound was obtained by performing substantially the same reaction as in Reference Example 1-1(1) except for using 1-iodopropane in place of hexachloroethane.

$^1$H NMR (300 MHz, CDCl$_3$) δ ppm 0.83-1.10 (m, 3H), 1.53-1.78 (m, 2H), 2.46-2.69 (m, 2H), 4.04 (s, 3H), 7.43-7.61 (m, 2H), 9.87-10.02 (m, 1H).

MS(+): 180 [M+H]$^+$.

Reference Example 4-15

(5R)-5-[(5-Chloro-6-methoxypyridin-2-yl)ethynyl]-1-(2,4-dimethoxybenzyl)pyrrolidin-2-one (5R)-1-(2,4-Dimethoxybenzyl)-5-ethynylpyrrolidin-2-one (600 mg, synthesized according to Tetrahedron Asymmetry, 1995, 239 using dimethyl (R)-glutamate hydrochloride as a raw material) in acetonitrile (6 mL) was added to a solution of 6-bromo-3-chloro-2-methoxypyridine (667 mg), bis(triphenylphosphine)palladium(II) dichloride (81 mg) and copper iodide (22 mg) in triethylamine (12 mL) in a nitrogen gas stream at 40° C. over 30 minutes. The mixture was stirred at room temperature for four hours. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (hexane:ethyl acetate=1:1→0:1) to give the title compound as a colorless oil (452 mg, 52%).

$^1$H NMR (300 MHz, CDCl$_3$) δ ppm 2.12-2.48 (m, 3H), 2.53-2.70 (m, 1H), 3.79 (s, 3H), 3.80 (s, 3H), 4.04 (s, 3H), 4.26 (d, J=15 Hz, 1H), 4.37-4.46 (m, 1H), 4.89 (d, J=15 Hz, 1H), 6.38-6.49 (m, 2H), 6.94 (d, J=7.8 Hz, 1H), 7.18-7.25 (m, 1H), 7.57 (d, J=7.8 Hz, 1H).

Reference Example 4-16

(5R)-5-[(5-Chloro-6-methoxypyridin-2-yl)ethynyl]pyrrolidin-2-one

Trifluoroacetic acid (4 mL) and anisole (2 mL) were added to (5R)-5-[(5-chloro-6-methoxypyridin-2-yl)ethynyl]-1-(2,4-dimethoxybenzyl)pyrrolidin-2-one (457 mg), and the mixture was stirred at 80° C. for two hours. The reaction solution was concentrated, and the residue was diluted with chloroform, washed with saturated aqueous sodium bicarbonate and brine and dried over anhydrous magnesium sulfate. After filtration, the solvent was evaporated under reduced pressure. The residue was purified by silica gel column chromatography (hexane:ethyl acetate=1:1→0:1) to give the title compound as a colorless oil (234 mg, 82%).

$^1$H NMR (300 MHz, CDCl$_3$) δ ppm 2.27-2.45 (m, 2H), 2.46-2.65 (m, 2H), 4.04 (s, 3H), 4.54-4.72 (m, 1H), 5.64-5.80 (m, 1H), 6.99 (d, J=7.8 Hz, 1H), 7.59 (d, J=7.8 Hz, 1H).

MS(+): 251 [M+H]$^+$.

Reference Example 4-17

(5R)-5-[(Z)-2-(5-Chloro-6-methoxypyridin-2-yl)ethenyl]pyrrolidin-2-one

Lindlar catalyst (50 mg) was added to a solution of (5R)-5-[(5-chloro-6-methoxypyridin-2-yl)ethynyl]pyrrolidin-2-one (232 mg) in methanol (5 mL), and the mixture was stirred at room temperature for eight hours in a hydrogen atmosphere. The reaction solution was filtered through celite, and then the solvent was evaporated. The residue was purified by silica gel column chromatography (hexane:ethyl acetate=1:1→0:1) to give the title compound as a colorless oil (166 mg, 71%).

$^1$H NMR (300 MHz, CDCl$_3$) δ ppm 1.85-2.01 (m, 1H), 2.25-2.64 (m, 3H), 4.02 (s, 3H), 5.43-5.60 (m, 1H), 5.72-5.85 (m, 1H), 5.86-6.04 (m, 1H), 6.28-6.45 (m, 1H), 6.77 (d, J=7.8 Hz, 1H), 7.60 (d, J=7.8 Hz, 1H).

Reference Example 4-18

(5R)-5-[(Z)-2-Bromo-2-(5-chloro-6-methoxypyridin-2-yl)ethenyl]pyrrolidin-2-one Bromine (80 μL) was added to a solution of (5R)-5-[(Z)-2-(5-chloro-6-methoxypyridin-2-yl)ethenyl]pyrrolidin-2-one (200 mg) in carbon tetrachloride (2 mL) under ice-cooling, and the mixture was stirred at the same temperature (0° C.) for 15 minutes. The reaction solution was concentrated and the residue was dissolved in chloroform. 1,8-Diazabicyclo[5.4.0]undec-7-ene (238 μL) was added under ice-cooling, and the mixture was stirred at room temperature for one hour. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (hexane:ethyl acetate=1:1→0:1) to give the title compound as a colorless powder (164 mg, 62%).

$^1$H NMR (300 MHz, CDCl$_3$) δ ppm 1.90-2.10 (m, 1H), 2.38-2.48 (m, 2H), 2.50-2.70 (m, 1H), 4.05 (s, 3H), 4.70-4.85 (m, 1H), 5.67-5.84 (m, 1H), 7.19 (d, J=7.9 Hz, 1H), 7.31 (d, J=8.1 Hz, 1H), 7.65 (d, J=7.9 Hz, 1H).

MS(+): 331 [M+H]$^+$.

Reference Example 4-19

6-{(Z)-1-Bromo-2-[(2R)-5-oxopyrrolidin-2-yl]ethenyl}-3-chloropyridin-2(1H)-one 48% hydrobromic acid (2 mL) was added to a solution of (5R)-5-[(Z)-2-bromo-2-(5-chloro-6-methoxypyridin-2-yl)ethenyl]pyrrolidin-2-one (115 mg) in 1,4-dioxane (3 mL), and the mixture was stirred at 65° C. for one hour. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (chloroform:methanol=10:0→4:1) to give the title compound as a colorless powder (40 mg, 37%).

$^1$H NMR (600 MHz, CDCl$_3$) δ ppm 2.05-2.14 (m, 1H), 2.32-2.41 (m, 1H), 2.44-2.55 (m, 2H), 4.67-4.76 (m, 1H), 6.59 (d, J=7.3 Hz, 1H), 7.04 (d, J=7.8 Hz, 1H), 7.48-7.55 (brs, 1H), 7.57 (d, J=7.8 Hz, 1H), 12.84-13.24 (brs, 1H).

MS(+): 317 [M+H]$^+$.

Reference Example 4-20

6-Bromo-3-cyclopropyl-2-methoxypyridine (1) A solution of sodium nitrite (5.44 g) in water (15 mL) was added dropwise to a suspension of 6-bromo-2-methoxypyridin-3-amine (16.0 g) in concentrated hydrochloric acid (130 mL) and water (175 mL) at an internal temperature of 5° C. or less, and the mixture was stirred as such for 20 minutes. This suspension was added dropwise to a solution of potassium iodide (39.2 g) in water (760 mL) at an internal temperature of 5° C. or less. The mixture was brought to room temperature and then stirred at 60° C. for two hours. The reaction solution was brought to room temperature and then extracted with ethyl acetate. The organic layer was washed with a saturated sodium thiosulfate solution and brine, dried over anhydrous magnesium sulfate and filtered, after which the filtrate was concentrated under reduced pressure. The resulting residue was purified by silica gel column chromatography (hexane:ethyl acetate=95:5→85:15) to give 6-bromo-3-iodo-2-methoxypyridine as a pale orange powder (21.1 g).

$^1$H NMR (600 MHz, CDCl$_3$) δ ppm 3.99 (s, 3H), 6.85 (d, J=7.8 Hz, 1H), 7.82 (d, J=7.8 Hz, 1H).

MS(+): 314 [M+H]$^+$.

(2) Palladium acetate (36 mg) was added to a suspension of 6-bromo-3-iodo-2-methoxypyridine (1.0 g), cyclopropylboronic acid (547 mg), triphenylphosphine (84 mg) and potassium carbonate (1.32 g) in toluene (20 mL) and water (1 mL), and the mixture was stirred at 110° C. for 4.5 hours. Water and ethyl acetate were added to the reaction solution, followed by extraction with ethyl acetate. The organic layer was dried over anhydrous magnesium sulfate and filtered. The filtrate was concentrated under reduced pressure. The resulting residue was purified by silica gel column chromatography (hexane:ethyl acetate=99:1→96:4) to give the title compound as a colorless oil (782 mg).

$^1$H NMR (600 MHz, CDCl$_3$) δ ppm 0.60-0.63 (m, 2H), 0.92-0.96 (m, 2H), 1.95-2.01 (m, 1H), 3.98 (s, 3H), 6.95 (s, 2H).

MS(+): 228 [M+H]$^+$.

Reference Example 4-21

(5R)-5-[(5-Cyclopropyl-6-methoxypyridin-2-yl) ethynyl]-1-(2,4-dimethoxybenzyl)pyrrolidin-2-one The title compound was obtained as a pale brown gum (6.84 g) by performing substantially the same reaction as in Reference Example 4-15 except for using 6-bromo-3-cyclopropyl-2-methoxypyridine in place of 6-bromo-3-chloro-2-methoxypyridine.

$^1$H NMR (600 MHz, CDCl$_3$) δ ppm 0.64-0.69 (m, 2H), 0.94-1.00 (m, 2H), 2.03-2.10 (m, 1H), 2.18-2.24 (m, 1H), 2.27-2.35 (m, 1H), 2.37-2.44 (m, 1H), 2.57-2.64 (m, 1H), 3.79 (s, 3H), 3.80 (s, 3H), 4.00 (s, 3H), 4.26 (d, J=15.1 Hz, 1H), 4.40 (dd, J=8.3, 4.1 Hz, 1H), 4.90 (d, J=14.7 Hz, 1H), 6.41-6.45 (m, 2H), 6.91 (d, J=7.3 Hz, 1H), 7.02 (d, J=7.3 Hz, 1H), 7.21-7.24 (m, 1H).

MS(+): 407 [M+H]$^+$.

Reference Example 4-22

(5R)-5-[(5-Cyclopropyl-6-methoxypyridin-2-yl) ethynyl]pyrrolidin-2-one

The title compound was obtained as a pale brown gum (14.6 g) by performing substantially the same reaction as in Reference Example 4-16 except for using (5R)-5-[(5-cyclopropyl-6-methoxypyridin-2-yl)ethynyl]-1-(2,4-dimethoxybenzyl)pyrrolidin-2-one.

$^1$H NMR (600 MHz, CDCl$_3$) δ ppm 0.63-0.68 (m, 2H), 0.95-1.00 (m, 2H), 2.05-2.10 (m, 1H), 2.31-2.39 (m, 2H), 2.49-2.58 (m, 2H), 3.99 (s, 3H), 4.63 (dd, J=7.6, 4.8 Hz, 1H), 5.73 (brs, 1H), 6.94 (d, J=7.3 Hz, 1H), 7.02 (d, J=7.3 Hz, 1H).

Reference Example 4-23

(5R)-5-[(Z)-2-(5-Cyclopropyl-6-methoxypyridin-2-yl)ethenyl]pyrrolidin-2-one

The title compound was obtained as a pale brown powder (10.2 g) by performing substantially the same reaction as in Reference Example 4-17 except for using (5R)-5-[(5-cyclopropyl-6-methoxypyridin-2-yl)ethynyl]pyrrolidin-2-one.

$^1$H NMR (600 MHz, CDCl$_3$) δ ppm 0.62-0.68 (m, 2H), 0.92-0.99 (m, 2H), 1.88-1.96 (m, 1H), 2.04-2.09 (m, 1H), 2.33-2.55 (m, 3H), 3.98 (s, 3H), 5.53-5.58 (m, 1H), 5.70 (dd, J=11.7, 8.0 Hz, 1H), 6.05 (brs, 1H), 6.33 (dd, J=11.7, 1.2 Hz, 1H), 6.70 (d, J=7.3 Hz, 1H), 7.07 (d, J=7.3 Hz, 1H).

MS(+): 259 [M+H]$^+$.

Reference Example 4-25

(5R)-5-[(Z)-2-Bromo-2-(5-cyclopropyl-6-methoxypyridin-2-yl)ethenyl]pyrrolidin-2-one The title compound was obtained as a pale brown powder (11.3 g) by performing substantially the same reaction as in Reference Example 4-18 except for using (5R)-5-[(Z)-2-(5-cyclopropyl-6-methoxypyridin-2-yl)ethenyl]pyrrolidin-2-one.

$^1$H NMR (300 MHz, CDCl$_3$) δ ppm 0.61-0.71 (m, 2H), 0.91-1.07 (m, 2H), 1.91-2.15 (m, 2H), 2.35-2.69 (m, 3H), 4.00 (s, 3H), 4.71-4.90 (m, 1H), 5.59-5.71 (m, 1H), 7.06-7.18 (m, 2H), 7.24 (d, J=7.6 Hz, 1H).

MS(+): 337 [M+H]$^+$.

Reference Example 4-25

6-[(Z)-1-Bromo-2-(tetrahydro-2H-pyran-4-yl)ethenyl]-3-chloro-2-methoxypyridine (1) A solution of lithium hexamethyldisilazide in tetrahydrofuran (1 M, 10 mL) was added to a solution of triphenyl (tetrahydro-2H-pyran-4-ylmethyl)phosphonium iodide (5.51 g) in tetrahydrofuran (20 mL) under ice-cooling, and the mixture was stirred at room temperature for one hour. A solution of 5-chloro-6-methoxypyridine-2-carbaldehyde (1.3 g) in tetrahydrofuran (20 mL) was slowly added to the reaction solution, and the mixture was stirred at room temperature for one hour. The reaction solution was poured into water, followed by extraction with ethyl acetate. The organic layer was washed with brine, dried over anhydrous magnesium sulfate and filtered. The solvent was then evaporated under reduced pressure. The filtrate was purified by silica gel column chromatography (hexane:ethyl acetate=4:1) to give 3-chloro-2-methoxy-6-[(Z)-2-(tetrahydro-2H-pyran-4-yl) ethenyl]pyridine as a colorless powder (1.62 g, 60%).

(2) The title compound was obtained as a colorless powder (1.97 g, 93%) by performing substantially the same reaction as in Reference Example 4-18 except for using 3-chloro-2-methoxy-6-[(Z)-2-(tetrahydro-2H-pyran-4-yl)ethenyl]pyridine.

$^1$H NMR (300 MHz, CDCl$_3$) δ ppm 1.57-1.70 (m, 2H), 1.71-1.82 (m, 2H), 2.80-3.04 (m, 1H), 3.41-3.61 (m, 2H), 3.94-4.07 (m, 5H), 6.99 (d, J=8.9 Hz, 1H), 7.28 (d, J=8.1 Hz, 1H), 7.61 (d, J=8.1 Hz, 1H).

Reference Example 4-26

(5R)-5-[(E)-2-(4-tert-Butylphenyl)-2-(tributylstannyl)ethenyl]-1-(2,4-dimethoxybenzyl)pyrrolidin-2-one (1) Copper iodide (74 mg) and bis(triphenylphosphine)palladium(II) dichloride (135 mg) were added to a solution of 4-tert-butyliodobenzene (3.0 g) in triethylamine (10 mL), and the mixture was stirred at room temperature for 15 minutes. (5R)-1-(2,4-Dimethoxybenzyl)-5-ethynylpyrrolidin-2-one (1.0 g) was added thereto over one hour, and the mixture was stirred at room temperature for three hours. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (hexane:ethyl acetate=1:0→1:1) to give (5R)-5-[(4-tert-butylphenyl)ethynyl]-1-(2,4-dimethoxybenzyl)pyrrolidin-2-one as a colorless powder (1.25 g, 84%).

(2) Bis(tricyclohexylphosphine)palladium(II) dichloride (230 mg) and tributyltin chloride (1.0 mL) were sequentially added to a solution of (5R)-5-[(4-tert-butylphenyl)ethynyl]-1-(2,4-dimethoxybenzyl)pyrrolidin-2-one (1.24 g) in tetrahydrofuran (15 mL) in a nitrogen gas stream, and the mixture was stirred at room temperature for two hours. The reaction solution was filtered through celite, and then the filtrate was concentrated. The residue was purified by silica gel column chromatography (hexane:ethyl acetate=4:1→2:1) to give the title compound as a colorless powder (2.16 g, 96%).

$^1$H NMR (300 MHz, CDCl$_3$) δ ppm 0.65-1.49 (m, 33H), 1.68-1.87 (m, 1H), 1.99-2.21 (m, 1H), 2.26-2.58 (m, 3H), 3.66 (s, 3H), 3.76 (s, 3H), 4.00-4.26 (m, 3H), 4.66 (d, J=16 Hz, 2H), 5.58 (s, 1H), 6.23-6.31 (m, 1H), 6.36 (s, 1H), 6.62 (d, J=8.5 Hz, 2H), 6.88 (s, 1H), 7.12 (d, J=8.5 Hz, 2H).

MS(+): 684 [M+H]$^+$.

The compounds of Examples 4-27 to 4-30 were synthesized by performing substantially the same reaction as in Reference Example 4-26 using corresponding aryl halides (1-iodo-4-isopropylbenzene, 1-chloro-4-iodobenzene, 1-iodo-4-(trifluoromethyl)benzene and 2-bromo-5-(trifluoromethyl)pyridine) in place of 4-tert-butyl-1-iodobenzene, respectively.

Reference Example 4-27

(5R)-1-(2,4-Dimethoxybenzyl)-5-[(E)-2-[4-(propan-2-yl)phenyl]-2-(tributylstannyl)ethenyl]pyrrolidin-2-one The title compound was obtained as a colorless oil (4.7 g).

$^1$H NMR (300 MHz, CDCl$_3$) δ ppm 0.72-0.93 (m, 15H), 1.13-1.31 (m, 12H), 1.32-1.48 (m, 6H), 1.68-1.88 (m, 1H), 2.04-2.18 (m, 1H), 2.26-2.60 (m, 2H), 2.71-2.93 (m, 1H), 3.67 (s, 3H), 3.76 (s, 3H), 4.03-4.22 (m, 2H), 4.66 (d, J=16 Hz, 1H), 5.56 (d, J=9.0 Hz, 1H), 6.24-6.33 (m, 1H), 6.33-6.41 (m, 1H), 6.55-6.69 (m, 2H), 6.88 (d, J=8.2 Hz, 1H), 6.93-7.03 (m, 2H).

MS(+): 670 [M+H]$^+$.

Reference Example 4-28

(5R)-5-[(E)-2-(4-Chlorophenyl)-2-(tributylstannyl)ethenyl]-1-(2,4-dimethoxybenzyl)pyrrolidin-2-one The title compound was obtained as a pale brown oil (12.8 g).

$^1$H NMR (300 MHz, CDCl$_3$) δ ppm 0.71-0.97 (m, 15H), 1.19-1.48 (m, 12H), 1.65-1.81 (m, 1H), 1.98-2.13 (m, 1H), 2.27-2.55 (m, 2H), 3.71 (s, 3H), 3.79 (s, 3H), 3.97-4.15 (m, 2H), 4.71 (d, J=15.2 Hz, 1H), 5.60 (d, J=9.0 Hz, 1H), 6.32 (dd, J=8.3, 2.4 Hz, 1H), 6.39 (d, J=2.3 Hz, 1H), 6.51-6.61 (m, 2H), 6.84 (d, J=8.2 Hz, 1H), 7.08 (d, J=8.5 Hz, 2H).

MS(+): 662 [M+H]$^+$.

Reference Example 4-29

(5R)-1-(2,4-Dimethoxybenzyl)-5-{(E)-2-(tributylstannyl)-2-[4-(trifluoromethyl)phenyl]ethenyl}pyrrolidin-2-one The title compound was obtained as a pale orange oil (8.9 g).

$^1$H NMR (300 MHz, CDCl$_3$) δ ppm 0.83-0.90 (m, 15H), 1.18-1.48 (m, 12H), 1.62-1.84 (m, 1H), 1.99-2.13 (m, 1H), 2.28-2.57 (m, 2H), 3.71 (s, 3H), 3.76 (brs, 3H), 3.91-4.03 (m, 1H), 4.08 (d, J=15.7 Hz, 1H), 4.73 (d, J=15.4 Hz, 1H), 5.63 (d, J=9.2 Hz, 1H), 6.29 (dd, J=8.3, 2.4 Hz, 1H), 6.39 (d, J=2.3 Hz, 1H), 6.71 (d, J=7.9 Hz, 2H), 6.80 (d, J=8.2 Hz, 1H), 7.35 (d, J=7.9 Hz, 2H).

MS(+): 696 [M+H]$^+$.

Reference Example 4-30

(5R)-1-(2,4-Dimethoxybenzyl)-5-{(E)-2-(tributylstannyl)-2-[5-(trifluoromethyl)pyridin-2-yl]ethenyl}pyrrolidin-2-one The title compound was obtained as a colorless powder (800 mg).

$^1$H NMR (300 MHz, CDCl$_3$) δ ppm 0.70-1.07 (m, 15H), 1.14-1.34 (m, 6H), 1.35-1.51 (m, 6H), 1.69-1.96 (m, 1H), 2.08-2.71 (m, 3H), 3.66 (s, 3H), 3.74 (s, 3H), 3.93-4.38 (m, 2H), 4.71-5.07 (m, 1H), 5.69-5.91 (m, 1H), 6.13-6.44 (m, 2H), 6.59-6.76 (m, 1H), 6.78-6.96 (m, 1H), 7.48-7.76 (m, 1H), 8.65-8.83 (m, 1H).

MS(+): 697 [M+H]$^+$.

Reference Example 4-31

3-Bromo-6-iodo-2-methoxypyridine (1) Sodium iodide (40 g), copper iodide (6.0 g) and N,N'-dimethylethylenediamine (7 mL) was added to a solution of 6-bromo-2-methoxypyridin-3-amine (26 g) in 1,4-dioxane (250 mL) in a nitrogen gas stream, and the mixture was stirred at 120° C. for 14 hours. The reaction solution was left to cool, and then water and ethyl acetate were added. Filtration through celite was followed by extraction. The organic layer was washed with a 20% sodium thiosulfate solution and brine, dried over anhydrous magnesium sulfate and filtered. The solvent was then evaporated under reduced pressure. The residue was purified by silica gel column chromatography (hexane:ethyl acetate=85:15→70:30) to give 6-iodo-2-methoxypyridin-3-amine as a colorless powder (25 g, 75%).

$^1$H NMR (300 MHz, CDCl$_3$) δ ppm 3.66-3.83 (brs, 2H), 3.96 (s, 3H), 6.58 (d, J=7.6 Hz, 1H), 7.09 (d, J=7.8 Hz, 1H).

MS(+): 251 [M+H]$^+$.

(2) tert-Butyl nitrite (6.2 mL), copper(I) bromide (5.0 g) and copper(II) bromide (6.5 g) were sequentially added to a solution of 6-iodo-2-methoxypyridin-3-amine (25 g) in acetonitrile (400 mL) under ice-cooling, and the mixture was stirred at 65° C. for two hours. The reaction solution was poured into 1 M hydrochloric acid, followed by extraction with ethyl acetate. The organic layer was washed with brine, dried over anhydrous magnesium sulfate and filtered. The solvent was then evaporated under reduced pressure. The residue was purified by silica gel column chromatography (hexane:ethyl acetate=70:30→0:100) to give the title compound (3.7 g) as a colorless powder.

$^1$H NMR (300 MHz, CDCl$_3$) δ ppm 4.00 (s, 3H), 7.19 (d, J=7.8 Hz, 1H), 7.40 (d, J=7.8 Hz, 1H).

MS(+): 313 [M+H]$^+$.

Reference Example 4-32

6-Iodo-2-[(4-methoxybenzyl)oxy]-3-propoxypyridine (1) Potassium carbonate (1.38 g) and n-propyl iodide (1.13 g) were added to a solution of 2-bromo-6-iodopyridin-3-ol (1.0 g, described in WO 2007088996) in N,N-dimethylformamide (10 mL), and the mixture was stirred at room temperature for two hours. The reaction solution was poured into water, followed by extraction with ethyl acetate. The organic layer was washed with brine, dried over anhydrous magnesium sulfate and filtered, after which the solvent was evaporated under reduced pressure to give 2-bromo-6-iodo-3-propoxypyridine as a crude product.

(2) 4-Methoxybenzyl alcohol (689 mg) was added to a solution of sodium hydride (200 mg) in N,N-dimethylformamide (4 mL) under ice-cooling, and the mixture was stirred at room temperature for 15 minutes. A solution of 2-bromo-6-iodo-3-propoxypyridine in N,N-dimethylformamide (2 mL) was added thereto, and the mixture was stirred at 85° C. for six hours. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (hexane:ethyl acetate=10:1→1:1) to give the title compound as a colorless powder (670 mg).

$^1$H NMR (300 MHz, CDCl$_3$) δ ppm 0.87-1.11 (m, 3H), 1.69-1.91 (m, 2H), 3.81 (s, 3H), 3.85-3.98 (m, 2H), 5.35 (s, 2H), 6.72 (d, J=8.1 Hz, 1H), 6.83-6.95 (m, 2H), 7.18 (d, J=7.9 Hz, 1H), 7.36-7.52 (m, 2H).

MS(+): 400 [M+H]$^+$.

The compounds of Reference Examples 4-33 to 4-35 were synthesized by performing substantially the same reaction as in Reference Example 4-32 except for using methyl iodide, methyl chlorodifluoroacetate and 2-iodopropane in place of 1-iodopropane.

Reference Example 4-33

6-Iodo-3-methoxy-2-[(4-methoxybenzyl)oxy]pyridine

The title compound was obtained as a colorless oil (660 mg, 29% (two steps)).

$^1$H NMR (300 MHz, CDCl$_3$) δ ppm 3.80 (s, 6H), 5.36 (s, 2H), 6.72 (d, J=8.1 Hz, 1H), 6.89 (d, J=8.7 Hz, 2H), 7.21 (d, J=8.1 Hz, 1H), 7.45 (d, J=8.7 Hz, 2H).

MS(+): 372 [M+H]$^+$.

Reference Example 4-34

3-(Difluoromethoxy)-6-iodo-2-[(4-methoxybenzyl)oxy]pyridine

The title compound (1.53 g, 23% (two steps)) was obtained as a colorless oil by performing reaction at 90° C.

$^1$H NMR (300 MHz, CDCl$_3$) δ ppm 3.82 (s, 3H), 5.36 (s, 2H), 6.22-6.81 (m, 1H), 6.86-6.95 (m, 2H), 7.08 (d, J=7.9 Hz, 1H), 7.29 (d, J=7.9 Hz, 1H), 7.41 (d, J=8.7 Hz, 2H).

Reference Example 4-35

6-Iodo-2-[(4-methoxybenzyl)oxy]-3-(propan-2-yloxy)pyridine

The title compound was obtained as a colorless powder (430 mg).

$^1$H NMR (300 MHz, CDCl$_3$) δ ppm 1.30 (d, J=6.1 Hz, 6H), 3.81 (s, 3H), 4.33-4.53 (m, 1H), 5.34 (s, 2H), 6.76 (d, J=7.9 Hz, 1H), 6.85-6.96 (m, 2H), 7.18 (d, J=7.9 Hz, 1H), 7.38-7.47 (m, 2H).

MS(+): 400 [M+H]$^+$.

Reference Example 4-36

6-Iodo-2-methoxypyridin-3-ol (1) Potassium carbonate (12 g) and 4-methoxybenzyl chloride (8.8 mL) were added to a solution of 2-bromo-6-iodopyridin-3-ol (12 g) in N,N-dimethylformamide (130 mL), and the mixture was stirred at room temperature for six hours. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (hexane:ethyl acetate=90:1→0:100) to give 2-bromo-6-iodo-3-[(4-methoxybenzyl)oxy]pyridine as a colorless powder (18 g, 100%).

(2) Sodium methoxide (11 g) was added to a solution of 2-bromo-6-iodo-3-[(4-methoxybenzyl)oxy]pyridine (17 g) in dimethyl sulfoxide (90 mL), and the mixture was stirred at 90° C. for three hours. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (hexane:ethyl acetate=95:5→70:30) to give 6-iodo-2-methoxy-3-[(4-methoxybenzyl)oxy]pyridine as a colorless powder (10 g, 71%).

(3) Triisopropylsilane (2.1 g) and trifluoroacetic acid (4.0 mL) were added to a solution of 6-iodo-2-methoxy-3-[(4-methoxybenzyl)oxy]pyridine (1 g) in chloroform (10 mL), and the mixture was stirred at 0° C. for one hour. The solvent was evaporated from the reaction solution under reduced pressure. The residue was purified by silica gel column chromatography (hexane:ethyl acetate=90:10→50:50) to give the title compound as a colorless powder (604 mg, 96%).

$^1$H NMR (300 MHz, CDCl$_3$) δ ppm 4.01 (s, 3H), 6.82 (d, J=7.9 Hz, 1H), 7.20 (d, J=7.8 Hz, 1H).

MS(+): 252 [M+H]$^+$.

The compounds of Reference Examples 4-37 to 4-39 were synthesized by performing substantially the same reaction as in Reference Example 4-36(1) except for using 6-iodo-2-methoxypyridin-3-ol obtained in Reference Example 4-36, using sodium hydride in place of potassium carbonate and using corresponding alkyl halides (cyclopentyl iodide, 3-bromopropoxy-tert-butyldimethylsilane and 3-bromo-2,2-dimethylpropoxy-tert-butyldiphenylsilane) in place of 4-methoxybenzyl chloride, respectively.

Reference Example 4-37

3-(Cyclopentyloxy)-6-iodo-2-methoxypyridine

The title compound was obtained as a light red oil (169 mg, 66%).

$^1$H NMR (300 MHz, CDCl$_3$) δ ppm 1.56-1.69 (m, 2H), 1.73-1.97 (m, 6H), 3.96 (s, 3H), 4.66-4.76 (m, 1H), 6.72 (d, J=8.4 Hz, 1H), 7.18 (d, J=7.9 Hz, 1H).
MS(+): 320 [M+H]$^+$.

Reference Example 4-38

3-(3-{[tert-Butyl(dimethyl)silyl]oxy}propoxy)-6-iodo-2-methoxypyridine

The title compound was obtained as a colorless oil (638 mg, 100%).

$^1$H NMR (300 MHz, CDCl$_3$) δ ppm 0.08 (s, 6H), 0.88 (s, 9H), 2.02-2.09 (m, 2H), 3.79 (t, J=5.8 Hz, 2H), 3.98 (s, 3H), 4.09 (t, J=6.5 Hz, 2H), 6.78 (d, J=7.9 Hz, 1H), 7.21 (d, J=7.9 Hz, 1H).
MS(+): 424 [M+H]$^+$.

Reference Example 4-39

3-(3-{[tert-Butyl(diphenyl)silyl]oxy}-2,2-dimethyl-propoxy)-6-iodo-2-methoxypyridine The title compound was obtained as a colorless oil (37 mg, 7%).

$^1$H NMR (300 MHz, CDCl$_3$) δ ppm 1.01 (s, 9H), 1.02 (s, 6H), 3.53 (s, 2H), 3.76 (s, 2H), 3.92 (s, 3H), 6.70 (d, J=7.9 Hz, 1H), 7.16 (d, J=7.9 Hz, 1H), 7.28-7.40 (m, 6H), 7.57-7.62 (m, 4H).
MS(+): 576 [M+H]$^+$.

Reference Example 4-40

1-(6-Bromo-2-methoxypyridin-3-yl)ethanone

A solution of 6-bromo-3-iodo-2-methoxypyridine (500 mg) in diethyl ether (15 mL) was cooled to −80° C. in a nitrogen atmosphere, and n-butyllithium (2.6 M, 0.735 mL) were added dropwise. After stirring at the same temperature for one hour, N,N-dimethylacetamide (0.37 mL) was added dropwise. The mixture was warmed to −40° C. over 1.5 hours to complete the reaction. Water and ethyl acetate was added to the reaction system. The organic layer was washed with brine and then dried over anhydrous magnesium sulfate and filtered, after which the solvent was evaporated under reduced pressure. The residue was purified by silica gel column chromatography (hexane:ethyl acetate=9:1→4:1) to give the title compound as a colorless powder (284 mg, 78%).

$^1$H NMR (300 MHz, CDCl$_3$) δ ppm 2.62 (s, 3H), 4.08 (s, 3H), 7.16 (d, J=7.8 Hz, 1H), 7.97 (d, J=7.8 Hz, 1H).
MS(+): 230 [M+H]$^+$.

Reference Example 4-41 tert-Butyl 3-(6-bromo-2-methoxypyridin-3-yl)propanoate (1) A solution of 6-bromo-3-iodo-2-methoxypyridine (1.0 g) in diethyl ether (38 mL) was cooled to −80° C. in a nitrogen atmosphere, and n-butyllithium (2.6 M, 0.735 mL) were added dropwise. After stirring at the same temperature for one hour, N,N-dimethylformamide (0.62 mL) was added dropwise. The mixture was stirred at the same temperature for one hour and water was added to the reaction system, followed by extraction with ethyl acetate. The organic layer was washed with brine, dried over anhydrous magnesium sulfate and filtered, after which the solvent was evaporated under reduced pressure. The residue was purified by silica gel column chromatography (hexane:ethyl acetate=94:6→9:1) to give 6-bromo-2-methoxynicotinaldehyde as a colorless powder (618 mg, 90%).

(2) (tert-Butoxycarbonylmethylene)triphenylphosphorane (1.74 g) was added to a solution of 6-bromo-2-methoxynicotinaldehyde (500 mg) in chloroform (5 mL) under ice-cooling, followed by stirring for one hour. The solvent was evaporated from the reaction solution under reduced pressure. The residue was purified by silica gel column chromatography (hexane:ethyl acetate=9:1) to give tert-butyl 3-(6-bromo-2-methoxypyridin-3-yl)acrylate as a colorless oil (726 mg, 100%).

(3) 10% platinum-activated carbon was added to a solution of tert-butyl 3-(6-bromo-2-methoxypyridin-3-yl)acrylate (727 mg) in ethyl acetate (7.3 mL), and the mixture was stirred for four hours in a hydrogen atmosphere. The reaction solution was filtered through celite and the filtrate was concentrated. The residue was purified by silica gel column chromatography (hexane:ethyl acetate=8:1) to give the title compound as a colorless oil (657 mg, 90%).

$^1$H NMR (300 MHz, CDCl$_3$) δ ppm 1.41 (s, 9H), 2.42-2.56 (m, 2H), 2.72-2.84 (m, 2H), 3.96 (s, 3H), 6.98 (d, J=7.6 Hz, 1H), 7.27 (d, J=7.6 Hz, 1H).
MS(+): 316 [M+H]$^+$.

Reference Example 4-42

(5R)-5-[(E)-2-(5-Bromo-6-methoxypyridin-2-yl)-2-(4-tert-butylphenyl)ethenyl]pyrrolidin-2-one (1) (5R)-5-[(E)-2-(4-tert-Butylphenyl)-2-(tributylstannyl) ethenyl]-1-(2,4-dimethoxybenzyl)pyrrolidin-2-one (4.0 g), 3-bromo-6-iodo-2-methoxypyridine (3.7 g), cesium fluoride (1.8 g) and copper iodide (1.3 g) were subjected to replacement with nitrogen and N,N-dimethylformamide (40 mL) was added, followed by degassing.

Tetrakis(triphenylphosphine)palladium(0) (693 mg) was added thereto and the mixture was stirred at 65° C. for two hours. After returning to room temperature, water and ethyl acetate were added and the mixture was filtered through celite. The filtrate was extracted with ethyl acetate. The organic layer was washed with water and brine, dried over anhydrous magnesium sulfate and filtered, after which the filtrate was concentrated under reduced pressure. The residue was purified by silica gel column chromatography (hexane: ethyl acetate=4:1→1:1) to give (5R)-5-[(E)-2-(5-bromo-6-methoxypyridin-2-yl)-2-(4-tert-butylphenyl)ethenyl]-1-(2, 4-dimethoxybenzyl)pyrrolidin-2-one as a brown powder (2.6 g, 77%).

$^1$H NMR (300 MHz, CDCl$_3$) δ ppm 1.32 (s, 9H), 1.80-1.95 (m, 1H), 2.06-2.20 (m, 1H), 2.32-2.46 (m, 1H), 2.48-2.61 (m, 1H), 3.59 (s, 3H), 3.76 (s, 3H) 3.98 (s, 3H), 4.01-4.11 (m, 1H), 4.17 (d, J=15.1 Hz, 1H), 4.63 (d, J=15.4 Hz, 1H), 6.23 (d, J=7.9 Hz, 1H), 6.27-6.34 (m, 2H), 6.79 (d, J=9.8 Hz, 1H), 6.87-6.98 (m, 3H), 7.26-7.32 (m, 2H), 7.80 (d, J=7.8 Hz, 1H).
MS(+): 579 [M+H]$^+$.

(2) Trifluoroacetic acid (10 mL) and anisole (5 mL) were added to (5R)-5-[(E)-2-(5-bromo-6-methoxypyridin-2-yl)-2-(4-tert-butylphenyl)ethenyl]-1-(2,4-dimethoxybenzyl)pyrrolidin-2-one (950 mg), and the mixture was stirred at 70° C.

for five hours. The reaction solution was concentrated under reduced pressure. The residue was purified by silica gel column chromatography (hexane:ethyl acetate=4:1→1:4) to give the title compound as a yellow amorphous (460 mg, 66%).

$^1$H NMR (300 MHz, CDCl$_3$) δ ppm 1.37 (s, 9H), 2.20-2.51 (m, 4H), 4.07 (s, 3H), 4.14-4.23 (m, 1H), 5.48-5.63 (brs, 1H), 6.29 (d, J=7.9 Hz, 1H), 6.89 (d, J=9.5 Hz, 1H), 7.08 (d, J=8.5 Hz, 2H), 7.44 (d, J=8.5 Hz, 2H), 7.61 (d, J=7.9 Hz, 1H).

MS(+): 429 [M+H]$^+$.

The compounds of Reference Examples 4-43 and 4-44 were synthesized by performing substantially the same reaction as in Reference Example 4-42(1) except for using (5R)-5-[(E)-2-(4-chlorophenyl)-2-(tributylstannyl)ethenyl]-1-(2,4-dimethoxybenzyl)pyrrolidin-2-one (Reference Example 4-28) and (5R)-1-(2,4-dimethoxybenzyl)-5-{(E)-2-(tributylstannyl)-2-[4-(trifluoromethyl)phenyl]ethenyl}pyrrolidin-2-one (Reference Example 4-29) in place of (5R)-5-[(E)-2-(4-tert-butylphenyl)-2-(tributylstannyl)ethenyl]-1-(2,4-dimethoxybenzyl)pyrrolidin-2-one.

Reference Example 4-43

(5R)-5-[(E)-2-(5-Bromo-6-methoxypyridin-2-yl)-2-(4-chlorophenyl)ethenyl]-1-(2,4-dimethoxybenzyl)pyrrolidin-2-one The title compound was obtained as a light yellow amorphous (2.37 g, 80%).

$^1$H NMR (300 MHz, CDCl$_3$) δ ppm 1.77-1.92 (m, 1H), 2.02-2.15 (m, 1H), 2.31-2.45 (m, 1H), 2.47-2.62 (m, 1H), 3.62 (s, 3H), 3.78 (s, 3H), 3.92-4.03 (m, 4H), 4.15 (d, J=15.1 Hz, 1H), 4.69 (d, J=15.2 Hz, 1H), 6.19 (d, J=7.9 Hz, 1H), 6.31-6.37 (m, 2H), 6.79 (d, J=9.8 Hz, 1H), 6.87 (d, J=8.5 Hz, 2H), 6.92 (d, J=8.9 Hz, 1H), 7.25 (d, J=9.5 Hz, 2H), 7.61 (d, J=7.9 Hz, 1H).

MS(+): 557 [M+H]$^+$.

Reference Example 4-44

(5R)-5-{(E)-2-(5-Bromo-6-methoxypyridin-2-yl)-2-[4-(trifluoromethyl)phenyl]ethenyl}-1-(2,4-dimethoxybenzyl)pyrrolidin-2-one The title compound was obtained as a light yellow amorphous (2.47 g, 82%).

$^1$H NMR (300 MHz, CDCl$_3$) δ ppm 1.79-1.94 (m, 1H), 2.05-2.17 (m, 1H), 2.33-2.46 (m, 1H), 2.49-2.62 (m, 1H), 3.62 (s, 3H), 3.77 (s, 3H), 3.89-4.02 (m, 4H), 4.15 (d, J=15.4 Hz, 1H), 4.70 (d, J=15.2 Hz, 1H), 6.16 (d, J=7.9 Hz, 1H), 6.28-6.36 (m, 2H), 6.82 (d, J=10.1 Hz, 1H), 6.89 (d, J=8.1 Hz, 1H), 7.05 (d, J=7.8 Hz, 2H), 7.52 (d, J=8.4 Hz, 2H), 7.61 (d, J=7.9 Hz, 1H).

MS(+): 591 [M+H]$^+$.

Reference Example 4-45

1-Propan-2-yl-3-[4-(4,4,5,5-tetramethyl-1,3,2-dioxaborolan-2-yl)phenyl]urea

The title compound was obtained as a yellow oil (2.2 g, 79% (two steps)) by performing substantially the same reaction as in Reference Example 4-26 except for using 1-(cyclopropylsulfonyl)-4-iodobenzene (Reference Example 5-55) in place of 1-tert-butyl-4-iodobenzene.

$^1$H NMR (300 MHz, CDCl$_3$) δ ppm 0.82-0.91 (m, 15H), 0.97-1.06 (m, 2H), 1.19-1.49 (m, 14H), 1.68-1.83 (m, 1H), 2.00-2.14 (m, 1H), 2.30-2.57 (m, 3H), 3.74 (s, 3H), 3.79 (s, 3H), 3.86-3.98 (m, 1H), 4.08 (d, J=15.7 Hz, 1H), 4.74 (d, J=15.7 Hz, 1H), 5.65 (d, J=9.2 Hz, 1H), 6.30 (dd, J=8.3, 2.4 Hz, 1H), 6.39 (d, J=2.3 Hz, 1H), 6.73-6.83 (m, 3H), 7.61 (d, J=8.5 Hz, 2H).

MS(+): 732 [M+H]$^+$.

The structures of Reference Examples 4-12 to 4-45 are shown below.

[Hyo 7-1]

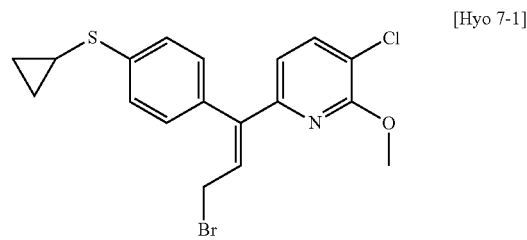

Reference Example 4-12

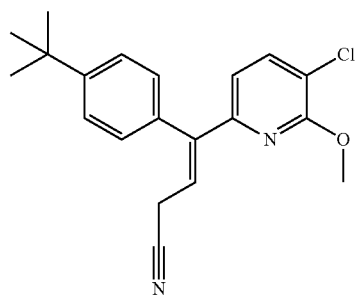

Reference Example 4-13

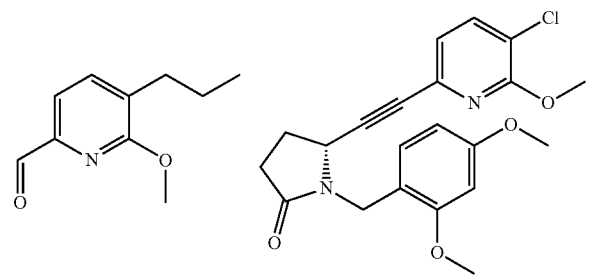

Reference Example 4-14  Reference Example 4-15

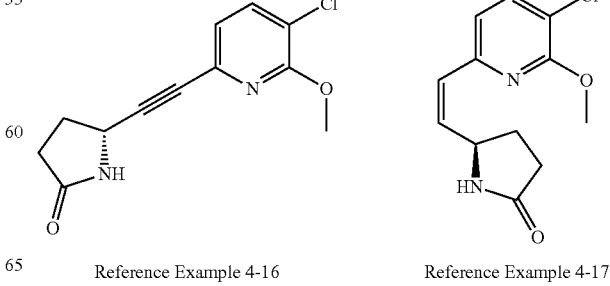

Reference Example 4-16  Reference Example 4-17

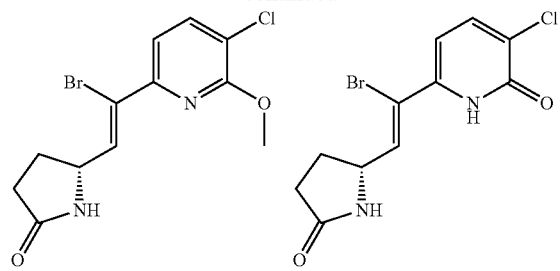
Reference Example 4-18　　Reference Example 4-19
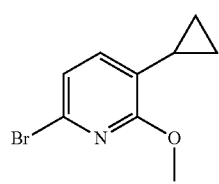
Reference Example 4-20
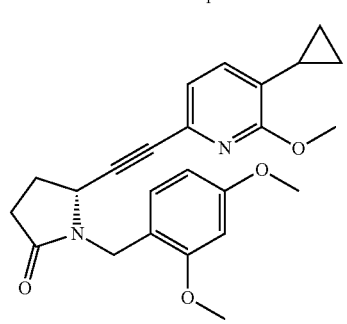
Reference Example 4-21
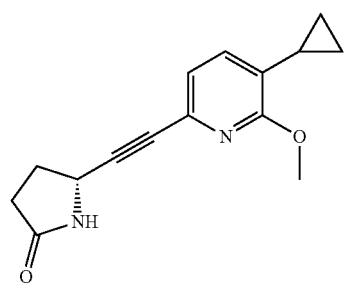
Reference Example 4-22
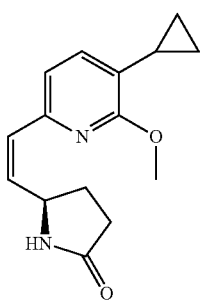
Reference Example 4-23
[Hyo 7-2]
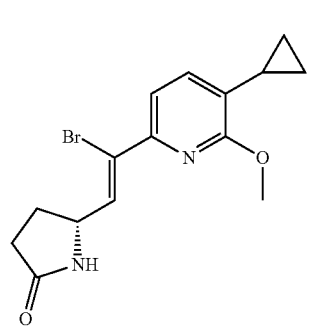
Reference Example 4-24
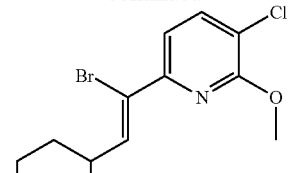
Reference Example 4-25
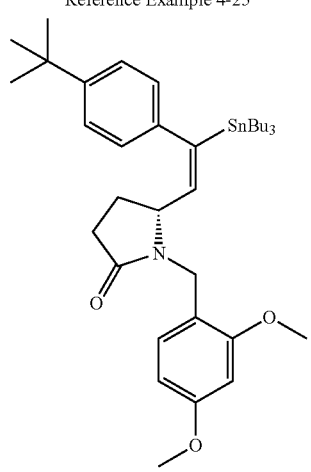
Reference Example 4-26
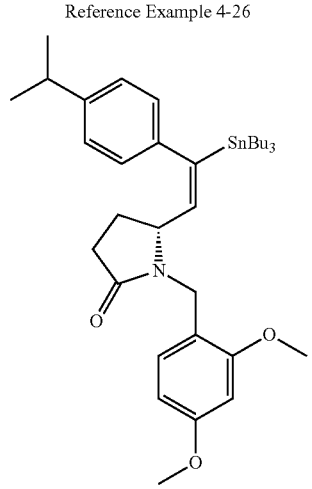
Reference Example 4-27
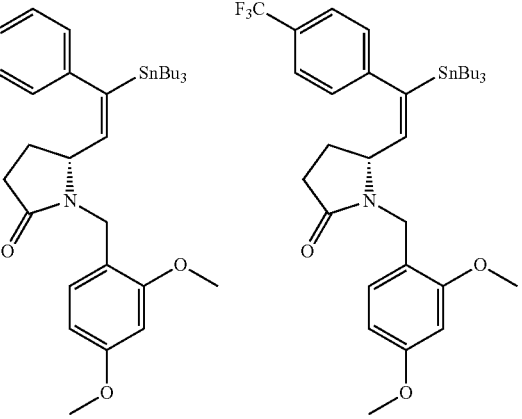
Reference Example 4-28　　Reference Example 4-29

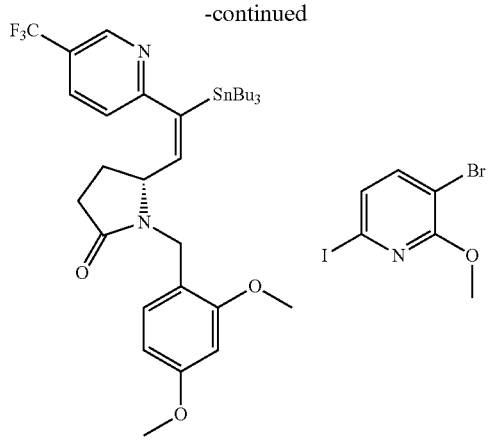
Reference Example 4-30
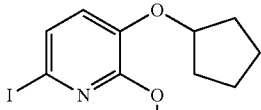
Reference Example 4-31
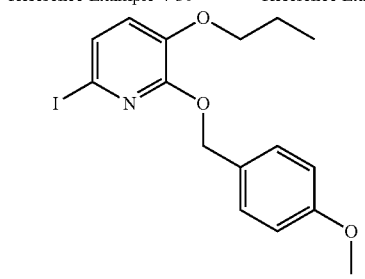
Reference Example 4-32
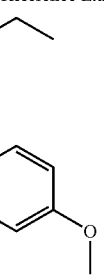
Reference Example 4-33
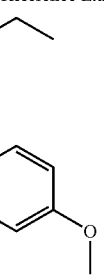
Reference Example 4-34
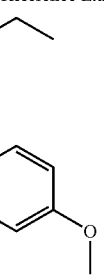
Reference Example 4-35
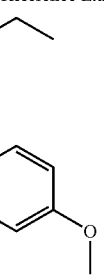
Reference Example 4-36
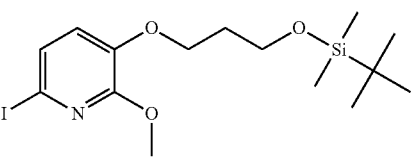
Reference Example 4-37
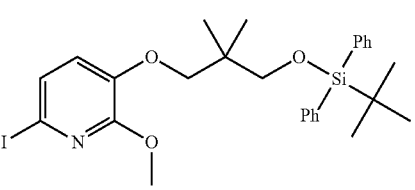
Reference Example 4-38
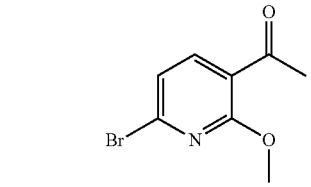
Reference Example 4-39
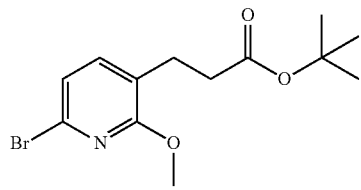
Reference Example 4-40
Reference Example 4-41
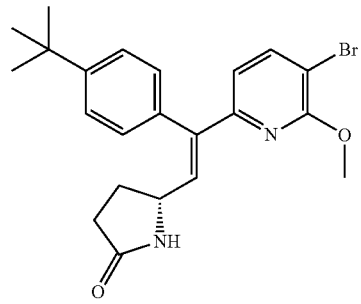
Reference Example 4-42
[Hyo 7-3]

-continued

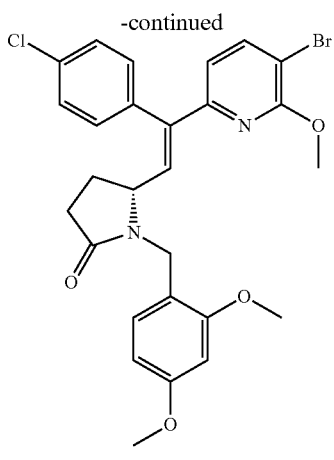

Reference Example 4-43

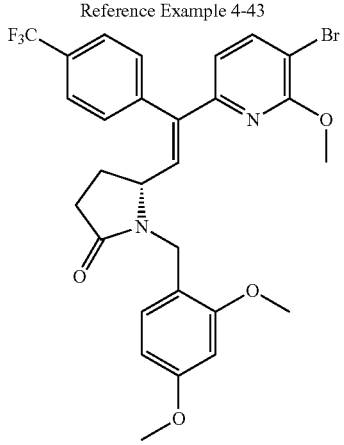

Reference Example 4-44

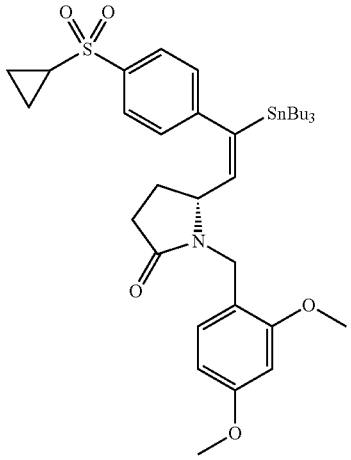

Reference Example 4-45

Reference Example 5-1

(4-Chloro-3-methoxyphenyl)boronic acid n-Butyllithium (2.76 M, 2.5 mL) was added dropwise to a solution of commercially available 4-bromo-2-chloroanisole (1.0 g) in toluene (8 mL) and tetrahydrofuran (3 mL) at −78° C., and the mixture was stirred as such for 30 minutes. Thereafter, trimethyl borate (1.0 mL) was added and the mixture was stirred at room temperature for 15 minutes. Dilute hydrochloric acid and ethyl acetate were added, followed by extraction with ethyl acetate. The organic layer was dried over anhydrous magnesium sulfate and filtered. The filtrate was concentrated under reduced pressure. The resulting residue was purified by silica gel column chromatography (hexane:ethyl acetate=100:0→98:2) to give the title compound as a colorless powder (535 mg).

$^1$H NMR (600 MHz, METHANOL-d4) δ ppm 3.88 (s, 3H), 7.15 (d, J=7.8 Hz, 1H) 7.24 (s, 1H) 7.34 (d, J=7.8 Hz, 1H).

Reference Example 5-2

[3-Chloro-4-(trifluoromethoxy)phenyl]boronic acid

The title compound was obtained by performing substantially the same reaction as in Reference Example 5-1 except for using 4-bromo-2-chloro-1-(trifluoromethoxy)benzene in place of 4-bromo-2-chloroanisole.

$^1$H NMR (600 MHz, METHANOL-d4) δ ppm 7.34-7.44 (m, 1H), 7.58-7.82 (m, 2H).

MS(−): 239 [M−H]$^−$.

Reference Example 5-3

[4-Chloro-3-(trifluoromethoxy)phenyl]boronic acid

The title compound was obtained by performing substantially the same reaction as in Reference Example 5-1 except for using 4-bromo-1-chloro-2-(trifluoromethoxy)benzene in place of 4-bromo-2-chloroanisole.

$^1$H NMR (600 MHz, CDCl$_3$) δ ppm 4.60 (s, 2H), 7.63-7.66 (m, 1H), 8.02-8.04 (m, 1H), 8.05-8.08 (m, 1H).

MS(−): 239 [M−H]$^−$.

Reference Example 5-4

[4-Chloro-3-(difluoromethoxy)phenyl]boronic acid (1) A suspension of 5-bromo-2-chloro-1-(difluoromethoxy)benzene (1.0 g), a 1,1'-bis(diphenylphosphino)ferrocenepalladium chloride-dichloromethane complex (317 mg), bis(pinacolato)diborane (1.48 g) and potassium acetate (1.14 g) in 1,4-dioxane (20 mL) were stirred at 80° C. for 14 hours. Ethyl acetate and a saturated ammonium chloride solution were added to the reaction solution, and the insoluble matter was filtered off through celite, after which the filtrate was extracted with ethyl acetate. The organic layer was dried over anhydrous magnesium sulfate and filtered. The filtrate was concentrated under reduced pressure. The resulting residue was purified by silica gel column chromatography (hexane:ethyl acetate=100:0→99:1) to give a crude product of 2-(4-chloro-3-difluoromethoxyphenyl)-4,4,5,5-tetramethyl-1,3,2-dioxaborolane (1.14 g).

(2) 2 M hydrochloric acid (10 mL) was added to the crude product of 2-(4-chloro-3-difluoromethoxyphenyl)-4,4,5,5-tetramethyl-1,3,2-dioxaborolane (1.14 g) in tetrahydrofuran (10 mL), and the mixture was stirred at room temperature for four hours. Water and ethyl acetate were added to the reaction solution, followed by extraction with ethyl acetate. The organic layer was extracted with a 2 M sodium hydroxide solution. The resulting solution was made acidic with concentrated hydrochloric acid and then extracted with ethyl acetate. The organic layer was dried over anhydrous magnesium sulfate and filtered. The filtrate was concentrated under reduced pressure. The resulting residue was purified by silica gel column chromatography (hexane:ethyl acetate=99:1→50:50) to give the title compound (93 mg).

$^1$H NMR (600 MHz, CDCl$_3$) δ ppm 6.64 (t, J=73.0 Hz, 1H), 7.60-7.63 (m, 1H), 7.96-8.01 (m, 2H).

Reference Example 5-5

2-[3-Chloro-4-(difluoromethyl)phenyl]-4,4,5,5-tetramethyl-1,3,2-dioxaborolane (1) Deoxo-fluoro(R) (5.63 mL) and ethanol (several drops) were added to a solution of 4-bromo-2-chlorobenzaldehyde (3.2 g) in chloroform (30 mL) under ice-cooling, and the mixture was stirred at 80° C. for two hours. The reaction solution was poured into saturated aqueous sodium bicarbonate, followed by extraction with chloroform. The organic layer was washed with brine, dried over anhydrous magnesium sulfate and filtered. The solvent was then evaporated under reduced pressure. The residue was purified by silica gel column chromatography (hexane:ethyl acetate=100:0→90:10) to give 4-bromo-2-chloro-1-(difluoromethyl)benzene (3.0 g) as a colorless oil.

(2) Bis(pinacolato)diborane (2.1 g), a 1,1'-bis(diphenylphosphino)ferrocene-palladium(II) dichloride-dichloromethane complex (346 mg) and potassium acetate (812 mg) were added to a solution of 4-bromo-2-chloro-1-(difluoromethyl)benzene (1.0 g) in 1,4-dioxane (10 mL), and the mixture was stirred at 65° C. for three hours. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (hexane:ethyl acetate=100:0→90:10) to give the title compound (780 mg, 65%) as a colorless oil.

$^1$H NMR (300 MHz, CDCl$_3$) δ ppm 1.35 (s, 12H), 6.71-7.17 (m, 1H), 7.58-7.69 (m, 1H), 7.73-7.80 (m, 1H), 7.81-7.88 (m, 1H).

The compounds of Reference Examples 5-6 to 5-9 were synthesized by performing substantially the same reaction as in Reference Example 5-5 except for using corresponding aldehydes (4-bromo-2-fluorobenzaldehyde, 4-bromo-2-methylbenzaldehyde, 4-bromo-2-methoxybenzaldehyde and 4-bromo-2-(methylsulfonyl)benzaldehyde) in place of 4-bromo-2-chlorobenzaldehyde, respectively.

Reference Example 5-6

2-[4-(Difluoromethyl)-3-fluorophenyl]-4,4,5,5-tetramethyl-1,3,2-dioxaborolane

The title compound was obtained as a colorless oil (540 mg).

$^1$H NMR (300 MHz, CDCl$_3$) δ ppm 1.35 (s, 12H), 6.61-7.18 (m, 1H), 7.41-7.73 (m, 3H).

Reference Example 5-7

2-[4-(Difluoromethyl)-3-methylphenyl]-4,4,5,5-tetramethyl-1,3,2-dioxaborolane

The title compound was obtained as a colorless powder (1.0 g).

$^1$H NMR (300 MHz, CDCl$_3$) δ ppm 1.35 (s, 12H), 2.43 (s, 3H), 6.50-7.07 (m, 1H), 7.41-7.56 (m, 1H), 7.62-7.83 (m, 2H).

Reference Example 5-8

2-[4-(Difluoromethyl)-3-methoxyphenyl]-4,4,5,5-tetramethyl-1,3,2-dioxaborolane

The title compound was obtained as a colorless oil (400 mg).

$^1$H NMR (300 MHz, CDCl$_3$) δ ppm 1.36 (s, 12H), 3.91 (s, 3H), 6.74-7.17 (m, 1H), 7.30-7.37 (m, 1H), 7.44-7.51 (m, 1H), 7.53-7.61 (m, 1H).

Reference Example 5-9

2-[4-(Difluoromethyl)-3-(methylsulfonyl)phenyl]-4,4,5,5-tetramethyl-1,3,2-dioxaborolane The title compound was obtained as a colorless powder (982 mg).

$^1$H NMR (300 MHz, CDCl$_3$) δ ppm 1.36 (s, 12H), 3.13 (s, 3H), 7.65 (s, 1H), 7.89 (d, J=7.6 Hz, 1H), 8.16 (d, J=7.1 Hz, 1H), 8.52 (d, J=0.8 Hz, 1H).

Reference Example 5-10

N-(2-{[tert-Butyl(dimethyl)silyl]oxy}ethyl)-N-methyl-4-(4,4,5,5-tetramethyl-1,3,2-dioxaborolan-2-yl)benzenesulfonamide (1) A solution of 4-bromobenzenesulfonyl chloride (1.10 g) in chloroform (10 mL) was stirred in an ice bath, during which N-methylethanolamine (5 mL) was slowly added dropwise thereto. The mixture was returned to room temperature and stirred for about 2.5 hours. The reaction solution was quenched with concentrated hydrochloric acid with stirring again in an ice bath. The mixed solution was poured into 6 M hydrochloric acid (10 mL) as such, followed by extraction with chloroform. The organic layer was dried over anhydrous magnesium sulfate and filtered, after which the filtrate was concentrated under reduced pressure to give a crude product of 4-bromo-N-(2-hydroxyethyl)-N-methylbenzenesulfonamide as a colorless oil (1.339 g, quant.).

(2) A solution of 4-bromo-N-(2-hydroxyethyl)-N-methylbenzenesulfonamide (1.339 g) in chloroform (15 mL) was stirred in an ice bath, during which tert-butyldimethylchlorosilane (1.04 g) and N,N-dimethyl-4-aminopyridine (84 mg) were added thereto. Triethylamine were added dropwise, and the mixture was returned to room temperature and stirred for 16 hours. The reaction solution was poured into water, followed by extraction with chloroform. The organic layer was dried over anhydrous magnesium sulfate and filtered. The filtrate was concentrated under reduced pressure. The resulting residue was purified by silica gel column chromatography (hexane:ethyl acetate=95:5→60:40) to give 4-bromo-N-(2-{[tert-butyl(dimethyl)silyl]oxy}ethyl)-N-methylbenzenesulfonamide as a colorless powder (1.77 g, 100%).

$^1$H NMR (600 MHz, CDCl$_3$) δ ppm 0.05 (s, 6H), 0.87 (s, 9H), 2.87 (s, 3H), 3.16 (t, J=5.7 Hz, 2H), 3.77 (t, J=5.7 Hz, 2H), 7.66 (s, 4H).

MS(+): 408 [M+H]$^+$.

(3) Bispinacol diborate (2.21 g), a 1,1'-bis(diphenylphosphino)ferrocenepalladium chloride-dichloromethane complex (355 mg) and potassium acetate (853 mg) were added to a solution of 4-bromo-N-(2-{[tert-butyl(dimethyl)silyl]oxy}ethyl)-N-methylbenzenesulfonamide (1.77 g) in 1,4-dioxane (18 mL), and the mixture was stirred at 84° C. for 2.5 hours. The reaction solution was poured into water, followed by extraction with chloroform. The organic layer was dried over anhydrous magnesium sulfate and filtered. The filtrate was concentrated under reduced pressure. The resulting residue was purified by silica gel column chromatography (hexane:ethyl acetate=95:5→60:40) to give the title compound as a colorless powder (2.461 g, quant.).

$^1$H NMR (600 MHz, CDCl$_3$) δ ppm 0.05 (s, 6H), 0.87 (s, 9H), 1.36 (s, 12H), 2.85 (s, 3H), 3.13 (t, J=5.7 Hz, 2H), 3.77 (t, J=5.7 Hz, 2H), 7.77 (d, J=8.3 Hz, 2H), 7.94 (d, J=8.3 Hz, 2H).

MS(+): 456 [M+H]$^+$.

The structures of Reference Examples 5-1 to 5-10 are shown below.

[Hyo 8]

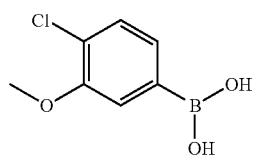

Reference Example 5-1

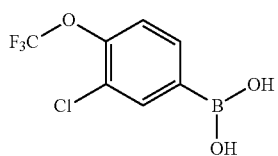

Reference Example 5-2

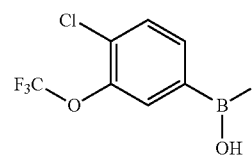

Reference Example 5-3

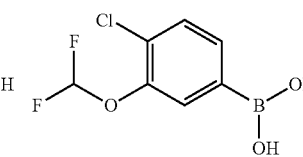

Reference Example 5-4

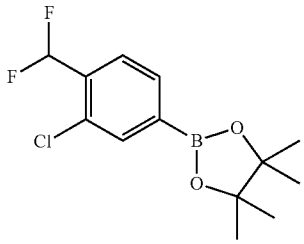

Reference Example 5-5

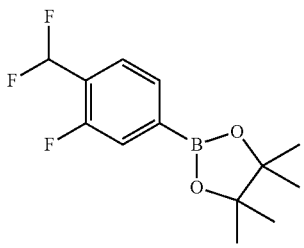

Reference Example 5-6

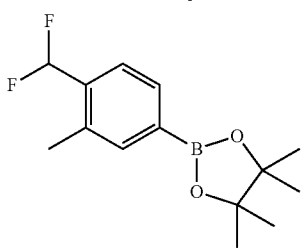

Reference Example 5-7

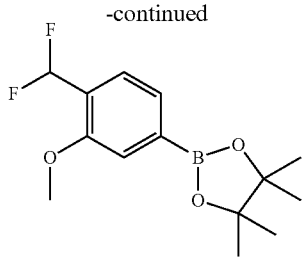

Reference Example 5-8

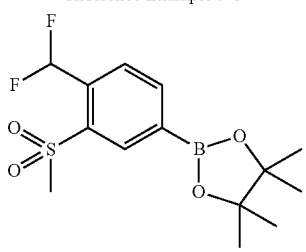

Reference Example 5-9

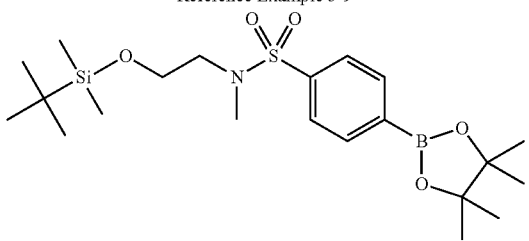

Reference Example 5-10

Reference Example 5-11

5,5-Dimethyl-2-[3-methyl-4-(trifluoromethyl)phenyl]-1,3,2-dioxaborinane

A solution of 4-bromo-2-methylbenzotrifluoride (500 mg) in tetrahydrofuran (5 mL) was cooled to an external temperature of −78° C. in a nitrogen atmosphere, and a solution of n-butyllithium in hexane (1.57 M, 2.0 mL) was added dropwise. After stirring at −78° C. for 30 minutes, triisopropyl borate (0.72 mL) was added dropwise and the mixture was stirred at room temperature overnight. Acetic acid (0.18 mL) and 2,2-dimethyl-1,3-propanediol (240 mg) were added, followed by stirring at room temperature for three hours. Water was added to the reaction solution, followed by extraction with ethyl acetate. The organic layer was washed with water and brine, dried over anhydrous magnesium sulfate and filtered. The solvent was then evaporated under reduced pressure. The residue was purified by silica gel column chromatography (hexane:ethyl acetate=10:1) to give the title compound as a colorless solid (353 mg, 62%).

$^1$H NMR (300 MHz, CDCl$_3$) δ ppm 1.03 (s, 6H), 2.48 (d, J=1.8 Hz, 3H), 3.78 (s, 4H), 7.56 (d, J=7.7 Hz, 1H), 7.67 (d, J=8.9 Hz, 1H), 7.69 (s, 1H).

Reference Example 5-12

6-(5,5-Dimethyl-1,3,2-dioxaborinan-2-yl)-2,2-dimethyl-3,4-dihydro-2H-chromene

The title compound was obtained as a white solid (72 mg, 13%) by performing substantially the same reaction as in Reference Example 5-11 except for using 6-bromo-2,2-dimethyl-3,4-dihydro-2H-chromene in place of 4-bromo-2-methylbenzotrifluoride and using trimethyl borate in place of triisopropyl borate.

$^1$H NMR (300 MHz, CDCl$_3$) δ ppm 1.01 (s, 6H), 1.32 (s, 6H), 1.79 (t, J=6.8 Hz, 2H), 2.77 (t, J=6.9 Hz, 2H), 3.73 (s, 4H), 6.75 (d, J=8.4 Hz, 1H), 7.46-7.58 (m, 2H).

Reference Example 5-13

2-(4-Cyclopropylphenyl)-5,5-dimethyl-1,3,2-dioxaborinane

The title compound was obtained as a colorless solid (721 mg, 63%) by performing substantially the same reaction as in Reference Example 5-11 except for using 4-bromo-1-cyclopropylbenzene in place of 4-bromo-2-methylbenzotrifluoride.

$^1$H NMR (300 MHz, CDCl$_3$) δ ppm 0.65-0.78 (m, 2H), 0.92-1.16 (m, 2H), 1.01 (s, 6H), 1.80-1.95 (m, 1H), 3.77 (s, 4H), 7.04 (d, J=7.7 Hz, 2H), 7.67 (d, J=8.3 Hz, 2H).

Reference Example 5-14

2-[3-Chloro-4-(cyclopropyloxy)phenyl]-5,5-dimethyl-1,3,2-dioxaborinane

The title compound (834 mg, 74%) was obtained by performing substantially the same reaction as in Reference Example 5-11 except for using 4-bromo-2-chloro-1-(cyclopropyloxy)benzene in place of 4-bromo-2-methylbenzotrifluoride.

$^1$H NMR (300 MHz, CDCl$_3$) δ ppm 0.78-0.91 (m, 4H), 1.01 (s, 6H), 3.74 (s, 4H), 3.78-3.86 (m, 1H), 7.25 (d, J=8.0 Hz, 1H), 7.64 (dd, J=8.3, 1.2 Hz, 1H), 7.76 (d, J=1.5 Hz, 1H).

Reference Example 5-15

2-[3-Chloro-4-(2,2,2-trifluoroethoxy)phenyl]-5,5-dimethyl-1,3,2-dioxaborinane (1) 2,2,2-Trifluoroethyliodide (15.2 g) and potassium carbonate (10.0 g) were added to a solution of 4-bromo-2-chlorophenol (5.0 g) in N,N-dimethylformamide (20 mL), and the mixture was stirred at 80° C. for 20 hours. The reaction solution was cooled to room temperature and water was added, followed by extraction with ethyl acetate. The organic layer was washed with brine, dried over anhydrous magnesium sulfate and filtered. The solvent was then evaporated under reduced pressure. The residue was purified by silica gel column chromatography (hexane only) to give 4-bromo-2-chloro-1-(2,2,2-trifluoroethoxy)benzene as a colorless oil (3.0 g, 43%).

(2) The title compound was obtained as a crude product (236 mg, 21%) by performing substantially the same reaction as in Reference Example 5-11 except for using 4-bromo-2-chloro-1-(2,2,2-trifluoroethoxy)benzene in place of 4-bromo-2-methylbenzotrifluoride.

Reference Example 5-16

4-Bromo-2-chloro-1-ethylbenzene

A solution of 4-bromo-2-chloro-1-ethenylbenzene (883 mg), iron(II) acetate (7 mg) and 5% rhodium-activated carbon (167 mg) in tetrahydrofuran (17 mL) was stirred at room temperature for three hours in a hydrogen atmosphere. The reaction solution was filtered through celite and the filtrate was evaporated under reduced pressure. The residue was purified by silica gel column chromatography (hexane only) to give the title compound as a colorless oil (414 mg, 46%).

$^1$H NMR (300 MHz, CDCl$_3$) δ ppm 1.21 (t, J=7.4 Hz, 3H), 2.70 (q, J=7.9 Hz, 2H), 7.09 (d, J=8.9 Hz, 1H), 7.31 (dd, J=8.9, 3.0 Hz, 1H), 7.49 (d, J=3.0 Hz, 1H).

Reference Example 5-17

2-(3-Chloro-4-ethylphenyl)-5,5-dimethyl-1,3,2-dioxaborinane

The title compound was obtained as a colorless oil (148 mg, 27%) by performing substantially the same reaction as in Reference Example 5-11 except for using 4-bromo-2-chloro-1-ethylbenzene obtained in Reference Example 5-16 in place of 4-bromo-2-methylbenzotrifluoride.

$^1$H NMR (300 MHz, CDCl$_3$) δ ppm 1.01 (s, 6H), 1.23 (t, J=7.4 Hz, 3H), 2.76 (q, J=7.4 Hz, 2H), 3.75 (s, 4H), 7.21 (d, J=7.4 Hz, 1H), 7.59 (d, J=7.4 Hz, 1H), 7.74 (s, 1H).

Reference Example 5-18

4-Bromo-1-(cyclopropylsulfanyl)-2-methylbenzene (1) Potassium t-butoxide (994 mg) and bromocyclopropane (2.92 g) were added to a solution of 2-methylbenzenethiol (1.05 g) in dimethyl sulfoxide (10 mL), and the mixture was stirred at 100° C. for 9.5 hours. The reaction solution was cooled to room temperature and brine was added, followed by extraction with ethyl acetate. The organic layer was dried over anhydrous magnesium sulfate and filtered. The solvent was then evaporated under reduced pressure. The residue was purified by silica gel column chromatography (hexane:ethyl acetate=10:1) to give 1-(cyclopropylsulfanyl)-2-methylbenzene as an orange oil (1.41 g, quant.).

(2) Bromine (0.42 mL) was added to a solution of 1-(cyclopropylsulfanyl)-2-methylbenzene (1.35 g) in acetic acid (10 mL) under ice-cooling, and the mixture was stirred at room temperature for 17 hours. The reaction solution was ice-cooled and a saturated sodium thiosulfate solution and brine were added, followed by extraction with ethyl acetate. The organic layer was dried over anhydrous magnesium sulfate and filtered. The solvent was then evaporated under reduced pressure. The residue was purified by silica gel column chromatography (hexane only) and the solvent was evaporated under reduced pressure. The precipitated solid was filtered and washed with hexane, after which the filtrate was evaporated under reduced pressure. The residue was purified by silica gel column chromatography (hexane only) to give the title compound as a pale yellow oil (1.59 g, 80%).

$^1$H NMR (300 MHz, CDCl$_3$) δ ppm 0.62-0.73 (m, 2H), 1.03-1.14 (m, 2H), 2.04-2.14 (m, 1H), 2.22 (s, 3H), 7.25 (d, J=1.1 Hz, 1H), 7.29 (dd, J=8.3, 1.9 Hz, 1H), 7.37 (d, J=8.3 Hz, 1H).

Reference Example 5-19

1-Bromo-4-[(3-methylbutoxy)methyl]benzene

Sodium hydride (purity: 55%, 700 mg) and 1-bromo-3-methylbutane (2.56 mL) were added to a solution of 4-bromobenzylalcohol (2.0 g) in N,N-dimethylformamide (40 mL) under ice-cooling, and the mixture was stirred at room temperature for five hours. A saturated ammonium chloride solution was added to the reaction solution, followed by extraction with a mixture of hexane-ethyl acetate (1:1). The organic layer was dried over sodium sulfate and filtered. The solvent was then evaporated under reduced pressure. The residue was purified by silica gel column chromatography (hexane:ethyl acetate=100:1→50:1→30:1) to give the title compound (2.31 g, 85%).

LC-Mass retention time 4.24 min
SunFire C18 3.5 μm 2.1×20 mm column temperature 40° C.
$H_2O:CH_3CN$ (0.1% $HCO_2H$ added)=
60:40 to 0:100 v/v 0.4 mL/min (0 to 3 min)
0:100 v/v 0.4 mL/min (3 to 5 min)

Reference Example 5-20

1-Bromo-4-[2-(2-methylpropoxy)ethyl]benzene

Potassium hydroxide (1.32 g) and 1-bromo-2-methylpropane (1.04 mL) were added to a solution of 2-(4-bromophenyl)ethylalcohol (140 μL) in dimethyl sulfoxide (2 mL), and the mixture was stirred at room temperature overnight. Water was added to the reaction solution, followed by extraction with dichloromethane. The organic layer was filtered through diatomaceous earth and the filtrate was evaporated under reduced pressure. The residue was purified by silica gel column chromatography (hexane only) to give the title compound as a colorless oil (180 mg, 70%).

$^1$H NMR (300 MHz, $CDCl_3$) δ ppm 0.88 (d, J=6.8 Hz, 6H), 1.84 (qt, J=6.8, 6.5 Hz, 1H), 2.83 (t, J=6.8 Hz, 2H), 3.18 (d, J=6.5 Hz, 2H), 3.59 (t, J=6.8 Hz, 2H), 7.11 (d, J=8.2 Hz, 2H), 7.39 (d, J=8.2 Hz, 2H).

Reference Example 5-21

[4-(4-Bromophenyl)butoxy](tert-butyl)dimethylsilane (1) Lithium aluminum hydride (759 mg) was added to a solution of 4-(4-bromophenyl)butyric acid (3.12 g) in tetrahydrofuran (90 mL) under ice-cooling, and the mixture was stirred under ice-cooling for one hour. Acetone and water were added to the reaction solution, followed by extraction with ethyl acetate. The organic layer was dried over sodium sulfate and filtered. The solvent was then evaporated under reduced pressure. The residue was purified by silica gel column chromatography (hexane:ethyl acetate=30:1→10:1→7:1 5:1) to give 4-(4-bromophenyl)butan-1-ol (2.29 g, quant.).

(2) tert-Butyldimethylchlorosilane (1.13 g) and imidazole (513 mg) were added to a solution of 4-(4-bromophenyl)butan-1-ol (1.15 g) in N,N-dimethylformamide (35 mL) under ice-cooling, and the mixture was stirred at room temperature for one hour. Water was added to the reaction solution, followed by extraction with a mixture of hexane-ethyl acetate (1:1). The organic layer was dried over sodium sulfate and filtered. The solvent was then evaporated under reduced pressure. The residue was purified by silica gel column chromatography (hexane:ethyl acetate=100:1→50:1→20:1) to give the title compound (1.78 g, quant.).

$^1$H NMR (300 MHz, $CDCl_3$) δ ppm 0.00 (s, 6H), 0.85 (s, 9H), 1.40-1.70 (m, 4H), 2.54 (t, J=7.3 Hz, 2H), 3.57 (t, J=6.1 Hz, 2H), 7.00 (d, J=8.6 Hz, 2H), 7.34 (d, J=8.0 Hz, 2H).

Reference Example 5-22

4-Bromo-2-chloro-1-(cyclopropylsulfanyl)benzene

The title compound was obtained as a yellow oil (2.18 g, 34% (two steps)) by performing substantially the same reaction as in Reference Example 5-18 except for using 2-chlorobenzenethiol in place of 2-methylbenzenethiol.

$^1$H NMR (300 MHz, $CDCl_3$) δ ppm 0.66-0.79 (m, 2H), 1.08-1.19 (m, 2H), 2.03-2.19 (m, 1H), 7.36 (dd, J=8.5, 1.9 Hz, 1H), 7.41 (d, J=8.5 Hz, 1H), 7.47 (d, J=1.9 Hz, 1H).

Reference Example 5-23

[3-(4-Bromophenoxy)propoxy](tert-butyl)dimethylsilane (1) Potassium carbonate (12.0 g) and 3-bromo-1-propanol (5.1 mL) were added to a solution of 4-bromophenol (5.0 g) in N,N-dimethylformamide (200 mL) under ice-cooling, and the mixture was stirred at room temperature for 8.5 hours. The reaction solution was ice-cooled and a saturated ammonium chloride solution and water were added, followed by extraction with a mixture of hexane-ethyl acetate (1:1). The organic layer was dried over sodium sulfate and filtered. The solvent was then evaporated under reduced pressure. The residue was purified by silica gel column chromatography (hexane:ethyl acetate=7:1→4:1→3:1) to give 3-(4-bromophenoxy)propan-1-ol as a crude product.

(2) tert-Butyldimethylchlorosilane (8.7 g) and imidazole (3.9 g) were added to a solution of 3-(4-bromophenoxy)propan-1-ol in N,N-dimethylformamide (193 mL) under ice-cooling, and the mixture was stirred at room temperature for 40 minutes. The reaction solution was ice-cooled and water and a saturated ammonium chloride solution were added, followed by extraction with a mixture of hexane-ethyl acetate (1:1). The organic layer was dried over sodium sulfate and filtered. The solvent was then evaporated under reduced pressure. The residue was purified by silica gel column chromatography (hexane:ethyl acetate=100:1). Pyrrolidine (4.82 mL) and triethylamine (8.86 mL) were added to a solution of the resulting crude product in tetrahydrofuran (145 mL) under ice-cooling, and the mixture was stirred at room temperature for 27 hours. The reaction solution was ice-cooled and a saturated ammonium chloride solution was added, followed by extraction with a mixture of hexane-chloroform (1:1). The organic layer was dried over sodium sulfate and filtered. The solvent was then evaporated under reduced pressure. The residue was purified by silica gel column chromatography (hexane:ethyl acetate=100:1→80:1) to give the title compound (7.88 g, 79% (two steps)).

$^1$H NMR (300 MHz, $CDCl_3$) δ ppm 0.05 (s, 6H), 0.89 (s, 9H), 1.90-2.05 (m, 2H), 3.79 (t, J=6.0 Hz, 2H), 4.03 (t, J=6.1 Hz, 2H), 6.78 (dd, J=6.8, 2.4 Hz, 2H), 7.36 (dd, J=6.8, 2.1 Hz, 2H).

Reference Example 5-24

3-[2-(4-Bromophenyl)-1,3-dioxolan-2-yl]-N,N-diethylpropan-1-amine (1) Diethylamine (180 mL) and triethylamine (90 mL) were added to a solution of 4'-bromo-4-chlorobutyrophenone (18.13 g) in acetonitrile (90 mL), and the mixture was stirred at 100° C. for one hour. The reaction solution was cooled to room temperature and water was added, followed by extraction with chloroform. The organic layer was dried over anhydrous magnesium sulfate and filtered. The solvent was then evaporated under reduced pressure. The residue was purified by silica gel column chromatography (hexane:ethyl acetate=5:1→ethyl acetate:methanol:triethylamine=40:4:1) to give 1-(4-bromophenyl)-4-(diethylamino)butan-1-one as a brown oil (9.02 g, 44%).

(2) Ethylene glycol (10 mL) and p-toluenesulfonic acid monohydrate (128 mg) were added to a solution of 1-(4-bromophenyl)-4-(diethylamino)butan-1-one (2.0 g) in toluene (80 mL), and the mixture was stirred at 150° C. for one hour. The reaction solution was cooled to room temperature and p-toluenesulfonic acid monohydrate (1.28 g) was added, after which the mixture was stirred at 150° C. for further one hour. The reaction solution was cooled to room temperature and neutralized with saturated aqueous sodium bicarbonate, followed by extraction with chloroform. The organic layer was dried over anhydrous magnesium sulfate and filtered. The solvent was then evaporated under reduced pressure. The residue was purified by silica gel column chromatography (chloroform:methanol=10:1) to give the title compound as a brown oil (2.09 g, 91%).

$^1$H NMR (300 MHz, CDCl$_3$) δ ppm 0.99 (t, J=7.2 Hz, 6H), 1.41-1.58 (m, 2H), 1.58 (t, J=7.8 Hz, 2H), 2.40 (t, J=7.8 Hz, 2H), 2.50 (q, J=7.2 Hz, 4H), 3.67-3.81 (m, 2H), 3.93-4.07 (m, 2H), 7.27-7.34 (m, 2H), 7.39-7.48 (m, 2H).

Reference Example 5-25

1-Bromo-4-(4-methoxybutyl)benzene

Sodium hydride (purity: 55%, 434 mg) and methyl iodide (0.62 mL) were added to a solution of 4-(4-bromophenyl)butan-1-ol obtained in Reference Example 5-21(1) in N,N-dimethylformamide (30 mL) under ice-cooling, and the mixture was stirred at room temperature for 7.5 hours. Water was added to the reaction solution, followed by extraction with a mixture of hexane-ethyl acetate (1:1). The organic layer was dried over sodium sulfate and filtered. The solvent was then evaporated under reduced pressure. The residue was purified by silica gel column chromatography (hexane:ethyl acetate=50:1→20:1→10:1) to give the title compound (1.06 g, 88%).

$^1$H NMR (300 MHz, CDCl$_3$) δ ppm 1.51-1.73 (m, 4H), 2.06 (t, J=7.4 Hz, 2H), 3.32 (s, 3H), 3.37 (t, J=6.1 Hz, 2H), 7.00-7.08 (m, 2H), 7.33-7.42 (m, 2H).

Reference Example 5-26

4-Bromo-2-chloro-1-(propan-2-yl)benzene

Triethylsilane (1.8 mL) and trifluoroacetic acid (5.8 mL) were added to a solution of 2-(4-bromo-2-chlorophenyl)propan-2-ol (1.9 g) in dichloromethane (76 mL), and the mixture was stirred at room temperature for one day. Water was added to the reaction solution, followed by extraction with ethyl acetate. The organic layer was dried over anhydrous magnesium sulfate and filtered. The solvent was then evaporated under reduced pressure. The residue was purified by silica gel column chromatography (hexane only) to give the title compound as a colorless oil (1.74 g, 98%).

LC-Mass retention time 5.82 min
SunFire C18 3.5 μm 2.1×20 mm column temperature 40° C.
H2O:CH3CN (0.1% HCO2H added)=
90:10 v/v 0.3 mL/min (0 to 1 min)
90:10 to 40:60 v/v 0.3 mL/min (1 to 4 min)
40:60 v/v 0.4 mL/min (4 to 5 min)
40:60 to 10:90 v/v 0.4 mL/min (5 to 5.1 min)
10:90 v/v 0.5 mL/min (5.1 to 5.3 min)
10:90 to 90:10 v/v 0.5 mL/min (5.3 to 5.5 min)
90:10 v/v 0.5 mL/min (5.5 to 8 min)

MS(+): 233 [M+H]$^+$.

Reference Example 5-27

4,4,5,5-Tetramethyl-2-[4-(2,2,2-trifluoroethyl)phenyl]-1,3,2-dioxaborolane

A solution of 1-bromo-4-(2,2,2-trifluoroethyl)benzene (510 mg), bis(pinacolato)diborane (1.08 g), a 1,1'-bis(diphenylphosphino)ferrocenepalladium chloride-dichloromethane complex (70 mg) and triethylamine (1.2 mL) in 1,4-dioxane (10 mL) was stirred at 80° C. for 7.5 hours in a nitrogen atmosphere. The reaction solution was cooled to room temperature and water was added, followed by extraction with ethyl acetate. The organic layer was washed with water and brine, dried over anhydrous magnesium sulfate and filtered. The solvent was then evaporated under reduced pressure. The residue was purified by silica gel column chromatography (hexane:ethyl acetate=10:0→10:1) to give the title compound as a colorless solid (68 mg, 12%).

$^1$H NMR (300 MHz, CDCl$_3$) δ ppm 1.34 (s, 12H), 3.37 (q, J=10.9 Hz, 2H), 7.29 (d, J=7.2 Hz, 2H), 7.80 (d, J=8.1 Hz, 2H).

Reference Example 5-28

2-[4-(3-Methoxypropyl)phenyl]-5,5-dimethyl-1,3,2-dioxaborinane (1) 1-Bromo-4-(3-methoxypropyl)benzene was obtained as a colorless oil (2.07 g, 84%) by performing substantially the same reaction as in Reference Example 5-25 except for using 3-(4-bromophenyl)propan-1-ol in place of 4-(4-bromophenyl)butan-1-ol.

(2) The title compound was obtained as a white solid (116.8 mg, 51%) by performing substantially the same reaction as in Reference Example 5-11 except for using 1-bromo-4-(3-methoxypropyl)benzene in place of 4-bromo-2-methylbenzotrifluoride.

$^1$H NMR (300 MHz, CDCl$_3$) δ ppm 1.02 (s, 6H), 1.82-1.96 (m, 2H), 2.69 (t, J=7.2 Hz, 2H), 3.33 (d, J=0.8 Hz, 3H), 3.37 (t, J=6.6 Hz, 2H), 3.76 (s, 4H), 7.19 (d, J=7.7 Hz, 2H), 7.72 (d, J=7.7 Hz, 2H).

Reference Example 5-29

2-[4-(Difluoromethyl)phenyl]-4,4,5,5-tetramethyl-1,3,2-dioxaborolane

The title compound was obtained as a pale yellow oil (238 mg, 36%) by performing substantially the same reaction as in Reference Example 5-27 except for using 1-bromo-4-(difluoromethyl)benzene in place of 1-bromo-4-(2,2,2-trifluoroethyl)benzene.

$^1$H NMR (300 MHz, CDCl$_3$) δ ppm 1.34 (s, 12H), 6.63 (t, J=56.4 Hz, 1H), 7.49 (d, J=7.8 Hz, 2H), 7.89 (d, J=7.5 Hz, 2H).

Reference Example 5-30

4-Bromo-2-chloro-1-(cyclopropylsulfonyl)benzene

Oxone(R) (20.3 g) was added to a solution of 4-bromo-2-chloro-1-(cyclopropylsulfanyl)benzene obtained in Reference Example 5-22 (964 mg) in tetrahydrofuran (20 mL)-methanol (20 mL)-water (10 mL), and the mixture was stirred at room temperature for one day. Oxone(R) (6.8 g) was further added and the mixture was stirred at room temperature for 18 hours. Water was added to the reaction solution, followed by extraction with chloroform. The organic layer was dried over anhydrous magnesium sulfate and filtered. The solvent was then evaporated under reduced pressure. The residue was purified by silica gel column chromatography (chloroform only) to give the title compound as a pale yellow amorphous (597 mg, 55%).

$^1$H NMR (300 MHz, CDCl$_3$) δ ppm 1.00-1.18 (m, 2H), 1.28-1.42 (m, 2H), 2.92-3.11 (m, 1H), 7.58 (dd, J=8.5, 1.9 Hz, 1H), 7.74 (d, J=1.9 Hz, 1H), 7.88 (d, J=8.3 Hz, 1H).

MS(+): 295 [M+H]$^+$.

Reference Example 5-31

2-[3-Chloro-4-(cyclopentyloxy)phenyl]-5,5-dimethyl-1,3,2-dioxaborinane (1) Potassium carbonate (2.0 g) and bromocyclopentane (0.775 mL) were added to a solution of 4-bromo-2-chlorophenol (1.0 g) in N,N-dimethylformamide (10 mL), and the mixture was stirred at room temperature for four days. Water was added to the reaction solution, followed by extraction with ethyl acetate. The organic layer was washed with a saturated ammonium chloride solution and water, dried over anhydrous magnesium sulfate and filtered. The solvent was then evaporated under reduced pressure. The residue was purified by silica gel column chromatography (hexane:ethyl acetate=10:1) to give 4-bromo-2-chloro-1-(cyclopentyloxy)benzene as a colorless oil (1.31 g, 98%).

(2) The title compound was obtained as a pale yellow solid (1.24 g, 86%) by performing substantially the same reaction as in Reference Example 5-11 except for using 4-bromo-2-chloro-1-(cyclopentyloxy)benzene in place of 4-bromo-2-methylbenzotrifluoride.

$^1$H NMR (300 MHz, CDCl$_3$) δ ppm 1.01 (s, 6H), 1.50-1.75 (m, 2H), 1.75-2.00 (m, 6H), 3.74 (s, 4H), 4.75-4.93 (m, 1H), 6.89 (d, J=8.4 Hz, 1H), 7.61 (dd, J=7.8, 1.8 Hz, 1H), 7.70 (d, J=1.2 Hz, 1H).

Reference Example 5-32

2-[3-Chloro-4-(difluoromethoxy)phenyl]-4,4,5,5-tetramethyl-1,3,2-dioxaborolane (1) A solution of 4-bromo-2-chlorophenol (830 mg) and a 30% potassium hydroxide solution (16 mL) in acetonitrile (16 mL) was cooled to −78° C. 2-Chloro-2,2-difluoroacetophenone (2.95 mL) was added and the mixture was stirred at 80° C. for 40 hours. The reaction solution was cooled to room temperature and extracted with diethyl ether. The organic layer was washed with water and brine, dried over anhydrous magnesium sulfate and filtered. The solvent was then evaporated under reduced pressure. The residue was purified by silica gel column chromatography (hexane:ethyl acetate=10:1→10:1) to give 4-bromo-2-chloro-1-(difluoromethoxy)benzene as a colorless oil (533 mg, 52%).

(2) A solution of 4-bromo-2-chloro-1-(difluoromethoxy)benzene (100 mg), potassium acetate (114 mg), bis(pinacolato)diborane (108 mg) and a 1,1'-bis(diphenylphosphino)ferrocenepalladium chloride-dichloromethane complex (15.8 mg) in 1,4-dioxane (1 mL) was stirred in a nitrogen atmosphere, at 100° C. for 19 hours. The reaction solution was cooled to room temperature and filtered through celite. After washing with ethyl acetate, the filtrate was evaporated under reduced pressure. The residue was purified by silica gel column chromatography (hexane:ethyl acetate=50:1→2:1) to give the title compound as a pale yellow oil (104 mg, 88%).

$^1$H NMR (300 MHz, CDCl$_3$) δ ppm 1.34 (s, 12H), 6.56 (t, J=73.3 Hz, 1H), 7.21 (d, J=7.8 Hz, 1H), 7.68 (dd, J=8.1, 1.5 Hz, 1H), 7.88 (d, J=1.8 Hz, 1H).

Reference Example 5-33

2-[4-(Cyclopentyloxy)phenyl]-5,5-dimethyl-1,3,2-dioxaborinane

The title compound was obtained as a colorless solid (1.27 g, 96%) by performing substantially the same reaction as in Reference Example 5-11 except for using 1-bromo-4-(cyclopentyloxy)benzene in place of 4-bromo-2-methylbenzotrifluoride.

$^1$H NMR (300 MHz, CDCl$_3$) δ ppm 1.01 (s, 6H), 1.50-1.70 (m, 2H), 1.70-2.00 (m, 6H), 3.75 (s, 4H), 4.71-4.85 (m, 1H), 6.85 (d, J=8.4 Hz, 2H), 7.71 (d, J=8.7 Hz, 2H).

Reference Example 5-34

2-(3-Chloro-4-methoxyphenyl)-5,5-dimethyl-1,3,2-dioxaborinane

The title compound (738 mg, 72%) was obtained by performing substantially the same reaction as in Reference Example 5-11 except for using 4-bromo-2-chloro-1-methoxybenzene in place of 4-bromo-2-methylbenzotrifluoride.

$^1$H NMR (300 MHz, CDCl$_3$) δ ppm 1.01 (s, 6H), 3.75 (s, 4H), 3.92 (s, 3H), 6.90 (d, J=8.3 Hz, 1H), 7.66 (dd, J=8.2, 1.6 Hz, 1H), 7.79 (d, J=1.2 Hz, 1H).

Reference Example 5-35

1-(Benzylsulfonyl)-4-bromo-2-chlorobenzene

A solution of 4-bromo-2-chlorobenzenesulfonyl chloride (1.16 g), sodium sulfite (1.01 g) and sodium bicarbonate (672 mg) in water (8 mL) was stirred at 100° C. for 1.5 hours. The reaction solution was cooled to 50° C. and tetrabutylammonium bromide (1.29 g) and benzyl bromide (1.43 mL) were added, after which the mixture was stirred at 70° C. for further three hours. The reaction solution was cooled to room temperature and water was added, followed by extraction with chloroform. The organic layer was dried over anhydrous magnesium sulfate and filtered. The solvent was then evaporated under reduced pressure. The residue was purified by silica gel column chromatography (hexane:ethyl acetate=9:1) to give the title compound as a white solid (1.29 g, 94%).

$^1$H NMR (300 MHz, CDCl$_3$) δ ppm 4.63 (s, 2H), 7.16-7.22 (m, 2H), 7.22-7.37 (m, 3H), 7.38-7.46 (m, 1H), 7.58 (d, J=8.5 Hz, 1H), 7.71-7.77 (m, 1H).

Reference Example 5-36

4,4,5,5-Tetramethyl-2-[4-(2,2,2-trifluoroethoxy)phenyl]-1,3,2-dioxaborolane

The title compound was obtained as a colorless oil (303 mg, 17%) by performing substantially the same reaction as in Reference Example 5-32 except for using 1-bromo-4-(2,2,2-trifluoroethoxy)benzene in place of 1-bromo-4-(2,2,2-trifluoroethyl)benzene.

$^1$H NMR (300 MHz, CDCl$_3$) δ ppm 1.30-1.40 (m, 12H), 4.25-4.44 (m, 2H), 6.85-6.97 (m, 2H), 7.69-7.84 (m, 2H).

The structures of Reference Examples 5-11 to 5-36 are shown below.
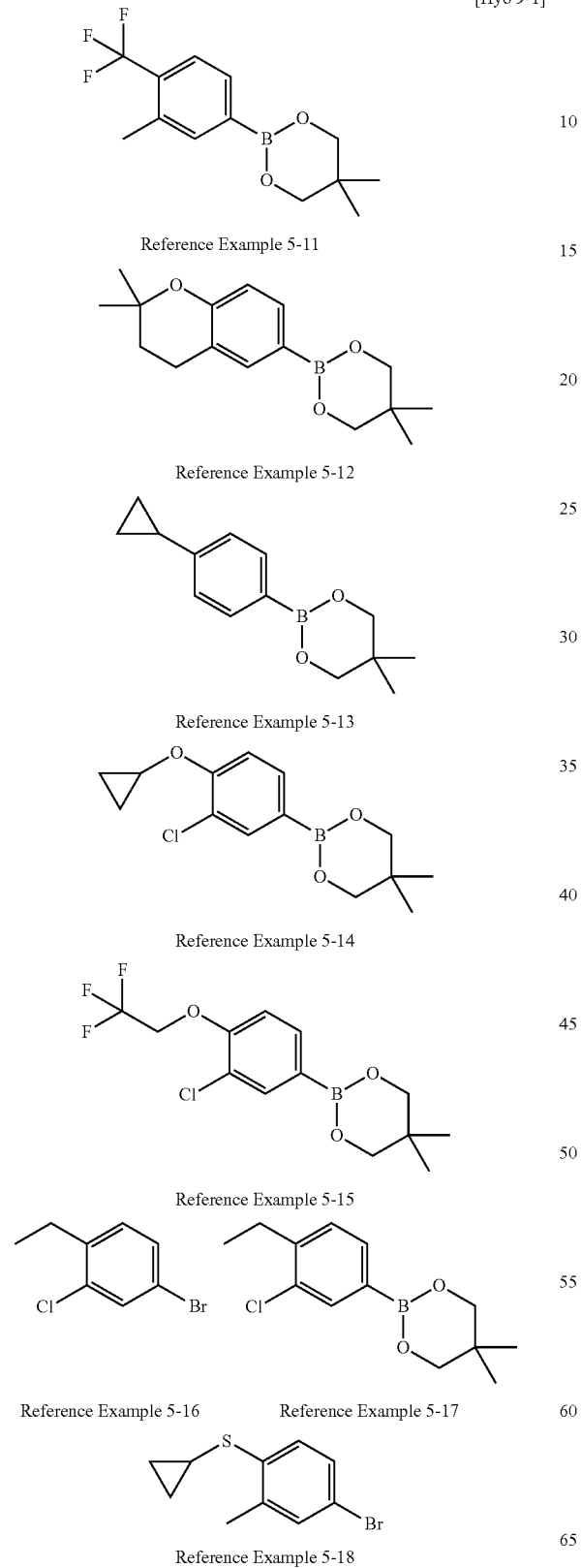
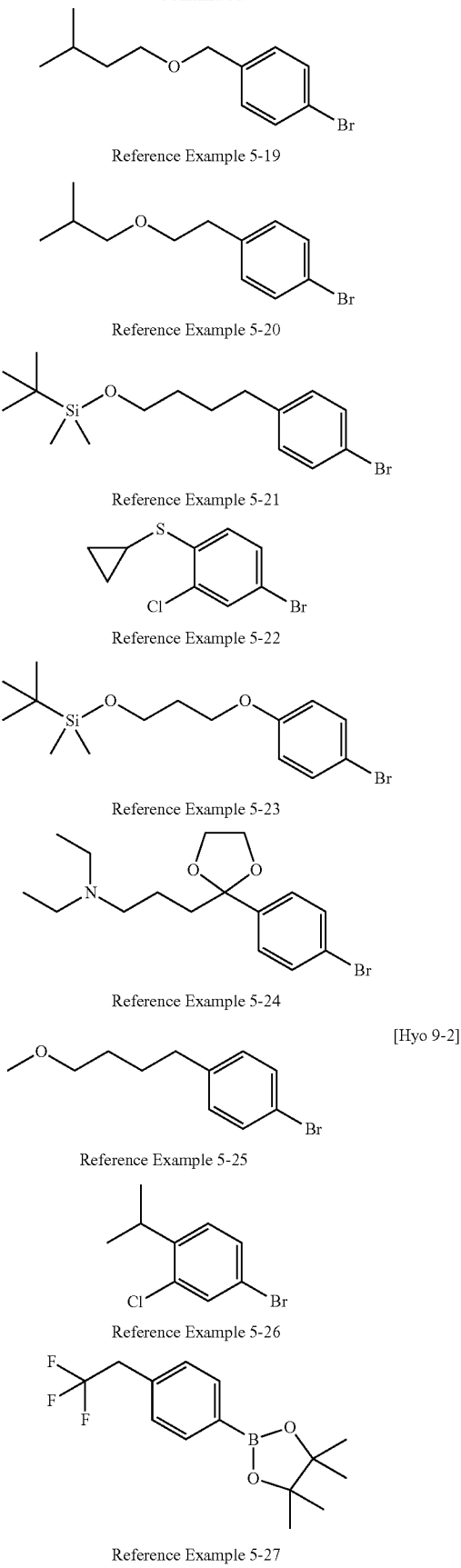

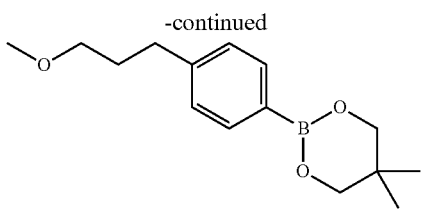

Reference Example 5-28

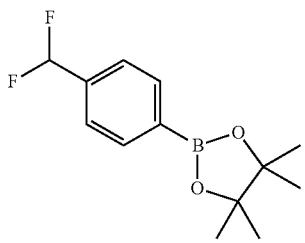

Reference Example 5-29

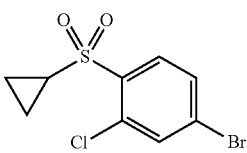

Reference Example 5-30

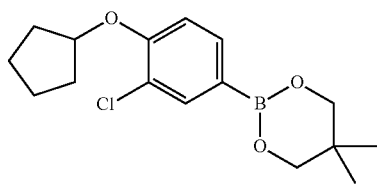

Reference Example 5-31

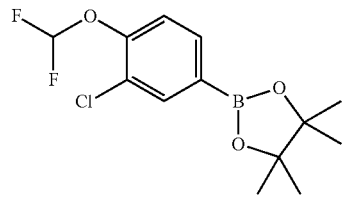

Reference Example 5-32

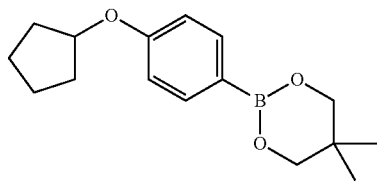

Reference Example 5-33

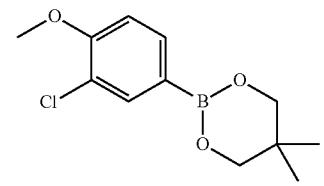

Reference Example 5-34

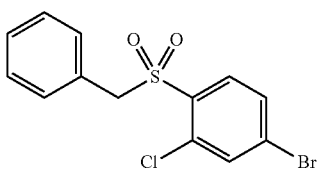

Reference Example 5-35

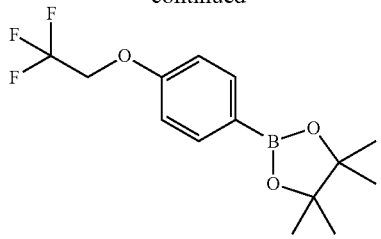

Reference Example 5-36

Reference Example 5-37

4-Bromo-2-chloro-1-(ethylsulfanyl)benzene

Sodium ethanethiolate (2.0 g) was added to a solution of 4-bromo-2-chloro-1-fluorobenzene (5.0 g) in N,N-dimethylformamide (20 mL), and the mixture was stirred at 65° C. for two hours. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (hexane:ethyl acetate=90:1→0:100) to give the title compound as a colorless oil (4.8 g).
$^1$H NMR (300 MHz, CDCl$_3$) δ ppm 1.22-1.41 (m, 3H), 2.83-3.07 (m, 2H), 7.01-7.18 (m, 1H), 7.31-7.40 (m, 1H), 7.48-7.61 (m, 1H).

Reference Example 5-38

1-Bromo-3-(cyclopropylsulfanyl)benzene

Potassium t-butoxide (4 g) and cyclopropyl bromide (7.6 mL) were added to a solution of 3-bromothiophenol (6 g) in dimethyl sulfoxide (30 mL), and the mixture was stirred at 80° C. for five hours. The reaction solution was poured into water, followed by extraction with ethyl acetate. The organic layer was sequentially washed with water and brine, dried over sodium sulfate and filtered, after which the solvent was evaporated under reduced pressure. The residue was purified by silica gel column chromatography (hexane:ethyl acetate=9:1→7:3) to give the title compound as a light yellow oil (1.6 g, 23%).
$^1$H NMR (300 MHz, CDCl$_3$) δ ppm 0.63-0.77 (m, 2H), 1.04-1.18 (m, 2H), 2.11-2.25 (m, 1H), 7.09-7.17 (m, 1H), 7.22-7.29 (m, 2H), 7.48-7.53 (m, 1H).
MS(+): 229 [M+H]$^+$.

Reference Example 5-39

[4-Bromo-2-(trifluoromethyl)phenoxy](tert-butyl)dimethylsilane (1) Tetra-n-butylammonium tribromide (37 g) was added in small portions to a solution of 2-hydroxybenzotrifluoride (10 g) in chloroform (350 mL), and the mixture was stirred at room temperature for eight hours. The solvent was evaporated from the reaction solution under reduced pressure and then 0.5 M hydrochloric acid was added to the residue, followed by extraction with ethyl acetate. The organic layer was sequentially washed with a 5% sodium thiosulfate solution, water and brine and dried over sodium sulfate. The solvent was evaporated under reduced pressure. The residue was purified by silica gel column chromatography (hexane:ethyl acetate=8:2→6:4) to give a mixture of 2-hydroxybenzotrifluoride and 4-bromo-2-(trifluoromethyl)phenol (16 g).

(2) Imidazole (6.8 g) and tert-butyldimethylsilyl chloride (12 g) were added to a solution of the mixture of 2-hydroxybenzotrifluoride and 4-bromo-2-(trifluoromethyl)phenol (16 g) in N,N-dimethylformamide (60 mL), and the mixture was stirred at room temperature for one hour. The reaction solution was poured into water, followed by extraction with ethyl acetate. The organic layer was sequentially washed with water and brine, dried over sodium sulfate and filtered, after which the solvent was evaporated under reduced pressure. The residue was purified by silica gel column chromatography (hexane:ethyl acetate=8:2→7:3) to give a mixture of [4-bromo-2-(trifluoromethyl)phenoxy](tert-butyl)dimethylsilane and [2-(trifluoromethyl)phenoxy](tert-butyl)dimethylsilane (17 g).

$^1$H NMR (300 MHz, CDCl$_3$) δ ppm 0.26 (s, 6H), 1.00 (s, 9H), 6.79 (d, J=9.0 Hz, 1H), 7.45-7.51 (m, 1H), 7.65 (d, J=2.8 Hz, 1H).

MS(+): 299 [M-tBu]$^+$.

Reference Example 5-40

{3-[(4-Bromo-2-chlorophenyl)sulfanyl]propoxy}(tert-butyl)dimethylsilane

The title compound was obtained as a colorless oil (4.0 g) by performing substantially the same reaction as in Reference Examples 5-37 and 5-39(2) sequentially except for using 3-hydroxy-1-propanethiol in place of sodium ethanethiolate.

$^1$H NMR (200 MHz, CDCl$_3$) δ ppm 0.06 (s, 6H), 0.90 (s, 9H), 1.77-1.97 (m, 2H), 2.91-3.09 (m, 2H), 3.63-3.82 (m, 2H), 7.10-7.21 (m, 1H), 7.28-7.37 (m, 1H), 7.44-7.57 (m, 1H).

Reference Example 5-41 tert-Butyl 3-[(4-bromophenyl)sulfanyl]azetidine-1-carboxylate

The title compound was obtained as a colorless oil (9.2 g) by performing substantially the same reaction as in Reference Example 5-38 except for using tert-butyl 3-[(phenylsulfonyl)oxy]azetidine-1-carboxylate in place of cyclopropylbromide and using 4-bromothiophenol.

$^1$H NMR (300 MHz, CDCl$_3$) δ ppm 1.43 (s, 9H), 3.78-3.89 (m, 2H), 3.92-4.04 (m, 1H), 4.25-4.45 (m, 2H), 7.03-7.14 (m, 2H), 7.38-7.49 (m, 2H).

MS(+): 366 [M+Na]$^+$.

Reference Example 5-42

{3-[(4-Bromophenyl)sulfanyl]propoxy}(tert-butyl)dimethylsilane

Potassium carbonate (4.1 g) and (3-bromopropoxy)-tert-butyldimethylsilane (4.1 g) were added to a solution of 4-bromothiophenol (3.0 g) in N,N-dimethylformamide, and the mixture was stirred at room temperature overnight. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (hexane:ethyl acetate=50:1→20:1) to give the title compound as a colorless oil (5.5 g).

$^1$H NMR (200 MHz, CDCl$_3$) δ ppm 0.05 (s, 6H), 0.90 (s, 9H), 1.64-1.95 (m, 2H), 2.81-3.13 (m, 2H), 3.60-3.79 (m, 2H), 7.09-7.24 (m, 2H), 7.34-7.49 (m, 2H).

Reference Example 5-43

(4-Bromo-2-fluorophenoxy)(tert-butyl)dimethylsilane

The title compound was obtained as a colorless oil (16 g) by performing substantially the same reaction as in Reference Example 5-39(2) except for using 4-bromo-2-fluorophenol in place of 4-bromo-2-(trifluoromethyl)phenol.

$^1$H NMR (300 MHz, CDCl$_3$) δ ppm 0.18 (d, J=1.1 Hz, 6H), 0.99 (s, 9H), 6.79 (t, J=8.7 Hz, 1H), 7.08-7.13 (m, 1H), 7.21 (dd, J=10.1, 2.3 Hz, 1H).

Reference Example 5-44

N,N-Dimethyl-N'-[4-(4,4,5,5-tetramethyl-1,3,2-dioxaborolan-2-yl)phenyl]sulfuric acid diamide Dimethylsulfamoyl chloride (492 mg) and triethylamine (0.95 mL) were added to a solution of 4-(4,4,5,5-tetramethyl-1,3,2-dioxaborolan-2-yl)aniline (500 mg) in chloroform (5 mL), and the mixture was stirred at room temperature overnight. The reaction solution was concentrated and the residue was purified by silica gel column chromatography (hexane:ethyl acetate=1:0→2:1) to give the title compound as a pale orange powder (427 mg).

$^1$H NMR (300 MHz, CDCl$_3$) δ ppm 1.34 (s, 12H), 2.84 (s, 6H), 6.47-6.54 (m, 1H), 7.14 (d, J=8.5 Hz, 2H), 7.76 (d, J=8.5 Hz, 2H).

MS(+): 327 [M+H]$^+$.

Reference Example 5-45

1-Propan-2-yl-3-[4-(4,4,5,5-tetramethyl-1,3,2-dioxaborolan-2-yl)phenyl]urea

The title compound was obtained as a colorless powder (514 mg) by performing substantially the same reaction as in Reference Example 5-44 except for using 2-isocyanatopropane in place of dimethylsulfamoyl chloride.

$^1$H NMR (300 MHz, CDCl$_3$) δ ppm 1.16 (s, 3H), 1.19 (s, 3H), 1.33 (s, 12H), 3.91-4.07 (m, 1H), 4.49-4.61 (m, 1H), 6.23-6.35 (m, 1H), 7.29 (d, J=8.5 Hz, 2H), 7.75 (d, J=8.4 Hz, 2H).

MS(+): 305 [M+H]$^+$.

The structures of Reference Examples 5-37 to 5-45 are shown below.

[Hyo 10]

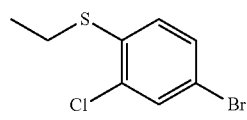

Reference Example 5-37

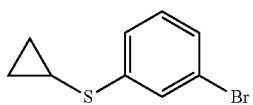

Reference Example 5-38

Reference Example 5-39

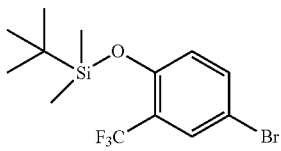

Reference Example 5-40

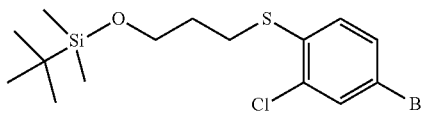

Reference Example 5-41

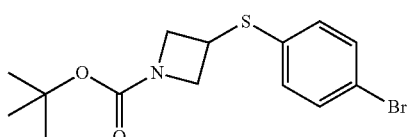

Reference Example 5-42

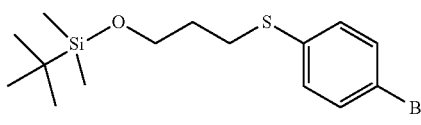

Reference Example 5-43

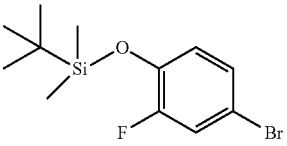

Reference Example 5-44

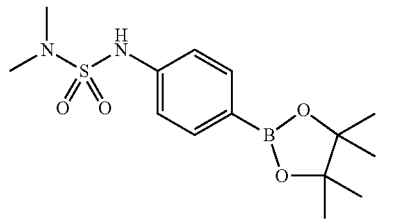

Reference Example 5-45

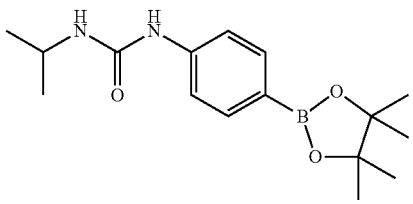

Reference Example 5-46

4-(5,5-Dimethyl-1,3,2-dioxaborinan-2-yl)-2-methyl-benzonitrile

A solution of 4-bromo-2-methylbenzonitrile (1.0 g) in tetrahydrofuran (16 mL) was cooled to an external temperature of −78° C. in a nitrogen atmosphere, and a solution of n-butyllithium in hexane (1.57 M, 3.5 mL) was added dropwise. After stirring at −78° C. for 40 minutes, triisopropyl borate (1.5 mL) was added dropwise and the mixture was stirred at room temperature for 1.5 hours. 1 M hydrochloric acid (10 mL) was added to the reaction solution, followed by extraction with diethyl ether. The organic layer was washed with water and brine, dried over sodium sulfate and filtered. The solvent was then evaporated under reduced pressure. The residue was dissolved in toluene (4 mL) and tetrahydrofuran (3 mL), and 2,2-dimethyl-1,3-propanediol (531 mg) and anhydrous magnesium sulfate (catalytic amount) were added, after which the mixture was stirred at room temperature for five minutes. The insoluble matter in the reaction solution was filtered off, and then the solvent was evaporated under reduced pressure. The residue was purified by silica gel column chromatography (hexane:ethyl acetate=50:1→20:1) to give the title compound as a colorless solid (778 mg, 67%).

$^1$H NMR (300 MHz, CDCl$_3$) δ ppm 1.02 (s, 6H), 2.54 (s, 3H), 3.78 (s, 4H), 7.56 (d, J=7.7 Hz, 1H), 7.66 (d, J=7.4 Hz, 1H), 7.73 (s, 1H).

Reference Example 5-47

4-Bromo-2-chloro-1-(propan-2-ylsulfonyl)benzene

The title compound was obtained as a colorless oil (432 mg, 36%) by performing substantially the same reaction as in Reference Example 5-35 except for using 2-bromopropane in place of benzyl bromide.

$^1$H NMR (300 MHz, CDCl$_3$) δ ppm 1.32 (d, J=6.9 Hz, 6H), 3.68-3.83 (m, 1H), 7.61 (dd, J=8.5, 1.9 Hz, 1H), 7.73 (d, J=1.9 Hz, 1H), 7.96 (d, J=8.3 Hz, 1H).

MS(+): 319 [M+Na]$^+$.

Reference Example 5-48

{3-[(4-Bromophenyl)sulfonyl]propoxy}(tert-butyl)dimethylsilane (1) 3-(4-Bromophenylsulfonyl)propan-1-ol was obtained as a colorless oil (784 mg, 70%) by performing substantially the same reaction as in Reference Example 5-35 except for using 3-bromo-1-propanol in place of benzyl bromide and using 4-bromobenzenesulfonyl chloride in place of 4-bromo-2-chlorobenzenesulfonyl chloride.

(2) tert-Butyldimethylchlorosilane (508 mg) and diisopropylethylamine (587 μL) were added to a solution of 3-(4-bromophenylsulfonyl)propan-1-ol (784 mg) in N,N-dimethylformamide (4 mL), and the mixture was stirred at room temperature for 2.5 hours. tert-Butyldimethylchlorosilane (127 mg) and diisopropylethylamine (147 μL) were added to the reaction solution, and the mixture was stirred at room temperature for further two hours. tert-Butyldimethylchlorosilane (254 mg) and diisopropylethylamine (1.17 mL) were added to the reaction solution, and the mixture was stirred at room temperature for further 30 minutes. Water was added to the reaction solution, followed by extraction with chloroform. The organic layer was dried over anhydrous magnesium sulfate and filtered. The solvent was then evaporated under reduced pressure. The residue was purified by silica gel column chromatography (hexane:ethyl acetate=50:1→33:1→19:1→9:1) to give the title compound as a white solid (720 mg, 65%).

$^1$H NMR (300 MHz, CDCl$_3$) δ ppm 0.00 (s, 6H), 0.84 (s, 9H), 1.82-1.96 (m, 2H), 3.14-3.26 (m, 2H), 3.64 (t, J=5.8 Hz, 2H), 7.64-7.83 (m, 4H).

MS(+): 393 [M+H]$^+$.

Reference Example 5-49

4-Bromo-2-chloro-1-(cyclopentylsulfonyl)benzene

The title compound was obtained as a white amorphous (308 mg, 24%) by performing substantially the same reaction as in Reference Example 5-35 except for using bromocyclopentane in place of benzyl bromide.

$^1$H NMR (300 MHz, CDCl$_3$) δ ppm 1.51-2.20 (m, 8H), 3.99-4.16 (m, 1H), 7.60 (dd, J=8.5, 1.9 Hz, 1H), 7.73 (d, J=1.9 Hz, 1H), 7.97 (d, J=8.3 Hz, 1H).

MS(+): 345 [M+Na]$^+$.

Reference Example 5-50

2-Chloro-5-(5,5-dimethyl-1,3,2-dioxaborinan-2-yl) benzonitrile

The title compound was obtained as a yellow solid (454 mg, 39%) by performing substantially the same reaction as in Reference Example 5-11 except for using 5-bromo-2-chlorobenzonitrile in place of 4-bromo-2-methylbenzotrifluoride.

$^1$H NMR (300 MHz, CDCl$_3$) δ ppm 1.02 (s, 6H), 3.77 (s, 4H), 7.48 (d, J=7.7 Hz, 1H), 7.91 (dd, J=7.9, 1.3 Hz, 1H), 8.09 (d, J=1.5 Hz, 1H).

Reference Example 5-51

2-[4-(Difluoromethoxy)-3-methoxyphenyl]-4,4,5,5-tetramethyl-1,3,2-dioxaborolane (1) Ethyl dichlorofluoroacetate (1.87 mL) and potassium carbonate (2.72 g) were added to a solution of 4-bromo-2-methoxyphenol (2.0 g) in N,N-dimethylformamide (20 mL), and the mixture was stirred at 70° C. for 23 hours. The reaction solution was cooled to room temperature and water was added, followed by extraction with ethyl acetate. The organic layer was washed with water and brine, dried over anhydrous magnesium sulfate and filtered. The solvent was then evaporated under reduced pressure. The residue was purified by silica gel column chromatography (hexane:ethyl acetate=20:1) and further purified by NH-silica gel column chromatography (hexane:ethyl acetate=30:1→20:1) to give 4-bromo-1-(difluoromethoxy)-2-methoxybenzene as a white solid (636 g, 26%).

(2) The title compound was obtained as a white solid (357 mg, 47%) by performing substantially the same reaction as in Reference Example 5-32 except for using 4-bromo-1-(difluoromethoxy)-2-methoxybenzene in place of 4-bromo-2-chloro-1-(difluoromethoxy)benzene.

$^1$H NMR (300 MHz, CDCl$_3$) δ ppm 1.34 (s, 12H), 3.92 (s, 3H), 6.56 (t, J=75.1 Hz, 1H), 7.14 (d, J=8.0 Hz, 1H), 7.39 (s, 1H), 7.40 (d, J=7.4 Hz, 1H).

Reference Example 5-52

2-[4-(Difluoromethoxy)-3-methylphenyl]-4,4,5,5-tetramethyl-1,3,2-dioxaborolane

The title compound was obtained as a pale yellow oil (1.21 g, 40% (two steps)) by performing substantially the same reaction as in Reference Example 5-51 except for using 4-bromo-2-methylphenol in place of 4-bromo-2-methoxyphenol.

$^1$H NMR (300 MHz, CDCl$_3$) δ ppm 1.34 (s, 12H), 2.28 (d, J=6.6 Hz, 3H), 6.52 (t, J=74.0 Hz, 1H), 7.04 (d, J=8.0 Hz, 1H), 7.63 (d, J=8.0 Hz, 1H), 7.68 (s, 1H).

Reference Example 5-53

2-[4-(Difluoromethoxy)-3-fluorophenyl]-4,4,5,5-tetramethyl-1,3,2-dioxaborolane

The title compound was obtained as a colorless oil (0.67 g, 24% (two steps)) by performing substantially the same reaction as in Reference Example 5-51 except for using 4-bromo-2-fluorophenol in place of 4-bromo-2-methoxyphenol.

$^1$H NMR (300 MHz, CDCl$_3$) δ ppm 1.34 (s, 12H), 6.57 (t, J=73.4 Hz, 1H), 7.15-7.24 (m, 1H), 7.48-7.63 (m, 2H).

Reference Example 5-54

4-Bromo-2-chloro-1-[(cyclopropylmethyl)sulfonyl] benzene

The title compound was obtained as a pale brown oil (444 mg, 36%) by performing substantially the same reaction as in Reference Example 5-35 except for using (bromomethyl) cyclopropane in place of benzyl bromide.

$^1$H NMR (300 MHz, CDCl$_3$) δ ppm 0.14-0.37 (m, 2H), 0.44-0.70 (m, 2H), 0.90-1.15 (m, 1H), 3.33 (d, J=7.2 Hz, 2H), 7.64 (dd, J=8.5, 1.9 Hz, 1H), 7.73 (d, J=1.9 Hz, 1H), 8.02 (d, J=8.5 Hz, 1H).

MS(+): 331 [M+Na]$^+$.

Reference Example 5-55

1-(Cyclopropylsulfonyl)-4-iodobenzene

The title compound was obtained as a colorless powder (2.19 g, 93%) by performing substantially the same reaction as in Reference Example 4-31(1) except for using 1-bromo-4-(cyclopropylsulfonyl)benzene (described in WO 2004009086).

$^1$H NMR (300 MHz, CDCl$_3$) δ ppm 0.98-1.11 (m, 2H) 1.29-1.41 (m, 2H) 2.36-2.53 (m, 1H) 7.61 (d, J=8.5 Hz, 2H) 7.92 (d, J=8.2 Hz, 2H).

MS(+): 309 [M+H]$^+$.

The structures of Reference Examples 5-46 to 5-55 are shown below.

[Hyo 11]

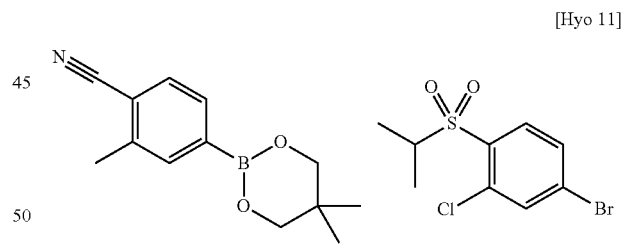

Reference Example 5-46    Reference Example 5-47

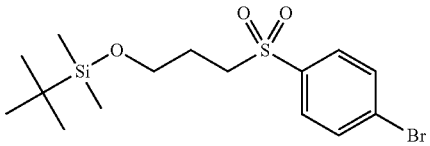

Reference Example 5-48

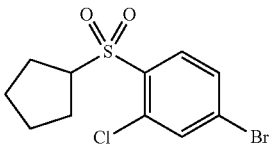

Reference Example 5-49

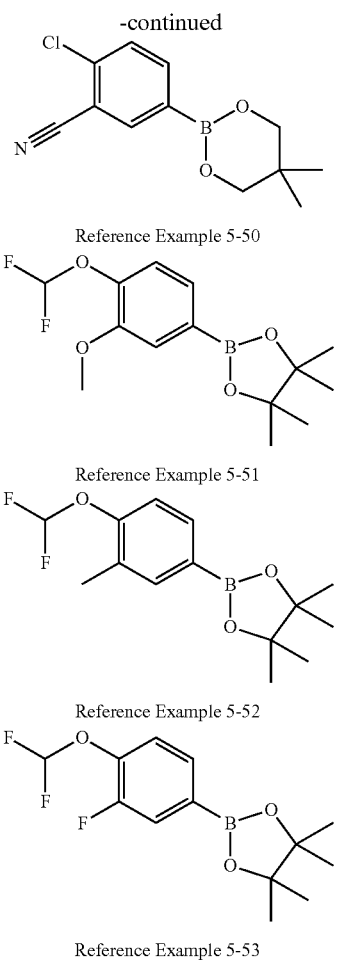

Reference Example 5-50

Reference Example 5-51

Reference Example 5-52

Reference Example 5-53

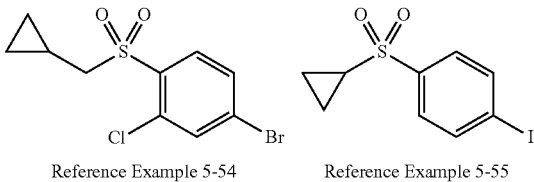

Reference Example 5-54    Reference Example 5-55

Example 1-1

3-Chloro-6-{(E)-2-Cyclopentyl-1-[4-(methylsulfa-nyl)phenyl]ethenyl}pyridin-2(1H)-one

[Ka 106]

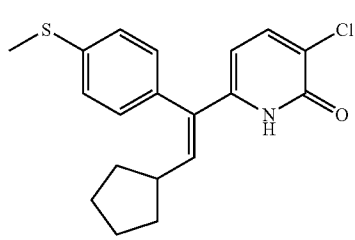

(1) A solution of lithiumhexamethyldisilazide in tetrahydrofuran (1 M, 5.22 mL) was added to a solution of (cyclopentylmethyl)triphenylphosphonium iodide (described in WO 2001044216) (2.46 g) in tetrahydrofuran (20 mL) in a nitrogen atmosphere under ice-cooling, and the mixture was stirred at room temperature for one hour. The reaction solution was ice-cooled again and a solution of (5-chloro-6-methoxypyridin-2-yl)[4-(methylsulfanyl)phenyl]methanone obtained in Reference Example 1-1 (1.0 g) in tetrahydrofuran (10 mL) was added, after which the mixture was stirred at room temperature for one hour. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (chloroform:hexane=1:1) to give 3-chloro-6-{(E)-2-cyclopentyl-1-[4-(methylsulfanyl)phenyl]ethenyl}-2-methoxypyridine (710 mg, 58%) as a colorless oil.

(2) 48% hydrobromic acid (1.5 mL) was added to a solution of 3-chloro-6-{(E)-2-cyclopentyl-1-[4-(methylsulfanyl)phenyl]ethenyl}-2-methoxypyridine (250 mg) in 1,4-dioxane (1.5 mL), and the mixture was stirred at 85° C. for one hour. The reaction solution was poured into water, followed by extraction with ethyl acetate. The organic layer was washed with brine, dried over anhydrous magnesium sulfate and filtered, after which the filtrate was concentrated under reduced pressure. The resulting residue was purified by silica gel column chromatography (chloroform:methanol=9:1) to give a pale brown oil. This was powdered with a hexane/ethyl acetate solution, and filtration operation gave the title compound as a pale brown powder (230 mg, 71%).

$^1$H NMR (300 MHz, CDCl$_3$) δ ppm 1.40-1.63 (m, 4H), 1.68-1.90 (m, 4H), 2.32-2.58 (m, 4H), 5.81 (d, J=7.8 Hz, 1H), 6.47 (d, J=10.1 Hz, 1H), 7.10 (d, J=8.5 Hz, 2H), 7.23-7.33 (m, 2H), 7.44 (d, J=7.8 Hz, 1H), 10.91-11.23 (brs, 1H).

MS(+): 345 [M+H]$^+$.

Example 1-2

3-Chloro-6-{(E)-2-Cyclopentyl-1-[4-(methylsulfonyl)phenyl]ethenyl}pyridin-2(1H)-one

[Ka 107]

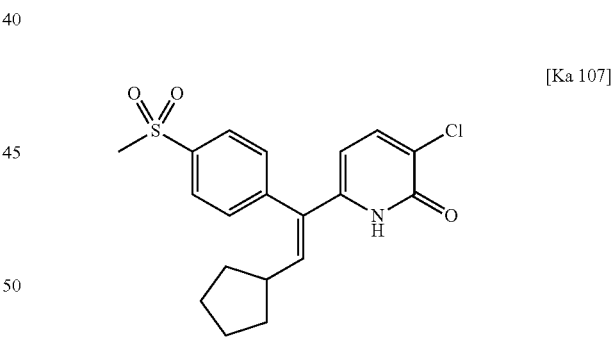

Water (3 mL) and Oxone(R) (853 mg) were sequentially added to a solution of 3-chloro-6-{(E)-2-cyclopentyl-1-[4-(methylsulfanyl)phenyl]ethenyl}pyridin-2(1H)-one obtained in Example 1-1 (160 mg) in THF-methanol (1:1, 6 mL), and the mixture was stirred at room temperature for one hour. The reaction solution was poured into water, followed by extraction with ethyl acetate. The organic layer was washed with brine, dried over anhydrous magnesium sulfate and filtered. The solvent was then evaporated under reduced pressure. The resulting residue was purified by silica gel column chromatography (chloroform:hexane=10:0→9:1). The resulting crude product was recrystallized from a chloroform:ethyl acetate:hexane (1:1:1, 6 mL) solution to give the title compound as a colorless powder (130 mg, 74%).

¹H NMR (300 MHz, CDCl₃) δ ppm 1.40-1.64 (m, 4H), 1.67-1.92 (m, 4H), 2.22-2.52 (m, 1H), 3.14 (s, 3H), 5.66 (d, J=7.6 Hz, 1H), 6.63 (d, J=10.1 Hz, 1H), 7.37-7.57 (m, 3H), 8.00 (d, J=8.5 Hz, 2H), 11.40-11.73 (brs, 1H).

MS(+): 378 [M+H]⁺.

Example 1-3

6-{(E)-2-Cyclopentyl-1-[4-(methylsulfanyl)phenyl]ethenyl}-3-(propan-2-yl)pyridin-2(1H)-one

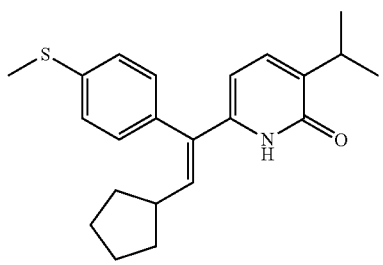

[Ka 108]

The title compound was obtained as a colorless powder (135 mg, 23% (two steps)) by performing substantially the same reaction as in Example 1-1 except for using [6-methoxy-5-(propan-2-yl)pyridin-2-yl][4-(methylsulfanyl)phenyl]methanone obtained in Reference Example 1-76.

¹H NMR (300 MHz, CDCl₃) δ ppm 1.17 (d, J=7.0 Hz, 6H), 1.32-1.81 (m, 8H), 2.35-2.51 (m, 1H), 2.53 (s, 3H), 3.08-3.28 (m, 1H), 5.86 (d, J=7.1 Hz, 1H), 6.19 (d, J=9.9 Hz, 1H), 7.03-7.18 (m, 3H), 7.23-7.32 (m, 2H), 9.34-9.59 (brs, 1H).

MS(+): 354 [M+H]⁺.

Example 1-4

6-{(E)-2-Cyclopentyl-1-[4-(methylsulfonyl)phenyl]ethenyl}-3-(propan-2-yl)pyridin-2(1H)-one

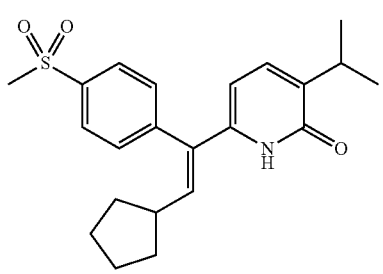

[Ka 109]

The title compound was obtained as a colorless powder (60 mg, 50%) by performing substantially the same reaction as in Example 1-2 except for using 6-{(E)-2-cyclopentyl-1-[4-(methylsulfanyl)phenyl]ethenyl}-3-(propan-2-yl)pyridin-2(1H)-one obtained in Example 1-3.

¹H NMR (300 MHz, CDCl₃) δ ppm 1.17 (d, J=6.8 Hz, 6H), 1.40-1.60 (m, 4H), 1.64-1.89 (m, 4H), 2.21-2.44 (m, 1H), 3.13 (s, 3H), 3.15-3.26 (m, 1H), 5.63 (d, J=7.3 Hz, 1H), 6.53 (d, J=10.1 Hz, 1H), 7.05-7.18 (m, 1H), 7.42 (d, J=8.5 Hz, 2H), 7.92-8.05 (m, 2H), 10.91-11.05 (brs, 1H).

MS(+): 386 [M+H]⁺.

Example 1-5

6-{(E)-2-Cyclopentyl-1-[4-(methylsulfanyl)phenyl]ethenyl}-3-cyclopropylpyridin-2(1H)-one

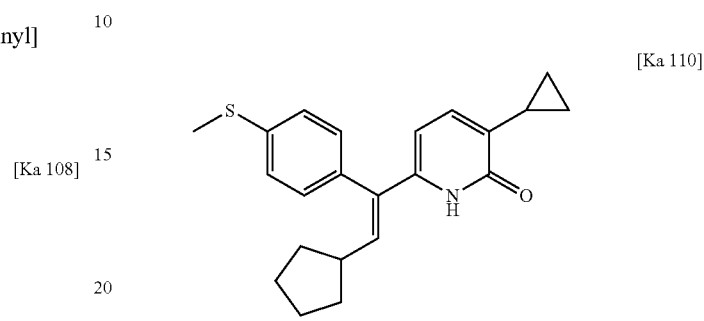

[Ka 110]

(1) 6-{(E)-2-Cyclopentyl-1-[4-(methylsulfanyl)phenyl]ethenyl}-3-cyclopropyl-2-methoxypyridine was obtained as a colorless oil (480 mg, 33%) by performing substantially the same reaction as in Example 1-1(1) except for using (5-cyclopropyl-6-methoxypyridin-2-yl)[4-(methylsulfanyl)phenyl]methanone obtained in Reference Example 1-51.

(2) A 4 M hydrogen chloride-1,4-dioxane solution (4.5 mL) was added to a suspension of 6-{(E)-2-cyclopentyl-1-[4-(methylsulfanyl)phenyl]ethenyl}-3-cyclopropyl-2-methoxypyridine (150 mg) in water (1.5 mL), and the mixture was stirred at 90° C. for 1.5 hours. The reaction solution was cooled to room temperature and extracted with chloroform twice. The organic layer was washed with brine, dried over anhydrous magnesium sulfate and filtered, after which the filtrate was concentrated under reduced pressure. The resulting residue was dissolved in a hexane-ethyl acetate solution with heating, and then recrystallization by cooling to room temperature gave the title compound as a colorless powder (111 mg, 77%).

¹H NMR (300 MHz, CDCl₃) δ ppm 0.54-0.63 (m, 2H), 0.87-0.98 (m, 2H), 1.29-1.82 (m, 8H), 2.03-2.15 (m, 1H), 2.36-2.51 (m, 1H), 2.51 (s, 3H), 5.80 (d, J=7.2 Hz, 1H), 6.18 (d, J=10.0 Hz, 1H), 6.80 (dd, J=7.3, 0.6 Hz, 1H), 7.05-7.13 (m, 2H), 7.23-7.30 (m, 2H), 9.34-9.65 (brs, 1H).

MS(+): 352 [M+H]⁺.

Example 1-6

6-{(E)-2-Cyclopentyl-1-[4-(methylsulfonyl)phenyl]ethenyl}-3-cyclopropylpyridin-2(1H)-one

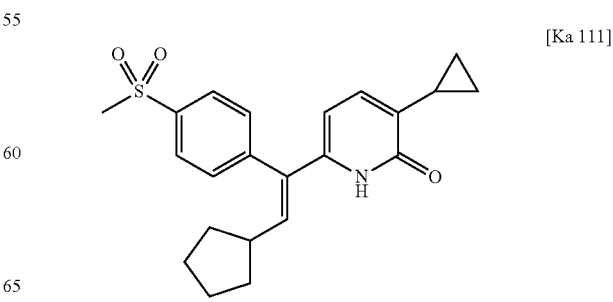

[Ka 111]

(1) A crude product containing 6-{(E)-2-cyclopentyl-1-[4-(methylsulfonyl)phenyl]ethenyl}-2-methoxy-3-cyclopropylpyridine was obtained by performing substantially the same reaction as in Example 1-2 except for using 6-{(E)-2-cyclopentyl-1-[4-(methylsulfanyl)phenyl]ethenyl}-3-cyclopropyl-2-methoxypyridine obtained in Example 1-5(1).

(2) The title compound was obtained as a colorless powder (132 mg, 84% (two steps)) by performing substantially the same reaction as in Example 1-5(2) except for using 6-{(E)-2-cyclopentyl-1-[4-(methylsulfonyl)phenyl]ethenyl}-2-methoxy-3-cyclopropylpyridine.

$^1$H NMR (300 MHz, CDCl$_3$) δ ppm 0.52-0.66 (m, 2H), 0.83-1.01 (m, 2H), 1.36-1.84 (m, 8H), 2.05-2.20 (m, 1H), 2.23-2.43 (m, 1H), 3.13 (s, 3H), 5.58 (d, J=7.2 Hz, 1H), 6.51 (d, J=10.1 Hz, 1H), 6.78 (d, J=7.2 Hz, 1H), 7.35-7.48 (m, 2H), 7.91-8.04 (m, 2H), 10.82-11.14 (brs, 1H).

MS(+): 384 [M+H]$^+$.

Example 1-7

6-{(E)-2-Cyclopentyl-1-[4-(methylsulfanyl)phenyl]ethenyl}-3-methylpyridin-2(1H)-one

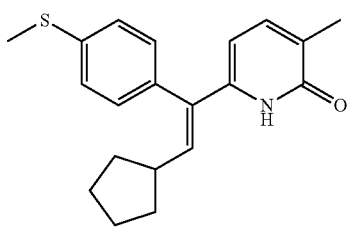

[Ka 112]

The title compound was obtained as a colorless amorphous (174 mg, 29% (two steps)) by performing substantially the same reaction as in Example 1-1 except for using (6-methoxy-5-methylpyridin-2-yl)[4-(methylsulfanyl)phenyl]methanone obtained in Reference Example 1-36.

$^1$H NMR (300 MHz, CDCl$_3$) δ ppm 1.10-1.85 (m, 8H), 2.12 (s, 3H), 2.35-2.55 (m, 1H), 2.53 (s, 3H), 5.85 (d, J=7.3 Hz, 1H), 6.12 (d, J=9.9 Hz, 1H), 7.00-7.30 (m, 5H), 8.90-9.35 (brs, 1H).

MS(+): 326 [M+H]$^+$.

Example 1-8

6-{(E)-2-Cyclopentyl-1-[4-(methylsulfonyl)phenyl]ethenyl}-3-methylpyridin-2(1H)-one

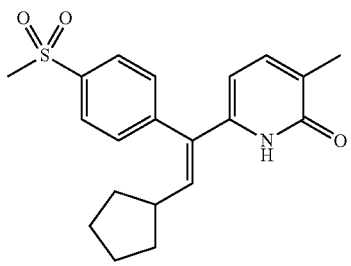

[Ka 113]

The title compound was obtained as a colorless powder (375 mg, 88% (two steps)) by performing substantially the same reaction as in Examples 1-2 and 1-1(2) sequentially except for using 6-{(E)-2-cyclopentyl-1-[4-(methylsulfanyl)phenyl]ethenyl}-2-methoxy-3-methylpyridine obtained in Example 1-7.

$^1$H NMR (300 MHz, CDCl$_3$) δ ppm 1.31-1.62 (m, 4H), 1.67-1.87 (m, 4H), 2.12 (s, 3H), 2.23-2.48 (m, 1H), 3.14 (s, 3H), 5.64 (d, J=7.0 Hz, 1H), 6.39 (d, J=10.1 Hz, 1H), 7.14 (d, J=8.2 Hz, 1H), 7.43 (d, J=8.4 Hz, 2H), 7.99 (d, J=8.4 Hz, 2H), 10.12-10.48 (brs, 1H).

MS(+): 358 [M+H]$^+$.

Example 1-9

6-{(E)-2-Cyclopentyl-1-[4-(ethylsulfanyl)phenyl]ethenyl}-3-methylpyridin-2(1H)-one

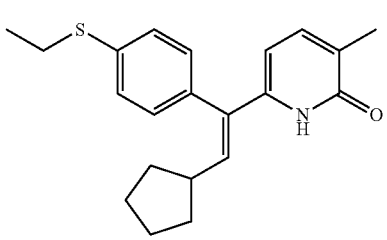

[Ka 114]

(1) 6-{(E)-2-Cyclopentyl-1-[4-(ethylsulfanyl)phenyl]ethenyl}-2-methoxy-3-methylpyridine was obtained as a colorless oil (470 mg, 31%) by performing substantially the same reaction as in Example 1-1(1) except for using [4-(ethylsulfanyl)phenyl](6-methoxy-5-methylpyridin-2-yl)methanone obtained in Reference Example 1-43.

(2) The title compound was obtained as a colorless powder (180 mg, 76%) by performing substantially the same reaction as in Example 1-1(2) except for using 6-{(E)-2-cyclopentyl-1-[4-(ethylsulfanyl)phenyl]ethenyl}-2-methoxy-3-methylpyridine.

$^1$H NMR (300 MHz, CDCl$_3$) δ ppm 1.28-1.86 (m, 8H), 1.38 (t, J=7.3, 3H), 2.12 (s, 3H), 2.34-2.63 (m, 1H), 3.00 (q, J=7.3 Hz, 2H), 5.82 (d, J=7.0 Hz, 1H), 6.20 (d, J=9.9 Hz, 1H), 7.09 (d, J=8.5 Hz, 2H), 7.14 (d, J=5.9 Hz, 1H), 7.32 (d, J=8.5 Hz, 2H), 9.52-9.80 (brs, 1H).

MS(+): 340 [M+H]$^+$.

Example 1-10

6-{(E)-2-Cyclopentyl-1-[4-(ethylsulfonyl)phenyl]ethenyl}-3-methylpyridin-2(1H)-one

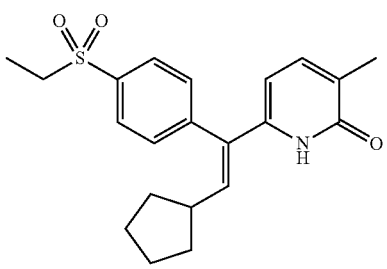

[Ka 115]

The title compound was obtained as a colorless powder (118 mg, 46% (two steps)) by performing substantially the same reaction as in Examples 1-2 and 1-1(2) sequentially except for using 6-{(E)-2-cyclopentyl-1-[4-(ethylsulfanyl)phenyl]ethenyl}-2-methoxy-3-methylpyridine obtained in Example 1-9(1).

$^1$H NMR (300 MHz, CDCl$_3$) δ ppm 1.27-1.42 (m, 3H), 1.42-1.64 (m, 4H), 1.66-1.83 (m, 4H), 2.12 (s, 3H), 2.25-2.48 (m, 1H), 3.19 (q, J=7.5 Hz, 2H), 5.60 (d, J=7.0 Hz, 1H), 6.36-6.57 (m, 1H), 7.08-7.18 (m, 1H), 7.35-7.52 (m, 2H), 7.88-8.08 (m, 2H), 10.56-10.85 (m, 1H).

MS(+): 372 [M+H]$^+$.

Example 1-11

6-{(E)-2-Cyclopentyl-1-[4-(cyclopropylsulfonyl)phenyl]ethenyl}-3-methylpyridin-2(1H)-one

[Ka 116]

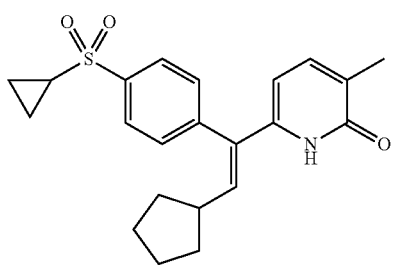

The title compound was obtained as a colorless powder (105 mg, 5.3% (three steps)) by performing substantially the same reaction as in Examples 1-1(1), 1-2 and 1-1(2) sequentially except for using [4-(cyclopropylsulfanyl)phenyl](6-methoxy-5-methylpyridin-2-yl)methanone obtained in Reference Example 1-37.

$^1$H NMR (300 MHz, CDCl$_3$) δ ppm 0.99-1.21 (m, 2H), 1.36-1.64 (m, 6H), 1.67-1.89 (m, 4H), 2.13 (s, 3H), 2.27-2.44 (m, 1H), 2.48-2.67 (m, 1H), 5.69 (d, J=7.0 Hz, 1H), 6.38 (d, J=10.1 Hz, 1H), 7.16 (d, J=6.9 Hz, 1H), 7.39 (d, J=8.4 Hz, 2H), 7.94 (d, J=8.5 Hz, 2H), 10.08-10.25 (brs, 1H).

MS(+): 384 [M+H]$^+$.

Example 1-12

6-[(E)-2-Cyclopentyl-1-{4-[(3-hydroxypropyl)sulfanyl]phenyl}ethenyl]-3-ethylpyridin-2(1H)-one

[Ka 117]

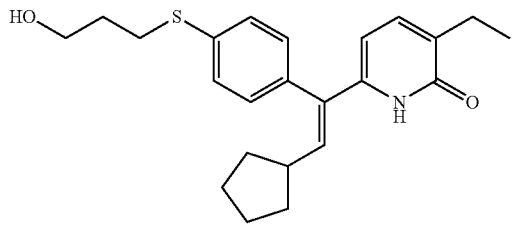

(1) 6-[1-{4-[(3-{[tert-Butyl(dimethyl)silyl]oxy}propyl)sulfanyl]phenyl}-2-cyclopentylethenyl]-3-ethyl-2-methoxypyridine (E:Z=1:1 mixture) was obtained as a colorless oil (800 mg) by performing substantially the same reaction as in Example 1-1(1) except for using {4-[(3-{[tert-butyl(dimethyl)silyl]oxy}propyl)sulfanyl]phenyl}(5-ethyl-6-methoxypyridin-2-yl)methanone obtained in Reference Example 1-47.

(2) The title compound was obtained as a colorless oil (50 mg, 33%) by performing substantially the same reaction as in Example 1-1(2) except for using 6-[1-{4-[(3-{[tert-butyl(dimethyl)silyl]oxy}propyl)sulfanyl]phenyl}-2-cyclopentylethenyl]-3-ethyl-2-methoxypyridine (E:Z=1:1 mixture).

$^1$H NMR (200 MHz, CDCl$_3$) δ ppm 1.17 (t, J=7.5 Hz, 3H), 1.30-1.85 (m, 8H), 1.90-2.07 (m, 2H), 2.33-2.62 (m, 3H), 3.01-3.20 (m, 2H), 3.71-3.91 (m, 2H), 5.88 (d, J=7.0 Hz, 1H), 6.13 (d, J=9.7 Hz, 1H), 6.99-7.20 (m, 3H), 7.37 (s, 2H).

MS(+): 384 [M+H]$^+$.

Example 1-13

6-[(E)-2-Cyclopentyl-1-{4-[(3-hydroxypropyl)sulfonyl]phenyl}ethenyl]-3-ethylpyridin-2(1H)-one

[Ka 118]

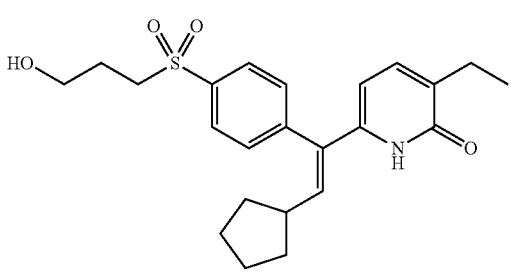

The title compound was obtained as a colorless powder (86 mg, 17% (two steps)) by performing substantially the same reaction as in Examples 1-2 and 1-1(2) sequentially except for using 6-[1-{4-[(3-{[tert-butyl(dimethyl)silyl]oxy}propyl)sulfanyl]phenyl}-2-cyclopentylethenyl]-3-ethyl-2-methoxypyridine (E:Z=1:1 mixture) obtained in Example 1-12(1).

$^1$H NMR (300 MHz, CDCl$_3$) δ ppm 1.17 (t, J=7.5 Hz, 3H), 1.35-1.63 (m, 4H), 1.67-1.88 (m, 4H), 1.98-2.14 (m, 2H), 2.25-2.43 (m, 1H), 2.54 (q, J=7.5 Hz, 2H), 3.22-3.42 (m, 2H), 3.71-3.85 (m, 2H), 5.69 (d, J=7.1 Hz, 1H), 6.41 (d, J=10.1 Hz, 1H), 7.13 (d, J=9.0 Hz, 1H), 7.42 (d, J=8.5 Hz, 2H), 7.97 (d, J=8.5 Hz, 2H).

MS(+): 416 [M+H]$^+$.

Example 1-14

4-[(E)-2-Cyclopentyl-1-(5-methyl-6-oxo-1,6-dihydropyridin-2-yl)ethenyl]-N,N-dimethylbenzenesulfonamide

[Ka 119]

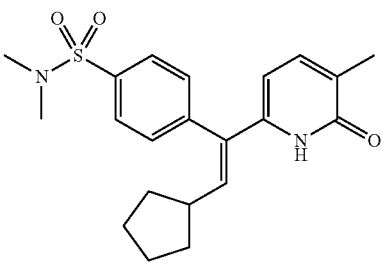

The title compound was obtained as a colorless powder (135 mg, 5.1% (two steps)) by performing substantially the same reaction as in Example 1-1 except for using 4-[(6-methoxy-5-methylpyridin-2-yl)carbonyl]-N,N-dimethylbenzenesulfonamide obtained in Reference Example 1-38.

$^1$H NMR (300 MHz, CDCl$_3$) δ ppm 1.34-1.59 (m, 4H), 1.64-1.87 (m, 4H), 2.13 (s, 3H), 2.27-2.48 (m, 1H), 2.80 (s, 6H), 5.66 (d, J=7.0 Hz, 1H), 6.37 (d, J=10.1 Hz, 1H), 7.15 (d, J=7.0 Hz, 1H), 7.38 (d, J=8.4 Hz, 2H), 7.82 (d, J=8.4 Hz, 2H), 10.12-10.37 (brs, 1H).

MS(+): 387 [M+H]$^+$.

Example 1-15

4-[(E)-2-Cyclopentyl-1-(5-methyl-6-oxo-1,6-dihydropyridin-2-yl)ethenyl]-N-(2-hydroxyethyl)-N-methylbenzenesulfonamide

[Ka 120]

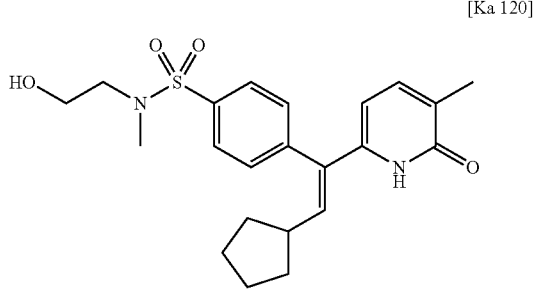 [SMILES: Cc1ccc(/C(=C/C2CCCC2)c2ccc(S(=O)(=O)N(C)CCO)cc2)[nH]c1=O]

The title compound was obtained as a colorless powder (132 mg, 16% (two steps)) by performing substantially the same reaction as in Example 1-1 except for using N-(2-{[tert-butyl(dimethyl)silyl]oxy}ethyl)-4-[(6-methoxy-5-methylpyridin-2-yl)carbonyl]-N-methylbenzenesulfonamide obtained in Reference Example 1-39.

$^1$H NMR (300 MHz, CDCl$_3$) δ ppm 1.33-1.61 (m, 6H), 1.65-1.86 (m, 2H), 2.12 (s, 3H), 2.23-2.52 (m, 1H), 2.94 (s, 3H), 3.21-3.39 (m, 2H), 3.69-3.94 (m, 2H), 5.72 (d, J=7.0 Hz, 1H), 6.38 (d, J=10.1 Hz, 1H), 7.10-7.20 (m, 1H), 7.37 (d, J=8.5 Hz, 2H), 7.85 (d, J=8.5 Hz, 2H).

MS(+): 417 [M+H]$^+$.

Example 1-16

6-[(E)-1-(3-Chloro-4-methoxyphenyl)-2-cyclopentylethenyl]-3-ethylpyridin-2(1H)-one

[Ka 121]

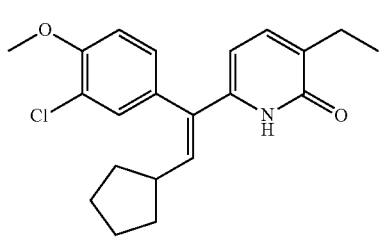

(1) 6-[(E)-1-(4-{[tert-Butyl(dimethyl)silyl]oxy}-3-chlorophenyl)-2-cyclopentylethenyl]-3-ethyl-2-methoxypyridine was obtained as a colorless amorphous (409 mg, 43%) by performing substantially the same reaction as in Example 1-1(1) except for using (4-{[tert-butyl(dimethyl)silyl]oxy}-3-chlorophenyl)(5-ethyl-6-methoxypyridin-2-yl)methanone obtained in Reference Example 1-50.

(2) A 1 M solution of tetrabutylammonium fluoride in tetrahydrofuran (1.73 mL) was added to a solution of 6-[(E)-1-(4-{[tert-butyl(dimethyl)silyl]oxy}-3-chlorophenyl)-2-cyclopentylethenyl]-3-ethyl-2-methoxypyridine (409 mg) in tetrahydrofuran (3 mL) under ice-boiling, and the mixture was stirred at room temperature for two hours. The reaction solution was poured into water and made acidic with 1 M hydrochloric acid, followed by extraction with ethyl acetate. The organic layer was washed with brine, dried over anhydrous magnesium sulfate and filtered. The solvent was then evaporated under reduced pressure. The residue was purified by silica gel column chromatography (hexane:ethyl acetate=10:1→1:1) to give 2-chloro-4-[(E)-2-cyclopentyl-1-(5-ethyl-6-methoxypyridin-2-yl)ethenyl]phenol as a yellow oil (306 mg, 99%).

(3) Potassium carbonate (188 mg) and methyl iodide (73 μL) were sequentially added to a solution of 2-chloro-4-[(E)-2-cyclopentyl-1-(5-ethyl-6-methoxypyridin-2-yl)ethenyl]phenol (163 mg) in N,N-dimethylformamide (3 mL), and the mixture was stirred at room temperature for four hours. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (hexane:ethyl acetate=10:0→2:1) to give 6-[(E)-1-(3-chloro-4-methoxyphenyl)-2-cyclopentylethenyl]-3-ethyl-2-methoxypyridine as a yellow oil (131 mg, 77%).

(4) The title compound was obtained as a colorless powder (50 mg, 39%) by performing substantially the same reaction as in Example 1-1(2) except for using 6-[(E)-1-(3-chloro-4-methoxyphenyl)-2-cyclopentylethenyl]-3-ethyl-2-methoxypyridine.

$^1$H NMR (300 MHz, CDCl$_3$) δ ppm 1.17 (t, J=7.5 Hz, 3H), 1.32-1.89 (m, 8H), 2.30-2.61 (m, 3H), 3.95 (s, 3H), 5.81 (d, J=7.0 Hz, 1H), 6.24 (d, J=10.0 Hz, 1H), 6.91-6.99 (m, 1H), 7.02-7.09 (m, 1H), 7.13 (d, J=7.2 Hz, 1H), 7.20 (s, 1H), 9.70-9.86 (brs, 1H).

MS(+): 358 [M+H]$^+$.

Example 1-17

6-[(E)-1-(3-Chloro-4-ethoxyphenyl)-2-cyclopentylethenyl]-3-ethylpyridin-2(1H)-one

[Ka 122]

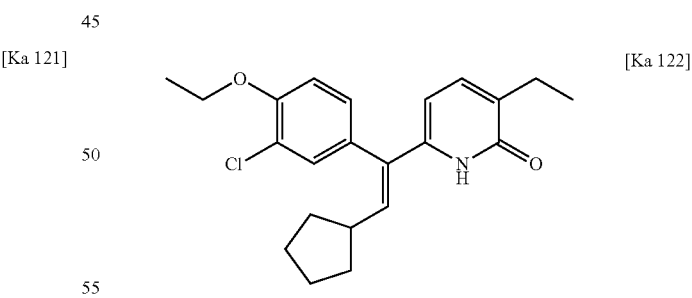

The title compound was obtained as a colorless powder (50 mg, 11% (four steps)) by performing substantially the same reaction as in Example 1-16 except for using ethyl iodide in place of methyl iodide.

$^1$H NMR (300 MHz, CDCl$_3$) δ ppm 1.17 (t, J=7.5 Hz, 3H), 1.29-1.85 (m, 11H), 2.31-2.67 (m, 3H), 4.15 (q, J=7.0 Hz, 2H), 5.82 (d, J=7.0 Hz, 1H), 6.22 (d, J=10.0 Hz, 1H), 6.88-6.97 (m, 1H), 6.99-7.06 (m, 1H), 7.12 (d, J=7.2 Hz, 1H), 7.19 (d, J=2.0 Hz, 1H), 9.61-9.79 (brs, 1H).

MS(+): 372 [M+H]$^+$.

Example 1-18

6-{(E)-1-[3-Chloro-4-(methylsulfanyl)phenyl]-2-cyclopentylethenyl}-3-methylpyridin-2(1H)-one

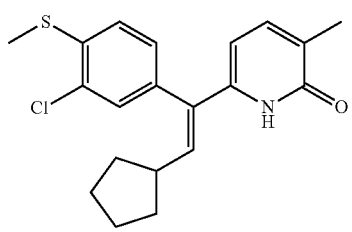

[Ka 123]

(1) 6-{(E)-1-[3-Chloro-4-(methylsulfanyl)phenyl]-2-cyclopentylethenyl}-2-methoxy-3-methylpyridine (196 mg, 25%) was obtained by performing substantially the same reaction as in Example 1-1(1) except for using [3-chloro-4-(methylsulfanyl)phenyl](6-methoxy-5-methylpyridin-2-yl)methanone obtained in Reference Example 1-40.

(2) The title compound was obtained as a colorless solid (162 mg, 89%) by performing substantially the same reaction as in Example 1-1(2) except for using 6-{(E)-1-[3-chloro-4-(methylsulfanyl)phenyl]-2-cyclopentylethenyl}-2-methoxy-3-methylpyridine.

$^1$H NMR (300 MHz, CDCl$_3$) δ ppm 1.35-1.60 (m, 4H), 1.60-1.85 (m, 4H), 2.14 (s, 3H), 2.35-2.50 (m, 1H), 2.52 (s, 3H), 5.85 (d, J=6.9 Hz, 1H), 6.26 (d, J=9.9 Hz, 1H), 7.07 (dd, J=8.1, 1.8 Hz, 1H), 7.15-7.25 (m, 3H), 9.80-10.00 (brs, 1H).
MS(+): 360 [M+H]$^+$.

Example 1-19

6-{(E)-1-[3-Chloro-4-(methylsulfonyl)phenyl]-2-cyclopentylethenyl}-3-methylpyridin-2(1H)-one

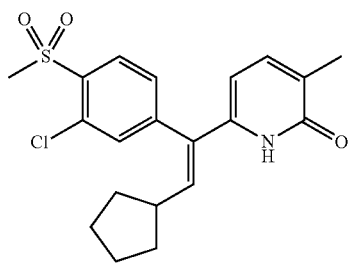

[Ka 124]

The title compound was obtained as a colorless solid (91 mg, 22% (two steps)) by performing substantially the same reaction as in Examples 1-2 and 1-1(2) sequentially except for using 6-{(E)-1-[3-chloro-4-(methylsulfanyl)phenyl]-2-cyclopentylethenyl}-2-methoxy-3-methylpyridine obtained in Example 1-18(1).

$^1$H NMR (300 MHz, CDCl$_3$) δ ppm 1.40-1.55 (m, 4H), 1.68-1.83 (m, 4H), 2.14 (s, 3H), 2.24-2.43 (m, 1H), 3.35 (s, 3H), 5.65 (d, J=7.2 Hz, 1H), 6.35 (d, J=10.5 Hz, 1H), 7.16 (dd, J=6.9, 0.9 Hz, 1H), 7.32 (dd, J=8.1, 1.5 Hz, 1H), 7.40 (d, J=1.5 Hz, 1H), 8.19 (d, J=8.1 Hz, 1H), 9.90-10.15 (brs, 1H).
MS(+): 392 [M+H]$^+$.

Example 1-20

6-{(E)-1-[3-Chloro-4-(methylsulfanyl)phenyl]-2-cyclopentylethenyl}-3-ethylpyridin-2(1H)-one

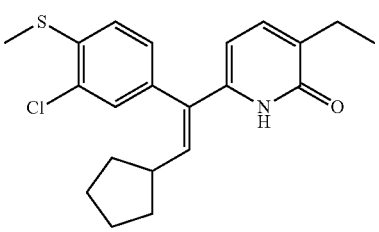

[Ka 125]

(1) 6-{(E)-1-[3-Chloro-4-(methylsulfanyl)phenyl]-2-cyclopentylethenyl}-3-ethyl-2-methoxypyridine was obtained as a pale yellow oil (60 mg, 10%) by performing substantially the same reaction as in Example 1-1(1) except for using [3-chloro-4-(methylsulfanyl)phenyl](5-ethyl-6-methoxypyridin-2-yl)methanone obtained in Reference Example 1-46.

(2) The title compound was obtained as a colorless powder (15 mg, 26%) by performing substantially the same reaction as in Example 1-1(2) except for using 6-{(E)-1-[3-chloro-4-(methylsulfanyl)phenyl]-2-cyclopentylethenyl}-3-ethyl-2-methoxypyridine.

$^1$H NMR (300 MHz, CDCl$_3$) δ ppm 1.17 (d, J=7.5 Hz, 3H), 1.33-1.84 (m, 8H), 2.52 (s, 3H), 2.33-2.61 (m, 3H), 5.77 (d, J=7.1 Hz, 1H), 6.26 (d, J=10.1 Hz, 1H), 6.98-7.23 (m, 4H), 10.25-10.42 (brs, 1H).
MS(+): 374 [M+H]$^+$.

Example 1-21

6-{(E)-1-[3-Chloro-4-(methylsulfonyl)phenyl]-2-cyclopentylethenyl}-3-ethylpyridin-2(1H)-one

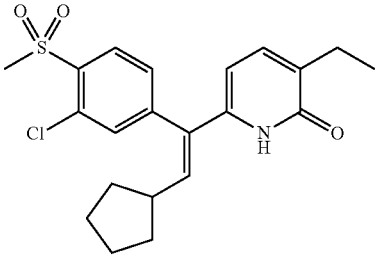

[Ka 126]

The title compound was obtained as a colorless powder (25 mg) by performing substantially the same reaction as in Examples 1-2 and 1-1(2) sequentially except for using 6-{(E)-1-[3-chloro-4-(methylsulfanyl)phenyl]-2-cyclopentylethenyl}-3-ethyl-2-methoxypyridine obtained in Example 1-20(1).

$^1$H NMR (300 MHz, CDCl$_3$) δ ppm 1.17 (t, J=7.5 Hz, 3H), 1.39-1.64 (m, 4H), 1.67-1.87 (m, 4H), 2.20-2.42 (m, 1H), 2.46-2.71 (m, 2H), 3.35 (s, 3H), 5.62 (d, J=7.1 Hz, 1H), 6.51 (d, J=10.3 Hz, 1H), 7.12 (d, J=7.3 Hz, 1H), 7.33 (dd, J=8.1, 1.6 Hz, 1H), 7.41 (d, J=1.6 Hz, 1H), 8.19 (d, J=8.1 Hz, 1H), 10.82-11.11 (brs, 1H).
MS(+): 406 [M+H]$^+$.

Example 1-22

6-[(E)-1-{3-Chloro-4-[(3-hydroxypropyl)sulfanyl]phenyl}-2-cyclopentylethenyl]-3-methylpyridin-2(1H)-one

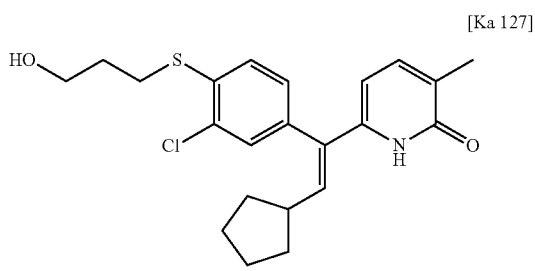 [SMILES: Cc1ccc(/C(=C/C2CCCC2)c2ccc(SCCCO)c(Cl)c2)[nH]c1=O]

[Ka 127]

(1) 6-[(E)-1-{4-[(3-{[tert-Butyl(dimethyl)silyl]oxy}propyl)sulfanyl]-3-chlorophenyl}-2-cyclopentylethenyl]-2-methoxy-3-methylpyridine was obtained as a colorless oil (1.24 g, 42%) by performing substantially the same reaction as in Example 1-1(1) except for using {4-[(3-{[tert-butyl(dimethyl)silyl]oxy}propyl)sulfanyl]-3-chlorophenyl}(6-methoxy-5-methylpyridin-2-yl)methanone obtained in Reference Example 1-41.

(2) The title compound was obtained as a colorless powder (77 mg, 40% (two steps)) by performing substantially the same reaction as in Example 1-1(2) except for using 6-[(E)-1-{4-[(3-{[tert-butyl(dimethyl)silyl]oxy}propyl)sulfanyl]-3-chlorophenyl}-2-cyclopentylethenyl]-2-methoxy-3-methylpyridine.

$^1$H NMR (300 MHz, CDCl$_3$) δ ppm 1.38-1.61 (m, 4H), 1.63-1.84 (m, 4H), 1.93-2.06 (m, 2H), 2.11 (s, 3H), 2.32-2.53 (m, 1H), 3.11 (t, J=7.2 Hz, 2H), 3.84 (t, J=6.0 Hz, 2H), 5.70 (d, J=7.2 Hz, 1H), 6.41 (d, J=10.0 Hz, 1H), 7.06 (dd, J=8.1, 1.9 Hz, 1H), 7.14 (dd, J=7.0, 1.1 Hz, 1H), 7.21 (d, J=1.9 Hz, 1H), 7.30 (d, J=8.1 Hz, 1H).

MS(+): 404 [M+H]$^+$.

Example 1-23

6-[(E)-1-{3-Chloro-4-[(3-hydroxypropyl)sulfonyl]phenyl}-2-cyclopentylethenyl]-3-methylpyridin-2(1H)-one

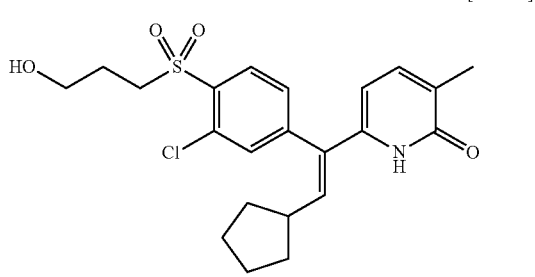

[Ka 128]

(1) 3-({2-chloro-4-[(E)-2-cyclopentyl-1-(6-methoxy-5-methylpyridin-2-yl)ethenyl]phenyl}sulfonyl)propan-1-ol was obtained as a colorless oil (148 mg, 88%) by performing substantially the same reaction as in Example 1-2 except for using 6-[(E)-1-{4-[(3-{[tert-butyl(dimethyl)silyl]oxy}propyl)sulfanyl]-3-chlorophenyl}-2-cyclopentylethenyl]-2-methoxy-3-methylpyridine obtained in Example 1-22 (1).

(2) The title compound was obtained as a colorless amorphous (31 mg, 72%) by performing substantially the same reaction as in Example 1-1(2) except for using 3-({2-chloro-4-[(E)-2-cyclopentyl-1-(6-methoxy-5-methylpyridin-2-yl)ethenyl]phenyl}sulfonyl)propan-1-ol.

$^1$H NMR (300 MHz, CDCl$_3$) δ ppm 1.38-1.88 (m, 8H), 2.01-2.16 (m, 5H), 2.25-2.44 (m, 1H), 3.58-3.66 (m, 2H), 3.81 (t, J=5.9 Hz, 2H), 5.62 (d, J=7.0 Hz, 1H), 6.47 (d, J=10.3 Hz, 1H), 7.13-7.19 (m, 1H), 7.32 (dd, J=8.1, 1.6 Hz, 1H), 7.41 (d, J=1.6 Hz, 1H), 8.16 (d, J=8.1 Hz, 1H).

MS(+): 436 [M+H]$^+$.

Example 1-24

6-[(E)-1-(3-Chloro-4-{[3-(diethylamino)propyl]sulfanyl}phenyl)-2-cyclopentylethenyl]-3-methylpyridin-2(1H)-one

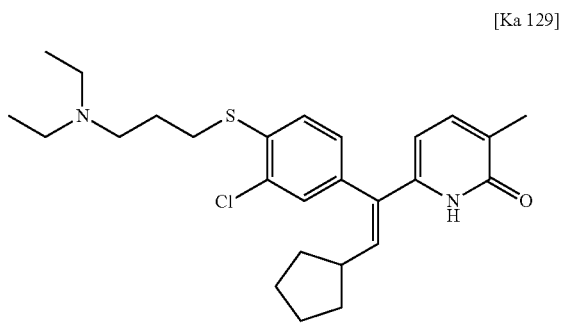 [SMILES: CCN(CC)CCCSc1ccc(/C(=C\C2CCCC2)c2ccc(C)c(=O)[nH]2)cc1Cl]

[Ka 129]

(1) Triethylamine (148 µL), trimethylamine hydrochloride (50 mg) and 4-methylbenzenesulfonyl chloride (74 mg) were sequentially added to a solution of 6-[(E)-1-{3-chloro-4-[(3-hydroxypropyl)sulfanyl]phenyl}-2-cyclopentylethenyl]-3-methylpyridin-2(1H)-one obtained in Example 1-22 (143 mg) in chloroform (5 mL) under ice-cooling, and the mixture was stirred at room temperature for one hour. Water and N,N-dimethylethylenediamine were added to the reaction solution, followed by extraction with chloroform. The organic layer was sequentially washed with 1 M hydrochloric acid and brine, dried over anhydrous magnesium sulfate and filtered. The solvent was then evaporated under reduced pressure. The residue was purified by silica gel chromatography (hexane:ethyl acetate=9:1→1:1) to give 3-({2-chloro-4-[(E)-2-cyclopentyl-1-(5-methyl-6-oxo-1,6-dihydropyridin-2-yl)ethenyl]phenyl}sulfanyl)propyl 4-methylbenzenesulfonate (33 mg, 18%) as a colorless amorphous.

(2) Potassium carbonate (290 mg) and diethylamine (219 µL) were sequentially added to a solution of 3-({2-chloro-4-[(E)-2-cyclopentyl-1-(5-methyl-6-oxo-1,6-dihydropyridin-2-yl)ethenyl]phenyl}sulfanyl)propyl 4-methylbenzenesulfonate (33 mg) in acetonitrile (3 mL), and the mixture was stirred at 90° C. for two hours. The reaction solution was poured into water, followed by extraction with chloroform. The organic layer was washed with brine, dried over anhydrous magnesium sulfate and filtered. The solvent was then evaporated under reduced pressure. The residue was purified by silica gel column chromatography (chloroform:methanol=10:0→9:1) to give the title compound (18 mg, 66%) as a colorless amorphous.

$^1$H NMR (300 MHz, CDCl$_3$) δ ppm 1.04 (t, J=7.2 Hz, 6H), 1.37-1.82 (m, 8H), 1.81-1.95 (m, 2H), 2.12 (d, J=0.9 Hz, 3H), 2.37-2.64 (m, 7H), 3.02 (t, J=7.3 Hz, 2H), 5.70 (d, J=7.0 Hz, 1H), 6.38 (d, J=10.0 Hz, 1H), 7.05 (dd, J=8.1, 1.7 Hz, 1H), 7.11-7.17 (m, 1H), 7.20 (d, J=1.9 Hz, 1H), 7.29 (d, J=8.2 Hz, 1H).

MS(+): 459 [M+H]$^+$.

Example 1-25

6-[(E)-1-(3-Chloro-4-{[3-(diethylamino)propyl]sulfonyl}phenyl)-2-cyclopentylethenyl]-3-methylpyridin-2(1H)-one

[Ka 130]

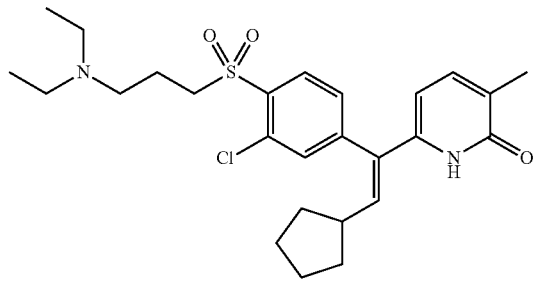

The title compound was obtained as a colorless amorphous (19 mg, 16% (three steps)) by performing substantially the same reaction as in Examples 1-24(1)(2) and 1-1(2) sequentially except for using 3-({2-chloro-4-[(E)-2-cyclopentyl-1-(6-methoxy-5-methylpyridin-2-yl)ethenyl]phenyl}sulfonyl)propan-1-ol obtained in Example 1-23(1).

$^1$H NMR (300 MHz, CDCl$_3$) δ ppm 1.34-1.89 (m, 14H), 2.13 (d, J=0.8 Hz, 3H), 2.27-2.71 (m, 3H), 3.09-3.43 (m, 6H), 3.62 (t, J=6.2 Hz, 2H), 5.63-5.72 (m, 1H), 6.38 (d, J=10.1 Hz, 1H), 7.16-7.22 (m, 1H), 7.35 (dd, J=8.1, 1.6 Hz, 1H), 7.43 (d, J=1.6 Hz, 1H), 8.14 (d, J=8.1 Hz, 1H).

MS(+): 491 [M+H]$^+$.

Example 1-26

6-[(E)-1-(3-Chloro-4-{[3-(diethylamino)propyl]sulfanyl}phenyl)-2-cyclopentylethenyl]-3-ethylpyridin-2(1H)-one

[Ka 131]

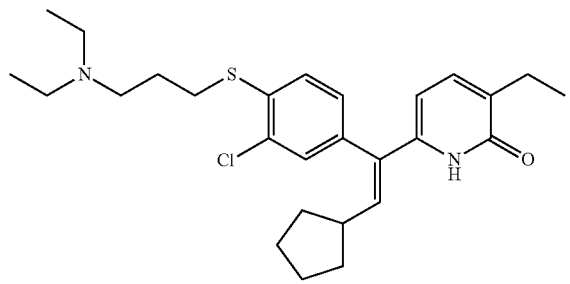

(1) 6-[(E)-1-{4-[(3-{[tert-Butyl(dimethyl)silyl]oxy}propyl)sulfanyl]-3-chlorophenyl}-2-cyclopentylethenyl]-3-ethyl-2-methoxypyridine was obtained as a colorless oil (273 mg, 37%) by performing substantially the same reaction as in Example 1-1(1) except for using {4-[(3-{[tert-butyl(dimethyl)silyl]oxy}propyl)sulfanyl]-3-chlorophenyl}(5-ethyl-6-methoxypyridin-2-yl)methanone obtained in Reference Example 1-48.

(2) 3-({2-Chloro-4-[(E)-2-cyclopentyl-1-(5-ethyl-6-methoxypyridin-2-yl)ethenyl]phenyl}sulfanyl)propan-1-ol was obtained as a colorless oil (195 mg, 86%) by performing substantially the same reaction as in Example 1-16(2) except for using 6-[(E)-1-{4-[(3-{[tert-butyl(dimethyl)silyl]oxy}propyl)sulfanyl]-3-chlorophenyl}-2-cyclopentylethenyl]-3-ethyl-2-methoxypyridine.

(3) Triethylamine (87 μL), trimethylamine hydrochloride (20 mg) and 4-methylbenzenesulfonyl chloride (60 mg) were sequentially added to a solution of 3-({2-chloro-4-[(E)-2-cyclopentyl-1-(5-ethyl-6-methoxypyridin-2-yl)ethenyl]phenyl}sulfanyl)propan-1-ol (95 mg) in chloroform (2 mL) under ice-cooling, and the mixture was stirred at room temperature for one hour. The reaction solution was poured into water, followed by extraction with ethyl acetate. The organic layer was washed with brine, dried over anhydrous magnesium sulfate and filtered, after which the solvent was evaporated under reduced pressure to give 3-({2-chloro-4-[(E)-2-cyclopentyl-1-(5-ethyl-6-methoxypyridin-2-yl)ethenyl]phenyl}sulfanyl)propyl 4-methylbenzenesulfonate (120 mg) as a yellow amorphous.

(4) Potassium carbonate (290 mg) and diethylamine (219 mL) were sequentially added to a solution of 3-({2-chloro-4-[(E)-2-cyclopentyl-1-(5-ethyl-6-methoxypyridin-2-yl)ethenyl]phenyl}sulfanyl)propyl 4-methylbenzenesulfonate (120 mg) in acetonitrile (3 mL), and the mixture was stirred at 90° C. for two hours. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (chloroform:methanol=10:0→9:1) to give 3-({2-chloro-4-[(E)-2-cyclopentyl-1-(5-ethyl-6-methoxypyridin-2-yl)ethenyl]phenyl}sulfanyl)-N,N-diethylpropan-1-amine (110 mg, 80%) as a colorless oil.

(5) The title compound was obtained as a colorless powder (45 mg) by performing substantially the same reaction as in Example 1-1(2) except for using 3-({2-chloro-4-[(E)-2-cyclopentyl-1-(5-ethyl-6-methoxypyridin-2-yl)ethenyl]phenyl}sulfanyl)-N,N-diethylpropan-1-amine.

$^1$H NMR (300 MHz, CDCl$_3$) δ ppm 1.04 (t, J=7.2 Hz, 6H), 1.14-1.23 (m, 3H), 1.33-1.97 (m, 12H), 2.31-2.68 (m, 7H), 2.93-3.13 (m, 2H), 5.78 (d, J=7.2 Hz, 1H), 6.24 (d, J=10.1 Hz, 1H), 7.04 (dd, J=8.1, 1.9 Hz, 1H), 7.10-7.15 (m, 1H), 7.19 (d, J=1.7 Hz, 1H), 7.29 (d, J=8.1 Hz, 1H), 9.67-9.89 (brs, 1H).

MS(+): 473 [M+H]$^+$.

Example 1-27

6-[(E)-1-(3-Chloro-4-{[3-(diethylamino)propyl]sulfonyl}phenyl)-2-cyclopentylethenyl]-3-ethylpyridin-2(1H)-one

[Ka 132]

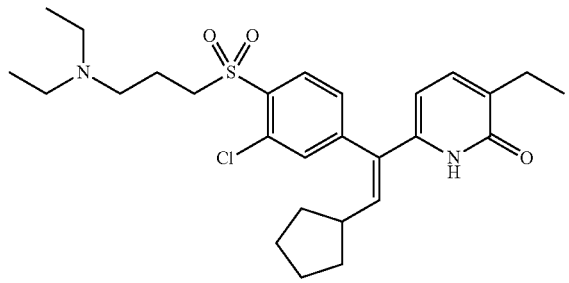

(1) 3-({2-Chloro-4-[(E)-2-cyclopentyl-1-(5-ethyl-6-methoxypyridin-2-yl)ethenyl]phenyl}sulfonyl)propan-1-ol was obtained as a colorless amorphous (82 mg, 66%) by performing substantially the same reaction as in Example 1-2 except for using 3-({2-chloro-4-[(E)-2-cyclopentyl-1-(5-ethyl-6-methoxypyridin-2-yl)ethenyl]phenyl}sulfanyl)propan-1-ol obtained in Example 1-26(2).

(2) The title compound was obtained as a colorless amorphous (40 mg) by performing substantially the same reaction as in Example 1-26(3)-(5) except for using 3-({2-chloro-4-[(E)-2-cyclopentyl-1-(5-ethyl-6-methoxypyridin-2-yl)ethenyl]phenyl}sulfonyl)propan-1-ol.

$^1$H NMR (300 MHz, CDCl$_3$) δ ppm 0.91-1.05 (m, 6H), 1.18 (t, J=7.5 Hz, 3H), 1.37-2.06 (m, 10H), 2.22-2.63 (m, 9H), 3.40-3.62 (m, 2H), 5.61 (d, J=7.0 Hz, 1H), 6.43 (d, J=10.3 Hz, 1H), 7.12 (d, J=7.8 Hz, 1H), 7.31 (dd, J=8.1, 1.6 Hz, 1H), 7.40 (d, J=1.6 Hz, 1H), 8.16 (d, J=8.1 Hz, 1H).
MS(+): 505 [M+H]$^+$.

Example 1-28

6-{(E)-2-Cyclopentyl-1-[4-(methylsulfonyl)phenyl]ethenyl}-3-(trifluoromethyl)pyridin-2(1H)-one

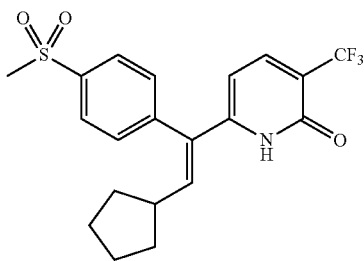

[Ka 133]

The title compound was obtained as a colorless powder (57 mg, 14% (three steps)) by performing substantially the same reaction as in Examples 1-1(1), 1-2 and 1-1(2) sequentially except for using [6-methoxy-5-(trifluoromethyl)pyridin-2-yl][4-(methylsulfanyl)phenyl]methanone obtained in Reference Example 1-67.

$^1$H NMR (300 MHz, CDCl$_3$) δ ppm 1.43-1.63 (m, 4H), 1.67-1.87 (m, 4H), 2.16-2.45 (m, 1H), 3.14 (s, 3H), 5.73 (d, J=7.5 Hz, 1H), 6.82 (d, J=10.1 Hz, 1H), 7.42 (d, J=8.5 Hz, 2H), 7.65 (d, J=7.5 Hz, 1H), 8.02 (d, J=8.5 Hz, 2H), 11.89-12.21 (brs, 1H).
MS(+): 412 [M+H]$^+$.

Example 1-29

6-{(E)-2-Cyclopentyl-1-[4-(cyclopropylsulfanyl)phenyl]ethenyl}-3-phenylpyridin-2(1H)-one

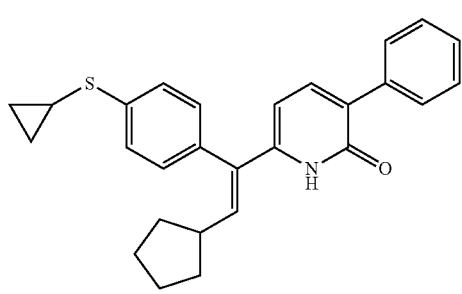

[Ka 134]

The title compound was obtained as a colorless powder (130 mg, 38% (two steps)) by performing substantially the same reaction as in Example 1-1 except for using [4-(cyclopropylsulfanyl)phenyl](6-methoxy-5-phenylpyridin-2-yl)methanone obtained in Reference Example 1-78

$^1$H NMR (300 MHz, CDCl$_3$) δ ppm 0.70-0.80 (m, 2H), 1.05-1.20 (m, 2H), 1.20-1.84 (m, 8H), 2.15-2.30 (m, 1H), 2.36-2.54 (m, 1H), 6.01 (d, J=7.3 Hz, 1H), 6.29 (d, J=9.9 Hz, 1H), 7.12 (d, J=7.9 Hz, 2H), 7.32 (d, J=6.6 Hz, 1H), 7.35-7.50 (m, 5H), 7.70 (d, J=8.3 Hz, 2H), 9.70-10.00 (brs, 1H).
MS(+): 414 [M+H]$^+$.

Example 1-30

6-{(E)-2-Cyclopentyl-1-[4-(cyclopropylsulfonyl)phenyl]ethenyl}-3-(hydroxymethyl)pyridin-2(1H)-one

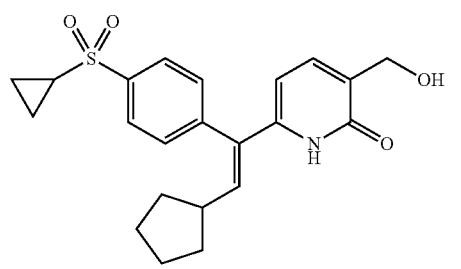

[Ka 135]

The title compound was obtained as a colorless powder (18 mg) by performing substantially the same reaction as in Examples 1-1(1), 1-16(2), 1-2 and 1-1(2) sequentially except for using [5-({[tert-butyl(diphenyl)silyl]oxy}methyl)-6-methoxypyridin-2-yl][4-(cyclopropylsulfanyl)phenyl]methanone obtained in Reference Example 1-77.

$^1$H NMR (300 MHz, CDCl$_3$) δ ppm 0.98-1.22 (m, 2H), 1.34-1.64 (m, 6H), 1.68-1.90 (m, 4H), 2.29-2.47 (m, 1H), 2.49-2.64 (m, 1H), 3.20-3.47 (brs, 1H), 4.44-4.65 (m, 2H), 5.83 (d, J=7.0 Hz, 1H), 6.40 (d, J=10.1 Hz, 1H), 7.21-7.32 (m, 1H), 7.35-7.42 (m, 2H), 7.96 (d, J=8.6 Hz, 2H), 10.43-10.67 (brs, 1H).
MS(+): 400 [M+H]$^+$.

Example 1-31

6-[(E)-2-Cyclopentyl-1-{4-[(1-ethylazetidin-3-yl)sulfanyl]phenyl}ethenyl]-3-methylpyridin-2(1H)-one

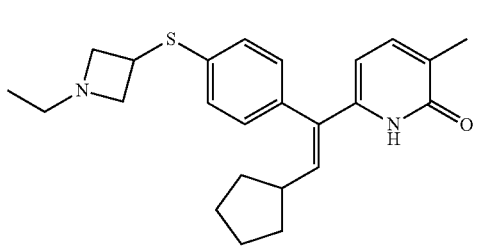

[Ka 136]

(1) tert-Butyl 3-({4-[(E)-2-cyclopentyl-1-(6-methoxy-5-methylpyridin-2-yl)ethenyl]phenyl}sulfanyl)azetidine-1-carboxylate was obtained as a colorless amorphous (505 mg, 33%) by performing substantially the same reaction as in Example 1-1(1) except for using tert-butyl 3-({4-[(6-methoxy-5-methylpyridin-2-yl)carbonyl]phenyl}sulfanyl)azetidine-1-carboxylate obtained in Reference Example 1-42.

(2) 4 M hydrochloric acid (4 mL, solution in 1,4-dioxane) was added to a solution of tert-butyl 3-({4-[(E)-2-cyclopentyl-1-(6-methoxy-5-methylpyridin-2-yl)ethenyl]phenyl}sulfanyl)azetidine-1-carboxylate (156 mg) in diethyl ether (4 mL), and the mixture was stirred at room temperature for two hours. The reaction solution was concentrated under reduced pressure to give a crude product containing 6-{(E)-1-[4-(azetidin-3-ylsulfanyl)phenyl]-2-cyclopentylethenyl}-2-methoxy-3-methylpyridine.

(3) 90% acetaldehyde (31 μL) and acetic acid were added to a solution of 6-{(E)-1-[4-(azetidin-3-ylsulfanyl)phenyl]-2-cyclopentylethenyl}-2-methoxy-3-methylpyridine in chloroform (2 mL), and the mixture was stirred at room temperature for 30 minutes. The reaction solution was cooled and sodium triacetoxyborohydride (206 mg) was added, after which the mixture was stirred at room temperature for 30 minutes. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (chloroform:methanol=100:0→93:7) to give 6-[(E)-2-cyclopentyl-1-{4-[(1-ethylazetidin-3-yl)sulfanyl]phenyl}ethenyl]-2-methoxy-3-methylpyridine as a colorless oil (78 mg, 58%).

(4) The title compound was obtained as a colorless powder (28 mg) by performing substantially the same reaction as in Example 1-1(2) except for using 6-[(E)-2-cyclopentyl-1-{4-[(1-ethylazetidin-3-yl)sulfanyl]phenyl}ethenyl]-2-methoxy-3-methylpyridine.

$^1$H NMR (300 MHz, CDCl$_3$) δ ppm 0.97 (t, J=7.2 Hz, 3H), 1.25-1.57 (m, 4H), 1.60-1.85 (m, 4H), 2.12 (s, 3H), 2.32-2.58 (m, 3H), 3.02-3.18 (m, 2H), 3.70-3.87 (m, 2H), 3.95-4.10 (m, 1H), 5.82 (d, J=7.0 Hz, 1H), 6.16 (d, J=10.1 Hz, 1H), 7.06-7.11 (m, 2H), 7.12-7.17 (m, 1H), 7.19-7.24 (m, 2H), 9.31-9.47 (brs, 1H).

MS(+): 395 [M+H]$^+$.

Example 1-32

6-[(E)-2-Cyclopentyl-1-{4-[(1-ethylazetidin-3-yl)sulfonyl]phenyl}ethenyl]-3-methylpyridin-2(1H)-one

[Ka 137]

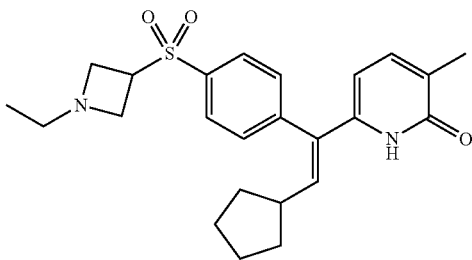

(1) tert-Butyl 3-({4-[(E)-2-cyclopentyl-1-(6-methoxy-5-methylpyridin-2-yl)ethenyl]phenyl}sulfonyl)azetidine-1-carboxylate was obtained as a colorless amorphous (240 mg, 68%) by performing substantially the same reaction as in Example 1-2 except for using tert-butyl 3-({4-[(E)-2-cyclopentyl-1-(6-methoxy-5-methylpyridin-2-yl)ethenyl]phenyl}sulfanyl)azetidine-1-carboxylate obtained in Example 1-31(1).

(2) The title compound was obtained as a colorless amorphous (103 mg, 48% (three steps)) by performing substantially the same reaction as in Example 1-31(2)-(4) except for using tert-butyl 3-({4-[(E)-2-cyclopentyl-1-(6-methoxy-5-methylpyridin-2-yl)ethenyl]phenyl}sulfonyl)azetidine-1-carboxylate.

$^1$H NMR (300 MHz, CDCl$_3$) δ ppm 0.95 (t, J=7.2 Hz, 3H), 1.38-1.59 (m, 4H), 1.62-1.84 (m, 4H), 2.12 (s, 3H), 2.23-2.42 (m, 1H), 2.47-2.61 (m, 2H), 3.41-3.68 (m, 4H), 3.91-4.19 (m, 1H), 5.59 (d, J=7.2 Hz, 1H), 6.44 (d, J=10.1 Hz, 1H), 7.08-7.20 (m, 1H), 7.34-7.48 (m, 2H), 7.82-7.98 (m, 2H), 10.54-10.81 (brs, 1H).

MS(+): 427 [M+H]$^+$.

Example 1-33

Methyl 4-[(E)-2-cyclopentyl-1-(5-methyl-6-oxo-1,6-dihydropyridin-2-yl)ethenyl]benzoate

[Ka 138]

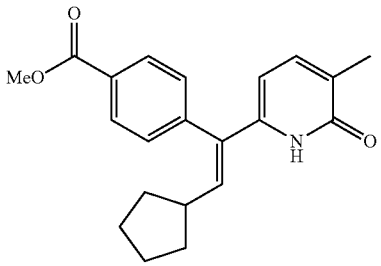

(1) 6-{(E)-2-Cyclopentyl-1-[4-(4,4-dimethyl-4,5-dihydro-1,3-oxazol-2-yl)phenyl]ethenyl}-2-methoxy-3-methylpyridine was obtained as a colorless oil (400 mg, 67%) by performing substantially the same reaction as in Example 1-1(1) except for using [4-(4,4-dimethyl-4,5-dihydrooxazol-2-yl)phenyl](6-methoxy-5-methylpyridin-2-yl)methanone obtained in Reference Example 1-44.

(2) 48% hydrobromic acid (1 mL) was added to a solution of 6-{(E)-2-cyclopentyl-1-[4-(4,4-dimethyl-4,5-dihydro-1,3-oxazol-2-yl)phenyl]ethenyl}-2-methoxy-3-methylpyridine (80 mg) in acetonitrile (1 mL), and the mixture was stirred at 100° C. for two hours and concentrated under reduced pressure. The residue was dissolved in methanol (1 mL) and 4 M hydrochloric acid (2 mL) was added, after which the mixture was stirred at 90° C. for four hours. The reaction solution was poured into water, followed by extraction with chloroform. The organic layer was washed with brine, dried over anhydrous magnesium sulfate and filtered. The solvent was then evaporated under reduced pressure. The residue was purified by silica gel column chromatography (hexane:ethyl acetate=4:1→1:1) to give the title compound as a colorless powder (15 mg, 21%).

$^1$H NMR (300 MHz, CDCl$_3$) δ ppm 1.31-1.62 (m, 4H), 1.64-1.86 (m, 4H), 2.12 (s, 3H), 2.28-2.52 (m, 1H), 3.95 (s, 3H), 5.68 (d, J=7.0 Hz, 1H), 6.26 (d, J=10.0 Hz, 1H), 7.13 (dd, J=7.0, 1.1 Hz, 1H), 7.22-7.38 (m, 2H), 8.00-8.13 (m, 2H), 9.49-9.88 (brs, 1H).

MS(+): 338 [M+H]$^+$.

Example 1-34

6-{(E)-2-Cyclopentyl-1-[6-(methylsulfanyl)pyridin-3-yl]ethenyl}-3-methylpyridin-2(1H)-one

[Ka 139]

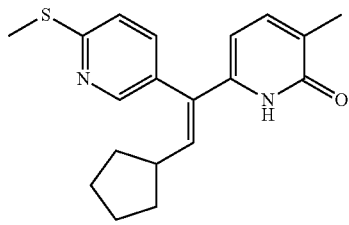

The title compound was obtained as a colorless powder (110 mg, 16% (two steps)) by performing substantially the same reaction as in Example 1-1 except for using (6-methoxy-5-methylpyridin-2-yl)[6-(methylsulfanyl)pyridin-3-yl]methanone obtained in Reference Example 1-45.

$^1$H NMR (300 MHz, CDCl$_3$) δ ppm 1.29-1.64 (m, 4H), 1.67-1.89 (m, 4H), 2.12 (s, 3H), 2.30-2.54 (m, 1H), 2.61 (s, 3H), 5.68 (d, J=7.0 Hz, 1H), 6.36 (d, J=9.9 Hz, 1H), 7.13 (d, J=8.2 Hz, 1H), 7.19-7.25 (m, 1H), 7.28-7.37 (m, 1H), 8.30 (d, J=3.0 Hz, 1H), 10.24-10.55 (brs, 1H).

MS(+): 327 [M+H]$^+$.

Example 1-35

6-{(E)-2-Cyclopentyl-1-[6-(methylsulfonyl)pyridin-3-yl]ethenyl}-3-methylpyridin-2(1H)-one

[Ka 140]

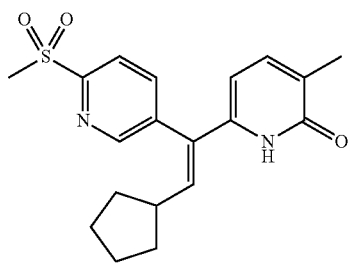

The title compound was obtained as a colorless powder (52 mg, 50%) by performing substantially the same reaction as in Example 1-2 except for using 6-{(E)-2-cyclopentyl-1-[6-(methylsulfanyl)pyridin-3-yl]ethenyl}-3-methylpyridin-2(1H)-one obtained in Example 1-34.

$^1$H NMR (300 MHz, CDCl$_3$) δ ppm 1.44-1.64 (m, 4H), 1.67-1.86 (m, 4H), 2.12 (s, 3H), 2.23-2.45 (m, 1H), 3.30 (s, 3H), 5.52 (d, J=7.1 Hz, 1H), 6.67 (d, J=10.3 Hz, 1H), 7.14 (dd, J=7.1, 1.2 Hz, 1H), 7.82 (dd, J=8.0, 2.1 Hz, 1H), 8.08-8.18 (m, 1H), 8.56-8.62 (m, 1H), 11.65-11.82 (brs, 1H).

MS(+): 359 [M+H]$^+$.

Example 1-36

6-{(1E)-3-Cyclopentyl-1-[4-(cyclopropylsulfanyl)phenyl]prop-1-en-1-yl}-3-methylpyridin-2(1H)-one

[Ka 141]

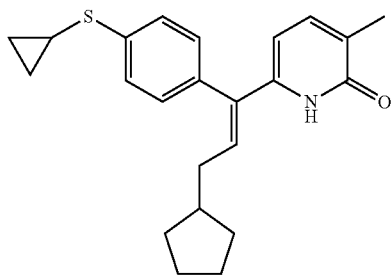

(1) 6-{(1E)-3-Cyclopentyl-1-[4-(cyclopropylsulfanyl)phenyl]prop-1-en-1-yl}-2-methoxy-3-methylpyridine was obtained as a colorless oil (564 mg, 44%) by performing substantially the same reaction as in Example 1-1(1) except for using (2-cyclopentylethyl)(triphenyl)phosphonium iodide in place of (cyclopentylmethyl)triphenylphosphonium iodide and using [4-(cyclopropylsulfanyl)phenyl](6-methoxy-5-methylpyridin-2-yl)methanone obtained in Reference Example 1-37.

(2) The title compound was obtained as a colorless powder (81 mg, 84%) by performing substantially the same reaction as in Example 1-1(2) except for using 6-{(1E)-3-cyclopentyl-1-[4-(cyclopropylsulfanyl)phenyl]prop-1-en-1-yl}-2-methoxy-3-methylpyridine.

$^1$H NMR (300 MHz, CDCl$_3$) δ ppm 0.70-0.78 (m, 2H), 1.01-1.19 (m, 4H), 1.41-1.65 (m, 4H), 1.71-1.86 (m, 2H), 1.87-2.01 (m, 1H), 2.04-2.26 (m, 6H), 5.79 (d, J=7.2 Hz, 1H), 6.48 (t, J=7.3 Hz, 1H), 7.03-7.11 (m, 2H), 7.14-7.20 (m, 1H), 7.33-7.41 (m, 2H).

MS(+): 366 [M+H]$^+$.

Example 1-37

6-{(1E)-3-Cyclopentyl-1-[4-(cyclopropylsulfonyl)phenyl]prop-1-en-1-yl}-3-methylpyridin-2(1H)-one

[Ka 142]

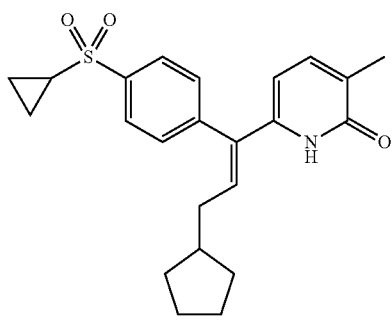

The title compound was obtained as a colorless powder (52 mg, 50%) by performing substantially the same reaction as in Examples 1-2 and 1-1(2) sequentially except for using 6-{(1E)-3-cyclopentyl-1-[4-(cyclopropylsulfanyl)phenyl]prop-1-en-1-yl}-2-methoxy-3-methylpyridine obtained in Example 1-36(1).

$^1$H NMR (300 MHz, CDCl$_3$) δ ppm 0.99-1.16 (m, 4H) 1.37-1.46 (m, 2H) 1.47-1.59 (m, 4H) 1.69-1.85 (m, 2H) 1.92-

1.98 (m, 1H) 2.03-2.11 (m, 2H) 2.12 (s, 3H) 2.54 (tt, J=8.0, 4.8 Hz, 1H) 5.69 (d, J=7.0 Hz, 1H) 6.55 (t, J=7.5 Hz, 1H) 7.15 (dd, J=7.1, 1.2 Hz, 1H) 7.32-7.43 (m, 2H) 7.90-7.99 (m, 2H) 10.35-10.56 (brs, 1H).

Example 1-38

6-{(E)-2-Cyclopentyl-1-[4-(4-hydroxybutyl)phenyl]ethenyl}-3-(trifluoromethyl)pyridin-2(1H)-one

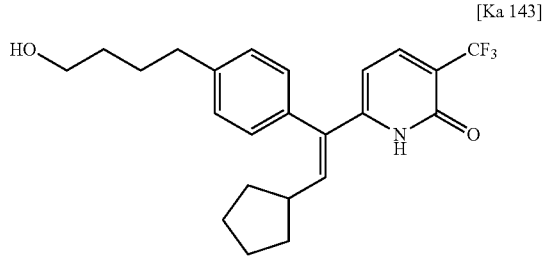 [SMILES: O=c1[nH]c(/C(=C/C2CCCC2)c2ccc(CCCCO)cc2)ccc1C(F)(F)F]

[Ka 143]

The title compound was obtained as a white solid (212 mg, 54% (two steps)) by performing substantially the same reaction as in Example 1-1 except for using [4-(4-{[tert-butyl(dimethyl)silyl]oxy}butyl)phenyl][6-methoxy-5-(trifluoromethyl)pyridin-2-yl]methanone obtained in Reference Example 1-72.

$^1$H NMR (300 MHz, CDCl$_3$) δ ppm 1.20-1.95 (m, 12H), 2.36-2.58 (m, 1H), 2.70 (t, J=7.4 Hz, 2H), 3.70 (t, J=6.3 Hz, 2H), 5.94 (d, J=7.4 Hz, 1H), 6.56 (d, J=10.1 Hz, 1H), 7.08 (dd, J=6.6, 1.8 Hz, 2H), 7.24 (d, J=8.0 Hz, 2H), 7.65 (d, J=7.4 Hz, 1H).

MS(+): 406 [M+H]$^+$.

Example 1-39

6-[(E)-2-Cyclopentyl-1-{4-[4-(diethylamino)butyl]phenyl}ethenyl]-3-(trifluoromethyl)pyridin-2(1H)-one

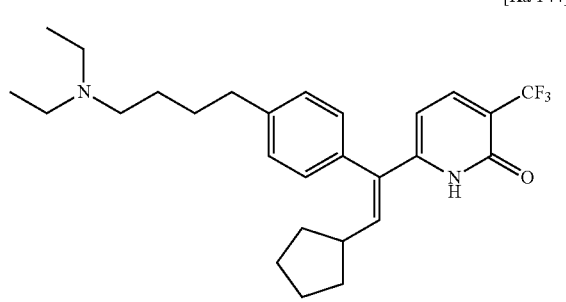

[Ka 144]

The title compound was obtained as a white solid (7.0 mg, 14% (two steps)) by performing substantially the same reaction as in Example 1-24 except for using 6-{(E)-2-cyclopentyl-1-[4-(4-hydroxybutyl)phenyl]ethenyl}-3-(trifluoromethyl)pyridin-2(1H)-one obtained in Example 1-38.

$^1$H NMR (300 MHz, CDCl$_3$) δ ppm 1.19 (t, J=7.0 Hz, 6H), 1.30-1.88 (m, 14H), 2.36-2.55 (m, 1H), 2.56-2.90 (m, 6H), 6.06 (d, J=7.4 Hz, 1H), 6.42 (d, J=10.1 Hz, 1H), 7.08 (d, J=8.0 Hz, 2H), 7.24 (d, J=11.3 Hz, 2H), 7.67 (d, J=8.0 Hz, 1H).

MS(+): 461 [M+H]$^+$.

Example 1-40

6-[(E)-2-Cyclopentyl-1-{4-[(3-hydroxypropyl)sulfonyl]phenyl}ethenyl]-3-(trifluoromethyl)pyridin-2(1H)-one

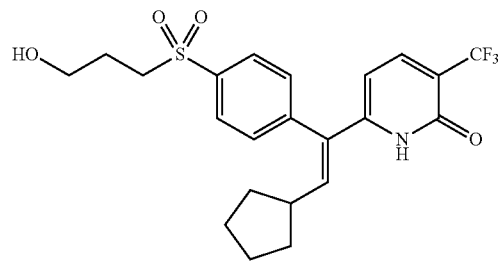

[Ka 145]

The title compound was obtained as a white solid (17 mg, 17% (three steps)) by performing substantially the same reaction as in Examples 1-1(1), 1-2 and 1-1(2) sequentially except for using {4-[(3-{[tert-butyl(dimethyl)silyl]oxy}propyl)sulfanyl]phenyl}[6-methoxy-5-(trifluoromethyl)pyridin-2-yl]methanone obtained in Reference Example 1-71.

$^1$H NMR (300 MHz, CDCl$_3$) δ ppm 1.40-1.63 (m, 4H), 1.65-1.85 (m, 4H), 2.01-2.14 (m, 2H), 2.25-2.45 (m, 1H), 3.32 (t, J=7.1 Hz, 2H), 3.78 (t, J=6.3 Hz, 2H), 5.85 (d, 7.1 Hz, 1H), 6.61 (d, J=8.6 Hz, 1H), 7.41 (d, J=8.0 Hz, 2H), 7.67 (d, J=8.0 Hz, 1H), 8.00 (d, J=8.3 Hz, 2H).

MS(+): 456 [M+H]$^+$.

Example 1-41

6-[(E)-2-Cyclopentyl-1-(4-{[3-(diethylamino)propyl]sulfonyl}phenyl)ethenyl]-3-(trifluoromethyl)pyridin-2(1H)-one

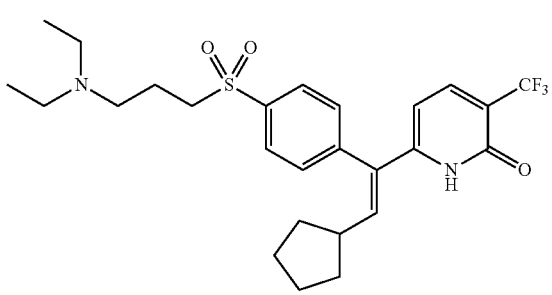

[Ka 146]

The title compound was obtained as a white solid (51 mg, 15% (five steps)) by performing substantially the same reaction as in Examples 1-1(1), 1-2, 1-24 and 1-1(2) sequentially except for using {4-[(3-{[tert-butyl(dimethyl)silyl]oxy}propyl)sulfanyl]phenyl}[6-methoxy-5-(trifluoromethyl)pyridin-2-yl]methanone obtained in Reference Example 1-71.

$^1$H NMR (300 MHz, CDCl$_3$) δ ppm 0.85-1.15 (m, 6H), 1.30-1.74 (m, 8H), 1.75-2.10 (m, 2H), 2.21-2.70 (m, 7H), 3.25 (t, J=7.7 Hz, 2H), 5.73 (d, J=7.4 Hz, 1H), 6.76 (d, J=10.1 Hz, 1H), 7.40 (d, J=8.3 Hz, 2H), 7.65 (d, J=8.3 Hz, 1H), 7.98 (d, J=8.3 Hz, 2H).

MS(+): 511 [M+H]+.

Example 1-42

6-[(E)-2-Cyclopentyl-1-{4-[4-(diethylamino)butanoyl]phenyl}ethenyl]-3-(trifluoromethyl)pyridin-2(1H)-one

[Ka 147]

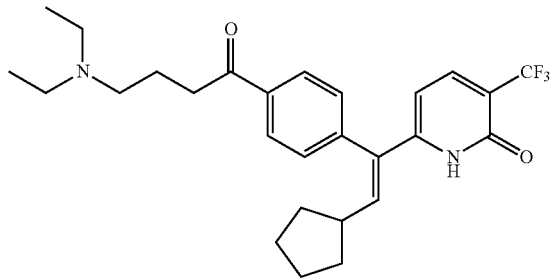

The title compound was obtained as a colorless solid (28 mg, 11% (two steps)) by performing substantially the same reaction as in Example 1-1 except for using (4-{2-[3-(diethylamino)propyl]-1,3-dioxolan-2-yl}phenyl)[6-methoxy-5-(trifluoromethyl)pyridin-2-yl]methanone obtained in Reference Example 1-75.

$^1$H NMR (300 MHz, CDCl$_3$) δ ppm 1.40-1.80 (m, 14H) 2.25-2.46 (m, 3H) 3.07-3.26 (m, 6H) 3.30 (t, J=6.6 Hz, 2H) 5.85 (d, J=7.7 Hz, 1H) 6.57 (d, J=10.1 Hz, 1H) 7.31 (d, J=8.0 Hz, 2H) 7.64 (d, J=7.7 Hz, 1H) 8.04 (d, J=8.0 Hz, 2H) 10.28-10.81 (brs, 1H).

MS(+): 475 [M+H]+.

Example 1-43

6-[(E)-2-Cyclopentyl-1-(4-{[3-(diethylamino)propyl]amino}phenyl)ethenyl]-3-(trifluoromethyl)pyridin-2(1H)-one

[Ka 148]

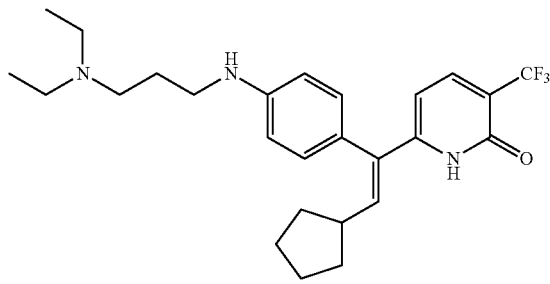

(1) 4-{(E)-2-Cyclopentyl-1-[6-methoxy-5-(trifluoromethylpyridin)-2-yl]ethenyl}phenol (256 mg, 63% (two steps)) was obtained by performing substantially the same reaction as in Example 1-16(1) and (2) except for using (4-{[tert-butyl (dimethyl)silyl]oxy}phenyl)[6-methoxy-5-(trifluoromethyl)pyridin-2-yl]methanone obtained in Reference Example 1-74.

(2) Trifluoromethanesulfonic anhydride (0.035 mL) and pyridine (0.017 mL) were sequentially added to a solution of 4-{(E)-2-cyclopentyl-1-[6-methoxy-5-(trifluoromethylpyridin)-2-yl]ethenyl}phenol (50 mg) in methylene chloride (4 mL) under ice-cooling, followed by stirring at room temperature. Trifluoromethanesulfonic anhydride (0.07 mL) and pyridine (0.034 mL) were further added. The mixture was stirred for 90 minutes in total. Separately, trifluoromethanesulfonic anhydride (0.241 mL) and pyridine (0.115 mL) were sequentially added to a solution of 4-{(E)-2-cyclopentyl-1-[6-methoxy-5-(trifluoromethylpyridin)-2-yl]ethenyl}phenol (130 mg) in methylene chloride (7.16 mL) under ice-cooling, and the mixture was stirred under ice-cooling for five minutes. Trifluoromethanesulfonic anhydride (0.6 mL) were further added under ice-cooling, and the mixture was stirred at room temperature for further four hours. Water was added to the respective reaction solutions, followed by extraction with chloroform. The organic layers were dried over anhydrous sodium sulfate and filtered. The solvent was then evaporated under reduced pressure. The resulting residues were combined and purified by silica gel column chromatography (hexane:ethyl acetate=50:1→30:1) to give 4-{(E)-2-cyclopentyl-1-[6-methoxy-5-(trifluoromethylpyridin)-2-yl]ethenyl}phenyl trifluoromethanesulfonate (243 mg, 99%).

(3) Cesium carbonate (30 mg), (2-biphenyl)dicyclohexylphosphine (4.3 mg) and palladium acetate (3 mg) were sequentially added to a solution of 4-{(E)-2-cyclopentyl-1-[6-methoxy-5-(trifluoromethylpyridin)-2-yl]ethenyl}phenyl trifluoromethanesulfonate (30 mg) and 3-(diethylamino)propylamine (0.012 mL) in toluene (3 mL) at room temperature in an argon atmosphere, and the mixture was stirred at 110° C. for three hours. The reaction solution was returned to room temperature, and sodium tert-butoxide (3.0 mg) was added in an argon atmosphere, after which the mixture was stirred at 110° C. for one hour. The reaction solution was returned to room temperature, and the solvent was evaporated under reduced pressure. The resulting residue was purified by silica gel column chromatography (chloroform:methanol=100:0→10:1) to give N'-(4-{(E)-2-cyclopentyl-1-[6-methoxy-5-(trifluoromethyl)pyridin-2-yl]ethenyl}phenyl)-N,N-diethyl-propane-1,3-diamine (16 mg, 57%).

(4) The title compound was obtained as a white solid (9.2 mg, 40%) by performing substantially the same reaction as in Example 1-1(2) except for using N'-(4-{(E)-2-cyclopentyl-1-[6-methoxy-5-(trifluoromethyl)pyridin-2-yl]ethenyl}phenyl)-N,N-diethylpropane-1,3-diamine.

$^1$H NMR (300 MHz, CDCl$_3$) δ ppm 1.31 (t, J=7.2 Hz, 6H), 1.35-2.16 (m, 10H), 2.48-2.64 (m, 1H), 2.90-3.10 (m, 6H), 3.32 (t, J=6.2 Hz, 2H), 6.15 (d, J=7.5 Hz, 1H), 6.37 (d, J=9.9 Hz, 1H), 6.64 (dd, J=6.8, 1.8 Hz, 2H), 6.95 (dd, J=6.6, 1.8 Hz, 2H), 7.67 (d, J=7.5 Hz, 1H)

MS(+): 462 [M+H]+.

Example 1-44

6-[(E)-1-{3-Chloro-4-[3-(ethylamino)propoxy]phenyl}-2-cyclopentylethenyl]-3-cyclopropylpyridin-2(1H)-one

[Ka 149]

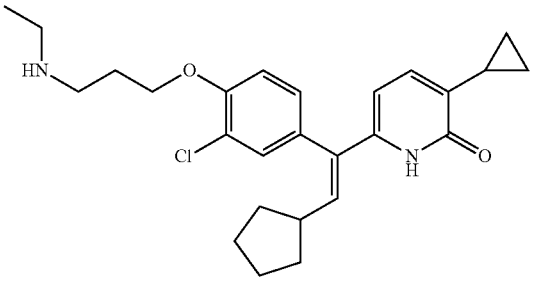

(1) 6-{(E)-1-[3-Chloro-4-(3-hydroxypropoxy)phenyl]-2-cyclopentylethenyl}-3-cyclopropyl-2-methoxypyridine was obtained as a colorless oil (140 mg, 46% (three steps)) by performing substantially the same reaction as in Example 1-16(1)-(3) except for using (4-{[tert-butyl(dimethyl)silyl]oxy}-3-chlorophenyl)(5-cyclopropyl-6-methoxypyridin-2-yl)methanone obtained in Reference Example 1-55 and using 3-bromo-1-propanol in place of methyl iodide.

(2) The title compound was obtained as a white solid (66 mg, 46% (three steps)) by performing substantially the same reaction as in Example 1-26(3)-(5) except for using 6-{(E)-1-[3-chloro-4-(3-hydroxypropoxy)phenyl]-2-cyclopentylethenyl}-3-cyclopropyl-2-methoxypyridine and a 2M ethylamine-methanol solution.

$^1$H NMR (300 MHz, DMSO-d$_6$) δ ppm 0.50-0.61 (m, 2H), 0.72-0.89 (m, 2H), 1.19 (t, J=7.7 Hz, 3H), 1.32-1.52 (m, 4H), 1.55-1.73 (m, 4H), 1.89-2.02 (m, 1H), 2.10 (t, J=6.0 Hz, 2H), 2.22-2.40 (m, 1H), 3.00 (q, J=7.7 Hz, 2H), 3.11 (t, J=7.4 Hz, 2H), 4.18 (t, J=6.0 Hz, 2H), 5.30-5.45 (m, 1H), 6.41 (d, J=9.2 Hz, 1H), 6.81 (d, J=7.1 Hz, 1H), 7.08 (dd, J=8.6, 1.5 Hz, 1H), 7.10-7.22 (m, 2H), 8.19-8.40 (brs, 1H), 11.22-11.38 (brs, 1H).

MS(+): 441 [M+H]$^+$.

Example 1-45

4-[(E)-2-Cyclopentyl-1-(5-cyclopropyl-6-oxo-1,6-dihydropyridin-2-yl)ethenyl]-N-[2-(diethylamino)ethyl]benzamide

[Ka 150]

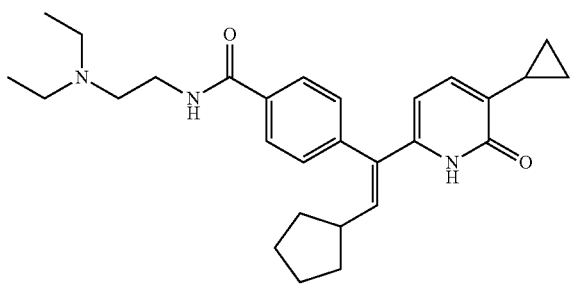

(1) 6-{(E)-2-Cyclopentyl-1-[4-(4,4-dimethyl-4,5-dihydro-1,3-oxazol-2-yl)phenyl]ethenyl}-3-cyclopropyl-2-methoxypyridine was obtained as a yellow oil (136 mg, 46%) by performing substantially the same reaction as in Example 1-1(1) except for using (5-cyclopropyl-6-methoxypyridin-2-yl)[4-(4,4-dimethyl-4,5-dihydro-1,3-oxazol-2-yl)phenyl]methanone obtained in Reference Example 1-59.

(2) 48% hydrobromic acid (4 mL) was added to a solution of 6-{(E)-2-cyclopentyl-1-[4-(4,4-dimethyl-4,5-dihydro-1,3-oxazol-2-yl)phenyl]ethenyl}-3-cyclopropyl-2-methoxypyridine (136 mg) in acetonitrile (4 mL) at room temperature. The mixture was stirred at room temperature for three hours and then stirred at 90° C. for three hours. The reaction solution was concentrated under reduced pressure. Methanol (2 mL) and 35% hydrochloric acid (2 mL) were added at room temperature, and the mixture was stirred at room temperature overnight. Water was added to the reaction solution, followed by extraction with ethyl acetate. The organic layer was concentrated under reduced pressure. Ethanol (6.5 mL) and a 1 M sodium hydroxide solution (1.2 mL) were added to the resulting crude product at room temperature, and the mixture was stirred at room temperature for three days. Water was added to the reaction solution, followed by extraction with ethyl acetate. The organic layer was concentrated under reduced pressure. The resulting residue was purified by silica gel column chromatography (chloroform:methanol=100:0→10:1) to give 4-[(E)-2-cyclopentyl-1-(5-cyclopropyl-6-oxo-1,6-dihydropyridin-2-yl)ethenyl]benzoic acid (100 mg, 88%).

(3) 1-Hydroxybenzotriazole (39 mg), triethylamine (0.04 mL), N,N-diethylethylenediamine (0.061 mL) and 1-(3-dimethylaminopropyl)-3-ethylcarbodiimide hydrochloride (55 mg) were sequentially added to a solution of 4-[(E)-2-cyclopentyl-1-(5-cyclopropyl-6-oxo-1,6-dihydropyridin-2-yl)ethenyl]benzoic acid (50 mg) in N,N-dimethylformamide at room temperature, and the mixture was stirred at room temperature overnight. Water was added to the reaction solution, followed by extraction with ethyl acetate. The organic layer was dried over anhydrous magnesium sulfate and filtered. The solvent was then evaporated under reduced pressure. The resulting residue was purified by preparative TLC (chloroform:methanol=20:1) and the resulting solid was washed with diethyl ether to give the title compound as a white solid (17 mg, 26%).

HPLC retention time 3.815 min

L-Column ODS 4.6×250 mm 0.01 M acetate buffer:MeCN=40:60 v/v, 40° C., 1.0 mL/min

MS(+): 448 [M+H]$^+$.

Example 1-46

3-Chloro-6-[(E)-2-cyclopentyl-1-{4-[(4-methylpiperazin-1-yl)sulfonyl]phenyl}ethenyl]pyridin-2(1H)-one

[Ka 151]

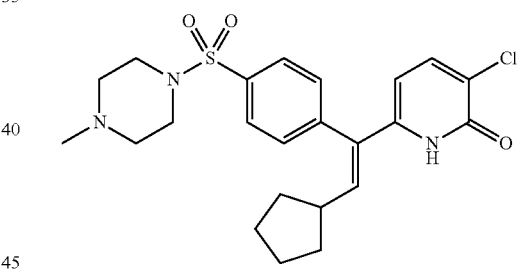

(1) tert-Butyl 4-({4-[(E)-1-(5-chloro-6-methoxypyridin-2-yl)-2-cyclopentylethenyl]phenyl}sulfonyl)piperazine-1-carboxylate was obtained as a colorless amorphous (178 mg, 17%) by performing substantially the same reaction as in Example 1-1(1) except for using tert-butyl 4-({4-[(5-chloro-6-methoxypyridin-2-yl)carbonyl]phenyl}sulfonyl)piperazine-1-carboxylate obtained in Reference Example 1-23.

(2) Trifluoroacetic acid (0.2 mL) was added to a solution of tert-butyl 4-({4-[(E)-1-(5-chloro-6-methoxypyridin-2-yl)-2-cyclopentylethenyl]phenyl}sulfonyl)piperazine-1-carboxylate (178 mg) in chloroform (3 mL), and the mixture was stirred at room temperature for three hours. The reaction solution was concentrated under reduced pressure to give 1-({4-[(E)-1-(5-chloro-6-methoxypyridin-2-yl)-2-cyclopentylethenyl]phenyl}sulfonyl)piperazine as a crude product.

(3) 1-({4-[(E)-1-(5-Chloro-6-methoxypyridin-2-yl)-2-cyclopentylethenyl]phenyl}sulfonyl)-4-methylpiperazine was obtained as a colorless amorphous (154 mg, 99%) by performing substantially the same reaction as in Example 1-31 (3) except for using a 37% formaldehyde solution in place of acetaldehyde and using 1-({4-[(E)-1-(5-chloro-6-methoxy-pyridin-2-yl)-2-cyclopentylethenyl]phenyl}sulfonyl)piperazine.

(4) The title compound was obtained as a colorless powder (66 mg, 44%) by performing substantially the same reaction as in Example 1-1(2) except for using 1-({4-[(E)-1-(5-chloro-6-methoxypyridin-2-yl)-2-cyclopentylethenyl]phenyl}sulfonyl)-4-methylpiperazine.

$^1$H NMR (300 MHz, CDCl$_3$) δ ppm 1.40-1.66 (m, 4H) 1.69-1.88 (m, 4H) 2.23-2.42 (m, 4H) 2.47-2.60 (m, 4H) 2.99-3.26 (m, 4H) 5.59 (d, J=7.6 Hz, 1H) 6.47 (d, J=10.3 Hz, 1H) 7.32-7.41 (m, 2H) 7.45 (d, J=7.6 Hz, 1H) 7.71-7.86 (m, 2H) 10.64-10.98 (brs, 1H).

MS(+): 462 [M+H]$^+$.

Example 1-47

3-Cyclopropyl-6-[(E)-1-[4-(methylsulfanyl)phenyl]-2-(tetrahydrofuran-3-yl)ethenyl]pyridin-2(1H)-one

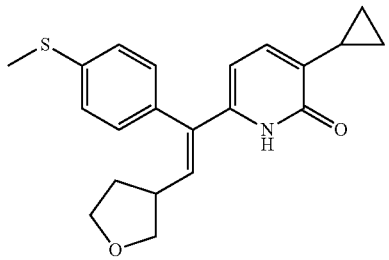

[Ka 152]

(1) A 1 M solution of lithium hexamethyldisilazide in tetrahydrofuran (5.14 mL) was added to a solution of 1-phenyl-5-[(tetrahydrofuran-3-ylmethyl)sulfonyl]-1H-tetrazole obtained in Reference Example 3-6 (1.51 g) in tetrahydrofuran (15 mL) in a nitrogen gas stream at −78° C., and the mixture was stirred at −78° C. for one hour. A solution of (5-cyclopropyl-6-methoxypyridin-2-yl)[4-(methylsulfanyl)phenyl]methanone obtained in Reference Example 1-51 (700 mg) in tetrahydrofuran (10 mL) was added, and the mixture was stirred at −78° C. to 0° C. for one hour. The reaction solution was poured into a saturated ammonium chloride solution, followed by extraction with ethyl acetate. The organic layer was washed with saturated aqueous sodium bicarbonate and brine, dried over anhydrous magnesium sulfate and filtered. The solvent was then evaporated under reduced pressure. The residue was purified by silica gel column chromatography (hexane:ethyl acetate=9:1→7:3) to give 3-cyclopropyl-2-methoxy-6-[(E)-1-[4-(methylsulfanyl)phenyl]-2-(tetrahydrofuran-3-yl)ethenyl]pyridine (122 mg, 14%) as a colorless oil.

(2) The title compound was obtained as a colorless powder (25 mg) by performing substantially the same reaction as in Example 1-1(2) except for using 3-cyclopropyl-2-methoxy-6-[(E)-1-[4-(methylsulfanyl)phenyl]-2-(tetrahydrofuran-3-yl)ethenyl]pyridine.

$^1$H NMR (300 MHz, CDCl$_3$) δ ppm 0.54-0.67 (m, 2H) 0.86-1.03 (m, 2H) 1.77-1.93 (m, 1H) 1.96-2.20 (m, 2H) 2.53 (s, 3H) 2.77-2.98 (m, 1H) 3.52-3.63 (m, 1H) 3.66-3.99 (m, 3H) 5.81 (d, J=7.3 Hz, 1H) 6.32 (d, J=9.9 Hz, 1H) 6.81 (d, J=7.3 Hz, 1H) 7.02-7.13 (m, 2H) 7.23-7.33 (m, 2H) 10.23-10.40 (brs, 1H).

MS(+): 354 [M+H]$^+$.

Example 1-48

6-{(E)-1-[4-(Cyclopropylsulfanyl)phenyl]-2-(tetrahydrofuran-3-yl)ethenyl}-3-(trifluoromethyl)pyridin-2(1H)-one

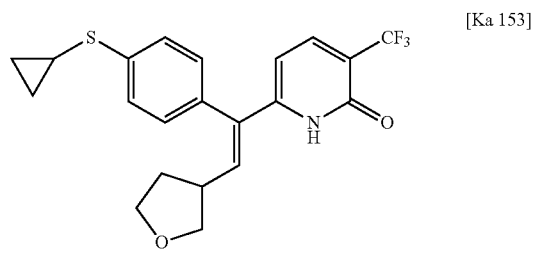 [SMILES: O=c1[nH]c(/C(=C/C2CCOC2)c2ccc(SC3CC3)cc2)ccc1C(F)(F)F]

[Ka 153]

The title compound was obtained as a colorless powder (37 mg) by performing substantially the same reaction as in Example 1-47 except for using [4-(cyclopropylsulfanyl)phenyl][6-methoxy-5-(trifluoromethyl)pyridin-2-yl]methanone obtained in Reference Example 1-68.

$^1$H NMR (300 MHz, CDCl$_3$) δ ppm 0.66-0.83 (m, 2H) 1.06-1.21 (m, 2H) 1.82-2.13 (m, 2H) 2.14-2.30 (m, 1H) 2.78-3.02 (m, 1H) 3.59 (t, J=8.2 Hz, 1H) 3.69-4.07 (m, 3H) 5.94 (d, J=7.5 Hz, 1H) 6.66 (d, J=9.8 Hz, 1H) 7.04-7.15 (m, 2H) 7.35-7.48 (m, 2H) 7.61-7.74 (m, 1H) 11.43-11.68 (brs, 1H).

MS(+): 408 [M+H]$^+$.

Example 1-49

3-Cyclopropyl-6-{(1E)-1-[4-(methylsulfanyl)phenyl]-3-(tetrahydrofuran-3-yl)prop-1-en-1-yl}pyridin-2(1H)-one

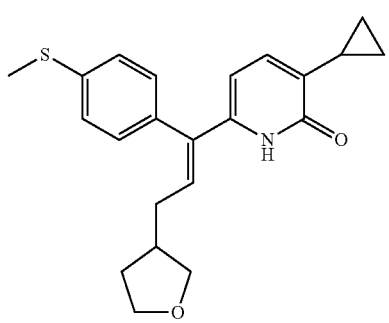

[Ka 154]

The title compound was obtained as a colorless powder (36 mg) by performing substantially the same reaction as in Example 1-47 except for using 1-phenyl-5-{[2-(tetrahydrofuran-3-yl)ethyl]sulfonyl}-1H-tetrazole obtained in Reference Example 3-8.

$^1$H NMR (300 MHz, CDCl$_3$) δ ppm 0.52-0.67 (m, 2H) 0.82-1.04 (m, 2H) 1.37-1.58 (m, 1H) 1.97-2.14 (m, 2H) 2.15-2.24 (m, 2H) 2.26-2.39 (m, 1H) 2.52 (s, 3H) 3.25-3.39 (m, 1H) 3.63-3.91 (m, 3H) 5.86 (d, J=7.1 Hz, 1H) 6.24 (t, J=7.3 Hz, 1H) 6.83 (d, J=7.3 Hz, 1H) 7.02-7.12 (m, 2H) 7.23-7.32 (m, 2H) 9.24-9.45 (brs, 1H)

MS(+): 368 [M+H]$^+$..

Example 1-50

6-[(1E)-1-(3-Chloro-4-methoxyphenyl)-3-(tetrahydrofuran-2-yl)prop-1-en-1-yl]-3-cyclopropylpyridin-2(1H)-one

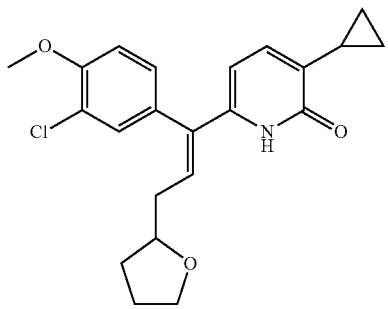

[Ka 155]

The title compound was obtained as a colorless powder (6.7 mg) by performing substantially the same reaction as in Examples 1-47(1) and 1-16(2)-(4) sequentially except for using 1-phenyl-5-{[2-(tetrahydrofuran-2-yl)ethyl]sulfonyl}-1H-tetrazole obtained in Reference Example 3-7 in place of 1-phenyl-5-[(tetrahydrofuran-3-ylmethyl)sulfonyl]-1H-tetrazole and using (4-{[tert-butyl(dimethyl)silyl]oxy}-3-chlorophenyl)(5-cyclopropyl-6-methoxypyridin-2-yl)methanone obtained in Reference Example 1-55.

$^1$H NMR (300 MHz, CDCl$_3$) δ ppm 0.54-0.69 (m, 2H) 0.86-1.02 (m, 2H) 1.35-1.52 (m, 1H) 1.79-2.16 (m, 4H) 2.24-2.41 (m, 2H) 3.66-3.79 (m, 1H) 3.80-4.00 (m, 5H) 5.87 (d, J=7.2 Hz, 1H) 6.30 (t, J=7.5 Hz, 1H) 6.82 (d, J=7.3 Hz, 1H) 6.91-6.99 (m, 1H) 7.02-7.10 (m, 1H) 7.22 (d, J=2.2 Hz, 1H) 9.01-9.27 (brs, 1H).

MS(+): 386 [M+H]$^+$.

Example 1-51

3-Cyclopropyl-6-[(E)-1-(4-methoxyphenyl)-2-(tetrahydro-2H-pyran-4-yl)ethenyl]pyridin-2(1H)-one

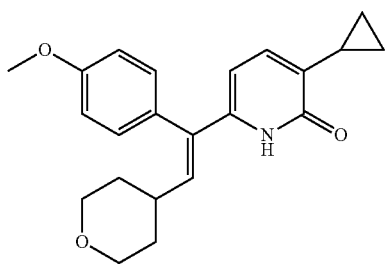

[Ka 156]

The title compound was obtained as a colorless powder (51 mg) by performing substantially the same reaction as in Example 1-16(1)-(4) except for using triphenyl(tetrahydro-2H-pyran-4-ylmethyl)phosphonium iodide (described in J. Med. Chem., 51(14), 2008, 4340-4345) in place of (cyclopentylmethyl)triphenylphosphonium iodide and using (4-{[tert-butyl(dimethyl)silyl]oxy}phenyl)(5-cyclopropyl-6-methoxypyridin-2-yl)methanone obtained in Reference Example 1-54.

$^1$H NMR (300 MHz, CDCl$_3$) δ ppm 0.53-0.67 (m, 2H) 0.88-0.99 (m, 2H) 1.40-1.71 (m, 4H) 2.03-2.17 (m, 1H) 2.25-2.43 (m, 1H) 3.17-3.37 (m, 2H) 3.86 (s, 3H) 3.87-3.94 (m, 2H) 5.85 (d, J=7.3 Hz, 1H) 6.10 (d, J=9.8 Hz, 1H) 6.75-6.86 (m, 1H) 6.89-6.99 (m, 2H) 7.03-7.13 (m, 2H) 9.53-9.71 (brs, 1H).

MS(+): 352 [M+H]$^+$.

Example 1-52

3-Cyclopropyl-6-[(E)-1-(4-ethoxyphenyl)-2-(tetrahydro-2H-pyran-4-yl)ethenyl]pyridin-2(1H)-one

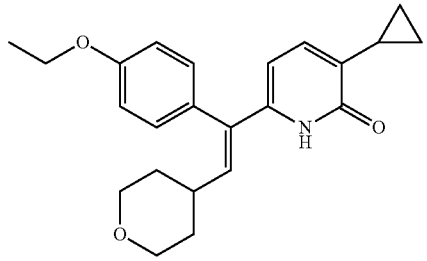

[Ka 157]

The title compound was obtained as a colorless powder (23 mg, (four steps)) by performing substantially the same reaction as in Example 1-51 except for using ethyl iodide in place of methyl iodide.

$^1$H NMR (300 MHz, CDCl$_3$) δ ppm 0.54-0.64 (m, 2H), 0.88-0.99 (m, 2H), 1.46 (t, J=7.0 Hz, 3H), 1.50-1.68 (m, 4H), 2.02-2.18 (m, 1H), 2.26-2.45 (m, 1H), 3.18-3.36 (m, 2H), 3.83-3.98 (m, 2H), 4.08 (q, J=7.0 Hz, 2H), 5.88 (d, J=7.2 Hz, 1H), 6.04 (d, J=9.6 Hz, 1H), 6.82 (d, J=7.9 Hz, 1H), 6.89-6.96 (m, 2H), 7.02-7.09 (m, 2H), 9.24-9.39 (brs, 1H).

MS(+): 366 [M+H]$^+$.

Example 1-53

6-[(E)-1-(3-Chloro-4-methoxyphenyl)-2-(tetrahydro-2H-pyran-4-yl)ethenyl]-3-cyclopropylpyridin-2(1H)-one

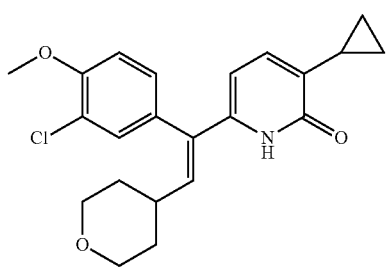

[Ka 158]

(1) 6-[(E)-1-(4-{[tert-Butyl(dimethyl)silyl]oxy}-3-chlorophenyl)-2-(tetrahydro-2H-pyran-4-yl)ethenyl]-3-cyclopropyl-2-methoxypyridine was obtained as a colorless powder (400 mg, 41%) by performing substantially the same reaction as in Example 1-1(1) except for using triphenyl (tetrahydro-2H-pyran-4-ylmethyl)phosphonium iodide in place of (cyclopentylmethyl)triphenylphosphonium iodide and using (4-{[tert-butyl(dimethyl)silyl]oxy}-3-chlorophenyl)(5-cyclopropyl-6-methoxypyridin-2-yl)methanone obtained in Reference Example 1-55.

(2) 4-[(E)-1-(5-Cyclopropyl-6-methoxypyridin-2-yl)-2-(tetrahydro-2H-pyran-4-yl)ethenyl]phenol was obtained as a yellow amorphous (300 mg, 97%) by performing substantially the same reaction as in Example 1-16(2) except for using 6-[(E)-1-(4-{[tert-butyl(dimethyl)silyl]oxy}-3-chlorophenyl)-2-(tetrahydro-2H-pyran-4-yl)ethenyl]-3-cyclopropyl-2-methoxypyridine.

(3) A crude product containing 3-cyclopropyl-2-methoxy-6-[(E)-1-(4-methoxyphenyl)-2-(tetrahydro-2H-pyran-4-yl)ethenyl]pyridine (134 mg) was obtained by performing substantially the same reaction as in Example 1-16(3) except for using 4-[(E)-1-(5-cyclopropyl-6-methoxypyridin-2-yl)-2-(tetrahydro-2H-pyran-4-yl)ethenyl]phenol.

(4) The title compound was obtained as a colorless powder (56 mg, 43%) by performing substantially the same reaction as in Example 1-16(4) except for using 3-cyclopropyl-2-methoxy-6-[(E)-1-(4-methoxyphenyl)-2-(tetrahydro-2H-pyran-4-yl)ethenyl]pyridine.

$^1$H NMR (300 MHz, CDCl$_3$) δ ppm 0.51-0.71 (m, 2H), 0.95 (dt, J=10.6, 4.3 Hz, 2H), 1.40-1.80 (m, 4H), 2.00-2.20 (m, 1H), 2.23-2.45 (m, 1H), 3.14-3.42 (m, 2H), 3.87-3.95 (m, 2H), 3.96 (s, 3H), 5.78 (d, J=7.2 Hz, 1H), 6.14 (d, J=9.8 Hz, 1H), 6.73-6.86 (m, 1H), 6.92-7.08 (m, 2H), 7.17 (d, J=2.0 Hz, 1H), 9.66-9.95 (brs, 1H).

MS(+): 386 [M+H]$^+$.

Example 1-54

6-[(E)-1-(3-Chloro-4-methoxyphenyl)-2-(tetrahydro-2H-pyran-4-yl)ethenyl]-3-(trifluoromethyl)pyridin-2(1H)-one

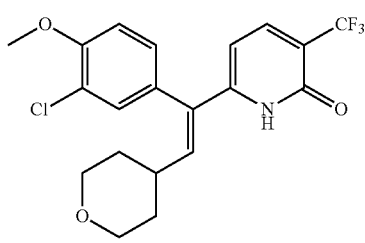
[Ka 159]

The title compound was obtained as a white solid (6.7 mg, 21% (two steps)) by performing substantially the same reaction as in Examples 1-53(1) and 1-1(2) sequentially except for using (3-chloro-4-methoxyphenyl)[6-methoxy-5-(trifluoromethyl)pyridin-2-yl]methanone obtained in Reference Example 1-73.

$^1$H NMR (300 MHz, CDCl$_3$) δ ppm 1.41-1.82 (m, 4H), 2.23-2.42 (m, 1H), 3.20-3.36 (m, 2H), 3.88-4.10 (m, 2H), 3.97 (s, 3H), 5.83 (d, J=7.7 Hz, 1H), 6.61 (d, J=9.8 Hz, 1H), 6.98 (d, J=8.3 Hz, 1H), 7.06 (dd, J=8.6, 2.1 Hz, 1H), 7.18 (d, J=2.1 Hz, 1H), 7.65 (d, J=7.4 Hz, 1H).

MS(+): 414 [M+H]$^+$.

Example 1-55

6-[(E)-1-[3-Chloro-4-(methylsulfanyl)phenyl]-2-(tetrahydro-2H-pyran-4-yl)ethenyl]-3-methylpyridin-2(1H)-one

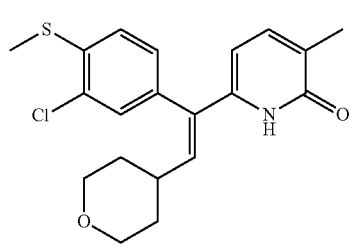
[Ka 160]

(1) 6-{(E)-1-[3-Chloro-4-(methylsulfanyl)phenyl]-2-(tetrahydro-2H-pyran-4-yl)ethenyl}-2-methoxy-3-methylpyridine was obtained as a colorless amorphous (400 mg, 35%) by performing substantially the same reaction as in Example 1-53(1) except for using [3-chloro-4-(methylsulfanyl)phenyl]-methoxy-5-methylpyridin-2-ylmethanone obtained in Reference Example 1-40.

(2) The title compound was obtained as a colorless powder (82 mg, 39%) by performing substantially the same reaction as in Example 1-1(2) except for using 6-{(E)-1-[3-chloro-4-(methylsulfanyl)phenyl]-2-(tetrahydro-2H-pyran-4-yl)ethenyl}-2-methoxy-3-methylpyridine.

$^1$H NMR (300 MHz, CDCl$_3$) δ ppm 1.40-1.80 (m, 4H), 2.14 (s, 3H), 2.21-2.40 (m, 1H), 2.54 (s, 3H), 3.21-3.38 (m, 2H), 3.81-4.03 (m, 2H), 5.72 (d, J=7.0 Hz, 1H), 6.29 (d, J=9.8 Hz, 1H), 7.02-7.10 (m, 1H), 7.11-7.23 (m, 3H), 10.53-10.71 (brs, 1H).

MS(+): 376 [M+H]$^+$.

Example 1-56

6-{(E)-1-[3-Chloro-4-(methylsulfonyl)phenyl]-2-(tetrahydro-2H-pyran-4-yl)ethenyl}-3-methylpyridin-2(1H)-one

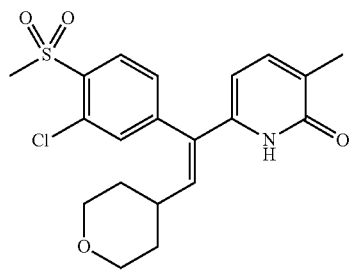
[Ka 161]

The title compound was obtained as a colorless powder (86 mg) by performing substantially the same reaction as in Examples 1-2 and 1-1(2) sequentially except for using 6-{(E)-1-[3-chloro-4-(methylsulfanyl)phenyl]-2-(tetrahydro-2H-pyran-4-yl)ethenyl}-2-methoxy-3-methylpyridine obtained in Example 1-55(1).

¹H NMR (300 MHz, CDCl₃) δ ppm 1.42-1.89 (m, 4H), 2.07-2.33 (m, 4H), 3.21-3.41 (m, 5H), 3.86-4.03 (m, 2H), 5.58 (d, J=7.0 Hz, 1H), 6.55 (d, J=9.9 Hz, 1H), 7.09-7.20 (m, 1H), 7.33 (dd, J=8.1, 1.6 Hz, 1H), 7.41 (s, 1H), 8.22 (d, J=8.1 Hz, 1H), 11.63-11.91 (brs, 1H).

MS(+): 430 [M+Na]⁺.

Example 1-57

6-[(E)-1-{3-Chloro-4-[3-(diethylamino)propoxy]phenyl}-2-(tetrahydro-2H-pyran-4-yl)ethenyl]-3-cyclopropylpyridin-2(1H)-one

[Ka 162]

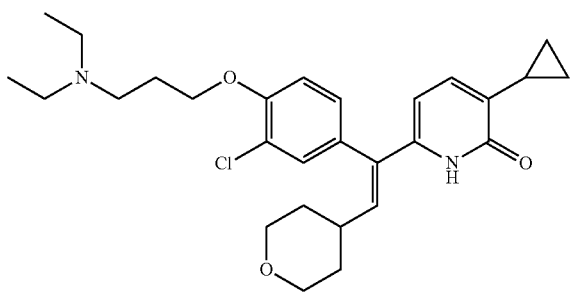

(1) Potassium carbonate (214 mg) and (3-bromopropoxy)(tert-butyl)dimethylsilane (240 μL) were added to a solution of 2-chloro-4-[(E)-1-(5-cyclopropyl-6-methoxypyridin-2-yl)-2-(tetrahydro-2H-pyran-4-yl)ethenyl]phenol obtained in Example 1-53(2) (200 mg) in N,N-dimethylformamide (4 mL), and the mixture was stirred at 65° C. for 1.5 hours and at room temperature overnight. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (hexane:ethyl acetate=4:1→1:1) to give 6-{(E)-1-[4-(3-{[tert-butyl(dimethyl)silyl]oxy}propoxy)-3-chlorophenyl]-2-(tetrahydro-2H-pyran-4-yl)ethenyl}-3-cyclopropyl-2-methoxypyridine as a colorless oil (245 mg, 80%).

(2) The title compound was obtained as a colorless powder (60 mg) by performing substantially the same reaction as in Example 1-26(2)-(5) except for using 6-{(E)-1-[4-(3-{[tert-butyl(dimethyl)silyl]oxy}propoxy)-3-chlorophenyl]-2-(tetrahydro-2H-pyran-4-yl)ethenyl}-3-cyclopropyl-2-methoxypyridine.

¹H NMR (300 MHz, CDCl₃) δ ppm 0.55-0.66 (m, 2H), 0.91-1.00 (m, 2H), 1.02-1.10 (m, 6H), 1.42-1.70 (m, 4H), 1.92-2.17 (m, 3H), 2.23-2.42 (m, 1H), 2.57 (q, J=7.2 Hz, 4H), 2.64-2.74 (m, 2H), 3.18-3.37 (m, 2H), 3.85-3.99 (m, 2H), 4.07-4.20 (m, 2H), 5.81 (d, J=7.3 Hz, 1H), 6.06 (d, J=9.8 Hz, 1H), 6.77-6.86 (m, 1H), 6.92-7.05 (m, 2H), 7.15 (d, J=1.7 Hz, 1H), 9.26-9.49 (brs, 1H).

MS(+): 485 [M+H]⁺.

Example 1-58

3-Cyclopropyl-6-{(E)-1-(4-ethylphenyl)-2-[(1S)-3-oxocyclopentyl]ethenyl}pyridin-2(1H)-one

[Ka 163]

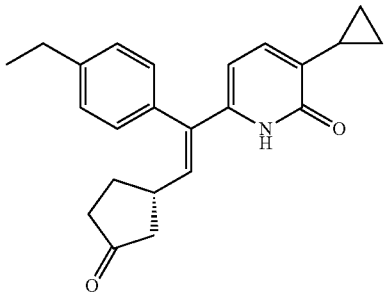

(1) A 1 M solution of lithium hexamethyldisilazide in tetrahydrofuran (4.0 mL) was added to a solution of 5-({[(2R,3R,7S)-2,3-diphenyl-1,4-dioxaspiro[4.4]non-7-yl]methyl}sulfonyl)-1-phenyl-1H-tetrazole obtained in Reference Example 3-1 (2.01 g) in tetrahydrofuran (20 mL) in a nitrogen gas stream at −78° C., and the mixture was stirred at −78° C. for one hour. A solution of (5-cyclopropyl-6-methoxypyridin-2-yl)(4-ethylphenyl)methanone obtained in Reference Example 1-53 (700 mg) in tetrahydrofuran (10 mL) was added, and the mixture was stirred at −78° C. to 0° C. for one hour. The reaction solution was poured into a saturated ammonium chloride solution, followed by extraction with ethyl acetate. The organic layer was washed with saturated aqueous sodium bicarbonate and brine, dried over anhydrous magnesium sulfate and filtered. The solvent was then evaporated under reduced pressure. The residue was purified by silica gel column chromatography (hexane:chloroform=1:1) to give 3-cyclopropyl-6-[(E)-2-[(2R,3R,7S)-2,3-diphenyl-1,4-dioxaspiro[4.4]non-7-yl]-1-(4-ethylphenyl)ethenyl]-2-methoxypyridine as a colorless amorphous (270 mg, 24%).

(2) The title compound was obtained as a colorless powder (56 mg, 33%) by performing substantially the same reaction as in Example 1-1(2) except for using 3-cyclopropyl-6-[(E)-2-[(2R,3R,7S)-2,3-diphenyl-1,4-dioxaspiro[4.4]non-7-yl]-1-(4-ethylphenyl)ethenyl]-2-methoxypyridine.

¹H NMR (300 MHz, CDCl₃) δ ppm 0.52-0.66 (m, 2H), 0.83-1.03 (m, 2H), 1.29 (t, J=7.6 Hz, 3H), 1.75-1.95 (m, 1H), 2.00-2.25 (m, 4H), 2.27-2.44 (m, 2H), 2.70 (q, J=7.5 Hz, 2H), 2.80-2.99 (m, 1H), 5.81 (d, J=7.3 Hz, 1H), 6.39 (d, J=9.5 Hz, 1H), 6.81 (d, J=8.1 Hz, 1H), 7.09 (d, J=8.1 Hz, 2H), 7.18-7.32 (m, 2H), 10.51-10.68 (brs, 1H).

MS(+): 348 [M+H]⁺.

Example 1-59

6-{(E)-1-(3-Chloro-4-ethoxyphenyl)-2-[(1S)-3-oxocyclopentyl]ethenyl}-3-ethylpyridin-2(1H)-one

[Ka 164]

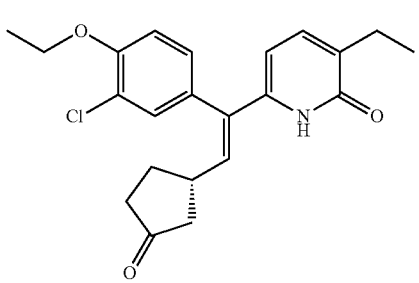

(1) 6-{(E)-1-(4-{[tert-Butyl(dimethyl)silyl]oxy}-3-chlorophenyl)-2-[(2R,3R,7S)-2,3-diphenyl-1,4-dioxaspiro[4.4]non-7-yl]ethenyl}-3-ethyl-2-methoxypyridine was obtained as a colorless powder (250 mg, 37%) by performing substantially the same reaction as in Example 1-58(1) except for using (4-{[tert-butyl(dimethyl)silyl]oxy}-3-chlorophenyl)(5-ethyl-6-methoxypyridin-2-yl)methanone obtained in Reference Example 1-50.

(2) The title compound was obtained as a pale yellow amorphous (71 mg, 49% (three steps)) by performing substantially the same reaction as in Example 1-16(2)-(4) except for using 6-{(E)-1-(4-{[tert-butyl(dimethyl)silyl]oxy}-3-chlorophenyl)-2-[(2R,3R,7S)-2,3-diphenyl-1,4-dioxaspiro[4.4]non-7-yl]ethenyl}-3-ethyl-2-methoxypyridine and using ethyl iodide in place of methyl iodide.

$^1$H NMR (300 MHz, CDCl$_3$) δ ppm 1.16 (t, J=7.5 Hz, 3H), 1.51 (t, J=6.9 Hz, 3H), 1.80-1.98 (m, 1H), 2.02-2.27 (m, 3H), 2.30-2.45 (m, 2H), 2.52 (q, J=7.7 Hz, 2H), 2.78-3.02 (m, 1H), 4.16 (q, J=7.0 Hz, 2H), 5.78 (d, J=7.2 Hz, 1H), 6.49 (d, J=9.6 Hz, 1H), 6.92-6.98 (m, 1H), 7.01-7.06 (m, 1H), 7.14 (d, J=7.2 Hz, 1H), 7.21 (d, J=2.0 Hz, 1H), 10.99-11.22 (brs, 1H).

MS(+): 386 [M+H]$^+$.

Example 1-60

6-{(E)-1-[4-(Cyclopropylsulfanyl)phenyl]-2-[(1S)-3-oxocyclopentyl]ethenyl}-3-methylpyridin-2(1H)-one

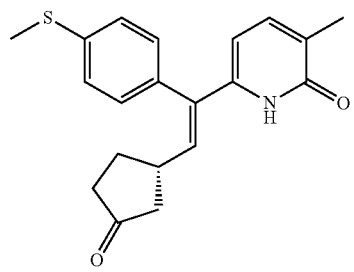

[Ka 165]

(1) 6-{(E)-1-[4-(Cyclopropylsulfanyl)phenyl]-2-[(2R,3R,7S)-2,3-diphenyl-1,4-dioxaspiro[4.4]non-7-yl]ethenyl}-2-methoxy-3-methylpyridine was obtained as a colorless amorphous (48 mg, 10%) by performing substantially the same reaction as in Example 1-58(1) except for using [4-(cyclopropylsulfanyl)phenyl](6-methoxy-5-methylpyridin-2-yl)methanone obtained in Reference Example 1-37.

(2) The title compound was obtained as a colorless powder (18 mg) by performing substantially the same reaction as in Example 1-1(2) except for using 6-{(E)-1-[4-(cyclopropylsulfanyl)phenyl]-2-[(2R,3R,7S)-2,3-diphenyl-1,4-dioxaspiro[4.4]non-7-yl]ethenyl}-2-methoxy-3-methylpyridine.

$^1$H NMR (300 MHz, CDCl$_3$) δ ppm 0.71-0.81 (m, 2H), 1.07-1.17 (m, 2H), 1.81-1.96 (m, 1H), 2.12-2.27 (m, 4H), 2.12 (s, 3H), 2.30-2.45 (m, 2H), 2.82-3.00 (m, 1H), 5.83 (d, J=7.0 Hz, 1H), 6.38 (d, J=9.6 Hz, 1H), 7.10 (d, J=8.5 Hz, 2H), 7.16 (dd, J=7.1, 1.2 Hz, 1H), 7.36-7.43 (brs, 2H).

MS(+): 366 [M+H]$^+$.

Example 1-61

6-{(E)-1-[4-(Cyclopropylsulfonyl)phenyl]-2-[(1S)-3-oxocyclopentyl]ethenyl}-3-methylpyridin-2(1H)-one

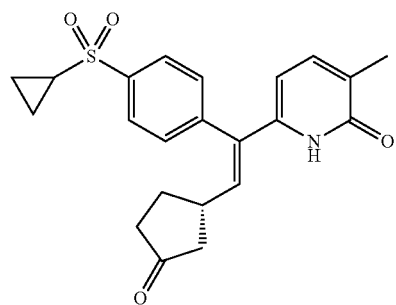

[Ka 166]

The title compound was obtained as a colorless powder (28 mg, 31% (two steps)) by performing substantially the same reaction as in Examples 1-2 and 1-1(2) sequentially except for using 6-{(E)-1-[4-(cyclopropylsulfanyl)phenyl]-2-[(2R,3R,7S)-2,3-diphenyl-1,4-dioxaspiro[4.4]non-7-yl]ethenyl}-2-methoxy-3-methylpyridine obtained in Example 1-60(1).

$^1$H NMR (300 MHz, CDCl$_3$) δ ppm 1.04-1.20 (m, 2H), 1.32-1.49 (m, 2H), 1.85-2.03 (m, 1H), 2.04-2.22 (m, 5H), 2.23-2.46 (m, 3H), 2.49-2.63 (m, 1H), 2.68-2.93 (m, 1H), 5.63 (d, J=7.0 Hz, 1H), 6.63 (d, J=9.6 Hz, 1H), 7.10-7.19 (m, 1H), 7.35-7.51 (m, 2H), 7.98 (d, J=8.4 Hz, 2H), 11.36-11.72 (brs, 1H).

MS(+): 398 [M+H]$^+$.

Example 1-62

6-{(E)-1-[4-(Cyclopropylsulfonyl)phenyl]-2-[(1S)-3-oxocyclopentyl]ethenyl}-3-ethylpyridin-2(1H)-one

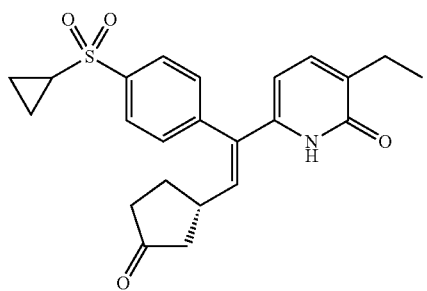

[Ka 167]

The title compound was obtained as a colorless powder (62 mg) by performing substantially the same reaction as in Examples 1-58(1), 1-2 and 1-1(2) sequentially except for using [4-(cyclopropylsulfanyl)phenyl](5-ethyl-6-methoxypyridin-2-yl)methanone obtained in Reference Example 1-49.

$^1$H NMR (300 MHz, CDCl$_3$) δ ppm 1.01-1.24 (m, 5H), 1.35-1.51 (m, 2H), 1.82-2.03 (m, 1H), 2.04-2.23 (m, 2H), 2.25-2.44 (m, 3H), 2.46-2.63 (m, 3H), 2.66-2.87 (m, 1H), 5.63 (d, J=7.1 Hz, 1H), 6.73 (d, J=9.8 Hz, 1H), 7.14 (d, J=7.3 Hz, 1H), 7.42 (d, J=8.4 Hz, 2H), 7.98 (d, J=8.4 Hz, 2H), 11.77-12.05 (brs, 1H).

MS(+): 412 [M+H]$^+$.

Example 1-63

6-{(E)-1-[4-(Cyclopropylsulfonyl)phenyl]-2-[(1S)-3-oxocyclopentyl]ethenyl}-3-(trifluoromethyl)pyridin-2(1H)-one

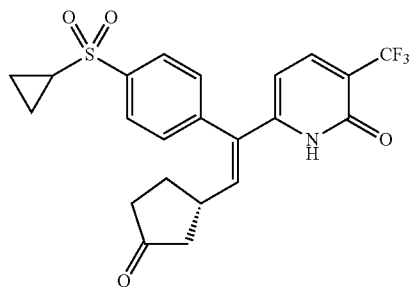

[Ka 168]

The title compound was obtained as a white solid (53 mg, 5% (three steps)) by performing substantially the same reaction as in Examples 1-58 and 1-2 sequentially except for using [4-(cyclopropylsulfanyl)phenyl][6-methoxy-5-(trifluoromethyl)pyridin-2-yl]methanone obtained in Reference Example 1-68.

$^1$H NMR (300 MHz, CDCl$_3$) δ ppm 1.08-1.17 (m, 2H), 1.40-1.48 (m, 2H), 1.97-2.16 (m, 3H), 2.26-2.43 (m, 3H), 2.50-2.61 (m, 1H), 2.68-2.83 (m, 1H), 5.72 (d, J=7.5 Hz, 1H), 7.05 (d, J=9.9 Hz, 1H), 7.41 (d, J=8.2 Hz, 2H), 7.67 (d, J=7.5 Hz, 1H), 8.00 (d, J=8.5 Hz, 2H).

MS(+): 452 [M+H]$^+$.

Example 1-64

6-{(E)-1-[4-(Methylsulfanyl)phenyl]-2-[(1S)-3-oxocyclopentyl]ethenyl}-3-(propan-2-yl)pyridin-2(1H)-one

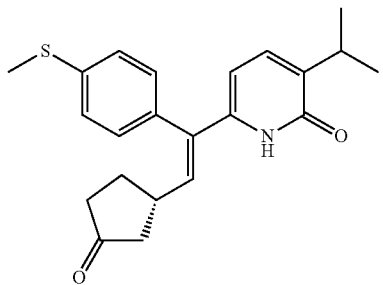

[Ka 169]

The title compound was obtained as a colorless powder (54 mg, 6% (two steps)) by performing substantially the same reaction as in Examples 1-58(1) and 1-1(2) sequentially except for using [6-methoxy-5-(propan-2-yl)pyridin-2-yl][4-(methylsulfanyl)phenyl]methanone obtained in Reference Example 1-76.

$^1$H NMR (300 MHz, CDCl$_3$) δ ppm 1.16 (d, J=6.8 Hz, 6H), 1.76-1.96 (m, 1H), 2.01-2.24 (m, 3H), 2.27-2.43 (m, 2H), 2.53 (s, 3H), 2.76-2.97 (m, 1H), 3.05-3.24 (m, 1H), 5.83 (d, J=7.1 Hz, 1H), 6.43 (d, J=9.5 Hz, 1H), 7.05-7.19 (m, 3H), 7.22-7.38 (m, 2H), 10.47-10.71 (brs, 1H).

MS(+): 368 [M+H]$^+$.

Example 1-65

3-Cyclopropyl-6-{(E)-1-[4-(methylsulfanyl)phenyl]-2-[(1S)-3-oxocyclopentyl]ethenyl}pyridin-2(1H)-one

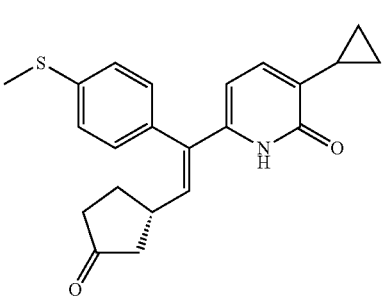

[Ka 170]

The title compound was obtained as a colorless powder (83 mg, 14% (two steps)) by performing substantially the same reaction as in Examples 1-58(1) and 1-1(2) sequentially except for using (5-cyclopropyl-6-methoxypyridin-2-yl)[4-(methylsulfanyl)phenyl]methanone obtained in Reference Example 1-51.

$^1$H NMR (300 MHz, CDCl$_3$) δ ppm 0.55-0.64 (m, 2H), 0.86-0.97 (m, 2H), 1.81-1.95 (m, 1H), 2.00-2.25 (m, 4H), 2.27-2.42 (m, 2H), 2.53 (s, 3H), 2.77-2.97 (m, 1H), 5.78 (d, J=7.3 Hz, 1H), 6.41 (d, J=9.6 Hz, 1H), 6.81 (dd, J=7.3, 0.6 Hz, 1H), 7.07-7.14 (m, 2H), 7.25-7.32 (m, 2H), 10.62-10.90 (brs, 1H).

MS(+): 366 [M+H]$^+$.

Example 1-66

3-Cyclopropyl-6-{(E)-1-{4-[3-(diethylamino)propoxy]phenyl}-2-[(1S)-3-oxocyclopentyl]ethenyl}pyridin-2(1H)-one

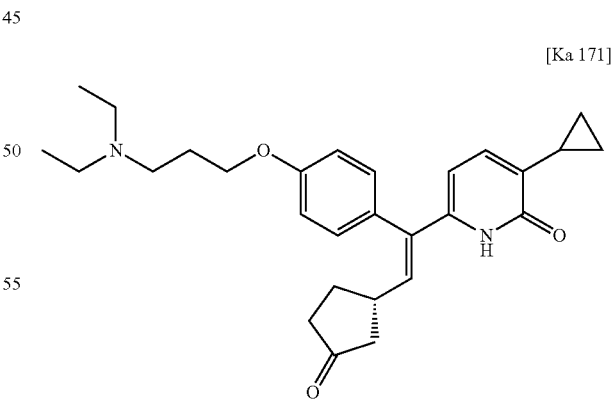

[Ka 171]

The title compound was obtained as a brown amorphous (18 mg, 8% (five steps)) by performing substantially the same reaction as in Examples 1-58(1) and 1-26(2)-(5) sequentially except for using [4-(3-{[tert-butyl(dimethyl)silyl]oxy}propoxy)phenyl](5-cyclopropyl-6-methoxypyridin-2-yl)methanone obtained in Reference Example 1-56.

$^1$H NMR (300 MHz, CDCl$_3$) δ ppm 0.52-0.65 (m, 2H), 0.85-0.96 (m, 2H), 1.06 (t, J=7.1 Hz, 6H), 1.75-2.42 (m, 9H), 2.51-2.72 (m, 6H), 2.80-2.98 (m, 1H), 4.05 (t, J=6.3 Hz, 2H), 5.78 (d, J=7.2 Hz, 1H), 6.44 (d, J=9.6 Hz, 1H), 6.80 (d, J=7.2 Hz, 1H), 6.93 (d, J=8.4 Hz, 2H), 7.09 (d, J=8.7 Hz, 2H).
MS(+): 449 [M+H]$^+$.

Example 1-67

6-{(E)-1-[3-Chloro-4-(methylsulfanyl)phenyl]-2-[(1S)-3-oxocyclopentyl]ethenyl}-3-methylpyridin-2(1H)-one

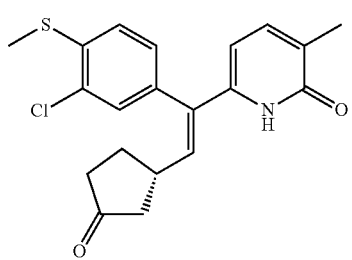

[Ka 172]

(1) 6-{(E)-1-[3-Chloro-4-(methylsulfanyl)phenyl]-2-[(2R,3R,7S)-2,3-diphenyl-1,4-dioxaspiro[4.4]non-7-yl]ethenyl}-2-methoxy-3-methylpyridine was obtained as a colorless amorphous (230 mg, 15%) by performing substantially the same reaction as in Example 1-58(1) except for using [3-chloro-4-(methylsulfanyl)phenyl](6-methoxy-5-methylpyridin-2-yl)methanone obtained in Reference Example 1-40.

(2) The title compound was obtained as a colorless powder (50 mg, 55%) by performing substantially the same reaction as in Example 1-1(2) except for using 6-{(E)-1-[3-chloro-4-(methylsulfanyl)phenyl]-2-[(2R,3R,7S)-2,3-diphenyl-1,4-dioxaspiro[4.4]non-7-yl]ethenyl}-2-methoxy-3-methylpyridine.

$^1$H NMR (600 MHz, CDCl$_3$) δ ppm 1.79-1.99 (m, 1H), 2.11 (s, 3H), 2.08-2.28 (m, 3H), 2.32-2.42 (m, 2H), 2.51 (s, 3H), 2.76-2.99 (m, 1H), 5.69 (d, J=6.9 Hz, 1H), 6.55 (d, J=9.6 Hz, 1H), 7.08 (d, J=7.8 Hz, 1H), 7.14 (d, J=7.3 Hz, 1H), 7.19 (s, 2H), 11.51-11.67 (brs, 1H).
MS(+): 374 [M+H]$^+$.

Example 1-68

6-{(E)-1-[3-Chloro-4-(methylsulfonyl)phenyl]-2-[(1S)-3-oxocyclopentyl]ethenyl}-3-methylpyridin-2(1H)-one

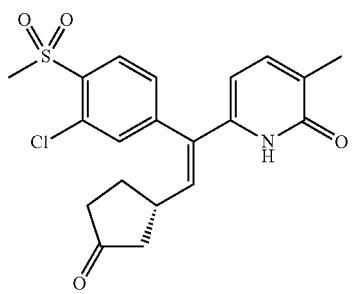

[Ka 173]

The title compound was obtained as a colorless powder (35 mg, 42% (two steps)) by performing substantially the same reaction as in Examples 1-2 and 1-1(2) sequentially except for using 6-{(E)-1-[3-chloro-4-(methylsulfanyl)phenyl]-2-[(2R,3R,7S)-2,3-diphenyl-1,4-dioxaspiro[4.4]non-7-yl]ethenyl}-2-methoxy-3-methylpyridine obtained in Example 1-67(1).

$^1$H NMR (600 MHz, CDCl$_3$) δ ppm 1.90-2.02 (m, 1H), 2.10 (s, 3H), 2.12-2.20 (m, 2H), 2.23-2.32 (m, 1H), 2.33-2.45 (m, 2H), 2.69-2.83 (m, 1H), 3.34 (s, 3H), 5.58 (d, J=6.9 Hz, 1H), 6.70 (d, J=9.6 Hz, 1H), 7.15-7.19 (m, 1H), 7.33 (dd, J=8.0, 1.6 Hz, 1H), 7.42 (d, J=1.4 Hz, 1H), 8.21 (d, J=8.3 Hz, 1H).
MS(+): 406 [M+H]$^+$.

Example 1-69

6-{(E)-1-[3-Chloro-4-(methylsulfanyl)phenyl]-2-[(1S)-3-oxocyclopentyl]ethenyl}-3-ethylpyridin-2(1H)-one

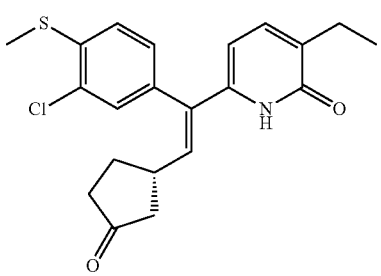

[Ka 174]

The title compound was obtained as a colorless powder (49 mg, 26% (two steps)) by performing substantially the same reaction as in Examples 1-58(1) and 1-1(2) sequentially except for using [3-chloro-4-(methylsulfanyl)phenyl](5-ethyl-6-methoxypyridin-2-yl)methanone obtained in Reference Example 1-46.

$^1$H NMR (300 MHz, CDCl$_3$) δ ppm 1.16 (t, J=7.5 Hz, 3H), 1.82-1.99 (m, 1H), 2.05-2.45 (m, 5H), 2.46-2.59 (m, 5H), 2.72-2.98 (m, 1H), 5.73 (d, J=7.1 Hz, 1H), 6.58 (d, J=9.6 Hz, 1H), 7.03-7.16 (m, 2H), 7.17-7.24 (m, 2H), 11.35-11.60 (brs, 1H).
MS(+): 388 [M+H]$^+$.

Example 1-70

6-{(E)-1-[3-Chloro-4-(methylsulfonyl)phenyl]-2-[(1S)-3-oxocyclopentyl]ethenyl}-3-ethylpyridin-2(1H)-one

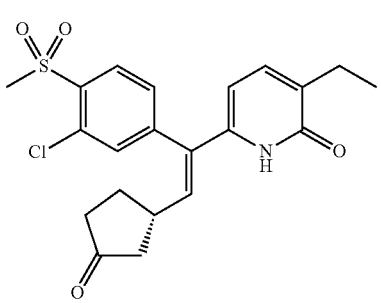

[Ka 175]

The title compound was obtained as a colorless powder (17 mg, 43%) by performing substantially the same reaction as in Example 1-2 except for using 6-{(E)-1-[3-chloro-4-(methylsulfanyl)phenyl]-2-[(1S)-3-oxocyclopentyl]ethenyl}-3-ethylpyridin-2(1H)-one obtained in Example 1-69.

$^1$H NMR (300 MHz, CDCl$_3$) δ ppm 1.16 (t, J=7.5 Hz, 3H), 1.84-2.03 (m, 1H), 2.06-2.24 (m, 2H), 2.26-2.45 (m, 3H), 2.52 (q, J=7.4 Hz, 2H), 2.65-2.89 (m, 1H), 3.35 (s, 3H), 5.61 (d, J=7.1 Hz, 1H), 6.78 (d, J=9.8 Hz, 1H), 7.15 (d, J=7.1 Hz, 1H), 7.30-7.39 (m, 1H), 7.44 (s, 1H), 8.23 (d, J=8.1 Hz, 1H), 12.01-12.39 (brs, 1H).
MS(+): 420 [M+H]$^+$.

Example 1-71

6-{(E)-1-[3-Chloro-4-(methylsulfanyl)phenyl]-2-[(1S)-3-oxocyclopentyl]ethenyl}-3-cyclopropylpyridin-2(1H)-one

[Ka 176]

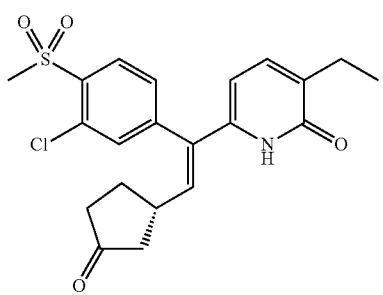

(1) 6-{(E)-1-[3-Chloro-4-(methylsulfanyl)phenyl]-2-[(2R,3R,7S)-2,3-diphenyl-1,4-dioxaspiro[4.4]non-7-yl]ethenyl}-3-cyclopropyl-2-methoxypyridine was obtained as a pale yellow powder (610 mg, 40%) by performing substantially the same reaction as in Example 1-58(1) except for using [3-chloro-4-(methylsulfanyl)phenyl] (5-cyclopropyl-6-methoxypyridin-2-yl)methanone obtained in Reference Example 1-52.

(2) The title compound was obtained as a colorless powder (131 mg, 68%) by performing substantially the same reaction as in Example 1-1(2) except for using 6-{(E)-1-[3-chloro-4-(methylsulfanyl)phenyl]-2-[(2R,3R,7S)-2,3-diphenyl-1,4-dioxaspiro[4.4]non-7-yl]ethenyl}-3-cyclopropyl-2-methoxypyridine.
$^1$H NMR (300 MHz, CDCl$_3$) δ ppm 0.51-0.67 (m, 2H), 0.84-1.05 (m, 2H), 1.81-2.00 (m, 1H), 2.02-2.24 (m, 3H), 2.25-2.46 (m, 3H), 2.52 (s, 3H), 2.74-2.97 (m, 1H), 5.68 (d, J=7.3 Hz, 1H), 6.61 (d, J=9.6 Hz, 1H), 6.81 (s, 1H), 7.04-7.16 (m, 1H), 7.15-7.22 (m, 2H), 11.63-11.95 (brs, 1H).
MS(+): 400 [M+H]$^+$.

Example 1-72

6-{(E)-1-[3-Chloro-4-(methylsulfonyl)phenyl]-2-[(1S)-3-oxocyclopentyl]ethenyl}-3-cyclopropylpyridin-2(1H)-one

[Ka 177]

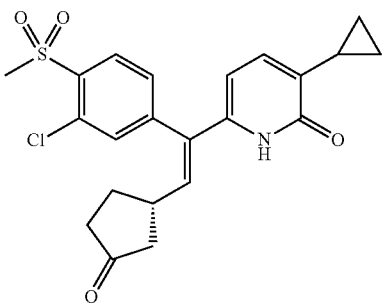

The title compound was obtained as a colorless powder (74 mg, 33% (two steps)) by performing substantially the same reaction as in Examples 1-2 and 1-1(2) sequentially except for using 6-{(E)-1-[3-chloro-4-(methylsulfanyl)phenyl]-2-[(2R,3R,7S)-2,3-diphenyl-1,4-dioxaspiro[4.4]non-7-yl]ethenyl}-3-cyclopropyl-2-methoxypyridine obtained in Example 1-71 (1).
$^1$H NMR (300 MHz, CDCl$_3$) δ ppm 0.54-0.67 (m, 2H), 0.86-1.01 (m, 2H), 1.85-2.23 (m, 4H), 2.25-2.51 (m, 3H), 2.64-2.91 (m, 1H), 3.35 (s, 3H), 5.57 (d, J=7.1 Hz, 1H), 6.70-6.91 (m, 2H), 7.31-7.38 (m, 1H), 7.43 (d, J=1.6 Hz, 1H), 8.22 (d, J=8.1 Hz, 1H), 12.13-12.38 (m, 1H).
MS(+): 432 [M+H]$^+$.

Example 1-73

6-{(E)-1-{3-Chloro-4-[(3-hydroxypropyl)sulfanyl]phenyl}-2-[(1S)-3-oxocyclopentyl]ethenyl}-3-methylpyridin-2(1H)-one

[Ka 178]

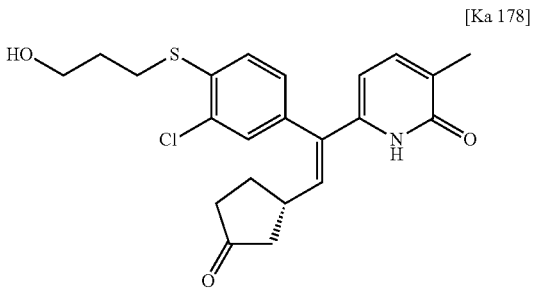 [SMILES: Cc1ccc(/C(=C/[C@H]2CCC(=O)C2)c2ccc(SCCCO)c(Cl)c2)[nH]c1=O]

(1) 6-{(E)-1-{4-[(3-{[tert-Butyl(dimethyl)silyl]oxy}propyl)sulfanyl]-3-chlorophenyl}-2-[(2R,3R,7S)-2,3-diphenyl-1,4-dioxaspiro[4.4]non-7-yl]ethenyl}-2-methoxy-3-methylpyridine was obtained as a colorless amorphous (510 mg, 37%) by performing substantially the same reaction as in Example 1-58(1) except for using {4-[(3-{[tert-butyl(dimethyl)silyl]oxy}propyl)sulfanyl]-3-chlorophenyl}(6-methoxy-5-methylpyridin-2-yl)methanone obtained in Reference Example 1-41.

(2) The title compound was obtained as a pale yellow powder (10 mg, 19%) by performing substantially the same reaction as in Example 1-5(2) except for using 6-{(E)-1-{4-[(3-{[tert-butyl(dimethyl)silyl]oxy}propyl)sulfanyl]-3-chlorophenyl}-2-[(2R,3R,7S)-2,3-diphenyl-1,4-dioxaspiro[4.4]non-7-yl]ethenyl}-2-methoxy-3-methylpyridine.
$^1$H NMR (300 MHz, CDCl$_3$) δ ppm 1.81-2.26 (m, 10H), 2.29-2.45 (m, 2H), 2.77-2.94 (m, 1H), 3.13 (t, J=7.2 Hz, 2H), 3.85 (t, J=6.0 Hz, 2H), 5.77 (d, J=7.2 Hz, 1H), 6.43 (d, J=9.6 Hz, 1H), 7.06 (dd, J=8.1, 1.9 Hz, 1H), 7.14-7.20 (m, 1H), 7.21 (d, J=1.7 Hz, 1H), 7.33 (d, J=8.1 Hz, 1H).
MS(+): 418 [M+H]$^+$.

Example 1-74

6-{(E)-1-{3-Chloro-4-[(3-hydroxypropyl)sulfonyl]phenyl}-2-[(1S)-3-oxocyclopentyl]ethenyl}-3-methylpyridin-2(1H)-one

[Ka 179]

The title compound was obtained as a colorless powder (6.5 mg, 10% (two steps)) by performing substantially the same reaction as in Examples 1-2 and 1-1(2) sequentially except for using 6-{(E)-1-{4-[(3-{[tert-butyl(dimethyl)silyl]oxy}propyl)sulfanyl]-3-chlorophenyl}-2-[(2R,3R,7S)-2,3-diphenyl-1,4-dioxaspiro[4.4]non-7-yl]ethenyl}-2-methoxy-3-methylpyridine obtained in Example 1-73(1).

$^1$H NMR (300 MHz, CDCl$_3$) δ ppm 1.85-2.48 (m, 11H), 2.68-2.86 (m, 1H), 3.57-3.67 (m, 2H), 3.81 (t, J=5.9 Hz, 2H), 5.61 (d, J=7.0 Hz, 1H), 6.72 (d, J=9.8 Hz, 1H), 7.15-7.23 (m, 1H), 7.31-7.37 (m, 1H), 7.43 (d, J=1.4 Hz, 1H), 8.19 (d, J=8.1 Hz, 1H).

MS(+): 450 [M+H]$^+$.

Example 1-75

6-{(E)-1-{3-Chloro-4-[(3-hydroxypropyl)sulfanyl]phenyl}-2-[(1S)-3-oxocyclopentyl]ethenyl}-3-ethylpyridin-2(1H)-one

[Ka 180]

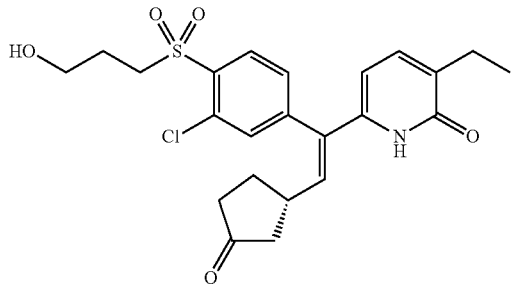

(1) 6-{(E)-1-{4-[(3-{[tert-Butyl(dimethyl)silyl]oxy}propyl)sulfanyl]-3-chlorophenyl}-2-[(2R,3R,7S)-2,3-diphenyl-1,4-dioxaspiro[4.4]non-7-yl]ethenyl}-3-ethyl-2-methoxypyridine was obtained as a colorless amorphous (570 mg, 39%) by performing substantially the same reaction as in Example 1-58(1) except for using {4-[(3-{[tert-butyl(dimethyl)silyl]oxy}propyl)sulfanyl]-3-chlorophenyl}(5-ethyl-6-methoxypyridin-2-yl)methanone obtained in Reference Example 1-48.

(2) The title compound was obtained as a pale yellow powder (24 mg, 42%) by performing substantially the same reaction as in Example 1-1(2) except for using 6-{(E)-1-{4-[(3-{[tert-butyl(dimethyl)silyl]oxy}propyl)sulfanyl]-3-chlorophenyl}-2-[(2R,3R,7S)-2,3-diphenyl-1,4-dioxaspiro[4.4]non-7-yl]ethenyl}-3-ethyl-2-methoxypyridine.

$^1$H NMR (300 MHz, CDCl$_3$) δ ppm 1.16 (t, J=7.5 Hz, 3H), 1.80-2.26 (m, 6H), 2.28-2.44 (m, 2H), 2.46-2.59 (m, 2H), 2.76-2.95 (m, 1H), 3.13 (t, J=7.2 Hz, 2H), 3.85 (t, J=6.0 Hz, 2H), 5.79 (d, J=7.2 Hz, 1H), 6.47 (d, J=9.8 Hz, 1H), 7.06 (dd, J=8.1, 1.9 Hz, 1H), 7.11-7.19 (m, 1H), 7.21 (d, J=1.7 Hz, 1H), 7.33 (d, J=8.1 Hz, 1H).

MS(+): 432 [M+H]$^+$.

Example 1-76

6-{(E)-1-{3-Chloro-4-[(3-hydroxypropyl)sulfonyl]phenyl}-2-[(1S)-3-oxocyclopentyl]ethenyl}-3-ethylpyridin-2(1H)-one

[Ka 181]

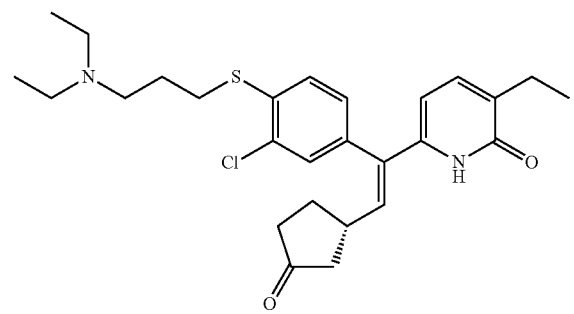

The title compound was obtained as a pale yellow powder (16 mg, 17% (two steps)) by performing substantially the same reaction as in Examples 1-2 and 1-1(2) sequentially except for using 6-{(E)-1-{4-[(3-{[tert-butyl(dimethyl)silyl]oxy}propyl)sulfanyl]-3-chlorophenyl}-2-[(2R,3R,7S)-2,3-diphenyl-1,4-dioxaspiro[4.4]non-7-yl]ethenyl}-3-ethyl-2-methoxypyridine obtained in Example 1-75(1).

$^1$H NMR (300 MHz, CDCl$_3$) δ ppm 1.17 (t, J=7.5 Hz, 3H), 1.84-2.59 (m, 10H), 2.68-2.86 (m, 1H), 3.58-3.67 (m, 2H), 3.82 (t, J=5.9 Hz, 2H), 5.65 (d, J=7.2 Hz, 1H), 6.71 (d, J=9.8 Hz, 1H), 7.14-7.20 (m, 1H), 7.34 (dd, J=8.1, 1.6 Hz, 1H), 7.43 (d, J=1.7 Hz, 1H), 8.20 (d, J=8.1 Hz, 1H).

MS(+): 464 [M+H]$^+$.

Example 1-77

6-{(E)-1-(3-Chloro-4-{[3-(diethylamino)propyl]sulfanyl}phenyl)-2-[(1S)-3-oxocyclopentyl]ethenyl}-3-ethylpyridin-2(1H)-one

[Ka 182]

(1) 3-({2-Chloro-4-[(E)-2-[(2R,3R,7S)-2,3-diphenyl-1,4-dioxaspiro[4.4]non-7-yl]-1-(5-ethyl-6-methoxypyridin-2-yl)ethenyl]phenyl}sulfanyl)propan-1-ol was obtained as a colorless amorphous (222 mg, 88%) by performing substantially the same reaction as in Example 1-16(2) except for using 6-{(E)-1-{4-[(3-{[tert-butyl(dimethyl)silyl]oxy}propyl)sulfanyl]-3-chlorophenyl}-2-[(2R,3R,7S)-2,3-diphenyl-1,4-dioxaspiro[4.4]non-7-yl]ethenyl}-3-ethyl-2-methoxypyridine obtained in Example 1-75(1).

(2) The title compound was obtained as a colorless amorphous (36 mg) by performing substantially the same reaction as in Example 1-26(3)-(5) except for using 3-({2-chloro-4-

[(E)-2-[(2R,3R,7S)-2,3-diphenyl-1,4-dioxaspiro[4.4]non-7-yl]-1-(5-ethyl-6-methoxypyridin-2-yl)ethenyl]phenyl}sulfanyl)propan-1-ol.

$^1$H NMR (300 MHz, CDCl$_3$) δ ppm 1.00-1.23 (m, 9H), 1.81-2.02 (m, 4H), 2.06-2.28 (m, 3H), 2.31-2.44 (m, 2H), 2.46-2.74 (m, 7H), 2.79-2.97 (m, 1H), 3.00-3.13 (m, 2H), 5.75 (d, J=7.2 Hz, 1H), 6.52 (d, J=9.5 Hz, 1H), 7.06 (dd, J=8.0, 1.8 Hz, 1H), 7.14 (d, J=7.2 Hz, 1H), 7.21 (d, J=1.9 Hz, 1H), 7.32 (d, J=8.2 Hz, 1H), 11.04-11.28 (brs, 1H).

MS(+): 487 [M+H]$^+$.

Example 1-78

6-{(E)-1-(3-Chloro-4-{[3-(diethylamino)propyl]sulfonyl}phenyl)-2-[(1S)-3-oxocyclopentyl]ethenyl}-3-ethylpyridin-2(1H)-one

[Ka 183]

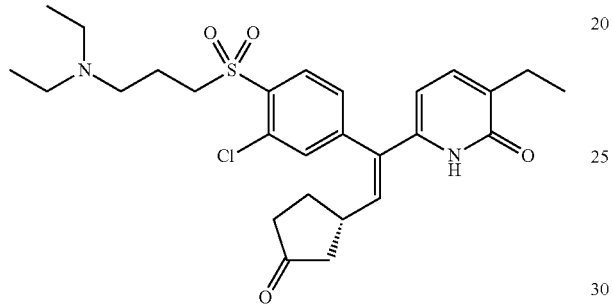

The title compound was obtained as a colorless amorphous (21 mg) by performing substantially the same reaction as in Example 1-27(1)-(2) except for using 3-({2-chloro-4-[(E)-2-[(2R,3R,7S)-2,3-diphenyl-1,4-dioxaspiro[4.4]non-7-yl]-1-(5-ethyl-6-methoxypyridin-2-yl)ethenyl]phenyl}sulfanyl)propan-1-ol obtained in Example 1-77(1).

$^1$H NMR (300 mhz, CDCl$_3$) δ ppm 0.93-1.05 (m, 6H), 1.16 (t, J=7.5 Hz, 3H), 1.86-2.05 (m, 4H), 2.07-2.25 (m, 3H), 2.26-2.63 (m, 9H), 2.67-2.88 (m, 1H), 3.46-3.70 (m, 2H), 5.58 (d, J=7.2 Hz, 1H), 6.79 (d, J=9.8 Hz, 1H), 7.15 (d, J=7.2 Hz, 1H), 7.34 (dd, J=8.0, 1.6 Hz, 1H), 7.42 (d, J=1.6 Hz, 1H), 8.19 (d, J=7.9 Hz, 1H).

MS(+): 519 [M+H]$^+$.

Example 1-79

6-{(E)-1-{3-Chloro-4-[3-(diethylamino)propoxy]phenyl}-2-[(1S)-3-oxocyclopentyl]ethenyl}-3-cyclopropylpyridin-2(1H)-one

[Ka 184]

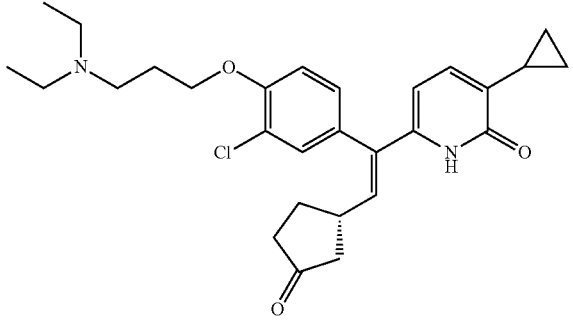

(1) 2-Chloro-4-{(E)-1-(5-cyclopropyl-6-methoxypyridin-2-yl)-2-[(2R,3R,7S)-2,3-diphenyl-1,4-dioxaspiro[4.4]non-7-yl]ethenyl}phenol (429 mg, 31% (two steps)) was obtained by performing substantially the same reaction as in Examples 1-58(1) and 1-16(2) sequentially using (4-{[tert-butyl(dimethyl)silyl]oxy}-3-chlorophenyl)(5-cyclopropyl-6-methoxypyridin-2-yl)methanone obtained in Reference Example 1-55.

(2) The title compound was obtained as a brown amorphous (167 mg, 48% (four steps)) by performing substantially the same reaction as in Examples 1-16(3) and 1-26(3)-(5) sequentially except for using 2-chloro-4-{(E)-1-(5-cyclopropyl-6-methoxypyridin-2-yl)-2-[(2R,3R,7S)-2,3-diphenyl-1,4-dioxaspiro[4.4]non-7-yl]ethenyl}phenol and using 3-bromo-1-propanol in place of methyl iodide.

$^1$H NMR (300 MHz, CDCl$_3$) δ ppm 0.56-0.63 (m, 2H), 0.86-0.97 (m, 2H), 1.05 (t, J=7.2 Hz, 6H), 1.88-2.44 (m, 9H), 2.56 (q, J=7.2 Hz, 4H), 2.68 (t, J=7.5 Hz, 2H), 2.77-2.96 (m, 1H), 4.12 (t, J=6.1 Hz, 2H), 5.74 (d, J=7.2 Hz, 1H), 6.43 (d, J=9.5 Hz, 1H), 6.80 (d, J=7.5 Hz, 1H), 6.92 (d, J=8.5 Hz, 1H), 7.01 (dd, J=8.5, 2.0 Hz, 1H), 7.18 (d, J=1.7 Hz, 1H), 10.78-11.02 (brs, 1H).

MS(+): 483 [M+H]$^+$.

Example 1-80

6-{(E)-1-{3-Chloro-4-[4-(diethylamino)butoxy]phenyl}-2-[(1S)-3-oxocyclopentyl]ethenyl}-3-cyclopropylpyridin-2(1H)-one

[Ka 185]

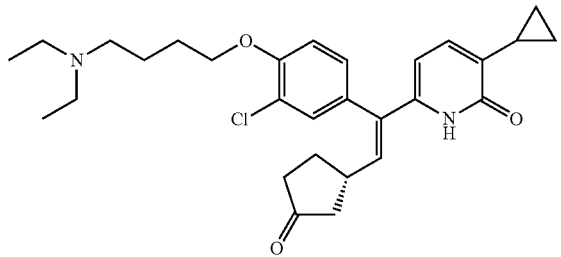

The title compound was obtained as a pale yellow amorphous (23 mg, 25% (four steps)) by performing substantially the same reaction as in Example 1-79(2) except for using 2-chloro-4-{(E)-1-(5-cyclopropyl-6-methoxypyridin-2-yl)-2-[(2R,3R,7S)-2,3-diphenyl-1,4-dioxaspiro[4.4]non-7-yl]ethenyl}phenol obtained in Example 1-79(1) and using 4-bromo-1-butanol in place of 3-bromo-1-propanol.

$^1$H NMR (300 MHz, CDCl$_3$) δ ppm 0.52-0.68 (m, 2H), 0.88-1.00 (m, 2H), 1.05 (t, J=7.0 Hz, 6H), 1.63-1.78 (m, 2H), 1.78-1.98 (m, 3H), 1.98-2.24 (m, 4H), 2.24-2.44 (m, 2H), 2.44-2.71 (m, 6H), 2.78-2.97 (m, 1H), 4.09 (t, J=6.1 Hz, 2H), 5.80 (d, J=7.4 Hz, 1H), 6.30 (d, J=9.4 Hz, 1H), 6.81 (d, J=7.4 Hz, 1H), 6.94 (d, J=8.6 Hz, 1H), 7.01 (dd, J=8.2, 2.0 Hz, 1H), 7.18 (d, J=2.0 Hz, 1H), 9.88-10.39 (brs, 1H).

MS(+): 497 [M+H]$^+$.

Example 1-81

6-{(E)-1-[3-Chloro-4-(3-hydroxypropoxy)phenyl]-2-[(1S)-3-oxocyclopentyl]ethenyl}-3-(trifluoromethyl)pyridin-2(1H)-one

[Ka 186]

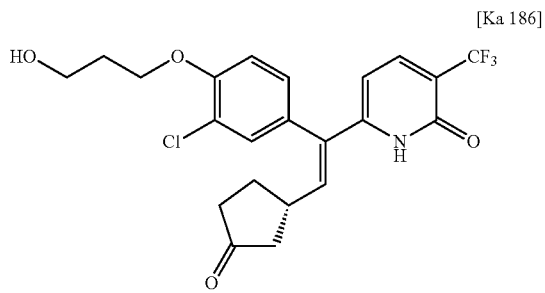 [SMILES: O=C1CC[C@H](/C=C(\c2ccc(OCCCO)c(Cl)c2)c2ccc(C(F)(F)F)c(=O)[nH]2)C1]

The title compound was obtained as a white solid (67 mg, 11% (four steps)) by performing substantially the same reaction as in Examples 1-58(1) and 1-16(2)-(4) sequentially except for using (4-{[tert-butyl(dimethyl)silyl]oxy}-3-chlorophenyl)[6-methoxy-5-(trifluoromethyl)pyridin-2-yl]methanone obtained in Reference Example 1-69 and using 3-bromo-1-propanol in place of methyl iodide.

$^1$H NMR (300 MHz, CDCl$_3$) δ ppm 1.78-2.50 (m, 8H), 2.74-2.98 (m, 1H), 3.94 (t, J=5.7 Hz, 2H), 4.26 (t, J=5.7 Hz, 2H), 5.84 (d, J=7.8 Hz, 1H), 6.86 (d, J=9.4 Hz, 1H), 6.97-7.08 (m, 2H), 7.20 (d, J=1.6 Hz, 1H), 7.66 (d, J=7.4 Hz, 1H), 12.11-12.29 (brs, 1H).

MS(+): 456 [M+H]$^+$.

Example 1-82

6-{(E)-1-{3-Chloro-4-[(3-hydroxypropyl)sulfanyl]phenyl}-2-[(1S)-3-oxocyclopentyl]ethenyl}-3-(trifluoromethyl)pyridin-2(1H)-one

[Ka 187]

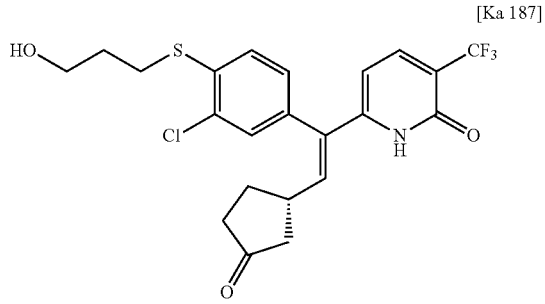 [SMILES: O=C1CC[C@H](/C=C(\c2ccc(SCCCO)c(Cl)c2)c2ccc(C(F)(F)F)c(=O)[nH]2)C1]

The title compound was obtained as a white solid (5.2 mg, 4% (two steps)) by performing substantially the same reaction as in Example 1-58 except for using {4-[(3-{[tert-butyl(dimethyl)silyl]oxy}propyl)sulfanyl]-3-chlorophenyl}[6-methoxy-5-(trifluoromethyl)pyridin-2-yl]methanone obtained in Reference Example 1-70.

$^1$H NMR (300 MHz, CDCl$_3$) δ ppm 1.74-2.20 (m, 5H), 2.20-2.48 (m, 3H), 2.73-2.94 (m, 1H), 3.14 (t, J=7.0 Hz, 2H), 3.85 (t, J=6.1 Hz, 2H), 5.84 (d, J=7.8 Hz, 1H), 6.90 (d, J=9.8 Hz, 1H), 7.06 (dd, J=8.2, 1.6 Hz, 1H), 7.20 (d, J=1.6 Hz, 1H), 7.35 (d, J=8.2 Hz, 1H), 7.67 (d, J=7.8 Hz, 1H), 12.21-12.42 (brs, 1H).

MS(+): 472 [M+H]$^+$.

Example 1-83

6-{(E)-1-{3-Chloro-4-[3-(diethylamino)propoxy]phenyl}-2-[(1S)-3-oxocyclopentyl]ethenyl}-3-(trifluoromethyl)pyridin-2(1H)-one

[Ka 188]

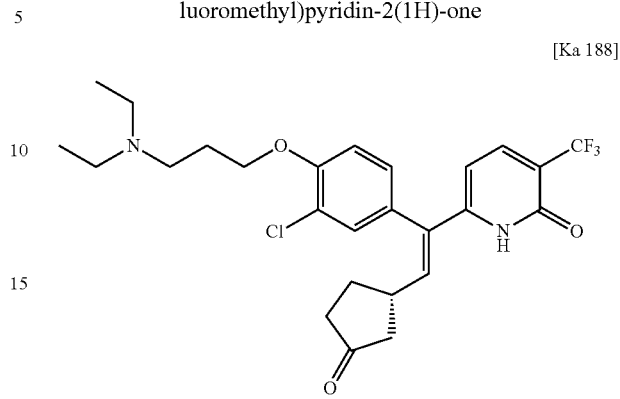

The title compound was obtained as a pale brown amorphous (137 mg, 7% (six steps)) by performing substantially the same reaction as in Example 1-79 except for using (4-{[tert-butyl(dimethyl)silyl]oxy}-3-chlorophenyl) [6-methoxy-5-(trifluoromethyl)pyridin-2-yl]methanone obtained in Reference Example 1-69.

$^1$H NMR (300 MHz, CDCl$_3$) δ ppm 1.06 (t, J=7.2 Hz, 6H), 1.90-2.44 (m, 8H), 2.50-2.63 (m, 4H), 2.63-2.76 (m, 2H), 2.76-2.93 (m, 1H), 4.14 (t, J=6.1 Hz, 2H), 5.84 (d, J=7.5 Hz, 1H), 6.87 (d, J=9.5 Hz, 1H), 6.98 (d, J=8.5 Hz, 1H), 7.02 (dd, J=8.5, 1.7 Hz, 1H), 7.18 (d, J=1.7 Hz, 1H), 7.66 (d, J=7.5 Hz, 1H).

MS(+): 511 [M+H]$^+$.

Example 1-84

6-{(E)-1-(3-Chloro-4-{[3-(diethylamino)propyl]sulfanyl}phenyl)-2-[(1S)-3-oxocyclopentyl]ethenyl}-3-(trifluoromethyl)pyridin-2(1H)-one

[Ka 189]

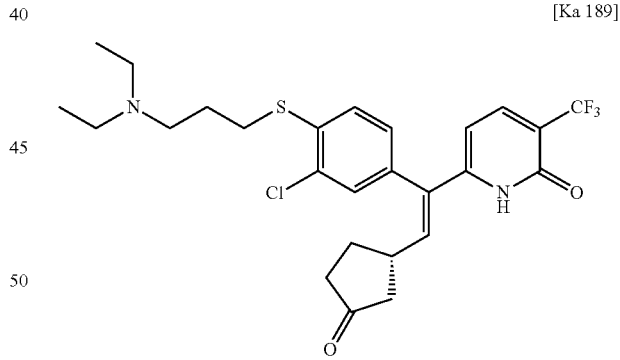

The title compound was obtained as a colorless amorphous (20 mg, 4% (five steps)) by performing substantially the same reaction as in Examples 1-58(1) and 1-26(2)-(5) sequentially except for using {4-[(3-{[tert-butyl(dimethyl)silyl]oxy}propyl)sulfanyl]-3-chlorophenyl}[6-methoxy-5-(trifluoromethyl)pyridin-2-yl]methanone obtained in Reference Example 1-70.

$^1$H NMR (300 MHz, CDCl$_3$) δ ppm 1.11 (t, J=7.2 Hz, 6H), 1.88-2.47 (m, 8H), 2.59-2.78 (m, 6H), 2.78-2.90 (m, 1H), 3.06 (t, J=7.2 Hz, 2H), 5.81 (d, J=7.5 Hz, 1H), 6.95 (d, J=9.5 Hz, 1H), 7.06 (dd, J=8.2, 1.7 Hz, 1H), 7.19 (d, J=1.7 Hz, 1H), 7.34 (d, J=7.8 Hz, 1H), 7.66 (d, J=7.8 Hz, 1H)

MS(+): 527 [M+H]$^+$..

Example 1-85

6-{(E)-1-[3-Chloro-4-(methylsulfanyl)phenyl]-2-[(1S)-3-hydroxycyclopentyl]ethenyl}-3-cyclopropylpyridin-2(1H)-one

[Ka 190]

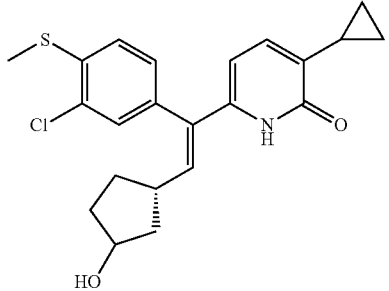

Sodium borohydride (11 mg) was added to a suspension of 6-{(E)-1-[3-chloro-4-(methylsulfanyl)phenyl]-2-[(1S)-3-oxocyclopentyl]ethenyl}-3-cyclopropylpyridin-2(1H)-one obtained in Example 1-71 (50 mg) in ethanol-tetrahydrofuran (2.5 mL, 4:1) under ice-cooling, and the mixture was stirred at room temperature for 30 minutes. The reaction solution was poured into 0.5 M hydrochloric acid, followed by extraction with chloroform. The organic layer was washed with brine, dried over anhydrous magnesium sulfate and filtered. The solvent was then evaporated under reduced pressure. The residue was purified by silica gel column chromatography (chloroform:methanol=10:0→9:1) to give the title compound (35 mg, 60%) as a colorless amorphous.

diastereomer mixture (colorless amorphous)
MS(+): 402 [M+H]$^+$.

Example 1-86

6-{(E)-1-{3-Chloro-4-[3-(diethylamino)propoxy]phenyl}-2-[(1S)-3-hydroxycyclopentyl]ethenyl}-3-(trifluoromethyl)pyridin-2(1H)-one

[Ka 191]

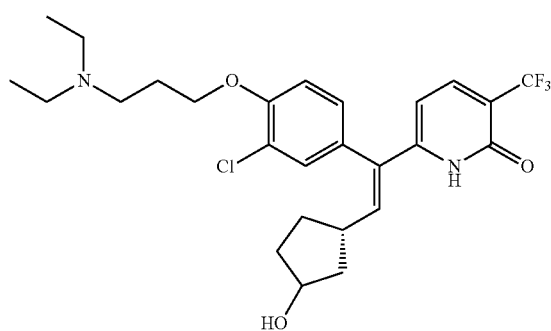

Sodium borohydride (4.4 mg) was added to a solution of 6-{(E)-1-{3-chloro-4-[3-(diethylamino)propoxy]phenyl}-2-[(1S)-3-oxocyclopentyl]ethenyl}-3-(trifluoromethyl)pyridin-2(1H)-one obtained in Example 1-83 (30 mg) in methanol (0.15 mL) at room temperature, and the mixture was stirred at room temperature for 30 minutes. Water and brine were added to the reaction solution, followed by extraction with chloroform. The organic layer was dried over anhydrous magnesium sulfate and filtered, after which the solvent was evaporated under reduced pressure. The residue was washed with diethyl ether to give the title compound (10 mg, 34%) as a pale yellow solid.
MS(+): 513 [M+H]$^+$.

Example 1-87

6-{(E)-1-{3-Chloro-4-[3-(diethylamino)propoxy]phenyl}-2-[(1S)-3-hydroxycyclopentyl]ethenyl}-3-cyclopropylpyridin-2(1H)-one

[Ka 192]

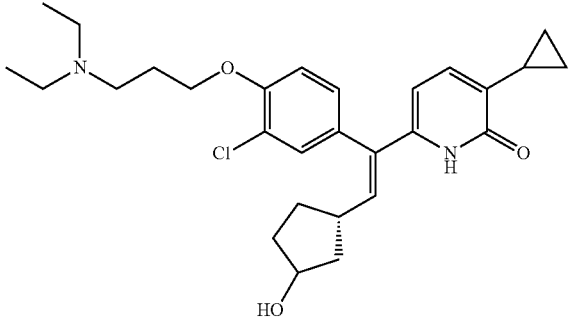

The title compound (4.4 mg, 15%) was obtained as a pale yellow solid by performing substantially the same reaction as in Example 1-86 except for using 6-{(E)-1-{3-chloro-4-[3-(diethylamino)propoxy]phenyl}-2-[(1S)-3-oxocyclopentyl]ethenyl}-3-cyclopropylpyridin-2(1H)-one obtained in Example 1-79.

diastereomer mixture (pale yellow solid)
MS(+): 485 [M+H]$^+$.

Example 1-88

6-[(E)-1-(3-Chloro-4-methoxyphenyl)-2-(cis-4-hydroxycyclohexyl)ethenyl]-3-cyclopropylpyridin-2(1H)-one

[Ka 193]

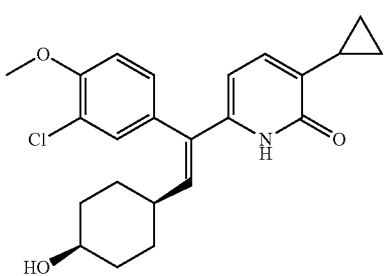

(1) 6-[(E)-1-(4-{[tert-Butyl(dimethyl)silyl]oxy}-3-chlorophenyl)-2-(cis-4-{[tert-butyl(dimethyl)silyl]oxy}cyclohexyl)ethenyl]-3-cyclopropyl-2-methoxypyridine was obtained as a pale yellow amorphous (620 mg, 61%) by performing substantially the same reaction as in Example 1-47(1) except for using 5-{[(cis-4-{[tert-butyl(dimethyl)silyl]oxy}cyclohexyl)methyl]sulfonyl}-1-phenyl-1H-tetrazole obtained in Reference Example 3-4 in place of 1-phenyl-5-[(tetrahydrofuran-3-ylmethyl)sulfonyl]-1H-tetrazole and using (4-{[tert-butyl(dimethyl)silyl]oxy}-3-chlorophenyl)(5-cyclopropyl-6-methoxypyridin-2-yl)methanone obtained in Reference Example 1-55.

(2) The title compound was obtained as a colorless powder (77 mg, 35% (three steps)) by performing substantially the same reaction as in Example 1-16(2)-(4) except for using 6-[(E)-1-(4-{[tert-butyl(dimethyl)silyl]oxy}-3-chlorophenyl)-2-(cis-4-{[tert-butyl(dimethyl)silyl]oxy}cyclohexyl)ethenyl]-3-cyclopropyl-2-methoxypyridine.

$^1$H NMR (300 MHz, CDCl$_3$) δ ppm 0.49-0.67 (m, 2H), 0.83-1.06 (m, 2H), 1.28-1.88 (m, 8H), 1.99-2.27 (m, 2H), 3.83-4.13 (m, 4H), 5.80 (d, J=7.3 Hz, 1H), 6.19 (d, J=10.0 Hz, 1H), 6.81 (d, J=7.3 Hz, 1H), 6.93-6.98 (m, 1H), 7.01-7.09 (m, 1H), 7.18 (d, J=2.0 Hz, 1H), 9.38-9.60 (brs, 1H).
MS(+): 400 [M+H]$^+$.

Example 1-89

6-[(E)-1-(3-Chloro-4-methoxyphenyl)-2-(trans-4-hydroxycyclohexyl)ethenyl]-3-cyclopropylpyridin-2(1H)-one

[Ka 194]

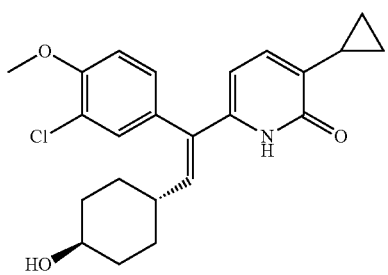

The title compound was obtained as a colorless powder (91 mg, 4.7% (four steps)) by performing substantially the same reaction as in Example 1-88(1)(2) except for using 5-{[(trans-4-{[tert-butyl(dimethyl)silyl]oxy}cyclohexyl)methyl]sulfonyl}-1-phenyl-1H-tetrazole obtained in Reference Example 3-5.

$^1$H NMR (300 MHz, CDCl$_3$) δ ppm 0.49-0.69 (m, 2H), 0.82-0.98 (m, 2H), 1.07-1.46 (m, 4H), 1.54-1.82 (m, 2H), 1.88-2.29 (m, 4H), 3.39-3.72 (m, 1H), 3.96 (s, 3H), 5.75 (d, J=7.3 Hz, 1H), 6.09 (d, J=10.0 Hz, 1H), 6.81 (s, 1H), 6.90-7.08 (m, 2H), 7.17 (d, J=2.0 Hz, 1H), 9.47-10.10 (brs, 1H).
MS(+): 400 [M+H]$^+$.

Example 1-90

6-[(E)-1-[4-(Cyclopropylsulfanyl)phenyl]-2-(trans-4-hydroxycyclohexyl)ethenyl]-3-(trifluoromethyl)pyridin-2(1H)-one

[Ka 195]

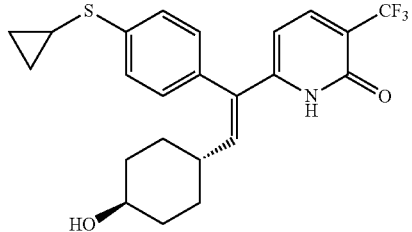

The title compound was obtained as a colorless powder (50 mg) by performing substantially the same reaction as in Example 1-89 except for using [4-(cyclopropylsulfanyl)phenyl][6-methoxy-5-(trifluoromethyl)pyridin-2-yl]methanone obtained in Reference Example 1-68.

$^1$H NMR (300 MHz, CDCl$_3$) δ ppm 0.65-0.83 (m, 2H), 1.05-1.50 (m, 6H), 1.62-1.76 (m, 2H), 1.96 (d, J=11.3 Hz, 3H), 2.15-2.28 (m, 1H), 3.49-3.70 (m, 1H), 5.83-5.95 (m, 1H), 6.45-6.59 (m, 1H), 7.07 (d, J=8.5 Hz, 2H), 7.42 (d, J=8.2 Hz, 2H), 7.65 (d, J=7.5 Hz, 1H).
MS(+): 436 [M+H]$^+$.

Example 1-91

6-[(E)-1-[4-(Cyclopropylsulfonyl)phenyl]-2-(trans-4-hydroxycyclohexyl)ethenyl]-3-(trifluoromethyl)pyridin-2(1H)-one

[Ka 196]

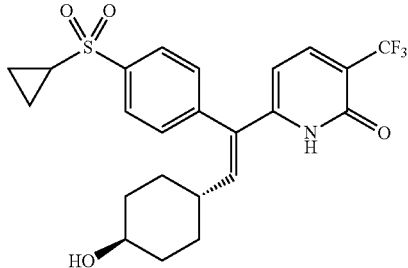

The title compound was obtained as a pale yellow powder (44 mg, 55%) by performing substantially the same reaction as in Example 1-2 except for using 6-[(E)-1-[4-(cyclopropylsulfanyl)phenyl]-2-(trans-4-hydroxycyclohexyl)ethenyl]-3-(trifluoromethyl)pyridin-2(1H)-one obtained in Example 1-90.

$^1$H NMR (300 MHz, DMSO-d$_6$) δ ppm 0.88-1.37 (m, 8H), 1.53-1.66 (m, 2H), 1.73-1.94 (m, 3H), 2.89-3.01 (m, 1H), 4.46 (d, J=4.5 Hz, 1H), 5.54-5.69 (m, 1H), 6.45-6.59 (m, 1H), 7.48 (d, J=8.4 Hz, 2H), 7.78 (d, J=8.2 Hz, 1H), 7.96 (d, J=8.4 Hz, 2H), 12.23-12.38 (brs, 1H).
MS(+): 468 [M+H]$^+$.

Example 1-92

3-Cyclopropyl-6-{(1E)-4-hydroxy-1-[4-(methylsulfanyl)phenyl]but-1-en-1-yl}pyridin-2(1H)-one

[Ka 197]

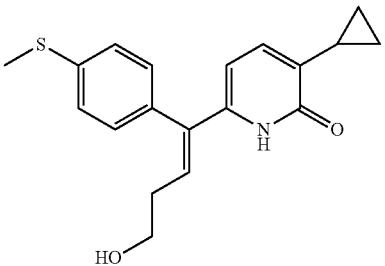

(1) 6-{(1E)-4-{[tert-Butyl(dimethyl)silyl]oxy}-1-[4-(methylsulfanyl)phenyl]but-1-en-1-yl}-3-cyclopropyl-2-methoxypyridine was obtained as a colorless oil (360 mg, 19%) by performing substantially the same reaction as in Example 1-47(1) except for using 5-[(3-{[tert-butyl(dimethyl)silyl]oxy}propyl)sulfonyl]-1-phenyl-1H-tetrazole.

(2) (3E)-4-(5-cyclopropyl-6-methoxypyridin-2-yl)-4-[4-(methylsulfanyl)phenyl]but-3-en-1-ol was obtained as a colorless oil (260 mg, 96%) by performing substantially the same reaction as in Example 1-16(2) except for using 6-{(1E)-4-{[tert-butyl(dimethyl)silyl]oxy}-1-[4-(methylsulfanyl)phenyl]but-1-en-1-yl}-3-cyclopropyl-2-methoxypyridine.

(3) The title compound was obtained as a colorless oil (45 mg, 40%) by performing substantially the same reaction as in Example 1-1(2) except for using (3E)-4-(5-cyclopropyl-6-methoxypyridin-2-yl)-4-[4-(methylsulfanyl)phenyl]but-3-en-1-ol.

$^1$H NMR (300 MHz, CDCl$_3$) δ ppm 0.49-0.59 (m, 2H), 0.86-1.00 (m, 2H), 2.03-2.16 (m, 1H), 2.36-2.48 (m, 2H), 2.51 (s, 3H), 3.69-3.78 (m, 2H), 3.91-3.40 (brs, 1H), 5.79 (d, J=7.3 Hz, 1H), 6.51 (t, J=7.4 Hz, 1H), 6.88 (dd, J=7.3, 0.8 Hz, 1H), 7.10-7.18 (m, 2H), 7.23-7.31 (m, 2H).

MS(+): 328 [M+H]$^+$.

Example 1-93

3-Cyclopropyl-6-{(1E)-4-hydroxy-1-[4-(methylsulfonyl)phenyl]but-1-en-1-yl}pyridin-2(1H)-one

[Ka 198]

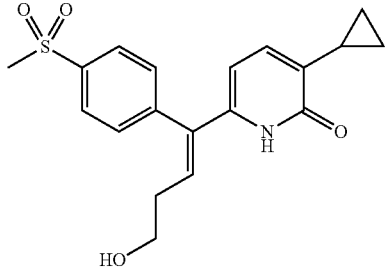

The title compound was obtained as a colorless oil (17 mg, 44%) by performing substantially the same reaction as in Example 1-2 except for using 3-cyclopropyl-6-{(1E)-4-hydroxy-1-[4-(methylsulfanyl)phenyl]but-1-en-1-yl}pyridin-2(1H)-one obtained in Example 1-92(3).

$^1$H NMR (300 MHz, CDCl$_3$) δ ppm 0.42-0.63 (m, 2H), 0.88-1.06 (m, 2H), 1.95-2.23 (m, 1H), 2.31-2.50 (m, 2H), 3.11 (s, 3H), 3.64-3.96 (m, 2H), 4.18-4.40 (brs, 1H), 5.68 (d, J=7.3 Hz, 1H), 6.63 (t, J=7.5 Hz, 1H), 6.92 (d, J=7.3 Hz, 1H), 7.47 (d, J=8.4 Hz, 2H), 7.98 (d, J=8.5 Hz, 2H), 12.26-12.55 (brs, 1H).

MS(+): 360 [M+H]$^+$.

Example 1-94

N-{(3E)-4-(5-Cyclopropyl-6-oxo-1,6-dihydropyridin-2-yl)-4-[4-(methylsulfanyl)phenyl]but-3-en-1-yl}acetamide

[Ka 199]

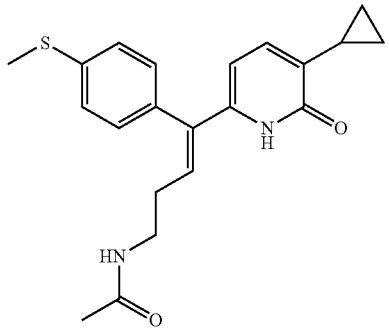

(1) Phthalimide (154 mg) and triphenylphosphine (275 mg) were added to a solution of (3E)-4-(5-cyclopropyl-6-methoxypyridin-2-yl)-4-[4-(methylsulfanyl)phenyl]but-3-en-1-ol obtained in Example 1-92(2) (275 mg) in tetrahydrofuran (10 mL), and the mixture was ice-cooled in a nitrogen gas stream. A 40% solution of diethyl azodicarboxylate in toluene (0.477 mL) was added thereto and the mixture was stirred at room temperature for three hours. The reaction solution was poured into water, followed by extraction with ethyl acetate. The organic layer was washed with brine, dried over anhydrous magnesium sulfate and filtered.

The solvent was then evaporated under reduced pressure. The residue was purified by silica gel column chromatography (hexane:ethyl acetate=9:1→1:1) to give 2-{(3E)-4-(5-cyclopropyl-6-methoxypyridin-2-yl)-4-[4-(methylsulfanyl)phenyl]but-3-en-1-yl}-1H-isoindole-1,3(2H)-dione as a colorless amorphous (320 mg, 84%).

(2) Hydrazine monohydrate (1 mL) was added to a solution of 2-{(3E)-4-(5-cyclopropyl-6-methoxypyridin-2-yl)-4-[4-(methylsulfanyl)phenyl]but-3-en-1-yl}-1H-isoindole-1,3(2H)-dione (320 mg) in ethanol (4 mL), and the mixture was stirred at 95° C. for one hour. The reaction solution was poured into a 3 M sodium hydroxide solution, followed by extraction with ethyl acetate. The organic layer was washed with brine, dried over anhydrous magnesium sulfate and filtered, after which the solvent was evaporated under reduced pressure to give (3E)-4-(5-cyclopropyl-6-methoxypyridin-2-yl)-4-[4-(methylsulfanyl)phenyl]but-3-en-1-amine as a colorless amorphous (225 mg, 97%).

(3) Acetic anhydride (85 mg) was added to a solution of (3E)-4-(5-cyclopropyl-6-methoxypyridin-2-yl)-4-[4-(methylsulfanyl)phenyl]but-3-en-1-amine (95 mg) in pyridine (1 mL) under ice-cooling, and the mixture was stirred at room temperature for one hour. The reaction solution was poured into 1 M hydrochloric acid, followed by extraction with ethyl acetate. The organic layer was washed with brine, dried over anhydrous magnesium sulfate and filtered. The solvent was then evaporated under reduced pressure. The residue was purified by silica gel column chromatography (hexane:ethyl acetate=4:1→0:1) to give N-{(3E)-4-(5-cyclopropyl-6-methoxypyridin-2-yl)-4-[4-(methylsulfanyl)phenyl]but-3-en-1-yl}acetamide as a colorless amorphous (87 mg, 81%).

(4) 48% hydrobromic acid (2 mL) was added to a solution of N-{(3E)-4-(5-cyclopropyl-6-methoxypyridin-2-yl)-4-[4-(methylsulfanyl)phenyl]but-3-en-1-yl}acetamide (87 mg) in 1,4-dioxane (2 mL), and the mixture was stirred at 80° C. for one hour. The reaction solution was poured into water, followed by extraction with ethyl acetate. The organic layer was washed with brine, dried over anhydrous magnesium sulfate and filtered. The solvent was then evaporated under reduced pressure. The residue was recrystallized from a mixed solvent of chloroform-ethyl acetate-hexane. Filtration gave the title compound as a colorless solid (54 mg, 64%).

$^1$H NMR (300 MHz, DMSO-d$_6$) δ ppm 0.47-0.65 (m, 2H), 0.76-0.91 (m, 2H), 1.76 (s, 3H), 1.89-2.05 (m, 1H), 2.12 (q, J=7.1 Hz, 2H), 2.51 (s, 3H), 3.04-3.18 (m, 2H), 5.38-5.55 (m, 1H), 6.22-6.43 (m, 1H), 6.84 (d, J=7.2 Hz, 1H), 7.04-7.15 (m, 2H), 7.22-7.36 (m, 2H), 7.77-7.96 (m, 1H), 11.11-11.33 (brs, 1H).

MS(+): 369 [M+H]$^+$.

Example 1-95

N-{(3E)-4-(5-Cyclopropyl-6-oxo-1,6-dihydropyridin-2-yl)-4-[4-(methylsulfonyl)phenyl]but-3-en-1-yl}acetamide

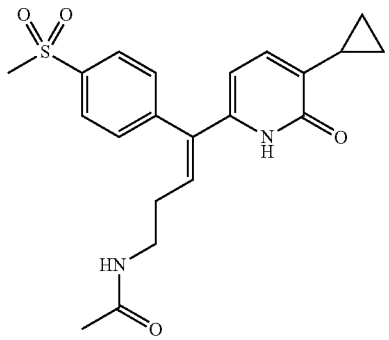

[Ka 200]

The title compound was obtained as a colorless oil (29 mg, 64%) by performing substantially the same reaction as in Example 1-2 except for using N-{(3E)-4-(5-cyclopropyl-6-oxo-1,6-dihydropyridin-2-yl)-4-[4-(methylsulfanyl)phenyl]but-3-en-1-yl}acetamide obtained in Example 1-94(4).

$^1$H NMR (300 MHz, CDCl$_3$) δ ppm 0.52-0.69 (m, 2H), 0.82-1.02 (m, 2H), 1.92-2.10 (m, 4H), 2.27-2.49 (m, 2H), 3.13 (s, 3H), 3.30-3.53 (m, 2H), 5.65 (d, J=7.5 Hz, 1H), 6.60 (t, J=7.5 Hz, 1H), 6.89 (d, J=7.9 Hz, 1H), 7.19-7.28 (m, 1H), 7.35-7.48 (m, 2H), 7.89-8.08 (m, 2H), 12.05-12.23 (brs, 1H).

MS(+): 401 [M+H]$^+$.

Example 1-96

3-Cyclopropyl-6-{(1E)-5-hydroxy-1-[4-(methylsulfanyl)phenyl]pent-1-en-1-yl}pyridin-2(1H)-one

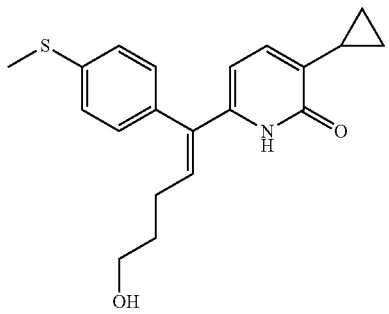

[Ka 201]

The title compound was obtained as a colorless powder (117 mg, 14% (two steps)) by performing substantially the same reaction as in Examples 1-47(1) and 1-1(2) sequentially except for using 5-[(4-{[tert-butyl(dimethyl)silyl]oxy}butyl)sulfonyl]-1-phenyl-1H-tetrazole.

$^1$H NMR (300 MHz, CDCl$_3$) δ ppm 0.49-0.67 (m, 2H), 0.86-1.08 (m, 2H), 1.62-1.77 (m, 2H), 2.00-2.14 (m, 1H), 2.21 (q, J=7.5 Hz, 2H), 3.62 (t, J=6.2 Hz, 2H), 5.85 (d, J=7.1 Hz, 1H), 6.31 (t, J=7.5 Hz, 1H), 6.83 (d, J=8.1 Hz, 1H), 7.09 (d, J=8.5 Hz, 2H), 7.27 (d, J=8.5 Hz, 2H),

MS(+): 342 [M+H]$^+$.

Example 1-97

3-Cyclopropyl-6-{(1E)-5-hydroxy-1-[4-(methylsulfonyl)phenyl]pent-1-en-1-yl}pyridin-2(1H)-one

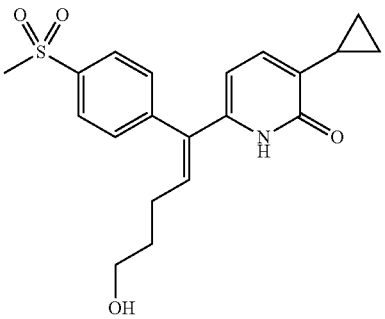

[Ka 202]

The title compound was obtained as a colorless oil (84 mg, 75%) by performing substantially the same reaction as in Example 1-2 except for using 3-cyclopropyl-6-{(1E)-5-hydroxy-1-[4-(methylsulfanyl)phenyl]pent-1-en-1-yl}pyridin-2(1H)-one obtained in Example 1-96.

$^1$H NMR (300 MHz, CDCl$_3$) δ ppm 0.47-0.74 (m, 2H), 0.84-1.04 (m, 2H), 1.49-1.88 (m, 1H), 1.98-2.13 (m, 2H), 2.14-2.29 (m, 2H), 3.13 (s, 3H), 3.54-3.71 (m, 2H), 5.65 (d, J=7.3 Hz, 1H), 6.53 (t, J=7.5 Hz, 1H), 6.85 (s, 1H), 7.42 (d, J=8.5 Hz, 2H), 7.99 (d, J=8.5 Hz, 2H).

MS(+): 374 [M+H]$^+$.

Example 1-98

6-{(1E)-1-[4-(Cyclopropylsulfanyl)phenyl]-5-hydroxypent-1-en-1-yl}-3-(trifluoromethyl)pyridin-2(1H)-one

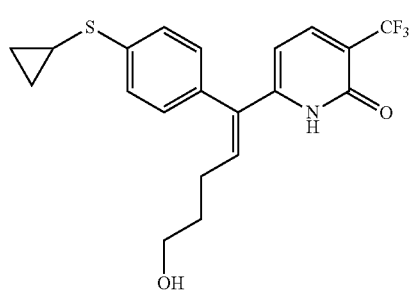

[Ka 203]

The title compound was obtained as a colorless powder (65 mg) by performing substantially the same reaction as in Example 1-96 except for using [4-(cyclopropylsulfanyl)phenyl][6-methoxy-5-(trifluoromethyl)pyridin-2-yl]methanone obtained in Reference Example 1-68.

$^1$H NMR (300 MHz, CDCl$_3$) δ ppm 0.68-0.82 (m, 2H), 1.06-1.18 (m, 2H), 1.69-1.86 (m, 2H), 2.13-2.37 (m, 3H), 3.58-3.71 (m, 2H), 5.93 (d, J=7.8 Hz, 1H), 6.79 (t, J=7.6 Hz, 1H), 7.03-7.14 (m, 2H), 7.37-7.46 (m, 2H), 7.67 (d, J=8.4 Hz, 1H), 11.34-11.66 (brs, 1H).

MS(+): 396 [M+H]$^+$.

Example 1-99

6-{(1E)-1-[4-(Cyclopropylsulfonyl)phenyl]-5-hydroxypent-1-en-1-yl}-3-(trifluoromethyl)pyridin-2(1H)-one

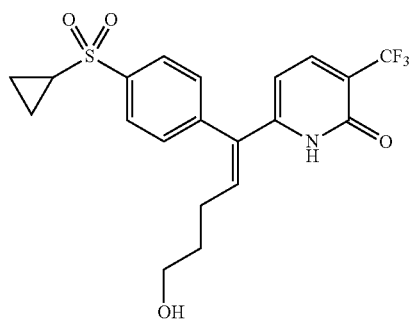

[Ka 204]

The title compound was obtained as a colorless oil (63 mg, 92%) by performing substantially the same reaction as in Example 1-2 except for using 6-{(1E)-1-[4-(cyclopropylsulfanyl)phenyl]-5-hydroxypent-1-en-1-yl}-3-(trifluoromethyl)pyridin-2(1H)-one obtained in Example 1-98.

$^1$H NMR (300 MHz, CDCl$_3$) δ ppm 0.98-1.17 (m, 2H), 1.34-1.48 (m, 2H), 1.69-1.92 (m, 2H), 2.14-2.32 (m, 2H), 2.44-2.62 (m, 1H), 3.47-3.79 (m, 2H), 5.77 (d, J=7.6 Hz, 1H), 6.98 (t, J=7.5 Hz, 1H), 7.34-7.49 (m, 2H), 7.68 (d, J=7.9 Hz, 1H), 7.92-8.05 (m, 2H), 12.21-12.59 (brs, 1H).

MS(+): 450 [M+Na]$^+$.

Example 1-100

6-{(E)-1-[4-(Cyclopropylsulfonyl)phenyl]-2-[1-(hydroxymethyl)cyclopropyl]ethenyl}-3-methylpyridin-2(1H)-one

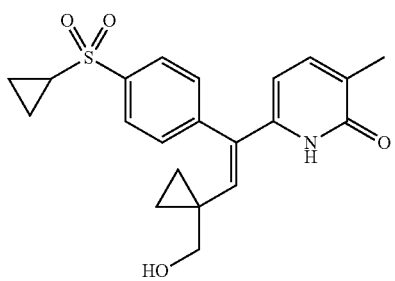

[Ka 205]

The title compound was obtained as a pale yellow solid (3.2 mg, 1% (three steps)) by performing substantially the same reaction as in Examples 1-47(1), 1-2 and 1-1(2) sequentially except for using [4-(cyclopropylsulfanyl)phenyl](6-methoxy-5-methylpyridin-2-yl)methanone obtained in Reference Example 1-37 and using 5-({[1-({[tert-butyl(dimethyl)silyl]oxy}methyl)cyclopropyl]methyl}sulfonyl)-1-phenyl-1H-tetrazole obtained in Reference Example 3-13 in place of 1-phenyl-5-[(tetrahydrofuran-3-ylmethyl)sulfonyl]-1H-tetrazole.

$^1$H NMR (500 MHz, CDCl$_3$) δ ppm 0.47-0.52 (m, 2H), 0.58-0.65 (m, 2H), 1.00-1.15 (m, 2H), 1.30-1.45 (m, 2H), 2.14 (s, 3H), 2.50-2.57 (m, 1H), 3.41 (s, 2H), 5.82 (d, J=7.1 Hz, 1H), 6.60 (s, 1H), 7.21 (d, J=7.0 Hz, 1H), 7.57 (d, J=8.3 Hz, 2H), 7.92 (d, J=8.3 Hz, 2H).

MS(+): 386 [M+H]$^+$.

Example 1-101

6-{(1E,3S)-1-[4-(Cyclopropylsulfonyl)phenyl]-4-hydroxy-3-methylbut-1-en-1-yl}-3-(trifluoromethyl)pyridin-2(1H)-one

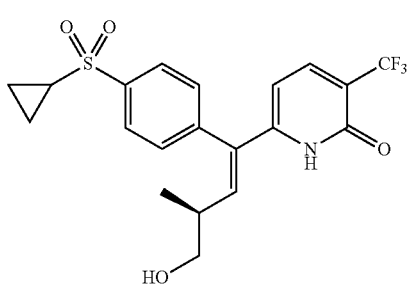

[Ka 206]

The title compound was obtained as a white solid (22 mg, 4% (three steps)) by performing substantially the same reaction as in Examples 1-47(1), 1-2 and 1-1(2) sequentially except for using [4-(cyclopropylsulfanyl)phenyl][6-methoxy-5-(trifluoromethyl)pyridin-2-yl]methanone obtained in Reference Example 1-68 and using 5-{[(2R)-3-{[tert-butyl(diphenyl)silyl]oxy}-2-methylpropyl]sulfonyl}-1-phenyl-1H-tetrazole obtained in Reference Example 3-14 in place of 1-phenyl-5-[(tetrahydrofuran-3-ylmethyl)sulfonyl]-1H-tetrazole.

$^1$H NMR (300 MHz, CDCl$_3$) δ ppm 1.02-1.18 (m, 5H), 1.38-1.47 (m, 2H), 2.42-2.60 (m, 2H), 3.52-3.65 (m, 2H), 5.82 (d, J=7.4 Hz, 1H), 6.62 (d, J=10.1 Hz, 1H), 7.44 (d, J=8.6 Hz, 2H), 7.70 (d, J=7.7 Hz, 1H), 7.97 (d, J=8.0 Hz, 2H).

MS(+): 428 [M+H]$^+$.

Example 1-102

6-{(1E,3R)-1-[4-(Cyclopropylsulfonyl)phenyl]-4-hydroxy-3-methylbut-1-en-1-yl}-3-(trifluoromethyl)pyridin-2(1H)-one

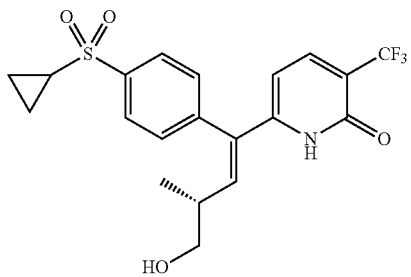

[Ka 207]

The title compound was obtained as a white solid (24 mg, 13% (three steps)) by performing substantially the same reaction as in Examples 1-47(1), 1-2 and 1-1(2) sequentially except for using [4-(cyclopropylsulfanyl)phenyl][6-methoxy-5-(trifluoromethyl)pyridin-2-yl]methanone obtained in Reference Example 1-68 and using 5-{[(2S)-3-{[tert-butyl(diphenyl)silyl]oxy}-2-methylpropyl]sulfonyl}-1-phenyl-1H-tetrazole obtained in Reference Example 3-15 in place of 1-phenyl-5-[(tetrahydrofuran-3-ylmethyl)sulfonyl]-1H-tetrazole.

$^1$H NMR (300 MHz, CDCl$_3$) δ ppm 1.00-1.20 (m, 5H), 1.38-1.47 (m, 2H), 2.20-2.39 (brs, 1H), 2.42-2.62 (m, 2H), 3.52-3.68 (m, 2H), 5.82 (d, J=7.4 Hz, 1H), 6.61 (d, J=10.7 Hz, 1H), 7.44 (d, J=8.3 Hz, 2H), 7.70 (d, J=7.4 Hz, 1H), 7.97 (d, J=8.0 Hz, 2H), 11.95-12.20 (brs, 1H).

MS(+): 428 [M+H]$^+$.

Example 1-103

3-Chloro-6-{(E)-2-cyclopentyl-1-[4-(cyclopropylsulfanyl)phenyl]ethenyl}pyridin-2(1H)-one

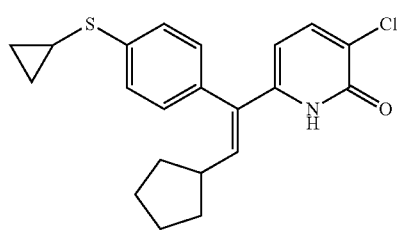

[Ka 208]

The title compound was obtained by performing substantially the same reaction as in Example 1-1 except for using (5-chloro-6-methoxypyridin-2-yl)[4-(cyclopropylsulfanyl)phenyl]methanone obtained in Reference Example 1-2.

$^1$H NMR (300 MHz, CDCl$_3$) δ ppm 0.57-0.65 (m, 2H), 1.07-1.17 (m, 2H), 1.35-1.55 (m, 4H), 1.58-1.75 (m, 4H), 2.24-2.36 (m, 2H), 5.48-5.60 (m, 1H), 6.45 (d, J=9.8 Hz, 1H), 7.11 (d, J=8.1 Hz, 2H), 7.40 (d, J=8.1 Hz, 2H), 7.58 (d, J=7.8 Hz, 1H), 11.93-12.18 (brs, 1H).

MS(+): 372 [M+H]$^+$.

Example 1-104

3-Chloro-6-{(E)-2-cyclopentyl-1-[4-(cyclopropylsulfonyl)phenyl]ethenyl}pyridin-2(1H)-one

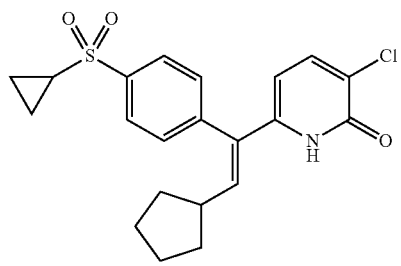

[Ka 209]

The title compound was obtained by performing substantially the same reaction as in Example 1-2 except for using 3-chloro-6-{(E)-2-cyclopentyl-1-[4-(cyclopropylsulfanyl)phenyl]ethenyl}pyridin-2(1H)-one obtained in Example 1-103.

$^1$H NMR (300 MHz, CDCl$_3$) δ ppm 1.07-1.17 (m, 2H), 1.38-1.47 (m, 2H), 1.49-1.59 (m, 4H), 1.71-1.84 (m, 4H), 2.31-2.44 (m, 1H), 2.49-2.61 (m, 1H), 5.77 (d, J=7.6 Hz, 1H), 6.49 (d, J=10.1 Hz, 1H), 7.39 (d, J=8.6 Hz, 2H), 7.47 (d, J=7.8 Hz, 1H), 7.96 (d, J=8.6 Hz, 2H), 10.42-10.75 (brs, 1H).

MS(+): 404 [M+H]$^+$.

Example 1-105

N-{4-[(E)-1-(5-Chloro-6-oxo-1,6-dihydropyridin-2-yl)-2-cyclopentylethenyl]phenyl}acetamide

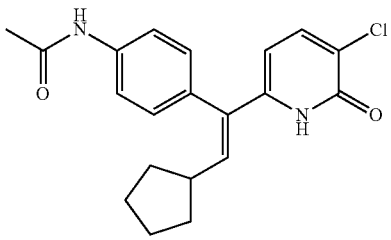

[Ka 210]

(1) 48% hydrobromic acid (2 mL) was added to a solution of tert-butyl {4-[(5-chloro-6-methoxypyridin-2-yl)carbonyl]phenyl}carbamate obtained in Reference Example 1-89 in 1,4-dioxane (5 mL), and the mixture was stirred at an external temperature of 65° C. for one hour. Saturated aqueous sodium bicarbonate was added to the reaction solution, followed by extraction with ethyl acetate. The organic layer was washed with brine and dried over sodium sulfate. After filtration, the solvent was evaporated under reduced pressure. The residue was purified by silica gel column chromatography (chloroform:methanol=10:0→9:1) to give 6-[(E)-1-(4-aminophenyl)-2-cyclopentylethenyl]-3-chloropyridin-2(1H)-one as a yellow oil (326 mg, quant.).

(2) Acetic anhydride (5 mL) was added to 6-[(E)-1-(4-aminophenyl)-2-cyclopentylethenyl]-3-chloropyridin-2(1H)-one (173 mg), and the mixture was stirred at room temperature for 15 minutes. Saturated aqueous sodium bicarbonate was added to the reaction solution, followed by extraction with ethyl acetate. The organic layer was washed with brine and dried over sodium sulfate. After filtration, the solvent was evaporated under reduced pressure, and the residue was purified by silica gel column chromatography (hexane:ethyl acetate=1:1→0:1). This was powdered with ethyl acetate, and filtration operation gave the title compound as a light yellow powder (75 mg, 38%).

$^1$H NMR (300 MHz, CDCl$_3$) δ ppm 1.34-1.54 (m, 4H), 1.63-1.83 (m, 4H), 2.22 (s, 3H), 2.40-2.55 (m, 1H), 5.94 (d, J=7.6 Hz, 1H), 6.20 (d, J=10.0 Hz, 1H), 7.13 (d, J=8.4 Hz, 2H), 7.22 (s, 1H), 7.47 (d, J=7.8 Hz, 1H), 7.56 (d, J=8.7 Hz, 2H).

MS(+): 357 [M+H]$^+$.

Example 1-106

1-{4-[(E)-1-(5-Chloro-6-oxo-1,6-dihydropyridin-2-yl)-2-cyclopentylethenyl]phenyl}urea

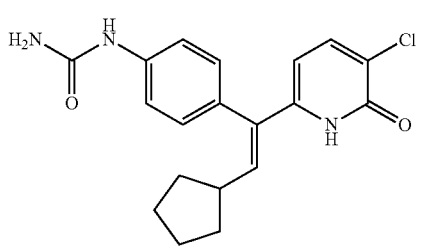

[Ka 211]

A solution of potassium cyanate (41 mg) in water (2 mL) was added to a solution of 6-[(E)-1-(4-aminophenyl)-2-cyclopentylethenyl]-3-chloropyridin-2(1H)-one obtained in Example 1-105(1) (153 mg) in acetic acid (2 mL)-water (1 mL), and the mixture was stirred at room temperature for 30 minutes. Saturated aqueous sodium bicarbonate and ethyl acetate were sequentially added to the reaction solution. The organic layer was separated, washed with saturated aqueous sodium bicarbonate and brine and dried over sodium sulfate. After filtration, the solvent was evaporated under reduced pressure, and the residue was purified by silica gel column chromatography (chloroform:methanol=9:1→8:2). This was powdered with ethyl acetate, and filtration operation gave the title compound as a light yellow powder (37 mg, 21%).

$^1$H NMR (300 MHz, CDCl$_3$) δ ppm 1.32-1.55 (m, 4H), 1.59-1.77 (m, 4H), 2.35-2.46 (m, 1H), 5.47-5.59 (m, 1H), 5.88 (s, 2H), 6.39 (d, J=10.0 Hz, 1H), 7.00 (d, J=8.6 Hz, 2H), 7.43 (d, J=8.7 Hz, 2H), 7.56 (d, J=7.6 Hz, 1H), 8.64 (s, 1H).
MS(+): 358 [M+H]$^+$.

Example 1-107

6-{(E)-1-[4-(Methylsulfonyl)phenyl]-2-[(1S)-3-oxocyclopentyl]ethenyl}-3-(propan-2-yl)pyridin-2(1H)-one The title compound was obtained as a colorless powder (18 mg) by performing substantially the same reaction as in Examples 1-58(1), 1-1(2) and 1-2 sequentially except for using [6-methoxy-5-(propan-2-yl)pyridin-2-yl][4-(methylsulfanyl)phenyl]methanone obtained in Reference Example 1-76.

$^1$H NMR (300 MHz, CDCl$_3$) δ ppm 0.99-1.32 (m, 6H), 1.75-2.50 (m, 6H), 2.61-2.88 (m, 1H), 2.98-3.30 (m, 4H), 5.50-5.80 (m, 1H), 6.66-6.83 (m, 1H), 7.06-7.21 (m, 1H), 7.38-7.55 (m, 2H), 7.89-8.16 (m, 2H), 11.66-12.13 (brs, 1H).
MS(+): 400 [M+H]$^+$.

Example 1-108

3-Cyclopropyl-6-{(E)-1-[4-(methylsulfonyl)phenyl]-2-[(1S)-3-oxocyclopentyl]ethenyl}pyridin-2(1H)-one The title compound was obtained as a colorless powder (55 mg) by performing substantially the same reaction as in Examples 1-58(1), 1-1(2) and 1-2 sequentially except for using (5-cyclopropyl-6-methoxypyridin-2-yl)[4-(methylsulfanyl)phenyl]methanone obtained in Reference Example 1-51.

$^1$H NMR (300 MHz, CDCl$_3$) δ ppm 0.53-0.68 (m, 2H), 0.82-1.05 (m, 2H), 1.84-2.48 (m, 7H), 2.63-2.89 (m, 1H), 3.08-3.21 (m, 3H), 5.46-5.64 (m, 1H), 6.65-6.92 (m, 2H), 7.38-7.52 (m, 2H), 7.95-8.09 (m, 2H), 11.84-12.19 (brs, 1H).
MS(+): 398 [M+H]$^+$.

Example 1-109

3-Chloro-6-[(E)-1-[4-(propan-2-yl)phenyl]-2-(tetrahydro-2H-pyran-4-yl)ethenyl]pyridin-2(1H)-one (1) 4-Isopropylphenylboronic acid (103 mg), tris(dibenzylideneacetone)dipalladium (38 mg), tri(2-furyl)phosphine (58 mg), cesium carbonate (273 mg) and water (0.5 mL) were added to a solution of 6-[(Z)-1-bromo-2-(tetrahydro-2H-pyran-4-yl)ethenyl]-3-chloro-2-methoxypyridine (140 mg) in 1,4-dioxane (3 mL), and the mixture was stirred at 90° C. for two hours. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (hexane:ethyl acetate=4:1→1:1) to give 3-chloro-2-methoxy-6-[(E)-1-[4-(propan-2-yl)phenyl]-2-(tetrahydro-2H-pyran-4-yl)ethenyl]pyridine containing impurities as a yellow oil (170 mg).

(2) The title compound was obtained as a colorless powder (61 mg) by performing substantially the same reaction as in Example 1-1(2) except for using 3-chloro-2-methoxy-6-[(E)-1-[4-(propan-2-yl)phenyl]-2-(tetrahydro-2H-pyran-4-yl)ethenyl]pyridine.

$^1$H NMR (300 MHz, CDCl$_3$) δ ppm 1.31 (d, J=7.0 Hz, 6H), 1.48-1.75 (m, 4H), 2.21-2.48 (m, 1H), 2.87-3.04 (m, 1H), 3.21-3.39 (m, 2H), 3.82-4.03 (m, 2H), 5.93 (d, J=7.6 Hz, 1H), 6.27 (d, J=9.8 Hz, 1H), 7.04-7.10 (m, 2H), 7.24-7.34 (m, 2H), 7.47 (d, J=7.6 Hz, 1H), 10.26-10.48 (brs, 1H).
MS(+): 358 [M+H]$^+$.

Example 1-110

3-Chloro-6-[(E)-1-[4-(cyclopropylsulfonyl)phenyl]-2-(tetrahydro-2H-pyran-4-yl)ethenyl]pyridin-2(1H)-one The title compound was obtained as a colorless powder (151 mg) by performing substantially the same reaction as in Examples 1-109(1), 1-1(2) and 1-2 sequentially except for using [4-(cyclopropylthio)phenyl]boronic acid in place of 4-isopropylphenylboronic acid.

$^1$H NMR (300 MHz, CDCl$_3$) δ ppm 0.90-1.25 (m, 2H), 1.30-1.49 (m, 2H), 1.48-1.62 (m, 2H), 1.65-1.93 (m, 2H), 2.05-2.36 (m, 1H), 2.45-2.70 (m, 1H), 3.09-3.51 (m, 2H), 3.76-4.17 (m, 2H), 5.67 (d, J=7.8 Hz, 1H), 6.62 (d, J=9.9 Hz, 1H), 7.36-7.43 (m, 2H), 7.47 (d, J=7.6 Hz, 1H), 7.93-8.03 (m, 2H), 12.08-12.18 (brs, 1H).
MS(+): 420 [M+H]$^+$.

Example 1-111

3-Chloro-6-[(E)-1-[4-(morpholin-4-yl)phenyl]-2-(tetrahydro-2H-pyran-4-yl)ethenyl]pyridin-2(1H)-one The title compound was obtained as a colorless powder (29 mg, 23% (two steps)) by performing substantially the same reaction as in Examples 1-109(1) and 1-1(2) sequentially except for using (4-morpholinophenyl)boronic acid in place of 4-isopropylphenylboronic acid.

$^1$H NMR (300 MHz, CDCl$_3$) δ ppm 1.45-1.80 (m, 4H), 2.27-2.54 (m, 1H), 3.14-3.42 (m, 6H), 3.73-4.03 (m, 6H), 5.99 (d, J=7.6 Hz, 1H), 6.19 (d, J=9.8 Hz, 1H), 6.86-7.00 (m, 2H), 7.01-7.10 (m, 2H), 7.47 (d, J=7.6 Hz, 1H), 9.87-10.15 (brs, 1H).

MS(+): 401[M+H]$^+$.

Example 1-112

6-[(E)-1-(4-Acetylphenyl)-2-(tetrahydro-2H-pyran-4-yl)ethenyl]-3-chloropyridin-2(1H)-one The title compound was obtained as a colorless powder (82 mg, 73% (two steps)) by performing substantially the same reaction as in Examples 1-109(1) and 1-1(2) sequentially except for using (4-acetylphenyl)boronic acid in place of 4-isopropylphenylboronic acid.

$^1$H NMR (300 MHz, CDCl$_3$) δ ppm 1.45-1.64 (m, 2H), 1.69-1.88 (m, 2H), 2.17-2.35 (m, 1H), 2.66 (s, 3H), 3.21-3.35 (m, 2H), 3.88-4.02 (m, 2H), 5.66 (d, J=7.6 Hz, 1H), 6.61 (d, J=9.8 Hz, 1H), 7.28-7.34 (m, 2H), 7.44 (d, J=7.6 Hz, 1H), 7.98-8.07 (m, 2H), 12.11-12.28 (brs, 1H).

MS(+): 358 [M+H]$^+$.

Example 1-113

3-Chloro-6-[(1E)-3-[4-(methylsulfonyl)phenyl]-1-(tetrahydro-2H-pyran-4-yl)prop-1-en-2-yl]pyridin-2(1H)-one (1) 1-(Bromomethyl)-4-(methylsulfonyl)benzene (110 mg), trimethylsilyl chloride (12.5 μL) and 1,2-dibromoethane (8.6 μL) were added to a solution of zinc powder (78 mg) in tetrahydrofuran (4 mL) in the presence of an argon gas, and the mixture was stirred at 80° C. for two hours. The reaction solution was returned to room temperature. A solution of tris(dibenzylideneacetone)dipalladium (45 mg), tri(2-furyl)phosphine (69 mg) and 6-[(Z)-1-bromo-2-(tetrahydro-2H-pyran-4-yl)ethenyl]-3-chloro-2-methoxypyridine (380 mg) in tetrahydrofuran (2 mL) was added and the mixture was stirred at 90° C. for two hours. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (hexane:ethyl acetate=1:1→0:1) to give 3-chloro-2-methoxy-6-[(1E)-3-[4-(methylsulfonyl)phenyl]-1-(tetrahydro-2H-pyran-4-yl)prop-1-en-2-yl]pyridine as a yellow oil (110 mg).

(2) The title compound was obtained as a colorless powder (64 mg) by performing substantially the same reaction as in Example 1-1(2) except for using 3-chloro-2-methoxy-6-[(1E)-3-[4-(methylsulfonyl)phenyl]-1-(tetrahydro-2H-pyran-4-yl)prop-1-en-2-yl]pyridine.

$^1$H NMR (300 MHz, CDCl$_3$) δ ppm 1.53-1.90 (m, 4H), 2.50-2.78 (m, 1H), 3.04 (s, 3H), 3.33-3.55 (m, 2H), 3.91-4.08 (m, 4H), 6.06 (d, J=7.6 Hz, 1H), 6.39 (d, J=9.3 Hz, 1H), 7.38 (d, J=8.2 Hz, 2H), 7.48 (d, J=7.7 Hz, 1H), 7.78-7.92 (m, 2H), 12.15-12.35 (brs, 1H).

MS(+): 408 [M+H]$^+$.

The structures of Examples 1-107 to 1-113 are shown below.

[Hyo 12]

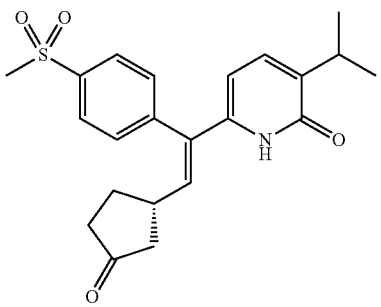

Example 1-107

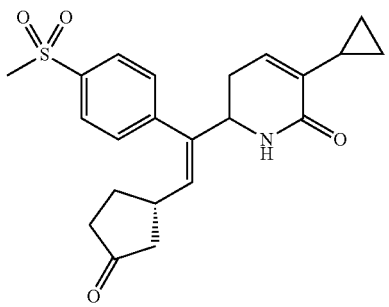

Example 1-108

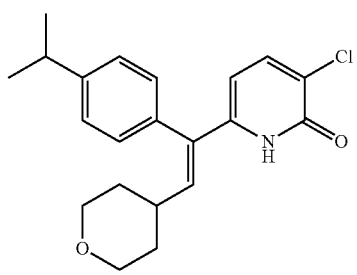

Example 1-109

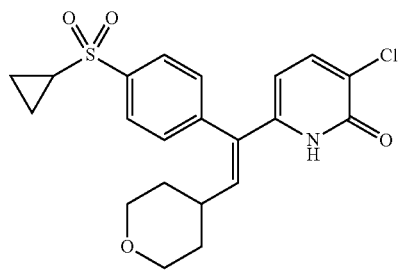

Example 1-110

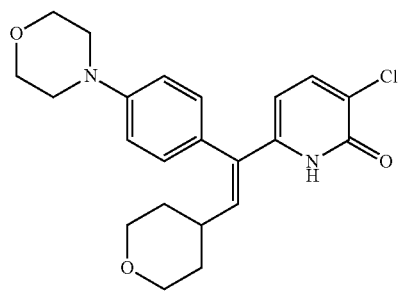

Example 1-111

-continued

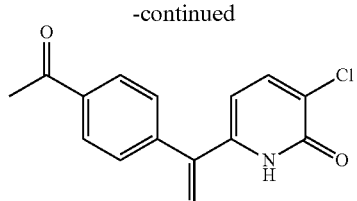

Example 1-112

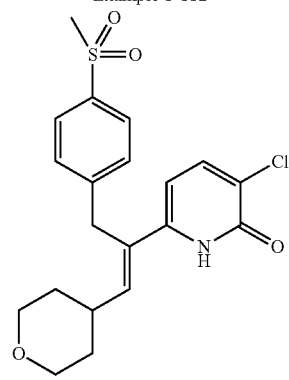

Example 1-113

Example 2-1

6-{2-Cyclopentyl-1-[4-(methylsulfanyl)phenyl]ethyl}-3-methylpyridin-2(1H)-one

[Ka 212]

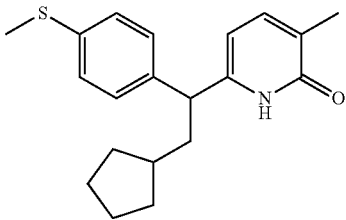

(1) A solution of 2.46 M n-butyllithium in hexane (1.11 mL) was added to a solution of 2-methoxy-3-methyl-6-[4-(methylsulfanyl)benzyl]pyridine obtained in Reference Example 2-1 (400 mg) in tetrahydrofuran (5 mL) in the presence of an argon gas at −78° C., and the mixture was stirred at −35° C. for 30 minutes. The reaction solution was cooled again to −78° C. and a solution of cyclopentylmethyl 4-methylbenzenesulfonate (549 mg) in tetrahydrofuran (3 mL) was added, after which the mixture was stirred at −78° C. to 0° C. for two hours. The reaction solution was poured into water, followed by extraction with ethyl acetate. The organic layer was washed with brine, dried over anhydrous magnesium sulfate and filtered. The solvent was then evaporated under reduced pressure. The residue was purified by preparative TLC (hexane:ethyl acetate=19:1) to give 6-{2-cyclopentyl-1-[4-(methylsulfanyl)phenyl]ethyl}-2-methoxy-3-methylpyridine as a colorless amorphous (220 mg, 42%).

(2) 48% hydrobromic acid (2 mL) was added to a solution of 6-{2-cyclopentyl-1-[4-(methylsulfanyl)phenyl]ethyl}-2-methoxy-3-methylpyridine (220 mg) in acetonitrile (2 mL), and the mixture was stirred at 110° C. for two hours. The reaction solution was poured into saturated aqueous sodium bicarbonate, followed by extraction with ethyl acetate. The organic layer was washed with brine, dried over anhydrous magnesium sulfate and filtered. The solvent was then evaporated under reduced pressure. The residue was purified by silica gel column chromatography (hexane:ethyl acetate=0:1) to give the title compound as a colorless amorphous (200 mg, 94%).

$^1$H NMR (300 MHz, CDCl$_3$) δ ppm 1.02-1.29 (m, 2H), 1.37-1.84 (m, 7H), 1.94-2.05 (m, 2H), 2.10 (s, 3H), 2.46 (s, 3H), 3.69-3.83 (m, 1H), 6.03 (d, J=6.8 Hz, 1H), 7.15-7.24 (m, 5H), 10.18-10.35 (m, 1H).

MS(+): 328 [M+H]$^+$.

Example 2-2

6-{2-Cyclopentyl-1-[4-(methylsulfonyl)phenyl]ethyl}-3-methylpyridin-2(1H)-one

[Ka 213]

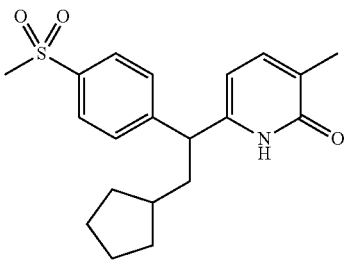

Potassium carbonate (324 mg) and Oxone(R) (1.45 g) were sequentially added to a solution of 6-{2-cyclopentyl-1-[4-(methylsulfanyl)phenyl]ethyl}-3-methylpyridin-2(1H)-one (154 mg) in acetone-water (10 mL) under ice-cooling, and the mixture was stirred at 0° C. for 30 minutes. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (hexane:ethyl acetate=0:1) to give the title compound as a colorless amorphous (20 mg, 12%).

$^1$H NMR (300 MHz, CDCl$_3$) δ ppm 1.02-1.29 (m, 2H), 1.38-1.87 (m, 7H), 1.95-2.16 (m, 5H), 3.03 (s, 3H), 3.88-4.02 (m, 1H), 6.10 (d, J=7.0 Hz, 1H), 7.18-7.30 (m, 1H), 7.49-7.60 (m, 2H), 7.80-7.90 (m, 2H), 11.38-11.57 (brs, 1H).

MS(+): 360 [M+H]$^+$.

Example 2-3

6-{2-Cyclopentyl-1-[4-(cyclopropylsulfonyl)phenyl]ethyl}-3-methylpyridin-2(1H)-one

[Ka 214]

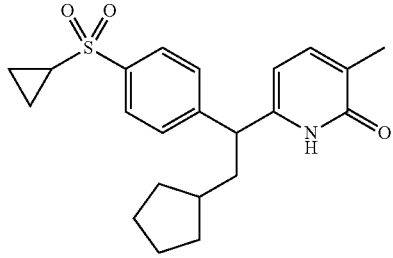

10% palladium-activated carbon (50 mg) was added to a mixed solution of 6-{(E)-2-cyclopentyl-1-[4-(cyclopropylsulfonyl)phenyl]ethenyl}-3-methylpyridin-2(1H)-one synthesized in Example 1-11 (50 mg) in tetrahydrofuran and methanol (2 mL, 1:1), and the mixture was stirred in a hydrogen gas stream at room temperature for three hours. The reaction solution was filtered through celite, and then the filtrate was concentrated under reduced pressure. The residue was purified by silica gel column chromatography (chloroform:methanol=1:1→0:1) to give the title compound as a colorless amorphous (33 mg, 60%).

$^1$H NMR (300 MHz, CDCl$_3$) δ ppm 0.96-1.26 (m, 3H), 1.29-1.39 (m, 2H), 1.42-1.83 (m, 8H), 1.98-2.10 (m, 2H), 2.13 (s, 3H), 2.33-2.51 (m, 1H), 3.83-4.04 (m, 1H), 6.10 (d, J=7.0 Hz, 1H), 7.20-7.29 (m, 1H), 7.45-7.55 (m, 2H), 7.76-7.86 (m, 2H), 11.31-11.48 (brs, 1H).

MS(+): 386 [M+H]$^+$.

The compounds of Examples 2-4 to 2-25 were synthesized by performing substantially the same reaction as in Example 1-2, 2-1 or 2-3.

Example 2-4

6-{1-[3-Chloro-4-(methylsulfanyl)phenyl]-2-cyclopentylethyl}-3-methylpyridin-2(1H)-one The title compound was obtained as a colorless amorphous (320 mg, 80%).

$^1$H NMR (300 MHz, CDCl$_3$) δ ppm 1.02-1.28 (m, 2H), 1.38-1.82 (m, 7H), 1.94-2.04 (m, 2H), 2.12 (d, J=0.9 Hz, 3H), 2.45 (s, 3H), 3.72-3.81 (m, 1H), 6.03 (d, J=7.0 Hz, 1H), 7.06-7.11 (m, 1H), 7.15-7.24 (m, 2H), 7.29 (d, J=1.9 Hz, 1H).

MS(+): 362 [M+H]$^+$.

Example 2-5

6-{1-[3-Chloro-4-(methylsulfonyl)phenyl]-2-cyclopentylethyl}-3-methylpyridin-2(1H)-one The title compound was obtained as a colorless amorphous (150 mg, 40%).

$^1$H NMR (300 MHz, CDCl$_3$) δ ppm 1.02-1.31 (m, 2H), 1.38-1.85 (m, 7H), 1.96-2.12 (m, 2H), 2.15 (d, J=0.9 Hz, 3H), 3.23 (s, 3H), 3.91-4.02 (m, 1H), 6.11 (d, J=7.0 Hz, 1H), 7.22-7.31 (m, 1H), 7.49 (dd, J=8.2, 1.7 Hz, 1H), 7.63 (d, J=1.7 Hz, 1H), 8.04 (d, J=8.2 Hz, 1H), 12.52-12.80 (brs, 1H).

MS(+): 394 [M+H]$^+$.

Example 2-6

6-{2-Cyclopentyl-1-[4-(methylsulfanyl)phenyl]ethyl}-3-ethylpyridin-2(1H)-one

The title compound was obtained as a colorless amorphous (200 mg, 25% (two steps)).

$^1$H NMR (300 MHz, CDCl$_3$) δ ppm 0.97-1.24 (m, 5H), 1.35-1.84 (m, 7H), 1.91-2.07 (m, 2H), 2.40-2.66 (m, 5H), 3.61-3.83 (m, 1H), 6.06 (d, J=7.0 Hz, 1H), 7.11-7.24 (m, 5H), 10.04-10.34 (brs, 1H).

MS(+): 342 [M+H]$^+$.

Example 2-7

6-{2-Cyclopentyl-1-[4-(methylsulfonyl)phenyl]ethyl}-3-ethylpyridin-2(1H)-one

The title compound was obtained as a colorless amorphous (180 mg, 82%).

$^1$H NMR (300 MHz, CDCl$_3$) δ ppm 1.04-1.30 (m, 5H), 1.35-1.84 (m, 7H), 1.98-2.19 (m, 2H), 2.48-2.64 (m, 2H), 3.02 (s, 3H), 3.92-4.08 (m, 1H), 6.13 (d, J=7.0 Hz, 1H), 7.24 (d, J=7.2 Hz, 1H), 7.61 (d, J=8.6 Hz, 2H), 7.84 (d, J=8.4 Hz, 2H), 12.53-12.71 (brs, 1H).

MS(+): 374 [M+H]$^+$.

Example 2-8

6-{2-Cyclopentyl-1-[4-(methylsulfanyl)phenyl]ethyl}-3-propylpyridin-2(1H)-one

The title compound was obtained as a colorless amorphous (80 mg, 20% (two steps)).

$^1$H NMR (300 MHz, CDCl$_3$) δ ppm 0.95 (t, J=7.38 Hz, 3H), 1.04-1.30 (m, 2H), 1.36-1.85 (m, 9H), 1.94-2.07 (m, 2H), 2.39-2.51 (m, 5H), 3.69-3.83 (m, 1H), 6.04 (d, J=6.8 Hz, 1H), 7.11-7.23 (m, 5H), 10.23-10.40 (brs, 1H).

MS(+): 356 [M+H]$^+$.

Example 2-9

6-{2-Cyclopentyl-1-[4-(methylsulfonyl)phenyl]ethyl}-3-propylpyridin-2(1H)-one

The title compound was obtained as a colorless amorphous (60 mg, 68%).

$^1$H NMR (300 MHz, CDCl$_3$) δ ppm 0.92-1.02 (m, 3H), 1.05-1.30 (m, 2H), 1.36-1.85 (m, 9H), 2.02-2.17 (m, 2H), 2.44-2.57 (m, 2H), 3.02 (s, 3H), 3.94-4.06 (m, 1H), 6.11 (d, J=7.0 Hz, 1H), 7.22 (d, J=7.0 Hz, 1H), 7.53-7.65 (m, 2H), 7.79-7.90 (m, 2H), 12.45-12.75 (brs, 1H).

MS(+): 388 [M+H]$^+$.

Example 2-10

6-{2-Cyclopentyl-1-[4-(methylsulfonyl)phenyl]ethyl}-3-cyclopropylpyridin-2(1H)-one The title compound was obtained as a colorless amorphous (102 mg, 35%).

$^1$H NMR (300 MHz, CDCl$_3$) δ ppm 0.64-0.74 (m, 2H), 0.87-0.99 (m, 2H), 1.03-1.31 (m, 2H), 1.34-1.84 (m, 7H), 1.97-2.17 (m, 3H), 3.02 (s, 3H), 3.98 (t, J=7.7 Hz, 1H), 6.10 (d, J=7.2 Hz, 1H), 6.95 (d, J=7.2 Hz, 1H), 7.51-7.62 (m, 2H), 7.79-7.89 (m, 2H), 11.92-12.24 (brs, 1H).

MS(+): 386 [M+H]$^+$.

Example 2-11

6-(2-Cyclopentyl-1-{4-[(3-hydroxypropyl)sulfonyl]phenyl}ethyl)-3-ethylpyridin-2(1H)-one The title compound was obtained as a colorless amorphous (26 mg, 52%).

$^1$H NMR (300 MHz, CDCl$_3$) δ ppm 1.02-1.27 (m, 4H), 1.38-1.85 (m, 8H), 1.90-2.23 (m, 4H), 2.44-2.64 (m, 2H), 3.08-3.28 (m, 2H), 3.61-3.78 (m, 2H), 3.87-4.06 (m, 1H), 6.15 (d, J=7.0 Hz, 1H), 7.24 (d, J=7.0 Hz, 1H), 7.44-7.61 (m, 2H), 7.76-7.86 (m, 2H), 11.54-11.91 (brs, 1H).

MS(+): 418 [M+H]$^+$.

Example 2-12

6-{2-Cyclopentyl-1-[4-(methylsulfonyl)phenyl]ethyl}-3-(propan-2-yl)pyridin-2(1H)-one The title compound was obtained as a colorless amorphous (36 mg, 97%).

¹H NMR (300 MHz, CDCl₃) δ ppm 1.02-1.29 (m, 7H), 1.39-1.88 (m, 8H), 2.02-2.20 (m, 2H), 3.02 (s, 3H), 3.06-3.23 (m, 1H), 3.89-4.06 (m, 1H), 6.15 (d, J=7.2 Hz, 1H), 7.23 (d, J=6.5 Hz, 1H), 7.53-7.69 (m, 2H), 7.81-7.96 (m, 2H), 12.18-12.41 (brs, 1H).
MS(+): 388 [M+H]⁺.

Example 2-13

6-[1-(3-Chloro-4-{[3-(diethylamino)propyl]sulfonyl}phenyl)-2-cyclopentylethyl]-3-methylpyridin-2(1H)-one The title compound was obtained as a colorless amorphous (315 mg).
¹H NMR (300 MHz, CDCl₃) δ ppm 1.05-1.90 (m, 15H), 2.07-2.32 (m, 5H), 2.34-2.56 (m, 2H), 3.02-3.42 (m, 6H), 3.45-3.64 (m, 2H), 4.34 (t, J=7.5 Hz, 1H), 6.82 (d, J=6.8 Hz, 1H), 7.57-7.80 (m, 3H), 8.06 (d, J=7.9 Hz, 1H), 10.87-11.13 (brs, 1H).
MS(+): 493 [M+H]⁺.

Example 2-14

6-(1-{3-Chloro-4-[(3-hydroxypropyl)sulfonyl]phenyl}-2-cyclopentylethyl)-3-methylpyridin-2(1H)-one The title compound was obtained as a colorless amorphous (36 mg, 51% (three steps)).
¹H NMR (300 MHz, CDCl₃) δ ppm 1.02-1.29 (m, 2H), 1.37-1.83 (m, 6H), 1.88-2.21 (m, 8H), 3.43-3.55 (m, 2H), 3.71 (t, J=5.9 Hz, 2H), 3.96 (t, J=8.0 Hz, 1H), 6.13 (d, J=7.0 Hz, 1H), 7.25-7.31 (m, 1H), 7.48 (dd, J=8.2, 1.7 Hz, 1H), 7.62 (d, J=1.7 Hz, 1H), 8.00 (d, J=8.1 Hz, 1H).
MS(+): 438 [M+H]⁺.

Example 2-15

6-{3-Cyclopentyl-1-[4-(cyclopropylsulfonyl)phenyl]propyl}-3-methylpyridin-2(1H)-one The title compound was obtained as a colorless amorphous (88 mg, 88%).
¹H NMR (300 MHz, CDCl₃) δ ppm 0.91-1.12 (m, 4H), 1.14-1.39 (m, 4H), 1.41-1.64 (m, 4H), 1.65-1.83 (m, 3H), 1.88-2.20 (m, 5H), 2.36-2.49 (m, 1H), 3.86 (t, J=7.7 Hz, 1H), 6.12 (d, J=7.0 Hz, 1H), 7.21-7.32 (m, 1H), 7.46-7.58 (m, 2H), 7.75-7.84 (m, 2H), 11.74-11.98 (brs, 1H).
MS(+): 400 [M+H]⁺.

Example 2-16

6-{2-Cyclohexyl-1-[4-(methylsulfanyl)phenyl]ethyl}-3-methylpyridin-2(1H)-one

The title compound was obtained as a colorless amorphous (750 mg, 55% (two steps)).
¹H NMR (300 MHz, CDCl₃) δ ppm 0.85-1.02 (m, 2H), 1.04-1.20 (m, 4H), 1.48-1.94 (m, 7H), 2.10 (s, 3H), 2.46 (s, 3H), 3.81-3.93 (m, 1H), 6.01 (d, J=6.8 Hz, 1H), 7.11-7.24 (m, 5H), 10.30-10.48 (brs, 1H).
MS(+): 342 [M+H]⁺.

Example 2-17

6-{2-Cyclohexyl-1-[4-(methylsulfonyl)phenyl]ethyl}-3-methylpyridin-2(1H)-one

The title compound was obtained as a colorless amorphous (105 mg, 87%).
¹H NMR (300 MHz, CDCl₃) δ ppm 0.82-1.23 (m, 6H), 1.52-2.06 (m, 7H), 2.13 (s, 3H), 3.02 (s, 3H), 4.00-4.18 (m, 1H), 6.08 (d, J=7.0 Hz, 1H), 7.18-7.31 (m, 1H), 7.49-7.63 (m, 2H), 7.78-7.90 (m, 2H), 12.13-12.38 (brs, 1H).
MS(+): 374 [M+H]⁺.

Example 2-18

3-Methyl-6-{1-[4-(methylsulfanyl)phenyl]-2-(tetrahydro-2H-pyran-4-yl)ethyl}pyridin-2(1H)-one The title compound was obtained as a colorless amorphous (220 mg, 65% (two steps)).
¹H NMR (300 MHz, CDCl₃) δ ppm 1.18-1.46 (m, 3H), 1.48-1.72 (m, 2H), 1.82-2.01 (m, 2H), 2.10 (s, 3H), 2.46 (s, 3H), 3.16-3.35 (m, 2H), 3.78-4.02 (m, 3H), 6.01 (d, J=6.8 Hz, 1H), 7.11-7.24 (m, 5H), 10.91-11.14 (brs, 1H).
MS(+): 344 [M+H]⁺.

Example 2-19

3-Methyl-6-{1-[4-(methylsulfonyl)phenyl]-2-(tetrahydro-2H-pyran-4-yl)ethyl}pyridin-2(1H)-one The title compound was obtained as a colorless amorphous (410 mg, 78%).
¹H NMR (300 MHz, CDCl₃) δ ppm 1.25-1.45 (m, 3H), 1.51-1.75 (m, 2H), 1.91-2.11 (m, 2H), 2.13 (d, J=0.9 Hz, 3H), 3.03 (s, 3H), 3.19-3.34 (m, 2H), 3.84-3.98 (m, 2H), 4.06-4.20 (m, 1H), 6.09 (d, J=7.0 Hz, 1H), 7.23-7.31 (m, 1H), 7.52-7.64 (m, 2H), 7.81-7.89 (m, 2H), 12.88-13.08 (brs, 1H).
MS(+): 376 [M+H]⁺.

Example 2-20

3-Methyl-6-{1-[4-(methylsulfanyl)phenyl]-2-(4-oxocyclohexyl)ethyl}pyridin-2(1H)-one The title compound was obtained as a colorless amorphous (22 mg, 12% (two steps)).
¹H NMR (300 MHz, CDCl₃) δ ppm 1.33-1.69 (m, 3H), 1.94-2.42 (m, 11H), 2.47 (s, 3H), 3.81-4.02 (m, 1H), 5.93-6.09 (m, 1H), 7.15-7.29 (m, 5H), 10.91-11.23 (brs, 1H).
MS(+): 356 [M+H]⁺.

Example 2-21

3-Methyl-6-{1-[4-(methylsulfonyl)phenyl]-2-(4-oxocyclohexyl)ethyl}pyridin-2(1H)-one The title compound was obtained as a colorless amorphous (56 mg, 20%).
¹H NMR (300 MHz, CDCl₃) δ ppm 1.39-1.59 (m, 3H), 1.97-2.43 (m, 11H), 3.04 (s, 3H), 4.03-4.18 (m, 1H), 6.09 (d, J=7.2 Hz, 1H), 7.23-7.31 (m, 1H), 7.54-7.67 (m, 2H), 7.81-7.93 (m, 2H), 12.49-12.72 (brs, 1H).
MS(+): 388 [M+H]⁺.

Example 2-22

3-Methyl-6-{1-[4-(methylsulfanyl)phenyl]-2-[(1R)-3-oxocyclopentyl]ethyl}pyridin-2(1H)-one The title compound was obtained as a colorless amorphous (170 mg, 13% (two steps)).
diastereomer mixture (colorless amorphous)
MS(+): 342 [M+H]⁺.

Example 2-23
3-Methyl-6-{1-[4-(methylsulfonyl)phenyl]-2-[(1R)-3-oxocyclopentyl]ethyl}pyridin-2(1H)-one
The title compound was obtained as a colorless amorphous (86 mg, 54%).
diastereomer mixture (colorless amorphous)
MS(+): 374 [M+H]$^+$.
The structures of Examples 2-4 to 2-23 are shown below.
[Hyo 13-1]
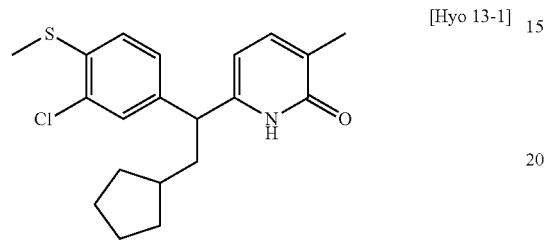
Example 2-4
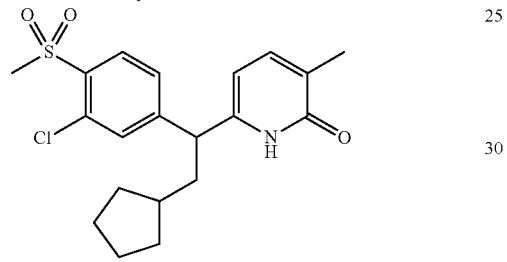
Example 2-5
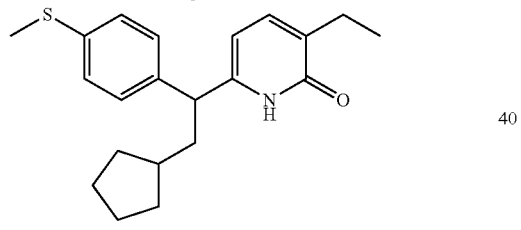
Example 2-6
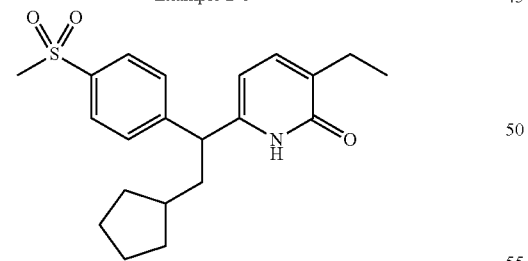
Example 2-7
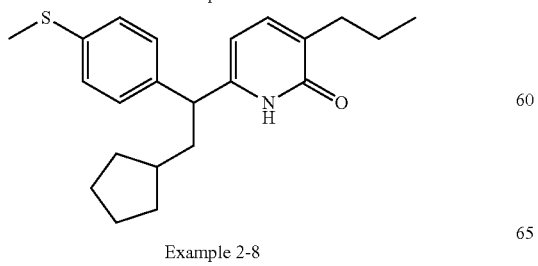
Example 2-8
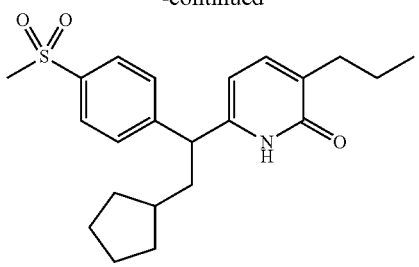
Example 2-9
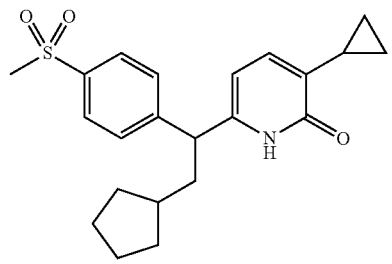
Example 2-10
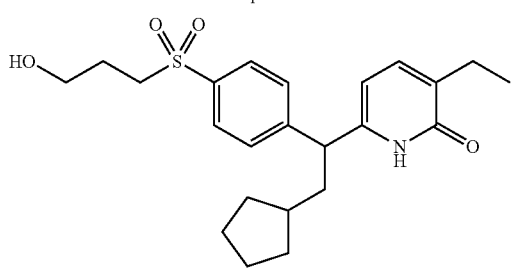
Example 2-11
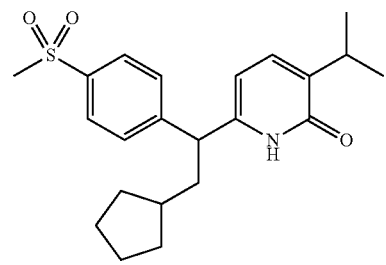
Example 2-12
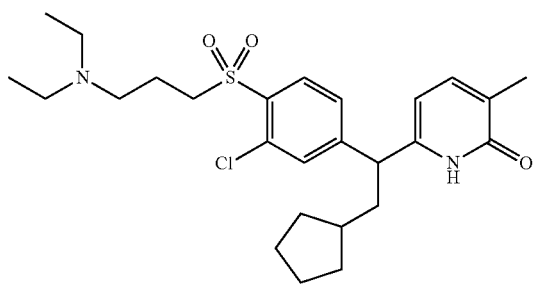
Example 2-13

Example 2-14

Example 2-15

Example 2-16

Example 2-17

Example 2-18

Example 2-19

Example 2-20

Example 2-21

Example 2-22

Example 2-23

Example 2-24

3-Chloro-6-(2-cyclopentyl-1-{4-[(4-methylpiper-azin-1-yl)sulfonyl]phenyl}ethyl)pyridin-2(1H)-one

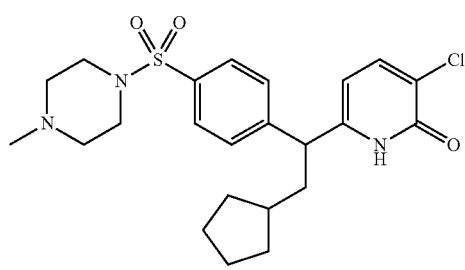

[Ka 215]

The title compound (183 mg, 90%) was obtained as a colorless amorphous.

$^1$H NMR (300 MHz, CDCl$_3$) δ ppm 1.07-1.28 (m, 2H), 1.42-1.80 (m, 7H), 2.04 (t, J=7.6 Hz, 2H), 2.26 (s, 3H), 2.45-2.52 (m, 4H), 2.99-3.09 (m, 4H), 3.93 (t, J=7.9 Hz, 1H), 6.11 (d, J=7.2 Hz, 1H), 7.46 (d, J=8.4 Hz, 2H), 7.55 (d, J=7.5 Hz, 1H), 7.68 (d, J=8.6 Hz, 2H).

MS(+): 464 [M+H]$^+$.

Example 2-25

3-Chloro-6-{2-cyclopentyl-1-[4-(cyclopropylsulfo-nyl)phenyl]ethyl}pyridin-2(1H)-one

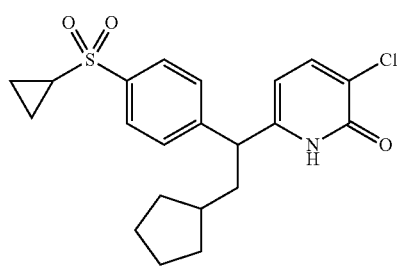

[Ka 216]

The title compound (70 mg, 49%) was obtained as a colorless powder.

$^1$H NMR (300 MHz, CDCl$_3$) δ ppm 0.83-0.93 (m, 2H), 0.98-1.85 (m, 11H), 2.00-2.12 (m, 2H), 2.37-2.52 (m, 1H), 3.97 (t, J=7.7 Hz, 1H), 6.18 (d, J=7.5 Hz, 1H), 7.51 (d, J=8.2 Hz, 2H), 7.57 (d, J=7.5 Hz, 1H), 7.82 (d, J=8.2 Hz, 2H), 11.67-12.04 (brs, 1H).

MS(+): 406 [M+H]$^+$.

Example 3-1 trans-6-{1-[3-Chloro-4-(methylsulfanyl)phenyl]-2-cyclopentylcyclopropyl}-3-methylpyridin-2(1H)-one

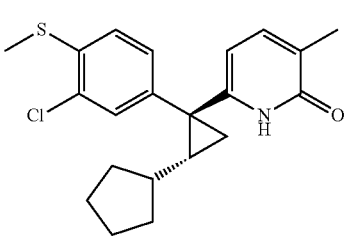

[Ka 217]

A 1.0 M solution of diethylzinc in n-hexane (0.6 mL) was added to a solution of 6-{(E)-1-[3-chloro-4-(methylsulfanyl)phenyl]-2-cyclopentylethenyl}-3-methylpyridin-2(1H)-one obtained in Example 1-18 (36.0 mg) in dichloromethane (2.5 mL) in a nitrogen atmosphere under ice-cooling, and a solution of diiodomethane (322 mg) in dichloromethane (1.5 mL) was subsequently added dropwise slowly. After stirring at room temperature for 12 hours, a saturated ammonium chloride solution was added to the reaction mixture. After extraction with ethyl acetate, the organic layer was washed with brine. The organic layer was dried over anhydrous sodium sulfate and then filtered, and the solvent was evaporated under reduced pressure. The resulting residue was purified by silica gel column chromatography (NH silica gel, chloroform:hexane=3:2→1:0) to give the title compound as a colorless solid (8.2 mg, 22%).

$^1$H NMR (300 MHz, CDCl$_3$) δ ppm 0.80-1.10 (m, 2H), 1.20-1.80 (m, 10H), 2.09 (s, 3H), 2.47 (s, 3H), 5.99 (d, J=6.9 Hz, 1H), 7.09 (d, J=8.4 Hz, 1H), 7.16 (d, J=7.2 Hz, 1H), 7.21 (dd, J=8.4, 1.8 Hz, 1H), 7.32 (d, J=1.5 Hz, 1H), 9.05-9.35 (brs, 1H).

MS(+): 374 [M+H]$^+$.

Example 3-2 trans-6-{1-[3-Chloro-4-(methylsulfonyl)phenyl]-2-cyclopentylcyclopropyl}-3-methylpyridin-2(1H)-one

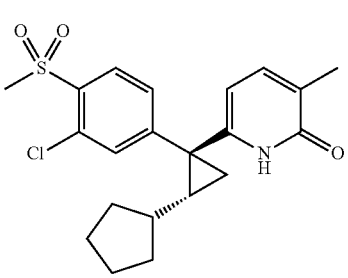

[Ka 218]

Water (0.2 mL) and Oxone(R) (99 mg) were added to a solution of trans-6-{1-[3-chloro-4-(methylsulfanyl)phenyl]-2-cyclopentylcyclopropyl}-3-methylpyridin-2(1H)-one obtained in Example 3-1 (20.0 mg) in methanol-tetrahydrofuran (1:1) (1.5 mL) under ice-cooling, and the mixture was stirred at room temperature for one day. Oxone(R) (99 mg and another 66 mg after four hours) was further added while confirming the progress of the reaction by LC/MS, and the mixture was stirred for 31 hours in total. Water and ethyl acetate were added to the reaction mixture, followed by extraction with ethyl acetate. The organic layer was washed with water, dried over anhydrous magnesium sulfate and then filtered. The solvent was evaporated under reduced pressure. The residue was purified by preparative TLC (NH silica gel, chloroform) to give the title compound as a colorless solid (7.7 mg, 41%).

$^1$H NMR (300 MHz, CDCl$_3$) δ ppm 0.80-0.98 (m, 2H), 1.20-1.50 (m, 7H), 1.50-1.78 (m, 3H), 2.13 (s, 3H), 3.25 (s, 3H), 6.13 (d, J=7.2 Hz, 1H), 7.21 (dd, J=6.9, 0.9 Hz, 1H), 7.53 (dd, J=8.1, 1.8 Hz, 1H), 7.68 (d, J=1.8 Hz, 1H), 8.04 (d, J=8.1 Hz, 1H), 11.15-11.45 (brs, 1H).

MS(+): 406 [M+H]$^+$.

Example 3-3 trans-6-{2-Cyclopentyl-1-[4-(methylsulfanyl)phenyl] cyclopropyl}-3-methylpyridin-2(1H)-one

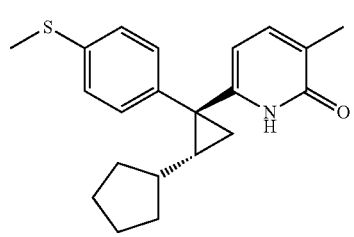

[Ka 219]

The title compound was obtained as a colorless amorphous (71 mg, 20%) by performing substantially the same reaction as in Example 3-1 except for using 6-{(E)-2-cyclopentyl-1-[4-(methylsulfanyl)phenyl]ethenyl}-3-methylpyridin-2(1H)-one obtained in Example 1-7.

$^1$H NMR (300 MHz, CDCl$_3$) δ ppm 0.84-1.77 (m, 12H), 2.07 (d, J=0.9 Hz, 3H), 2.49 (s, 3H), 5.96 (d, J=6.9 Hz, 1H), 7.15 (dd, J=6.9, 0.9 Hz, 1H), 7.21 (s, 4H), 8.40-8.50 (brs, 1H).

MS(+): 340 [M+H]$^+$.

Example 3-4 trans-6-{2-Cyclopentyl-1-[4-(methylsulfonyl)phenyl]cyclopropyl}-3-methylpyridin-2(1H)-one

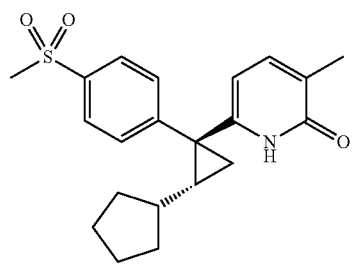

[Ka 220]

The title compound was obtained as a colorless amorphous (28 mg, 42%) by performing substantially the same reaction as in Example 3-2 except for using trans-6-{2-cyclopentyl-1-[4-(methylsulfanyl)phenyl]cyclopropyl}-3-methylpyridin-2(1H)-one obtained in Example 3-3.

$^1$H NMR (300 MHz, CDCl$_3$) δ ppm 0.75-1.00 (m, 1H), 1.20-1.75 (m, 11H), 2.10 (s, 3H), 3.05 (s, 3H), 6.11 (d, J=7.0 Hz, 1H), 7.20 (dd, J=8.2, 1.2 Hz, 1H), 7.62 (d, J=8.2 Hz, 2H), 7.85 (d, J=8.2 Hz, 2H), 10.40-11.00 (brs, 1H).

MS(+): 372 [M+H]$^+$.

Example 3-5 cis-6-{2-Cyclopentyl-1-[4-(methylsulfanyl)phenyl] cyclopropyl}-3-methylpyridin-2(1H)-one

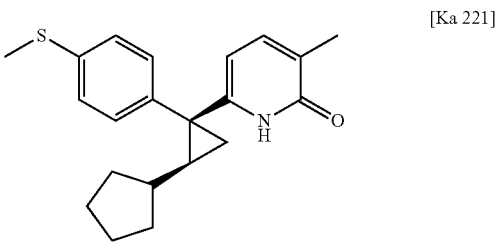

[Ka 221]

(1) A solution of lithiumhexamethyldisilazide in tetrahydrofuran (1 M, 5.5 mL) was added to a solution of (cyclopentylmethyl)triphenylphosphonium iodide (1.73 g, 3.66 mmol) in tetrahydrofuran (5 mL) in a nitrogen atmosphere under ice-cooling, and the mixture was stirred under ice-cooling for one hour. A solution of (6-methoxy-5-methylpyridin-2-yl)[4-(methylsulfanyl)phenyl]methanone obtained in Reference Example 1-36 (1.0 g) in tetrahydrofuran (2.5 mL) was added to the reaction solution under ice-cooling, and the mixture was stirred at room temperature for 16 hours. Water was added to the reaction solution, followed by extraction with ethyl acetate. The organic layer was dried over anhydrous magnesium sulfate and then filtered. The solvent was evaporated under reduced pressure. The residue was purified by silica gel column chromatography (chloroform:hexane=1:9→1:2) to give (Z)-6-{2-cyclopentyl-1-[4-(methylsulfanyl)phenyl]ethenyl}-2-methoxy-3-methylpyridine (493 mg, 40%) as a more polar product.

(2) A 1.0 M solution of diethylzinc in n-hexane (5.96 mL) was added to a solution of (Z)-6-{2-cyclopentyl-1-[4-(methylsulfanyl)phenyl]ethenyl}-2-methoxy-3-methylpyridine (405 mg) in dichloromethane (20 mL) in a nitrogen atmosphere under ice-cooling, and a solution of diiodomethane (3.2 g) in dichloromethane (8 mL) was subsequently added dropwise slowly. After stirring at room temperature for 4 hours, a saturated ammonium chloride solution was added to the reaction mixture. After extraction with ethyl acetate, the organic phase was washed with brine. The organic layer was dried over anhydrous sodium sulfate and filtered, after which the solvent was evaporated under reduced pressure. The resulting residue was purified by silica gel column chromatography (chloroform:hexane=1:5) to give cis-6-{2-cyclopentyl-1-[4-(methylsulfanyl)phenyl]cyclopropyl}-2-methoxy-3-methylpyridine (127 mg, 30%).

(3) 48% hydrobromic acid (1.0 mL) was added to a solution of cis-6-{2-cyclopentyl-1-[4-(methylsulfanyl)phenyl]cyclopropyl}-2-methoxy-3-methylpyridine (100 mg) in acetonitrile (1.0 mL), and the mixture was stirred at 95° C. for one hour. Water was added to the reaction solution, followed by extraction with ethyl acetate. The organic layer was washed with brine, dried over anhydrous sodium sulfate and filtered, after which the filtrate was concentrated under reduced pressure. The resulting residue was purified by silica gel column chromatography (NH silica gel, chloroform:hexane=1:1) to give the title compound as a colorless amorphous (91 mg, 94%).

$^1$H NMR (300 MHz, DMSO-$d_6$) δ ppm 0.94-1.04 (m, 1H), 1.10-1.90 (m, 11H), 1.92 (s, 3H), 2.42 (s, 3H), 6.11 (d, J=5.3 Hz, 1H), 7.16-7.20 (brs, 4H), 7.24 (d, J=7.0 Hz, 1H), 11.20-11.40 (brs, 1H).

MS(+): 340 [M+H]$^+$.

Example 3-6 cis-6-{2-Cyclopentyl-1-[4-(methylsulfonyl)phenyl]cyclopropyl}-3-methylpyridin-2(1H)-one

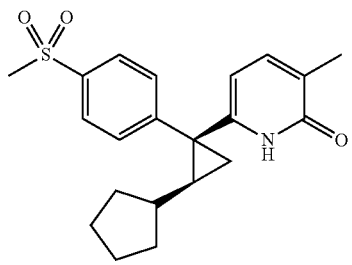
[Ka 222]

The title compound was obtained as a colorless amorphous (71 mg, 72%) by performing substantially the same reaction as in Example 3-2 except for using cis-6-{2-cyclopentyl-1-[4-(methylsulfanyl)phenyl]cyclopropyl}-3-methylpyridin-2(1H)-one obtained in Example 3-5.

$^1$H NMR (300 MHz, CDCl$_3$) δ ppm 1.15-1.90 (m, 12H), 2.09 (s, 3H), 3.01 (s, 3H), 6.18 (d, J=7.0 Hz, 1H), 7.24 (dd, J=7.0, 1.2 Hz, 1H), 7.45 (d, J=8.2 Hz, 2H), 7.80 (d, J=8.2 Hz, 2H), 10.20-10.85 (brs, 1H).

MS(+): 372 [M+H]$^+$.

Example 4-1

3-Cyclopropyl-6-{(E)-1-[4-(methylsulfanyl)phenyl]-2-[(2R)-5-oxopyrrolidin-2-yl]ethenyl}pyridin-2(1H)-one

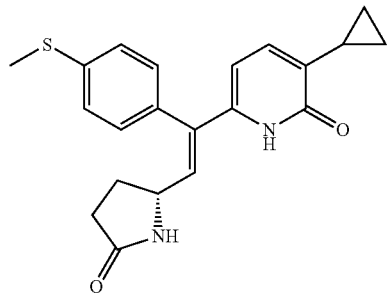
[Ka 223]

(1) A 1 M solution of lithiumhexamethyldisilazide in tetrahydrofuran (6.68 mL) was added to a solution of (5R)-5-{[(1-phenyl-1H-tetrazol-5-yl)sulfonyl]methyl}pyrrolidin-2-one obtained in Reference Example 3-2 (1.07 g) in tetrahydrofuran (10 mL) at −78° C. in a nitrogen gas stream, and the mixture was stirred at −78° C. for 30 minutes. A solution of (5-cyclopropyl-6-methoxypyridin-2-yl)[4-(methylsulfanyl)phenyl]methanone obtained in Reference Example 1-51 (500 mg) in tetrahydrofuran (10 mL) was added, and the mixture was stirred at −78° C. for one hour. The reaction solution was poured into a saturated ammonium chloride solution, followed by extraction with ethyl acetate. The organic layer was washed with saturated aqueous sodium bicarbonate and brine, dried over anhydrous magnesium sulfate and filtered. The solvent was then evaporated under reduced pressure. The residue was purified by silica gel column chromatography (chloroform:ethyl acetate=1:2) to give (5R)-5-{(E)-2-(5-cyclopropyl-6-methoxypyridin-2-yl)-2-[4-(methylsulfanyl)phenyl]ethenyl}pyrrolidin-2-one as a colorless oil (50.6 mg, 8%).

(2) The title compound was obtained as a colorless powder (21 mg, 45%) by performing substantially the same reaction as in Example 1-1(2) except for using (5R)-5-{(E)-2-(5-cyclopropyl-6-methoxypyridin-2-yl)-2-[4-(methylsulfanyl)phenyl]ethenyl}pyrrolidin-2-one.

$^1$H NMR (300 MHz, CDCl$_3$) δ ppm 0.46-0.75 (m, 2H), 0.85-1.11 (m, 2H), 2.00-2.18 (m, 2H), 2.21-2.43 (m, 3H), 2.53 (s, 3H), 4.12-4.31 (m, 1H), 5.78 (d, J=7.3 Hz, 1H), 6.25-6.34 (brs, 1H), 6.43 (s, 1H), 6.83 (d, J=7.9 Hz, 1H), 7.08 (d, J=8.5 Hz, 2H), 7.23-7.34 (m, 2H), 11.47-11.66 (brs, 1H).

MS(+): 367 [M+H]$^+$.

Example 4-2

3-Chloro-6-{(E)-1-(3-chloro-4-ethoxyphenyl)-2-[(2R)-5-oxopyrrolidin-2-yl]ethenyl}pyridin-2(1H)-one

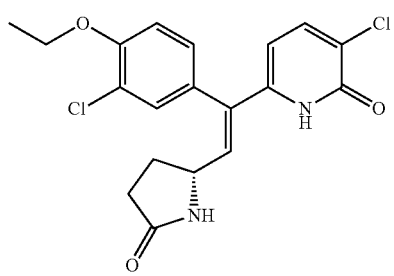
[Ka 224]

(1) (5R)-5-[(E)-2-(3-Chloro-4-ethoxyphenyl)-2-(5-chloro-6-methoxypyridin-2-yl)ethenyl]pyrrolidin-2-one was obtained as a colorless oil (180 mg, 17%) by performing substantially the same reaction as in Example 4-1(1) except for using (3-chloro-4-ethoxyphenyl)(5-chloro-6-methoxypyridin-2-yl)methanone obtained in Reference Example 1-24 and using (5R)-5-[(1,3-benzothiazol-2-ylsulfonyl)methyl]pyrrolidin-2-one obtained in Reference Example 3-12 in place of (5R)-5-{[(1-phenyl-1H-tetrazol-5-yl)sulfonyl]methyl}pyrrolidin-2-one. (5R)-5-[2-(3-Chloro-4-ethoxyphenyl)-2-(5-chloro-6-methoxypyridin-2-yl)ethenyl]pyrrolidin-2-one (E:Z=1:1 mixture) was also obtained as a colorless oil (182 mg).

(2) The title compound was obtained as a colorless powder (118 mg, 73%) by performing substantially the same reaction as in Example 1-1(2) except for using (5R)-5-[(E)-2-(3-chloro-4-ethoxyphenyl)-2-(5-chloro-6-methoxypyridin-2-yl)ethenyl]pyrrolidin-2-one.

¹H NMR (300 MHz, CDCl₃) δ ppm 1.51 (t, J=7.0 Hz, 3H), 2.19-2.57 (m, 4H), 4.09-4.30 (m, 3H), 5.78 (d, J=7.8 Hz, 1H), 6.50 (d, J=9.2 Hz, 1H), 6.94-7.01 (m, 1H), 7.05-7.14 (m, 2H), 7.22 (d, J=2.2 Hz, 1H), 7.48 (d, J=7.8 Hz, 1H), 12.84-13.14 (brs, 1H).
MS(+): 393 [M+H]⁺.

Example 4-3

3-Chloro-6-{1-(3-chloro-4-ethoxyphenyl)-2-[(2R)-5-oxopyrrolidin-2-yl]ethyl}pyridin-2(1H)-one

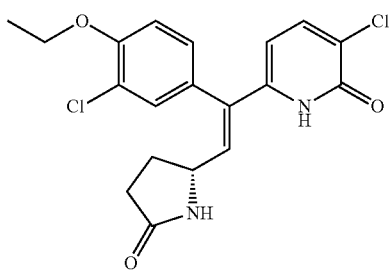

[Ka 225]

(1) (5R)-5-[2-(3-Chloro-4-ethoxyphenyl)-2-(5-chloro-6-methoxypyridin-2-yl)ethyl]pyrrolidin-2-one was obtained as a colorless amorphous (73 mg, 91%) by performing substantially the same reaction as in Example 2-3 except for using the mixture of (5R)-5-[2-(3-chloro-4-ethoxyphenyl)-2-(5-chloro-6-methoxypyridin-2-yl)ethenyl]pyrrolidin-2-one (E:Z=1:1) obtained in Example 4-2(1).

(2) The title compound was obtained as a colorless amorphous (43 mg, 61%) by performing substantially the same reaction as in Example 1-1(2) except for using (5R)-5-[2-(3-chloro-4-ethoxyphenyl)-2-(5-chloro-6-methoxypyridin-2-yl)ethyl]pyrrolidin-2-one.

¹H NMR (300 MHz, CDCl₃) δ ppm 1.46 (t, J=7.0 Hz, 3H), 1.71-1.92 (m, 2H), 2.09-2.49 (m, 4H), 3.46-3.69 (m, 1H), 3.89-4.15 (m, 3H), 6.00-6.05 (m, 1H), 6.85-6.91 (m, 1H), 7.13-7.25 (m, 1H), 7.29-7.35 (m, 1H), 7.50-7.51 (m, 1H).
MS(+): 395 [M+H]⁺.

The compounds of Examples 4-4 to 4-38 were synthesized by performing substantially the same reaction as in Example 4-1 or 4-2.

Example 4-4

3-Cyclopropyl-6-{(E)-1-(4-methylphenyl)-2-[(2R)-5-oxopyrrolidin-2-yl]ethenyl}pyridin-2(1H)-one The title compound was obtained as a white solid (78 mg, 21% (two steps)).
¹H NMR (300 MHz, CDCl₃) δ ppm 0.50-0.67 (m, 2H), 0.92-1.03 (m, 2H), 1.98-2.19 (m, 2H), 2.19-2.47 (m, 3H), 2.40 (s, 3H), 4.08-4.22 (m, 1H), 5.79 (d, J=7.4 Hz, 1H), 6.26 (s, 1H), 6.40 (d, J=9.1 Hz, 1H), 6.83 (d, J=7.2 Hz, 1H), 7.05 (d, J=8.0 Hz, 2H), 7.22 (d, J=7.7 Hz, 2H), 11.28-11.48 (brs, 1H).
MS(+): 335 [M+H]⁺.

Example 4-5

3-Cyclopropyl-6-{(E)-1-(4-ethylphenyl)-2-[(2R)-5-oxopyrrolidin-2-yl]ethenyl}pyridin-2(1H)-one The title compound was obtained as a colorless solid (30 mg, 12% (two steps)).

¹H NMR (300 MHz, CDCl₃) δ ppm 0.50-0.70 (m, 2H), 0.80-1.05 (m, 2H), 1.29 (t, J=7.8 Hz, 3H), 1.95-2.19 (m, 2H), 2.19-2.43 (m, 3H), 2.70 (q, J=7.8 Hz, 2H), 4.08-4.25 (m, 1H), 5.84 (d, J=7.3 Hz, 1H), 5.95 (s, 1H), 6.31 (d, J=9.2 Hz, 1H), 6.85 (d, J=7.3 Hz, 1H), 7.06 (d, J=8.3 Hz, 2H), 7.25 (d, J=8.3 Hz, 2H), 10.50-10.73 (brs, 1H).
MS(+): 349 [M+H]⁺.

Example 4-6

3-Cyclopropyl-6-{(E)-1-(4-ethoxyphenyl)-2-[(2R)-5-oxopyrrolidin-2-yl]ethenyl}pyridin-2(1H)-one The title compound was obtained as a colorless solid (44 mg, 16% (two steps)).
¹H NMR (300 MHz, CDCl₃) δ ppm 0.55-0.70 (m, 2H), 0.91-1.06 (m, 2H), 1.45 (t, J=7.0 Hz, 3H), 1.97-2.20 (m, 2H), 2.22-2.46 (m, 3H), 4.07 (q, J=7.0 Hz, 2H), 4.21 (dd, J=16.0, 7.0 Hz, 1H), 5.86 (d, J=7.4 Hz, 1H), 6.08 (s, 1H), 6.29 (d, J=9.1 Hz, 1H), 6.84 (d, J=7.4 Hz, 1H), 6.92 (d, J=9.1 Hz, 2H), 7.06 (d, J=9.1 Hz, 2H), 10.73-10.92 (brs, 1H).
MS(+): 365 [M+H]⁺.

Example 4-7

3-Cyclopropyl-6-{(E)-1-(3-ethoxyphenyl)-2-[(2R)-5-oxopyrrolidin-2-yl]ethenyl}pyridin-2(1H)-one The title compound was obtained as a white solid (46 mg, 18% (two steps)).
¹H NMR (300 MHz, CDCl₃) δ ppm 0.54-0.63 (m, 2H), 0.90-1.05 (m, 2H), 1.43 (t, J=6.9 Hz, 3H), 1.92-2.17 (m, 2H), 2.20-2.48 (m, 3H), 3.95-4.28 (m, 3H), 5.67-5.79 (m, 1H), 5.94 (d, J=7.2 Hz, 1H), 6.25 (d, J=9.3 Hz, 1H), 6.60-6.68 (m, 1H), 6.71 (d, J=7.5 Hz, 1H), 6.85 (d, J=7.2 Hz, 1H), 6.94 (dd, J=8.1, 2.1 Hz, 1H).
MS(+): 365 [M+H]⁺.

Example 4-8

3-Cyclopropyl-6-{(E)-1-[3-(3-hydroxypropoxy)phenyl]-2-[(2R)-5-oxopyrrolidin-2-yl]ethenyl}pyridin-2(1H)-one The title compound was obtained as a colorless solid (17 mg, 9% (two steps)).
¹H NMR (300 MHz, CDCl₃) δ ppm 0.58-0.64 (m, 2H), 0.94-1.00 (m, 2H), 2.00-2.16 (m, 5H), 2.21-2.41 (m, 3H), 3.86 (t, J=5.7 Hz, 2H), 4.08-4.22 (m, 3H), 5.87 (d, J=7.4 Hz, 1H), 6.12-6.18 (brs, 1H), 6.33 (d, J=8.9 Hz, 1H), 6.65-6.75 (m, 2H), 6.83 (d, J=7.4 Hz, 1H), 6.86-6.95 (m, 1H), 7.32 (t, J=8.0 Hz, 1H), 10.63-11.02 (brs, 1H).
MS(+): 395 [M+H]⁺.

Example 4-9

3-Cyclopropyl-6-{(E)-1-[3-(4-hydroxybutoxy)phenyl]-2-[(2R)-5-oxopyrrolidin-2-yl]ethenyl}pyridin-2(1H)-one The title compound was obtained as a colorless solid (16 mg, 6% (two steps)).
¹H NMR (300 MHz, CDCl₃) δ ppm 0.45-0.70 (m, 2H), 0.85-1.05 (m, 2H), 1.62-2.45 (m, 10H), 3.71 (t, J=6.3 Hz, 2H), 3.92-4.08 (m, 2H), 4.10-4.23 (m, 1H), 5.75 (d, J=7.4 Hz, 1H), 6.50 (d, J=8.9 Hz, 1H), 6.69 (s, 1H), 6.73 (d, J=7.4 Hz, 1H), 6.80 (d, J=7.4 Hz, 2H), 6.91 (d, J=7.7 Hz, 1H), 7.30 (t, J=7.9 Hz, 1H).
MS(+): 409 [M+H]$^+$.

Example 4-10

6-{(E)-1-(3-Chloro-4-ethoxyphenyl)-2-[(2R)-5-oxopyrrolidin-2-yl]ethenyl}-3-cyclopropylpyridin-2(1H)-one The title compound was obtained as a colorless solid (17 mg, 12% (two steps)).
$^1$H NMR (300 MHz, CDCl$_3$) δ ppm 0.50-0.68 (m, 2H), 0.90-1.05 (m, 2H), 1.51 (t, J=6.9 Hz, 3H), 2.00-2.20 (m, 2H), 2.20-2.45 (m, 3H), 4.10-4.23 (m, 3H), 5.75 (d, J=7.2 Hz, 1H), 6.44 (d, J=8.7 Hz, 1H), 6.54 (s, 1H), 6.84 (d, J=7.5 Hz, 1H), 6.94 (d, J=8.4 Hz, 1H), 7.01 (dd, J=8.1, 2.1 Hz, 1H), 7.16 (d, J=2.1 Hz, 1H), 11.70-11.90 (brs, 1H).
MS(+): 399 [M+H]$^+$.

Example 4-11

6-{(E)-1-[3-Chloro-4-(4-hydroxybutoxy)phenyl]-2-[(2R)-5-oxopyrrolidin-2-yl]ethenyl}-3-cyclopropylpyridin-2(1H)-one The title compound was obtained as a white solid (22 mg, 9% (two steps)).
$^1$H NMR (300 MHz, CDCl$_3$) δ ppm 0.50-0.75 (m, 2H), 0.92-1.07 (m, 2H), 1.75-1.90 (m, 2H), 1.90-2.20 (m, 4H), 2.20-2.48 (m, 3H), 3.77 (t, J=6.1 Hz, 2H), 4.04-4.23 (m, 3H), 5.77 (d, J=7.4 Hz, 1H), 6.36-6.50 (m, 2H), 6.85 (d, J=7.4 Hz, 1H), 6.90-7.07 (m, 2H), 7.17 (s, 1H), 11.50-11.80 (brs, 1H).
MS(+): 443 [M+H]$^+$.

Example 4-12

3-Cyclopropyl-6-{(E)-1-[4-(cyclopropylsulfanyl)-3-methylphenyl]-2-[(2R)-5-oxopyrrolidin-2-yl]ethenyl}pyridin-2(1H)-one The title compound was obtained as a white solid (54 mg, 3% (two steps)).
$^1$H NMR (300 MHz, CDCl$_3$) δ ppm 0.57-0.68 (m, 2H), 0.70-0.78 (m, 2H), 0.92-1.04 (m, 2H), 1.10-1.21 (m, 2H), 1.92-2.20 (m, 3H), 2.26 (s, 3H), 2.28-2.50 (m, 3H), 4.20-4.27 (m, 1H), 5.93 (d, J=7.3 Hz, 1H), 5.98 (s, 1H), 6.26 (d, J=9.2 Hz, 1H), 6.82-6.92 (m, 2H), 6.97 (dd, J=7.9, 2.0 Hz, 1H), 7.57 (d, J=8.3 Hz, 1H), 10.27-10.64 (brs, 1H).
MS(+): 407 [M+H]$^+$.

Example 4-13

3-Chloro-6-{(E)-1-[3-chloro-4-(cyclopropylsulfanyl)phenyl]-2-[(2R)-5-oxopyrrolidin-2-yl]ethenyl}pyridin-2(1H)-one The title compound was obtained as a white solid (156 mg, 32% (two steps)).
$^1$H NMR (300 MHz, CDCl$_3$) δ ppm 0.70-0.82 (m, 2H), 1.10-1.29 (m, 2H), 2.06-2.20 (m, 1H), 2.20-2.60 (m, 4H), 4.12-4.30 (m, 1H), 5.81 (d, J=7.9 Hz, 1H), 6.53 (d, J=9.2 Hz, 1H), 6.94 (s, 1H), 7.12 (dd, J=8.3, 1.7 Hz, 1H), 7.17 (d, J=1.7 Hz, 1H), 7.50 (d, J=7.9 Hz, 1H), 7.63 (d, J=8.3 Hz, 1H), 12.93-13.01 (brs, 1H).
MS(+): 421 [M+H]$^+$.

Example 4-14

3-Chloro-6-{(E)-1-(4-ethylphenyl)-2-[(2R)-5-oxopyrrolidin-2-yl]ethenyl}pyridin-2(1H)-one The title compound was obtained as a colorless solid (64 mg, 15% (two steps)).
$^1$H NMR (300 MHz, CDCl$_3$) δ ppm 1.29 (t, J=7.5 Hz, 3H), 1.65-1.95 (brs, 1H), 2.18-2.58 (m, 4H), 2.70 (q, J=7.5 Hz, 2H), 4.13-4.35 (m, 1H), 5.78 (d, J=7.5 Hz, 1H), 6.50 (d, J=9.0 Hz, 1H), 7.12 (d, J=7.8 Hz, 2H), 7.26 (d, J=7.8 Hz, 2H), 7.46 (d, J=7.5 Hz, 1H).
MS(+): 343 [M+H]$^+$.

Example 4-15

3-Chloro-6-{(E)-2-[(2R)-5-oxopyrrolidin-2-yl]-1-[4-(propan-2-yl)phenyl]ethenyl}pyridin-2(1H)-one The title compound was obtained as a colorless solid (21 mg, 5% (two steps)).
$^1$H NMR (300 MHz, CDCl$_3$) δ ppm 1.29 (s, 3H), 1.31 (s, 3H), 2.07-2.50 (m, 4H), 2.90-3.02 (m, 1H), 4.17-4.28 (m, 1H), 5.93 (d, J=7.5 Hz, 1H), 6.04-6.15 (m, 1H), 6.38 (d, J=9.0 Hz, 1H), 7.09 (d, J=7.8 Hz, 2H), 7.29 (d, J=8.1 Hz, 2H), 7.50 (d, J=7.5 Hz, 1H), 11.50-11.84 (brs, 1H).

Example 4-16

3-Chloro-6-[(E)-2-[(2R)-5-oxopyrrolidin-2-yl]-1-(4-propylphenyl)ethenyl]pyridin-2(1H)-one The title compound was obtained as a white solid (21 mg, 7% (two steps)).
$^1$H NMR (300 MHz, CDCl$_3$) δ ppm 0.99 (t, J=7.4 Hz, 3H), 1.69 (qt, J=7.5, 7.5 Hz, 2H), 2.12-2.51 (m, 4H) 2.64 (t, J=7.6 Hz, 2H), 4.15-4.27 (m, 1H), 5.89 (d, J=7.4 Hz, 1H), 6.23 (s, 1H), 6.41 (d, J=9.0 Hz, 1H), 7.08 (d, J=7.8 Hz, 2H), 7.21-7.27 (m, 2H), 7.50 (d, J=7.8 Hz, 1H), 12.03-12.12 (brs, 1H).
MS(+): 357 [M+H]$^+$.

Example 4-17

6-{(E)-1-(4-Butylphenyl)-2-[(2R)-5-oxopyrrolidin-2-yl]ethenyl}-3-chloropyridin-2(1H)-one The title compound was obtained as a white solid (51 mg, 15% (two steps)).
$^1$H NMR (300 MHz, CDCl$_3$) δ ppm 0.96 (t, J=7.4 Hz, 3H), 1.40 (qt, J=7.5, 7.5 Hz, 2H), 1.57-1.70 (m, 2H), 2.16-2.52 (m, 4H), 2.66 (t, J=7.8 Hz, 2H), 4.16-4.26 (m, 1H), 5.82 (d, J=7.4 Hz, 1H), 6.46 (d, J=9.4 Hz, 1H), 6.63 (s, 1H), 7.09 (d, J=8.2 Hz, 2H), 7.24 (d, J=8.2 Hz, 2H), 7.48 (d, J=7.8 Hz, 1H), 12.60-12.67 (brs, 1H).
MS(+): 371 [M+H]$^+$.

Example 4-18

6-{(E)-1-(4-tert-Butylphenyl)-2-[(2R)-5-oxopyrrolidin-2-yl]ethenyl}-3-chloropyridin-2(1H)-one The title compound was obtained as a white solid (52 mg, 14% (two steps)).
$^1$H NMR (300 MHz, CDCl$_3$) δ ppm 1.38 (s, 9H), 2.10-2.25 (m, 1H), 2.30-2.55 (m, 3H), 4.15-4.35 (m, 1H), 5.97 (d, J=7.7

Hz, 1H), 6.01-6.15 (brs, 1H), 6.37 (d, J=9.2 Hz, 1H), 7.10 (dd, J=6.6, 1.5 Hz, 2H), 7.46 (d, J=6.6 Hz, 2H), 7.52 (d, J=7.4 Hz, 1H), 11.30-11.70 (brs, 1H).
MS(+): 371 [M+H]$^+$.

Example 4-19

3-Chloro-6-{(E)-2-[(2R)-5-oxopyrrolidin-2-yl]-1-[4-(trifluoromethyl)phenyl]ethenyl}pyridin-2(1H)-one The title compound was obtained as a white solid (125 mg, 37% (two steps)).
$^1$H NMR (300 MHz, CDCl$_3$) δ ppm 2.20-2.42 (m, 4H), 4.08-4.17 (m, 1H), 5.66 (d, J=7.8 Hz, 1H), 6.65 (d, J=9.4 Hz, 1H), 7.41 (d, J=8.2 Hz, 2H), 7.47 (d, J=7.8 Hz, 1H), 7.68-7.75 (m, 3H), 13.19-13.30 (brs, 1H).
MS(+): 383 [M+H]$^+$.

Example 4-20

3-Chloro-6-{(E)-1-[3-chloro-4-(3-methylbutoxy)phenyl]-2-[(2R)-5-oxopyrrolidin-2-yl]ethenyl}pyridin-2(1H)-one The title compound was obtained as a colorless solid (27 mg, 21% (two steps)).
$^1$H NMR (300 MHz, CDCl$_3$) δ ppm 0.99 (s, 3H), 1.01 (s, 3H), 1.78 (td, J=6.6 Hz, 6.6 Hz, 2H), 1.84-1.97 (m, 1H), 2.12-2.55 (m, 4H), 4.08 (t, J=6.3 Hz, 2H), 4.17-4.22 (m, 1H), 5.85 (d, J=7.8 Hz, 1H), 6.43 (d, J=9.6 Hz, 1H), 6.40-6.52 (m, 1H), 6.97 (d, J=8.7 Hz, 1H), 7.05 (dd, J=8.6, 2.0 Hz, 1H), 7.19 (d, J=2.1 Hz, 1H), 7.51 (d, J=7.5 Hz, 1H), 12.30-12.74 (brs, 1H).
MS(+): 435 [M+H]$^+$.

Example 4-21

3-Chloro-6-{(E)-1-{3-chloro-4-[(4-methylpentyl)oxy]phenyl}-2-[(2R)-5-oxopyrrolidin-2-yl]ethenyl}pyridin-2(1H)-one The title compound was obtained as a colorless solid (21 mg, 7% (two steps)).
$^1$H NMR (300 MHz, CDCl$_3$) δ ppm 0.95 (d, J=6.5 Hz, 6H), 1.31-1.71 (m, 3H), 1.80-1.98 (m, 2H), 2.10-2.53 (m, 4H), 4.06 (t, J=6.5 Hz, 2H), 4.22 (dd, J=16.0, 7.8 Hz, 1H), 5.87 (d, J=7.4 Hz, 1H), 6.28 (s, 1H), 6.41 (d, J=9.0 Hz, 1H), 6.96 (d, J=8.2 Hz, 1H), 7.03 (dd, J=8.2, 2.0 Hz, 1H), 7.19 (d, J=2.0 Hz, 1H), 7.51 (d, J=7.8 Hz, 1H), 12.15-12.30 (brs, 1H).
MS(+): 449 [M+H]$^+$.

Example 4-22

3-Chloro-6-{(E)-1-[3-chloro-4-(2-methylpropoxy)phenyl]-2-[(2R)-5-oxopyrrolidin-2-yl]ethenyl}pyridin-2(1H)-one The title compound was obtained as a colorless solid (5 mg, 5% (two steps)).
$^1$H NMR (300 MHz, CDCl$_3$) δ ppm 1.09 (d, J=7.0 Hz, 6H), 2.09-2.52 (m, 5H), 3.83 (d, J=6.1 Hz, 2H), 4.22 (dd, J=16.0, 7.0 Hz, 1H), 5.81 (d, J=7.8 Hz, 1H), 6.47 (d, J=9.0 Hz, 1H), 6.77 (s, 1H), 6.95 (d, J=8.6 Hz, 1H), 7.06 (dd, J=8.6, 2.0 Hz, 1H), 7.20 (d, J=2.0 Hz, 1H), 7.50 (d, J=7.8 Hz, 1H), 12.70-12.92 (brs, 1H).
MS(+): 421 [M+H]$^+$.

Example 4-23

3-Chloro-6-{(E)-1-(3,4-dimethylphenyl)-2-[(2R)-5-oxopyrrolidin-2-yl]ethenyl}pyridin-2(1H)-one The title compound was obtained as a white solid (56 mg, 12% (two steps)).
$^1$H NMR (300 MHz, CDCl$_3$) δ ppm 2.14-2.27 (m, 2H), 2.29 (s, 3H), 2.31 (s, 3H), 2.33-2.52 (m, 2H), 4.15-4.25 (m, 1H), 5.86 (d, J=7.8 Hz, 1H), 6.44 (d, J=9.0 Hz, 1H), 6.47 (s, 1H), 6.87-6.95 (m, 2H), 7.19 (d, J=7.4 Hz, 1H), 7.48 (d, J=7.8 Hz, 1H), 12.35-12.45 (brs, 1H).
MS(+): 343 [M+H]$^+$.

Example 4-24

3-Chloro-6-{(E)-1-(3-chloro-4-methylphenyl)-2-[(2R)-5-oxopyrrolidin-2-yl]ethenyl}pyridin-2(1H)-one The title compound was obtained as a white solid (40 mg, 10% (two steps)).
$^1$H NMR (300 MHz, CDCl$_3$) δ ppm 2.16-2.40 (m, 3H), 2.43 (s, 3H), 2.45-2.54 (m, 1H), 4.11-4.22 (m, 1H), 5.78 (d, J=7.8 Hz, 1H), 6.54 (d, J=9.4 Hz, 1H), 6.80 (s, 1H), 7.01 (d, J=7.8 Hz, 1H), 7.19 (s, 1H), 7.30 (d, J=7.8 Hz, 1H), 7.48 (d, J=7.4 Hz, 1H), 12.88-12.98 (brs, 1H).
MS(+): 363 [M+H]$^+$.

Example 4-25

3-Chloro-6-{(E)-1-[4-methyl-3-(trifluoromethyl)phenyl]-2-[(2R)-5-oxopyrrolidin-2-yl]ethenyl}pyridin-2(1H)-one The title compound was obtained as a white solid (41 mg, 18% (two steps)).
$^1$H NMR (300 MHz, CDCl$_3$) δ ppm 2.20-2.50 (m, 4H), 2.57 (s, 3H), 4.05-4.35 (brs, 1H), 5.73 (d, J=6.6 Hz, 1H), 6.40-6.85 (m, 2H), 7.35-7.45 (m, 3H), 7.46-7.60 (m, 1H), 12.50-13.40 (brs, 1H).
MS(+): 397 [M+H]$^+$.

Example 4-26

3-Chloro-6-{(E)-1-[4-(4-hydroxybutyl)phenyl]-2-[(2R)-5-oxopyrrolidin-2-yl]ethenyl}pyridin-2(1H)-one The title compound was obtained as a white solid (15 mg, 4% (two steps)).
$^1$H NMR (300 MHz, CDCl$_3$) δ ppm 1.40-1.90 (m, 5H), 2.10-2.58 (m, 4H), 2.69 (t, J=7.4 Hz, 2H), 3.69 (t, J=6.1 Hz, 2H), 4.10-4.28 (m, 1H), 5.78 (d, J=7.7 Hz, 1H), 6.48 (d, J=8.9 Hz, 1H), 6.80-6.95 (brs, 1H), 7.10 (d, J=8.0 Hz, 2H), 7.24 (d, J=7.1 Hz, 2H), 7.46 (d, J=7.7 Hz, 1H), 12.60-13.00 (brs, 1H).
MS(+): 387 [M+H]$^+$.

Example 4-27

3-Chloro-6-{(E)-1-[3-chloro-4-(ethylsulfanyl)phenyl]-2-[(2R)-5-oxopyrrolidin-2-yl]ethenyl}pyridin-2(1H)-one The title compound was obtained as a colorless amorphous (315 mg (two steps)).

¹H NMR (300 MHz, CDCl₃) δ ppm 1.43 (t, J=7.4 Hz, 3H), 2.17-2.57 (m, 4H), 3.02 (q, J=7.4 Hz, 2H), 4.10-4.33 (m, 1H), 5.79 (d, J=7.8 Hz, 1H), 6.53 (d, J=9.2 Hz, 1H), 6.92-7.04 (brs, 1H), 7.10 (dd, J=8.1, 2.0 Hz, 1H), 7.21 (d, J=1.9 Hz, 1H), 7.29 (d, J=8.1 Hz, 1H), 7.50 (d, J=7.6 Hz, 1H), 12.92-13.10 (brs, 1H).
MS(+): 431 [M+Na]⁺.

Example 4-28

3-Chloro-6-{(E)-1-{4-[2-(2-methylpropoxy)ethyl]phenyl}-2-[(2R)-5-oxopyrrolidin-2-yl]ethenyl}pyridin-2(1H)-one The title compound was obtained as a white solid (24 mg, 9% (two steps)).
¹H NMR (300 MHz, CDCl₃) δ ppm 0.89 (d, J=6.5 Hz, 6H), 1.79-1.93 (m, 1H), 2.11-2.54 (m, 4H), 2.93 (t, J=6.8 Hz, 2H), 3.22 (d, J=6.5 Hz, 2H), 3.67 (t, J=7.0 Hz, 2H), 4.20 (dd, J=16.0, 7.8 Hz, 1H), 5.79 (d, J=7.8 Hz, 1H), 6.48 (d, J=9.0 Hz, 1H), 6.55-6.72 (brs, 1H), 7.11 (d, J=8.2 Hz, 2H), 7.30 (d, J=8.2 Hz, 2H), 7.47 (d, J=7.8 Hz, 1H), 12.55-12.78 (brs, 1H).
MS(+): 415 [M+H]⁺.

Example 4-29

3-Chloro-6-{(E)-1-[4-(2-methylpropyl)phenyl]-2-[(2R)-5-oxopyrrolidin-2-yl]ethenyl}pyridin-2(1H)-one The title compound was obtained as a colorless solid (56 mg, 20% (two steps)).
¹H NMR (300 MHz, CDCl₃) δ ppm 0.94 (s, 3H), 0.96 (s, 3H), 1.84-1.98 (m, 1H), 2.12-2.47 (m, 4H), 2.52 (d, J=7.2 Hz, 2H), 4.16-4.26 (m, 1H), 5.86 (d, J=8.1 Hz, 1H), 6.32 (s, 1H), 6.43 (d, J=9.0 Hz, 1H), 7.08 (d, J=8.1 Hz, 2H), 7.21 (d, J=8.4 Hz, 2H), 7.49 (d, J=7.5 Hz, 1H), 12.17-12.37 (brs, 1H).
MS(+): 371 [M+H]⁺.

Example 4-30

3-Chloro-6-{(E)-2-[(2R)-5-oxopyrrolidin-2-yl]-1-[4-(trifluoromethoxy)phenyl]ethenyl}pyridin-2(1H)-one The title compound was obtained as a white solid (57 mg, 19% (two steps)).
¹H NMR (300 MHz, CDCl₃) δ ppm 2.22-2.60 (m, 4H), 4.10-4.21 (m, 1H), 5.71 (d, J=7.5 Hz, 1H), 6.56 (d, J=9.6 Hz, 1H), 7.25-7.40 (m, 4H), 7.47 (d, J=7.5 Hz, 1H), 12.95-13.20 (brs, 1H).
MS(+): 399 [M+H]⁺.

Example 4-31

3-Chloro-6-{(E)-1-(2,4-dimethylphenyl)-2-[(2R)-5-oxopyrrolidin-2-yl]ethenyl}pyridin-2(1H)-one The title compound was obtained as a white solid (6.9 mg, 2% (two steps)).
¹H NMR (300 MHz, CDCl₃) δ ppm 2.00-2.55 (m, 10H) 3.92-4.10 (m, 1H) 5.64-5.78 (m, 0.5H) 5.80-5.92 (m, 1.5H) 6.45-6.65 (m, 1H) 6.95-7.00 (m, 1H) 7.02-7.15 (m, 2H) 7.47 (d, J=7.7 Hz, 1H).
MS(+): 343 [M+H]⁺.

Example 4-32

3-Chloro-6-{(E)-1-[3-chloro-4-(propan-2-yloxy)phenyl]-2-[(2R)-5-oxopyrrolidin-2-yl]ethenyl}pyridin-2(1H)-one The title compound was obtained as a white solid (71 mg, 22% (two steps)).
¹H NMR (300 MHz, CDCl₃) δ ppm 1.42 (s, 3H) 1.44 (s, 3H) 2.05-2.60 (m, 4H) 4.10-4.30 (m, 1H) 4.55-4.75 (m, 1H) 5.87 (d, J=7.7 Hz, 1H) 6.25-6.36 (brs, 1H) 6.41 (d, J=8.6 Hz, 1H) 6.95-7.05 (m, 2H) 7.18 (s, 1H) 7.51 (d, J=7.7 Hz, 1H) 12.20-12.45 (brs, 1H).
MS(+): 407 [M+H]⁺.

Example 4-33

3-Chloro-6-{(E)-1-[4-(cyclopentylsulfanyl)phenyl]-2-[(2R)-5-oxopyrrolidin-2-yl]ethenyl}pyridin-2(1H)-one The title compound was obtained as a colorless amorphous (71 mg (two steps)).
¹H NMR (300 MHz, CDCl₃) δ ppm 1.59-1.89 (m, 6H), 2.04-2.59 (m, 6H), 3.51-3.79 (m, 1H), 4.14-4.31 (m, 1H), 5.83 (d, J=7.6 Hz, 1H), 6.46 (d, J=9.0 Hz, 1H), 6.60-6.75 (brs, 1H), 7.09 (d, J=8.4 Hz, 2H), 7.36 (d, J=8.4 Hz, 2H), 7.49 (d, J=7.8 Hz, 1H), 12.53-12.78 (brs, 1H).
MS(+): 415 [M+H]⁺.

Example 4-34

3-Chloro-6-{(E)-1-[4-(cyclopropylsulfanyl)-3-methylphenyl]-2-[(2R)-5-oxopyrrolidin-2-yl]ethenyl}pyridin-2(1H)-one The title compound was obtained as a white solid (94 mg, 16% (two steps)).
¹H NMR (300 MHz, CDCl₃) δ ppm 0.70-0.78 (m, 2H), 1.12-1.21 (m, 2H), 2.08-2.52 (m, 5H), 2.26 (s, 3H), 4.20-4.32 (m, 1H), 5.90 (d, J=7.6 Hz, 1H), 6.30-6.50 (m, 2H), 6.92 (s, 1H), 7.00 (d, J=7.9 Hz, 1H), 7.51 (d, J=7.6 Hz, 1H), 7.58 (d, J=8.3 Hz, 1H), 12.10-12.36 (brs, 1H).
MS(+): 401 [M+H]⁺.

Example 4-35

3-Chloro-6-{(E)-1-[4-(methylsulfanyl)-3-(trifluoromethyl)phenyl]-2-[(2R)-5-oxopyrrolidin-2-yl]ethenyl}pyridin-2(1H)-one The title compound was obtained as a white solid (108 mg, 15% (two steps)).
¹H NMR (300 MHz, CDCl₃) δ ppm 2.21-2.53 (m, 4H), 2.58 (s, 3H), 4.17 (dd, J=16.0, 7.4 Hz, 1H), 5.70-5.78 (m, 1H), 6.51-6.63 (m, 1H), 6.95 (s, 1H), 7.30-7.52 (m, 4H), 13.01-13.28 (brs, 1H).
MS(+): 429 [M+H]⁺.

Example 4-36

3-Chloro-6-{(E)-1-[3-(cyclopropylsulfanyl)phenyl]-2-[(2R)-5-oxopyrrolidin-2-yl]ethenyl}pyridin-2(1H)-one The title compound was obtained as a pale brown powder (3.2 mg).

<sup>1</sup>H NMR (300 MHz, CDCl₃) δ ppm 0.65-0.75 (m, 2H), 1.05-1.16 (m, 2H), 2.14-2.54 (m, 5H), 4.15-4.27 (m, 1H), 5.82 (d, J=7.8 Hz, 1H), 6.54 (d, J=9.2 Hz, 1H), 6.69 (s, 1H), 6.95 (dt, J=7.4, 1.4 Hz, 1H), 7.15 (t, J=1.6 Hz, 1H), 7.31-7.53 (m, 4H).

MS(+): 409 [M+Na]⁺.

Example 4-37

3-Chloro-6-{(E)-1-[4-(cyclopropylsulfanyl)phenyl]-2-[(2R)-5-oxopyrrolidin-2-yl]ethenyl}pyridin-2(1H)-one The title compound was obtained as a pale brown powder (55 mg).

$^1$H NMR (300 MHz, CDCl₃) δ ppm 0.60-0.83 (m, 2H), 1.01-1.21 (m, 2H), 2.01-2.58 (m, 5H), 4.10-4.38 (m, 1H), 5.85 (d, J=7.6 Hz, 1H), 6.46 (d, J=9.0 Hz, 1H), 6.60-6.73 (brs, 1H), 7.11 (d, J=8.4 Hz, 2H), 7.43 (d, J=8.4 Hz, 2H), 7.49 (d, J=7.6 Hz, 1H), 12.47-12.79 (m, 1H).

MS(+): 409 [M+Na]⁺.

Example 4-38

3-Chloro-6-{(E)-1-[3-chloro-4-(4-hydroxybutoxy)phenyl]-2-[(2R)-5-oxopyrrolidin-2-yl]ethenyl}pyridin-2(1H)-one The title compound was obtained as a colorless solid (64 mg, 18% (two steps)).

$^1$H NMR (300 MHz, CDCl₃) δ ppm 1.76-1.88 (m, 2H), 1.94-2.04 (m, 2H), 2.10-2.56 (m, 4H), 3.78 (t, J=6.2 Hz, 2H), 4.14 (t, J=6.0 Hz, 2H), 4.16-4.28 (m, 1H), 5.84 (d, J=7.5 Hz, 1H), 6.44 (d, J=9.0 Hz, 1H), 6.39-6.52 (brs, 1H), 6.97 (d, J=8.4 Hz, 1H), 7.05 (dd, J=8.6, 2.0 Hz, 1H), 7.20 (d, J=2.1 Hz, 1H), 7.51 (d, J=7.5 Hz, 1H), 12.34-12.64 (brs, 1H).

MS(+): 437 [M+H]⁺.

The structures of Examples 4-4 to 4-38 are shown below.

[Hyo 14-1]

Example 4-4

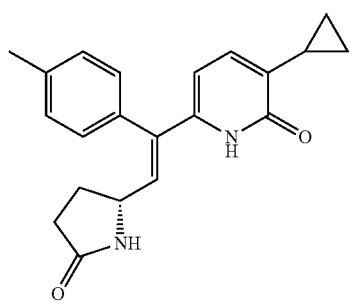

Example 4-5

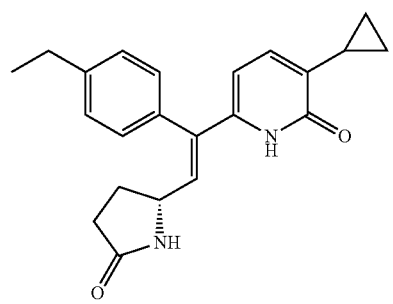

Example 4-6

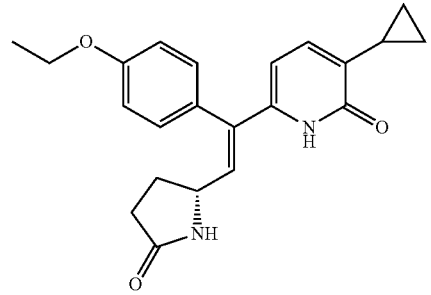

Example 4-7

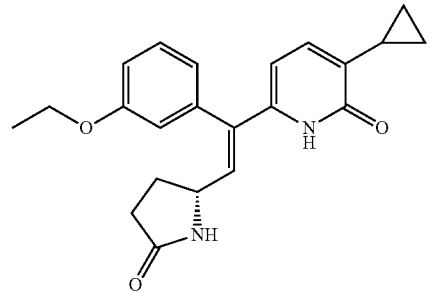

Example 4-8

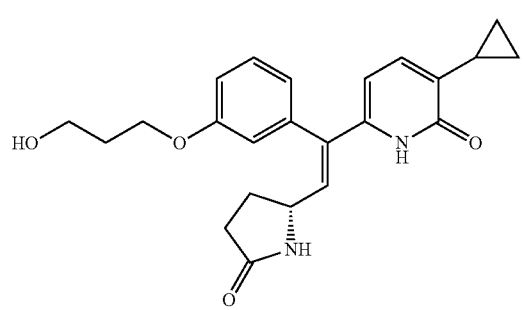

Example 4-9

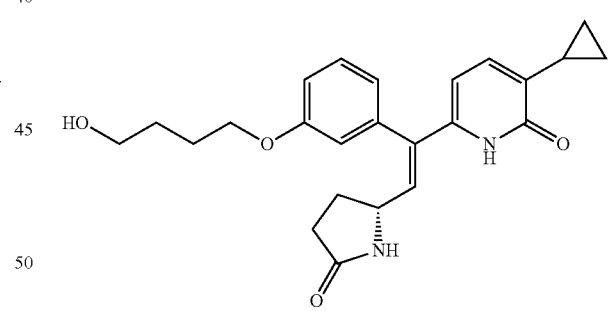

Example 4-10

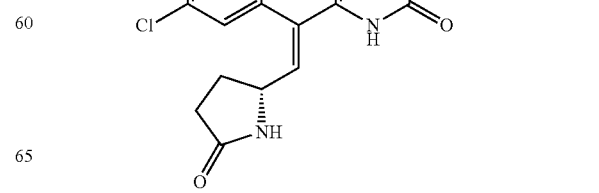

Example 4-11
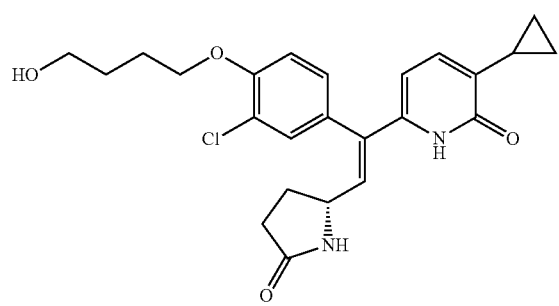
Example 4-12
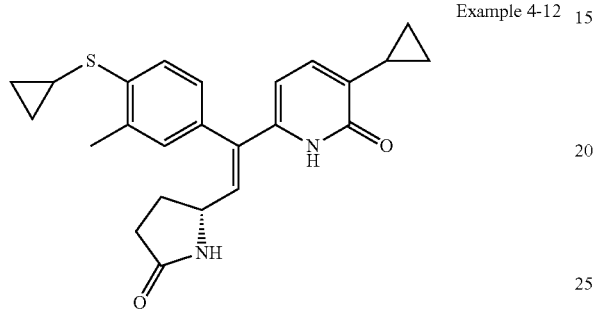
Example 4-13
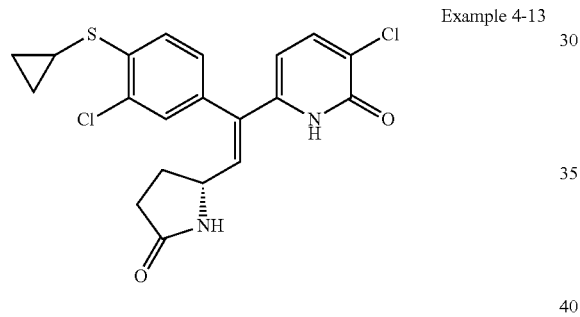
Example 4-14
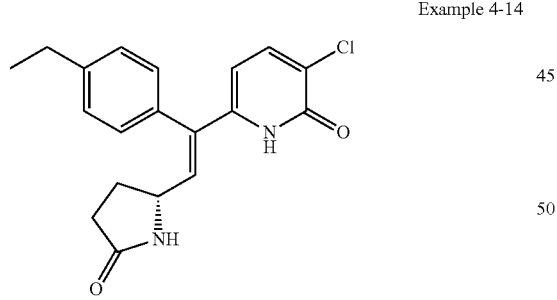
Example 4-15
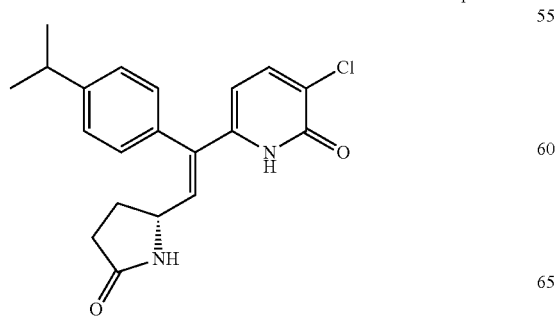
Example 4-16
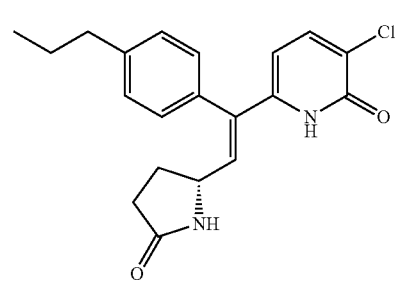
Example 4-17
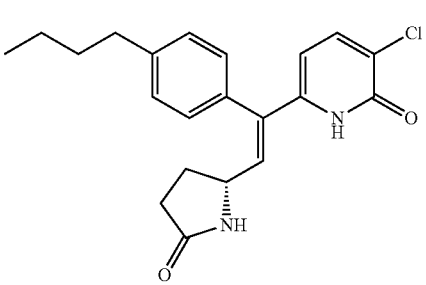
Example 4-18
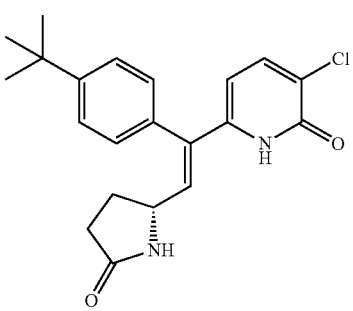
Example 4-19
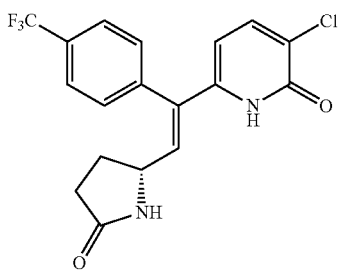
Example 4-20
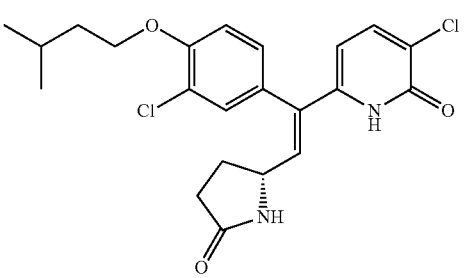

-continued
Example 4-21
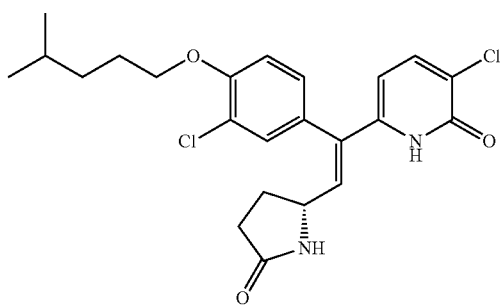
Example 4-22
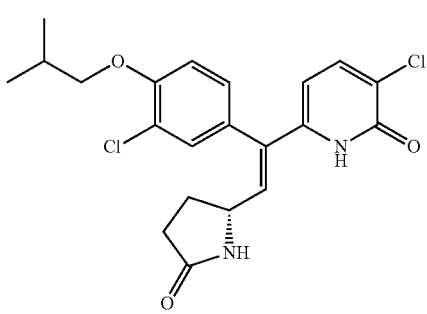
Example 4-23
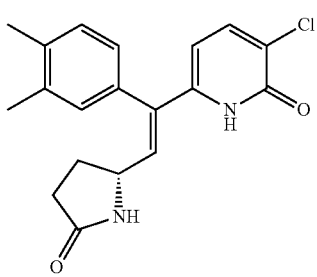
Example 4-24
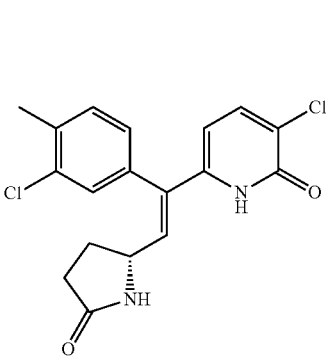
Example 4-25
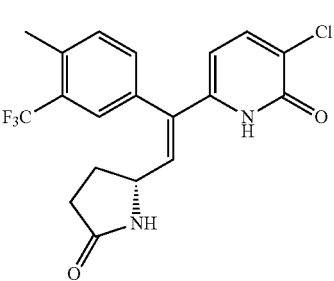
Example 4-26
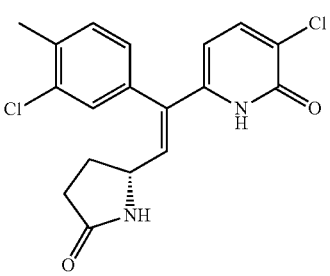
Example 4-27
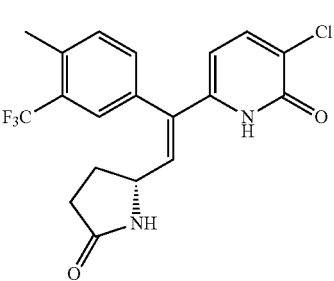
Example 4-28

Example 4-29
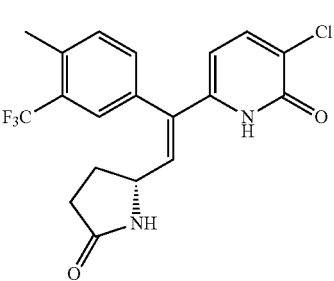
Example 4-30

Example 4-31
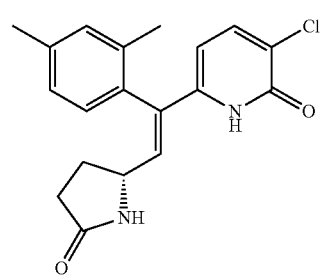

Example 4-32
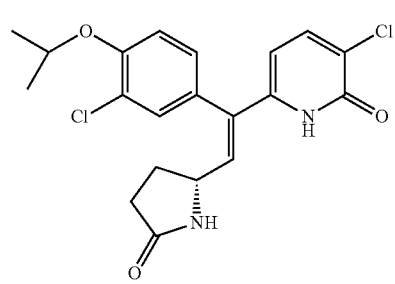

Example 4-33
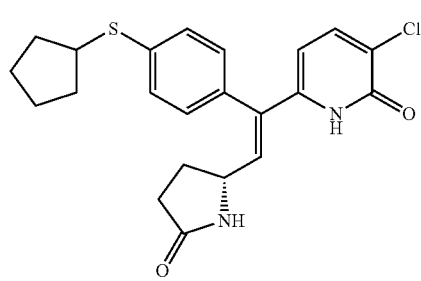

Example 4-34
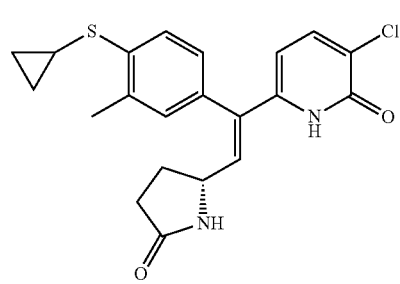

Example 4-35
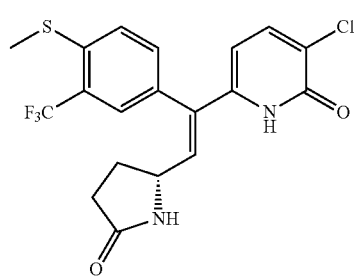

Example 4-36
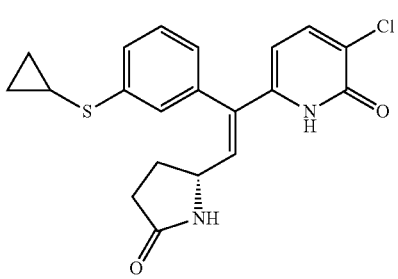

Example 4-37
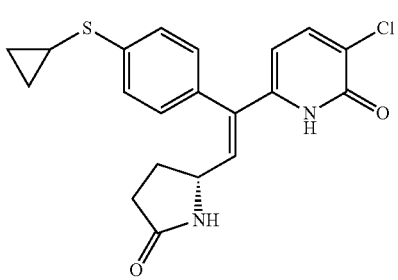

Example 4-38
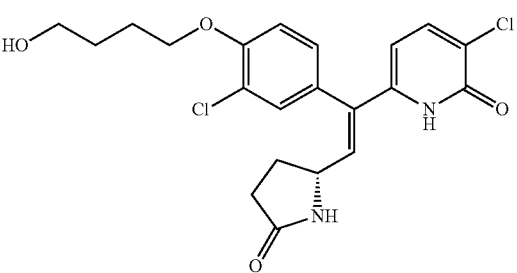

Example 4-39

6-{(E)-2-[(3R)-1-Acetylpyrrolidin-3-yl]-1-[4-(methylsulfanyl)phenyl]ethenyl}-3-cyclopropylpyridin-2(1H)-one

[Ka 226]

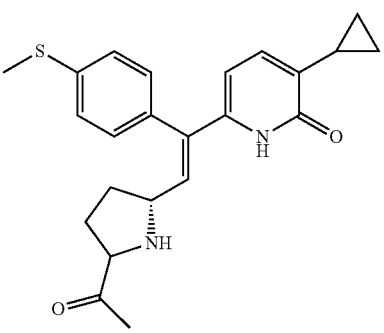

The title compound was obtained as a pale yellow amorphous (52 mg) by performing substantially the same reaction as in Example 4-1 except for using 1-[(3S)-3-{[(1-phenyl-1H-tetrazol-5-yl)sulfonyl]methyl}pyrrolidin-1-yl]ethanone obtained in Reference Example 3-10.

MS(+): 417 [M+Na]$^+$.

Example 4-40

6-[(E)-2-[(3R)-1-Acetylpyrrolidin-3-yl]-1-(4-ethylphenyl)ethenyl]-3-chloropyridin-2(1H)-one

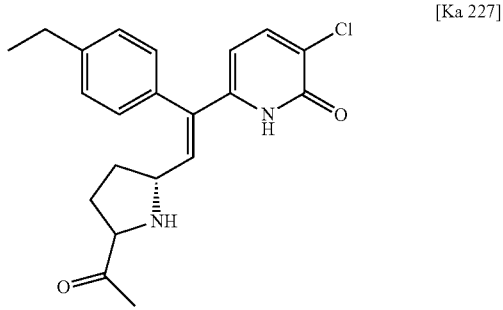

[Ka 227]

The title compound was obtained as a colorless solid (24 mg, 9% (two steps)) by performing substantially the same reaction as in Example 4-39 except for using (5-chloro-6-methoxypyridin-2-yl)(4-ethylphenyl)methanone obtained in Reference Example 1-9 and using 1-{(3S)-3-[(1,3-benzothiazol-2-ylsulfonyl)methyl]pyrrolidin-1-yl}ethanone obtained in Reference Example 3-17 in place of 1-[(3S)-3-{[(1-phenyl-1H-tetrazol-5-yl)sulfonyl]methyl}pyrrolidin-1-yl]ethanone.

$^1$H NMR (300 MHz, CDCl$_3$) δ ppm 1.18-1.34 (m, 3H), 1.94-2.34 (m, 6H), 2.58-3.03 (m, 3H), 3.21-3.43 (m, 1H), 3.55 (d, J=8.7 Hz, 1H), 3.60-3.80 (m, 1H), 5.73 (dd, J=7.8, 2.7 Hz, 1H), 6.69 (dd, J=14.6, 9.5 Hz, 1H), 7.06-7.14 (m, 2H), 7.21-7.31 (m, 2H), 7.45 (dd, J=7.7, 1.7 Hz, 1H), 12.41-13.19 (brs, 1H).

MS(+): 371 [M+H]$^+$.

Example 4-41

6-[(E)-2-[(3R)-1-Acetylpyrrolidin-3-yl]-1-(3-chloro-4-ethoxyphenyl)ethenyl]-3-chloropyridin-2(1H)-one

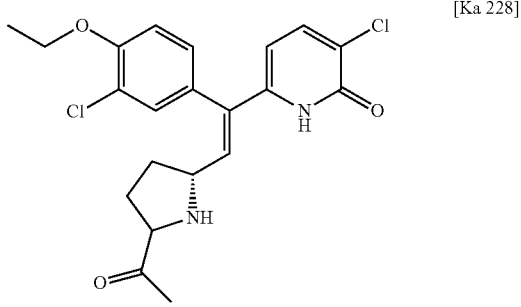

[Ka 228]

The title compound was obtained as a white solid (24 mg, 6% (two steps)) by performing substantially the same reaction as in Example 4-40 except for using (3-chloro-4-ethoxyphenyl)(5-chloro-6-methoxypyridin-2-yl)methanone obtained in Reference Example 1-24.

$^1$H NMR (300 MHz, CDCl$_3$) δ ppm 1.35-1.60 (m, 3H) 2.03 (s, 3H), 2.08-2.20 (m, 1H), 2.75-3.05 (m, 1H), 3.25-3.47 (m, 2H), 3.50-3.80 (m, 3H), 4.10-4.20 (m, 2H), 5.75-5.85 (m, 1H), 6.43-6.63 (m, 1H), 6.82-7.05 (m, 2H), 7.19 (dd, J=3.6, 2.1 Hz, 1H), 7.47 (d, J=7.1 Hz, 1H).

MS(+): 421 [M+H]$^+$.

Example 4-42

6-{(E)-2-(1-Acetylpiperidin-4-yl)-1-[4-(methylsulfanyl)phenyl]ethenyl}-3-cyclopropylpyridin-2(1H)-one

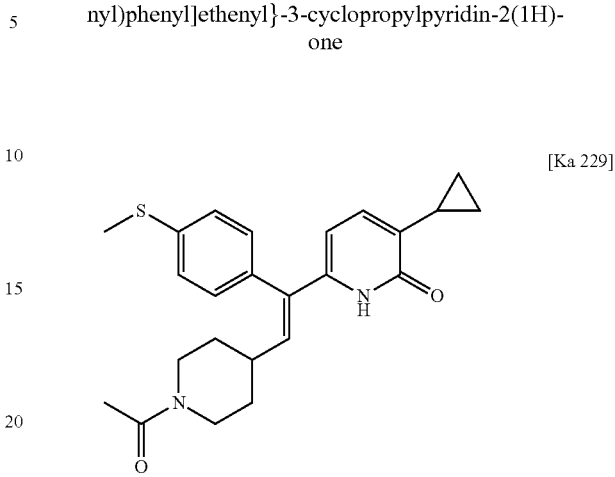

[Ka 229]

The title compound was obtained as a colorless powder (52 mg, 3.5% (two steps)) by performing substantially the same reaction as in Example 4-1 except for using 1-(4-{[(1-phenyl-1H-tetrazol-5-yl)sulfonyl]methyl}piperidin-1-yl)ethanone obtained in Reference Example 3-9.

$^1$H NMR (300 MHz, CDCl$_3$) δ ppm 0.55-0.64 (m, 2H), 0.87-0.97 (m, 2H), 1.35-1.54 (m, 1H), 1.66-1.74 (m, 2H), 2.06 (s, 3H), 2.07-2.14 (m, 2H), 2.23-2.38 (m, 1H), 2.38-2.51 (m, 1H), 2.54 (s, 3H), 2.87-3.00 (m, 1H), 3.76 (d, J=12.4 Hz, 1H), 4.56 (d, J=13.8 Hz, 1H), 5.72-5.80 (m, 1H), 6.15-6.25 (m, 1H), 6.79 (d, J=7.5 Hz, 1H), 7.08 (d, J=8.4 Hz, 2H), 7.28 (d, J=8.5 Hz, 2H), 10.11-10.45 (brs, 1H).

MS(+): 409 [M+H]$^+$.

Example 4-43

6-{(E)-2-(1-Acetylpiperidin-4-yl)-1-[4-(methylsulfonyl)phenyl]ethenyl}-3-cyclopropylpyridin-2(1H)-one

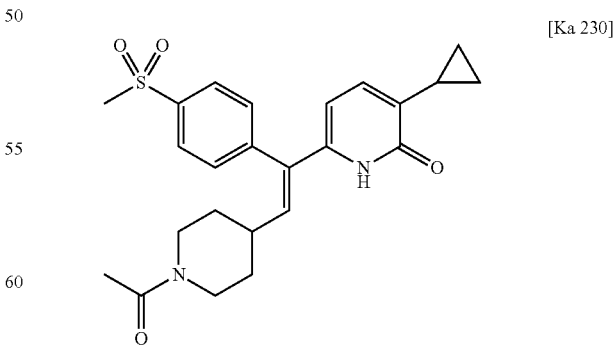

[Ka 230]

The title compound was obtained as a colorless powder (20 mg, 31%) by performing substantially the same reaction as in Example 1-2 except for using 6-{(E)-2-(1-acetylpiperidin-4- yl)-1-[4-(methylsulfanyl)phenyl]ethenyl}-3-cyclopropylpyridin-2(1H)-one obtained in Example 4-42.

$^1$H NMR (300 MHz, DMSO-d$_6$) δ ppm 0.53-0.61 (m, 2H), 0.77-0.87 (m, 2H), 1.18-1.46 (m, 2H), 1.48-1.64 (m, 2H), 1.90-1.95 (m, 1H), 1.97 (s, 3H), 2.06-2.20 (m, 1H), 2.85-3.01 (m, 1H), 3.28 (s, 3H), 3.29-3.30 (m, 1H), 3.73 (d, J=13.5 Hz, 1H), 4.20 (d, J=13.2 Hz, 1H), 5.27-5.45 (m, 1H), 6.44 (d, J=10.1 Hz, 1H), 6.83 (d, J=7.5 Hz, 1H), 7.46 (d, J=8.4 Hz, 2H), 7.97 (d, J=8.4 Hz, 2H), 11.31-11.55 (brs, 1H).

MS(+): 463 [M+Na]$^+$.

Example 4-44

6-{(E)-2-(1-Acetylazetidin-3-yl)-1-[4-(methylsulfanyl)phenyl]ethenyl}-3-cyclopropylpyridin-2(1H)-one

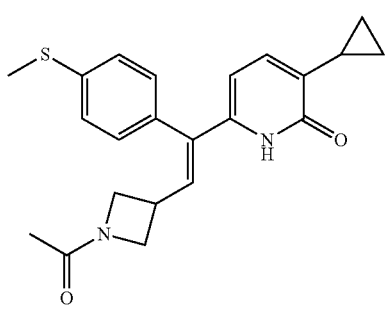

[Ka 231]

The title compound was obtained as a colorless powder (7.3 mg) by performing substantially the same reaction as in Example 4-1 except for using 1-(3-{[(1-phenyl-1H-tetrazol-5-yl)sulfonyl]methyl}azetidin-1-yl)ethanone obtained in Reference Example 3-11.

$^1$H NMR (300 MHz, CDCl$_3$) δ ppm 0.55-0.69 (m, 2H), 0.91-1.03 (m, 2H), 1.82 (s, 3H), 2.01-2.19 (m, 1H), 2.53 (s, 3H), 3.27-3.43 (m, 1H), 3.87-3.99 (m, 1H), 4.01-4.26 (m, 3H), 5.78-5.89 (m, 1H), 6.63-6.78 (m, 1H), 6.82 (d, J=7.3 Hz, 1H), 6.99 (d, J=8.4 Hz, 2H), 7.27 (d, J=8.4 Hz, 2H).

MS(+): 381 [M+H]$^+$.

Example 4-45

3-Cyclopropyl-6-{(E)-2-[(2R)-1-methyl-5-oxopyrrolidin-2-yl]-1-[4-(methylsulfanyl)phenyl]ethenyl}pyridin-2(1H)-one

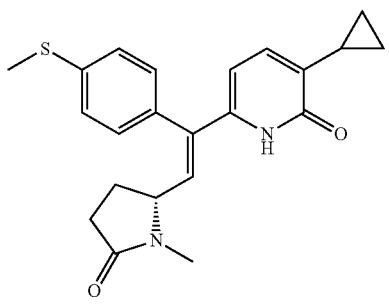

[Ka 232]

The title compound was obtained as a colorless powder (9.5 mg) by performing substantially the same reaction as in Example 4-1 except for using (5R)-1-methyl-5-{[(1-phenyl-1H-tetrazol-5-yl)sulfonyl]methyl}pyrrolidin-2-one obtained in Reference Example 3-3.

$^1$H NMR (300 MHz, CDCl$_3$) δ ppm 0.52-0.66 (m, 2H), 0.88-1.06 (m, 2H), 1.85-2.49 (m, 5H), 2.53 (s, 3H), 2.75 (s, 3H), 3.93-4.09 (m, 1H), 5.79 (d, J=7.3 Hz, 1H), 6.45 (d, J=9.6 Hz, 1H), 6.79 (d, J=6.8 Hz, 1H), 7.09 (d, J=8.4 Hz, 2H), 7.25-7.43 (m, 2H), 10.98-11.32 (brs, 1H).

MS(+): 381 [M+H]$^+$.

Example 4-46

3-Chloro-6-{(E)-1-[4-(cyclopropylsulfonyl)phenyl]-2-[(3R)-1-propanoylpyrrolidin-3-yl]ethenyl}pyridin-2(1H)-one

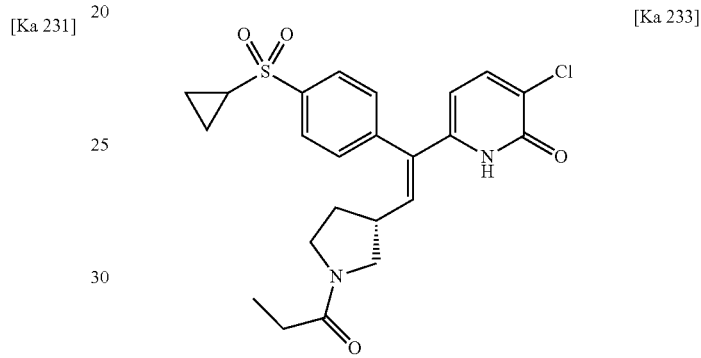

[Ka 233]

(1) tert-Butyl (3R)-3-{2-(5-chloro-6-methoxypyridin-2-yl)-2-[4-(cyclopropylsulfanyl)phenyl]ethenyl}pyrrolidine-1-carboxylate (EZ mixture) was obtained as a crude product (630 mg) by performing substantially the same reaction as in Example 4-2(1) except for using (5-chloro-6-methoxypyridin-2-yl)[4-(cyclopropylsulfanyl)phenyl]methanone obtained in Reference Example 1-2 (406 mg) and using tert-butyl (3S)-3-[(1,3-benzothiazol-2-ylsulfonyl)methyl]pyrrolidine-1-carboxylate obtained in Reference Example 3-16.

(2) Trifluoroacetic acid (1.5 mL) was added to a solution of tert-butyl (3R)-3-{2-(5-chloro-6-methoxypyridin-2-yl)-2-[4-(cyclopropylsulfanyl)phenyl]ethenyl}pyrrolidine-1-carboxylate (EZ mixture) (296 mg) in dichloromethane (3 mL) under ice-cooling, followed by stirring for three hours. The reaction solution was concentrated under reduced pressure to give 3-chloro-6-{1-[4-(cyclopropylsulfanyl)phenyl]-2-[(3R)-pyrrolidin-3-yl]ethenyl}-2-methoxypyridine (EZ mixture) as a crude product (235 mg).

(3) Propionyl chloride (58 µL) was added to a solution of 3-chloro-6-{1-[4-(cyclopropylsulfanyl)phenyl]-2-[(3R)-pyrrolidin-3-yl]ethenyl}-2-methoxypyridine (EZ mixture) (235 mg) and triethylamine (83 µL) in tetrahydrofuran (6 mL) under ice-cooling, and the mixture was stirred at room temperature for four hours. Water was added to the reaction solution, followed by extraction with ethyl acetate. The organic layer was washed with water and brine, dried over anhydrous magnesium sulfate and filtered, after which the solvent was evaporated under reduced pressure. The residue was purified by silica gel column chromatography (hexane: ethyl acetate=1:5) to give 1-[(3R)-3-{2-(5-chloro-6-methoxypyridin-2-yl)-2-[4-(cyclopropylsulfanyl)phenyl]ethenyl}pyrrolidin-1-yl]propan-1-one (EZ mixture) as a crude product (363 mg).

(4) 1-[(3R)-3-{(E)-2-(5-Chloro-6-methoxypyridin-2-yl)-2-[4-(cyclopropylsulfonyl)phenyl]ethenyl}pyrrolidin-1-yl]propan-1-one was obtained as a colorless solid (215 mg, 66%) by performing substantially the same reaction as in Example 1-2 except for using 1-[(3R)-3-{2-(5-chloro-6-methoxypyridin-2-yl)-2-[4-(cyclopropylsulfanyl)phenyl]ethenyl}pyrrolidin-1-yl]propan-1-one (EZ mixture) (303 mg). 1-[(3R)-3-{2-(5-Chloro-6-methoxypyridin-2-yl)-2-[4-(cyclopropylsulfonyl)phenyl]ethenyl}pyrrolidin-1-yl]propan-1-one (EZ mixture) was also obtained as a colorless amorphous (49 mg, 15%).

(5) The title compound was obtained as a colorless solid (47 mg, 84%) by performing substantially the same reaction as in Example 1-1(2) except for using 1-[(3R)-3-{(E)-2-(5-chloro-6-methoxypyridin-2-yl)-2-[4-(cyclopropylsulfonyl)phenyl]ethenyl}pyrrolidin-1-yl]propan-1-one.

$^1$H NMR (300 MHz, CDCl$_3$) δ ppm 1.06-1.16 (m, 5H), 1.38-1.47 (m, 2H), 1.60-2.38 (m, 2H), 2.25 (q, J=7.8 Hz, 2H), 2.50-2.60 (m, 1H), 2.60-2.91 (m, 1H), 3.20-3.88 (m, 4H), 5.59-5.65 (m, 1H), 6.83 (t, J=10.5 Hz, 1H), 7.42 (dd, J=8.3, 2.3 Hz, 2H), 7.48 (d, J=7.8 Hz, 1H), 7.95-8.03 (m, 2H), 12.8-13.3 (brs, 1H).

MS(+): 461 [M+H]$^+$.
MS(−): 459 [M−H]$^−$.

Example 4-47

6-[(E)-2-[(2R)-1-Acetylpyrrolidin-2-yl]-1-(4-ethylphenyl)ethenyl]-3-chloropyridin-2(1H)-one

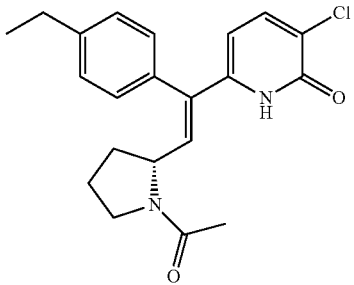

[Ka 234]

(1) 3-Chloro-6-{1-(4-ethylphenyl)-2-[(2R)-pyrrolidin-2-yl]ethenyl}pyridin-2(1H)-one (E:Z=1:3 mixture) was obtained as a yellow solid (230 mg, 73% (two steps)) by performing substantially the same reaction as in Example 4-1 except for using (5-chloro-6-methoxypyridin-2-yl)(4-ethylphenyl)methanone obtained in Reference Example 1-9 and using tert-butyl (2R)-2-[(1,3-benzothiazol-2-ylsulfonyl)methyl]pyrrolidine-1-carboxylate obtained in Reference Example 3-18 in place of (5R)-5-{[(1-phenyl-1H-tetrazole 5-yl)sulfonyl]methyl}pyrrolidin-2-one.

(2) Triethylamine (15.3 μL) was added to a solution of 3-chloro-6-{1-(4-ethylphenyl)-2-[(2R)-pyrrolidin-2-yl]ethenyl}pyridin-2(1H)-one (E:Z=1:3 mixture) (32.9 mg) in methylene chloride (1 mL) at room temperature, and acetyl chloride (7.8 μL) was added under ice-cooling, after which the mixture was stirred under ice-cooling for 30 minutes. Triethylamine (15.3 μL) and acetyl chloride (7.8 μL) were added under ice-cooling and the mixture was stirred under ice-cooling for further 30 minutes. Water was added to the reaction solution, followed by extraction with methylene chloride. The organic layer was filtered through diatomaceous earth, and then the solvent was concentrated under reduced pressure. Acetonitrile (329 μL) and 48% hydrobromic acid (329 μL) were added to the resulting residue, and the mixture was stirred at 50° C. for one hour. Separately, triethylamine (121 μL) and acetyl chloride (61.6 μL) were added to a solution of 3-chloro-6-{1-(4-ethylphenyl)-2-[(2R)-pyrrolidin-2-yl]ethenyl}pyridin-2(1H)-one (E:Z=1:3 mixture) (190 mg) in methylene chloride (2 mL) under ice-cooling, and the mixture was stirred under ice-cooling for 30 minutes. Water was added to the reaction solution, followed by extraction with methylene chloride. The organic layer was filtered through diatomaceous earth, and then the solvent was concentrated under reduced pressure. Acetonitrile (1.9 mL) and 48% hydrobromic acid (1.9 mL) were added to the resulting residue, and the mixture was stirred at room temperature for 30 minutes. The reaction solutions were neutralized respectively with saturated aqueous sodium bicarbonate at room temperature, combined and extracted with ethyl acetate. The organic layer was filtered through diatomaceous earth, and then the solvent was concentrated under reduced pressure. The resulting residue was purified by NH-silica gel column chromatography (hexane:ethyl acetate=1:1→ethyl acetate:methanol=4:1) to give a yellow oil. This was powdered with acetonitrile, and filtration operation gave the title compound as a colorless solid (49 mg, 23%).

$^1$H NMR (300 MHz, CDCl$_3$) δ ppm 1.20-1.40 (m, 3H), 1.76-2.32 (m, 7H), 2.60-2.80 (m, 2H), 3.38-3.74 (m, 2H), 4.16-4.29 (m, 0.45H), 4.39-4.52 (m, 0.55H), 5.88 (d, J=7.8 Hz, 0.55H), 6.02 (d, J=7.8 Hz, 0.45H), 6.21-6.35 (m, 0.55H), 6.35-6.49 (m, 0.45H), 7.07 (d, J=7.8 Hz, 0.9H), 7.22-7.30 (m, 3.1H), 7.42 (d, J=7.5 Hz, 0.55H), 7.49 (d, J=7.5 Hz, 0.45H), 10.38-10.55 (brs, 1H).

MS(+): 371 [M+H]$^+$.

Example 4-48

3-Chloro-6-{(E)-1-(4-ethoxyphenyl)-2-[(2R)-5-oxopyrrolidin-2-yl]ethenyl}pyridin-2(1H)-one

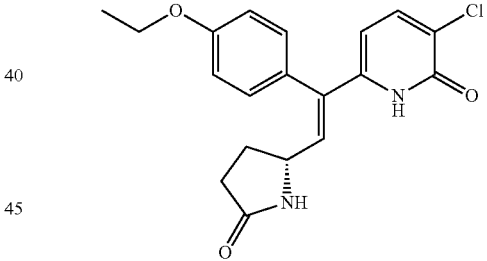

[Ka 235]

(1) A 1 M solution of lithiumhexamethyldisilazide in tetrahydrofuran (35 mL) was added to a solution of (5R)-5-[(1,3-benzothiazol-2-ylsulfonyl)methyl]pyrrolidin-2-one obtained in Reference Example 3-12 (5.01 g) in tetrahydrofuran (150 mL) at −78° C. in a nitrogen gas stream, and the mixture was stirred at −78° C. for 40 minutes. A solution of (4-{[tert-butyl(dimethyl)silyl]oxy}phenyl)(5-chloro-6-methoxypyridin-2-yl)methanone obtained in Reference Example 1-28 (3.2 g) in tetrahydrofuran (20 mL) was added, and the mixture was stirred at −78° C. for two hours. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (chloroform:ethyl acetate=7:3→3:7) to give (5R)-5-[(E)-2-(4-{[tert-butyl(dimethyl)silyl]oxy}phenyl)-2-(5-chloro-6-methoxypyridin-2-yl)ethenyl]pyrrolidin-2-one as a colorless oil (688 mg, 17%).

(2) The title compound was obtained as a colorless powder (62 mg, 43% (three steps)) by performing substantially the same reaction as in Examples 1-16(2)-(3) and 1-1(2) sequentially except for using (5R)-5-[(E)-2-(4-{[tert-butyl(dimethyl)silyl]oxy}phenyl)-2-(5-chloro-6-methoxypyridin-2-yl)ethenyl]pyrrolidin-2-one and using ethyl iodide in place of methyl iodide.

$^1$H NMR (300 MHz, CDCl$_3$) δ ppm 1.45 (t, J=7.0 Hz, 3H), 2.11-2.54 (m, 4H), 4.00-4.13 (m, 2H), 4.17-4.33 (m, 1H), 5.83 (d, J=7.8 Hz, 1H), 6.42 (d, J=9.0 Hz, 1H), 6.64-6.81 (brs, 1H), 6.87-6.99 (m, 2H), 7.05-7.15 (m, 2H), 7.48 (d, J=7.6 Hz, 1H), 12.56-12.78 (brs, 1H).

MS(+): 359 [M+H]$^+$.

Example 4-49

3-Chloro-6-{(E)-1-(4-ethoxy-3-fluorophenyl)-2-[(2R)-5-oxopyrrolidin-2-yl]ethenyl}pyridin-2(1H)-one

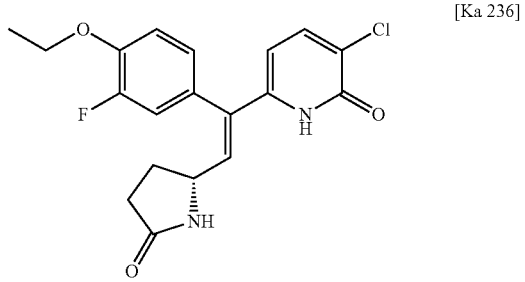 [SMILES: CCOc1ccc(/C(=C\[C@H]2CCC(=O)N2)c2ccc(Cl)c(=O)[nH]2)cc1F]

[Ka 236]

The title compound was obtained as a colorless powder (22 mg) by performing substantially the same reaction as in Example 4-48(1)(2) except for using (4-{[tert-butyl(dimethyl)silyl]oxy}-3-fluorophenyl)(5-chloro-6-methoxypyridin-2-yl)methanone obtained in Reference Example 1-26.

$^1$H NMR (300 MHz, CDCl$_3$) δ ppm 1.50 (t, J=7.0 Hz, 3H), 2.11-2.53 (m, 4H), 4.18-4.30 (m, 3H), 5.86 (d, J=7.6 Hz, 1H), 6.29-6.37 (brs, 1H), 6.42 (d, J=9.0 Hz, 1H), 6.86-7.07 (m, 3H), 7.51 (d, J=7.6 Hz, 1H).

MS(+): 377 [M+H]$^+$.

Example 4-50

3-Chloro-6-{(E)-1-(4-ethoxy-3-methylphenyl)-2-[(2R)-5-oxopyrrolidin-2-yl]ethenyl}pyridin-2(1H)-one

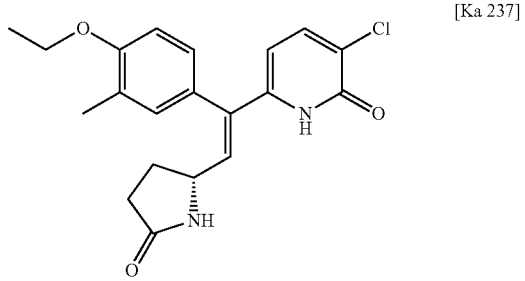 [SMILES: CCOc1ccc(/C(=C\[C@H]2CCC(=O)N2)c2ccc(Cl)c(=O)[nH]2)cc1C]

[Ka 237]

(1) (5R)-5-[(E)-2-(4-{[tert-Butyl(dimethyl)silyl]oxy}-3-methylphenyl)-2-(5-chloro-6-methoxypyridin-2-yl)ethenyl]pyrrolidin-2-one was obtained as a colorless amorphous (1.41 g, 24%) by performing substantially the same reaction as in Example 4-48(1) except for using (4-{[tert-butyl(dimethyl)silyl]oxy}-3-methylphenyl)(5-chloro-6-methoxypyridin-2-yl)methanone obtained in Reference Example 1-25.

(2) (5R)-5-[(E)-2-(5-Chloro-6-methoxypyridin-2-yl)-2-(4-hydroxy-3-methylphenyl)ethenyl]pyrrolidin-2-one was obtained as a colorless amorphous (610 mg, 94%) by performing substantially the same reaction as in Example 1-16 (2) except for using (5R)-5-[(E)-2-(4-{[tert-butyl(dimethyl)silyl]oxy}-3-methylphenyl)-2-(5-chloro-6-methoxypyridin-2-yl)ethenyl]pyrrolidin-2-one.

(3) (5R)-5-[(E)-2-(5-Chloro-6-methoxypyridin-2-yl)-2-(4-ethoxy-3-methylphenyl)ethenyl]pyrrolidin-2-one was obtained as a pale blue amorphous (356 mg, 95%) by performing substantially the same reaction as in Example 1-16 (3) except for using (5R)-5-[(E)-2-(5-chloro-6-methoxypyridin-2-yl)-2-(4-hydroxy-3-methylphenyl)ethenyl]pyrrolidin-2-one and using ethyl iodide in place of methyl iodide.

(4) The title compound was obtained as a colorless powder (140 mg, 40%) by performing substantially the same reaction as in Example 1-1(2) except for using (5R)-5-[(E)-2-(5-chloro-6-methoxypyridin-2-yl)-2-(4-ethoxy-3-methylphenyl)ethenyl]pyrrolidin-2-one.

$^1$H NMR (300 MHz, CDCl$_3$) δ ppm 1.46 (t, J=7.0 Hz, 3H), 2.23 (s, 3H), 2.26-2.55 (m, 4H), 4.08 (q, J=7.0 Hz, 2H), 4.19-4.30 (m, 1H), 5.87 (d, J=7.6 Hz, 1H), 6.39 (d, J=9.0 Hz, 1H), 6.61 (s, 1H), 6.84 (d, J=8.1 Hz, 1H), 6.91-7.00 (m, 2H), 7.48 (d, J=7.8 Hz, 1H), 12.38-12.57 (brs, 1H).

MS(+): 373 [M+H]$^+$.

Example 4-51

3-Chloro-6-{(E)-1-[4-ethoxy-3-(trifluoromethyl)phenyl]-2-[(2R)-5-oxopyrrolidin-2-yl]ethenyl}pyridin-2(1H)-one

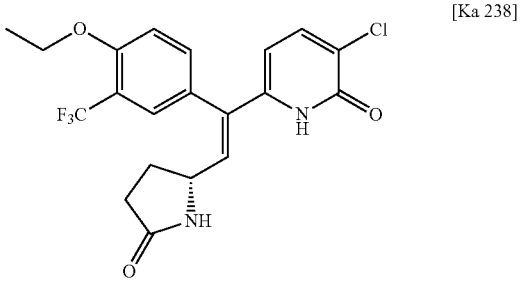 [SMILES: CCOc1ccc(/C(=C\[C@H]2CCC(=O)N2)c2ccc(Cl)c(=O)[nH]2)cc1C(F)(F)F]

[Ka 238]

The title compound was obtained as a colorless powder (45 mg) by performing substantially the same reaction as in Example 4-48(1)(2) except for using [4-{[tert-butyl(dimethyl)silyl]oxy}-3-(trifluoromethyl)phenyl] (5-chloro-6-methoxypyridin-2-yl)methanone obtained in Reference Example 1-27.

$^1$H NMR (300 MHz, CDCl$_3$) δ ppm 1.49 (t, J=7.0 Hz, 3H), 2.19-2.54 (m, 4H), 4.12-4.23 (m, 3H), 5.77 (d, J=7.8 Hz, 1H), 6.50 (d, J=9.2 Hz, 1H), 6.73 (s, 1H), 7.06 (d, J=8.7 Hz, 1H), 7.30-7.36 (m, 1H), 7.39 (d, J=2.2 Hz, 1H), 7.51 (d, J=7.6 Hz, 1H), 12.83-12.92 (brs, 1H).

MS(+): 427 [M+H]$^+$.

Example 4-52

3-Chloro-6-{(E)-1-[4-(3-hydroxypropoxy)-3-methylphenyl]-2-[(2R)-5-oxopyrrolidin-2-yl]ethenyl}pyridin-2(1H)-one

[Ka 239]

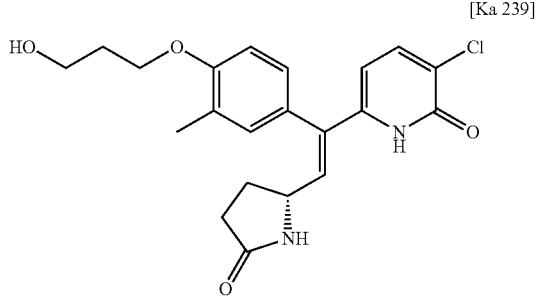 [SMILES: Cc1cc(/C(=C\[C@H]2CCC(=O)N2)c2ccc(Cl)c(=O)[nH]2)ccc1OCCCO]

(1) Potassium carbonate (470 mg) and (3-bromopropoxy)-tert-butyldimethylsilane (600 μL) were sequentially added to a solution of (5R)-5-[(E)-2-(5-chloro-6-methoxypyridin-2-yl)-2-(4-hydroxy-3-methylphenyl)ethenyl]pyrrolidin-2-one obtained in Example 4-50(2) (610 mg) in N,N-dimethylformamide (10 mL), and the mixture was stirred at room temperature for 15 hours and at 65° C. for three hours. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (hexane:ethyl acetate=6:4→2:8) to give (5R)-5-[(E)-2-[4-(3-{[tert-butyl(dimethyl)silyl]oxy}propoxy)-3-methylphenyl]-2-(5-chloro-6-methoxypyridin-2-yl)ethenyl]pyrrolidin-2-one as a colorless amorphous (879 mg, 97%).

(2) The title compound was obtained as a colorless powder (34 mg, 23%) by performing substantially the same reaction as in Example 1-1(2) except for using (5R)-5-[(E)-2-[4-(3-{[tert-butyl(dimethyl)silyl]oxy}propoxy)-3-methylphenyl]-2-(5-chloro-6-methoxypyridin-2-yl)ethenyl]pyrrolidin-2-one.

$^1$H NMR (300 MHz, CDCl$_3$) δ ppm 2.04-2.19 (m, 2H), 2.24 (s, 3H), 2.28-2.54 (m, 4H), 3.82-3.99 (m, 2H), 4.07-4.34 (m, 3H), 5.90 (d, J=7.6 Hz, 1H), 6.23-6.46 (m, 2H), 6.72-7.08 (m, 3H), 7.50 (d, J=7.6 Hz, 1H), 11.89-12.21 (br, 1H).
MS(+): 403 [M+H]$^+$.

Example 4-53

3-Cyclopropyl-6-{(E)-1-[4-(methylsulfonyl)phenyl]-2-[(2R)-5-oxopyrrolidin-2-yl]ethenyl}pyridin-2(1H)-one

[Ka 240]

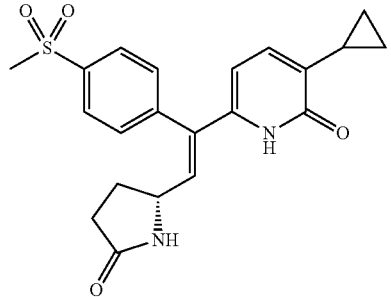

The title compound was obtained as a colorless powder (27 mg, 42%) by performing substantially the same reaction as in Example 1-2 except for using 3-cyclopropyl-6-{(E)-1-[4-(methylsulfanyl)phenyl]-2-[(2R)-5-oxopyrrolidin-2-yl]ethenyl}pyridin-2(1H)-one obtained in Example 4-1.

$^1$H NMR (300 MHz, CDCl$_3$) δ ppm 0.49-0.72 (m, 2H), 0.88-1.10 (m, 2H), 1.97-2.19 (m, 2H), 2.22-2.48 (m, 3H), 3.14 (s, 3H), 3.95-4.21 (m, 1H), 5.67 (d, J=7.1 Hz, 1H), 6.38-6.51 (brs, 1H), 6.56 (d, J=9.6 Hz, 1H), 6.85 (d, J=7.1 Hz, 1H), 7.36-7.49 (m, 2H), 7.93-8.13 (m, 2H).
MS(+): 399 [M+H]$^+$.

Example 4-54

3-Cyclopropyl-6-{(E)-1-[4-(cyclopropylsulfonyl)-3-methylphenyl]-2-[(2R)-5-oxopyrrolidin-2-yl]ethenyl}pyridin-2(1H)-one

[Ka 241]

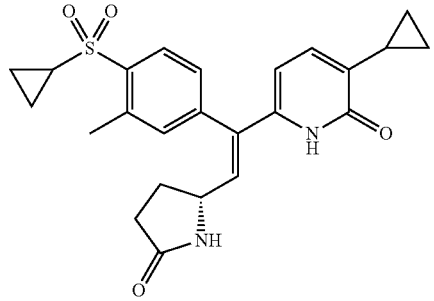

The title compound was obtained as a colorless solid (11 mg, 26%) by performing substantially the same reaction as in Example 1-2 except for using 3-cyclopropyl-6-{(E)-1-[4-(cyclopropylsulfanyl)-3-methylphenyl]-2-[(2R)-5-oxopyrrolidin-2-yl]ethenyl}pyridin-2(1H)-one obtained in Example 4-12.

$^1$H NMR (300 MHz, CDCl$_3$) δ ppm 0.50-0.70 (m, 2H), 0.92-1.05 (m, 2H), 1.05-1.18 (m, 2H), 1.35-1.45 (m, 2H), 2.00-2.20 (m, 2H), 2.20-2.50 (m, 3H), 2.60-2.70 (m, 1H), 2.78 (s, 3H), 4.03-4.18 (m, 1H), 5.66 (d, J=6.9 Hz, 1H), 6.57 (d, J=9.0 Hz, 1H), 6.83 (d, J=7.5 Hz, 1H), 6.95 (s, 1H), 7.15-7.25 (m, 2H), 7.99 (d, J=8.7 Hz, 1H), 11.80-12.30 (brs, 1H).
MS(+): 439 [M+H]$^+$.

Example 4-55

3-Chloro-6-{(E)-1-[4-(cyclopropylsulfonyl)-3-methylphenyl]-2-[(2R)-5-oxopyrrolidin-2-yl]ethenyl}pyridin-2(1H)-one

[Ka 242]

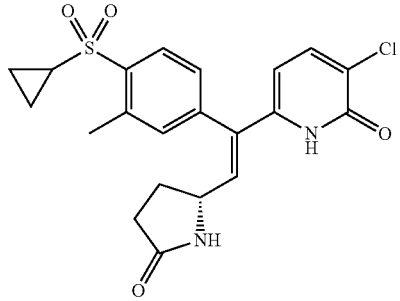

The title compound was obtained as a white solid (27 mg, 42%) by performing substantially the same reaction as in Example 1-2 except for using 3-chloro-6-{(E)-1-[4-(cyclopropylsulfanyl)-3-methylphenyl]-2-[(2R)-5-oxopyrrolidin-2-yl]ethenyl}pyridin-2(1H)-one obtained in Example 4-34.

¹H NMR (300 MHz, CDCl₃) δ ppm 1.05-1.18 (m, 2H), 1.34-1.45 (m, 2H), 2.20-2.45 (m, 3H), 2.45-2.60 (m, 1H), 2.60-2.73 (m, 1H), 2.80 (s, 3H), 4.08-4.19 (m, 1H), 5.69 (d, J=7.9 Hz, 1H), 6.64 (d, J=9.2 Hz, 1H), 7.26-7.29 (m, 2H), 7.48 (d, J=7.6 Hz, 1H), 7.88 (s, 1H), 8.01 (d, J=8.3 Hz, 1H), 13.12-13.28 (brs, 1H).

MS(+): 433 [M+H]⁺.

Example 4-56

3-Chloro-6-{(E)-1-[4-(methylsulfonyl)-3-(trifluoromethyl)phenyl]-2-[(2R)-5-oxopyrrolidin-2-yl]ethenyl}pyridin-2(1H)-one

[Ka 243]

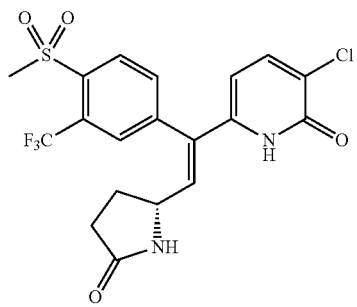

The title compound was obtained as a white solid (20 mg, 29%) by performing substantially the same reaction as in Example 1-2 except for using 3-chloro-6-{(E)-1-[4-(methylsulfanyl)-3-(trifluoromethyl)phenyl]-2-[(2R)-5-oxopyrrolidin-2-yl]ethenyl}pyridin-2(1H)-one obtained in Example 4-35.

¹H NMR (300 MHz, CDCl₃) δ ppm 1.98-2.49 (m, 4H), 3.24 (s, 3H), 3.88-4.04 (m, 1H), 5.49-5.60 (m, 1H), 6.49-6.61 (m, 1H), 6.99-7.10 (m, 1H), 7.41-7.46 (m, 1H), 7.65-7.78 (m, 2H), 8.28-8.39 (m, 1H), 12.02-12.28 (brs, 1H).

MS(+): 461 [M+H]⁺.

Example 4-57

3-Chloro-6-{(E)-1-[4-(cyclopropylsulfonyl)phenyl]-2-[(2R)-5-oxopyrrolidin-2-yl]ethenyl}pyridin-2(1H)-one

[Ka 244]

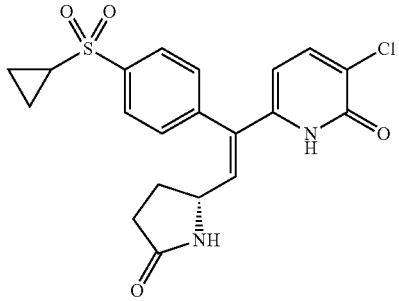

The title compound was obtained as a pale brown powder (31 mg) by performing substantially the same reaction as in Example 1-2 except for using 3-chloro-6-{(E)-1-[4-(cyclopropylsulfanyl)phenyl]-2-[(2R)-5-oxopyrrolidin-2-yl]ethenyl}pyridin-2(1H)-one obtained in Example 4-37.

¹H NMR (300 MHz, CDCl₃) δ ppm 0.99-1.25 (m, 2H), 1.36-1.48 (m, 2H), 2.16-2.43 (m, 3H), 2.46-2.63 (m, 2H), 3.98-4.27 (m, 1H), 5.67 (d, J=7.8 Hz, 1H), 6.66 (d, J=9.5 Hz, 1H), 7.39-7.54 (m, 3H), 7.59-7.75 (brs, 1H), 8.00 (d, J=8.5 Hz, 2H), 13.00-13.33 (brs, 1H).

MS(+): 441 [M+Na]⁺.

Example 4-58

3-Chloro-6-{(E)-1-[3-chloro-4-(ethylsulfonyl)phenyl]-2-[(2R)-5-oxopyrrolidin-2-yl]ethenyl}pyridin-2(1H)-one

[Ka 245]

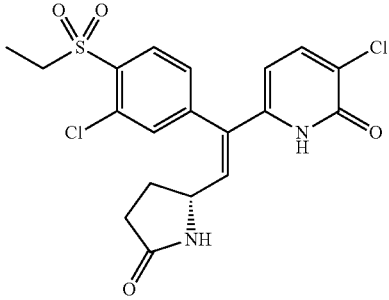

The title compound was obtained as a colorless powder (54 mg) by performing substantially the same reaction as in Example 1-2 except for using 3-chloro-6-{(E)-1-[3-chloro-4-(ethylsulfanyl)phenyl]-2-[(2R)-5-oxopyrrolidin-2-yl]ethenyl}pyridin-2(1H)-one obtained in Example 4-27.

¹H NMR (300 MHz, CDCl₃) δ ppm 1.30-1.46 (m, 3H), 2.22-2.61 (m, 4H), 3.38-3.58 (m, 2H), 4.01-4.20 (m, 1H), 5.67 (d, J=7.8 Hz, 1H), 6.68 (d, J=9.5 Hz, 1H), 7.42 (dd, J=8.1, 1.7 Hz, 1H), 7.47-7.56 (m, 2H), 7.57-7.66 (brs, 1H), 8.23 (d, J=8.1 Hz, 1H), 13.08-13.37 (brs, 1H).

MS(+): 463 [M+Na]⁺.

Example 4-59

3-Chloro-6-{(E)-1-[3-chloro-4-(cyclopropylsulfonyl)phenyl]-2-[(2R)-5-oxopyrrolidin-2-yl]ethenyl}pyridin-2(1H)-one

[Ka 246]

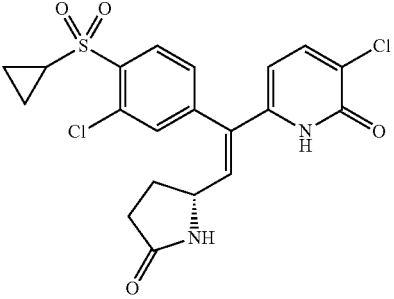

The title compound was obtained as a white solid (33 mg, 32%) by performing substantially the same reaction as in Example 1-2 except for using 3-chloro-6-{(E)-1-[3-chloro-4-(cyclopropylsulfanyl)phenyl]-2-[(2R)-5-oxopyrrolidin-2-yl]ethenyl}pyridin-2(1H)-one obtained in Example 4-13.

¹H NMR (300 MHz, CDCl₃) δ ppm 1.10-1.20 (m, 2H), 1.37-1.50 (m, 2H), 2.21-2.48 (m, 3H), 2.48-2.64 (m, 1H), 3.00-3.19 (m, 1H), 4.06-4.21 (m, 1H), 5.70 (d, J=7.9 Hz, 1H), 6.67 (d, J=8.9 Hz, 1H), 7.37 (dd, J=7.9, 1.3 Hz, 1H), 7.48 (d, J=1.3 Hz, 1H), 7.52 (d, J=7.6 Hz, 1H), 8.12 (d, J=7.9 Hz, 1H), 12.97-13.33 (brs, 1H)

MS(+): 453 [M+H]⁺..

Example 4-60

3-Chloro-6-{(E)-1-[4-(cyclopentylsulfonyl)phenyl]-2-[(2R)-5-oxopyrrolidin-2-yl]ethenyl}pyridin-2(1H)-one

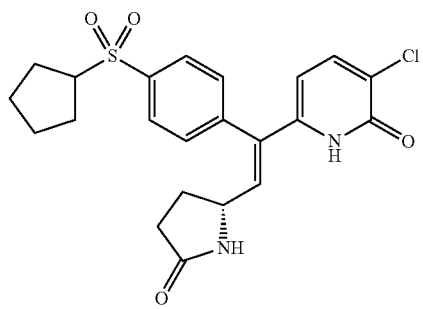
[Ka 247]

The title compound was obtained as a colorless powder (13 mg) by performing substantially the same reaction as in Example 1-2 except for using 3-chloro-6-{(E)-1-[4-(cyclopropylsulfonyl)phenyl]-2-[(2R)-5-oxopyrrolidin-2-yl]ethenyl}pyridin-2(1H)-one obtained in Example 4-33.

$^1$H NMR (300 MHz, CDCl$_3$) δ ppm 1.58-1.74 (m, 2H), 1.75-2.02 (m, 4H), 2.06-2.23 (m, 2H), 2.24-2.44 (m, 3H), 2.44-2.62 (m, 1H), 3.44-3.73 (m, 1H), 3.97-4.20 (m, 1H), 5.64 (d, J=7.6 Hz, 1H), 6.66 (d, J=9.3 Hz, 1H), 7.42-7.55 (m, 3H), 7.59-7.70 (brs, 1H), 8.00 (d, J=8.2 Hz, 2H), 13.06-13.34 (brs, 1H).

MS(+): 447 [M+H]$^+$.

Example 4-61

3-Chloro-6-{(E)-1-{4-[(4-methylpiperazin-1-yl)sulfonyl]phenyl}-2-[(2R)-5-oxopyrrolidin-2-yl]ethenyl}pyridin-2(1H)-one

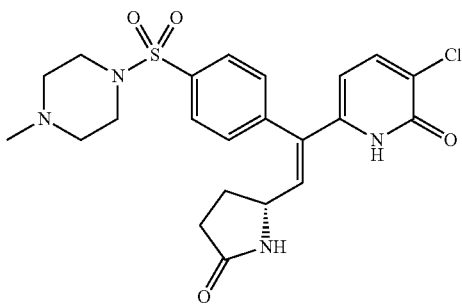
[Ka 248]

(1) tert-Butyl 4-[(4-{(E)-1-(5-chloro-6-methoxypyridin-2-yl)-2-[(2R)-5-oxopyrrolidin-2-yl]ethenyl}phenyl)sulfonyl]piperazine-1-carboxylate was obtained as a colorless amorphous (620 mg, 28%) by performing substantially the same reaction as in Example 4-48(1) except for using tert-butyl 4-({4-[(5-chloro-6-methoxypyridin-2-yl)carbonyl]phenyl}sulfonyl)piperazine-1-carboxylate obtained in Reference Example 1-23.

(2) A crude product containing (5R)-5-{(E)-2-(5-chloro-6-methoxypyridin-2-yl)-2-[4-(piperazin-1-ylsulfonyl)phenyl]ethenyl}pyrrolidin-2-one was obtained by performing substantially the same reaction as in Example 1-46(2) except for using tert-butyl 4-[(4-{(E)-1-(5-chloro-6-methoxypyridin-2-yl)-2-[(2R)-5-oxopyrrolidin-2-yl]ethenyl}phenyl)sulfonyl]piperazine-1-carboxylate.

(3) (5R)-5-[(E)-2-(5-chloro-6-methoxypyridin-2-yl)-2-{4-[(4-methylpiperazin-1-yl)sulfonyl]phenyl}ethenyl]pyrrolidin-2-one was obtained as a colorless amorphous (234 mg, 98%) by performing substantially the same reaction as in Example 1-46(3) except for using (5R)-5-{(E)-2-(5-chloro-6-methoxypyridin-2-yl)-2-[4-(piperazin-1-ylsulfonyl)phenyl]ethenyl}pyrrolidin-2-one.

(4) The title compound (69 mg, 30%) was obtained by performing substantially the same reaction as in Example 1-1(2) except for using (5R)-5-[(E)-2-(5-chloro-6-methoxypyridin-2-yl)-2-{4-[(4-methylpiperazin-1-yl)sulfonyl]phenyl}ethenyl]pyrrolidin-2-one.

$^1$H NMR (300 MHz, CDCl$_3$) δ ppm 2.17-2.43 (m, 7H), 2.46-2.64 (m, 4H), 3.01-3.21 (m, 4H), 3.90-4.22 (m, 1H), 5.63 (d, J=7.6 Hz, 1H), 6.63 (d, J=9.5 Hz, 1H), 7.34-7.64 (m, 4H), 7.82-7.88 (m, 2H).

MS(+): 477 [M+H]$^+$.

Example 4-62

6-{(E)-1-{3-Chloro-4-[4-(diethylamino)butoxy]phenyl}-2-[(2R)-5-oxopyrrolidin-2-yl]ethenyl}-3-cyclopropylpyridin-2(1H)-one

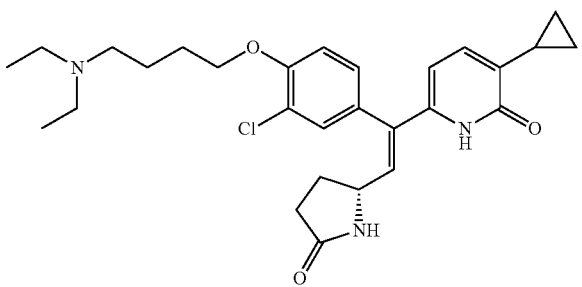
[Ka 249]

The title compound was obtained as a colorless solid (20 mg, 6% (three steps)) by performing substantially the same reaction as in Examples 4-2(1) and 1-26(4)-(5) sequentially except for using 4-{2-chloro-4-[(5-cyclopropyl-6-methoxypyridin-2-yl)carbonyl]phenoxy}butyl 4-methylbenzenesulfonate obtained in Reference Example 1-65.

$^1$H NMR (300 MHz, CDCl$_3$) δ ppm 0.56-0.67 (m, 2H), 0.96-1.10 (m, 8H), 1.65-1.76 (m, 2H), 1.84-1.94 (m, 2H), 2.00-2.16 (m, 2H), 2.24-2.42 (m, 3H), 2.50-2.62 (m, 6H), 4.10 (t, J=6.3 Hz, 2H), 4.14-4.24 (m, 1H), 5.84 (d, J=7.2 Hz, 1H), 6.02 (s, 1H), 6.29 (d, J=9.0 Hz, 1H), 6.85 (d, J=7.2 Hz, 1H), 6.92-7.02 (m, 2H), 7.16 (d, J=1.8 Hz, 1H), 10.50-11.00 (brs, 1H).

MS(+): 498 [M+H]$^+$.

Example 4-63

3-Chloro-6-{(E)-1-{3-chloro-4-[4-(diethylamino)butoxy]phenyl}-2-[(2R)-5-oxopyrrolidin-2-yl]ethenyl}pyridin-2(1H)-one

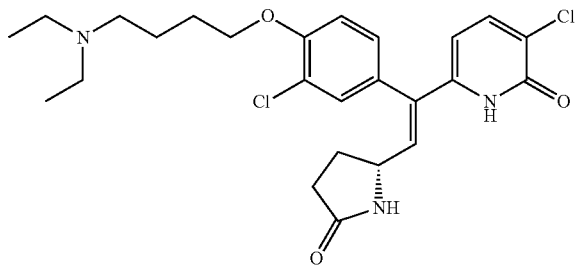
[Ka 250]

The title compound was obtained as a white solid (48 mg, 21% (three steps)) by performing substantially the same reaction as in Examples 4-2(1) and 1-26(4)-(5) sequentially except for using 4-{2-chloro-4-[(5-chloro-6-methoxypyridin-2-yl)carbonyl]phenoxy}butyl 4-methylbenzenesulfonate obtained in Reference Example 1-35.

¹H NMR (300 MHz, CDCl₃) δ ppm 1.04 (t, J=7.2 Hz, 6H), 1.61-1.77 (m, 2H), 1.77-1.97 (m, 2H), 2.18-2.61 (m, 10H), 4.10 (t, J=6.3 Hz, 2H), 4.17-4.28 (m, 1H), 5.81 (d, J=7.8 Hz, 1H), 6.47 (d, J=9.0 Hz, 1H), 6.75 (s, 1H), 6.97 (d, J=8.6 Hz, 1H), 7.06 (dd, J=8.6, 2.0 Hz, 1H), 7.20 (d, J=2.0 Hz, 1H), 7.49 (d, J=7.8 Hz, 1H).

MS(+): 492 [M+H]⁺.

Example 4-64

3-Chloro-6-{(E)-1-{3-chloro-4-[4-(pyrrolidin-1-yl)butoxy]phenyl}-2-[(2R)-5-oxopyrrolidin-2-yl]ethenyl}pyridin-2(1H)-one

[Ka 251]

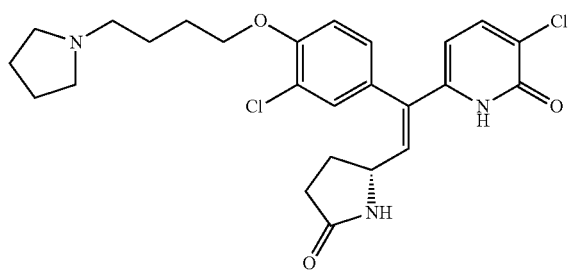

The title compound was obtained as a colorless solid (3 mg, 0.9% (three steps)) by performing substantially the same reaction as in Example 4-63 except for using pyrrolidine in place of diethylamine.

¹H NMR (300 MHz, CDCl₃) δ ppm 1.71-2.68 (m, 18H), 4.11 (t, J=6.3 Hz, 2H), 4.22 (ddd, J=7.8 Hz, 7.8 Hz, 7.8 Hz, 1H), 5.84 (d, J=7.8 Hz, 1H), 6.45 (d, J=9.0 Hz, 1H), 6.49-6.58 (brs, 1H), 6.96 (d, J=8.4 Hz, 1H), 7.05 (dd, J=8.3, 2.3 Hz, 1H), 7.19 (d, J=1.8 Hz, 1H), 7.50 (d, J=7.5 Hz, 1H).

Example 4-65

3-Cyclopropyl-6-{(E)-1-{4-[3-(diethylamino)propoxy]phenyl}-2-[(2R)-5-oxopyrrolidin-2-yl]ethenyl}pyridin-2(1H)-one

[Ka 252]

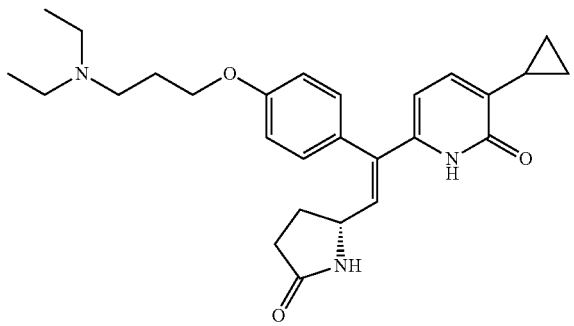

(1) (5R)-5-[(E)-2-[4-(3-{[tert-Butyl(dimethyl)silyl]oxy}propoxy)phenyl]-2-(5-cyclopropyl-6-methoxypyridin-2-yl)ethenyl]pyrrolidin-2-one (77 mg, 16%) was obtained by performing substantially the same reaction as in Example 4-2(1) except for using [4-(3-{[tert-butyl(dimethyl)silyl]oxy}propoxy)phenyl](5-cyclopropyl-6-methoxypyridin-2-yl)methanone obtained in Reference Example 1-56.

(2) Triethylamine (0.031 mL), di-tert-butyl dicarbonate (39 mg) and 4-dimethylaminopyridine (18 mg) were sequentially added to a solution of (5R)-5-[(E)-2-[4-(3-{[tert-butyl(dimethyl)silyl]oxy}propoxy)phenyl]-2-(5-cyclopropyl-6-methoxypyridin-2-yl)ethenyl]pyrrolidin-2-one (77 mg) in tetrahydrofuran (3 mL) at room temperature. The mixture was stirred at room temperature for 20 hours, during which di-tert-butyl dicarbonate was further added several times. Water was added to the reaction solution, followed by extraction with ethyl acetate. The organic layers were dried over anhydrous sodium sulfate and filtered. The solvent was then evaporated under reduced pressure. The resulting residue was purified by silica gel column chromatography (hexane:ethyl acetate=100:0→4:1) to give tert-butyl (2R)-2-[(E)-2-[4-(3-{[tert-butyl(dimethyl)silyl]oxy}propoxy)phenyl]-2-(5-cyclopropyl-6-methoxypyridin-2-yl)ethenyl]-5-oxopyrrolidine-1-carboxylate (89 mg, 97%).

(3) The title compound was obtained as a white solid (19 mg, 31% (four steps)) by performing substantially the same reaction as in Example 1-26(2)-(5) except for using tert-butyl (2R)-2-[(E)-2-[4-(3-{[tert-butyl(dimethyl)silyl]oxy}propoxy)phenyl]-2-(5-cyclopropyl-6-methoxypyridin-2-yl)ethenyl]-5-oxopyrrolidine-1-carboxylate.

¹H NMR (300 MHz, CDCl₃) δ ppm 0.48-0.58 (m, 2H) 0.89-1.05 (m, 2H) 1.06 (t, J=7.1 Hz, 6H) 1.85-2.45 (m, 7H) 2.50-2.70 (m, 6H) 4.04 (t, J=6.4 Hz, 2H) 4.12-4.25 (m, 1H) 5.77 (d, J=7.4 Hz, 1H) 6.39 (d, J=8.9 Hz, 1H) 6.45-6.60 (brs, 1H) 6.82 (d, J=7.4 Hz, 1H) 6.91 (d, J=8.6 Hz, 2H) 7.06 (d J=8.6 Hz, 2H)

MS(+): 450 [M+H]⁺.

Example 4-66

3-Chloro-6-{(E)-2-[(2R)-5-oxopyrrolidin-2-yl]-1-[4-(pyrrolidin-1-ylmethyl)phenyl]ethenyl}pyridin-2(1H)-one

[Ka 253]

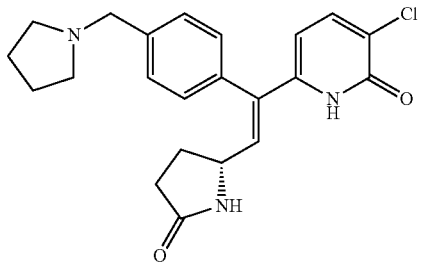

(1) (5R)-5-[2-(5-Chloro-6-methoxypyridin-2-yl)-2-{4-[(3-methylbutoxy)methyl]phenyl}ethenyl]pyrrolidin-2-one (E:Z=1:2 mixture) (448 mg, 95%) by performing substantially the same reaction as in Example 4-2(1) except for using (5-chloro-6-methoxypyridin-2-yl){4-[(3-methylbutoxy)methyl]phenyl}methanone obtained in Reference Example 1-10.

(2) 48% hydrobromic acid (4 mL) was added to a solution of (5R)-5-[2-(5-chloro-6-methoxypyridin-2-yl)-2-{4-[(3-methylbutoxy)methyl]phenyl}ethenyl]pyrrolidin-2-one (E:Z=1:2 mixture) (396 mg) in acetonitrile (4 mL) at room temperature, and the mixture was stirred at 70° C. for three hours. Saturated aqueous sodium bicarbonate and water were sequentially added to the reaction solution at room temperature, followed by extraction with chloroform. The organic layers were dried over anhydrous sodium sulfate and filtered. The solvent was then evaporated under reduced pressure. The resulting residue was purified by silica gel column chromatography (chloroform:methanol=50:1→5:1) to give 6-{1-[4-(bromomethyl)phenyl]-2-[(2R)-5-oxopyrrolidin-2-yl]ethenyl}-3-chloropyridin-2(1H)-one (E:Z=1:2 mixture) (321 mg, 85%).

(3) Pyrrolidine (0.062 mL) was added to a solution of 6-{1-[4-(bromomethyl)phenyl]-2-[(2R)-5-oxopyrrolidin-2-yl]ethenyl}-3-chloropyridin-2(1H)-one (E:Z=1:2 mixture) (30 mg) in acetonitrile (1.2 mL) at room temperature, and the mixture was stirred at room temperature for five hours.

Separately, pyrrolidine (0.424 mL) was added to a solution of 6-{1-[4-(bromomethyl)phenyl]-2-[(2R)-5-oxopyrrolidin-2-yl]ethenyl}-3-chloropyridin-2(1H)-one (E:Z=1:2 mixture) (206 mg) in acetonitrile (8.24 mL) at room temperature, and the mixture was stirred at room temperature for one hour. Water and a saturated ammonium chloride solution were sequentially added to the reaction solutions at room temperature, and the mixtures were combined, followed by extraction with chloroform. The organic layers were dried over anhydrous sodium sulfate and filtered. The solvent was then evaporated under reduced pressure. The resulting residue was purified by preparative TLC (chloroform:methanol=5:1) to give the title compound as a white solid (70 mg, 30%).

$^1$H NMR (300 MHz, CDCl$_3$) δ ppm 1.70-1.90 (m, 4H), 2.15-2.65 (m, 8H), 3.65 (d, J=1.8 Hz, 2H), 4.10-4.26 (m, 1H), 5.76 (d, J=7.7 Hz, 1H), 6.50 (d, J=9.5 Hz, 1H), 7.06 (s, 1H), 7.14 (d, J=7.7 Hz, 2H), 7.39 (d, J=7.7 Hz, 2H), 7.45 (d, J=7.7 Hz, 1H).

MS(+): 398[M+H]$^+$.

Example 4-67

3-Cyclopropyl-6-{(E)-2-[(2R)-5-oxopyrrolidin-2-yl]-1-[4-(propan-2-yl)phenyl]ethenyl}pyridin-2(1H)-one

[Ka 254]

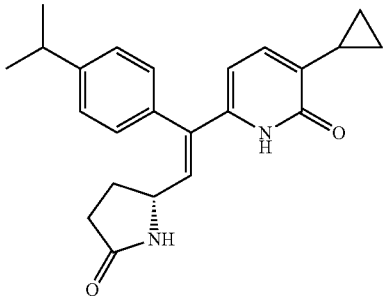

(1) (5R)-5-{2-(5-Cyclopropyl-6-methoxypyridin-2-yl)-2-[4-(propan-2-yl)phenyl]ethenyl}pyrrolidin-2-one (E:Z=7:2) was obtained as a colorless amorphous (67 mg, 14%) by performing substantially the same reaction as in Example 4-2(1) except for using (5-cyclopropyl-6-methoxypyridin-2-yl)[4-(propan-2-yl)phenyl]methanone obtained in Reference Example 1-79. (5R)-5-{(Z)-2-(5-Cyclopropyl-6-methoxypyridin-2-yl)-2-[4-(propan-2-yl)phenyl]ethenyl}pyrrolidin-2-one was also obtained as a colorless amorphous (236 mg, 49%).

(2) The title compound was obtained as a colorless solid (34 mg) by performing substantially the same reaction as in Example 1-1(2) except for using (5R)-5-{2-(5-cyclopropyl-6-methoxypyridin-2-yl)-2-[4-(propan-2-yl)phenyl]ethenyl}pyrrolidin-2-one (E:Z=7:2).

$^1$H NMR (300 MHz, CDCl$_3$) δ ppm 0.55-0.70 (m, 2H) 0.94-1.06 (m, 2H) 1.30 (s, 3H) 1.32 (s, 3H) 1.99-2.19 (m, 2H) 2.24-2.49 (m, 3H) 2.90-3.03 (m, 1H) 4.15-4.28 (m, 1H) 5.84-5.98 (brs, 1H) 5.94 (d, J=7.4 Hz, 1H) 6.27 (d, J=8.9 Hz, 1H) 6.87 (d, J=7.4 Hz, 1H) 7.07 (d, J=8.3 Hz, 2H) 7.21-7.34 (m, 2H) 10.17-10.47 (brs, 1H).

MS(+): 363 [M+H]$^+$.

Example 4-68

6-{(E)-1-(4-tert-Butylphenyl)-2-[(3R)-1-propanoylpyrrolidin-3-yl]ethenyl}-3-chloropyridin-2(1H)-one

[Ka 255]

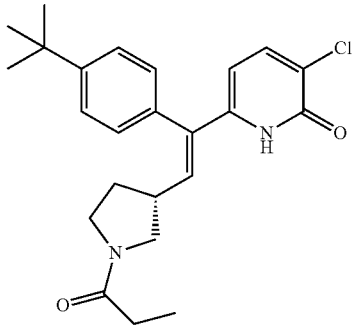

The title compound was obtained as a white solid (48 mg, 38% (two steps)) by performing substantially the same reaction as in Example 4-1 except for using (4-tert-butylphenyl)(5-chloro-6-methoxypyridin-2-yl)methanone obtained in Reference Example 1-7 and using 1-{(3S)-3-[(1,3-benzothiazol-2-ylsulfonyl)methyl]pyrrolidin-1-yl}propan-1-one obtained in Reference Example 3-19 in place of (5R)-5-{[(1-phenyl-1H-tetrazol-5-yl)sulfonyl]methyl}pyrrolidin-2-one.

$^1$H NMR (300 MHz, CDCl$_3$) δ ppm 1.13 (td, J=7.4, 2.0 Hz, 3H) 1.36 (d, J=2.0 Hz, 9H) 1.87-2.32 (m, 4H) 2.76-3.02 (m, 1H) 3.25-3.79 (m, 4H) 5.88 (dd, J=13.1, 7.8 Hz, 1H) 6.48 (dd, J=31.7, 9.6, 1H) 7.10 (dd, J=8.2, 2.5 Hz, 2H) 7.41-7.49 (m, 3H)

MS(+): 413 [M+H]$^+$.

Examples 4-69 and 4-70

6-{1-(4-tert-Butylphenyl)-2-[(2R)-5-oxopyrrolidin-2-yl]ethyl}-3-chloropyridin-2(1H)-one

[Ka 256]

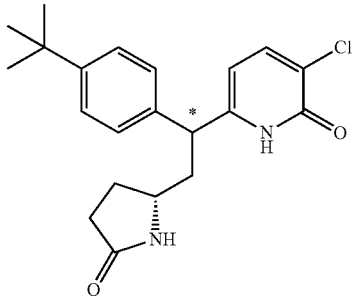

(1) (5R)-5-[2-(4-tert-Butylphenyl)-2-(5-chloro-6-methoxypyridin-2-yl)ethenyl]pyrrolidin-2-one (E:Z≥9:1) (110 mg, 28%) was obtained by performing substantially the same reaction as in Example 4-2(1) except for using (4-tert-butylphenyl)(5-chloro-6-methoxypyridin-2-yl)methanone obtained in Reference Example 1-7. (5R)-5-[2-(4-tert-Butylphenyl)-2-(5-chloro-6-methoxypyridin-2-yl)ethenyl]pyrrolidin-2-one (E:Z=2:8) (172 mg, 44%) was also obtained.

(2) 5% palladium-activated carbon (30 mg) was added to a solution of (5R)-5-[2-(4-tert-butylphenyl)-2-(5-chloro-6-methoxypyridin-2-yl)ethenyl]pyrrolidin-2-one (E:Z=2:8) (150 mg) in methanol in a hydrogen gas stream, and the mixture was stirred at room temperature for seven hours. The reaction solution was filtered through celite, and the solvent was evaporated under reduced pressure. The resulting residue was purified by NH-silica gel column chromatography (chloroform) and further purified by preparative TLC (chloroform) to give (5R)-5-[2-(4-tert-butylphenyl)-2-(5-chloro-6-methoxypyridin-2-yl)ethyl]pyrrolidin-2-one as a pale brown amorphous (110 mg, 73%).

(3) 48% hydrobromic acid (1 mL) was added to a solution of (5R)-5-[2-(4-tert-butylphenyl)-2-(5-chloro-6-methoxypyridin-2-yl)ethyl]pyrrolidin-2-one (100 mg) in 1,4-dioxane (2 mL), and the mixture was stirred at room temperature for 30 minutes and at 65° C. for 30 minutes. The reaction solution was extracted with ethyl acetate. The organic layer was washed with brine, dried over anhydrous magnesium sulfate and filtered. The solvent was then evaporated under reduced pressure. The resulting residue was purified by preparative TLC (chloroform:methanol=10:1) to give 6-{1-(4-tert-butylphenyl)-2-[(2R)-5-oxopyrrolidin-2-yl]ethyl}-3-chloropyridin-2(1H)-one, which was separated by preparative HPLC (Inertsil ODS-3 (20 mm i.d.×250 mm L, GL Sciences Inc.), 40° C., flow rate: 10 mL/min, acetonitrile:water=40:60). The fraction containing a single diastereomer eluted with a retention time of 43 minutes was concentrated to give the title compound as a white solid (18 mg, 19%) (Example 4-69).

$^1$H NMR (300 MHz, CDCl$_3$) δ ppm 1.30 (s, 9H) 1.80-2.00 (m, 1H) 2.12-2.55 (m, 5H) 3.60-3.78 (m, 1H) 3.95-4.10 (m, 1H) 6.09 (d, J=8.0 Hz, 1H) 7.21 (d, J=8.3 Hz, 2H) 7.30-7.43 (m, 3H) 7.52 (d, J=7.4 Hz, 1H) 12.15-12.40 (brs, 1H).

MS(+): 373 [M+H]$^+$.

The fraction containing a single diastereomer eluted with a retention time of 48 minutes was concentrated to give the title compound as a white solid (28 mg, 29%) (Example 4-70).

$^1$H NMR (300 MHz, CDCl$_3$) δ ppm 1.30 (s, 9H) 1.63-1.85 (m, 1H) 2.10-2.55 (m, 5H) 3.41-3.62 (m, 1H) 3.95 (dd, J=9.5, 6.3 Hz, 1H) 6.03 (d, J=7.4 Hz, 1H) 7.02-7.18 (brs, 1H) 7.23 (d, J=8.0 Hz, 2H) 7.36 (d, J=8.0 Hz, 2H) 7.49 (d, J=7.4 Hz, 1H) 11.30-11.65 (brs, 1H).

MS(+): 373 [M+H]$^+$.

Example 4-71

6-{(E)-1-(4-tert-Butyl-3-chlorophenyl)-2-[(2R)-5-oxopyrrolidin-2-yl]ethenyl}-3-chloropyridin-2(1H)-one

[Ka 257]

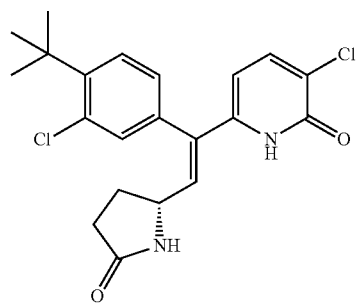

The title compound was obtained as a colorless solid (10 mg) by performing substantially the same reaction as in Example 4-2 except for using the mixture of (4-tert-butyl-3-chlorophenyl)(5-chloro-6-methoxypyridin-2-yl)methanone and (5-chloro-6-methoxypyridin-2-yl)[3-chloro-4-(prop-1-en-2-yl)phenyl]methanone (1:1) obtained in Reference Example 1-80.

$^1$H NMR (300 MHz, CDCl$_3$) δ ppm 1.52 (s, 9H) 2.09-2.26 (m, 1H) 2.26-2.54 (m, 3H) 4.21 (td, J=7.6, 8.0 Hz, 1H) 5.89 (d, J=8.0 Hz, 1H) 6.15-6.22 (m, 1H) 6.42 (d, J=9.5 Hz, 1H) 7.01 (dd, J=8.2, 1.6 Hz, 1H) 7.16 (d, J=1.8 Hz, 1H) 7.45-7.54 (m, 2H) 11.95-12.19 (brs, 1H).

MS(+): 405 [M+H]$^+$.

Example 4-72

6-{(E)-1-(4-tert-Butylphenyl)-2-[(3R)-1-(ethylsulfonyl)pyrrolidin-3-yl]ethenyl}-3-chloropyridin-2(1H)-one

[Ka 258]

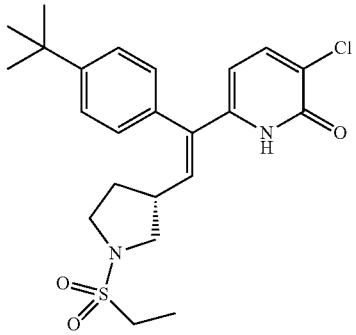

The title compound was obtained as a white solid (65 mg, 25% (two steps)) by performing substantially the same reaction as in Example 4-1 except for using (4-tert-butylphenyl)(5-chloro-6-methoxypyridin-2-yl)methanone obtained in Reference Example 1-7 and using 2-({[(3S)-1-(ethylsulfonyl)pyrrolidin-3-yl]methyl}sulfonyl)-1,3-benzothiazole obtained in Reference Example 3-20 in place of (5R)-5-{[(1-phenyl-1H-tetrazol-5-yl)sulfonyl]methyl}pyrrolidin-2-one.

$^1$H NMR (300 MHz, CDCl$_3$) δ ppm 1.34 (t, J=7.6 Hz, 3H) 1.37 (s, 9H) 2.05-2.17 (m, 2H) 2.87-3.06 (m, 3H) 3.26-3.39 (m, 2H) 3.53-3.57 (m, 2H) 5.86 (d, J=7.6 Hz, 1H) 6.53 (d, J=9.6 Hz, 1H) 7.08 (d, J=8.3 Hz, 2H) 7.44-7.47 (m, 3H) 11.70-11.73 (brs, 1H).

MS(+): 449 [M+H]$^+$.

Example 4-73

3-Chloro-6-{(E)-1-[4-(4-methoxybutyl)phenyl]-2-[(2R)-5-oxopyrrolidin-2-yl]ethenyl}pyridin-2(1H)-one

[Ka 259]

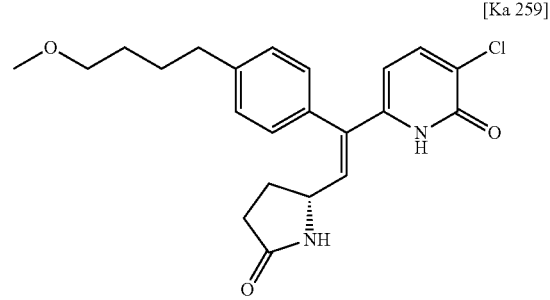 [SMILES: COCCCCc1ccc(/C(=C\[C@H]2CCC(=O)N2)c2ccc(Cl)c(=O)[nH]2)cc1]

The title compound was obtained as a white solid (70 mg, 9% (two steps)) by performing substantially the same reaction as in Example 4-2 except for using (5-chloro-6-methoxypyridin-2-yl)[4-(4-methoxybutyl)phenyl]methanone obtained in Reference Example 1-81.

$^1$H NMR (300 MHz, CDCl$_3$) δ ppm 1.40-1.98 (m, 4H) 2.11-2.85 (m, 6H) 3.34 (s, 3H) 3.41 (t, J=6.0 Hz, 2H) 4.08-4.33 (m, 1H) 5.76 (d, J=7.7 Hz, 1H) 6.50 (d, J=8.9 Hz, 1H) 6.93-7.37 (m, 5H) 7.45 (d, J=7.7 Hz, 1H) 12.75-13.20 (brs, 1H).

MS(+): 401 [M+H]$^+$.

Example 4-74

6-{(E)-1-(4-tert-Butylphenyl)-2-[(2R)-5-oxopyrrolidin-2-yl]ethenyl}-3-(trifluoromethyl)pyridin-2(1H)-one

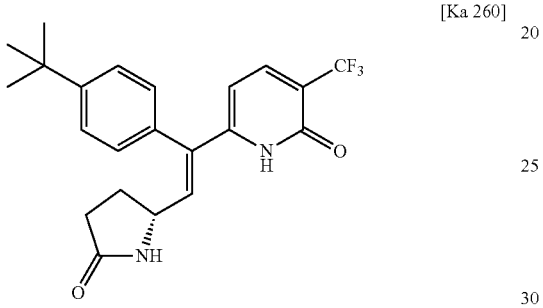

[Ka 260]

The title compound was obtained as a white solid (122 mg, 19% (two steps)) by performing substantially the same reaction as in Example 4-2 except for using (4-tert-butylphenyl)[6-methoxy-5-(trifluoromethyl)pyridin-2-yl]methanone obtained in Reference Example 1-82.

$^1$H NMR (300 MHz, CDCl$_3$) δ ppm 1.36 (s, 9H) 2.10-2.58 (m, 4H) 4.14-4.30 (m, 1H) 5.90 (d, J=7.4 Hz, 1H) 6.60 (d, J=6.3 Hz, 1H) 6.70-6.98 (brs, 1H) 7.12 (d, J=8.3 Hz, 2H) 7.45 (d, J=8.3 Hz, 2H) 7.66 (d, J=7.7 Hz, 1H).

MS(+): 405 [M+H]$^+$.

Example 4-75

6-{(E)-1-(4-tert-Butylphenyl)-2-[(2S)-5-oxopyrrolidin-2-yl]ethenyl}-3-chloropyridin-2(1H)-one

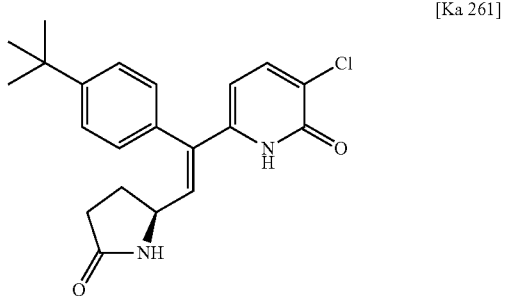 [SMILES: CC(C)(C)c1ccc(/C(=C\[C@@H]2CCC(=O)N2)c2ccc(Cl)c(=O)[nH]2)cc1]

[Ka 261]

(1) (5S)-5-[2-(4-tert-Butylphenyl)-2-(5-chloro-6-methoxypyridin-2-yl)ethenyl]pyrrolidin-2-one (EZ mixture) (750 mg, 99%) was obtained by performing substantially the same reaction as in Example 4-1(1) except for using (4-tert-butylphenyl)(5-chloro-6-methoxypyridin-2-yl)methanone obtained in Reference Example 1-7 and using (5S)-5-[(1,3-benzothiazol-2-ylsulfonyl)methyl]pyrrolidin-2-one obtained in Reference Example 3-21 in place of (5R)-5-{[(1-phenyl-1H-tetrazol-5-yl)sulfonyl]methyl}pyrrolidin-2-one.

(2) The title compound was obtained as a white solid (11 mg, 3%) by performing substantially the same reaction as in Example 1-1(2) except for using (5S)-5-[2-(4-tert-butylphenyl)-2-(5-chloro-6-methoxypyridin-2-yl)ethenyl]pyrrolidin-2-one (EZ mixture).

$^1$H NMR (300 MHz, CDCl$_3$) δ ppm 1.36 (s, 9H) 2.02-2.22 (m, 1H) 2.25-2.53 (m, 3H) 4.15-4.32 (m, 1H) 5.93 (s, 1H) 5.99 (d, J=7.4 Hz, 1H) 6.33 (d, J=8.9 Hz, 1H) 7.08 (d, J=8.0 Hz, 2H) 7.45 (d, J=8.3 Hz, 2H) 7.51 (d, J=8.0 Hz, 1H) 11.02-11.25 (brs, 1H).

MS(+): 371 [M+H]$^+$.

Examples 4-76 and 4-77

6-{1-(4-tert-Butylphenyl)-2-[(2S)-5-oxopyrrolidin-2-yl]ethyl}-3-chloropyridin-2(1H)-one

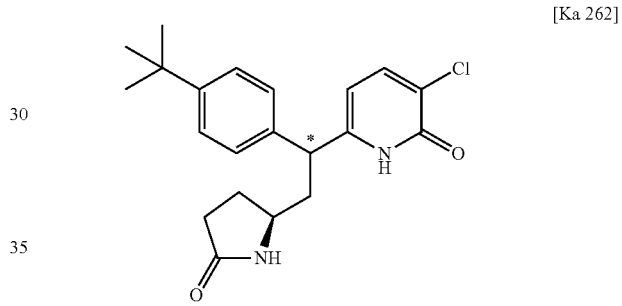

[Ka 262]

The title compound was obtained as a white solid (46 mg, 13% (two steps)) by performing substantially the same reaction as in Examples 4-69 and 4-70(2)(3) sequentially except for using (5S)-5-[2-(4-tert-butylphenyl)-2-(5-chloro-6-methoxypyridin-2-yl)ethenyl]pyrrolidin-2-one (EZ mixture) obtained in Example 4-75(1), separating the mixture by preparative HPLC (Inertsil ODS-3 (20 mm i.d.×250 mm L, GL Sciences Inc.), 40° C., flow rate: 10 mL/min, acetonitrile:water=40:60) and concentrating the fraction containing a single diastereomer eluted with a retention time of 44 minutes (Example 4-76).

$^1$H NMR (300 MHz, CDCl$_3$) δ ppm 1.30 (s, 9H) 1.80-2.05 (m, 1H) 2.10-2.55 (m, 5H) 3.59-3.75 (m, 1H) 3.95-4.11 (m, 1H) 6.07 (d, J=7.7 Hz, 1H) 7.22 (d, J=8.0 Hz, 2H) 7.34 (d, J=8.3 Hz, 2H) 7.52 (d, J=7.7 Hz, 1H) 7.55-7.73 (m, 1H) 12.50-12.90 (brs, 1H).

MS(+): 373 [M+H]$^+$.

The fraction containing a single diastereomer eluted with a retention time of 49 minutes was concentrated to give the title compound as a white solid (55 mg, 15% (two steps)) (Example 4-77).

$^1$H NMR (300 MHz, CDCl$_3$) δ ppm 1.30 (s, 9H) 1.60-1.90 (m, 1H) 2.11-2.52 (m, 5H) 3.41-3.62 (m, 1H) 3.90-4.08 (m, 1H) 6.03 (d, J=7.7 Hz, 1H) 7.29 (d, J=8.6 Hz, 2H) 7.35 (d, J=8.3 Hz, 2H) 7.38-7.45 (brs, 1H) 7.49 (d, J=7.4 Hz, 1H) 11.70-12.10 (brs, 1H).

MS(+): 373 [M+H]$^+$.

Example 4-78

6-{(E)-1-(4-Chlorophenyl)-2-[(3R)-1-(cyclopropylcarbonyl)pyrrolidin-3-yl]ethenyl}-3-cyclopropylpyridin-2(1H)-one

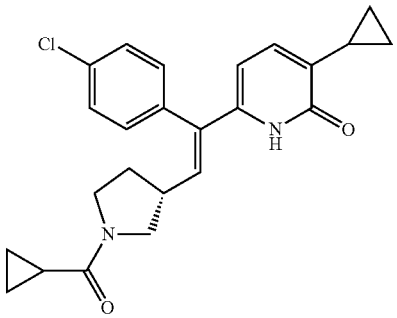

(1) tert-Butyl (3R)-3-[2-(4-chlorophenyl)-2-(5-cyclopropyl-6-methoxypyridin-2-yl)ethenyl]pyrrolidine-1-carboxylate (EZ mixture) (1.03 g, 63%) and tert-butyl (3R)-3-[(E)-2-(4-chlorophenyl)-2-(5-cyclopropyl-6-methoxypyridin-2-yl)ethenyl]pyrrolidine-1-carboxylate (358 mg, 22%) were obtained by performing substantially the same reaction as in Example 4-46(1) except for using (4-chlorophenyl)(5-cyclopropyl-6-methoxypyridin-2-yl)methanone obtained in Reference Example 1-95.

(2) {(3R)-3-[(E)-2-(4-Chlorophenyl)-2-(5-cyclopropyl-6-methoxypyridin-2-yl)ethenyl]pyrrolidin-1-yl}(cyclopropyl)methanone was obtained as a brown amorphous (79 mg, 83% (two steps)) by performing substantially the same reaction as in Example 4-46(2)(3) sequentially except for using tert-butyl (3R)-3-[(E)-2-(4-chlorophenyl)-2-(5-cyclopropyl-6-methoxypyridin-2-yl)ethenyl]pyrrolidine-1-carboxylate and using cyclopropanecarbonyl chloride as an acylating reagent.

(3) The title compound was obtained as a white solid (62 mg, 83%) by performing substantially the same reaction as in Example 1-1(2) except for using {(3R)-3-[(E)-2-(4-chlorophenyl)-2-(5-cyclopropyl-6-methoxypyridin-2-yl)ethenyl]pyrrolidin-1-yl}(cyclopropyl)methanone.

L-Column ODS 4.6×250 mm
0.01 M acetate buffer:MeCN=40:60 v/v, 40° C., 1.0 mL/min, 254 nm
Rt=7.843 min
MS(+): 409 [M+H]$^+$.
MS(−): 407 [M−H]$^-$.

Example 4-79

3-Chloro-6-{(E)-1-(4-methyl-3,4-dihydro-2H-1,4-benzoxazin-7-yl)-2-[(2R)-5-oxopyrrolidin-2-yl]ethenyl}pyridin-2(1H)-one

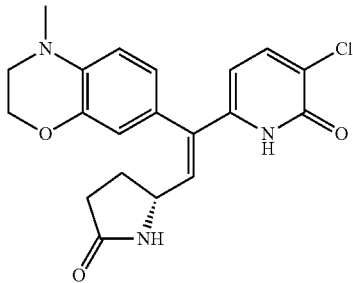

The title compound was obtained as a colorless solid (10 mg, 4% (two steps)) by performing substantially the same reaction as in Example 4-2 except for using (5-chloro-6-methoxypyridin-2-yl)(4-methyl-3,4-dihydro-2H-1,4-benzoxazin-7-yl)methanone obtained in Reference Example 1-83.

$^1$H NMR (300 MHz, CDCl$_3$) δ ppm 1.98-2.12 (m, 1H) 2.29-2.50 (m, 3H) 2.94 (s, 3H) 3.32-3.38 (m, 2H) 4.27-4.36 (m, 3H) 5.67-5.74 (brs, 1H) 6.11-6.19 (m, 2H) 6.51 (d, J=1.2 Hz, 1H) 6.54-6.60 (m, 1H) 6.60-6.68 (m, 1H) 7.50-7.55 (m, 1H) 9.81-10.14 (brs, 1H).

MS(+): 386 [M+H]$^+$.

Example 4-80

3-Cyclopropyl-6-{(1R)-2-[(2R)-5-oxopyrrolidin-2-yl]-1-[4-(propan-2-yl)phenyl]ethyl}pyridin-2(1H)-one

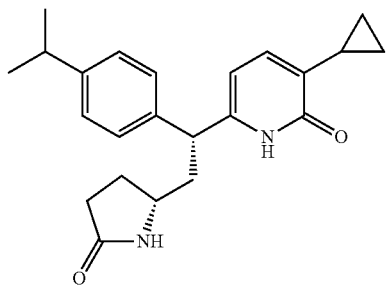

(1) tert-Butyl (2R)-2-{(Z)-2-(5-cyclopropyl-6-methoxypyridin-2-yl)-2-[4-(propan-2-yl)phenyl]ethenyl}-5-oxopyrrolidine-1-carboxylate was obtained as a colorless oil (235 mg, 93%) by performing substantially the same reaction as in Example 4-65(2) except for using (5R)-5-{(Z)-2-(5-cyclopropyl-6-methoxypyridin-2-yl)-2-[4-(propan-2-yl)phenyl]ethenyl}pyrrolidin-2-one obtained in Example 4-67(1).

(2) tert-Butyl (2R)-2-{2-(5-cyclopropyl-6-methoxypyridin-2-yl)-2-[4-(propan-2-yl)phenyl]ethyl}-5-oxopyrrolidine-1-carboxylate was obtained as a colorless amorphous (211 mg, 89%) by performing substantially the same reaction as in Example 4-69 and 4-70(2) except for using tert-butyl (2R)-2-{(Z)-2-(5-cyclopropyl-6-methoxypyridin-2-yl)-2-[4-(propan-2-yl)phenyl]ethenyl}-5-oxopyrrolidine-1-carboxylate.

(3) Trifluoroacetic acid (1 mL) was added to a solution of tert-butyl (2R)-2-{2-(5-cyclopropyl-6-methoxypyridin-2-yl)-2-[4-(propan-2-yl)phenyl]ethyl}-5-oxopyrrolidine-1-carboxylate (211 mg) in methylene chloride (2 mL) under ice-cooling, and the mixture was stirred under ice-cooling for 75 minutes. Saturated aqueous sodium bicarbonate was added to the reaction solution, followed by extraction with chloroform. The organic layer was dried over anhydrous magnesium sulfate and filtered, after which the solvent was evaporated under reduced pressure to give (5R)-5-{2-(5-cyclopropyl-6-methoxypyridin-2-yl)-2-[4-(propan-2-yl)phenyl]ethyl}pyrrolidin-2-one (176.5 mg, quant.).

(4) The title compound was obtained as a colorless solid (12 mg, 15%) by performing substantially the same reaction as in Example 1-1(2) except for using (5R)-5-{2-(5-cyclopropyl-6-methoxypyridin-2-yl)-2-[4-(propan-2-yl)phenyl]ethyl}pyrrolidin-2-one, separating the mixture by preparative HPLC (Inertsil ODS-3 (20 mm i.d.×250 mm L, GL Sciences Inc.), 40° C., flow rate: 10 mL/min, acetonitrile:water=40:60)

and concentrating the fraction containing a single diastereomer eluted with a retention time of 39 minutes.

¹H NMR (300 MHz, CDCl₃) δ ppm 0.51-0.70 (m, 2H) 0.81-1.06 (m, 2H) 1.21 (s, 3H) 1.24 (s, 3H) 1.62-1.81 (m, 1H) 1.91-2.48 (m, 6H) 2.79-2.96 (m, 1H) 3.42-3.58 (m, 1H) 3.93-4.05 (m, 1H) 5.97 (d, J=7.2 Hz, 1H) 6.91 (d, J=6.9 Hz, 1H) 7.18 (d, J=7.8 Hz, 2H) 7.21-7.34 (m, 2H) 7.43 (s, 1H) 11.75-12.08 (brs, 1H).

MS(+): 365 [M+H]⁺.

Example 4-81

6-{(E)-1-[3-Chloro-4-(propan-2-yl)phenyl]-2-[(2R)-5-oxopyrrolidin-2-yl]ethenyl}-3-cyclopropylpyridin-2(1H)-one

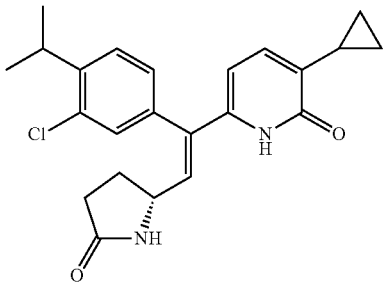

[Ka 266]

(1) (5R)-5-[(E)-2-[3-Chloro-4-(propan-2-yl)phenyl]-2-(5-cyclopropyl-6-methoxypyridin-2-yl)ethenyl]pyrrolidin-2-one was obtained as a colorless amorphous (37 mg, 19%) by performing substantially the same reaction as in Example 4-2(1) except for using [3-chloro-4-(propan-2-yl)phenyl](5-cyclopropyl-6-methoxypyridin-2-yl)methanone obtained in Reference Example 1-84. (5R)-5-[(Z)-2-[3-Chloro-4-(propan-2-yl)phenyl]-2-(5-cyclopropyl-6-methoxypyridin-2-yl)ethenyl]pyrrolidin-2-one was also obtained as a colorless amorphous (65 mg, 32%).

(2) The title compound was obtained as a colorless solid (17 mg, 48%) by performing substantially the same reaction as in Example 1-1(2) except for using (5R)-5-[(E)-2-[3-chloro-4-(propan-2-yl)phenyl]-2-(5-cyclopropyl-6-methoxypyridin-2-yl)ethenyl]pyrrolidin-2-one.

¹H NMR (300 MHz, CDCl₃) δ ppm 0.51-0.68 (m, 2H) 0.92-1.08 (m, 2H) 1.28 (s, 3H) 1.30 (s, 3H) 2.00-2.19 (m, 2H) 2.23-2.49 (m, 3H) 3.37-3.52 (m, 1H) 4.13-4.23 (m, 1H) 5.75-5.80 (m, 1H) 6.04-6.30 (brs, 1H) 6.30-6.48 (m, 1H) 6.86 (d, J=7.5 Hz, 1H) 6.98-7.07 (m, 1H) 7.14 (d, J=1.5 Hz, 1H) 7.34 (d, J=8.1 Hz, 1H) 10.65-11.79 (brs, 1H).

MS(+): 397 [M+H]⁺.

Example 4-82

3-Chloro-6-{(Z)-2-[(2R)-5-oxopyrrolidin-2-yl]-1-[4-(propan-2-yl)phenyl]ethenyl}pyridin-2(1H)-one

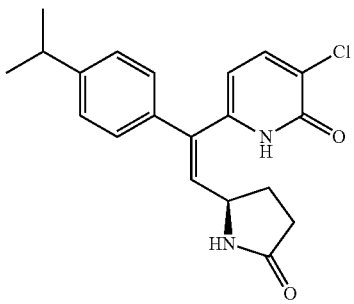

[Ka 267]

(1) (5R)-5-{(E)-2-(5-Chloro-6-methoxypyridin-2-yl)-2-[4-(propan-2-yl)phenyl]ethenyl}pyrrolidin-2-one (38 mg) was obtained by performing substantially the same reaction as in Example 4-2(1) except for using (5-chloro-6-methoxypyridin-2-yl)[4-(propan-2-yl)phenyl]methanone obtained in Reference Example 1-11. (5R)-5-{(Z)-2-(5-Chloro-6-methoxypyridin-2-yl)-2-[4-(propan-2-yl)phenyl]ethenyl}pyrrolidin-2-one (223 mg) and an EZ mixture (230 mg) were also obtained.

(2) The title compound was obtained as a colorless solid (37 mg, 20%) by performing substantially the same reaction as in Example 1-1(2) except for using (5R)-5-{(Z)-2-(5-chloro-6-methoxypyridin-2-yl)-2-[4-(propan-2-yl)phenyl]ethenyl}pyrrolidin-2-one.

¹H NMR (300 MHz, CDCl₃) δ ppm 1.23 (s, 3H) 1.25 (s, 3H) 1.85-2.00 (m, 1H) 2.24-2.50 (m, 3H) 2.84-2.98 (m, 1H) 4.32 (td, J=8.1, 8.6 Hz, 1H) 6.08-6.18 (m, 2H) 7.11-7.35 (m, 4H) 7.59-7.68 (m, 1H) 12.53-13.01 (brs, 1H).

MS(+): 357 [M+H]⁺.

Example 4-83

6-{(E)-1-(4-tert-Butylphenyl)-2-[(2R)-5-oxopyrrolidin-2-yl]ethenyl}-3-cyclopropylpyridin-2(1H)-one

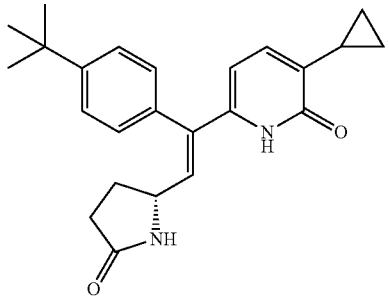

[Ka 268]

(1) (5R)-5-[(E)-2-(4-tert-Butylphenyl)-2-(5-cyclopropyl-6-methoxypyridin-2-yl)ethenyl]pyrrolidin-2-one (216 mg, 55%) was obtained by performing substantially the same reaction as in Example 4-2(1) except for using (4-tert-butylphenyl)(5-cyclopropyl-6-methoxypyridin-2-yl)methanone obtained in Reference Example 1-85. (5R)-5-[(Z)-2-(4-tert-Butylphenyl)-2-(5-cyclopropyl-6-methoxypyridin-2-yl)ethenyl]pyrrolidin-2-one (93 mg, 24%) and an EZ mixture (46 mg, 12%) were also obtained.

(2) The title compound was obtained as a white solid (74 mg, 36%) by performing substantially the same reaction as in Example 1-1(2) except for using (5R)-5-[(E)-2-(4-tert-butylphenyl)-2-(5-cyclopropyl-6-methoxypyridin-2-yl)ethenyl]pyrrolidin-2-one.

¹H NMR (300 MHz, CDCl₃) δ ppm 0.50-0.65 (m, 2H) 0.90-1.04 (m, 2H) 1.36 (s, 9H) 2.00-2.18 (m, 2H) 2.22-2.46 (m, 3H) 4.16-4.27 (m, 1H) 5.86 (d, J=7.2 Hz, 1H) 6.15-6.25 (brs, 1H) 6.35 (d, J=9.8 Hz, 1H) 6.85 (d, J=7.2 Hz, 1H) 7.08 (d, J=7.8 Hz, 2H) 7.42 (d, J=8.4 Hz, 2H) 10.92-11.20 (brs, 1H).

MS(+): 377 [M+H]⁺.

Example 4-84

3-Chloro-6-{(E)-1-[3-chloro-4-(propan-2-yl)phenyl]-2-[(2R)-5-oxopyrrolidin-2-yl]ethenyl}pyridin-2(1H)-one

[Ka 269]

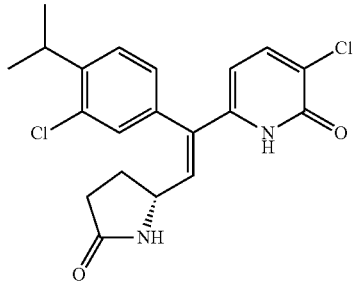

(1) (5R)-5-{(E)-2-(5-Chloro-6-methoxypyridin-2-yl)-2-[3-chloro-4-(propan-2-yl)phenyl]ethenyl}pyrrolidin-2-one was obtained as a colorless amorphous (77 mg, 26%) by performing substantially the same reaction as in Example 4-2(1) except for using (5-chloro-6-methoxypyridin-2-yl)[3-chloro-4-(propan-2-yl)phenyl]methanone obtained in Reference Example 1-86. (5R)-5-{2-(5-Chloro-6-methoxypyridin-2-yl)-2-[3-chloro-4-(propan-2-yl)phenyl]ethenyl}pyrrolidin-2-one (EZ mixture) was also obtained as a colorless amorphous (179 mg, 60%).

(2) The title compound was obtained as a colorless solid (53 mg, 71%) by performing substantially the same reaction as in Example 1-1(2) except for using (5R)-5-{(E)-2-(5-chloro-6-methoxypyridin-2-yl)-2-[3-chloro-4-(propan-2-yl)phenyl]ethenyl}pyrrolidin-2-one.

$^1$H NMR (300 MHz, CDCl$_3$) δ ppm 1.29 (s, 3H) 1.31 (s, 3H) 2.12-2.54 (m, 4H) 3.25-3.50 (m, 1H) 4.22 (td, J=7.8, 7.4 Hz, 1H) 5.85 (d, J=7.5 Hz, 1H) 6.40 (s, 1H) 6.47 (d, J=9.8 Hz, 1H) 7.06 (dd, J=7.8, 1.8 Hz, 1H) 7.17 (d, J=1.5 Hz, 1H) 7.36 (d, J=7.8 Hz, 1H) 7.51 (d, J=7.5 Hz, 1H) 12.44-12.56 (brs, 1H).

MS(+): 391 [M+H]$^+$.

Example 4-85

3-Chloro-6-{2-[(2R)-5-oxopyrrolidin-2-yl]-1-[4-(propan-2-yl)phenyl]ethyl}pyridin-2(1H)-one

[Ka 270]

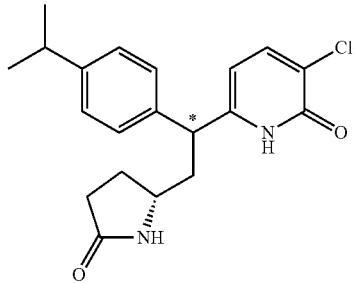

The title compound was obtained as a colorless solid (58 mg, 17% (two steps)) by performing substantially the same reaction as in Examples 4-69 and 4-70(2)(3) sequentially except for using (5R)-5-{2-(5-chloro-6-methoxypyridin-2-yl)-2-[4-(propan-2-yl)phenyl]ethenyl}pyrrolidin-2-one (EZ mixture) obtained in Example 4-82(1), separating the mixture by preparative HPLC (Inertsil ODS-3 (20 mm i.d.×250 mm L, GL Sciences Inc.), 40° C., flow rate: 10 mL/min, acetonitrile:water=40:60) and concentrating the fraction containing a single diastereomer eluted with a retention time of 35 minutes.

$^1$H NMR (300 MHz, CDCl$_3$) δ ppm 1.22 (s, 3H) 1.24 (s, 3H) 1.61-1.85 (m, 1H) 2.13-2.55 (m, 5H) 2.80-2.97 (m, 1H) 3.45-3.59 (m, 1H) 3.90-4.04 (m, 1H) 6.02 (d, J=7.7 Hz, 1H) 7.15-7.28 (m, 4H) 7.28-7.40 (brs, 1H) 7.49 (d, J=7.1 Hz, 1H) 11.67-11.99 (brs, 1H).

MS(+): 359 [M+H]$^+$.

Example 4-86

3-Chloro-6-{1-[3-chloro-4-(propan-2-yl)phenyl]-2-[(2R)-5-oxopyrrolidin-2-yl]ethyl}pyridin-2(1H)-one

[Ka 271]

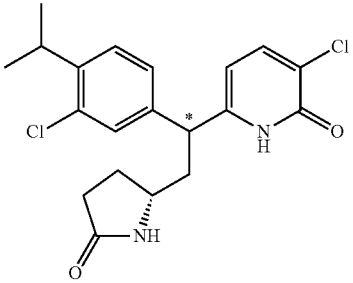

The title compound was obtained as a colorless solid (83 mg, 5% (two steps)) by performing substantially the same reaction as in Examples 4-69 and 4-70(2)(3) sequentially except for using (5R)-5-{2-(5-chloro-6-methoxypyridin-2-yl)-2-[3-chloro-4-(propan-2-yl)phenyl]ethenyl}pyrrolidin-2-one (EZ mixture) obtained in Example 4-84(1), separating the mixture by preparative HPLC (CHIRALPAK IA (10 mm i.d.×250 mm L, Daicel Chemical Industries, LTD.), 40° C., flow rate: 3 mL/min, ethanol:hexane=20:80) and concentrating the fraction containing a single diastereomer eluted with a retention time of 32 minutes.

$^1$H NMR (300 MHz, CDCl$_3$) δ ppm 1.21 (s, 3H) 1.23 (s, 3H) 1.68-1.82 (m, 1H) 2.15-2.51 (m, 5H) 3.28-3.42 (m, 1H) 3.47-3.59 (m, 1H) 3.92-4.03 (m, 1H) 6.02 (d, J=7.7 Hz, 1H) 7.22-7.29 (m, 2H) 7.32 (s, 1H) 7.50 (d, J=7.4 Hz, 1H) 7.47-7.57 (brs, 1H) 12.14-12.40 (brs, 1H).

MS(+): 393 [M+H]$^+$.

Example 4-87

6-{1-(3-Chloro-4-ethoxyphenyl)-2-[(2R)-5-oxopyrrolidin-2-yl]ethyl}-3-cyclopropylpyridin-2(1H)-one

[Ka 272]

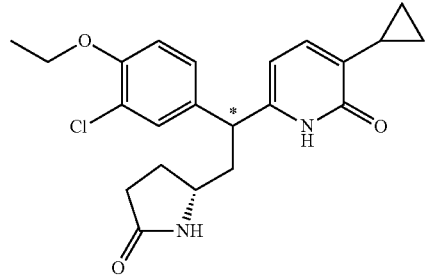

(1) (5R)-5-[(E)-2-(3-Chloro-4-ethoxyphenyl)-2-(5-cyclopropyl-6-methoxypyridin-2-yl)ethenyl]pyrrolidin-2-one (1.32 g, 35%) was obtained by performing substantially the same reaction as in Example 4-2(1) except for using (3-chloro-4-ethoxyphenyl)(5-cyclopropyl-6-methoxypyridin-2-yl)methanone obtained in Reference Example 1-62. (5R)-5-[(Z)-2-(3-Chloro-4-ethoxyphenyl)-2-(5-cyclopropyl-6-methoxypyridin-2-yl)ethenyl]pyrrolidin-2-one (0.97 g, 26%) and an EZ mixture (1.28 mg, 34%) were also obtained.

(2) The title compound was obtained as a white solid (16 mg, 4% (two steps)) by performing substantially the same reaction as in Examples 4-69 and 4-70(2)(3) sequentially except for using (5R)-5-[2-(3-chloro-4-ethoxyphenyl)-2-(5-cyclopropyl-6-methoxypyridin-2-yl)ethenyl]pyrrolidin-2-one (EZ mixture), separating the mixture by preparative HPLC (Inertsil ODS-3 (20 mm i.d.×250 mm L, GL Sciences Inc.), 40° C., flow rate: 10 mL/min, acetonitrile:water=35:65) and concentrating the fraction containing a single diastereomer eluted with a retention time of 65 minutes.

$^1$H NMR (300 MHz, CDCl$_3$) δ ppm 0.53-0.72 (m, 2H) 0.91-1.02 (m, 2H) 1.46 (t, J=6.9 Hz, 3H) 1.60-1.85 (m, 1H) 2.07-2.46 (m, 6H) 3.41-3.58 (m, 1H) 3.87-3.98 (m, 1H) 4.08 (q, J=6.9 Hz, 2H) 5.95 (d, J=6.9 Hz, 1H) 6.82-6.96 (m, 2H) 7.03-7.11 (brs, 1H) 7.20 (dd, J=8.2, 2.3 Hz, 1H) 7.34 (d, J=2.3 Hz, 1H) 11.67-11.88 (brs, 1H).

MS(+): 401 [M+H]$^+$.

Example 4-88

3-Chloro-6-{(E)-1-(4-cyclopropylphenyl)-2-[(2R)-5-oxopyrrolidin-2-yl]ethenyl}pyridin-2(1H)-one

[Ka 273]

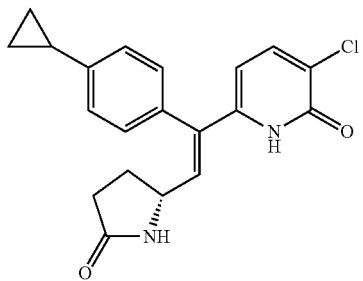

(1) (5R)-5-[2-(5-Chloro-6-methoxypyridin-2-yl)-2-(4-cyclopropylphenyl)ethenyl]pyrrolidin-2-one (EZ mixture) was obtained as a colorless solid (322 mg, 72%) by performing substantially the same reaction as in Example 4-2(1) except for using (5-chloro-6-methoxypyridin-2-yl)(4-cyclopropylphenyl)methanone obtained in Reference Example 1-87.

(2) The title compound was obtained as a colorless solid (48 mg, 50%) by performing substantially the same reaction as in Example 1-1(2) except for using (5R)-5-[2-(5-chloro-6-methoxypyridin-2-yl)-2-(4-cyclopropylphenyl)ethenyl]pyrrolidin-2-one (EZ mixture).

$^1$H NMR (300 MHz, CDCl$_3$) δ ppm 0.72-0.78 (m, 2H) 1.00-1.08 (m, 2H) 1.89-1.99 (m, 1H) 2.10-2.50 (m, 4H) 4.21 (td, J=7.4 Hz, 7.8 Hz, 1H) 5.88 (d, J=7.7 Hz, 1H) 6.16-6.20 (brs, 1H) 6.39 (d, J=9.2 Hz, 1H) 7.04 (d, J=8.0 Hz, 2H) 7.12 (d, J=8.3 Hz, 2H) 7.48 (d, J=7.7 Hz, 1H) 11.90-12.07 (brs, 1H).

MS(+): 355 [M+H]$^+$.

Example 4-89

3-Chloro-6-(1-{4-[(4-methylpiperazin-1-yl)sulfonyl]phenyl}-2-[(2R)-5-oxopyrrolidin-2-yl]ethyl)pyridin-2(1H)-one

[Ka 274]

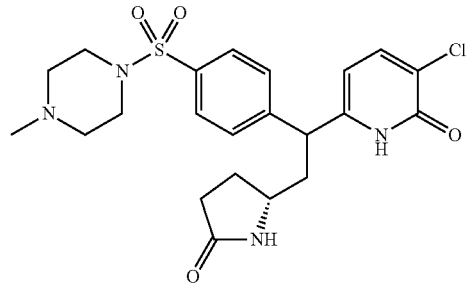

The title compound was obtained by performing substantially the same reaction as in Example 2-3 except for using 3-chloro-6-{(E)-1-{4-[(4-methylpiperazin-1-yl)sulfonyl]phenyl}-2-[(2R)-5-oxopyrrolidin-2-yl]ethenyl}pyridin-2(1H)-one obtained in Example 4-61.

$^1$H NMR (300 MHz, CDCl$_3$) δ ppm 1.73-1.98 (m, 2H), 2.19-2.60 (m, 11H), 2.88-3.16 (m, 4H), 3.48-3.86 (m, 1H), 4.04-4.23 (m, 1H), 6.05-6.15 (m, 1H), 7.47-7.64 (m, 3H), 7.67-7.77 (m, 2H).

MS(+): 479 [M+H]$^+$.

Example 4-90

3-Chloro-6-{(E)-1-[4-(cyclopropyloxy)phenyl]-2-[(2R)-5-oxopyrrolidin-2-yl]ethenyl}pyridin-2(1H)-one

[Ka 275]

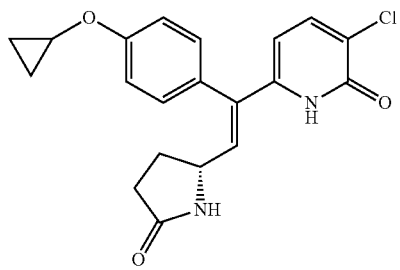

The title compound was obtained by performing substantially the same reaction as in Example 4-2 except for using (5-chloro-6-methoxypyridin-2-yl)[4-(cyclopropyloxy)phenyl]methanone obtained in Reference Example 1-88.

$^1$H NMR (300 MHz, CDCl$_3$) δ ppm 0.76-0.88 (m, 4H), 2.07-2.23 (m, 1H), 2.26-2.50 (m, 3H), 3.71-3.84 (m, 1H), 4.18-4.30 (m, 1H), 5.95 (d, J=7.6 Hz, 1H), 6.10 (s, 1H), 6.35 (d, J=9.0 Hz, 1H), 7.04-7.15 (m, 4H), 7.52 (d, J=7.6 Hz, 1H).

MS(+): 371 [M+H]$^+$.

Example 4-91

6-{(E)-1-(4-tert-Butylphenyl)-2-[(3R)-pyrrolidin-3-yl]ethenyl}-3-chloropyridin-2(1H)-one (1) tert-Butyl (3R)-3-[2-(4-tert-butylphenyl)-2-(5-chloro-6-methoxypyridin-2-yl)ethenyl]pyrrolidine-1-carboxylate (EZ mixture) was obtained as a white amorphous (964 mg, 86%) by performing substantially the same reaction as in Example 4-2(1) except for using (4-tert-butylphenyl)(5-chloro-6-methoxypyridin-2-yl)methanone obtained in Reference Example 1-7 and using tert-butyl (3S)-3-[(1,3-benzothiazol-2-ylsulfonyl)methyl]pyrrolidine-1-carboxylate obtained in Reference Example 3-16.

(2) 6-{(E)-1-(4-tert-Butylphenyl)-2-[(3R)-pyrrolidin-3-yl]ethenyl}-3-chloro-2-methoxypyridine (131 mg, 62%) was obtained by performing the same reaction as in Example 4-46(2) using tert-butyl (3R)-3-[2-(4-tert-butylphenyl)-2-(5-chloro-6-methoxypyridin-2-yl)ethenyl]pyrrolidine-1-carboxylate (EZ mixture).

(3) The title compound was obtained as a white solid (50 mg, 41%) by performing substantially the same reaction as in Example 1-1(2) except for using 6-{(E)-1-(4-tert-butylphenyl)-2-[(3R)-pyrrolidin-3-yl]ethenyl}-3-chloro-2-methoxypyridine.

$^1$H NMR (300 MHz, CDCl$_3$) δ ppm 1.36 (s, 9H), 1.68-1.73 (m, 1H), 1.92-1.99 (m, 1H), 2.67-2.82 (m, 2H), 2.88-2.92 (m, 1H), 3.01-3.11 (m, 2H), 5.95 (d, J=7.8 Hz, 1H), 6.40 (d, J=9.8 Hz, 1H), 7.09 (d, J=8.6 Hz, 2H), 7.42 (d, J=8.6 Hz, 2H), 7.47 (d, J=7.4 Hz, 1H).

MS(+): 357 [M+H]$^+$.
MS(−): 355 [M−H]$^-$.

Example 4-92

6-{(E)-1-(4-tert-Butylphenyl)-2-[(3R)-1-(cyclopropylcarbonyl)pyrrolidin-3-yl]ethenyl}-3-chloropyridin-2(1H)-one (1) 6-{1-(4-tert-Butylphenyl)-2-[(3R)-pyrrolidin-3-yl]ethenyl}-3-chloro-2-methoxypyridine (EZ mixture) (3.01 g, 94%) was obtained by performing the same reaction as in Example 4-46(2) using tert-butyl (3R)-3-[2-(4-tert-butylphenyl)-2-(5-chloro-6-methoxypyridin-2-yl)ethenyl]pyrrolidine-1-carboxylate (EZ mixture) obtained in Example 4-91 (1).

(2) {(3R)-3-[2-(4-tert-Butylphenyl)-2-(5-chloro-6-methoxypyridin-2-yl)ethenyl]pyrrolidin-1-yl}(cyclopropyl)methanone (EZ mixture) (106 mg, 91%) was obtained by performing substantially the same reaction as in Example 4-46(3) except for using 6-{1-(4-tert-butylphenyl)-2-[(3R)-pyrrolidin-3-yl]ethenyl}-3-chloro-2-methoxypyridine (EZ mixture) and using cyclopropanecarbonyl chloride as an acylating reagent.

(3) The title compound was obtained as a white solid (57 mg, 55%) by performing substantially the same reaction as in Example 1-1(2) except for using {(3R)-3-[2-(4-tert-butylphenyl)-2-(5-chloro-6-methoxypyridin-2-yl)ethenyl]pyrrolidin-1-yl}(cyclopropyl)methanone (EZ mixture).

L-Column ODS 4.6×250 mm
0.01 M acetate buffer:MeCN=40:60 v/v, 40° C., 1.0 mL/min, 254 nm
Rt=10.331 min
MS(+): 425 [M+H]$^+$.
MS(−): 423 [M−H]$^-$.

Example 4-93

6-{(E)-1-(4-tert-Butylphenyl)-2-[(3R)-1-(tetrahydro-2H-pyran-4-ylcarbonyl)pyrrolidin-3-yl]ethenyl}-3-chloropyridin-2(1H)-one The title compound was obtained as a white solid (55 mg, 42% (two steps)) by performing substantially the same reaction as in Example 4-92(2)(3) sequentially except for using tetrahydro-2H-pyran-4-carbonylchloride as an acylating reagent.

L-Column ODS 4.6×250 mm
0.01 M acetate buffer:MeCN=40:60 v/v, 40° C., 1.0 mL/min, 254 nm
Rt=12.228 min
MS(+): 469 [M+H]$^+$.
MS(−): 467 [M−H]$^-$.

Example 4-94

6-{(E)-1-(4-tert-Butylphenyl)-2-[(3R)-1-(3,4-difluorobenzyl)pyrrolidin-3-yl]ethenyl}-3-chloropyridin-2(1H)-one (1) The title compound was obtained as a colorless oil (34 mg, 15% (two steps)) by performing substantially the same reaction as in Example 4-92(2)(3) sequentially except for using 4-(chloromethyl)-1,2-difluorobenzene as an alkylating reagent.

(2) A 4 M hydrogen chloride-1,4-dioxane solution (1 mL) was added to the title compound (34 mg). After sonication for one minute, the solvent was evaporated to give a monohydrochloride of the title compound as a white solid (31 mg, 95%).

L-Column ODS 4.6×250 mm
0.01 M acetate buffer:MeCN=40:60 v/v, 40° C., 1.0 mL/min, 254 nm
Rt=6.553 min
MS(+): 483 [M+H]$^+$.
MS(−): 481 [M−H]$^-$.

Example 4-95

6-{(E)-1-(4-tert-Butylphenyl)-2-[(3R)-1-(2-methylpropyl)pyrrolidin-3-yl]ethenyl}-3-chloropyridin-2(1H)-one The title compound was obtained as a colorless amorphous (68 mg, 41% (two steps)) by performing substantially the same reaction as in Example 4-92(2)(3) sequentially except for using 1-chloro-2-methylpropane as an alkylating reagent.

$^1$H NMR (300 MHz, CDCl$_3$) δ ppm 0.89 (dd, J=6.5, 2.5 Hz, 6H), 1.35 (s, 9H), 1.65-1.80 (m, 2H), 1.94-2.08 (m, 1H), 2.13-2.24 (m, 2H), 2.27-2.33 (m, 1H), 2.42-2.50 (m, 1H), 2.61-2.78 (m, 2H), 2.80-2.93 (m, 1H), 5.97 (d, J=7.4 Hz, 1H), 6.42 (d, J=10.2 Hz, 1H), 7.06 (d, J=8.2 Hz, 2H), 7.40 (d, J=8.2 Hz, 2H), 7.47 (d, J=7.8 Hz, 1H), 10.04-10.28 (brs, 1H).

MS(+): 413 [M+H]$^+$.
MS(−): 411 [M−H]$^-$.

Examples 4-96 and 4-97

6-{1-(4-tert-Butylphenyl)-2-[(3S)-1-(cyclopropylcarbonyl)pyrrolidin-3-yl]ethyl}-3-chloropyridin-2(1H)-one One diastereomer (A) of the title compound was obtained as a white solid (60 mg, 23% (two steps)) by performing substantially the same reaction as in Examples 4-69 and 4-70 (2)(3) sequentially except for using {(3R)-3-[2-(4-tert-butylphenyl)-2-(5-chloro-6-methoxypyridin-2-yl)ethenyl]pyrrolidin-1-yl}(cyclopropyl)methanone (EZ mixture) obtained in Example 4-92(2), separating the mixture by preparative HPLC (CHIRALPAK IB (20 mm i.d.×250 mm L, Daicel Chemical Industries, LTD.), 40° C., flow rate: 10 mL/min, ethanol:hexane=20:80) and concentrating the fraction eluted with a retention time of 15 minutes. The fraction eluted with a retention time of 21 minutes was concentrated to give the other diastereomer (B) of the title compound as a white solid (73 mg, 28% (two steps)).

Diastereomer (A);
 CHIRALPAK IB 4.6×250 mm 5 μm (DAICEL)
 Hexane:EtOH=90:10 v/v, 40° C., 1.0 mL/min, 254 nm
 Rt=19.675 min
 MS(+): 427 [M+H]$^+$.
 MS(−): 425 [M−H]$^−$.

Diastereomer (B);
 CHIRALPAK IB 4.6×250 mm 5 μm (DAICEL)
 Hexane:EtOH=90:10 v/v, 40° C., 1.0 mL/min, 254 nm
 Rt=27.095 min
 MS(+): 427 [M+H]$^+$.
 MS(−): 425 [M−H]$^−$.

The structures of Examples 4-91 to 4-97 are shown below.

[Hyo 15]

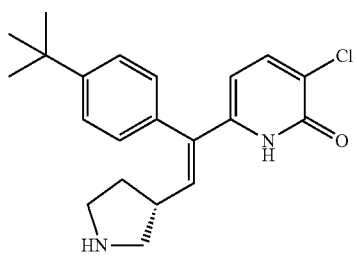

Example 4-91

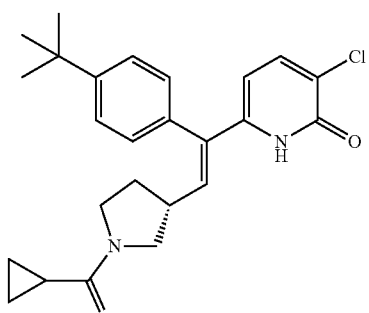

Example 4-92

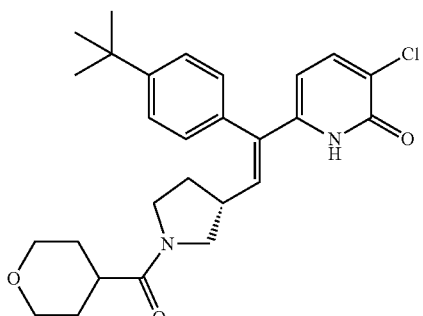

Example 4-93

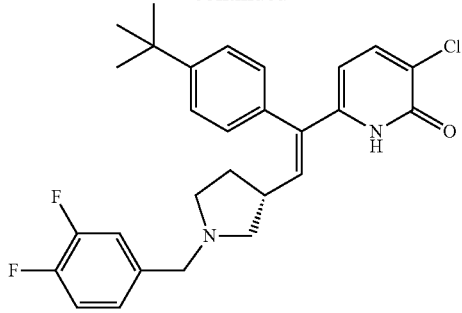

Example 4-94

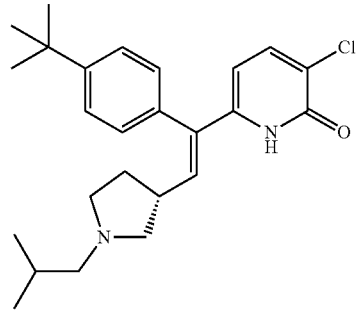

Example 4-95

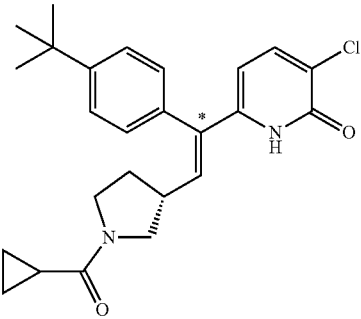

Example 4-96, 97

Example 4-98

6-{(E)-1-(4-Chlorophenyl)-2-[(2R)-5-oxopyrrolidin-2-yl]ethenyl}-3-cyclopropylpyridin-2(1H)-one (1) 1,4-Dioxane (4 mL) and water (0.4 mL) were added to a mixture of (5R)-5-[(Z)-2-bromo-2-(5-cyclopropyl-6-methoxypyridin-2-yl)ethenyl]pyrrolidin-2-one obtained in Reference Example 4-24 (170 mg), 4-chlorophenylboronic acid (160 mg), tris(dibenzylideneacetone) dipalladium (45 mg), tri(2-furyl)phosphine (69 mg) and cesium carbonate (492 mg), and the mixture was stirred at 90° C. for 2.5 hours. Water and ethyl acetate were added to the reaction solution and the insoluble matter was filtered off through celite, followed by extraction with ethyl acetate. The organic layer was dried over anhydrous magnesium sulfate and filtered. The filtrate was concentrated under reduced pressure. The resulting residue was purified by silica gel column chromatography (hexane:ethyl acetate=50:50→0:100) to give (5R)-5-[(E)-2-(4-chlorophenyl)-2-(5-cyclopropyl-6-methoxypyridin-2-yl)ethenyl]pyrrolidin-2-one as a crude product (250 mg).

(2) 1,4-Dioxane (4 mL) and 48% hydrobromic acid (2 mL) were added to (5R)-5-[(E)-2-(4-chlorophenyl)-2-(5-cyclopropyl-6-methoxypyridin-2-yl)ethenyl]pyrrolidin-2-one (250 mg), and the mixture was stirred at 65° C. for two hours. The reaction solution was poured into water, followed by extraction with ethyl acetate. The organic layer was dried over anhydrous magnesium sulfate and filtered. The filtrate was concentrated under reduced pressure. The resulting residue was purified by silica gel column chromatography (chloroform:methanol=100:0→90:10) to give the title compound as a colorless powder (65 mg, 68% (two steps)).
$^1$H NMR (300 MHz, CDCl$_3$) δ ppm 0.48-0.70 (m, 2H), 0.92-1.12 (m, 2H), 1.95-2.18 (m, 2H), 2.16-2.55 (m, 3H), 3.94-4.28 (m, 1H), 5.67-5.85 (m, 1H), 6.16-6.28 (m, 1H), 6.45 (d, J=9.0 Hz, 1H), 6.83 (d, J=7.3 Hz, 1H), 7.07-7.17 (m, 2H), 7.35-7.51 (m, 2H), 11.36-11.69 (brs, 1H).
MS(+): 355 [M+H]$^+$.

The compounds of Examples 4-99 to 4-142 were synthesized by performing substantially the same reaction as in Example 4-98 except for using, in place of 4-chlorophenylboronic acid, corresponding boronic acids or boronate esters ([4-(trifluoromethyl)phenyl]boronic acid, (4-fluorophenyl)boronic acid, (3,4-dichlorophenyl)boronic acid, (2-fluoro-4-methylphenyl)boronic acid, [3-chloro-4-(trifluoromethyl)phenyl]boronic acid, (3-chloro-4-fluorophenyl)boronic acid, [4-chloro-3-(trifluoromethyl)phenyl]boronic acid, (3-chloro-4-methylphenyl)boronic acid, (4-chloro-3-methylphenyl)boronic acid, [6-(trifluoromethyl)pyridin-3-yl]boronic acid, (2-chloro-4-methylphenyl)boronic acid, [4-chloro-2-(trifluoromethyl)phenyl]boronic acid, (4-chloro-3-fluorophenyl)boronic acid, (3,4-difluorophenyl)boronic acid, (4-fluoro-3-methylphenyl)boronic acid, (3-fluoro-4-methylphenyl)boronic acid, (3,4-dimethylphenyl)boronic acid, [3-fluoro-4-(trifluoromethyl)phenyl]boronic acid, [4-fluoro-3-(trifluoromethyl)phenyl]boronic acid, [2,4-bis(trifluoromethyl)phenyl]boronic acid, [3,5-bis(trifluoromethyl)phenyl]boronic acid, (6-chloropyridin-3-yl)boronic acid, (6-fluoropyridin-3-yl)boronic acid, (4-fluoro-2-hydroxyphenyl)boronic acid, 2,3-dihydro-1-benzofuran-5-ylboronic acid, (4-chloro-3-methoxyphenyl)boronic acid, (4-chloro-3-ethylphenyl)boronic acid, [4-(trifluoromethoxy)phenyl]boronic acid, [4-(difluoromethoxy)phenyl]boronic acid, [3-chloro-4-(trifluoromethoxy)phenyl]boronic acid (Reference Example 5-2), [4-chloro-3-(trifluoromethoxy)phenyl]boronic acid (Reference Example 5-3), [4-chloro-3-(difluoromethoxy)phenyl]boronic acid (Reference Example 5-4), 2-[4-(difluoromethyl)-3-fluorophenyl]-4,4,5,5-tetramethyl-1,3,2-dioxaborolane (Reference Example 5-6), 2-[3-chloro-4-(difluoromethyl)phenyl]-4,4,5,5-tetramethyl-1,3,2-dioxaborolane (Reference Example 5-5), 2-[4-(difluoromethyl)-3-methylphenyl]-4,4,5,5-tetramethyl-1,3,2-dioxaborolane (Reference Example 5-7), [4-methoxy-3-(trifluoromethyl)phenyl]boronic acid, 2-[4-(difluoromethyl)-3-methoxyphenyl]-4,4,5,5-tetramethyl-1,3,2-dioxaborolane (Reference Example 5-8), 1-{[4-(4,4,5,5-tetramethyl-1,3,2-dioxaborolan-2-yl)phenyl]sulfonyl}pyrrolidine, 4-(4,4,5,5-tetramethyl-1,3,2-dioxaborolan-2-yl)benzenesulfonamide, [4-(morpholin-4-ylsulfonyl)phenyl]boronic acid, N,N-dimethyl-N'-[4-(4,4,5,5-tetramethyl-1,3,2-dioxaborolan-2-yl)phenyl]sulfuric acid diamide (Reference Example 5-44), N-(2-{[tert-butyl(dimethyl)silyl]oxy}ethyl)-N-methyl-4-(4,4,5,5-tetramethyl-1,3,2-dioxaborolan-2-yl)benzenesulfonamide (Reference Example 5-10), 4,4,5,5-tetramethyl-2-{4-[(trifluoromethyl)sulfanyl]phenyl}-1,3,2-dioxaborolane and [6-(methylsulfonyl)pyridin-3-yl]boronic acid), respectively.

Example 4-99

3-Cyclopropyl-6-{(E)-2-[(2R)-5-oxopyrrolidin-2-yl]-1-[4-(trifluoromethyl)phenyl]ethenyl}pyridin-2 (1H)-one The title compound was obtained as a colorless powder (100 mg, 56% (two steps)).
$^1$H NMR (300 MHz, DMSO-d$_6$) δ ppm 0.49-0.65 (m, 2H), 0.73-0.95 (m, 2H), 1.69-2.33 (m, 5H), 3.72-3.86 (m, 1H), 5.27-5.59 (m, 1H), 6.43-6.59 (m, 1H), 6.78-6.91 (m, 1H), 7.36-7.56 (m, 2H), 7.72-7.86 (m, 3H), 11.32-11.62 (brs, 1H).
MS(+): 389 [M+H]$^+$.

Example 4-100

3-Cyclopropyl-6-{(E)-1-(4-fluorophenyl)-2-[(2R)-5-oxopyrrolidin-2-yl]ethenyl}pyridin-2(1H)-one The title compound was obtained as a colorless powder (42 mg, 41% (two steps)).
$^1$H NMR (300 MHz, CDCl$_3$) δ ppm 0.49-0.73 (m, 2H), 0.93-1.06 (m, 2H), 2.00-2.18 (m, 2H), 2.19-2.48 (m, 3H), 4.06-4.21 (m, 1H), 5.71 (d, J=7.2 Hz, 1H), 6.33-6.50 (m, 2H), 6.83 (d, J=7.3 Hz, 1H), 7.04-7.22 (m, 4H), 11.53-11.85 (brs, 1H).
MS(+): 339 [M+H]$^+$.

Example 4-101

3-Cyclopropyl-6-{(E)-1-(3,4-dichlorophenyl)-2-[(2R)-5-oxopyrrolidin-2-yl]ethenyl}pyridin-2(1H)-one The title compound was obtained as a colorless powder (20 mg, 17% (two steps)).
$^1$H NMR (300 MHz, CDCl$_3$) δ ppm 0.45-0.77 (m, 2H), 0.89-1.13 (m, 2H), 1.98-2.18 (m, 2H), 2.20-2.49 (m, 3H), 4.00-4.23 (m, 1H), 5.67 (d, J=7.3 Hz, 1H), 6.57 (d, J=9.2 Hz, 1H), 6.62-6.74 (m, 1H), 6.83 (dd, J=7.4, 0.7 Hz, 1H), 7.04 (dd, J=8.2, 2.0 Hz, 1H), 7.28 (d, J=2.0 Hz, 1H), 7.51 (d, J=8.2 Hz, 1H), 12.05-12.29 (brs, 1H).
MS(+): 389 [M+H]$^+$.

Example 4-102

3-Cyclopropyl-6-{(E)-1-(2-fluoro-4-methylphenyl)-2-[(2R)-5-oxopyrrolidin-2-yl]ethenyl}pyridin-2(1H)-one The title compound was obtained as a colorless powder (60 mg, 57% (two steps)).
$^1$H NMR (300 MHz, CDCl$_3$) δ ppm 0.54-0.69 (m, 2H), 0.92-1.03 (m, 2H), 1.98-2.17 (m, 2H), 2.21-2.38 (m, 3H), 2.41 (s, 3H), 4.00-4.18 (m, 1H), 5.78 (d, J=7.2 Hz, 1H), 5.82-5.91 (m, 1H), 6.56 (d, J=9.2 Hz, 1H), 6.82 (d, J=7.5 Hz, 1H), 6.90-7.08 (m, 3H), 11.13-11.37 (brs, 1H).
MS(+): 353 [M+H]$^+$.

Example 4-103

6-{(E)-1-[3-Chloro-4-(trifluoromethyl)phenyl]-2-[(2R)-5-oxopyrrolidin-2-yl]ethenyl}-3-cyclopropylpyridin-2(1H)-one The title compound was obtained as a colorless powder (67 mg, 45% (two steps)).

¹H NMR (600 MHz, CDCl₃) δ ppm 0.52-0.66 (m, 2H), 0.93-1.04 (m, 2H), 2.03-2.14 (m, 2H), 2.23-2.45 (m, 3H), 4.04-4.13 (m, 1H), 5.62 (d, J=7.3 Hz, 1H), 6.61 (d, J=9.2 Hz, 1H), 6.68 (s, 1H), 6.83 (d, J=7.3 Hz, 1H), 7.18-7.24 (m, 1H), 7.35 (s, 1H), 7.75 (d, J=7.8 Hz, 1H), 12.11-12.24 (brs, 1H).
MS(+): 423 [M+H]$^+$.

Example 4-104

6-{(E)-1-(3-Chloro-4-fluorophenyl)-2-[(2R)-5-oxopyrrolidin-2-yl]ethenyl}-3-cyclopropylpyridin-2 (1H)-one The title compound was obtained as a colorless powder (56 mg, 42% (two steps)).
¹H NMR (600 MHz, CDCl₃) δ ppm 0.55-0.65 (m, 2H), 0.95-1.03 (m, 2H), 2.03-2.14 (m, 2H), 2.23-2.43 (m, 3H), 4.09-4.15 (m, 1H), 5.71 (d, J=7.3 Hz, 1H), 6.20-6.22 (m, 1H), 6.43 (d, J=9.2 Hz, 1H), 6.84 (d, J=7.3 Hz, 1H), 7.03-7.08 (m, 1H), 7.18-7.24 (m, 2H), 11.36-11.49 (brs, 1H).
MS(+): 373 [M+H]$^+$.

Example 4-105

6-{(E)-1-[4-Chloro-3-(trifluoromethyl)phenyl]-2-[(2R)-5-oxopyrrolidin-2-yl]ethenyl}-3-cyclopropylpyridin-2(1H)-one The title compound was obtained as a colorless powder (60 mg, 40% (two steps)).
¹H NMR (600 MHz, CDCl₃) δ ppm 0.54-0.67 (m, 2H), 0.94-1.06 (m, 2H), 2.08-2.16 (m, 2H), 2.23-2.44 (m, 3H), 4.06-4.11 (m, 1H), 5.63 (d, J=7.3 Hz, 1H), 6.40 (brs, 1H), 6.55 (d, J=9.2 Hz, 1H), 6.84 (d, J=7.3 Hz, 1H), 7.31-7.35 (m, 1H), 7.48-7.51 (m, 1H), 7.59 (d, J=8.3 Hz, 1H), 11.84-12.04 (brs, 1H).
MS(+): 423 [M+H]$^+$.

Example 4-106

6-{(E)-1-(3-Chloro-4-methylphenyl)-2-[(2R)-5-oxopyrrolidin-2-yl]ethenyl}-3-cyclopropylpyridin-2 (1H)-one The title compound was obtained as a colorless powder (54 mg, 48% (two steps)).
¹H NMR (300 MHz, CDCl₃) δ ppm 0.56-0.64 (m, 2H), 0.95-1.02 (m, 2H), 2.01-2.17 (m, 2H), 2.24-2.41 (m, 3H), 2.43 (s, 3H), 4.10-4.21 (m, 1H), 5.79 (d, J=7.2 Hz, 1H), 6.08 (brs, 1H), 6.40 (d, J=9.0 Hz, 1H), 6.84 (d, J=7.3 Hz, 1H), 6.93-6.99 (m, 1H), 7.12-7.17 (m, 1H), 7.26-7.33 (m, 1H).
MS(+): 369 [M+H]$^+$.

Example 4-107

6-{(E)-1-(4-Chloro-3-methylphenyl)-2-[(2R)-5-oxopyrrolidin-2-yl]ethenyl}-3-cyclopropylpyridin-2 (1H)-one The title compound was obtained as a colorless powder (38 mg, 36% (two steps)).
¹H NMR (300 MHz, CDCl₃) δ ppm 0.56-0.64 (m, 2H), 0.95-1.02 (m, 2H), 2.03-2.17 (m, 2H), 2.21-2.39 (m, 3H), 2.40 (s, 3H), 4.09-4.19 (m, 1H), 5.74 (d, J=7.3 Hz, 1H), 6.36 (brs, 1H) 6.45 (d, J=9.2 Hz, 1H), 6.83 (d, J=7.3 Hz, 1H), 6.90-6.98 (m, 1H), 7.02-7.05 (m, 1H) 7.36-7.42 (m, 1H).
MS(+): 369 [M+H]$^+$.

Example 4-108

3-Cyclopropyl-6-{(E)-2-[(2R)-5-oxopyrrolidin-2-yl]-1-[6-(trifluoromethyl)pyridin-3-yl]ethenyl}pyridin-2(1H)-one The title compound was obtained as a colorless powder (22 mg, 18% (two steps)).
MS(+): 390 [M+H]$^+$.

Example 4-109

6-{(E)-1-(2-Chloro-4-methylphenyl)-2-[(2R)-5-oxopyrrolidin-2-yl]ethenyl}-3-cyclopropylpyridin-2 (1H)-one The title compound was obtained as a colorless powder (40 mg, 36% (two steps)).
¹H NMR (300 MHz, CDCl₃) δ ppm 0.54-0.70 (m, 2H), 0.91-1.03 (m, 2H), 1.94-2.44 (m, 8H), 3.87-4.06 (m, 1H), 5.60-5.72 (m, 1H), 5.79-5.96 (m, 1H), 6.57-6.72 (m, 1H), 6.75-6.84 (m, 1H), 7.00-7.10 (m, 1H), 7.11-7.19 (m, 1H), 7.29-7.34 (m, 1H), 11.21-11.47 (brs, 1H).
MS(+): 369 [M+H]$^+$.

Example 4-110

6-{(E)-1-[4-Chloro-2-(trifluoromethyl)phenyl]-2-[(2R)-5-oxopyrrolidin-2-yl]ethenyl}-3-cyclopropylpyridin-2(1H)-one The title compound was obtained as a colorless powder (35 mg, 28% (two steps)).
MS(+): 423 [M+H]$^+$.

Example 4-111

6-{(E)-1-(4-Chloro-3-fluorophenyl)-2-[(2R)-5-oxopyrrolidin-2-yl]ethenyl}-3-cyclopropylpyridin-2 (1H)-one The title compound was obtained as a colorless powder (46 mg, 35% (two steps)).
¹H NMR (600 MHz, CDCl₃) δ ppm 0.53-0.64 (m, 2H), 0.93-1.02 (m, 2H), 2.07-2.17 (m, 2H), 2.21-2.44 (m, 3H), 4.09-4.16 (m, 1H), 5.65 (d, J=7.3 Hz, 1H), 6.60 (d, J=9.2 Hz, 1H), 6.82 (d, J=7.8 Hz, 1H), 6.93-6.97 (m, 1H), 6.99-7.04 (m, 2H), 7.45 (t, J=7.8 Hz, 1H), 12.26-12.59 (brs, 1H).
MS(+): 373 [M+H]$^+$.

Example 4-112

3-Cyclopropyl-6-{(E)-1-(3,4-difluorophenyl)-2-[(2R)-5-oxopyrrolidin-2-yl]ethenyl}pyridin-2(1H)-one The title compound was obtained as a colorless powder (47 mg, 37% (two steps)).
¹H NMR (600 MHz, CDCl₃) δ ppm 0.55-0.66 (m, 2H), 0.94-1.04 (m, 2H), 2.06-2.15 (m, 2H), 2.24-2.44 (m, 3H), 4.11-4.16 (m, 1H), 5.70 (d, J=7.3 Hz, 1H), 6.40-6.42 (m, 1H), 6.48 (d, J=9.2 Hz, 1H), 6.84 (d, J=7.3 Hz, 1H), 6.91-6.95 (m, 1H), 6.99-7.05 (m, 1H), 7.20-7.26 (m, 1H), 11.68-11.76 (brs, 1H).
MS(+): 357 [M+H]$^+$.

Example 4-113

3-Cyclopropyl-6-{(E)-1-(4-fluoro-3-methylphenyl)-2-[(2R)-5-oxopyrrolidin-2-yl]ethenyl}pyridin-2(1H)-one The title compound was obtained as a colorless powder (43 mg, 34% (two steps)).

$^1$H NMR (600 MHz, CDCl$_3$) δ ppm 0.55-0.66 (m, 2H), 0.93-1.03 (m, 2H), 2.01-2.16 (m, 2H), 2.22-2.44 (m, 3H), 2.30 (d, J=1.4 Hz, 3H), 4.10-4.20 (m, 1H), 5.79 (d, J=7.3 Hz, 1H), 6.13 (brs, 1H), 6.36 (d, J=9.2 Hz, 1H), 6.83 (s, 1H), 6.92-7.00 (m, 2H), 7.02-7.10 (m, 1H), 10.95-11.11 (brs, 1H).

MS(+): 353 [M+H]$^+$.

Example 4-114

3-Cyclopropyl-6-{(E)-1-(3-fluoro-4-methylphenyl)-2-[(2R)-5-oxopyrrolidin-2-yl]ethenyl}pyridin-2(1H)-one The title compound was obtained as a colorless powder (15 mg, 12% (two steps)).

$^1$H NMR (600 MHz, CDCl$_3$) δ ppm 0.56-0.65 (m, 2H), 0.96-1.01 (m, 2H), 2.01-2.15 (m, 2H), 2.24-2.42 (m, 3H), 2.33 (s, 3H), 4.14-4.19 (m, 1H), 5.81 (d, J=7.3 Hz, 1H), 6.05 (brs, 1H), 6.37 (d, J=9.2 Hz, 1H), 6.83 (s, 3H), 7.22-7.26 (m, 1H), 10.96-11.12 (brs, 1H).

MS(+): 353 [M+H]$^+$.

Example 4-115

3-Cyclopropyl-6-{(E)-1-(3,4-dimethylphenyl)-2-[(2R)-5-oxopyrrolidin-2-yl]ethenyl}pyridin-2(1H)-one The title compound was obtained as a colorless powder (93 mg, 75% (two steps)).

$^1$H NMR (600 MHz, CDCl$_3$) δ ppm 0.57-0.65 (m, 2H), 0.94-1.00 (m, 2H), 2.00-2.13 (m, 2H), 2.23-2.42 (m, 3H), 2.28 (s, 3H), 2.31 (s, 3H), 4.16-4.21 (m, 1H), 5.87 (brs, 1H), 5.92 (d, J=7.3 Hz, 1H), 6.26 (d, J=9.2 Hz, 1H), 6.84 (d, J=6.9 Hz, 1H), 6.86-6.91 (m, 2H), 7.18 (d, J=7.8 Hz, 1H), 10.29-10.42 (brs, 1H).

MS(+): 349 [M+H]$^+$.

Example 4-116

3-Cyclopropyl-6-{(E)-1-[3-fluoro-4-(trifluoromethyl)phenyl]-2-[(2R)-5-oxopyrrolidin-2-yl]ethenyl}pyridin-2(1H)-one The title compound was obtained as a colorless powder (102 mg, 71% (two steps)).

$^1$H NMR (600 MHz, CDCl$_3$) δ ppm 0.54-0.66 (m, 2H), 0.95-1.04 (m, 2H), 2.07-2.18 (m, 2H), 2.24-2.46 (m, 3H), 4.06-4.14 (m, 1H), 5.63 (d, J=7.3 Hz, 1H), 6.61 (d, J=9.2 Hz, 1H), 6.81 (brs, 1H), 6.84 (d, J=7.3 Hz, 1H), 7.06-7.14 (m, 2H), 7.68 (t, J=7.6 Hz, 1H), 12.16-12.36 (m, 1H).

MS(+): 407 [M+H]$^+$.

Example 4-117

3-Cyclopropyl-6-{(E)-1-[4-fluoro-3-(trifluoromethyl)phenyl]-2-[(2R)-5-oxopyrrolidin-2-yl]ethenyl}pyridin-2(1H)-one The title compound was obtained as a colorless powder (116 mg, 80% (two steps)).

$^1$H NMR (600 MHz, CDCl$_3$) δ ppm 0.53-0.66 (m, 2H), 0.95-1.05 (m, 2H), 2.07-2.16 (m, 2H), 2.23-2.45 (m, 3H), 4.05-4.11 (m, 1H), 5.62 (d, J=7.3 Hz, 1H), 6.50-6.59 (m, 2H), 6.81-6.90 (m, 1H), 7.29 (t, J=9.6 Hz, 1H), 7.37-7.44 (m, 2H), 11.96-12.13 (m, 1H).

MS(+): 407 [M+H]$^+$.

Example 4-118

6-{(E)-1-[2,4-Bis(trifluoromethyl)phenyl]-2-[(2R)-5-oxopyrrolidin-2-yl]ethenyl}-3-cyclopropylpyridin-2(1H)-one The title compound was obtained as a colorless powder (25 mg, 15% (two steps)).

$^1$H NMR (600 MHz, CDCl$_3$) δ ppm 0.57-0.69 (m, 2H), 0.93-1.04 (m, 2H), 2.00-2.18 (m, 3H), 2.19-2.31 (m, 1H), 2.32-2.46 (m, 1H), 3.76-3.82 (m, 1H), 5.40 (dd, J=7.3, 1.4 Hz, 1H), 6.78 (dd, J=7.3, 3.7 Hz, 1H), 6.79-6.86 (m, 1H), 7.39-7.52 (m, 1H), 7.89-7.94 (m, 1H), 8.05 (d, J=12.8 Hz, 1H).

MS(+): 457 [M+H]$^+$.

Example 4-119

6-{(E)-1-[3,5-Bis(trifluoromethyl)phenyl]-2-[(2R)-5-oxopyrrolidin-2-yl]ethenyl}-3-cyclopropylpyridin-2(1H)-one The title compound was obtained as a colorless powder (90 mg, 55% (two steps)).

$^1$H NMR (600 MHz, CDCl$_3$) δ ppm 0.50-0.56 (m, 1H), 0.61-0.66 (m, 1H), 0.96-1.05 (m, 2H), 2.10-2.18 (m, 2H), 2.23-2.30 (m, 1H), 2.31-2.43 (m, 2H), 3.98-4.04 (m, 1H), 5.55 (d, J=7.3 Hz, 1H), 6.74 (d, J=9.2 Hz, 1H), 6.85 (d, J=7.3 Hz, 1H), 7.64 (s, 2H), 7.95 (s, 1H).

MS(+): 457 [M+H]$^+$.

Example 4-120

6-{(E)-1-(6-Chloropyridin-3-yl)-2-[(2R)-5-oxopyrrolidin-2-yl]ethenyl}-3-cyclopropylpyridin-2(1H)-one The title compound was obtained as a colorless powder (49 mg, 39% (two steps)).

$^1$H NMR (600 MHz, CDCl$_3$) δ ppm 0.55-0.59 (m, 1H), 0.61-0.66 (m, 1H), 0.97-1.07 (m, 2H), 2.08-2.16 (m, 2H), 2.26-2.44 (m, 3H), 4.09-4.14 (m, 1H), 5.64 (d, J=7.3 Hz, 1H), 6.49-6.53 (m, 1H), 6.62 (d, J=9.2 Hz, 1H), 6.85 (d, J=7.3 Hz, 1H), 7.41 (d, J=8.3 Hz, 1H), 7.51 (dd, J=8.3, 2.3 Hz, 1H), 8.24 (d, J=1.8 Hz, 1H).

MS(+): 356 [M+H]$^+$.

Example 4-121

3-Cyclopropyl-6-{(E)-1-(6-fluoropyridin-3-yl)-2-[(2R)-5-oxopyrrolidin-2-yl]ethenyl}pyridin-2(1H)-one The title compound was obtained as a colorless powder (2 mg, 2% (two steps)).

$^1$H NMR (600 MHz, CDCl$_3$) δ ppm 0.56-0.67 (m, 2H), 0.97-1.07 (m, 2H), 2.06-2.15 (m, 2H), 2.27-2.45 (m, 3H), 4.10-4.15 (m, 1H), 5.68 (d, J=7.3 Hz, 1H), 6.11 (brs, 1H), 6.50 (d, J=9.2 Hz, 1H), 6.85 (d, J=7.3 Hz, 1H), 7.03 (dd, J=8.5, 2.5 Hz, 1H), 7.63 (td, J=7.9, 2.5 Hz, 1H), 8.06-8.09 (m, 1H), 11.43-11.55 (brs, 1H).

MS(+): 340 [M+H]$^+$.

Example 4-122

3-Cyclopropyl-6-{(E)-1-(4-fluoro-2-hydroxyphenyl)-2-[(2R)-5-oxopyrrolidin-2-yl]ethenyl}pyridin-2(1H)-one The title compound was obtained as a colorless powder (30 mg, 24% (two steps)).

$^1$H NMR (600 MHz, CDCl$_3$) δ ppm 0.52-0.61 (m, 2H), 1.24-1.32 (m, 2H), 2.03-2.10 (m, 2H), 2.22 (dd, J=12.8, 5.0 Hz, 1H), 2.30-2.38 (m, 2H), 4.08-4.14 (m, 1H), 5.76-5.84 (m, 1H), 6.62 (td, J=8.2, 2.3 Hz, 2H), 6.77 (dd, J=10.1, 2.3 Hz, 1H), 6.79-6.83 (m, 1H), 6.89-6.94 (m, 1H), 6.96-7.02 (m, 1H).

MS(+): 355 [M+H]$^+$.

Example 4-123

3-Cyclopropyl-6-{(E)-1-(2,3-dihydro-1-benzofuran-5-yl)-2-[(2R)-5-oxopyrrolidin-2-yl]ethenyl}pyridin-2(1H)-one The title compound was obtained as a colorless powder (40 mg, 31% (two steps)).

$^1$H NMR (300 MHz, CDCl$_3$) δ ppm 0.51-0.67 (m, 2H), 0.89-1.04 (m, 2H), 1.98-2.19 (m, 2H), 2.21-2.55 (m, 3H), 3.14-3.29 (m, 2H), 4.12-4.30 (m, 1H), 4.55-4.75 (m, 2H), 5.82-5.91 (m, 1H), 6.23-6.36 (m, 2H), 6.76-6.94 (m, 3H), 6.95-7.00 (m, 1H), 11.03-11.23 (brs, 1H).

MS(+): 363 [M+H]$^+$.

Example 4-124

6-{(E)-1-(4-Chloro-3-methoxyphenyl)-2-[(2R)-5-oxopyrrolidin-2-yl]ethenyl}-3-cyclopropylpyridin-2(1H)-one The title compound was obtained as a colorless powder (45 mg, 33% (two steps)).

$^1$H NMR (600 MHz, CDCl$_3$) δ ppm 0.55-0.67 (m, 2H), 0.94-1.03 (m, 2H), 2.04-2.15 (m, 2H), 2.22-2.45 (m, 3H), 3.89 (s, 3H), 4.14-4.19 (m, 1H), 5.77 (d, J=7.3 Hz, 1H), 6.36 (brs, 1H), 6.44 (d, J=9.2 Hz, 1H), 6.71-6.75 (m, 2H), 6.83 (d, J=7.3 Hz, 1H), 7.42 (d, J=8.7 Hz, 1H), 11.41-11.59 (brs, 1H).

MS(+): 385 [M+H]$^+$.

Example 4-125

6-{(E)-1-(4-Chloro-3-ethylphenyl)-2-[(2R)-5-oxopyrrolidin-2-yl]ethenyl}-3-cyclopropylpyridin-2(1H)-one The title compound was obtained as a colorless powder (49 mg, 36% (two steps)).

$^1$H NMR (600 MHz, CDCl$_3$) δ ppm 0.55-0.66 (m, 2H), 0.94-1.03 (m, 2H), 1.24 (t, J=7.6 Hz, 3H), 2.03-2.15 (m, 2H), 2.22-2.43 (m, 3H), 2.78 (q, J=7.5 Hz, 2H), 4.11-4.17 (m, 1H), 5.77 (d, J=7.3 Hz, 1H), 6.94 (dd, J=8.0, 2.1 Hz, 1H), 7.03 (d, J=1.8 Hz, 1H), 7.39 (d, J=8.3 Hz, 1H), 11.21-11.33 (brs, 1H).

MS(+): 383 [M+H]$^+$.

Example 4-126

3-Cyclopropyl-6-{(E)-2-[(2R)-5-oxopyrrolidin-2-yl]-1-[4-(trifluoromethoxy)phenyl]ethenyl}pyridin-2(1H)-one The title compound was obtained as a colorless powder (52 mg, 49% (two steps)).

$^1$H NMR (600 MHz, CDCl$_3$) δ ppm 0.55-0.65 (m, 2H), 0.94-1.04 (m, 2H), 2.05-2.16 (m, 2H), 2.24-2.44 (m, 3H), 4.10-4.16 (m, 1H), 5.70 (d, J=7.3 Hz, 1H), 6.36 (brs, 1H), 6.49 (d, J=9.2 Hz, 1H), 6.81-6.86 (m, 1H), 7.20-7.24 (m, 2H), 7.25-7.30 (m, 2H), 11.59-11.73 (brs, 1H).

MS(+): 405 [M+H]$^+$.

Example 4-127

3-Cyclopropyl-6-{(E)-1-[4-(difluoromethoxy)phenyl]-2-[(2R)-5-oxopyrrolidin-2-yl]ethenyl}pyridin-2(1H)-one The title compound was obtained as a colorless powder (41 mg, 30% (two steps)).

$^1$H NMR (600 MHz, CDCl$_3$) δ ppm 0.55-0.66 (m, 2H), 0.95-1.03 (m, 2H), 2.04-2.15 (m, 2H), 2.24-2.43 (m, 3H), 4.11-4.18 (m, 1H), 5.73 (d, J=7.3 Hz, 1H), 6.26 (brs, 1H), 6.44 (d, J=9.2 Hz, 1H), 6.57 (t, J=73.0 Hz, 1H), 6.84 (d, J=7.3 Hz, 1H), 7.18 (s, 4H), 11.40-11.51 (brs, 1H).

MS(+): 387 [M+H]$^+$.

Example 4-128

6-{(E)-1-[3-Chloro-4-(trifluoromethoxy)phenyl]-2-[(2R)-5-oxopyrrolidin-2-yl]ethenyl}-3-cyclopropylpyridin-2(1H)-one The title compound was obtained as a colorless powder (59 mg, 45% (two steps)).

$^1$H NMR (600 MHz, CDCl$_3$) δ ppm 0.54-0.66 (m, 2H), 0.95-1.05 (m, 2H), 2.07-2.16 (m, 2H), 2.26-2.44 (m, 3H), 4.10-4.16 (m, 1H), 5.68 (d, J=7.3 Hz, 1H), 6.50 (brs, 1H), 6.53 (d, J=9.2 Hz, 1H), 6.85 (d, J=6.9 Hz, 1H), 7.11-7.15 (m, 1H), 7.30-7.32 (m, 1H), 7.37-7.41 (m, 1H), 11.83-12.01 (brs, 1H).

MS(+): 439 [M+H]$^+$.

Example 4-129

6-{(E)-1-[4-Chloro-3-(trifluoromethoxy)phenyl]-2-[(2R)-5-oxopyrrolidin-2-yl]ethenyl}-3-cyclopropylpyridin-2(1H)-one The title compound was obtained as a colorless powder (72 mg, 61% (two steps)).
$^1$H NMR (600 MHz, CDCl$_3$) δ ppm 0.53-0.67 (m, 2H), 0.95-1.05 (m, 2H), 2.07-2.15 (m, 2H), 2.23-2.44 (m, 3H), 4.08-4.16 (m, 1H), 5.66 (d, J=7.3 Hz, 1H), 6.51 (brs, 1H), 6.57 (d, J=9.2 Hz, 1H), 6.84 (d, J=7.3 Hz, 1H), 7.10 (dd, J=8.0, 2.1 Hz, 1H), 7.17 (s, 1H), 7.54 (d, J=8.3 Hz, 1H), 12.12-12.27 (brs, 1H).
MS(+): 439 [M+H]$^+$.

Example 4-130

6-{(E)-1-[4-Chloro-3-(difluoromethoxy)phenyl]-2-[(2R)-5-oxopyrrolidin-2-yl]ethenyl}-3-cyclopropylpyridin-2(1H)-one The title compound was obtained as a colorless powder (12 mg, 41% (two steps)).
$^1$H NMR (600 MHz, CDCl$_3$) δ ppm 0.56-0.66 (m, 2H), 0.95-1.04 (m, 2H), 2.04-2.15 (m, 2H), 2.25-2.44 (m, 3H), 4.11-4.16 (m, 1H), 5.72 (d, J=7.3 Hz, 1H), 6.27 (brs, 1H), 6.45 (d, J=9.2 Hz, 1H), 6.62 (t, J=72.9 Hz, 1H), 6.84 (d, J=7.3 Hz, 1H), 7.00-7.03 (m, 1H), 7.10 (brs, 1H), 7.51 (d, J=8.3 Hz, 1H), 11.40-11.56 (brs, 1H).
MS(+): 421 [M+H]$^+$.

Example 4-131

3-Cyclopropyl-6-{(E)-1-[4-(difluoromethyl)-3-fluorophenyl]-2-[(2R)-5-oxopyrrolidin-2-yl]ethenyl}pyridin-2(1H)-one The title compound was obtained as a colorless powder (20 mg, 32% (two steps)).
$^1$H NMR (300 MHz, CDCl$_3$) δ ppm 0.48-0.69 (m, 2H), 0.93-1.05 (m, 2H), 2.06-2.20 (m, 2H), 2.22-2.48 (m, 3H), 4.03-4.21 (m, 1H), 5.60-5.69 (m, 1H), 6.55-6.64 (m, 1H), 6.69-7.14 (m, 5H), 7.62-7.73 (m, 1H), 12.11-12.36 (brs, 1H).
MS(+): 389 [M+H]$^+$.

Example 4-132

6-{(E)-1-[3-Chloro-4-(difluoromethyl)phenyl]-2-[(2R)-5-oxopyrrolidin-2-yl]ethenyl}-3-cyclopropylpyridin-2(1H)-one The title compound was obtained as a colorless powder (50 mg, 46% (two steps)).
$^1$H NMR (300 MHz, CDCl$_3$) δ ppm 0.50-0.79 (m, 2H), 0.88-1.08 (m, 2H), 2.02-2.20 (m, 2H), 2.22-2.48 (m, 3H), 4.02-4.19 (m, 1H), 5.55-5.70 (m, 1H), 6.57-6.68 (m, 1H), 6.75-7.18 (m, 3H), 7.20-7.30 (m, 1H), 7.66-7.79 (m, 1H), 12.16-12.44 (brs, 1H).
MS(+): 405 [M+H]$^+$.

Example 4-133

3-Cyclopropyl-6-{(E)-1-[4-(difluoromethyl)-3-methylphenyl]-2-[(2R)-5-oxopyrrolidin-2-yl]ethenyl}pyridin-2(1H)-one The title compound was obtained as a colorless powder (50 mg, 36% (two steps)).
$^1$H NMR (300 MHz, CDCl$_3$) δ ppm 0.50-0.70 (m, 2H), 0.88-1.10 (m, 2H), 2.01-2.41 (m, 5H), 2.43-2.49 (m, 3H), 4.05-4.22 (m, 1H), 5.64-5.76 (m, 1H), 6.43-6.57 (m, 2H), 6.60-7.01 (m, 2H), 7.03-7.15 (m, 2H), 7.49-7.62 (m, 1H), 11.75-12.02 (brs, 1H).
MS(+): 385 [M+H]$^+$.

Example 4-134

3-Cyclopropyl-6-{(E)-1-[4-methoxy-3-(trifluoromethyl)phenyl]-2-[(2R)-5-oxopyrrolidin-2-yl]ethenyl}pyridin-2(1H)-one The title compound was obtained as a colorless powder (70 mg, 47% (two steps)).
$^1$H NMR (300 MHz, CDCl$_3$) δ ppm 0.42-0.75 (m, 2H), 0.93-1.09 (m, 2H), 2.03-2.19 (m, 2H), 2.21-2.42 (m, 3H), 3.96 (s, 3H), 4.06-4.20 (m, 1H), 5.62-5.74 (m, 1H), 6.45-6.54 (m, 1H), 6.55-6.64 (m, 1H), 6.79-6.88 (m, 1H), 7.01-7.12 (m, 1H), 7.27-7.41 (m, 2H), 11.90-12.10 (brs, 1H).
MS(+): 419 [M+H]$^+$.

Example 4-135

3-Cyclopropyl-6-{(E)-1-[4-(difluoromethyl)-3-methoxyphenyl]-2-[(2R)-5-oxopyrrolidin-2-yl]ethenyl}pyridin-2(1H)-one The title compound was obtained as a colorless powder (12 mg, 8.4% (two steps)).
$^1$H NMR (300 MHz, CDCl$_3$) δ ppm 0.44-0.73 (m, 2H), 0.87-1.17 (m, 2H), 1.93-2.55 (m, 5H), 3.78-3.93 (m, 3H), 4.04-4.38 (m, 1H), 5.72 (d, J=7.2 Hz, 1H), 6.39-7.21 (m, 6H), 7.57-7.74 (m, 1H).
MS(+): 401 [M+H]$^+$.

Example 4-136

3-Cyclopropyl-6-{(E)-2-[(2R)-5-oxopyrrolidin-2-yl]-1-[4-(pyrrolidin-1-ylsulfonyl)phenyl]ethenyl}pyridin-2(1H)-one The title compound was obtained as a colorless powder (69 mg, 43% (two steps)).
$^1$H NMR (600 MHz, CDCl$_3$) δ ppm 0.54-0.67 (m, 2H), 0.94-1.04 (m, 2H), 1.81-1.89 (m, 4H), 2.04-2.15 (m, 2H), 2.26-2.45 (m, 3H), 3.29-3.37 (m, 4H), 4.04-4.11 (m, 1H), 5.66-5.73 (m, 1H), 6.41-6.49 (m, 1H), 6.84 (d, J=7.3 Hz, 1H), 7.34 (d, J=8.3 Hz, 2H), 7.90 (d, J=8.3 Hz, 2H).
MS(+): 454 [M+H]$^+$.

Example 4-137

4-{(E)-1-(5-Cyclopropyl-6-oxo-1,6-dihydropyridin-2-yl)-2-[(2R)-5-oxopyrrolidin-2-yl]ethenyl}benzenesulfonamide The title compound was obtained as a light brown powder (35 mg, 37% (two steps)).

¹H NMR (600 MHz, DMSO-d6) δ ppm 0.53-0.62 (m, 2H), 0.80-0.89 (m, 2H), 1.79-1.90 (m, 1H), 1.95-2.02 (m, 1H), 2.03-2.14 (m, 2H), 2.15-2.26 (m, 1H), 3.76-3.85 (m, 1H), 5.37 (brs, 1H), 6.49 (d, J=8.7 Hz, 1H), 6.85 (brs, 1H), 7.39-7.46 (m, 4H), 7.79 (s, 1H), 7.86 (d, J=8.3 Hz, 2H), 11.32-11.58 (brs, 1H).
MS(+): 400 [M+H]⁺.

Example 4-138

3-Cyclopropyl-6-{(E)-1-[4-(morpholin-4-ylsulfonyl)phenyl]-2-[(2R)-5-oxopyrrolidin-2-yl]ethenyl}pyridin-2(1H)-one The title compound was obtained as a colorless powder (12 mg, 11% (two steps)).
¹H NMR (600 MHz, DMSO-d6) δ ppm 0.55-0.66 (m, 2H), 0.80-0.89 (m, 2H), 1.83-1.93 (m, 1H), 1.95-2.04 (m, 1H), 2.05-2.15 (m, 2H), 2.16-2.27 (m, 1H), 2.88-2.96 (m, 4H), 3.60-3.70 (m, 4H), 3.80-3.89 (m, 1H), 5.43 (brs, 1H), 6.44-6.57 (m, 1H), 6.86 (brs, 1H), 7.50 (d, J=8.3 Hz, 2H), 7.77 (d, J=8.3 Hz, 2H), 7.80 (s, 1H), 11.49 (brs, 1H).
MS(+): 470 [M+H]⁺.

Example 4-139

N'-(4-{(E)-1-(5-Cyclopropyl-6-oxo-1,6-dihydropyridin-2-yl)-2-[(2R)-5-oxopyrrolidin-2-yl]ethenyl}phenyl)-N,N-dimethylsulfuric acid diamide The title compound was obtained as a gray powder (24 mg, 18% (two steps)).
¹H NMR (300 MHz, DMSO-d6) δ ppm 0.52-0.64 (m, 2H), 0.75-0.90 (m, 2H), 1.73-2.30 (m, 5H), 2.73 (s, 6H), 3.75-3.96 (m, 1H), 5.53 (s, 1H), 6.21-6.45 (m, 1H), 6.73-6.92 (m, 1H), 7.03-7.29 (m, 4H), 7.74 (s, 1H), 9.93-10.14 (m, 1H), 11.26-11.49 (m, 1H).
MS(+): 443 [M+H]⁺.

Example 4-140

4-{(E)-1-(5-Cyclopropyl-6-oxo-1,6-dihydropyridin-2-yl)-2-[(2R)-5-oxopyrrolidin-2-yl]ethenyl}-N-(2-hydroxyethyl)-N-methylbenzenesulfonamide The title compound was obtained as a colorless powder (40 mg, 24% (two steps)).
¹H NMR (600 MHz, DMSO-d6) δ ppm 0.55-0.61 (m, 2H), 0.81-0.87 (m, 2H), 1.79-2.25 (m, 5H), 3.03-3.09 (m, 2H), 3.29 (s, 3H), 3.49-3.56 (m, 2H), 3.77-3.87 (m, 1H), 4.80 (t, J=5.5 Hz, 1H), 5.34-5.44 (m, 1H), 6.43-6.53 (m, 1H), 6.78-6.88 (m, 1H), 7.41-7.49 (m, 2H), 7.74-7.83 (m, 2H).
MS(−): 456 [M−H]⁻.

Example 4-141

3-Cyclopropyl-6-[(E)-2-[(2R)-5-oxopyrrolidin-2-yl]-1-{4-[(trifluoromethyl)sulfanyl]phenyl}ethenyl]pyridin-2(1H)-one The title compound was obtained as a colorless powder (62 mg, 79% (two steps)).
¹H NMR (600 MHz, METHANOL-d4) δ ppm 0.60-0.65 (m, 2H), 0.91-0.95 (m, 2H), 1.97-2.06 (m, 2H), 2.22-2.44 (m, 3H), 4.10-4.17 (m, 1H), 5.79 (d, J=7.3 Hz, 1H), 6.34 (d, J=9.2 Hz, 1H), 7.00 (d, J=7.3 Hz, 1H), 7.35-7.40 (m, 2H), 7.78 (d, J=7.8 Hz, 2H).
MS(+): 421 [M+H]⁺.

Example 4-142

3-Cyclopropyl-6-{(E)-1-[6-(methylsulfonyl)pyridin-3-yl]-2-[(2R)-5-oxopyrrolidin-2-yl]ethenyl}pyridin-2(1H)-one The title compound was obtained as a colorless powder (42 mg, 53% (two steps)).
¹H NMR (600 MHz, METHANOL-d4) δ ppm 0.60-0.66 (m, 2H), 0.91-0.96 (m, 2H), 1.99-2.09 (m, 2H), 2.25-2.35 (m, 2H), 2.37-2.45 (m, 1H), 3.28 (s, 3H), 4.05-4.15 (m, 1H), 5.75-5.84 (m, 1H), 6.51 (d, J=9.6 Hz, 1H), 7.00 (d, J=7.3 Hz, 1H), 7.99 (dd, J=7.8, 1.8 Hz, 1H), 8.17 (d, J=8.3 Hz, 1H), 8.63 (d, J=2.3 Hz, 1H).
MS(+): 400 [M+H]⁺.

Example 4-143

6-{(E)-1-[3-Chloro-4-(tetrahydro-2H-pyran-4-yloxy)phenyl]-2-[(2R)-5-oxopyrrolidin-2-yl]ethenyl}-3-cyclopropylpyridin-2(1H)-one (1) (5R)-5-[(E)-2-(3-Chloro-4-hydroxyphenyl)-2-(5-cyclopropyl-6-methoxypyridin-2-yl)ethenyl]pyrrolidin-2-one was obtained as a brown oil (160 mg, 69%) by performing substantially the same reaction as in Example 4-98(1) except for using 3-chloro-4-hydroxyphenylboronic acid in place of 4-chlorophenylboronic acid.
(2) Tetrahydro-4-pyranol (127 mg), a 2.2 M solution of diisopropyl azodicarboxylate in toluene (0.655 mL) and triphenylphosphine (326 mg) were added to a solution of (5R)-5-[(E)-2-(3-chloro-4-hydroxyphenyl)-2-(5-cyclopropyl-6-methoxypyridin-2-yl)ethenyl]pyrrolidin-2-one (160 mg) in tetrahydrofuran (3 mL), and the mixture was stirred at room temperature for four hours. The reaction solution was concentrated, and the residue was purified by silica gel column chromatography (hexane:ethyl acetate=1:1→0:1) to give (5R)-5-[(E)-2-[3-chloro-4-(tetrahydro-2H-pyran-4-yloxy)phenyl]-2-(5-cyclopropyl-6-methoxypyridin-2-yl)ethenyl]pyrrolidin-2-one as a colorless amorphous (120 mg, 61%).
(3) The title compound was obtained as a colorless powder (40 mg, 34%) by performing the same reaction as in Example 4-98(2) except for using (5R)-5-[(E)-2-[3-chloro-4-(tetrahydro-2H-pyran-4-yloxy)phenyl]-2-(5-cyclopropyl-6-methoxypyridin-2-yl)ethenyl]pyrrolidin-2-one.
¹H NMR (300 MHz, CDCl₃) δ ppm 0.44-0.72 (m, 2H), 0.91-1.10 (m, 2H), 1.78-1.97 (m, 2H), 1.99-2.19 (m, 4H), 2.23-2.50 (m, 3H), 3.54-3.72 (m, 2H), 3.94-4.09 (m, 2H), 4.10-4.29 (m, 1H), 4.50-4.70 (m, 1H), 5.79 (d, J=7.3 Hz, 1H), 6.31-6.49 (m, 2H), 6.80-6.90 (m, 1H), 6.92-7.06 (m, 2H), 7.14-7.21 (m, 1H), 11.37-11.65 (brs, 1H).
MS(+): 455 [M+H]⁺.

Example 4-144

3-Cyclopropyl-6-[(E)-2-[(2R)-5-oxopyrrolidin-2-yl]-1-(pyridin-4-yl)ethenyl]pyridin-2(1H)-one (1) 4-Pyridyltributyltin (218 mg), tris(dibenzylideneacetone)dipalladium (27 mg) and tri(2-furyl)phosphine (42 mg) were added to a solution of (5R)-5-[(Z)-2-bromo-2-(5-cyclopropyl-6-methoxypyridin-2-yl)ethenyl]pyrrolidin-2-one obtained in Reference Example 4-24 (100 mg) in 1,4-dioxane (2 mL), and the mixture was stirred at 90° C. for four hours. The reaction solution was poured into water, followed by extraction with ethyl acetate. The organic layer was washed with brine, dried over anhydrous magnesium sulfate and filtered. The solvent was then evaporated under reduced pressure. The residue was purified by NH-silica gel column chromatography (hexane:ethyl acetate=1:1→0:1) to give (5R)-5-[(E)-2-(5-cyclopropyl-6-methoxypyridin-2-yl)-2-(pyridin-4-yl)ethenyl]pyrrolidin-2-one as a colorless amorphous (42 mg).

(2) The title compound was obtained as a colorless powder (20 mg) by performing substantially the same reaction as in Example 4-98(2) except for using (5R)-5-[(E)-2-(5-cyclopropyl-6-methoxypyridin-2-yl)-2-(pyridin-4-yl)ethenyl]pyrrolidin-2-one.

$^1$H NMR (300 MHz, CDCl$_3$) δ ppm 0.51-0.69 (m, 2H), 0.88-1.05 (m, 2H), 1.95-2.17 (m, 2H), 2.23-2.63 (m, 3H), 3.93-4.21 (m, 1H), 5.66 (d, J=7.3 Hz, 1H), 6.49 (d, J=9.3 Hz, 1H), 6.84 (d, J=7.5 Hz, 1H), 7.07-7.23 (m, 2H), 8.53-8.77 (m, 2H).

MS(+): 322 [M+H]$^+$.

Example 4-145

6-{(E)-1-(3-Chloro-4-hydroxyphenyl)-2-[(2R)-5-oxopyrrolidin-2-yl]ethenyl}-3-cyclopropylpyridin-2(1H)-one A 1 M solution of boron tribromide in hexane (0.8 mL) was added to a solution of 6-{(E)-1-(3-chloro-4-ethoxyphenyl)-2-[(2R)-5-oxopyrrolidin-2-yl]ethenyl}-3-cyclopropylpyridin-2(1H)-one obtained in Example 4-10 (110 mg) in chloroform (2 mL), and the mixture was stirred at room temperature for two hours. The reaction solution was poured into water, followed by extraction with ethyl acetate. The organic layer was washed with brine, dried over anhydrous magnesium sulfate and filtered. The solvent was then evaporated under reduced pressure. The residue was purified by silica gel column chromatography (chloroform:methanol=100:0→90:10) to give the title compound as a colorless amorphous (17.5 mg).

$^1$H NMR (300 MHz, DMSO-d6) δ ppm 0.51-0.66 (m, 2H), 0.76-0.92 (m, 2H), 1.73-2.30 (m, 5H), 3.83-4.00 (m, 1H), 5.53 (d, J=7.3 Hz, 1H), 6.35 (d, J=9.5 Hz, 1H), 6.85 (d, J=7.3 Hz, 1H), 6.92-7.06 (m, 2H), 7.12-7.24 (m, 1H), 7.74-7.89 (m, 1H).

MS(+): 371 [M+H]$^+$.

Example 4-146

6-{(E)-1-(4-tert-Butylphenyl)-2-[(2R)-1-methyl-5-oxopyrrolidin-2-yl]ethenyl}-3-chloropyridin-2(1H)-one (1) 1,4-Dioxane (8 mL) and water (2 mL) were added to a mixture of (5R)-5-[(Z)-2-bromo-2-(5-chloro-6-methoxypyridin-2-yl)ethenyl]pyrrolidin-2-one obtained in Reference Example 4-18 (531 mg), 4-tert-butylphenylboronic acid (570 mg), tris(dibenzylideneacetone)dipalladium (147 mg), tri(2-furyl)phosphine (224 mg) and cesium carbonate (1.04 g), and the mixture was stirred at 90° C. for 2.5 hours. Water and ethyl acetate were added to the reaction solution and the insoluble matter was filtered off through celite, followed by extraction with ethyl acetate. The organic layer was dried over anhydrous magnesium sulfate and filtered. The filtrate was concentrated under reduced pressure. The resulting residue was purified by silica gel column chromatography (hexane:ethyl acetate=90:10→60:40) to give (5R)-5-[(E)-2-(4-tert-butylphenyl)-2-(5-chloro-6-methoxypyridin-2-yl)ethenyl]pyrrolidin-2-one as a pale yellow amorphous (597 mg).

(2) 60% sodium hydride (27 mg) was added to a solution of (5R)-5-[(E)-2-(4-tert-butylphenyl)-2-(5-chloro-6-methoxypyridin-2-yl)ethenyl]pyrrolidin-2-one (185 mg) in tetrahydrofuran (5 mL), and the mixture was stirred at room temperature for 20 minutes. Methyl iodide (60 μL) was then added and the mixture was stirred at room temperature for 4.5 hours. Water and ethyl acetate were added to the reaction solution, followed by extraction with ethyl acetate. The organic layer was washed with brine, dried over anhydrous magnesium sulfate and filtered, after which the filtrate was concentrated under reduced pressure. The resulting residue was purified by NH-silica gel column chromatography (hexane:ethyl acetate=80:20) to give (5R)-5-[(E)-2-(4-tert-butylphenyl)-2-(5-chloro-6-methoxypyridin-2-yl)ethenyl]-1-methylpyrrolidin-2-one as a colorless powder (180 mg).

(3) 48% hydrobromic acid (3 mL) was added to a solution of (5R)-5-[(E)-2-(4-tert-butylphenyl)-2-(5-chloro-6-methoxypyridin-2-yl)ethenyl]-1-methylpyrrolidin-2-one (152 mg) in 1,4-dioxane (6 mL), and the mixture was stirred at 65° C. for one hour. The reaction solution was poured into water, followed by extraction with ethyl acetate. The organic layer was dried over anhydrous magnesium sulfate and filtered. The filtrate was concentrated under reduced pressure. The resulting residue was purified by NH-silica gel column chromatography (chloroform:methanol=100:0→98:2) to give a colorless powder (151 mg). This was recrystallized from ethyl acetate-hexane to give the title compound as a colorless powder (99 mg).

$^1$H NMR (600 MHz, CDCl$_3$) δ ppm 1.37 (s, 9H), 2.01-2.09 (m, 1H), 2.15-2.23 (m, 1H), 2.29-2.36 (m, 1H), 2.49-2.57 (m, 1H), 2.79 (s, 3H), 4.03-4.08 (m, 1H), 5.94 (d, J=7.8 Hz, 1H), 6.43 (d, J=9.6 Hz, 1H), 7.11 (d, J=8.3 Hz, 2H), 7.44-7.51 (m, 3H), 11.24-11.34 (brs, 1H).

MS(+): 385 [M+H]$^+$.

Example 4-147

3-Chloro-6-{(E)-2-[(2R)-1-methyl-5-oxopyrrolidin-2-yl]-1-[4-(propan-2-yl)phenyl]ethenyl}pyridin-2(1H)-one (1) 6-bromo-3-chloro-2-methoxypyridine (361 mg), cesium fluoride (246 mg), copper iodide (170 mg) and tetrakis(triphenylphosphine)palladium(0) (92 mg) were added to a solution of (5R)-1-(2,4-dimethoxybenzyl)-5-[(E)-2-[4-(propan-2-yl)phenyl]-2-(tributylstannyl)ethenyl]pyrrolidin-2-one obtained in Reference Example 4-27 (543 mg) in N,N-dimethylformamide (6 mL), and the mixture was stirred at 65° C. for 1.5 hours. Water and ethyl acetate were added to the reaction solution. After filtration through celite, the organic layer was washed with brine. The organic layer dried over anhydrous magnesium sulfate and filtered, after which the solvent was evaporated under reduced pressure. The residue was purified by silica gel column chromatography (hexane:ethyl acetate=4:1→0:1) to give (5R)-5-{(E)-2-(5-chloro-6-methoxypyridin-2-yl)-2-[4-(propan-2-yl)phenyl]ethenyl}-1-(2,4-dimethoxybenzyl)pyrrolidin-2-one as a yellow oil (268 mg).

(2) The title compound was obtained as a colorless powder (65 mg, 65% (two steps)) by performing substantially the same reaction as in Reference Example 4-16 and Example 4-146(2)(3) except for using (5R)-5-{(E)-2-(5-chloro-6-methoxypyridin-2-yl)-2-[4-(propan-2-yl)phenyl]ethenyl}-1-(2,4-dimethoxybenzyl)pyrrolidin-2-one.

$^1$H NMR (300 MHz, CDCl$_3$) δ ppm 1.31 (d, J=7.0 Hz, 6H), 1.98-2.41 (m, 3H), 2.46-2.63 (m, 1H), 2.80 (s, 3H), 2.88-3.13 (m, 1H), 3.92-4.19 (m, 1H), 5.88 (d, J=7.8 Hz, 1H), 6.50 (d, J=9.8 Hz, 1H), 7.10 (d, J=8.2 Hz, 2H), 7.32 (d, J=8.2 Hz, 2H), 7.48 (d, J=7.8 Hz, 1H), 11.77-11.94 (brs, 1H).
MS(+): 371 [M+H]$^+$.

The compounds of Examples 4-148 to 4-157 were synthesized by performing substantially the same reaction as in Example 4-146(1) and (3) except for using, in place of 4-tert-butylphenylboronic acid, corresponding boronic acids or boronate esters ((4-tert-butyl-2-methoxyphenyl)boronic acid, naphthalen-2-ylboronic acid, naphthalen-1-ylboronic acid, biphenyl-4-ylboronic acid, (4-phenoxyphenyl)boronic acid, (3-carbamoylphenyl)boronic acid, [4-(benzyloxy)phenyl]boronic acid, {4-[(methylsulfonyl)amino]phenyl}boronic acid, 1-propan-2-yl-3-[4-(4,4,5,5-tetramethyl-1,3,2-dioxaborolan-2-yl)phenyl]urea (Reference Example 5-45) and 2-[4-(difluoromethyl)-3-(methylsulfonyl)phenyl]-4,4,5,5-tetramethyl-1,3,2-dioxaborolane (Reference Example 5-9)), respectively.

Example 4-148

6-{(E)-1-(4-tert-Butyl-2-methoxyphenyl)-2-[(2R)-5-oxopyrrolidin-2-yl]ethenyl}-3-chloropyridin-2(1H)-one The title compound was obtained as a colorless powder (100 mg, 57% (two steps)).
$^1$H NMR (300 MHz, CDCl$_3$) δ ppm 1.37 (s, 9H), 2.02-2.58 (m, 4H), 3.78 (s, 3H), 3.97-4.24 (m, 1H), 5.73-5.88 (m, 1H), 5.96 (d, J=7.6 Hz, 1H), 6.46 (d, J=9.2 Hz, 1H), 6.87-7.11 (m, 3H), 7.49 (d, J=7.6 Hz, 1H), 10.98-11.27 (brs, 1H).
MS(+): 401 [M+H]$^+$.

Example 4-149

3-Chloro-6-{(E)-1-(naphthalen-2-yl)-2-[(2R)-5-oxopyrrolidin-2-yl]ethenyl}pyridin-2(1H)-one The title compound was obtained as a colorless powder (45 mg, 82% (two steps)).
$^1$H NMR (600 MHz, METHANOL-d4) δ ppm 2.03-2.09 (m, 1H), 2.25-2.32 (m, 2H), 2.35-2.42 (m, 1H), 4.22-4.27 (m, 1H), 5.90 (d, J=7.3 Hz, 1H), 6.43 (d, J=9.2 Hz, 1H), 7.31 (dd, J=8.5, 1.6 Hz, 1H), 7.54-7.56 (m, 2H), 7.61 (d, J=7.8 Hz, 1H), 7.78-7.79 (m, 1H), 7.90-7.93 (m, 2H), 7.95 (d, J=8.7 Hz, 1H).
MS(+): 365 [M+H]$^+$.

Example 4-150

3-Chloro-6-{(E)-1-(naphthalen-1-yl)-2-[(2R)-5-oxopyrrolidin-2-yl]ethenyl}pyridin-2(1H)-one The title compound was obtained as a colorless powder (68 mg, 52% (two steps)).
$^1$H NMR (600 MHz, CDCl$_3$) δ ppm 1.98-2.06 (m, 1H), 2.21-2.28 (m, 2H), 2.43-2.50 (m, 1H), 3.90-4.01 (m, 1H), 5.76 (dd, J=7.6, 5.3 Hz, 1H), 6.96 (m, J=8.7 Hz, 1H), 7.35-7.44 (m, 2H), 7.50-7.63 (m, 3H), 7.73 (dd, J=12.8, 8.3 Hz, 1H), 7.97 (dd, J=12.6, 8.0 Hz, 2H).
MS(+): 365 [M+H]$^+$.

Example 4-151

6-{(E)-1-(Biphenyl-4-yl)-2-[(2R)-5-oxopyrrolidin-2-yl]ethenyl}-3-chloropyridin-2(1H)-one The title compound was obtained as a colorless powder (80 mg, 57% (two steps)).
$^1$H NMR (600 MHz, CDCl$_3$) δ ppm 2.22-2.31 (m, 1H), 2.31-2.40 (m, 2H), 2.44-2.52 (m, 1H), 4.26-4.31 (m, 1H), 5.89 (d, J=7.8 Hz, 1H), 6.53 (d, J=8.7 Hz, 1H), 6.57 (s, 1H), 7.28 (d, J=8.3 Hz, 2H), 7.37-7.42 (m, 1H), 7.46-7.53 (m, 3H), 7.61-7.64 (m, 2H), 7.66-7.68 (m, 2H),
MS(+): 391 [M+H]$^+$.

Example 4-152

3-Chloro-6-[(E)-2-[(2R)-5-oxopyrrolidin-2-yl]-1-(4-phenoxyphenyl)ethenyl]pyridin-2(1H)-one The title compound was obtained as a colorless powder (81 mg, 55% (two steps)).
$^1$H NMR (600 MHz, CDCl$_3$) δ ppm 2.14-2.20 (m, 1H), 2.29-2.39 (m, 2H), 2.41-2.48 (m, 1H), 4.22-4.27 (m, 1H), 5.91 (d, J=7.8 Hz, 1H), 6.29 (s, 1H), 6.41 (d, J=9.2 Hz, 1H), 7.03 (d, J=8.7 Hz, 2H), 7.08-7.14 (m, 4H), 7.19 (t, J=7.3 Hz, 1H), 7.40 (dd, J=8.5, 7.6 Hz, 2H), 7.52 (d, J=7.8 Hz, 1H).
MS(+): 407 [M+H]$^+$.

Example 4-153

3-{(E)-1-(5-Chloro-6-oxo-1,6-dihydropyridin-2-yl)-2-[(2R)-5-oxopyrrolidin-2-yl]ethenyl}benzamide The title compound was obtained as a colorless powder (40 mg, 37% (two steps)).
$^1$H NMR (300 MHz, DMSO-d6) δ ppm 1.73-2.32 (m, 4H), 3.77-3.94 (m, 1H), 5.44-5.70 (m, 1H), 6.46-6.57 (m, 1H), 7.26-8.06 (m, 8H), 11.93-12.22 (brs, 1H).
MS(−): 356 [M−H]$^−$.

Example 4-154

6-{(E)-1-[4-(Benzyloxy)phenyl]-2-[(2R)-5-oxopyrrolidin-2-yl]ethenyl}-3-chloropyridin-2(1H)-one The title compound was obtained as a yellow powder (45 mg, 35% (two steps)).
$^1$H NMR (600 MHz, CDCl$_3$) δ ppm 2.11-2.18 (m, 1H), 2.29-2.38 (m, 2H), 2.40-2.47 (m, 1H), 4.21-4.26 (m, 1H), 5.11 (s, 2H), 5.92 (d, J=7.8 Hz, 1H), 6.11 (s, 1H), 6.34 (d, J=8.7 Hz, 1H), 7.01-7.05 (m, 2H), 7.07-7.11 (m, 2H), 7.35-7.47 (m, 5H), 7.50 (d, J=7.8 Hz, 1H).
MS(+): 421 [M+H]$^+$.

Example 4-155

N-(4-{(E)-1-(5-Chloro-6-oxo-1,6-dihydropyridin-2-yl)-2-[(2R)-5-oxopyrrolidin-2-yl]ethenyl}phenyl)methanesulfonamide The title compound was obtained as a gray powder (79 mg, 92% (two steps)).
$^1$H NMR (300 MHz, METHANOL-d4) δ ppm 1.92-2.08 (m, 1H), 2.23-2.45 (m, 3H), 3.03 (s, 3H), 4.14-4.31 (m, 1H), 5.93 (d, J=7.6 Hz, 1H), 6.31 (d, J=9.3 Hz, 1H), 7.16-7.25 (m, 2H), 7.31-7.37 (m, 2H), 7.63 (d, J=7.8 Hz, 1H).
MS(+): 408 [M+H]$^+$.

Example 4-156

1-(4-{(E)-1-(5-Chloro-6-oxo-1,6-dihydropyridin-2-yl)-2-[(2R)-5-oxopyrrolidin-2-yl]ethenyl}phenyl)-3-propan-2-ylurea The title compound was obtained as a colorless powder (58 mg, 33% (two steps)).

¹H NMR (300 MHz, DMSO-d6) δ ppm 1.10 (d, J=6.5 Hz, 6H), 1.75-1.96 (m, 1H), 2.01-2.24 (m, 3H), 3.67-3.84 (m, 1H), 3.92-4.03 (m, 1H), 5.48-5.70 (m, 1H), 6.00-6.08 (m, 1H), 6.26-6.43 (m, 1H), 7.07 (d, J=8.4 Hz, 2H), 7.42 (d, J=8.4 Hz, 2H), 7.62 (d, J=7.6 Hz, 1H), 7.77 (s, 1H), 8.42 (s, 1H), 11.89-12.16 (brs, 1H).
MS(+): 415 [M+H]$^+$.

Example 4-157

3-Chloro-6-{(E)-1-[4-(difluoromethyl)-3-(methylsulfonyl)phenyl]-2-[(2R)-5-oxopyrrolidin-2-yl]ethenyl}pyridin-2(1H)-one The title compound was obtained as a colorless powder (46 mg, 42% (two steps)).
¹H NMR (300 MHz, CDCl$_3$) δ ppm 2.20-2.58 (m, 4H), 3.21 (s, 3H), 4.02-4.12 (m, 1H), 5.68 (d, J=7.6 Hz, 1H), 6.72 (d, J=9.3 Hz, 1H), 7.02-7.11 (brs, 1H), 7.43-7.87 (m, 3H), 7.93-8.06 (m, 2H), 12.98-13.26 (brs, 1H).
MS(+): 443 [M+H]$^+$.

The compounds of Examples 4-158 to 4-160 were synthesized by performing substantially the same reaction as in Example 4-146(1) except for using corresponding boronic acids or boronate esters ([4-(methylsulfinyl)phenyl]boronic acid, [4-(methylcarbamoyl)phenyl]boronic acid and (4-carbamoylphenyl)boronic acid) in place of 4-tert-butylphenylboronic acid, respectively, and using 6-{(Z)-1-bromo-2-[(2R)-5-oxopyrrolidin-2-yl]ethenyl}-3-chloropyridin-2(1H)-one (Reference Example 4-19) in place of (5R)-5-[(Z)-2-bromo-2-(5-chloro-6-methoxypyridin-2-yl)ethenyl]pyrrolidin-2-one (Reference Example 4-18).

Example 4-158

3-Chloro-6-{(E)-1-[4-(methylsulfinyl)phenyl]-2-[(2R)-5-oxopyrrolidin-2-yl]ethenyl}pyridin-2(1H)-one The title compound was obtained as a colorless powder (7.7 mg, 6.5%).
¹H NMR (300 MHz, CDCl$_3$) δ ppm 2.20-2.41 (m, 3H), 2.42-2.62 (m, 1H), 2.82 (s, 3H), 4.07-4.23 (m, 1H), 5.64-5.75 (m, 1H), 6.62 (d, J=10.3 Hz, 1H), 7.34 (d, J=12.3 Hz, 1H), 7.43 (d, J=8.4 Hz, 2H), 7.48 (d, J=7.6 Hz, 1H), 7.75 (m, J=6.8 Hz, 2H), 12.88-13.22 (brs, 1H).
MS(+): 377 [M+H]$^+$.

Example 4-159

4-{(E)-1-(5-Chloro-6-oxo-1,6-dihydropyridin-2-yl)-2-[(2R)-5-oxopyrrolidin-2-yl]ethenyl}-N-methylbenzamide The title compound was obtained as a colorless powder (11 mg, 10%).
¹H NMR (600 MHz, METHANOL-d4) δ ppm 1.96-2.05 (m, 1H), 2.21-2.32 (m, 2H), 2.33-2.42 (m, 1H), 2.92 (s, 3H), 4.08-4.19 (m, 1H), 5.84 (d, J=7.3 Hz, 1H), 6.37 (d, J=9.6 Hz, 1H), 7.33 (d, J=8.3 Hz, 2H), 7.60 (d, J=7.8 Hz, 1H), 7.88 (s, 2H).
MS(+): 372 [M+H]$^+$.

Example 4-160

4-{(E)-1-(5-Chloro-6-oxo-1,6-dihydropyridin-2-yl)-2-[(2R)-5-oxopyrrolidin-2-yl]ethenyl}benzamide The title compound was obtained as a colorless powder (2 mg, 4.4%).
¹H NMR (600 MHz, METHANOL-d4) δ ppm 1.91-2.02 (m, 1H), 2.13-2.40 (m, 3H), 4.04-4.13 (m, 1H), 5.75 (d, J=7.8 Hz, 1H), 6.54 (d, J=9.6 Hz, 1H), 7.27-7.36 (m, 3H), 7.90 (d, J=8.3 Hz, 2H).
MS(+): 358 [M+H]$^+$.

Example 4-161

4-{(E)-1-(5-Chloro-6-oxo-1,6-dihydropyridin-2-yl)-2-[(2R)-5-oxopyrrolidin-2-yl]ethenyl}-N,N-dimethylbenzamide (1) 4-{(E)-1-(5-Chloro-6-methoxypyridin-2-yl)-2-[(2R)-5-oxopyrrolidin-2-yl]ethenyl}benzoic acid was obtained as a brown oil (131 mg, 97%) by performing substantially the same reaction as in Example 4-146(1) except for using 4-carboxyphenylboronic acid in place of 4-tert-butylphenylboronic acid.
(2) Dimethylamine hydrochloride (43 mg), 1-ethyl-3-(3-dimethylaminopropyl)carbodiimide hydrochloride (121 mg), 1-hydroxybenzotriazole monohydrate (97 mg) and triethylamine were added to a mixed solution of 4-{(E)-1-(5-chloro-6-methoxypyridin-2-yl)-2-[(2R)-5-oxopyrrolidin-2-yl]ethenyl}benzoic acid (131 mg) in chloroform and N,N-dimethylformamide (4 mL, 3:1), and the mixture was stirred at room temperature for three hours. The reaction solution was concentrated and the resulting residue was purified by silica gel chromatography (chloroform:methanol=100:0→80:20) to give 4-{(E)-1-(5-chloro-6-methoxypyridin-2-yl)-2-[(2R)-5-oxopyrrolidin-2-yl]ethenyl}-N,N-dimethylbenzamide as a brown oil (139 mg, 99%).
(3) The title compound was obtained as a light brown powder (5 mg, 3%) by performing substantially the same reaction as in Example 4-146(3) except for using 4-{(E)-1-(5-chloro-6-methoxypyridin-2-yl)-2-[(2R)-5-oxopyrrolidin-2-yl]ethenyl}-N,N-dimethylbenzamide.
¹H NMR (600 MHz, METHANOL-d4) δ ppm 1.96-2.05 (m, 1H), 2.22-2.44 (m, 3H), 3.03 (s, 3H), 3.10 (s, 3H), 4.14-4.21 (m, 1H), 5.88 (d, J=7.8 Hz, 1H), 6.37 (d, J=9.6 Hz, 1H), 7.32 (d, J=7.8 Hz, 2H), 7.50 (d, J=7.8 Hz, 2H), 7.61 (d, J=7.8 Hz, 1H).
MS(+): 386 [M+H]$^+$.

Example 4-162

6-{(E)-1-(4-tert-Butyl-2-hydroxyphenyl)-2-[(2R)-5-oxopyrrolidin-2-yl]ethenyl}-3-chloropyridin-2(1H)-one The title compound was obtained as a colorless powder (35 mg) by performing substantially the same reaction as in Example 4-145 except for using 6-{(E)-1-(4-tert-butyl-2-methoxyphenyl)-2-[(2R)-5-oxopyrrolidin-2-yl]ethenyl}-3-chloropyridin-2(1H)-one obtained in Example 4-148 in place of 6-{(E)-1-(3-chloro-4-ethoxyphenyl)-2-[(2R)-5-oxopyrrolidin-2-yl]ethenyl}-3-cyclopropylpyridin-2(1H)-one.
¹H NMR (300 MHz, DMSO-d6) δ ppm 1.27 (s, 9H), 1.73-1.92 (m, 1H), 1.95-2.33 (m, 3H), 3.77-3.94 (m, 1H), 5.40-5.59 (m, 1H), 6.35-6.51 (m, 1H), 6.80-6.96 (m, 2H), 6.99-7.07 (m, 1H), 7.60 (d, J=7.6 Hz, 1H), 7.65-7.72 (brs, 1H).
MS(+): 387 [M+H]$^+$.

Example 4-163

N-(3-{(E)-1-(5-Chloro-6-oxo-1,6-dihydropyridin-2-yl)-2-[(2R)-5-oxopyrrolidin-2-yl]ethenyl}phenyl)acetamide A crude product was obtained by performing substantially the same reaction as in Example 4-146(1) and (3) except for using (3-acetamidophenyl)boronic acid in place of 4-tert-butylphenylboronic acid. Acetic anhydride (0.5 mL) was added thereto and the mixture was stirred at room temperature for 30 minutes. The reaction solution was poured into 1 M hydrochloric acid, followed by extraction with ethyl acetate. The organic layer was washed with brine, dried over anhydrous magnesium sulfate and filtered. The solvent was then evaporated under reduced pressure. The residue was purified by silica gel column chromatography (chloroform:methanol=100:0→90:10) to give the title compound as a colorless powder (6.0 mg).

$^1$H NMR (300 MHz, CDCl$_3$) δ ppm 2.14 (s, 3H), 2.29-2.75 (m, 4H), 4.02-4.19 (m, 1H), 5.72-5.87 (m, 1H), 6.63-6.74 (m, 1H), 6.87-6.95 (m, 1H), 7.04-7.14 (m, 1H), 7.35-7.50 (m, 2H), 8.17-8.27 (m, 1H), 8.31-8.39 (m, 1H), 8.94-9.05 (m, 1H), 13.19-13.33 (brs, 1H).

MS(+): 372 [M+H]$^+$.

Example 4-164

6-{(E)-1-(4-tert-Butylphenyl)-2-[(2R)-5-oxopyrrolidin-2-yl]ethenyl}-3-methoxypyridin-2(1H)-one (1) 6-Iodo-3-methoxy-2-[(4-methoxybenzyl)oxy]pyridine obtained in Reference Example 4-33 (657 mg), cesium fluoride (269 mg), copper iodide (185 mg) and tetrakis(triphenylphosphine)palladium(0) (102 mg) were added to a solution of (5R)-5-[(E)-2-(4-tert-butylphenyl)-2-(tributylstannyl)ethenyl]-1-(2,4-dimethoxybenzyl)pyrrolidin-2-one obtained in Reference Example 4-26 (604 mg) in N,N-dimethylformamide (6 mL), and the mixture was stirred at 65° C. for 1.5 hours. Water and ethyl acetate were added to the reaction solution. After filtration through celite, the organic layer was washed with brine. The organic layer dried over anhydrous magnesium sulfate and filtered, after which the solvent was evaporated under reduced pressure. The residue was purified by silica gel column chromatography (hexane:ethyl acetate=3:1→1:1) to give (5R)-5-[(E)-2-(4-tert-butylphenyl)-2-{5-methoxy-6-[(4-methoxybenzyl)oxy]-pyridin-2-yl}ethenyl]-1-(2,4-dimethoxybenzyl)pyrrolidin-2-one as a yellow oil (449 mg).

(2) Water (0.2 mL) and 2,3-dichloro-5,6-dicyano-1,4-benzoquinone (72 mg) were added to a solution of (5R)-5-[(E)-2-(4-tert-butylphenyl)-2-{5-methoxy-6-[(4-methoxybenzyl)oxy]-pyridin-2-yl}ethenyl]-1-(2,4-dimethoxybenzyl)pyrrolidin-2-one (202 mg) in chloroform (4 mL), and the mixture was stirred at 65° C. for 21 hours. Chloroform was added. After filtration, the solvent was evaporated under reduced pressure. The resulting residue was purified by silica gel column chromatography (chloroform:methanol=1:0→95:5 9:1) to give 6-{(E)-1-(4-tert-butylphenyl)-2-[(2R)-1-(2,4-dimethoxybenzyl)-5-oxopyrrolidin-2-yl]ethenyl}-3-methoxypyridin-2(1H)-one (65 mg).

(3) Anisole (1 mL) was added to a solution of 6-{(E)-1-(4-tert-butylphenyl)-2-[(2R)-1-(2,4-dimethoxybenzyl)-5-oxopyrrolidin-2-yl]ethenyl}-3-methoxypyridin-2(1H)-one (65 mg) in trifluoroacetic acid (2 mL), and the mixture was stirred at 80° C. for nine hours. The solvent was evaporated under reduced pressure. The residue was purified by silica gel column chromatography (chloroform:methanol=1:0→9:1) to give the title compound as a colorless powder (29 mg).

$^1$H NMR (300 MHz, CDCl$_3$) δ ppm 1.36 (s, 9H), 2.02-2.19 (m, 1H), 2.24-2.49 (m, 3H), 3.87 (s, 3H), 4.13-4.28 (m, 1H), 5.91 (d, J=7.8 Hz, 1H), 6.17 (d, J=9.0 Hz, 1H), 6.47-6.56 (m, 1H), 6.64 (d, J=7.9 Hz, 1H), 7.09 (d, J=8.5 Hz, 2H), 7.42 (d, J=8.5 Hz, 2H)

MS(+): 367 [M+H]$^+$. .

Example 4-165

6-{(E)-1-(4-tert-Butylphenyl)-2-[(2R)-5-oxopyrrolidin-2-yl]ethenyl}-3-(difluoromethoxy)pyridin-2(1H)-one (1) 3-(Difluoromethoxy)-6-iodo-2-[(4-methoxybenzyl)oxy]pyridine obtained in Reference Example 4-34 (727 mg), cesium fluoride (270 mg), copper iodide (187 mg) and tetrakis(triphenylphosphine)palladium (103 mg) were added to a solution of (5R)-5-[(E)-2-(4-tert-butylphenyl)-2-(tributylstannyl)ethenyl]-1-(2,4-dimethoxybenzyl)pyrrolidin-2-one obtained in Reference Example 4-26 (609 mg) in N,N-dimethylformamide (6 mL), and the mixture was stirred at 75° C. for two hours. Water and ethyl acetate were added to the reaction solution. After filtration through celite, the organic layer was washed with brine. The organic layer dried over anhydrous magnesium sulfate and filtered, after which the solvent was evaporated under reduced pressure. The residue was purified by silica gel column chromatography (hexane: ethyl acetate=95:5→1:1) to give (5R)-5-[(E)-2-(4-tert-butylphenyl)-2-{5-(difluoromethoxy)-6-[(4-methoxybenzyl)oxy]-pyridin-2-yl}ethenyl]-1-(2,4-dimethoxybenzyl)pyrrolidin-2-one as a colorless gum (511 mg).

(2) Water (0.4 mL) and 2,3-dichloro-5,6-dicyano-1,4-benzoquinone (1.72 g) were added to a solution of (5R)-5-[(E)-2-(4-tert-butylphenyl)-2-{5-(difluoromethoxy)-6-[(4-methoxybenzyl)oxy]-pyridin-2-yl}ethenyl]-1-(2,4-dimethoxybenzyl)pyrrolidin-2-one (511 mg) in chloroform (8 mL), and the mixture was stirred at 65° C. for 16 hours. Water was added to the reaction solution. After filtration, the solvent was evaporated under reduced pressure. The residue was purified by silica gel column chromatography (hexane: ethyl acetate=1:0→1:1→chloroform:methanol=1:0→95:5→9:1) to give the title compound as a colorless oil (96 mg).

$^1$H NMR (300 MHz, CDCl$_3$) δ ppm 1.20-1.25 (m, 1H), 1.36 (s, 9H), 2.04-2.22 (m, 1H), 2.24-2.53 (m, 3H), 4.15-4.28 (m, 1H), 5.87 (d, J=7.8 Hz, 1H), 6.37 (d, J=9.0 Hz, 1H), 6.46-6.59 (m, 1H), 6.69-7.25 (m, 1H), 7.10 (d, J=8.2 Hz, 2H), 7.44 (d, J=8.4 Hz, 2H), 12.11-12.46 (brs, 1H).

MS(+): 403 [M+H]$^+$.

Example 4-166

6-{(E)-1-(4-tert-Butylphenyl)-2-[(2R)-5-oxopyrrolidin-2-yl]ethenyl}-3-(propan-2-yloxy)pyridin-2(1H)-one The title compound was obtained as a colorless amorphous (170 mg, 60% (two steps)) by performing substantially the same reaction as in Example 4-164(1) and (3) except for using 6-iodo-2-[(4-methoxybenzyl)oxy]-3-(propan-2-yloxy)pyridine obtained in Reference Example 4-35 in place of 6-iodo-3-methoxy-2-[(4-methoxybenzyl)oxy]pyridine.

$^1$H NMR (300 MHz, DMSO-d6) δ ppm 1.21 (d, J=6.1 Hz, 6H), 1.31 (s, 9H), 1.72-1.92 (m, 1H), 1.97-2.31 (m, 3H), 3.77-3.96 (m, 1H), 4.34-4.67 (m, 1H), 5.29-5.53 (m, 1H), 6.17-6.35 (m, 1H), 6.66-6.83 (m, 1H), 7.07-7.22 (m, 2H), 7.36-7.56 (m, 2H), 7.69-7.84 (m, 1H), 11.38-11.59 (brs, 1H).

MS(+): 395 [M+H]$^+$.

Example 4-167

6-{(E)-1-(4-tert-Butylphenyl)-2-[(2R)-5-oxopyrrolidin-2-yl]ethenyl}-3-propoxypyridin-2(1H)-one The title compound was obtained as a colorless amorphous (170 mg, 73% (two steps)) by performing substantially the same reaction as in Example 4-164(1) and (3) except for using 6-iodo-2-[(4-methoxybenzyl)oxy]-3-propoxypyridine obtained in Reference Example 4-32 in place of 6-iodo-3-methoxy-2-[(4-methoxybenzyl)oxy]pyridine.

$^1$H NMR (300 MHz, DMSO-d6) δ ppm 0.95 (t, J=7.4 Hz, 3H), 1.31 (s, 9H), 1.62-1.75 (m, 2H), 1.77-1.93 (m, 1H), 1.97-2.26 (m, 3H), 3.72-3.93 (m, 3H), 5.34-5.50 (m, 1H), 6.20-6.32 (m, 1H), 6.63-6.77 (m, 1H), 7.07-7.21 (m, 2H), 7.39-7.50 (m, 2H), 7.68-7.83 (m, 1H), 11.40-11.54 (brs, 1H), MS(+): 395 [M+H]$^+$.

Example 4-168

3-(Cyclopentyloxy)-6-{(E)-2-[(2R)-5-oxopyrrolidin-2-yl]-1-[4-(trifluoromethyl)phenyl]ethenyl}pyridin-2(1H)-one (1) Tetrakis(triphenylphosphine)palladium(0) (30 mg) was added to a solution of (5R)-1-(2,4-dimethoxybenzyl)-5-{(E)-2-(tributylstannyl)-2-[4-(trifluoromethyl)phenyl]ethenyl}pyrrolidin-2-one obtained in Reference Example 4-29 (184 mg), 3-(cyclopentyloxy)-6-iodo-2-methoxypyridine obtained in Reference Example 4-37 (169 mg), cesium fluoride (80 mg) and copper iodide (60 mg) in N,N-dimethylformamide (2 mL) in a nitrogen atmosphere, and the mixture was stirred at 65° C. for three hours. The reaction solution was left to cool, and then water and ethyl acetate were added, followed by filtration through celite. The filtrate was extracted with ethyl acetate. The organic layer was washed with water and brine and dried over anhydrous magnesium sulfate, after which the solvent was evaporated under reduced pressure. The residue was purified by silica gel column chromatography (hexane:ethyl acetate=19:1→1:1) to give (5R)-5-{(E)-2-[5-(cyclopentyloxy)-6-methoxypyridin-2-yl]-2-[4-(trifluoromethyl)phenyl]ethenyl}-1-(2,4-dimethoxybenzyl)pyrrolidin-2-one as a light yellow oil (184 mg).

(2) 48% hydrobromic acid (3 mL) was added to a solution of (5R)-5-{(E)-2-[5-(cyclopentyloxy)-6-methoxypyridin-2-yl]-2-[4-(trifluoromethyl)phenyl]ethenyl}-1-(2,4-dimethoxybenzyl)pyrrolidin-2-one (184 mg) in 1,4-dioxane (2 mL), and the mixture was stirred at 65° C. for 30 minutes. Water was added to the reaction solution, followed by extraction with ethyl acetate. The organic layer was washed with brine and dried over anhydrous magnesium sulfate, after which the solvent was evaporated under reduced pressure. A solution of the residue in trifluoroacetic acid (4 mL) and anisole (2 mL) was stirred at 80° C. for six hours. The solvent was evaporated from the reaction solution under reduced pressure. The residue was purified by silica gel column chromatography (chloroform:methanol=100:1→4:1) and powdered with ethyl acetate-diethyl ether-hexane to give the title compound as a colorless amorphous (59 mg, 47%).

$^1$H NMR (300 MHz, CDCl$_3$) δ ppm 1.50-1.60 (m, 2H), 1.74-2.00 (m, 6H), 2.15-2.53 (m, 4H), 4.01-4.17 (m, 1H), 4.59-4.71 (m, 1H), 5.63 (d, J=7.8 Hz, 1H), 6.34 (d, J=9.2 Hz, 1H), 6.57 (d, J=8.1 Hz, 1H), 6.96-7.06 (brs, 1H), 7.37 (d, J=7.9 Hz, 2H), 7.70 (d, J=8.1 Hz, 2H), 12.29-12.52 (brs, 1H).
MS(+): 433 [M+H]$^+$.

Example 4-169

6-{(E)-1-(4-Chlorophenyl)-2-[(2R)-5-oxopyrrolidin-2-yl]ethenyl}-3-(3-hydroxypropoxy)pyridin-2(1H)-one The title compound was obtained as a light brown amorphous (56 mg, 69% (two steps)) by performing substantially the same reaction as in Example 4-168(1)(2) except for using 3-(3-{[tert-butyl(dimethyl)silyl]oxy}propoxy)-6-iodo-2-methoxypyridine obtained in Reference Example 4-38 and (5R)-5-[(E)-2-(4-chlorophenyl)-2-(tributylstannyl)ethenyl]-1-(2,4-dimethoxybenzyl)pyrrolidin-2-one obtained in Reference Example 4-28.

$^1$H NMR (600 MHz, METHANOL-d4) δ ppm 1.92-2.02 (m, 3H), 2.18-2.32 (m, 2H), 2.32-2.40 (m, 1H), 3.72 (t, J=6.2 Hz, 2H), 4.03 (t, J=6.2 Hz, 2H), 4.07-4.13 (m, 1H), 5.78 (d, J=7.8 Hz, 1H), 6.18 (d, J=9.6 Hz, 1H), 6.83 (d, J=7.8 Hz, 1H), 7.20 (d, J=8.3 Hz, 2H), 7.44 (d, J=8.7 Hz, 2H).
MS(+): 389 [M+H]$^+$.

Example 4-170

3-(3-Hydroxypropoxy)-6-{(E)-2-[(2R)-5-oxopyrrolidin-2-yl]-1-[4-(trifluoromethyl)phenyl]ethenyl}pyridin-2(1H)-one The title compound was obtained as a colorless amorphous (47 mg, 58% (two steps)) by performing substantially the same reaction as in Example 4-168(1)(2) except for using 3-(3-{[tert-butyl(dimethyl)silyl]oxy}propoxy)-6-iodo-2-methoxypyridine obtained in Reference Example 4-38 in place of 3-(cyclopentyloxy)-6-iodo-2-methoxypyridine.

$^1$H NMR (600 MHz, METHANOL-d4) δ ppm 1.94-2.03 (m, 3H), 2.19-2.32 (m, 2H), 2.33-2.41 (m, 1H), 3.72 (t, J=6.2 Hz, 2H), 4.00-4.10 (m, 3H), 5.73 (d, J=7.8 Hz, 1H), 6.25 (d, J=9.2 Hz, 1H), 6.82 (d, J=7.8 Hz, 1H), 7.43 (d, J=8.3 Hz, 2H), 7.75 (d, J=7.8 Hz, 2H).
MS(+): 423 [M+H]$^+$.

Example 4-171

3-(3-Hydroxy-2,2-dimethylpropoxy)-6-{(E)-2-[(2R)-5-oxopyrrolidin-2-yl]-1-[4-(trifluoromethyl)phenyl]ethenyl}pyridin-2(1H)-one The title compound was obtained as a colorless amorphous (8 mg, 33% (two steps)) by performing substantially the same reaction as in Example 4-168(1)(2) except for using 3-(3-{[tert-butyl(diphenyl)silyl]oxy}-2,2-dimethylpropoxy)-6-iodo-2-methoxypyridine obtained in Reference Example 4-39 in place of 3-(cyclopentyloxy)-6-iodo-2-methoxypyridine.

$^1$H NMR (300 MHz, CDCl$_3$) δ ppm 1.10 (d, J=5.3 Hz, 6H), 2.04-2.52 (m, 4H), 3.65-3.83 (m, 2H), 4.04-4.17 (m, 1H), 4.23-4.37 (m, 2H), 5.66 (d, J=7.8 Hz, 1H), 6.31 (d, J=9.5 Hz, 1H), 6.64 (d, J=7.8 Hz, 1H), 7.28-7.33 (brs, 1H), 7.38 (d, J=7.8 Hz, 2H), 7.70 (d, J=7.9 Hz, 2H).
MS(+): 451 [M+H]$^+$.

Example 4-172

3-Cyclopropyl-6-{(Z)-2-[(2R)-5-oxopyrrolidin-2-yl]-1-[5-(trifluoromethyl)pyridin-2-yl]ethenyl}pyridin-2(1H)-one The title compound was obtained as a colorless amorphous (45 mg, 10% (two steps)) by performing substantially the same reaction as in Example 4-168(1)(2) except for using 6-bromo-3-cyclopropyl-2-methoxypyridine obtained in Reference Example 4-20 and (5R)-1-(2,4-dimethoxybenzyl)-5-{(E)-2-(tributylstannyl)-2-[5-(trifluoromethyl)pyridin-2-yl]ethenyl}pyrrolidin-2-one obtained in Reference Example 4-30.

$^1$H NMR (300 MHz, CDCl$_3$) δ ppm 0.49-0.70 (m, 2H), 0.86-1.07 (m, 2H), 1.97-2.22 (m, 2H), 2.31-2.60 (m, 3H), 4.16-4.34 (m, 1H), 5.77 (d, J=7.3 Hz, 1H), 6.43-6.55 (m, 1H), 6.60 (d, J=9.0 Hz, 1H), 6.80-6.94 (m, 1H), 7.36-7.48 (m, 1H), 7.89-8.04 (m, 1H), 8.88-9.04 (m, 1H), 12.19-12.44 (brs, 1H).
MS(+): 390 [M+H]$^+$.

Example 4-173

3-Amino-6-{(E)-1-(4-tert-butylphenyl)-2-[(2R)-5-oxopyrrolidin-2-yl]ethenyl}pyridin-2(1H)-one (1) Tetrakis(triphenylphosphine)palladium(0) (50 mg) was added to a solution of (5R)-5-[(E)-2-(4-tert-butylphenyl)-2-(tributylstannyl)ethenyl]-1-(2,4-dimethoxybenzyl)pyrrolidin-2-one obtained in Reference Example 4-26 (296 mg), 6-iodo-2-methoxypyridin-3-amine obtained in Reference Example 4-31(1) (220 mg), cesium fluoride (135 mg) and copper iodide (93 mg) in N,N-dimethylformamide (1.5 mL) in a nitrogen atmosphere, and the mixture was stirred at 65° C. for three hours. The reaction solution was left to cool, and then water and ethyl acetate were added, followed by filtration through celite. The filtrate was extracted with ethyl acetate. The organic layer was washed with water and brine and dried over anhydrous magnesium sulfate, after which the solvent was evaporated under reduced pressure. The residue was purified by silica gel column chromatography (hexane:ethyl acetate=4:1→1:4) to give (5R)-5-[(E)-2-(5-amino-6-methoxypyridin-2-yl)-2-(4-tert-butylphenyl)ethenyl]-1-(2,4-dimethoxybenzyl)pyrrolidin-2-one as a light brown amorphous (152 mg, 68%).

(2) A solution of (5R)-5-[(E)-2-(5-amino-6-methoxypyridin-2-yl)-2-(4-tert-butylphenyl)ethenyl]-1-(2,4-dimethoxybenzyl)pyrrolidin-2-one (198 mg) in trifluoroacetic acid (4 mL) and anisole (2 mL) was stirred at 80° C. for six hours. Saturated aqueous sodium bicarbonate was added to the reaction solution, followed by extraction with ethyl acetate. The organic layer was washed with brine and dried over anhydrous magnesium sulfate, after which the solvent was evaporated under reduced pressure. The residue was purified by silica gel column chromatography (hexane:ethyl acetate=4:1→1:4) to give (5R)-5-[(E)-2-(5-amino-6-methoxypyridin-2-yl)-2-(4-tert-butylphenyl)ethenyl]pyrrolidin-2-one as a light brown solid (61 mg, 44%).

(3) 48% hydrobromic acid (0.5 mL) was added to a solution of (5R)-5-[(E)-2-(5-amino-6-methoxypyridin-2-yl)-2-(4-tert-butylphenyl)ethenyl]pyrrolidin-2-one (20 mg) in 1,4-dioxane (1 mL), and the mixture was stirred at 65° C. for 30 minutes. Water was added to the reaction solution, followed by extraction with ethyl acetate. The organic layer was washed with brine and dried over anhydrous magnesium sulfate, after which the solvent was evaporated under reduced pressure. The residue was purified by silica gel column chromatography (chloroform:methanol=10:0→4:1) and crystallized from chloroform-ethyl acetate to give the title compound as a light brown powder (8 mg, 44%).
$^1$H NMR (300 MHz, METHANOL-d4) δ ppm 1.26 (s, 9H), 1.80-1.96 (m, 1H), 2.08-2.33 (m, 3H), 3.99-4.09 (m, 1H), 5.66 (d, J=7.8 Hz, 1H), 5.94 (d, J=9.3 Hz, 1H), 6.46 (d, J=7.6 Hz, 1H), 7.05 (d, J=8.5 Hz, 2H), 7.39 (d, J=8.5 Hz, 2H).
MS(+): 352 [M+H]$^+$.

Example 4-174

6-{(E)-1-(4-tert-Butylphenyl)-2-[(2R)-5-oxopyrrolidin-2-yl]ethenyl}-3-(dimethylamino)pyridin-2(1H)-one (1) A 37% formamide solution (40 μL) was added to a solution of (5R)-5-[(E)-2-(5-amino-6-methoxypyridin-2-yl)-2-(4-tert-butylphenyl)ethenyl]pyrrolidin-2-one obtained in Example 4-173(2) (40 mg) in acetonitrile (2 mL) under ice-cooling, followed by stirring for 10 minutes. Sodium triacetoxyborohydride (120 mg) was added thereto and the mixture was stirred at room temperature for 15 hours. Saturated aqueous sodium bicarbonate was added to the reaction solution, followed by extraction with ethyl acetate. The organic layer was washed with brine and dried over anhydrous sodium sulfate, after which the solvent was evaporated under reduced pressure to give (5R)-5-{(E)-2-(4-tert-butylphenyl)-2-[5-(dimethylamino)-6-methoxypyridin-2-yl]ethenyl}pyrrolidin-2-one as a yellow oil (41 mg).

(2) 48% hydrobromic acid (0.5 mL) was added to a solution of (5R)-5-{(E)-2-(4-tert-butylphenyl)-2-[5-(dimethylamino)-6-methoxypyridin-2-yl]ethenyl}pyrrolidin-2-one (41 mg) in 1,4-dioxane (1 mL), and the mixture was stirred at 65° C. for 30 minutes. Water was added to the reaction solution, followed by extraction with ethyl acetate. The organic layer was washed with brine and dried over anhydrous magnesium sulfate, after which the solvent was evaporated under reduced pressure. The residue was purified by silica gel column chromatography (chloroform:methanol=10:0→4:1) and crystallized from chloroform-ethyl acetate to give the title compound as a light yellow powder (11 mg, 26% (two steps)).
$^1$H NMR (300 MHz, CDCl$_3$) δ ppm 1.36 (s, 9H), 1.92-2.06 (m, 1H), 2.22-2.47 (m, 3H), 2.89 (s, 6H), 4.11-4.22 (m, 1H), 5.72-5.80 (brs, 1H), 5.97 (d, J=7.6 Hz, 1H), 6.05 (d, J=9.2 Hz, 1H), 6.54 (d, J=9.9 Hz, 1H), 7.07 (d, J=8.4 Hz, 2H), 7.43 (d, J=8.4 Hz, 2H).
MS(+): 380 [M+H]$^+$.

Example 4-175

3-Acetyl-6-{(E)-1-(4-tert-butylphenyl)-2-[(2R)-5-oxopyrrolidin-2-yl]ethenyl}pyridin-2(1H)-one (1) Tetrakis(triphenylphosphine)palladium(0) (170 mg) was added to a solution of (5R)-5-[(E)-2-(4-tert-butylphenyl)-2-(tributylstannyl)ethenyl]-1-(2,4-dimethoxybenzyl)pyrrolidin-2-one obtained in Reference Example 4-26 (1.00 g), 1-(6-bromo-2-methoxypyridin-3-yl)ethanone obtained in Reference Example 4-40 (674 mg), cesium fluoride (447 mg) and copper iodide (308 mg) in N,N-dimethylformamide (10 mL) in a nitrogen atmosphere, and the mixture was stirred at 65° C. for one hour. The reaction solution was left to cool, and then water and ethyl acetate were added, followed by filtration through celite. The filtrate was extracted with ethyl acetate. The organic layer was washed with water and brine and dried over anhydrous magnesium sulfate, after which the solvent was evaporated under reduced pressure. The residue was purified by silica gel column chromatography (hexane:ethyl acetate=1:1) to give (5R)-5-[(E)-2-(5-acetyl-6-methoxypyridin-2-yl)-2-(4-tert-butylphenyl)ethenyl]-1-(2,4-dimethoxybenzyl)pyrrolidin-2-one as a pale yellow amorphous (773 mg).

(2) 48% hydrobromic acid (3.0 mL) was added to a solution of (5R)-5-[(E)-2-(5-acetyl-6-methoxypyridin-2-yl)-2-(4-tert-butylphenyl)ethenyl]-1-(2,4-dimethoxybenzyl)pyrrolidin-2-one (300 mg) in 1,4-dioxane (3.0 mL), and the mixture was stirred at 65° C. for 0.5 hour. Water was added to the reaction solution, followed by extraction with ethyl acetate. The organic layer was washed with brine and dried over anhydrous magnesium sulfate, after which the solvent was evaporated under reduced pressure. Anisole (2 mL) was added to a solution of the residue (278 mg) in trifluoroacetic acid (1 mL), and the mixture was stirred at 80° C. for 4.5 hours. The solvent was evaporated under reduced pressure.

The residue was purified by silica gel column chromatography (chloroform:methanol=1:0→9:1) to give the title compound as a yellow powder (103 mg).

$^1$H NMR (300 MHz, METHANOL-d4) δ ppm 1.36 (s, 9H), 1.94-2.11 (m, 1H), 2.18-2.48 (m, 3H), 2.61 (s, 3H), 4.18-4.32 (m, 1H), 6.04-6.17 (m, 1H), 6.46 (d, J=9.3 Hz, 1H), 7.18 (d, J=8.5 Hz, 2H), 7.53 (d, J=8.5 Hz, 2H), 8.03-8.17 (m, 1H).

MS(+): 379 [M+H]$^+$.

Example 4-176

6-{(E)-1-(4-tert-Butylphenyl)-2-[(2R)-5-oxopyrrolidin-2-yl]ethenyl}-3-ethylpyridin-2(1H)-one (1) Sodium borohydride (108 mg) was added to a solution of (5R)-5-[(E)-2-(5-acetyl-6-methoxypyridin-2-yl)-2-(4-tert-butylphenyl)ethenyl]-1-(2,4-dimethoxybenzyl)pyrrolidin-2-one obtained in Example 4-175(1) (773 mg) in methanol under ice-cooling, followed by stirring for 40 minutes. The reaction solution was poured into water and extracted with chloroform. The organic layer was dried over anhydrous magnesium sulfate. After filtration, the solvent was evaporated under reduced pressure. The residue was purified by silica gel column chromatography (hexane:ethyl acetate=1:0→1:1) to give (5R)-5-{(E)-2-(4-tert-butylphenyl)-2-[5-(1-hydroxyethyl)-6-methoxypyridin-2-yl]ethenyl}-1-(2,4-dimethoxybenzyl)pyrrolidin-2-one as a colorless amorphous (388 mg).

(2) Sodium hydride (22 mg, 60% in oil) was added to a solution of (5R)-5-{(E)-2-(4-tert-butylphenyl)-2-[5-(1-hydroxyethyl)-6-methoxypyridin-2-yl]ethenyl}-1-(2,4-dimethoxybenzyl)pyrrolidin-2-one (100 mg) in tetrahydrofuran (2 mL) under ice-cooling, and the mixture was stirred at the same temperature for 15 minutes. The reaction solution was warmed to room temperature and carbon disulfide (66.7 μL) was added, followed by stirring for 30 minutes. Methyl iodide (68.5 μL) was added and the mixture was stirred for 3.5 hours. Water was added to the reaction solution, followed by extraction with chloroform. The organic layer was dried over anhydrous magnesium sulfate, after which the solvent was evaporated under reduced pressure. The residue was purified by silica gel column chromatography (hexane:ethyl acetate=2:1→1:1) to give O-[1-(6-{(E)-1-(4-tert-butylphenyl)-2-[(2R)-1-(2,4-dimethoxybenzyl)-5-oxopyrrolidin-2-yl]ethenyl}-2-methoxypyridin-3-yl)ethyl] S-methyl carbonodithioate as a colorless oil (109 mg).

(3) Tributyltin hydride (91 μL) and azobisisobutyronitrile (8.5 mg) were added to a solution of O-[1-(6-{(E)-1-(4-tert-butylphenyl)-2-[(2R)-1-(2,4-dimethoxybenzyl)-5-oxopyrrolidin-2-yl]ethenyl}-2-methoxypyridin-3-yl)ethyl] S-methyl carbonodithioate (109 mg) in toluene (2 mL), and the mixture was stirred at 120° C. for 30 minutes. Water was added to the reaction solution, followed by extraction with chloroform. The organic layer was dried over anhydrous magnesium sulfate and filtered. The solvent was then evaporated under reduced pressure. The residue was purified by silica gel column chromatography (hexane:ethyl acetate=3:1) to give (5R)-5-[(E)-2-(4-tert-butylphenyl)-2-(5-ethyl-6-methoxypyridin-2-yl)ethenyl]-1-(2,4-dimethoxybenzyl)pyrrolidin-2-one as a colorless oil (65 mg).

(4) 48% hydrobromic acid (0.6 mL) was added to a solution of (5R)-5-[(E)-2-(4-tert-butylphenyl)-2-(5-ethyl-6-methoxypyridin-2-yl)ethenyl]-1-(2,4-dimethoxybenzyl)pyrrolidin-2-one (59 mg) in 1,4-dioxane (0.6 mL), and the mixture was stirred at 65° C. for 1.5 hours. Water was added to the reaction solution, followed by extraction with ethyl acetate. The organic layer was washed with brine and dried over anhydrous magnesium sulfate, after which the solvent was evaporated under reduced pressure. The resulting residue was purified by silica gel column chromatography (chloroform:methanol=10:0→3:1) to give 6-{(E)-1-(4-tert-butylphenyl)-2-[(2R)-1-(2,4-dimethoxybenzyl)-5-oxopyrrolidin-2-yl]ethenyl}-3-ethylpyridin-2(1H)-one as a colorless oil (49 mg).

(5) Anisole (0.25 mL) was added to a solution of 6-{(E)-1-(4-tert-butylphenyl)-2-[(2R)-1-(2,4-dimethoxybenzyl)-5-oxopyrrolidin-2-yl]ethenyl}-3-ethylpyridin-2(1H)-one (49 mg) in trifluoroacetic acid (0.5 mL), and the mixture was stirred at 65° C. for seven hours. Trifluoroacetic acid (0.5 mL) was added and the mixture was stirred for further five hours, after which the solvent was evaporated under reduced pressure. The residue was purified by silica gel column chromatography (chloroform:methanol=1:0→9:1). The resulting crystals (25 mg) were recrystallized from ethyl acetate-hexane to give the title compound as a colorless powder (20 mg).

$^1$H NMR (300 MHz, CDCl$_3$) δ ppm 1.18 (t, J=7.5 Hz, 3H), 1.36 (s, 9H), 1.99-2.09 (m, 1H), 2.24-2.44 (m, 3H), 2.50-2.60 (m, 2H), 4.16-4.26 (m, 1H), 5.59-5.70 (m, 1H), 6.04 (d, J=6.8 Hz, 1H), 6.20 (d, J=9.0 Hz, 1H), 7.07 (d, J=8.5 Hz, 2H), 7.18 (d, J=7.1 Hz, 1H), 7.44 (d, J=8.5 Hz, 2H).

MS(+): 365 [M+H]$^+$.

Example 4-177

3-Bromo-6-{(E)-1-(4-tert-butylphenyl)-2-[(2R)-5-oxopyrrolidin-2-yl]ethenyl}pyridin-2(1H)-one The title compound was obtained as a light yellow amorphous (13 mg, 21%) by performing substantially the same reaction as in Example 4-98(2) except for using (5R)-5-[(E)-2-(5-bromo-6-methoxypyridin-2-yl)-2-(4-tert-butylphenyl)ethenyl]pyrrolidin-2-one obtained in Reference Example 4-42.

$^1$H NMR (600 MHz, CDCl$_3$) δ ppm 1.36 (s, 9H), 2.10-2.19 (m, 1H), 2.31-2.42 (m, 2H), 2.44-2.53 (m, 1H), 4.18-4.33 (m, 1H), 5.94 (d, J=7.79 Hz, 1H), 6.21 (brs., 1H), 6.37 (d, J=9.2 Hz, 1H), 7.03-7.12 (m, 2H), 7.46 (d, J=8.3 Hz, 2H), 7.74 (d, J=7.8 Hz, 1H).

Example 4-178

6-{(E)-1-(4-tert-Butylphenyl)-2-[(2R)-5-oxopyrrolidin-2-yl]ethenyl}-3-phenylpyridin-2(1H)-one (1) Phenylboronic acid (57 mg), tris(dibenzylideneacetone)dipalladium(0) (19 mg), tri(2-furyl)phosphine (32 mg) and cesium carbonate (151 mg) were added to a solution of (5R)-5-[(E)-2-(5-bromo-6-methoxypyridin-2-yl)-2-(4-tert-butylphenyl)ethenyl]pyrrolidin-2-one obtained in Reference Example 4-42 (80 mg) in 1,4-dioxane (1.5 mL)-water (0.5 mL), and the mixture was stirred at an external temperature of 65° C. for three hours. The reaction solution was left to cool, diluted with ethyl acetate and filtered. The filtrate was washed with brine and dried over sodium sulfate. After filtration, the solvent was evaporated under reduced pressure. The residue was purified by silica gel column chromatography (hexane:ethyl acetate=9:1→3:2) to give (5R)-5-[(E)-2-(4-tert-butylphenyl)-2-(6-methoxy-5-phenylpyridin-2-yl)ethenyl]pyrrolidin-2-one as an orange oil (81 mg).

(2) 48% hydrobromic acid (1 mL) was added to a solution of (5R)-5-[(E)-2-(4-tert-butylphenyl)-2-(6-methoxy-5-phenylpyridin-2-yl)ethenyl]pyrrolidin-2-one (81 mg) in 1,4-dioxane (2 mL), and the mixture was stirred at 65° C. for 30 minutes. Water was added to the reaction solution, followed by extraction with ethyl acetate. The organic layer was washed with brine and dried over anhydrous magnesium sulfate, after which the solvent was evaporated under reduced pressure. The residue was purified by silica gel column chromatography (chloroform:methanol=10:0→4:1) and solidified with ethyl acetate-hexane to give the objective product as a light yellow amorphous (41 mg, 43% (two steps)).

$^1$H NMR (300 MHz, CDCl$_3$) δ ppm 1.37 (s, 9H), 1.84-1.98 (m, 1H), 2.11-2.34 (m, 3H), 4.09-4.23 (m, 1H), 5.99-6.04 (brs, 1H), 6.08 (d, J=7.3 Hz, 1H), 6.31 (d, J=9.3 Hz, 1H), 7.12 (d, J=8.5 Hz, 2H), 7.30-7.49 (m, 6H), 7.64-7.71 (m, 2H).

MS(+): 413 [M+H]$^+$.

The compounds of Examples 4-179 to 4-184 were synthesized by performing substantially the same reaction as in Example 4-178(1)(2) except for using, in place of phenylboronic acid, corresponding boronic acids or boronate esters (pyridin-4-ylboronic acid, pyridin-3-ylboronic acid, 2,4-dimethyl-5-(4,4,5,5-tetramethyl-1,3,2-dioxaborolan-2-yl)-1,3-thiazole, 1-(2-methylpropyl)-4-(4,4,5,5-tetramethyl-1,3,2-dioxaborolan-2-yl)-1H-pyrazole, 1-methyl-4-(4,4,5,5-tetramethyl-1,3,2-dioxaborolan-2-yl)-1H-pyrazole and 4-(4,4,5,5-tetramethyl-1,3,2-dioxaborolan-2-yl)-1,2-oxazole), respectively.

Example 4-179

6-{(E)-1-(4-tert-Butylphenyl)-2-[(2R)-5-oxopyrrolidin-2-yl]ethenyl}-3,4'-bipyridin-2(1H)-one The title compound was obtained as a light yellow amorphous (37 mg, 37% (two steps)).

$^1$H NMR (300 MHz, CDCl$_3$) δ ppm 1.37 (s, 9H), 1.87-2.04 (m, 1H), 2.15-2.42 (m, 3H), 4.09-4.25 (m, 1H), 6.13 (d, J=7.5 Hz, 1H), 6.37 (d, J=9.2 Hz, 1H), 6.53-6.61 (brs, 1H), 7.12 (d, J=8.2 Hz, 2H), 7.46 (d, J=8.2 Hz, 2H), 7.59 (d, J=7.6 Hz, 1H), 7.66 (d, J=5.8 Hz, 2H), 8.62 (d, J=5.4 Hz, 2H).

MS(+): 414 [M+H]$^+$.

Example 4-180

6-{(E)-1-(4-tert-Butylphenyl)-2-[(2R)-5-oxopyrrolidin-2-yl]ethenyl}-3,3'-bipyridin-2(1H)-one The title compound was obtained as a light yellow amorphous (39 mg, 55% (two steps)).

$^1$H NMR (300 MHz, CDCl$_3$) δ ppm 1.37 (s, 9H), 1.87-2.01 (m, 1H), 2.19-2.38 (m, 3H), 4.14-4.27 (m, 1H), 6.14 (d, J=7.5 Hz, 1H), 6.17-6.22 (brs, 1H), 6.34 (d, J=9.2 Hz, 1H), 7.12 (d, J=8.4 Hz, 2H), 7.31-7.37 (m, 1H), 7.46 (d, J=8.4 Hz, 2H), 7.53 (d, J=7.3 Hz, 1H), 8.08-8.14 (m, 1H), 8.53-8.59 (m, 1H), 8.84-8.90 (m, 1H).

MS(+): 414 [M+H]$^+$.

Example 4-181

6-{(E)-1-(4-tert-Butylphenyl)-2-[(2R)-5-oxopyrrolidin-2-yl]ethenyl}-3-(2,4-dimethyl-1,3-thiazol-5-yl)pyridin-2(1H)-one The title compound was obtained as a light orange amorphous (17 mg, 16% (two steps)).

$^1$H NMR (300 MHz, CDCl$_3$) δ ppm 1.37 (s, 9H), 1.97-2.08 (m, 1H), 2.26-2.43 (m, 3H), 2.45 (s, 3H), 2.66 (s, 3H), 4.15-4.27 (m, 1H), 6.14 (d, J=7.6 Hz, 1H), 6.28-6.32 (m, 2H), 7.13 (d, J=8.4 Hz, 2H), 7.44-7.52 (m, 3H).

MS(+): 448 [M+H]$^+$.

Example 4-182

6-{(E)-1-(4-tert-Butylphenyl)-2-[(2R)-5-oxopyrrolidin-2-yl]ethenyl}-3-[1-(2-methylpropyl)-1H-pyrazol-4-yl]pyridin-2(1H)-one The title compound was obtained as a light yellow amorphous (13 mg, 21% (two steps)).

$^1$H NMR (600 MHz, CDCl$_3$) δ ppm 0.93 (d, J=6.4 Hz, 6H), 1.37 (s, 9H), 2.11-2.29 (m, 2H), 2.31-2.43 (m, 2H), 2.50-2.58 (m, 1H), 3.96 (d, J=7.3 Hz, 2H), 4.25-4.31 (m, 1H), 6.28-6.33 (m, 2H), 6.39-6.44 (m, 1H), 7.10 (d, J=8.3 Hz, 2H), 7.47 (d, J=8.7 Hz, 2H), 7.81 (d, J=7.8 Hz, 1H), 7.89 (s, 1H), 8.25 (s, 1H).

MS(+): 459 [M+H]$^+$.

Example 4-183

6-{(E)-1-(4-tert-Butylphenyl)-2-[(2R)-5-oxopyrrolidin-2-yl]ethenyl}-3-(1-methyl-1H-pyrazol-4-yl)pyridin-2(1H)-one The title compound was obtained as a light yellow amorphous (46 mg, 64% (two steps)).

$^1$H NMR (300 MHz, CDCl$_3$) δ ppm 1.37 (s, 9H), 1.93-2.09 (m, 1H), 2.24-2.51 (m, 3H), 3.92 (s, 3H), 4.17-4.28 (m, 1H), 6.02 (s, 1H), 6.13-6.22 (m, 2H), 7.11 (d, J=8.2 Hz, 2H), 7.46 (d, J=8.4 Hz, 2H), 7.59 (d, J=7.3 Hz, 1H), 7.84 (s, 1H), 8.30 (s, 1H).

MS(+): 417 [M+H]$^+$.

Example 4-184

6-{(E)-1-(4-tert-Butylphenyl)-2-[(2R)-5-oxopyrrolidin-2-yl]ethenyl}-3-(1,2-oxazol-4-yl)pyridin-2(1H)-one The title compound was obtained as a light yellow amorphous (16 mg, 31% (two steps)).

$^1$H NMR (300 MHz, CDCl$_3$) δ ppm 1.37 (s, 9H), 1.95-2.16 (m, 1H), 2.23-2.53 (m, 3H), 4.20-4.32 (m, 1H), 6.17 (d, J=7.5 Hz, 1H), 6.32 (d, J=9.3 Hz, 1H), 6.51-6.57 (brs, 1H), 7.12 (d, J=8.5 Hz, 2H), 7.47 (d, J=8.5 Hz, 2H), 7.58 (d, J=7.5 Hz, 1H), 8.63 (s, 1H), 9.35 (s, 1H).

MS(+): 404 [M+H]$^+$.

Example 4-185

6-{(E)-1-(4-tert-Butylphenyl)-2-[(2R)-5-oxopyrrolidin-2-yl]ethenyl}-3-phenoxypyridin-2(1H)-one (1) Cesium carbonate (151 mg) was added to a solution of (5R)-5-[(E)-2-(5-bromo-6-methoxypyridin-2-yl)-2-(4-tert-butylphenyl)ethenyl]pyrrolidin-2-one obtained in Reference Example 4-42 (100 mg) and phenol (43 mg) in N-methylpyrrolidine (2 mL) in a nitrogen atmosphere, and the mixture was stirred at room temperature for five minutes. Copper iodide (22 mg) and 2,2,6,6-tetramethyl-3,5-heptanedione (10 mg) were added thereto, and the mixture was stirred at 120° C. for six hours. Water and ethyl acetate were added to the reaction solution, followed by filtration through celite. The filtrate was extracted with ethyl acetate. The organic layer was washed with brine and dried over anhydrous magnesium sulfate, after which the solvent was evaporated under reduced pressure. The residue was purified by silica gel column chromatography (hexane:ethyl acetate=4:1→1:4) to give a mixture of (5R)-5-[(E)-2-(4-tert-butylphenyl)-2-(6-methoxy-5-phenoxypyridin-2-yl)ethenyl]pyrrolidin-2-one and (5R)-5-[(E)-2-(4-tert-butylphenyl)-2-(6-methoxypyridin-2-yl)ethenyl] pyrrolidin-2-one (61 mg).

(2) 48% hydrobromic acid (2 mL) was added to a solution of the mixture of (5R)-5-[(E)-2-(4-tert-butylphenyl)-2-(6-methoxy-5-phenoxypyridin-2-yl)ethenyl]pyrrolidin-2-one and (5R)-5-[(E)-2-(4-tert-butylphenyl)-2-(6-methoxypyridin-2-yl)ethenyl]pyrrolidin-2-one (61 mg) in 1,4-dioxane (1 mL), and the mixture was stirred at 65° C. for 30 minutes. Water was added to the reaction solution, followed by extraction with ethyl acetate. The organic layer was washed with brine and dried over anhydrous magnesium sulfate, after which the solvent was evaporated under reduced pressure. The residue was purified by preparative HPLC (Waters Sunfire 19×150 mm 5 μm, rate: 20 mL/min, eluent: A=acetonitrile, B=0.1% trifluoroacetic acid solution, gradient: 10 to 90%) and solidified with ethyl acetate-hexane to give the title compound as a colorless amorphous (22 mg, 22% (two steps)). A crude product of (5R)-5-[(E)-2-(4-tert-butylphenyl)-2-(6-methoxypyridin-2-yl)ethenyl]pyrrolidin-2-one (15 mg) was also obtained.

$^1$H NMR (300 MHz, CDCl$_3$) δ ppm 1.35 (s, 9H), 2.00-2.11 (m, 1H), 2.19-2.42 (m, 3H), 4.09-4.22 (m, 1H), 5.87 (d, J=7.8 Hz, 1H), 6.17-6.27 (m, 2H), 6.79 (d, J=7.8 Hz, 1H), 7.04-7.15 (m, 5H), 7.30-7.37 (m, 2H), 7.42 (d, J=8.4 Hz, 2H).

MS(+): 429 [M+H]$^+$.

Example 4-186

6-{(E)-1-(4-tert-Butylphenyl)-2-[(2R)-5-oxopyrrolidin-2-yl]ethenyl}pyridin-2(1H)-one 48% hydrobromic acid (0.5 mL) was added to a solution of the crude product of (5R)-5-[(E)-2-(4-tert-butylphenyl)-2-(6-methoxypyridin-2-yl)ethenyl]pyrrolidin-2-one obtained in Example 4-185(2) (15 mg) in 1,4-dioxane (1 mL), and the mixture was stirred at 65° C. for 30 minutes. Water was added to the reaction solution, followed by extraction with ethyl acetate. The organic layer was washed with brine and dried over anhydrous magnesium sulfate, after which the solvent was evaporated under reduced pressure. The residue was purified by silica gel column chromatography (chloroform:methanol=10:0→4:1). This was powdered with ethyl acetate-hexane to give the title compound as an orange powder (2 mg).

$^1$H NMR (300 MHz, CDCl$_3$) δ ppm 1.36 (s, 9H), 2.01-2.14 (m, 1H), 2.30-2.49 (m, 3H), 4.15-4.30 (m, 1H), 5.98-6.03 (m, 1H), 6.21-6.25 (brs, 1H), 6.28 (d, J=9.2 Hz, 1H), 6.50-6.56 (m, 1H), 7.09 (d, J=8.4 Hz, 2H), 7.31-7.39 (m, 1H), 7.44 (d, J=8.4 Hz, 2H).

MS(+): 337 [M+H]$^+$.

The compounds of Examples 4-187 to 4-189 were synthesized by performing substantially the same reaction as in Example 4-185(1)(2) except for using corresponding phenols (p-cresol, 4-chlorophenol and 4-(trifluoro)phenol) in place of phenol, respectively.

Example 4-187

6-{(E)-1-(4-tert-Butylphenyl)-2-[(2R)-5-oxopyrrolidin-2-yl]ethenyl}-3-(4-methylphenoxy)pyridin-2 (1H)-one The title compound was obtained as a colorless powder (17 mg, 17% (two steps)).

$^1$H NMR (300 MHz, CDCl$_3$) δ ppm 1.35 (s, 9H), 2.03-2.12 (m, 1H), 2.23-2.47 (m, 6H), 4.11-4.24 (m, 1H), 5.91 (d, J=7.8 Hz, 1H), 6.06-6.13 (brs, 1H), 6.18 (d, J=9.0 Hz, 1H), 6.74 (d, J=7.8 Hz, 1H), 6.99 (d, J=8.2 Hz, 2H), 7.08 (d, J=8.4 Hz, 2H), 7.14 (d, J=8.1 Hz, 2H), 7.43 (d, J=8.4 Hz, 2H).

MS(+): 443 [M+H]$^+$.

Example 4-188

6-{(E)-1-(4-tert-Butylphenyl)-2-[(2R)-5-oxopyrrolidin-2-yl]ethenyl}-3-(4-chlorophenoxy)pyridin-2 (1H)-one The title compound was obtained as a colorless amorphous (9 mg, 8% (two steps)).

$^1$H NMR (300 MHz, CDCl$_3$) δ ppm 1.35 (s, 9H), 2.00-2.16 (m, 1H), 2.21-2.54 (m, 3H), 4.14-4.26 (m, 1H), 5.88 (d, J=7.8 Hz, 1H), 6.28 (d, J=9.2 Hz, 1H), 6.89 (d, J=7.8 Hz, 1H), 6.92-6.97 (brs, 1H), 7.01 (d, J=8.9 Hz, 2H), 7.08 (d, J=8.2 Hz, 2H), 7.27-7.31 (m, 2H), 7.42 (d, J=8.2 Hz, 2H).

MS(+): 463 [M+H]$^+$.

Example 4-189

6-{(E)-1-(4-tert-Butylphenyl)-2-[(2R)-5-oxopyrrolidin-2-yl]ethenyl}-3-[4-(trifluoromethyl)phenoxy] pyridin-2(1H)-one The title compound was obtained as a colorless amorphous (3 mg, 2% (two steps)).

$^1$H NMR (300 MHz, CDCl$_3$) δ ppm 1.36 (s, 9H), 2.02-2.15 (m, 1H), 2.22-2.58 (m, 3H), 4.16-4.29 (m, 1H), 6.03 (d, J=7.9 Hz, 1H), 6.27 (d, J=9.2 Hz, 1H), 6.80-6.89 (brs, 1H), 7.04-7.15 (m, 5H), 7.45 (d, J=8.2 Hz, 2H), 7.58 (d, J=8.5 Hz, 2H).

MS(+): 497 [M+H]$^+$.

Example 4-190

6-{(E)-1-(4-tert-Butylphenyl)-2-[(2R)-5-oxopyrrolidin-2-yl]ethenyl}-3-(4-hydroxybutyl)pyridin-2(1H)-one (1) trans-4-(tert-Butyldimethylsiloxy)-1-buten-1-ylboronic acid pinacol ester (296 mg), tris(dibenzylideneacetone) dipalladium(0) (48 mg), tri(2-furyl)phosphine (73 mg) and cesium carbonate (354 mg) were added to a solution of (5R)-5-[(E)-2-(5-bromo-6-methoxypyridin-2-yl)-2-(4-tert-butylphenyl)ethenyl]-1-(2,4-dimethoxybenzyl)pyrrolidin-2-one obtained in Reference Example 4-42(1) (300 mg) in 1,4-dioxane (3 mL)-water (1 mL), and the mixture was stirred at an external temperature of 65° C. for three hours. The reaction solution was left to cool, diluted with ethyl acetate and filtered through celite. The filtrate was washed with brine and dried over sodium sulfate. After filtration, the solvent was evaporated under reduced pressure. The residue was purified by silica gel column chromatography (hexane:ethyl acetate=9:1→3:2) to give (5R)-5-[(E)-2-{5-[(1E)-4-{[tert-butyl(dimethyl)silyl]oxy}but-1-en-1-yl]-6-methoxypyridin-2-yl}-2-(4-tert-butylphenyl)ethenyl]-1-(2,4-dimethoxybenzyl)pyrrolidin-2-one as a yellow oil (399 mg, 100%).

(2) 10% palladium-activated carbon (50 mg) and zinc(II) bromide (25 mg) were added to a solution of (5R)-5-[(E)-2-{5-[(1E)-4-{[tert-butyl(dimethyl)silyl]oxy}but-1-en-1-yl]-6-methoxypyridin-2-yl}-2-(4-tert-butylphenyl)ethenyl]-1-(2,4-dimethoxybenzyl)pyrrolidin-2-one (226 mg) in methanol (5 mL), and the mixture was stirred at room temperature for five hours in a hydrogen atmosphere. The reaction solution was diluted with ethyl acetate and filtered through celite. The filtrate was sequentially washed with water and brine and dried over anhydrous magnesium sulfate, after which the solvent was evaporated under reduced pressure. The residue was purified by silica gel column chromatography (hexane:ethyl acetate=7:3→1:9) to give (5R)-5-[(E)-2-[5-(4-{[tert-butyl(dimethyl)silyl]oxy}butyl)-6-methoxypyridin-2-yl]-2-(4-tert-butylphenyl)ethenyl]-1-(2,4-dimethoxybenzyl)pyrrolidin-2-one as a colorless oil (140 mg, 62%).

(3) 48% hydrobromic acid (0.5 mL) was added to a solution of (5R)-5-[(E)-2-[5-(4-{[tert-butyl(dimethyl)silyl]oxy}butyl)-6-methoxypyridin-2-yl]-2-(4-tert-butylphenyl)ethenyl]-1-(2,4-dimethoxybenzyl)pyrrolidin-2-one (24 mg) in 1,4-dioxane (1 mL), and the mixture was stirred at 65° C. for 30 minutes. The reaction solution was poured into water, followed by extraction with ethyl acetate. The organic layer was washed with brine and dried over anhydrous magnesium sulfate, after which the solvent was evaporated under reduced pressure.

A solution of the resulting residue in trifluoroacetic acid (2 mL) and anisole (1 mL) was stirred at 70° C. for five hours. The solvent was evaporated from the reaction solution under reduced pressure. The residue was purified by silica gel column chromatography (chloroform:methanol=100:1→4:1) and preparative HPLC (Waters Sunfire 19×150 mm 5 µm, rate: 20 mL/min, eluent: A=acetonitrile, B=0.1% trifluoroacetic acid solution, gradient: 10 to 90%) to give the title compound as a colorless amorphous (4 mg, 26%).

$^1$H NMR (300 MHz, CDCl$_3$) δ ppm 1.36 (s, 9H), 1.53-1.75 (m, 4H), 1.99-2.13 (m, 1H), 2.23-2.43 (m, 3H), 2.51-2.67 (m, 2H), 3.62-3.73 (m, 2H), 4.15-4.26 (m, 1H), 5.83 (d, J=7.1 Hz, 1H), 6.40 (d, J=9.2 Hz, 1H), 6.49-6.57 (brs, 1H), 7.09 (d, J=8.5 Hz, 2H), 7.15-7.23 (m, 1H), 7.41 (s, 2H).

MS(+): 409 [M+H]$^+$.

Example 4-191

6-{(E)-1-(4-tert-Butylphenyl)-2-[(2R)-5-oxopyrrolidin-2-yl]ethenyl}-3-[4-(dimethylamino)butyl]pyridin-2(1H)-one (1) A solution of tetra-n-butylammonium fluoride in tetrahydrofuran (1 mL) was added to a solution of (5R)-5-[(E)-2-[5-(4-{[tert-butyl(dimethyl)silyl]oxy}butyl)-6-methoxypyridin-2-yl]-2-(4-tert-butylphenyl)ethenyl]-1-(2,4-dimethoxybenzyl)pyrrolidin-2-one (140 mg) in tetrahydrofuran (4 mL), and the mixture was stirred at room temperature for three hours. The solvent was evaporated from the reaction solution under reduced pressure. The residue was purified by silica gel column chromatography (hexane:ethyl acetate=1:1→0:10) to give (5R)-5-{(E)-2-(4-tert-butylphenyl)-2-[5-(4-hydroxybutyl)-6-methoxypyridin-2-yl]ethenyl}-1-(2,4-dimethoxybenzyl)pyrrolidin-2-one as a colorless oil (101 mg, 86%).

(2) Triethylamine (50 µL) and methanesulfonyl chloride (25 µL) were added to a solution of (5R)-5-{(E)-2-(4-tert-butylphenyl)-2-[5-(4-hydroxybutyl)-6-methoxypyridin-2-yl]ethenyl}-1-(2,4-dimethoxybenzyl)pyrrolidin-2-one (144 mg) in chloroform (2 mL), and the mixture was stirred at room temperature for three hours. Triethylamine (50 µL) and methanesulfonyl chloride (25 µL) were further added thereto and the mixture was stirred at room temperature for one hour. The reaction solution was poured into water, followed by extraction with ethyl acetate. The organic layer was washed with water and brine and dried over anhydrous magnesium sulfate. The solvent was evaporated under reduced pressure to give 4-(6-{(E)-1-(4-tert-butylphenyl)-2-[(2R)-1-(2,4-dimethoxybenzyl)-5-oxopyrrolidin-2-yl]ethenyl}-2-methoxypyridin-3-yl)butyl methanesulfonate as a crude product. 2 M dimethylamine (solution in methanol) (3 mL) was added to 4-(6-{(E)-1-(4-tert-butylphenyl)-2-[(2R)-1-(2,4-dimethoxybenzyl)-5-oxopyrrolidin-2-yl]ethenyl}-2-methoxypyridin-3-yl)butyl methanesulfonate, and the mixture was stirred at room temperature for 17 hours. The solvent was evaporated from the reaction solution and then water was added, followed by extraction with ethyl acetate. The organic layer was washed with brine, dried over anhydrous magnesium sulfate and filtered, after which the solvent was evaporated under reduced pressure. The residue was purified by silica gel column chromatography (chloroform:methanol=100:0→4:1) to give (5R)-5-[(E)-2-(4-tert-butylphenyl)-2-{5-[4-(dimethylamino)butyl]-6-methoxypyridin-2-yl}ethenyl]-1-(2,4-dimethoxybenzyl)pyrrolidin-2-one as a colorless oil.

(3) 48% hydrobromic acid (1.5 mL) was added to a solution of (5R)-5-[(E)-2-(4-tert-butylphenyl)-2-{5-[4-(dimethylamino)butyl]-6-methoxypyridin-2-yl}ethenyl]-1-(2,4-dimethoxybenzyl)pyrrolidin-2-one in 1,4-dioxane (2 mL), and the mixture was stirred at 65° C. for 30 minutes. The reaction solution was poured into saturated aqueous sodium bicarbonate, followed by extraction with ethyl acetate. The organic layer was washed with brine and dried over anhydrous magnesium sulfate, after which the solvent was evaporated under reduced pressure. A solution of the residue in trifluoroacetic acid (4 mL) and anisole (2 mL) was stirred at 80° C. for five hours. The reaction solution was poured into saturated aqueous sodium bicarbonate, followed by extraction with chloroform. The organic layer was washed with brine, dried over anhydrous magnesium sulfate and filtered, after which the solvent was evaporated under reduced pressure. The residue was purified by silica gel column chromatography (chloroform:methanol=100:1→3:1) and solidified with diethyl ether-hexane to give the title compound as a light yellow amorphous (13 mg, 12% (four steps)).

$^1$H NMR (300 MHz, CDCl$_3$) δ ppm 1.36 (s, 9H), 1.47-1.58 (m, 4H), 2.00-2.09 (m, 1H), 2.21 (s, 6H), 2.25-2.44 (m, 5H), 2.49-2.58 (m, 2H), 4.16-4.27 (m, 1H), 5.72-5.77 (brs, 1H), 6.03 (d, J=7.1 Hz, 1H), 6.17 (d, J=9.2 Hz, 1H), 7.07 (d, J=8.5 Hz, 2H), 7.18 (d, J=7.1 Hz, 1H), 7.44 (d, J=8.5 Hz, 2H).

MS(+): 436 [M+H]$^+$.

The compounds of Examples 4-192 to 4-198 were synthesized by performing substantially the same reaction as in Example 4-190(1)-(3) except for using corresponding boronic acids or boronate esters ((1E)-prop-1-en-1-ylboronic acid, (1E)-pent-1-en-1-ylboronic acid, cyclopent-1-en-1-ylboronic acid, [(E)-2-cyclohexylethenyl]boronic acid, [(E)-2-phenylethenyl]boronic acid, [(1E)-3-phenylprop-1-en-1-yl]boronic acid and tert-butyl(dimethyl){[(2E)-3-(4,4,5,5-tetramethyl-1,3,2-dioxaborolan-2-yl)prop-2-en-1-yl]oxy}silane) in place of trans-4-(tert-butyldimethylsiloxy)-1-buten-1-ylboronic acid pinacol ester, respectively.

Example 4-192

6-{(E)-1-(4-tert-Butylphenyl)-2-[(2R)-5-oxopyrrolidin-2-yl]ethenyl}-3-propylpyridin-2(1H)-one The title compound was obtained as a colorless powder (6.1 mg, 6% (three steps)).

$^1$H NMR (300 MHz, CDCl$_3$) δ ppm 0.95 (t, J=7.4 Hz, 3H), 1.36 (s, 9H), 1.50-1.72 (m, 2H), 1.96-2.13 (m, 1H), 2.22-2.45 (m, 3H), 2.50 (t, J=7.5 Hz, 2H), 4.14-4.29 (m, 1H), 5.88-6.03

(m, 2H), 6.24 (d, J=9.2 Hz, 1H), 7.09 (d, J=8.1 Hz, 2H), 7.16 (d, J=7.0 Hz, 1H), 7.44 (d, J=7.8 Hz, 2H), 9.95-10.21 (brs, 1H).
MS(+): 379 [M+H]$^+$.

Example 4-193

6-{(E)-1-(4-tert-Butylphenyl)-2-[(2R)-5-oxopyrrolidin-2-yl]ethenyl}-3-pentylpyridin-2(1H)-one The title compound was obtained as a colorless powder (4 mg, 4% (four steps)).
$^1$H NMR (300 MHz, CDCl$_3$) δ ppm 0.82-0.94 (m, 3H), 1.27-1.41 (m, 13H), 1.51-1.62 (m, 2H), 1.98-2.16 (m, 1H), 2.22-2.44 (m, 3H), 2.48-2.57 (m, 2H), 4.13-4.27 (m, 1H), 5.91 (d, J=7.1 Hz, 1H), 6.29 (d, J=9.2 Hz, 1H), 6.33-6.39 (brs, 1H), 7.10 (d, J=8.4 Hz, 2H), 7.15 (d, J=7.1 Hz, 1H), 7.43 (d, J=8.4 Hz, 2H).
MS(+): 407 [M+H]$^+$.

Example 4-194

6-{(E)-1-(4-tert-Butylphenyl)-2-[(2R)-5-oxopyrrolidin-2-yl]ethenyl}-3-cyclopentylpyridin-2(1H)-one The title compound was obtained as a colorless powder (15 mg, 14% (three steps)).
$^1$H NMR (300 MHz, CDCl$_3$) δ ppm 1.36 (s, 9H), 1.41-1.54 (m, 2H), 1.64-1.79 (m, 4H), 1.94-2.12 (m, 3H), 2.22-2.51 (m, 3H), 3.12-3.29 (m, 1H), 4.13-4.27 (m, 1H), 5.90-6.01 (m, 1H), 6.06-6.15 (m, 1H), 6.19-6.28 (m, 1H), 7.01-7.12 (m, 2H), 7.16-7.22 (m, 1H), 7.36-7.47 (m, 2H), 9.97-10.31 (brs, 1H).
MS(+): 405 [M+H]$^+$.

Example 4-195

6-{(E)-1-(4-tert-Butylphenyl)-2-[(2R)-5-oxopyrrolidin-2-yl]ethenyl}-3-(2-cyclohexylethyl)pyridin-2(1H)-one The title compound was obtained as a colorless amorphous (19 mg, 16% (three steps)).
$^1$H NMR (300 MHz, METHANOL-d4) δ ppm 0.86-1.04 (m, 2H), 1.13-1.40 (m, 13H), 1.41-1.51 (m, 2H), 1.60-1.86 (m, 5H), 1.92-2.07 (m, 1H), 2.20-2.42 (m, 3H), 2.44-2.56 (m, 2H), 4.14-4.27 (m, 1H), 5.90 (d, J=7.1 Hz, 1H), 6.24 (d, J=9.3 Hz, 1H), 7.17 (d, J=8.1 Hz, 2H), 7.28 (d, J=7.3 Hz, 1H), 7.51 (d, J=8.1 Hz, 2H).
MS(+): 447 [M+H]$^+$.

Example 4-196

6-{(E)-1-(4-tert-Butylphenyl)-2-[(2R)-5-oxopyrrolidin-2-yl]ethenyl}-3-(2-phenylethyl)pyridin-2(1H)-one The title compound was obtained as a yellow powder (13 mg, 11% (three steps)).
$^1$H NMR (300 MHz, METHANOL-d4) δ ppm 1.32-1.38 (m, 9H), 1.91-2.09 (m, 1H), 2.21-2.41 (m, 3H), 2.69-2.93 (m, 4H), 4.13-4.26 (m, 1H), 5.85 (d, J=7.1 Hz, 1H), 6.25 (d, J=9.5 Hz, 1H), 7.07-7.28 (m, 8H), 7.50 (d, J=8.5 Hz, 2H).
MS(+): 441 [M+H]$^+$.

Example 4-197

6-{(E)-1-(4-tert-Butylphenyl)-2-[(2R)-5-oxopyrrolidin-2-yl]ethenyl}-3-(3-phenylpropyl)pyridin-2(1H)-one The title compound was obtained as a colorless powder (30 mg, 46% (three steps)).
$^1$H NMR (300 MHz, CDCl$_3$) δ ppm 1.36 (s, 9H), 1.86-1.97 (m, 2H), 2.04 (m, J=17.6 Hz, 1H), 2.27-2.46 (m, 3H), 2.54-2.62 (m, 2H), 2.63-2.71 (m, 2H), 4.15-4.26 (m, 1H), 5.76-5.86 (brs, 1H), 6.01 (d, J=7.0 Hz, 1H), 6.19 (d, J=8.9 Hz, 1H), 7.07 (d, J=8.4 Hz, 2H), 7.13-7.25 (m, 6H), 7.44 (d, J=8.5 Hz, 2H).
MS(+): 455 [M+H]$^+$.

Example 4-198

6-{(E)-1-(4-tert-Butylphenyl)-2-[(2R)-5-oxopyrrolidin-2-yl]ethenyl}-3-(3-hydroxypropyl)pyridin-2(1H)-one The title compound was obtained as a colorless powder (14 mg, 26% (three steps)).
$^1$H NMR (300 MHz, CDCl$_3$) δ ppm 1.36 (s, 9H), 1.95-2.15 (m, 3H), 2.28-2.45 (m, 3H), 2.63 (t, J=7.5 Hz, 2H), 4.15-4.27 (m, 1H), 4.38 (t, J=6.5 Hz, 2H), 5.81-5.88 (brs, 1H), 6.02 (d, J=7.1 Hz, 1H), 6.23 (d, J=9.0 Hz, 1H), 7.08 (d, J=8.4 Hz, 2H), 7.19 (d, J=7.1 Hz, 1H), 7.45 (d, J=8.4 Hz, 2H).
MS(+): 395 [M+H]$^+$.

The compounds of Examples 4-199 and 4-200 were synthesized by performing substantially the same reaction as in Example 4-190(1)-(3) except for using (5R)-5-[(E)-2-(4-chlorophenyl)-2-(tributylstannyl)ethenyl]-1-(2,4-dimethoxybenzyl)pyrrolidin-2-one (Reference Example 4-28) and (5R)-1-(2,4-dimethoxybenzyl)-5-{(E)-2-(tributylstannyl)-2-[4-(trifluoromethyl)phenyl]ethenyl}pyrrolidin-2-one (Reference Example 4-29) in place of (5R)-5-[(E)-2-(5-bromo-6-methoxypyridin-2-yl)-2-(4-tert-butylphenyl)ethenyl]-1-(2,4-dimethoxybenzyl)pyrrolidin-2-one.

Example 4-199

6-{(E)-1-(4-Chlorophenyl)-2-[(2R)-5-oxopyrrolidin-2-yl]ethenyl}-3-(4-hydroxybutyl)pyridin-2(1H)-one The title compound was obtained as a colorless amorphous (50 mg, 32% (three steps)).
$^1$H NMR (300 MHz, METHANOL-d4) δ ppm 1.48-1.70 (m, 4H), 1.92-2.09 (m, 1H), 2.18-2.41 (m, 3H), 2.45-2.56 (m, 2H), 3.52-3.60 (m, 2H), 4.08-4.22 (m, 1H), 5.85 (d, J=7.1 Hz, 1H), 6.31 (d, J=9.6 Hz, 1H), 7.23 (d, J=8.5 Hz, 2H), 7.31 (d, J=7.3 Hz, 1H), 7.47 (d, J=8.5 Hz, 2H).
MS(+): 387 [M+H]$^+$.

Example 4-200

3-(4-Hydroxybutyl)-6-{(E)-2-[(2R)-5-oxopyrrolidin-2-yl]-1-[4-(trifluoromethyl)phenyl]ethenyl}pyridin-2(1H)-one The title compound was obtained as a colorless amorphous (39 mg, 28% (three steps)).
$^1$H NMR (300 MHz, METHANOL-d4) δ ppm 2.23-2.40 (m, 4H), 2.66-2.84 (m, 1H), 2.92-3.15 (m, 3H), 3.19-3.28 (m, 2H), 4.25-4.33 (m, 2H), 4.78-4.91 (m, 1H), 6.53 (d, J=7.1 Hz, 1H), 7.12 (d, J=9.5 Hz, 1H), 8.05 (d, J=7.1 Hz, 1H), 8.18 (d, J=8.1 Hz, 2H), 8.50 (d, J=8.2 Hz, 2H).

MS(+): 421 [M+H]$^+$.

Example 4-201

3-(6-{(E)-1-(4-tert-Butylphenyl)-2-[(2R)-5-oxopyrrolidin-2-yl]ethenyl}-2-oxo-1,2-dihydropyridin-3-yl)propanamide (1) Tetrakis(triphenylphosphine)palladium(0) (80 mg) was added to a solution of (5R)-5-[(E)-2-(4-tert-butylphenyl)-2-(tributylstannyl)ethenyl]-1-(2,4-dimethoxybenzyl)pyrrolidin-2-one obtained in Reference Example 4-26 (471 mg), tert-butyl 3-(6-bromo-2-methoxypyridin-3-yl)propanoate obtained in Reference Example 4-41 (436 mg), cesium fluoride (209 mg) and copper iodide (144 mg) in N,N-dimethylformamide (4.5 mL) in a nitrogen atmosphere, and the mixture was stirred at 65° C. for one hour. The reaction solution was left to cool, and then water and ethyl acetate were added, followed by filtration through celite. The filtrate was extracted with ethyl acetate. The organic layer was washed with water and brine and dried over anhydrous magnesium sulfate, after which the solvent was evaporated under reduced pressure. The residue was purified by silica gel column chromatography (hexane:ethyl acetate=1:1) to give tert-butyl 3-(6-{(E)-1-(4-tert-butylphenyl)-2-[(2R)-1-(2,4-dimethoxybenzyl)-5-oxopyrrolidin-2-yl]ethenyl}-2-methoxypyridin-3-yl)propanoate as a brown oil (293 mg).

(2) Anisole (1 mL) was added to a solution of tert-butyl 3-(6-{(E)-1-(4-tert-butylphenyl)-2-[(2R)-1-(2,4-dimethoxybenzyl)-5-oxopyrrolidin-2-yl]ethenyl}-2-methoxypyridin-3-yl)propanoate (293 mg) in trifluoroacetic acid (2 mL), and the mixture was stirred at 65° C. for two hours. The solvent was evaporated under reduced pressure. The resulting residue was purified by silica gel column chromatography (chloroform:methanol=1:0→9:1) to give 3-(6-{(E)-1-(4-tert-butylphenyl)-2-[(2R)-1-(2,4-dimethoxybenzyl)-5-oxopyrrolidin-2-yl]ethenyl}-2-methoxypyridin-3-yl)propanoic acid as a colorless amorphous (172 mg).

(3) 48% hydrobromic acid (1.7 mL) was added to a solution of 3-(6-{(E)-1-(4-tert-butylphenyl)-2-[(2R)-1-(2,4-dimethoxybenzyl)-5-oxopyrrolidin-2-yl]ethenyl}-2-methoxypyridin-3-yl)propanoic acid (172 mg) in 1,4-dioxane (1.7 mL), and the mixture was stirred at 65° C. for two hours. Water was added to the reaction solution, followed by extraction with ethyl acetate. The organic layer was washed with brine and dried over anhydrous magnesium sulfate, after which the solvent was evaporated under reduced pressure. The resulting residue was purified by silica gel column chromatography (chloroform:methanol=10:0→9:1) to give 3-(6-{(E)-1-(4-tert-butylphenyl)-2-[(2R)-1-(2,4-dimethoxybenzyl)-5-oxopyrrolidin-2-yl]ethenyl}-2-oxo-1,2-dihydropyridin-3-yl)propanoic acid as a yellow oil (153 mg).

(4) 1,1'-Carbonyldiimidazole (24.8 mg) was added to a solution of 3-(6-{(E)-1-(4-tert-butylphenyl)-2-[(2R)-1-(2,4-dimethoxybenzyl)-5-oxopyrrolidin-2-yl]ethenyl}-2-oxo-1,2-dihydropyridin-3-yl)propanoic acid (77.8 mg) in tetrahydrofuran (1.6 mL). 28% aqueous ammonia (0.2 mL) was further added, followed by stirring for 15 hours. The reaction system was concentrated under reduced pressure. The resulting residue was purified by silica gel column chromatography (chloroform:methanol=10:0→9:1) to give 3-(6-{(E)-1-(4-tert-butylphenyl)-2-[(2R)-1-(2,4-dimethoxybenzyl)-5-oxopyrrolidin-2-yl]ethenyl}-2-oxo-1,2-dihydropyridin-3-yl)propanamide as a colorless amorphous (82.6 mg).

(5) Anisole (0.3 mL) was added to a solution of 3-(6-{(E)-1-(4-tert-butylphenyl)-2-[(2R)-1-(2,4-dimethoxybenzyl)-5-oxopyrrolidin-2-yl]ethenyl}-2-oxo-1,2-dihydropyridin-3-yl)propanamide (82.6 mg) in trifluoroacetic acid (0.6 mL), and the mixture was stirred at 80° C. for 19 hours. The solvent was evaporated under reduced pressure. The residue was purified by silica gel column chromatography (chloroform:methanol=1:0→9:1) to give the title compound as a colorless oil (14 mg).

$^1$H NMR (300 MHz, METHANOL-d4) δ ppm 1.31-1.38 (m, 9H), 1.90-2.09 (m, 1H), 2.19-2.41 (m, 3H), 2.44-2.60 (m, 2H), 2.72-2.83 (m, 2H), 4.14-4.26 (m, 1H), 5.86-5.93 (m, 1H), 6.28 (d, J=9.3 Hz, 1H), 7.10-7.20 (m, 2H), 7.30-7.37 (m, 1H), 7.45-7.53 (m, 2H).

MS(+): 408 [M+H]$^+$.

Example 4-202

6-{(E)-1-(4-tert-Butylphenyl)-2-[(2R)-5-oxopyrrolidin-2-yl]ethenyl}-2-oxo-1,2-dihydropyridine-3-carbonitrile (1) Copper cyanide (27 mg) was added to a solution of (5R)-5-[(E)-2-(5-bromo-6-methoxypyridin-2-yl)-2-(4-tert-butylphenyl)ethenyl]-1-(2,4-dimethoxybenzyl)pyrrolidin-2-one obtained in Reference Example 4-42(1) (90 mg) in N,N-dimethylformamide (5 mL), and the mixture was stirred at an external temperature of 180° C. for two hours. Water was added to the reaction solution, followed by extraction with ethyl acetate. The organic layer was washed with saline, dried over magnesium sulfate and filtered. The solvent was then evaporated under reduced pressure. The residue was purified by silica gel column chromatography (hexane:ethyl acetate=4:1→1:1) to give 6-{(E)-1-(4-tert-butylphenyl)-2-[(2R)-1-(2,4-dimethoxybenzyl)-5-oxopyrrolidin-2-yl]ethenyl}-2-methoxypyridine-3-carbonitrile (32 mg, 40%).

(2) Trifluoroacetic acid (1 mL) was added to a solution of 6-{(E)-1-(4-tert-butylphenyl)-2-[(2R)-1-(2,4-dimethoxybenzyl)-5-oxopyrrolidin-2-yl]ethenyl}-2-methoxypyridine-3-carbonitrile (32 mg) in anisole (1 mL), and the mixture was stirred at 85° C. overnight. The solvent was evaporated under reduced pressure, and then the residue was purified by silica gel column chromatography (hexane:ethyl acetate=1:1→1:5). The resulting compound was dissolved in 1,4-dioxane (1 mL) and 48% hydrobromic acid (1 mL) was added, after which the mixture was stirred at 65° C. for one hour. Saturated aqueous sodium bicarbonate was added to the reaction solution, followed by extraction with ethyl acetate. The organic layer was washed with brine and dried over anhydrous magnesium sulfate, after which the solvent was evaporated under reduced pressure. The residue was purified by silica gel column chromatography (hexane:ethyl acetate=1:5→chloroform:methanol=5:1) to give the title compound (8 mg, 36%) as a colorless solid.

$^1$H NMR (600 MHz, CDCl$_3$) δ ppm 1.37 (s, 9H), 2.22-2.43 (m, 3H), 2.54-2.62 (m, 1H), 4.24-4.30 (m, 1H), 6.06-6.11 (m, 1H), 6.52-6.65 (m, 2H), 7.09 (d, J=8.3 Hz, 2H), 7.48 (d, J=8.3 Hz, 2H), 7.78 (d, J=7.3 Hz, 1H).

MS(+): 362 [M+H]$^+$.

Examples 4-203 and 4-204

6-{1-(4-tert-Butylphenyl)-2-[(2R)-5-oxopyrrolidin-2-yl]ethenyl}-3-(1-hydroxycyclobutyl)pyridin-2(1H)-one (1) (5R)-5-[(E)-2-(5-Bromo-6-methoxypyridin-2-yl)-2-(4-tert-butylphenyl)ethenyl]-1-(2,4-dimethoxybenzyl)pyrrolidin-2-one obtained in Reference Example 4-42(1) (100 mg) was dissolved in tetrahydrofuran (5 mL), and n-butyllithium was added at −78° C. After stirring for 30 minutes, cyclobutanone was added dropwise. The mixture was stirred for further 30 minutes and then an ammonium chloride solution was added to the reaction solution, followed by extraction with ethyl acetate. The organic layer was dried over sodium sulfate, and then the solvent was evaporated under reduced pressure. The residue was purified by silica gel column chromatography (hexane:ethyl acetate=4:1→1:1) to give 5-{2-(4-tert-butylphenyl)-2-[5-(1-hydroxycyclobutyl)-6-methoxypyridin-2-yl]ethenyl}-1-(2,4-dimethoxybenzyl)pyrrolidin-2-one (EZ mixture) (35 mg).

(2) Trifluoroacetic acid (1 mL) was added to a solution of 5-{2-(4-tert-butylphenyl)-2-[5-(1-hydroxycyclobutyl)-6-methoxypyridin-2-yl]ethenyl}-1-(2,4-dimethoxybenzyl)pyrrolidin-2-one (EZ mixture) (35 mg) in anisole (1 mL), and the mixture was stirred at 85° C. overnight. The solvent was evaporated under reduced pressure, and then the residue was purified by silica gel column chromatography (hexane:ethyl acetate=1:1→1:5). The resulting compound was dissolved in 1,4-dioxane (1 mL) and 48% hydrobromic acid (1 mL) was added, after which the mixture was stirred at 65° C. for one hour. Aqueous sodium bicarbonate was added to the reaction solution, followed by extraction with ethyl acetate. The organic layer was washed with brine and dried over anhydrous magnesium sulfate, after which the solvent was evaporated under reduced pressure. The residue was purified by preparative HPLC (Waters Sunfire 19×150 mm 5 μm, rate: 20 mL/min, eluent: A=acetonitrile, B=0.1% trifluoroacetic acid solution, gradient: 10 to 90%) to give one isomer (A) of the title compound (1 mg, 8%) and the other isomer (B) of the title compound (1.0 mg, 8%) as colorless powders.

Isomer (A)

$^1$H NMR (600 MHz, CDCl$_3$) δ ppm 1.34 (s, 9H), 1.55-1.66 (m, 1H), 1.83-2.52 (m, 9H), 2.71 (t, J=9.6 Hz, 1H), 4.14-4.22 (m, 1H), 6.16 (d, J=6.4 Hz, 1H), 6.28 (d, J=8.7 Hz, 1H), 6.43 (brs, 1H), 6.65 (d, J=9.2 Hz, 1H), 7.05-7.12 (m, 2H), 7.44-7.53 (m, 3H).

MS(+): 407[M+H]$^+$.

Isomer (B)

$^1$H NMR (600 MHz, CDCl$_3$) δ ppm 1.36 (s, 9H), 1.55-1.66 (m, 1H), 1.84-2.49 (m, 9H), 2.97-3.04 (m, 1H), 4.20-4.30 (m, 1H), 6.28 (d, J=7.3 Hz, 1H), 6.41 (d, J=9.2 Hz, 1H), 6.60 (brs, 1H), 6.73 (d, J=8.7 Hz, 1H), 7.09 (d, J=8.3 Hz, 2H), 7.47 (s, 2H), 7.57-7.66 (m, 1H).

MS(+): 407[M+H]$^+$.

Example 4-205

3-Benzyl-6-{(E)-1-(4-tert-butylphenyl)-2-[(2R)-5-oxopyrrolidin-2-yl]ethenyl}pyridin-2(1H)-one (1) 0.05 M benzylzinc(II) bromide (385 μL), tris(dibenzylideneacetone)dipalladium(0) (8.0 mg) and tri(2-furyl)phosphine (15 mg) were added to a solution of (5R)-5-[(E)-2-(5-bromo-6-methoxypyridin-2-yl)-2-(4-tert-butylphenyl)ethenyl]pyrrolidin-2-one obtained in Reference Example 4-42(2) (30 mg) in tetrahydrofuran (2 mL), and the mixture was stirred under microwave irradiation at 110° C. for one hour. An ammonium chloride solution was added to the reaction solution, followed by extraction with ethyl acetate. The organic layer was dried over sodium sulfate and then the solvent was evaporated under reduced pressure. The residue was purified by silica gel column chromatography (hexane:ethyl acetate=1:1→1:0) to give (5R)-5-[(E)-2-(5-benzyl-6-methoxypyridin-2-yl)-2-(4-tert-butylphenyl)ethenyl]pyrrolidin-2-one (23 mg).

(2) 48% hydrobromic acid (1 mL) was added to a solution of (5R)-5-[(E)-2-(5-benzyl-6-methoxypyridin-2-yl)-2-(4-tert-butylphenyl)ethenyl]pyrrolidin-2-one (23 mg) in 1,4-dioxane (2 mL), and the mixture was stirred at 65° C. for one hour. Water was added to the reaction solution, followed by extraction with ethyl acetate. The organic layer was dried over anhydrous magnesium sulfate, after which the solvent was evaporated under reduced pressure. The residue was purified by preparative HPLC (Waters Sunfire 19×150 mm 5 μm, rate: 20 mL/min, eluent: A=acetonitrile, B=0.1% trifluoroacetic acid solution, gradient: 10 to 90%) to give the title compound (11 mg, 50%) as a colorless solid.

$^1$H NMR (600 MHz, CDCl$_3$) δ ppm 1.35 (s, 9H), 1.96-2.06 (m, 1H), 2.24-2.35 (m, 2H), 2.35-2.47 (m, 1H), 3.81-3.95 (m, 2H), 4.15-4.27 (m, 1H), 5.73-5.88 (m, 1H), 5.90-6.04 (m, 1H), 6.19 (brs, 1H), 7.05 (d, J=7.8 Hz, 2H), 7.18-7.25 (m, 3H), 7.27-7.31 (m, 2H), 7.42 (d, J=8.3 Hz, 2H).

MS(+): 427 [M+H]$^+$.

Example 4-206

6-{(E)-1-(4-tert-Butylphenyl)-2-[(2R)-5-oxopyrrolidin-2-yl]ethenyl}-3-(methylsulfanyl)pyridin-2(1H)-one (1) Sodium thiomethoxide (44 mg) was added to a solution of (5R)-5-[(E)-2-(5-bromo-6-methoxypyridin-2-yl)-2-(4-tert-butylphenyl)ethenyl]-1-(2,4-dimethoxybenzyl)pyrrolidin-2-one obtained in Reference Example 4-42(1) (150 mg) in N,N-dimethylformamide (1.5 mL), and the mixture was stirred at room temperature for 20 hours. Water was added to the reaction solution, followed by extraction with ethyl acetate. The organic layer was washed with water and brine, dried over anhydrous magnesium sulfate and filtered, after which the solvent was evaporated under reduced pressure. The residue was purified by silica gel column chromatography (hexane:ethyl acetate=9:1→0:10) to give (5R)-5-{(E)-2-(4-tert-butylphenyl)-2-[6-methoxy-5-(methylsulfanyl)pyridin-2-yl]ethenyl}-1-(2,4-dimethoxybenzyl)pyrrolidin-2-one as a colorless oil (53 mg, 34%).

(2) 48% hydrobromic acid (1.5 mL) was added to a solution of (5R)-5-{(E)-2-(4-tert-butylphenyl)-2-[6-methoxy-5-(methylsulfanyl)pyridin-2-yl]ethenyl}-1-(2,4-dimethoxybenzyl)pyrrolidin-2-one (53 mg) in 1,4-dioxane (2 mL), and the mixture was stirred at 65° C. for 30 minutes. Water was added to the reaction solution, followed by extraction with ethyl acetate. The organic layer was washed with brine and dried over anhydrous magnesium sulfate, after which the solvent was evaporated under reduced pressure. A solution of the residue in trifluoroacetic acid (4 mL) and anisole (2 mL) was stirred at 80° C. for six hours. The solvent was evaporated from the reaction solution under reduced pressure. The residue was purified by silica gel column chromatography (chloroform:methanol=100:1→3:1) and preparative HPLC (Waters Sunfire 19×150 mm 5 μm, rate: 20 mL/min, eluent: A=acetonitrile, B=0.1% trifluoroacetic acid solution, gradient: 10 to 90%) and powdered with ethyl acetate-hexane to give the title compound as a colorless powder (10 mg, 27%).

$^1$H NMR (300 MHz, CDCl$_3$) δ ppm 1.36 (s, 9H), 2.10-2.22 (m, 1H), 2.25-2.47 (m, 6H), 4.15-4.26 (m, 1H), 5.92-5.99 (m, 2H), 6.39 (d, J=9.0 Hz, 1H), 6.99 (d, J=7.6 Hz, 1H), 7.09 (d, J=8.4 Hz, 2H), 7.44 (d, J=8.4 Hz, 2H)

MS(+): 383 [M+H]$^+$. .

Examples 4-207 and 4-208

3-Cyclopropyl-6-{(1R)-1-(3,4-dichlorophenyl)-2-[(2R)-5-oxopyrrolidin-2-yl]ethyl}pyridin-2(1H)-one (Example 4-207)

3-Cyclopropyl-6-{(1S)-1-(3,4-dichlorophenyl)-2-[(2R)-5-oxopyrrolidin-2-yl]ethyl}pyridin-2(1H)-one (Example 4-208)

(1) 1,4-Dioxane (4 mL) and water (0.5 mL) were added to a mixture of (5R)-5-[(Z)-2-bromo-2-(5-cyclopropyl-6-methoxypyridin-2-yl)ethenyl]pyrrolidin-2-one (300 mg), 3,4-dichlorophenylboric acid (340 mg), tris(dibenzylideneacetone)dipalladium (81 mg), tri(2-furyl) phosphine (124 mg) and cesium carbonate (867 mg), and the mixture was stirred at 90° C. for three hours. Water and ethyl acetate were added to the reaction solution and the insoluble matter was filtered off through celite, followed by extraction with ethyl acetate. The organic layer was dried over anhydrous magnesium sulfate and filtered. The filtrate was concentrated under reduced pressure. The resulting residue was purified by silica gel column chromatography (hexane:ethyl acetate=50:50→0:100) to give (5R)-5-[(E)-2-(5-cyclopropyl-6-methoxypyridin-2-yl)-2-(3,4-dichlorophenyl)ethenyl]pyrrolidin-2-one as a colorless amorphous (250 mg, 69%).

(2) Zinc bromide (20 mg) and 10% palladium-activated carbon (40 mg) were added to a solution of (5R)-5-[(E)-2-(5-cyclopropyl-6-methoxypyridin-2-yl)-2-(3,4-dichlorophenyl)ethenyl]pyrrolidin-2-one (100 mg) in methanol (3 mL), and the mixture was stirred at room temperature for 18 hours in a hydrogen atmosphere. The reaction solution was filtered through celite, after which the filtrate was concentrated under reduced pressure to give a crude product of (5R)-5-[2-(5-cyclopropyl-6-methoxypyridin-2-yl)-2-(3,4-dichlorophenyl)ethyl]pyrrolidin-2-one as an amorphous (120 mg).

(3) 48% hydrobromic acid (2 mL) was added to a solution of (5R)-5-[2-(5-cyclopropyl-6-methoxypyridin-2-yl)-2-(3,4-dichlorophenyl)ethyl]pyrrolidin-2-one (120 mg) in 1,4-dioxane (4 mL), and the mixture was stirred at 65° C. for one hour. The reaction solution was poured into water, followed by extraction with ethyl acetate. The organic layer was dried over anhydrous magnesium sulfate and filtered. The filtrate was concentrated under reduced pressure. The resulting residue was purified by silica gel column chromatography (chloroform:methanol=100:0→90:10) to give an (R,S) mixture of the title compound as a brown amorphous (78 mg). This was preparatively isolated by a chiral HPLC column (CHIRALPAK IB, hexane:ethanol=20:80 v/v, 40° C., 10 mL/min, 210 nm) to give 3-cyclopropyl-6-{(1R)-1-(3,4-dichlorophenyl)-2-[(2R)-5-oxopyrrolidin-2-yl]ethyl}pyridin-2(1H)-one as a colorless amorphous (33 mg) and 3-cyclopropyl-6-{(1S)-1-(3,4-dichlorophenyl)-2-[(2R)-5-oxopyrrolidin-2-yl]ethyl}pyridin-2(1H)-one as a colorless amorphous (21 mg).

Example 4-207

$^1$H NMR (300 MHz, CDCl$_3$) δ ppm 0.52-0.68 (m, 2H), 0.93-1.07 (m, 2H), 1.70-1.85 (m, 1H), 2.07-2.40 (m, 6H), 3.49-3.65 (m, 1H), 3.97-4.12 (m, 1H), 5.92-6.04 (m, 1H), 6.90-7.02 (m, 1H), 7.07-7.15 (m, 1H), 7.15-7.22 (m, 1H), 7.29-7.36 (m, 1H), 7.62-7.74 (m, 1H), 13.04-13.16 (brs, 1H).

MS(+): 391 [M+H]$^+$.

CHIRALPAK IB 4.6×250 mm 5 μm (DAICEL), hexane:ethanol=50:50 v/v, 40° C., 1.0 mL/min, 210 nm, Rt=4.670 min.

Example 4-208

$^1$H NMR (300 MHz, CDCl$_3$) δ ppm 0.53-0.66 (m, 2H), 0.93-1.14 (m, 2H), 1.72-1.87 (m, 1H), 2.08-2.48 (m, 6H), 3.49-3.66 (m, 1H), 4.03-4.18 (m, 1H), 5.94-6.06 (m, 1H), 6.89-7.02 (m, 1H), 7.12-7.22 (m, 1H), 7.36-7.47 (m, 2H), 7.78-7.88 (m, 1H), 13.28-13.51 (brs, 1H),

MS(+): 391 [M+H]$^+$.

CHIRALPAK IB 4.6×250 mm 5 μm (DAICEL), hexane:ethanol=50:50 v/v, 40° C., 1.0 mL/min, 210 nm, Rt=9.879 min.

Examples 4-209 and 4-210

3-Cyclopropyl-6-{1-(2,3-dihydro-1-benzofuran-5-yl)-2-[(2R)-5-oxopyrrolidin-2-yl]ethyl}pyridin-2(1H)-one (1) (5R)-5-[(E)-2-(5-Cyclopropyl-6-methoxypyridin-2-yl)-2-(2,3-dihydro-1-benzofuran-5-yl)ethenyl]pyrrolidin-2-one was obtained as a colorless amorphous substance (240 mg) by performing substantially the same reaction as in Examples 4-207 and 4-208(1) except for using 2,3-dihydro-1-benzofuran-5-ylboronic acid.

(2) 10% palladium-activated carbon (50 mg) was added to a solution of (5R)-5-[(E)-2-(5-cyclopropyl-6-methoxypyridin-2-yl)-2-(2,3-dihydro-1-benzofuran-5-yl)ethenyl]pyrrolidin-2-one (240 mg) in methanol (3 mL), and the mixture was stirred at room temperature for four hours in a hydrogen atmosphere. The reaction solution was filtered through celite, and then the filtrate was concentrated under reduced pressure. The residue was purified by silica gel column chromatography (hexane:ethyl acetate=1:1→0:1) to give (5R)-5-[2-(5-cyclopropyl-6-methoxypyridin-2-yl)-2-(2,3-dihydro-1-benzofuran-5-yl)ethyl]pyrrolidin-2-one as an amorphous (200 mg).

(3) An (R,S) mixture of the title compound was obtained as a yellow amorphous (78 mg) by performing substantially the same reaction as in Examples 4-207 and 4-208(3) except for using (5R)-5-[2-(5-cyclopropyl-6-methoxypyridin-2-yl)-2-(2,3-dihydro-1-benzofuran-5-yl)ethyl]pyrrolidin-2-one. This was preparatively isolated by a chiral HPLC column (CHIRALPAK IB, hexane:ethanol=30:70 v/v, 40° C., 10 mL/min, 210 nm) to give one diastereomer (A) of the title compound as a colorless amorphous (50 mg) and the other diastereomer (B) of the title compound as a colorless amorphous (45 mg).

Diastereomer (A);

$^1$H NMR (300 MHz, CDCl$_3$) δ ppm 0.49-0.70 (m, 2H), 0.84-1.03 (m, 2H), 1.71-1.83 (m, 1H), 1.97-2.47 (m, 6H), 3.07-3.24 (m, 2H), 3.44-3.62 (m, 1H), 3.86-4.02 (m, 1H), 4.47-4.66 (m, 2H), 5.86-6.03 (m, 1H), 6.66-6.78 (m, 1H), 6.85-6.96 (m, 1H), 7.00-7.08 (m, 1H), 7.09-7.18 (m, 2H).

MS(+): 365 [M+H]$^+$.

CHIRALPAK IB 4.6×250 mm 5 μm (DAICEL), hexane:ethanol=40:60 v/v, 40° C., 1.0 mL/min, 210 nm, Rt=4.949 min.

Diastereomer (B);

$^1$H NMR (300 MHz, CDCl$_3$) δ ppm 0.47-0.71 (m, 2H), 0.88-1.11 (m, 2H), 1.68-1.85 (m, 1H), 2.07-2.42 (m, 6H), 3.11-3.30 (m, 2H), 3.49-3.70 (m, 1H), 3.91-4.09 (m, 1H), 4.50-4.65 (m, 2H), 5.90-6.09 (m, 1H), 6.67-6.78 (m, 1H), 6.90-6.98 (m, 1H), 7.05 (dd, J=8.16, 1.79 Hz, 1H), 7.09-7.18 (m, 1H), 7.35-7.51 (m, 1H), 12.59-12.84 (brs, 1H).
MS(+): 365 [M+H]$^+$.
CHIRALPAK IB 4.6×250 mm 5 μm (DAICEL), hexane:ethanol=40:60 v/v, 40° C., 1.0 mL/min, 210 nm, Rt=7.756 min.

The compounds of Examples 4-211 to 4-234 were obtained by performing substantially the same reaction as in Examples 4-207 and 4-208 or in Examples 4-209 and 4-210 using corresponding boronic acids ((3-chloro-4-fluorophenyl)boronic acid, (4-chloro-3-methylphenyl)boronic acid, (3-chloro-4-methylphenyl)boronic acid, (4-chloro-3-fluorophenyl)boronic acid, [3-fluoro-4-(trifluoromethyl)phenyl]boronic acid, [4-chloro-3-(trifluoromethyl)phenyl]boronic acid, (4-fluoro-3-methylphenyl)boronic acid, 2-[3-chloro-4-(difluoromethyl)phenyl]-4,4,5,5-tetramethyl-1,3,2-dioxaborolane (Reference Example 5-5), (4-chloro-3-methoxyphenyl)boronic acid, [4-(difluoromethoxy)phenyl]boronic acid, 2-[4-(difluoromethyl)-3-methylphenyl]-4,4,5,5-tetramethyl-1,3,2-dioxaborolane (Reference Example 5-7) and 2-[4-(difluoromethyl)-3-fluorophenyl]-4,4,5,5-tetramethyl-1,3,2-dioxaborolane (Reference Example 5-6)), respectively.

Examples 4-211 and 4-212

6-{1-(3-Chloro-4-fluorophenyl)-2-[(2R)-5-oxopyrrolidin-2-yl]ethyl}-3-cyclopropylpyridin-2(1H)-one Separation by CHIRALPAK IB (40° C., flow rate: 10 mL/min, ethanol:hexane=50:50) gave one diastereomer (A) of the title compound as a colorless amorphous (65 mg) and the other diastereomer (B) of the title compound as a colorless amorphous (37 mg).
Diastereomer (A);
$^1$H NMR (600 MHz, CDCl$_3$) δ ppm 0.59-0.67 (m, 2H), 0.94-1.00 (m, 2H), 1.70-1.77 (m, 1H), 2.07-2.40 (m, 6H), 3.47-3.52 (m, 1H), 3.97 (dd, J=9.6, 6.0 Hz, 1H), 5.98 (d, J=7.3 Hz, 1H), 6.93 (d, J=7.3 Hz, 1H), 7.03 (brs, 1H), 7.10 (t, J=8.5 Hz, 1H), 7.22-7.27 (m, 1H), 7.41-7.45 (m, 1H), 11.97-12.10 (brs, 1H).
MS(+): 375 [M+H]$^+$.
CHIRALPAK IB 4.6×250 mm 5 μm (DAICEL), hexane:ethanol=40:60 v/v, 40° C., 1.0 mL/min, 210 nm, Rt=4.360 min.
Diastereomer (B);
$^1$H NMR (600 MHz, CDCl$_3$) δ ppm 0.57-0.65 (m, 2H), 0.98-1.07 (m, 2H), 1.74-1.82 (m, 1H), 2.12-2.18 (m, 1H), 2.21-2.40 (m, 5H), 3.55-3.60 (m, 1H), 4.08 (dd, J=10.3, 5.3 Hz, 1H), 5.98 (d, J=7.3 Hz, 1H), 6.97 (d, J=7.3 Hz, 1H), 7.10 (t, J=8.5 Hz, 1H), 7.18-7.22 (m, 1H), 7.38 (dd, J=6.7, 2.1 Hz, 1H), 7.71 (brs, 1H), 13.17-13.26 (brs, 1H).
MS(+): 375 [M+H]$^+$.
CHIRALPAK IB 4.6×250 mm 5 μm (DAICEL), hexane:ethanol=40:60 v/v, 40° C., 1.0 mL/min, 210 nm, Rt=7.915 min.

Examples 4-213 and 4-214

6-{1-(4-Chloro-3-methylphenyl)-2-[(2R)-5-oxopyrrolidin-2-yl]ethyl}-3-cyclopropylpyridin-2(1H)-one Separation by CHIRALPAK IB (40° C., flow rate: 10 mL/min, ethanol:hexane=20:80) gave one diastereomer (A) of the title compound as a colorless amorphous (33 mg) and the other diastereomer (B) of the title compound as a colorless amorphous (21 mg).

Diastereomer (A);
$^1$H NMR (300 MHz, CDCl$_3$) δ ppm 0.51-0.73 (m, 2H), 0.83-1.04 (m, 2H), 1.68-1.83 (m, 1H), 2.02-2.38 (m, 9H), 3.36-3.59 (m, 1H), 3.86-4.01 (m, 1H), 5.87-6.04 (m, 1H), 6.85-6.96 (m, 1H), 7.06-7.18 (m, 1H), 7.20-7.34 (m, 3H), 11.89-12.11 (brs, 1H).
MS(+): 371 [M+H]$^+$.
CHIRALPAK IB 4.6×250 mm 5 μm (DAICEL), hexane:ethanol=50:50 v/v, 40° C., 1.0 mL/min, 210 nm, Rt=4.503 min.
Diastereomer (B);
$^1$H NMR (300 MHz, CDCl$_3$) δ ppm 0.49-0.68 (m, 2H), 0.93-1.13 (m, 2H), 1.70-1.86 (m, 1H), 2.06-2.41 (m, 9H), 3.48-3.67 (m, 1H), 4.00-4.10 (m, 1H), 5.93-6.01 (m, 1H), 6.87-6.99 (m, 1H), 7.06-7.14 (m, 1H), 7.14-7.21 (m, 1H), 7.26-7.36 (m, 1H), 7.68-7.80 (m, 1H), 13.04-13.24 (brs, 1H).
MS(+): 371 [M+H]$^+$.
CHIRALPAK IB 4.6×250 mm 5 μm (DAICEL), hexane:ethanol=50:50 v/v, 40° C., 1.0 mL/min, 210 nm, Rt=8.440 min.

Examples 4-215 and 4-216

6-{1-(3-Chloro-4-methylphenyl)-2-[(2R)-5-oxopyrrolidin-2-yl]ethyl}-3-cyclopropylpyridin-2(1H)-one Separation by CHIRALPAK IB (40° C., flow rate: 10 mL/min, ethanol:hexane=20:80) gave one diastereomer (A) of the title compound as a colorless amorphous (48 mg) and the other diastereomer (B) of the title compound as a colorless amorphous (35 mg).
Diastereomer (A);
$^1$H NMR (300 MHz, CDCl$_3$) δ ppm 0.51-0.68 (m, 2H), 0.90-1.02 (m, 2H), 1.62-1.74 (m, 1H), 1.99-2.41 (m, 9H), 3.40-3.57 (m, 1H), 3.90-4.01 (m, 1H), 5.93-6.03 (m, 1H), 6.87-6.96 (m, 1H), 7.07-7.21 (m, 2H), 7.26-7.31 (m, 1H), 7.33-7.37 (m, 1H), 11.98-12.20 (brs, 1H).
MS(+): 371 [M+H]$^+$.
CHIRALPAK IB 4.6×250 mm 5 μm (DAICEL), hexane:ethanol=50:50 v/v, 40° C., 1.0 mL/min, 210 nm, Rt=4.520 min.
Diastereomer (B);
$^1$H NMR (300 MHz, CDCl$_3$) δ ppm 0.52-0.68 (m, 2H), 0.93-1.07 (m, 2H), 1.70-1.85 (m, 1H), 2.07-2.40 (m, 9H), 3.49-3.65 (m, 1H), 3.97-4.12 (m, 1H), 5.92-6.04 (m, 1H), 6.90-7.02 (m, 1H), 7.07-7.15 (m, 1H), 7.15-7.22 (m, 1H), 7.29-7.36 (m, 1H), 7.62-7.74 (m, 1H), 13.04-13.16 (brs, 1H).
MS(+): 371 [M+H]$^+$.
CHIRALPAK IB 4.6×250 mm 5 μm (DAICEL), hexane:ethanol=50:50 v/v, 40° C., 1.0 mL/min, 210 nm, Rt=9.608 min.

Examples 4-217 and 4-218

6-{1-(4-Chloro-3-fluorophenyl)-2-[(2R)-5-oxopyrrolidin-2-yl]ethyl}-3-cyclopropylpyridin-2(1H)-one Separation by CHIRALPAK IB (40° C., flow rate: 10 mL/min, ethanol:hexane=50:50) gave one diastereomer (A) of the title compound as a colorless amorphous (50 mg) and the other diastereomer (B) of the title compound as a colorless amorphous (33 mg).
Diastereomer (A);
$^1$H NMR (600 MHz, CDCl$_3$) δ ppm 0.58-0.67 (m, 2H), 0.93-0.99 (m, 2H), 1.70-1.78 (m, 1H), 2.06-2.12 (m, 1H), 2.14-2.40 (m, 5H), 3.46-3.54 (m, 1H), 3.96-4.02 (m, 1H), 5.99 (d, J=7.3 Hz, 1H), 6.93 (d, J=7.3 Hz, 1H), 7.05 (brs, 1H), 7.09-7.13 (m, 1H), 7.21-7.25 (m, 1H), 7.32-7.37 (m, 1H), 12.11-12.26 (m, 1H).

MS(+): 375 [M+H]$^+$.

CHIRALPAK IB 4.6×250 mm 5 µm (DAICEL), hexane:ethanol=50:50 v/v, 40° C., 1.0 mL/min, 210 nm, Rt=4.820 min.

Diastereomer (B);
$^1$H NMR (600 MHz, CDCl$_3$) δ ppm 0.56-0.65 (m, 2H), 0.97-1.07 (m, 2H), 1.74-1.82 (m, 1H), 2.13-2.19 (m, 1H), 2.20-2.40 (m, 5H), 3.55-3.61 (m, 1H), 4.06-4.12 (m, 1H), 5.98 (d, J=7.3 Hz, 1H), 6.97 (d, J=7.3 Hz, 1H), 7.04-7.08 (m, 1H), 7.13-7.17 (m, 1H), 7.35 (t, J=8.0 Hz, 1H), 7.68 (brs, 1H), 13.15-13.27 (m, 1H).

MS(+): 375 [M+H]$^+$.

CHIRALPAK IB 4.6×250 mm 5 µm (DAICEL), hexane:ethanol=50:50 v/v, 40° C., 1.0 mL/min, 210 nm, Rt=9.481 min.

Examples 4-219 and 4-220

3-Cyclopropyl-6-{1-[3-fluoro-4-(trifluoromethyl)phenyl]-2-[(2R)-5-oxopyrrolidin-2-yl]ethyl}pyridin-2(1H)-one Separation by CHIRALPAK IB (40° C., flow rate: 10 mL/min, ethanol:hexane=50:50) gave one diastereomer (A) of the title compound as a colorless amorphous (68 mg) and the other diastereomer (B) of the title compound as a colorless amorphous (36 mg).

Diastereomer (A);
$^1$H NMR (600 MHz, CDCl$_3$) δ ppm 0.59-0.68 (m, 2H), 0.94-1.00 (m, 2H), 1.71-1.79 (m, 1H), 2.06-2.13 (m, 1H), 2.18-2.44 (m, 5H), 3.47-3.54 (m, 1H), 4.05-4.10 (m, 1H), 6.02 (d, J=7.3 Hz, 1H), 6.95 (d, J=6.9 Hz, 1H), 7.09 (brs, 1H), 7.27-7.34 (m, 2H), 7.52-7.58 (m, 1H), 12.32-12.45 (brs, 1H).

MS(+): 409 [M+H]$^+$.

CHIRALPAK IB 4.6×250 mm 5 µm (DAICEL), hexane:ethanol=40:60 v/v, 40° C., 1.0 mL/min, 210 nm, Rt=4.098 min.

Diastereomer (B);
$^1$H NMR (600 MHz, CDCl$_3$) δ ppm 0.57-0.66 (m, 2H), 0.98-1.08 (m, 2H), 1.76-1.83 (m, 1H), 2.15-2.42 (m, 6H), 3.56-3.62 (m, 1H), 4.15-4.20 (m, 1H), 6.01 (d, J=7.3 Hz, 1H), 6.98 (d, J=7.3 Hz, 1H), 7.22 (d, J=9.6 Hz, 2H), 7.56 (t, J=7.8 Hz, 1H), 7.79 (brs, 1H), 13.30-13.42 (brs, 1H).

MS(+): 409 [M+H]$^+$.

CHIRALPAK IB 4.6×250 mm 5 µm (DAICEL), hexane:ethanol=40:60 v/v, 40° C., 1.0 mL/min, 210 nm, Rt=7.120 min.

Examples 4-221 and 4-222

6-{1-[4-Chloro-3-(trifluoromethyl)phenyl]-2-[(2R)-5-oxopyrrolidin-2-yl]ethyl}-3-cyclopropylpyridin-2(1H)-one Separation by CHIRALPAK IB (40° C., flow rate: 10 mL/min, ethanol:hexane=50:50) gave one diastereomer (A) of the title compound as a colorless amorphous (87 mg) and the other diastereomer (B) of the title compound as a colorless amorphous (42 mg).

Diastereomer (A);
$^1$H NMR (600 MHz, CDCl$_3$) δ ppm 0.58-0.67 (m, 2H), 0.92-0.99 (m, 2H), 1.71-1.79 (m, 1H), 2.06-2.12 (m, 1H), 2.17-2.45 (m, 5H), 3.47-3.53 (m, 1H), 4.07 (dd, J=9.2, 6.4 Hz, 1H), 5.99 (d, J=7.3 Hz, 1H), 6.93 (d, J=6.9 Hz, 1H), 7.14 (brs, 1H), 7.47 (d, J=8.4 Hz, 1H), 7.55 (dd, J=8.4, 2.2 Hz, 1H), 7.71 (d, J=2.2 Hz, 1H), 12.37-12.49 (brs, 1H).

MS(+): 425 [M+H]$^+$.

CHIRALPAK IB 4.6×250 mm 5 µm (DAICEL), hexane:ethanol=40:60 v/v, 40° C., 1.0 mL/min, 210 nm, Rt=4.100 min.

Diastereomer (B);
$^1$H NMR (600 MHz, CDCl$_3$) δ ppm 0.57-0.65 (m, 2H), 0.98-1.08 (m, 2H), 1.75-1.82 (m, 1H), 2.13-2.19 (m, 1H), 2.21-2.41 (m, 5H), 3.56-3.62 (m, 1H), 4.15 (dd, J=10.6, 5.0 Hz, 1H), 5.98 (d, J=7.3 Hz, 1H), 6.98 (d, J=7.3 Hz, 1H), 7.44-7.49 (m, 2H), 7.64 (d, J=1.4 Hz, 1H), 7.77 (brs, 1H), 13.18-13.31 (brs, 1H).

MS(+): 425 [M+H]$^+$.

CHIRALPAK IB 4.6×250 mm 5 µm (DAICEL), hexane:ethanol=40:60 v/v, 40° C., 1.0 mL/min, 210 nm, Rt=7.961 min.

Examples 4-223 and 4-224

3-Cyclopropyl-6-{1-(4-fluoro-3-methylphenyl)-2-[(2R)-5-oxopyrrolidin-2-yl]ethyl}pyridin-2(1H)-one Separation by CHIRALPAK IB (40° C., flow rate: 10 mL/min, ethanol:hexane=50:50) gave one diastereomer (A) of the title compound as a colorless amorphous (40 mg) and the other diastereomer (B) of the title compound as a colorless amorphous (24 mg).

Diastereomer (A);
$^1$H NMR (600 MHz, CDCl$_3$) δ ppm 0.57-0.65 (m, 2H), 0.92-0.98 (m, 2H), 1.69-1.76 (m, 1H), 2.06-2.39 (m, 6H), 2.25 (d, J=1.4 Hz, 3H), 3.46-3.51 (m, 1H), 3.89 (dd, J=9.9, 5.7 Hz, 1H), 5.97 (d, J=6.9 Hz, 1H), 6.79 (brs, 1H), 6.91 (d, J=7.3 Hz, 1H), 6.95-6.99 (m, 1H), 7.08-7.13 (m, 2H), 11.10-11.21 (brs, 1H).

MS(+): 355 [M+H]$^+$.

CHIRALPAK IB 4.6×250 mm 5 µm (DAICEL), hexane:ethanol=40:60 v/v, 40° C., 1.0 mL/min, 210 nm, Rt=4.246 min.

Diastereomer (B);
$^1$H NMR (600 MHz, CDCl$_3$) δ ppm 0.56-0.63 (m, 2H), 0.96-1.04 (m, 2H), 1.74-1.81 (m, 1H), 2.13-2.37 (m, 6H), 2.26 (d, J=1.4 Hz, 3H), 3.54-3.60 (m, 1H), 4.01 (dd, J=9.4, 6.2 Hz, 1H), 5.98 (d, J=7.3 Hz, 1H), 6.93-6.99 (m, 2H), 7.07-7.12 (m, 2H), 7.39 (brs, 1H), 12.52-12.64 (brs, 1H).

MS(+): 355 [M+H]$^+$.

CHIRALPAK IB 4.6×250 mm 5 µm (DAICEL), hexane:ethanol=40:60 v/v, 40° C., 1.0 mL/min, 210 nm, Rt=6.970 min.

Examples 4-225 and 4-226

6-{1-[3-Chloro-4-(difluoromethyl)phenyl]-2-[(2R)-5-oxopyrrolidin-2-yl]ethyl}-3-cyclopropylpyridin-2(1H)-one Separation by CHIRALPAK IB (40° C., flow rate: 10 mL/min, ethanol:hexane=30:70) gave one diastereomer (A) of the title compound as a colorless amorphous (70 mg) and the other diastereomer (B) of the title compound as a colorless amorphous (40 mg).

Diastereomer (A);
$^1$H NMR (300 MHz, CDCl$_3$) δ ppm 0.56-0.70 (m, 2H), 0.93-1.02 (m, 2H), 1.71-1.79 (m, 1H), 2.03-2.46 (m, 6H), 3.43-3.56 (m, 1H), 4.01-4.14 (m, 1H), 5.98-6.07 (m, 1H), 6.66-7.13 (m, 2H), 7.30-7.38 (m, 2H), 7.39-7.46 (m, 1H), 7.48-7.54 (m, 1H), 7.56-7.65 (m, 1H), 12.41-12.59 (brs, 1H).

MS(+): 407 [M+H]$^+$.

CHIRALPAK IB 4.6×250 mm 5 μm (DAICEL), hexane:ethanol=30:70 v/v, 40° C., 1.0 mL/min, 210 nm, Rt=6.895 min.

Diastereomer (B);
$^1$H NMR (300 MHz, CDCl$_3$) δ ppm 0.52-0.71 (m, 2H), 0.90-1.14 (m, 2H), 1.70-1.91 (m, 1H), 2.08-2.47 (m, 6H), 3.47-3.67 (m, 1H), 4.10-4.20 (m, 1H), 5.93-6.08 (m, 1H), 6.68-7.15 (m, 2H), 7.31-7.47 (m, 2H), 7.56-7.68 (m, 1H), 7.83-7.97 (m, 1H), 13.30-13.49 (brs, 1H).
MS(+): 407 [M+H]$^+$.
CHIRALPAK IB 4.6×250 mm 5 μm (DAICEL), hexane:ethanol=30:70 v/v, 40° C., 1.0 mL/min, 210 nm, Rt=8.434 min.

Examples 4-227 and 4-228

6-{1-(4-Chloro-3-methoxyphenyl)-2-[(2R)-5-oxopyrrolidin-2-yl]ethyl}-3-cyclopropylpyridin-2(1H)-one Separation by CHIRALPAK IB (40° C., flow rate: 10 mL/min, ethanol:hexane=50:50) gave one diastereomer (A) of the title compound as a colorless amorphous (52 mg) and the other diastereomer (B) of the title compound as a colorless amorphous (29 mg).
Diastereomer (A);
$^1$H NMR (600 MHz, CDCl$_3$) δ ppm 0.57-0.64 (m, 2H), 0.91-0.98 (m, 2H), 1.70-1.78 (m, 1H), 2.07-2.13 (m, 1H), 2.17-2.40 (m, 5H), 3.48-3.54 (m, 1H), 3.88 (s, 3H), 3.95 (dd, J=9.9, 5.7 Hz, 1H), 5.99 (d, J=6.9 Hz, 1H), 6.87 (dd, J=8.0, 2.1 Hz, 1H), 6.90 (d, J=6.9 Hz, 1H), 7.02 (d, J=1.9 Hz, 1H), 7.05 (brs, 1H), 7.32 (d, J=8.3 Hz, 1H), 11.76-11.86 (brs, 1H).
MS(+): 387 [M+H]$^+$.
CHIRALPAK IB 4.6×250 mm 5 μm (DAICEL), hexane:ethanol=50:50 v/v, 40° C., 1.0 mL/min, 210 nm, Rt=5.090 min.

Diastereomer (B);
$^1$H NMR (600 MHz, CDCl$_3$) δ ppm 0.57-0.63 (m, 2H), 0.96-1.04 (m, 2H), 1.74-1.80 (m, 1H), 2.16-2.38 (m, 6H), 3.58-3.64 (m, 1H), 3.89 (s, 3H), 4.06 (dd, J=9.2, 6.0 Hz, 1H), 6.00 (d, J=7.3 Hz, 1H), 6.86-6.90 (m, 2H), 6.95 (d, J=7.3 Hz, 1H), 7.32 (d, J=8.3 Hz, 1H), 7.57 (brs, 1H), 12.98-13.07 (brs, 1H).
MS(+): 387 [M+H]$^+$.
CHIRALPAK IB 4.6×250 mm 5 μm (DAICEL), hexane:ethanol=50:50 v/v, 40° C., 1.0 mL/min, 210 nm, Rt=8.486 min.

Examples 4-229 and 4-230

3-Cyclopropyl-6-{1-[4-(difluoromethoxy)phenyl]-2-[(2R)-5-oxopyrrolidin-2-yl]ethyl}pyridin-2(1H)-one Separation by CHIRALPAK IB (40° C., flow rate: 10 mL/min, ethanol:hexane=50:50) gave one diastereomer (A) of the title compound as a colorless amorphous (59 mg) and the other diastereomer (B) of the title compound as a colorless amorphous (35 mg).
Diastereomer (A);
$^1$H NMR (600 MHz, CDCl$_3$) δ ppm 0.57-0.65 (m, 2H), 0.92-0.98 (m, 2H), 1.69-1.77 (m, 1H), 2.06-2.13 (m, 1H), 2.15-2.24 (m, 2H), 2.26-2.39 (m, 3H), 3.46-3.52 (m, 1H), 3.99 (dd, J=9.6, 6.0 Hz, 1H), 5.97 (d, J=7.3 Hz, 1H), 6.49 (t, J=73.8 Hz, 1H), 6.92 (d, J=7.3 Hz, 1H), 6.99 (brs, 1H), 7.09 (d, J=8.7 Hz, 2H), 7.35 (d, J=8.7 Hz, 2H), 11.65-11.77 (brs, 1H).
MS(+): 389 [M+H]$^+$.
CHIRALPAK IB 4.6×250 mm 5 μm (DAICEL), hexane:ethanol=50:50 v/v, 40° C., 1.0 mL/min, 210 nm, Rt=4.742 min.

Diastereomer (B);
$^1$H NMR (600 MHz, CDCl$_3$) δ ppm 0.56-0.64 (m, 2H), 0.96-1.05 (m, 2H), 1.74-1.81 (m, 1H), 2.14-2.38 (m, 6H), 3.56-3.61 (m, 1H), 4.10 (dd, J=9.9, 5.7 Hz, 1H), 5.98 (d, J=7.3 Hz, 1H), 6.49 (t, J=73.8 Hz, 1H), 6.96 (d, J=7.3 Hz, 1H), 7.09 (d, J=8.3 Hz, 2H), 7.32 (d, J=8.7 Hz, 2H), 7.63 (brs, 1H), 12.98-13.09 (brs, 1H).
MS(+): 389 [M+H]$^+$.
CHIRALPAK IB 4.6×250 mm 5 μm (DAICEL), hexane:ethanol=50:50 v/v, 40° C., 1.0 mL/min, 210 nm, Rt=7.778 min.

Examples 4-231 and 4-232

3-Cyclopropyl-6-{1-[4-(difluoromethyl)-3-methylphenyl]-2-[(2R)-5-oxopyrrolidin-2-yl]ethyl}pyridin-2(1H)-one Separation by CHIRALPAK IB (40° C., flow rate: 10 mL/min, ethanol:hexane=30:70) gave one diastereomer (A) of the title compound as a colorless amorphous (65 mg) and the other diastereomer (B) of the title compound as a colorless amorphous (50 mg).
Diastereomer (A);
$^1$H NMR (300 MHz, CDCl$_3$) δ ppm 0.45-0.68 (m, 2H), 0.85-1.08 (m, 2H), 1.64-1.83 (m, 1H), 2.01-2.49 (m, 9H), 3.36-3.62 (m, 1H), 3.88-4.10 (m, 1H), 5.91-6.03 (m, 1H), 6.48-6.97 (m, 2H), 7.13-7.33 (m, 3H), 7.42-7.52 (m, 1H).
MS(+): 387 [M+H]$^+$.
CHIRALPAK IB 4.6×250 mm 5 μm (DAICEL), hexane:ethanol=50:50 v/v, 40° C., 1.0 mL/min, 210 nm, Rt=4.923 min.

Diastereomer (B);
$^1$H NMR (300 MHz, CDCl$_3$) δ ppm 0.50-0.68 (m, 2H), 0.92-1.10 (m, 2H), 1.71-1.89 (m, 1H), 2.11-2.38 (m, 6H), 2.41 (s, 3H), 3.52-3.67 (m, 1H), 4.04-4.18 (m, 1H), 5.92-6.06 (m, 1H), 6.51-6.92 (m, 1H), 6.93-6.99 (m, 1H), 7.13-7.31 (m, 2H), 7.43-7.52 (m, 1H), 7.74-7.87 (m, 1H), 13.04-13.29 (brs, 1H).
MS(+): 387 [M+H]$^+$.
CHIRALPAK IB 4.6×250 mm 5 μm (DAICEL), hexane:ethanol=50:50 v/v, 40° C., 1.0 mL/min, 210 nm, Rt=9.239 min.

Examples 4-233 and 4-234

3-Cyclopropyl-6-{1-[4-(difluoromethyl)-3-fluorophenyl]-2-[(2R)-5-oxopyrrolidin-2-yl]ethyl}pyridin-2(1H)-one Separation by CHIRALPAK IB (40° C., flow rate: 10 mL/min, ethanol:hexane=30:70) gave one diastereomer (A) of the title compound as a colorless amorphous (40 mg) and the other diastereomer (B) of the title compound as a colorless amorphous (40 mg).
Diastereomer (A);
$^1$H NMR (300 MHz, CDCl$_3$) δ ppm 0.53-0.70 (m, 2H), 0.89-1.02 (m, 2H), 1.68-1.85 (m, 1H), 2.00-2.48 (m, 6H), 3.39-3.63 (m, 1H), 3.99-4.18 (m, 1H), 5.95-6.04 (m, 1H), 6.59-7.07 (m, 2H), 7.19-7.39 (m, 3H), 7.47-7.62 (m, 1H), 12.38-12.66 (brs, 1H).
MS(+): 391 [M+H]$^+$.

CHIRALPAK IB 4.6×250 mm 5 μm (DAICEL), hexane:ethanol=50:50 v/v, 40° C., 1.0 mL/min, 210 nm, Rt=4.843 min.

Diastereomer (B);
$^1$H NMR (300 MHz, CDCl$_3$) δ ppm 0.51-0.74 (m, 2H), 0.91-1.14 (m, 2H), 1.72-1.89 (m, 1H), 2.09-2.51 (m, 6H), 3.52-3.68 (m, 1H), 4.08-4.25 (m, 1H), 5.95-6.10 (m, 1H), 6.64-7.06 (m, 2H), 7.12-7.25 (m, 2H), 7.48-7.60 (m, 1H), 7.80-7.94 (m, 1H), 13.26-13.57 (brs, 1H).

MS(+): 391 [M+H]$^+$.

CHIRALPAK IB 4.6×250 mm 5 μm (DAICEL), hexane:ethanol=50:50 v/v, 40° C., 1.0 mL/min, 210 nm, Rt=9.704 min.

Examples 4-235 and 4-236

3-Chloro-6-{1-(4-ethoxyphenyl)-2-[(2R)-5-oxopyrrolidin-2-yl]ethyl}pyridin-2(1H)-one An (R,S) mixture of the title compound was obtained as a colorless amorphous (240 mg) by performing substantially the same reaction as in Examples 1-16(2)(3) and 4-209 and 4-210(2)(3) sequentially except for using (5R)-5-[2-(4-{[tert-butyl(dimethyl)silyl]oxy}phenyl)-2-(5-chloro-6-methoxypyridin-2-yl)ethenyl]pyrrolidin-2-one obtained in Example 4-48(1) and using ethyl iodide in place of methyl iodide. This was separated by chiral HPLC (CHIRALCEL OD-H, 40° C., flow rate: 7 mL/min, ethanol:hexane=0:100) to give one diastereomer (A) of the title compound as a colorless amorphous (38 mg) and the other diastereomer (B) of the title compound as a colorless amorphous (35 mg).

Diastereomer (A);
$^1$H NMR (300 MHz, CDCl$_3$) δ ppm 1.20-1.54 (m, 3H), 1.59-1.90 (m, 1H), 2.00-2.72 (m, 5H), 3.35-3.64 (m, 1H), 3.77-4.28 (m, 3H), 5.98 (d, J=7.6 Hz, 1H), 6.78-6.95 (m, 2H), 7.16-7.29 (m, 2H), 7.28-7.36 (m, 1H), 7.49 (d, J=7.5 Hz, 1H), 11.75-12.12 (brs, 1H).

MS(+): 361 [M+H]$^+$.

CHIRALCEL OD-H 4.6×250 mm 5 μm (DAICEL), hexane:i-PrOH=50:50 v/v, 40° C., 1.0 mL/min, 210 nm, Rt=9.196 min.

Diastereomer (B);
$^1$H NMR (300 MHz, CDCl$_3$) δ ppm 1.41 (t, J=7.0 Hz, 3H), 1.82-2.01 (m, 1H), 2.09-2.58 (m, 5H), 3.53-3.73 (m, 1H), 3.95-4.07 (m, 3H), 6.00 (d, J=7.6 Hz, 1H), 6.69-6.95 (m, 2H), 7.14-7.24 (m, 2H), 7.51 (d, J=7.6 Hz, 2H), 12.64-13.05 (brs, 1H).

MS(+): 361 [M+H]$^+$.

CHIRALCEL OD-H 4.6×250 mm 5 μm (DAICEL), hexane:i-PrOH=50:50 v/v, 40° C., 1.0 mL/min, 210 nm, Rt=11.535 min.

The compounds of Examples 4-237 to 4-241 were obtained by performing substantially the same reaction as in Examples 4-235 and 4-236.

Examples 4-237 and 4-238

3-Chloro-6-{1-[4-ethoxy-3-(trifluoromethyl)phenyl]-2-[(2R)-5-oxopyrrolidin-2-yl]ethyl}pyridin-2(1H)-one Separation by CHIRALCEL OD-H (40° C., flow rate: 7 mL/min, ethanol:hexane=0:100) gave one diastereomer (A) of the title compound as a colorless amorphous (60 mg) and the other diastereomer (B) of the title compound as a colorless amorphous (40 mg).

Diastereomer (A);
$^1$H NMR (300 MHz, CDCl$_3$) δ ppm 1.43 (t, J=6.9 Hz, 3H), 1.69-1.81 (m, 1H), 2.15-2.50 (m, 5H), 3.45-3.60 (m, 1H), 3.96-4.05 (m, 1H), 4.11 (q, J=6.9 Hz, 2H), 6.00 (d, J=7.5 Hz, 1H), 6.97 (d, J=8.6 Hz, 1H), 7.41-7.47 (m, 1H), 7.48-7.57 (m, 3H), 12.38-12.50 (brs, 1H).

MS(+): 429 [M+H]$^+$.

CHIRALCEL OD-H 4.6×250 mm 5 μm (DAICEL), EtOH v/v, 40° C., 1.0 mL/min, 210 nm, Rt=7.749 min.

Diastereomer (B);
$^1$H NMR (300 MHz, CDCl$_3$) δ ppm 1.43 (t, J=7.0 Hz, 3H), 1.82-2.00 (m, 1H), 2.11-2.54 (m, 5H), 3.61-3.75 (m, 1H), 4.01-4.17 (m, 3H), 6.04 (d, J=7.6 Hz, 1H), 6.95 (d, J=8.4 Hz, 1H), 7.41-7.51 (m, 2H), 7.54 (d, J=7.6 Hz, 1H), 7.82-7.90 (brs, 1H), 13.06-13.21 (brs, 1H).

MS(+): 429 [M+H]$^+$.

CHIRALCEL OD-H 4.6×250 mm 5 μm (DAICEL), EtOH v/v, 40° C., 1.0 mL/min, 210 nm, Rt=10.645 min.

Examples 4-239 and 4-240

3-Chloro-6-{1-(4-ethoxy-3-methylphenyl)-2-[(2R)-5-oxopyrrolidin-2-yl]ethyl}pyridin-2(1H)-one Separation by CHIRALCEL OD-H (40° C., flow rate: 7 mL/min, ethanol:hexane=0:100) gave one diastereomer (A) of the title compound as a colorless amorphous (38 mg) and the other diastereomer (B) of the title compound as a colorless amorphous (21 mg).

Diastereomer (A);
$^1$H NMR (300 MHz, CDCl$_3$) δ ppm 1.19-1.51 (m, 3H), 1.58-1.86 (m, 2H), 2.05-2.70 (m, 7H), 3.32-3.69 (m, 1H), 3.78-4.07 (m, 3H), 6.00 (d, J=7.6 Hz, 1H), 6.77 (d, J=8.2 Hz, 1H), 7.00-7.15 (m, 2H), 7.21-7.35 (m, 1H), 7.49 (d, J=7.6 Hz, 1H), 11.63-11.95 (brs, 1H).

MS(+): 375 [M+H]$^+$.

CHIRALCEL OD-H 4.6×250 mm 5 μm (DAICEL), hexane:i-PrOH=50:50 v/v, 40° C., 1.0 mL/min, 210 nm, Rt=8.549 min.

Diastereomer (B);
$^1$H NMR (300 MHz, CDCl$_3$) δ ppm 1.42 (t, J=7.0 Hz, 3H), 1.79-1.98 (m, 1H), 2.11-2.57 (m, 8H), 3.55-3.74 (m, 1H), 3.88-4.12 (m, 3H), 6.02 (d, J=7.6 Hz, 1H), 6.76 (d, J=8.2 Hz, 1H), 6.99-7.11 (m, 2H), 7.22-7.27 (m, 1H), 7.51 (d, J=7.6 Hz, 1H), 12.52-12.81 (brs, 1H).

MS(+): 375 [M+H]$^+$.

CHIRALCEL OD-H 4.6×250 mm 5 μm (DAICEL), hexane:i-PrOH=50:50 v/v, 40° C., 1.0 mL/min, 210 nm, Rt=10.983 min.

Example 4-241

3-Chloro-6-{1-(4-ethoxy-3-fluorophenyl)-2-[(2R)-5-oxopyrrolidin-2-yl]ethyl}pyridin-2(1H)-one Separation by CHIRALCEL OD-H (40° C., flow rate: 7 mL/min, ethanol:hexane=0:100) gave one diastereomer of the title compound as a colorless amorphous (19 mg).

$^1$H NMR (300 MHz, CDCl$_3$) δ ppm 1.35-1.53 (m, 3H), 1.64-1.83 (m, 1H), 2.06-2.55 (m, 5H), 3.41-3.62 (m, 1H), 3.90-4.00 (m, 1H), 4.09 (q, J=7.0 Hz, 2H), 6.00 (d, J=7.6 Hz, 1H), 6.85-6.97 (m, 1H), 7.02-7.14 (m, 2H), 7.35-7.45 (m, 1H), 7.51 (d, J=7.6 Hz, 1H), 12.12-12.39 (brs, 1H).

MS(+): 379 [M+H]$^+$.

CHIRALCEL OD-H 4.6×250 mm 5 μm (DAICEL), hexane:i-PrOH=50:50 v/v, 40° C., 1.0 mL/min, 210 nm, Rt=8.798 min.

Examples 4-242 and 4-243

6-{2-[(2R)-5-Oxopyrrolidin-2-yl]-1-[4-(trifluoromethyl)phenyl]ethyl}-3-propylpyridin-2(1H)-one An (R,S) mixture of the title compound was obtained as a colorless amorphous (50 mg) by performing substantially the same reaction as in Examples 4-207 and 4-208(2) except for using 3-cyclopropyl-6-{(E)-2-[(2R)-5-oxopyrrolidin-2-yl]-1-[4-(trifluoromethyl)phenyl]ethenyl}pyridin-2(1H)-one obtained in Example 4-99.

Separation by CHIRALPAK IB (40° C., flow rate: 10 mL/min, ethanol:hexane=50:50) gave one diastereomer (A) of the title compound as a colorless amorphous (21 mg) and the other diastereomer (B) of the title compound as a colorless amorphous (21 mg).

Diastereomer (A);
$^1$H NMR (300 MHz, CDCl$_3$) δ ppm 0.97 (t, J=7.4 Hz, 3H), 1.54-1.82 (m, 3H), 2.14-2.41 (m, 5H), 2.46-2.56 (m, 2H), 3.42-3.58 (m, 1H), 4.02-4.18 (m, 1H), 6.02 (d, J=7.2 Hz, 1H), 7.13-7.25 (m, 2H), 7.47-7.65 (m, 4H), 12.06-12.25 (brs, 1H).
MS(+): 393 [M+H]$^+$.
CHIRALPAK IB 4.6×250 mm 5 μm (DAICEL), hexane:ethanol=50:50 v/v, 40° C., 1.0 mL/min, 210 nm, Rt=3.957 min.

Diastereomer (B);
$^1$H NMR (300 MHz, CDCl$_3$) δ ppm 0.98 (t, J=7.3 Hz, 3H), 1.58-1.72 (m, 2H), 1.74-1.89 (m, 1H), 2.10-2.46 (m, 5H), 2.49-2.72 (m, 2H), 3.49-3.67 (m, 1H), 4.11-4.27 (m, 1H), 5.97-6.11 (m, 1H), 7.20-7.31 (m, 1H), 7.42-7.52 (m, 2H), 7.55-7.64 (m, 2H), 7.65-7.73 (m, 1H), 12.87-13.37 (brs, 1H).
MS(+): 393 [M+H]$^+$.
CHIRALPAK IB 4.6×250 mm 5 μm (DAICEL), hexane:ethanol=50:50 v/v, 40° C., 1.0 mL/min, 210 nm, Rt=5.234 min.

Examples 4-244 and 4-245

6-{1-(4-tert-Butylphenyl)-2-[(2R)-5-oxopyrrolidin-2-yl]ethyl}-3-methoxypyridin-2(1H)-one An (R,S) mixture of the title compound was obtained by performing substantially the same reaction as in Examples 4-207 and 4-208(2) except for using 6-{(E)-1-(4-tert-butylphenyl)-2-[(2R)-5-oxopyrrolidin-2-yl]ethenyl}-3-methoxypyridin-2(1H)-one obtained in Example 4-164. This was preparatively isolated by a chiral HPLC column (CHIRALCEL OD-H, hexane:ethanol=50:50 v/v, 40° C., 7.0 mL/min, 210 nm) to give one diastereomer (A) of the title compound as a colorless amorphous (9.5 mg) and the other diastereomer (B) of the title compound as a colorless powder (11.9 mg).

Diastereomer (A);
$^1$H NMR (300 MHz, CDCl$_3$) δ ppm 1.30 (s, 9H), 1.64-1.80 (m, 1H), 2.02-2.53 (m, 5H), 3.43-3.57 (m, 1H), 3.83 (s, 3H), 3.87-3.99 (m, 1H), 5.98 (d, J=7.6 Hz, 1H), 6.64 (d, J=7.6 Hz, 1H), 7.15-7.25 (m, 2H), 7.30-7.37 (m, 2H), 7.39-7.46 (m, 1H).
MS(+): 369 [M+H]$^+$.
CHIRALCEL OD-H 4.6×250 mm 5 μm (DAICEL), hexane:EtOH=50:50 v/v, 40° C., 1.0 mL/min, 210 nm, Rt=5.136 min Diastereomer (B);
$^1$H NMR (300 MHz, CDCl$_3$) δ ppm 1.30 (s, 9H), 1.79-1.94 (m, 1H), 2.09-2.47 (m, 5H), 3.49-3.62 (m, 1H), 3.80 (s, 3H), 3.89-3.99 (m, 1H), 5.95 (d, J=7.5 Hz, 1H), 6.65 (d, J=7.8 Hz, 1H), 7.19 (d, J=8.4 Hz, 2H), 7.34 (d, J=8.5 Hz, 2H), 7.43-7.50 (m, 1H).
MS(+): 369 [M+H]$^+$.
CHIRALCEL OD-H 4.6×250 mm 5 μm (DAICEL), hexane:EtOH=50:50 v/v, 40° C., 1.0 mL/min, 210 nm, Rt=6.333 min.

Examples 4-246 and 4-247

6-{-1-(4-tert-Butylphenyl)-2-[(2R)-5-oxopyrrolidin-2-yl]ethyl}-3-(difluoromethoxy)pyridin-2(1H)-one An (R,S) mixture of the title compound was obtained by performing substantially the same reaction as in Examples 4-207 and 4-208(2) except for using 6-{(E)-1-(4-tert-butylphenyl)-2-[(2R)-5-oxopyrrolidin-2-yl]ethenyl}-3-(difluoromethoxy)pyridin-2(1H)-one obtained in Example 4-165. This was preparatively isolated by a chiral HPLC column (CHIRALCEL OD-H, hexane:ethanol=50:50 v/v, 40° C., 7.0 mL/min, 210 nm) to give one diastereomer (A) of the title compound as a colorless amorphous (20 mg) and the other diastereomer (B) of the title compound as a colorless powder (24 mg).

Diastereomer (A);
$^1$H NMR (300 MHz, CDCl$_3$) δ ppm 1.30 (s, 9H), 1.62-1.81 (m, 1H), 2.13-2.46 (m, 5H), 3.44-3.58 (m, 1H), 4.00 (t, J=7.8 Hz, 1H), 6.02 (d, J=7.6 Hz, 1H), 6.68-7.18 (m, 1H), 7.20-7.28 (m, 3H), 7.31-7.39 (m, 2H), 7.63-7.74 (m, 1H), 12.22-12.67 (brs, 1H).
MS(+): 405 [M+H]$^+$.
CHIRALCEL OD-H 4.6×250 mm 5 μm (DAICEL), hexane:EtOH=50:50 v/v, 40° C., 1.0 mL/min, 210 nm, Rt=4.094 min.

Diastereomer (B);
$^1$H NMR (300 MHz, CDCl$_3$) δ ppm 1.30 (s, 9H), 1.74-1.94 (m, 1H), 2.14-2.50 (m, 5H), 3.51-3.65 (m, 1H), 4.02 (t, J=7.8 Hz, 1H), 6.11 (d, J=7.8 Hz, 1H), 6.59-7.17 (m, 1H), 7.22 (d, J=8.4 Hz, 2H), 7.29 (d, J=7.6 Hz, 1H), 7.33-7.40 (m, 2H), 7.64-7.74 (brs, 1H).
MS(+): 405 [M+H]$^+$.
CHIRALCEL OD-H 4.6×250 mm 5 μm (DAICEL), hexane:EtOH=50:50 v/v, 40° C., 1.0 mL/min, 210 nm, Rt=5.620 min.

The structures of Examples 4-98 to 4-247 are shown below.

[Hyo 16-1]

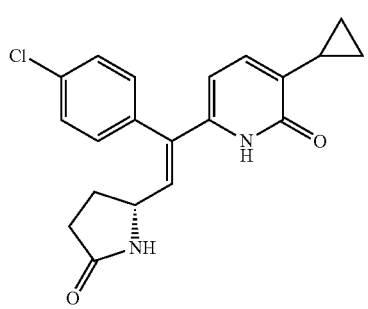

Example 4-98

Example 4-99
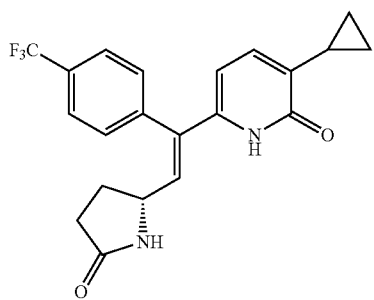
Example 4-100
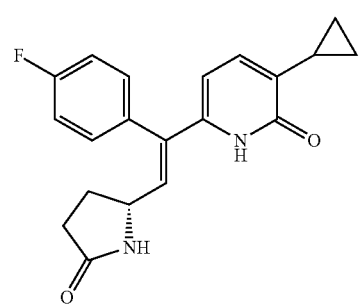
Example 4-101
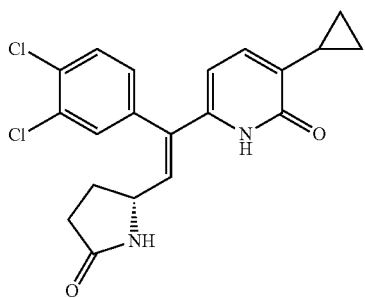
Example 4-102
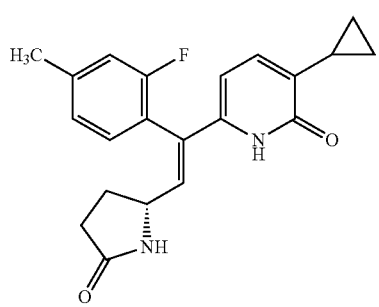
Example 4-103
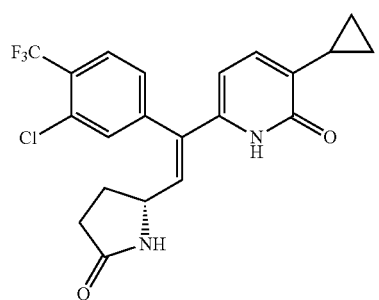
Example 4-104
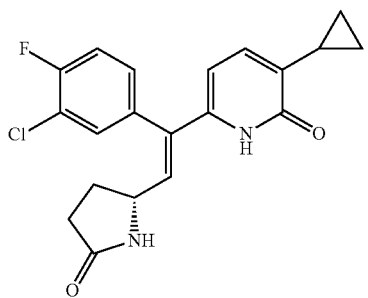
Example 4-105
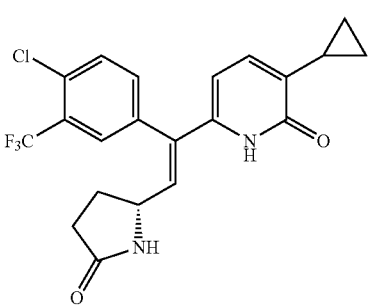
Example 4-106
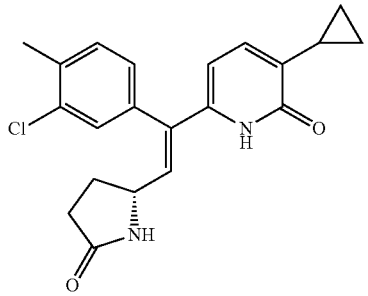
Example 4-107
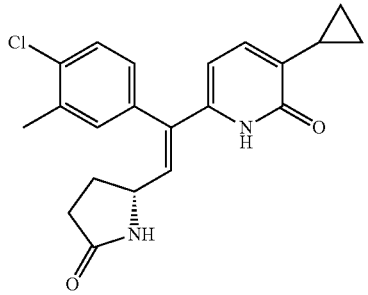
Example 4-108
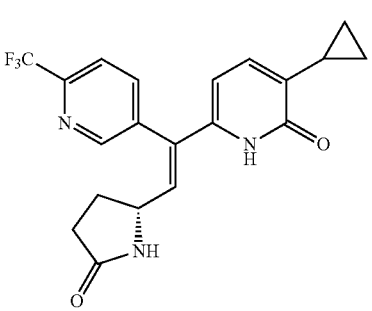

-continued
Example 4-109
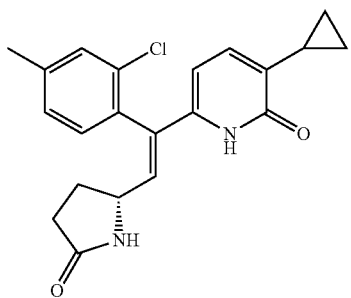
Example 4-110
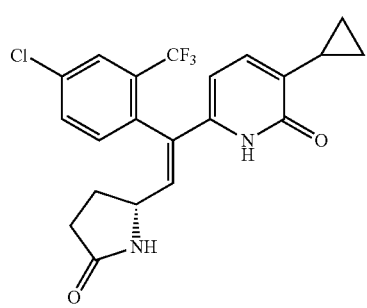
Example 4-111
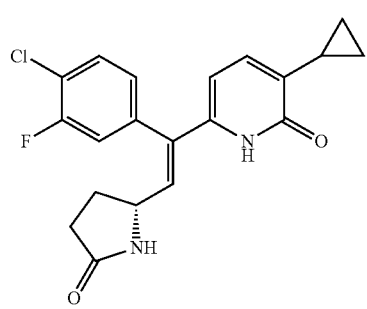
Example 4-112
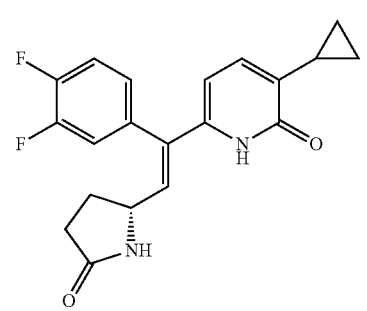
Example 4-113
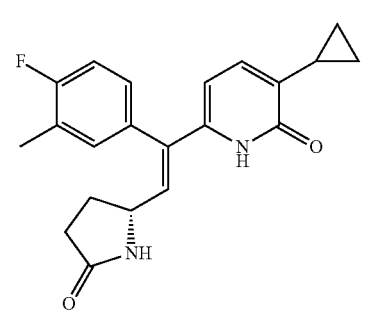
-continued
Example 4-114
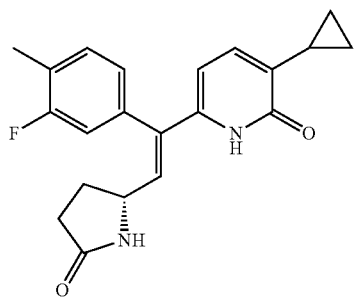
Example 4-115
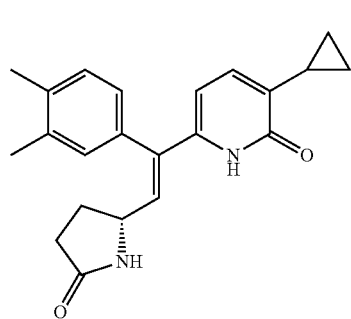
Example 4-116
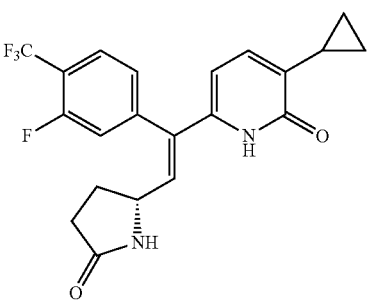
Example 4-117
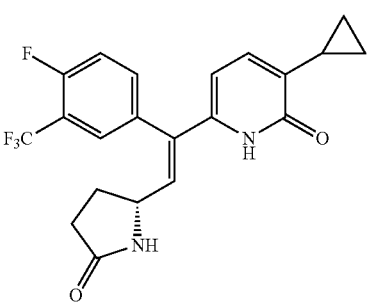
Example 4-118
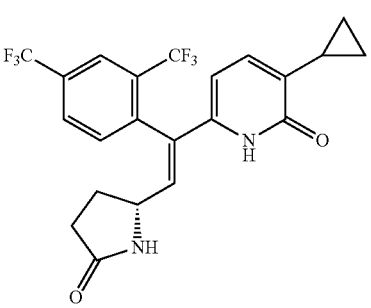

Example 4-119
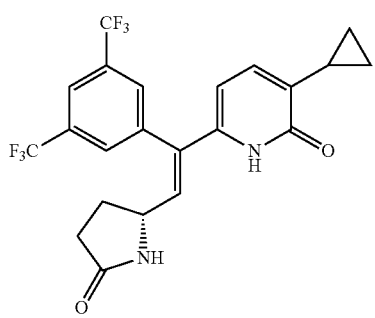
Example 4-120
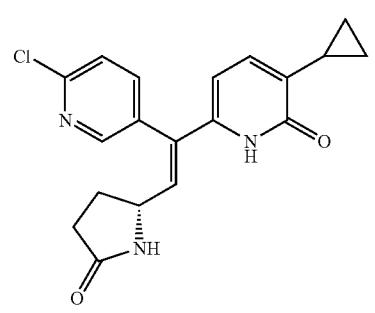
Example 4-121
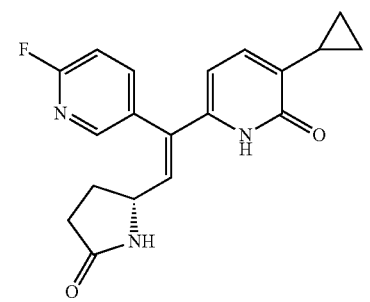
Example 4-122
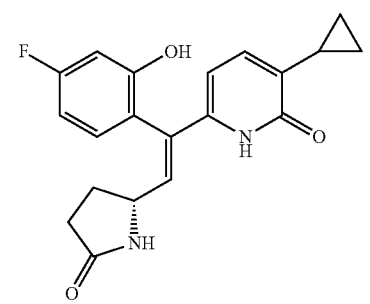
Example 4-123
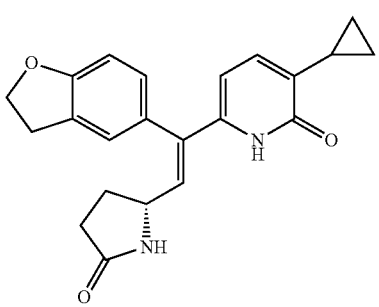
Example 4-124
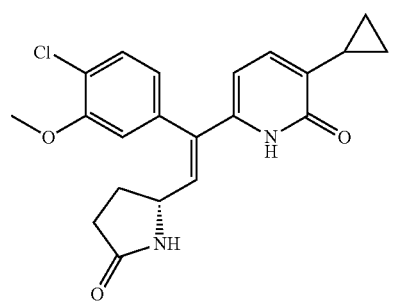
Example 4-125
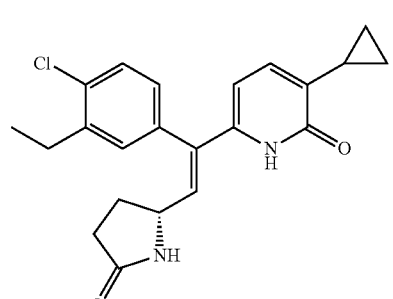
Example 4-126
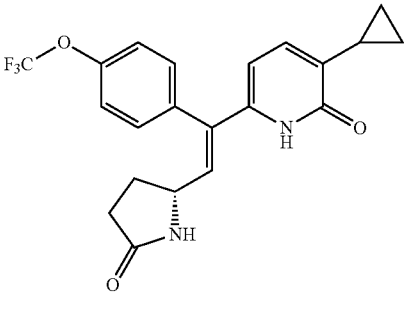
Example 4-127
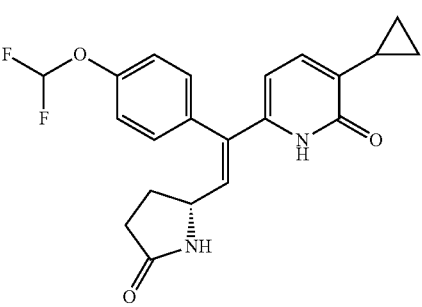
Example 4-128
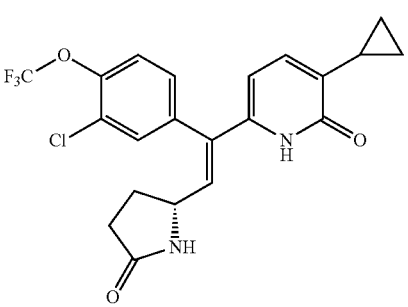

Example 4-129
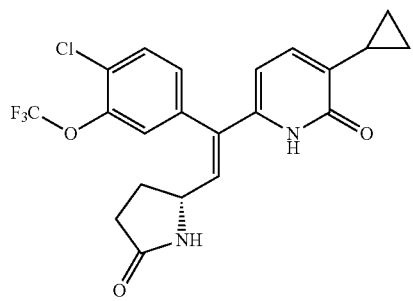
Example 4-130
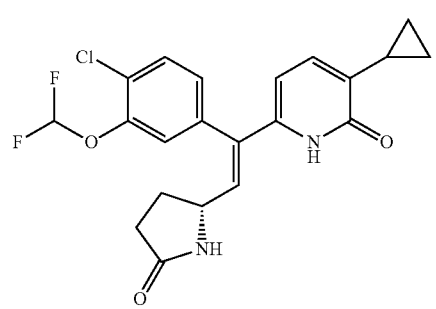
Example 4-131
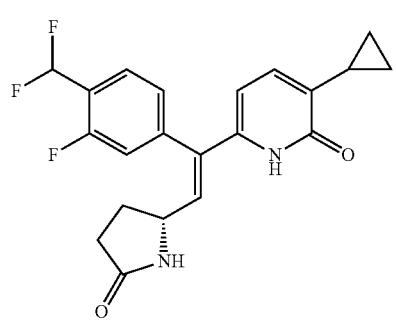
Example 4-132
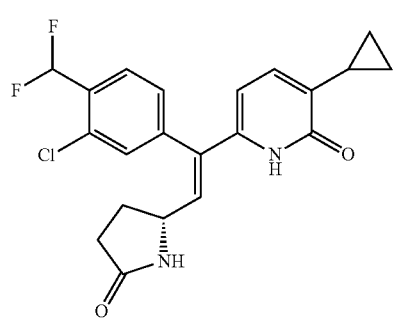
Example 4-133
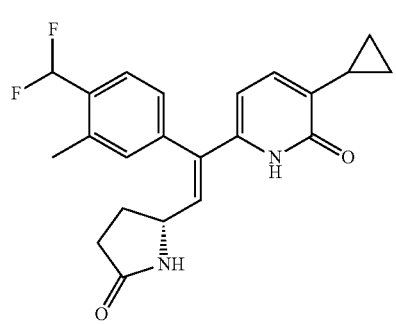
Example 4-134
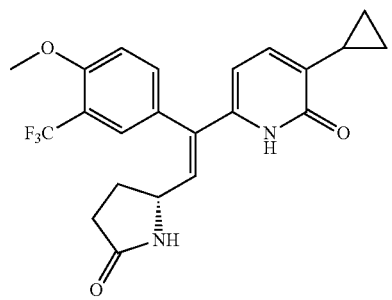
Example 4-135
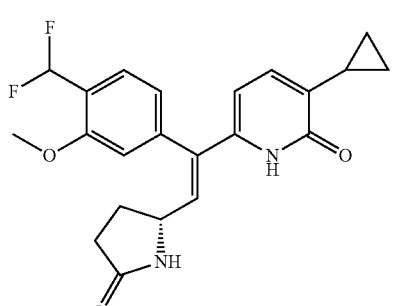
Example 4-136
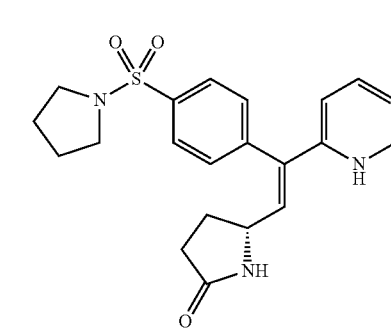
Example 4-137
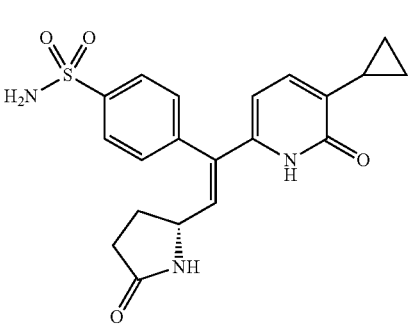
Example 4-138
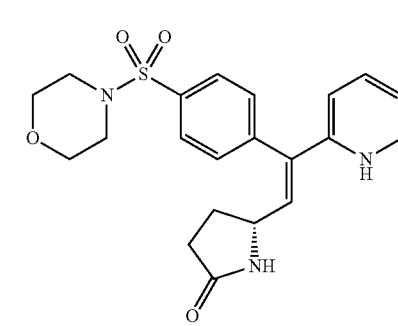

Example 4-139
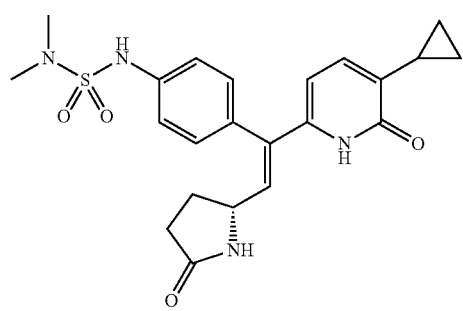
Example 4-144
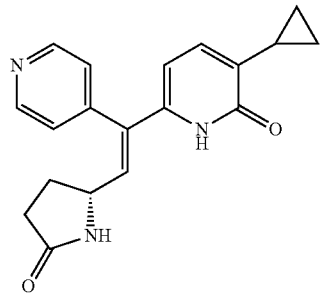
Example 4-140
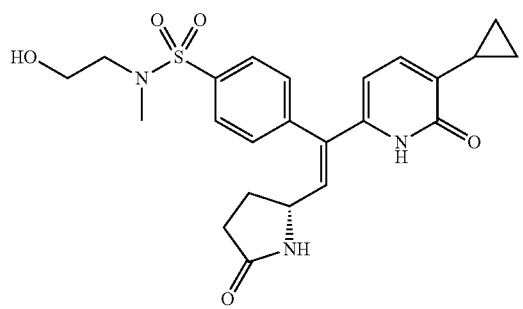
Example 4-145
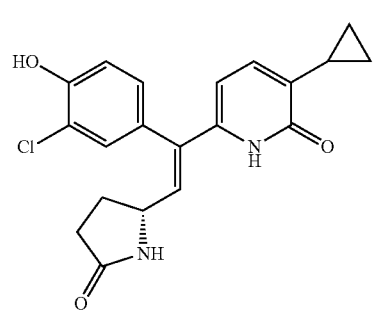
Example 4-141
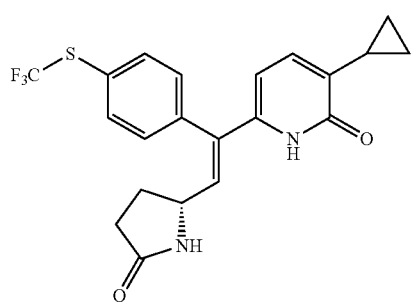
Example 4-146
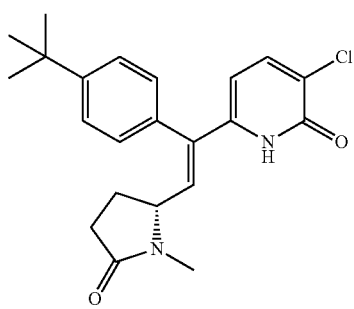
Example 4-142
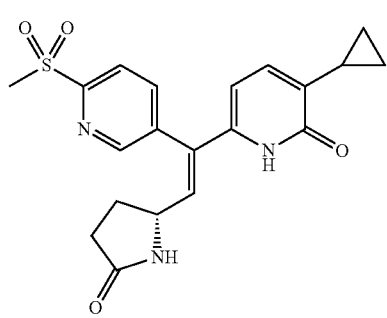
Example 4-147
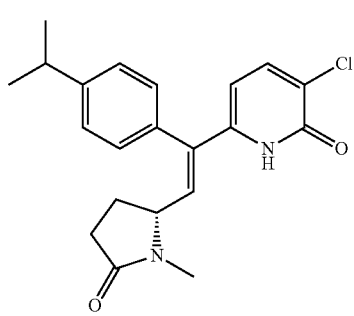
Example 4-143
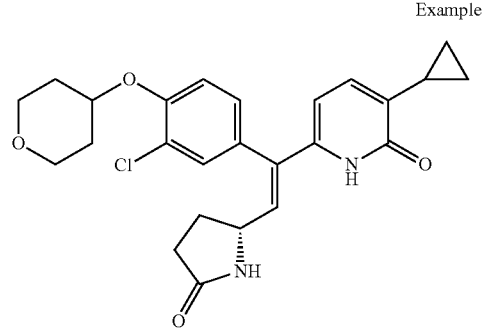
Example 4-148
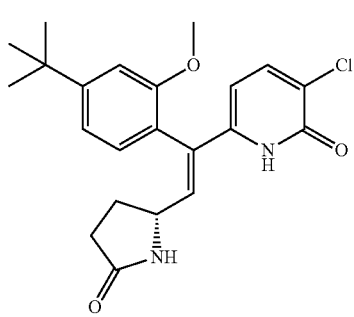

Example 4-149
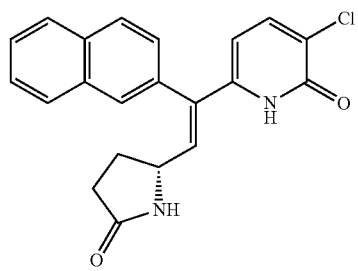
Example 4-150
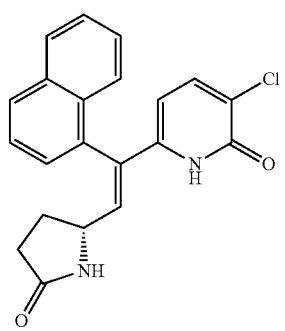
Example 4-151
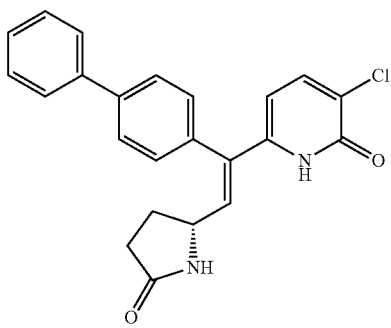
Example 4-152
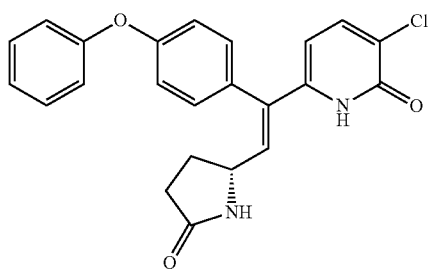
Example 4-153
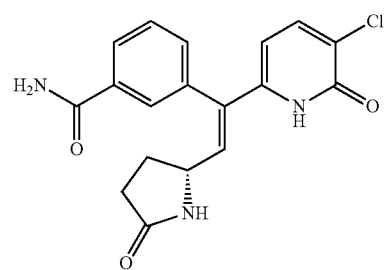
Example 4-154
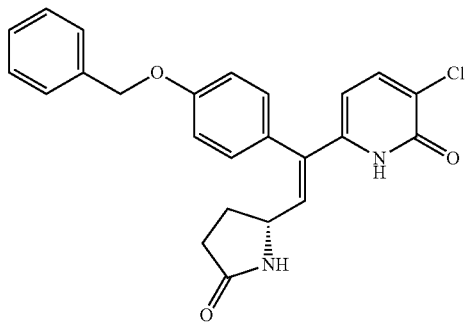
Example 4-155
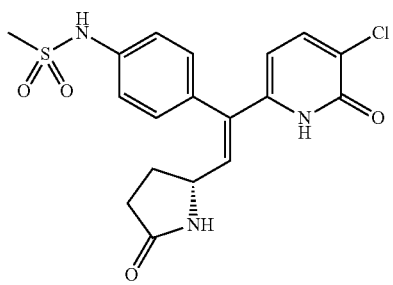
Example 4-156
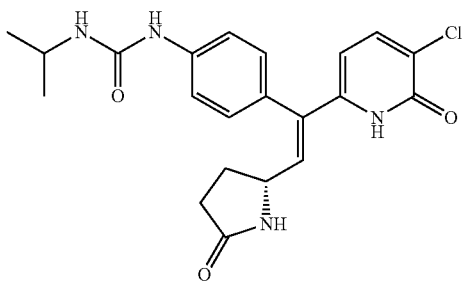
Example 4-157
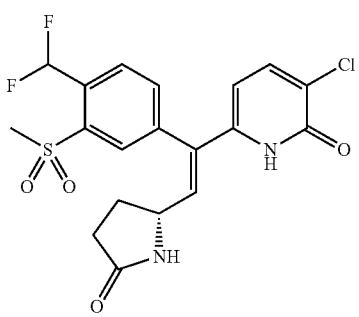
Example 4-158
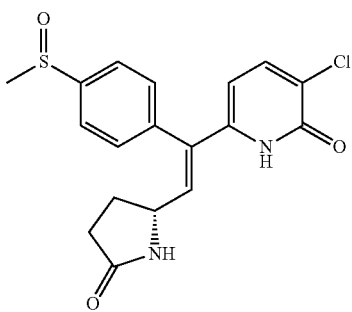

Example 4-159
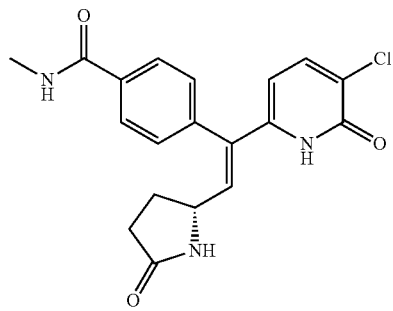
Example 4-164
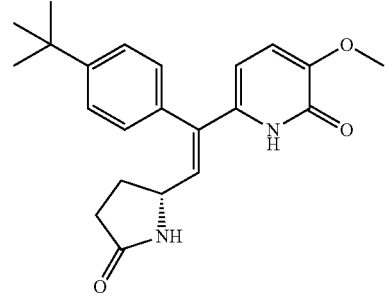
Example 4-160
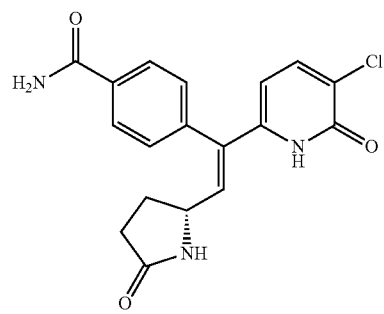
Example 4-165
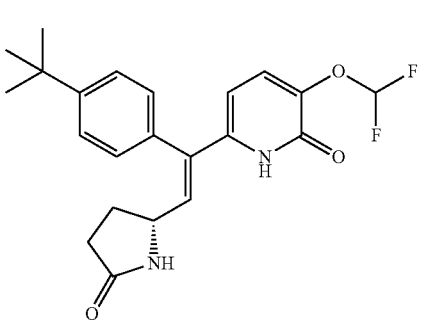
Example 4-161
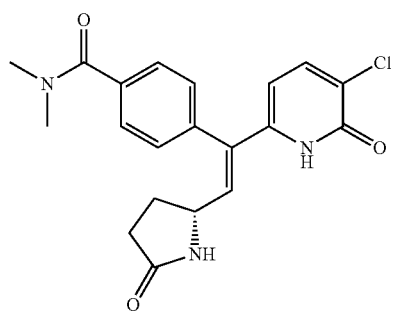
Example 4-166
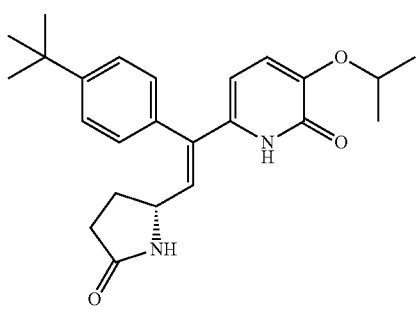
Example 4-162
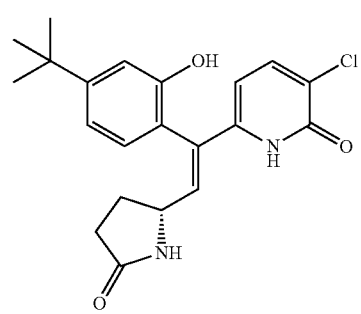
Example 4-167
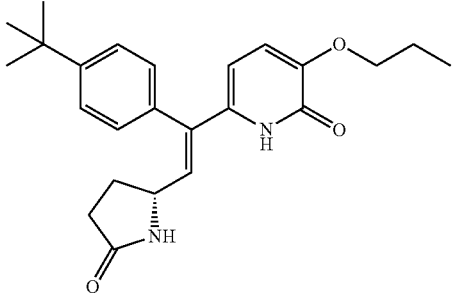
Example 4-163
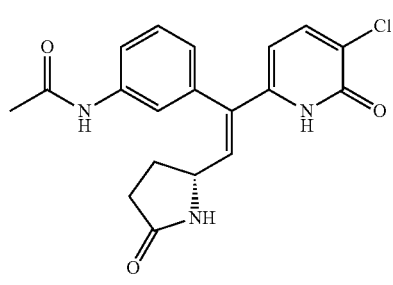
Example 4-168
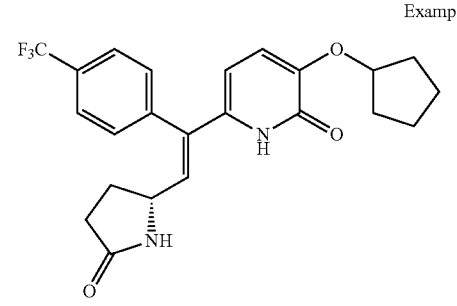

Example 4-169
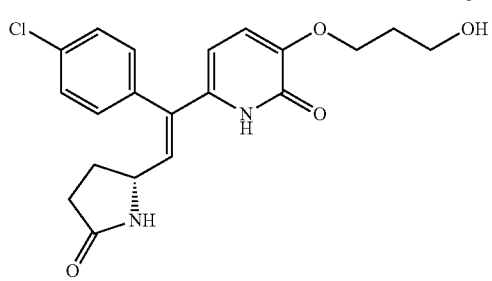
Example 4-170
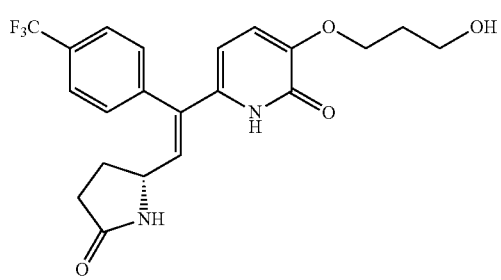
Example 4-171
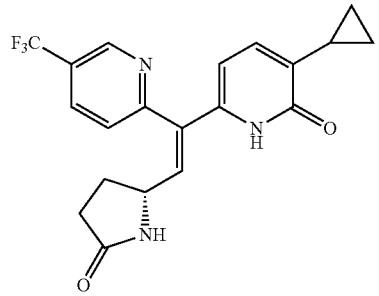
Example 4-172
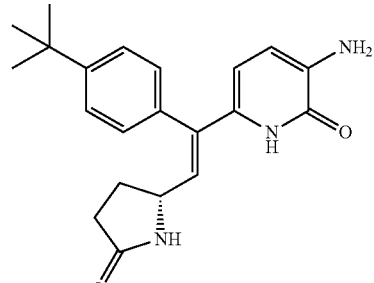
Example 4-173
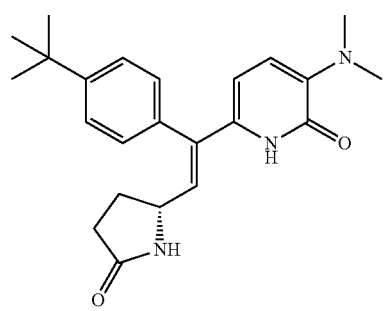
Example 4-174
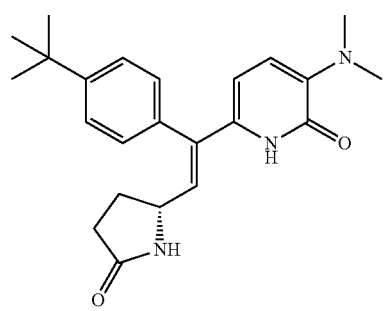
Example 4-175
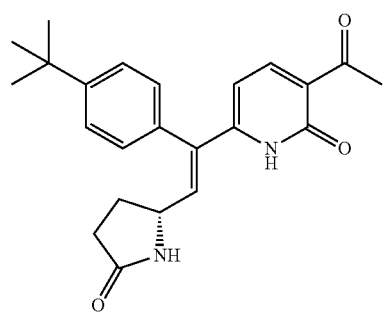
Example 4-176
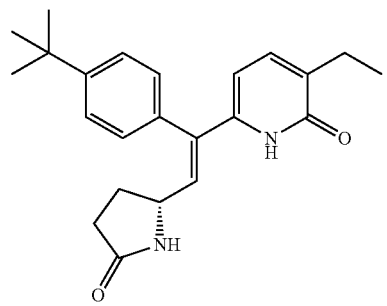
Example 4-177
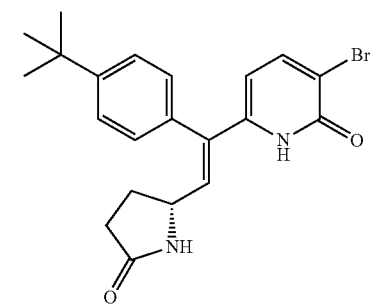
Example 4-178
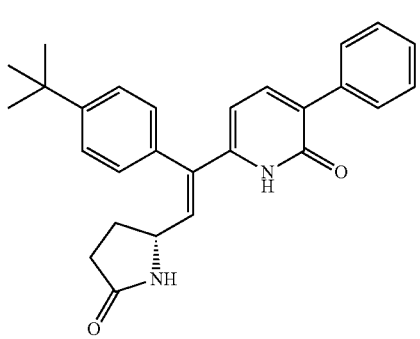

Example 4-179
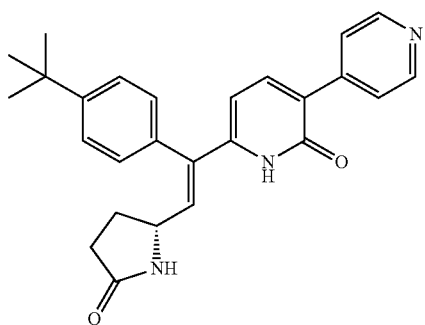
Example 4-180
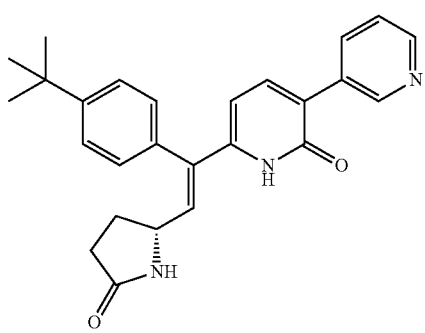
Example 4-181
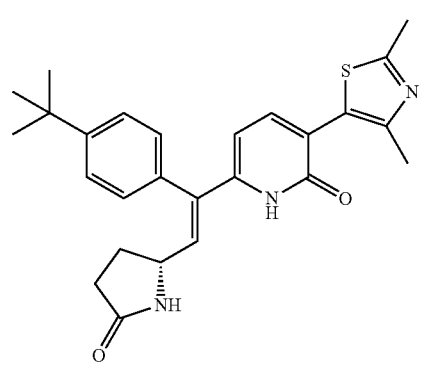
Example 4-182
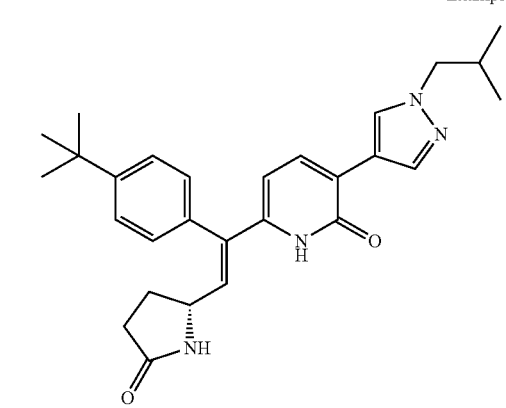
Example 4-183
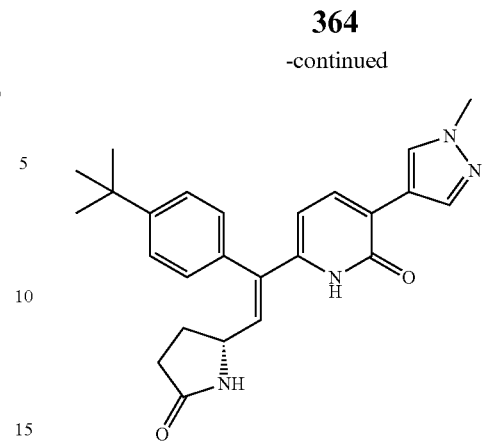
Example 4-184
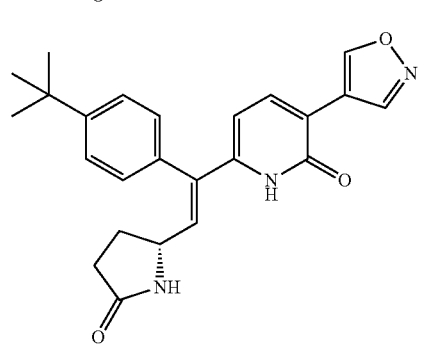
Example 4-185
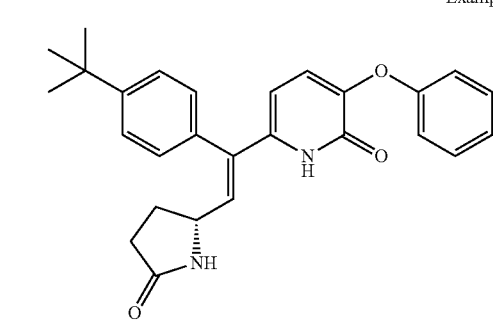
Example 4-186
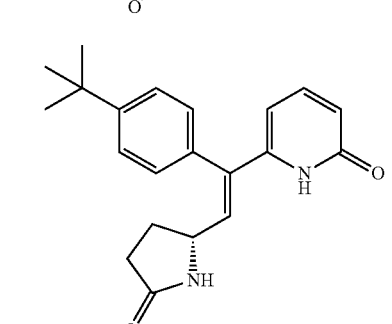
Example 4-187
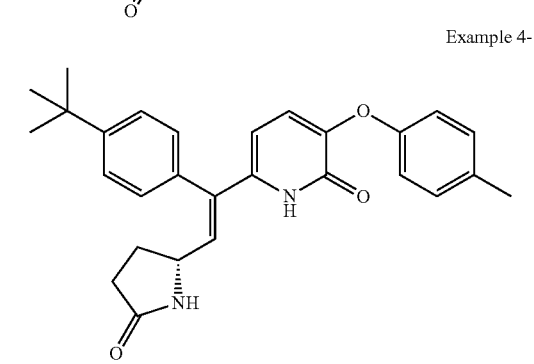

Example 4-188
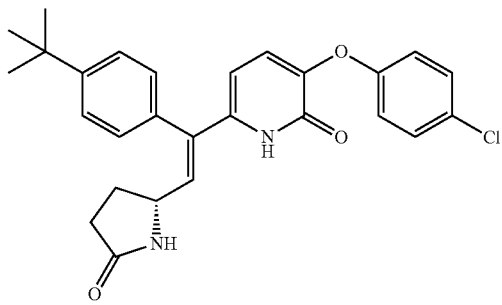
Example 4-189
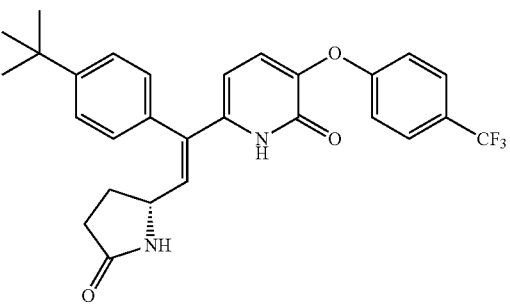
Example 4-190
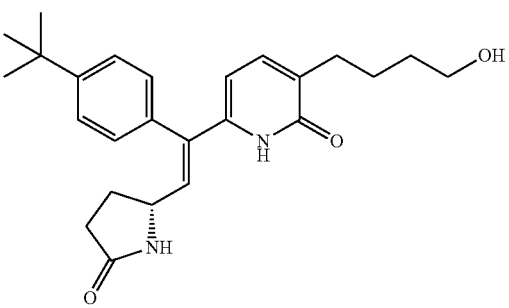
Example 4-191
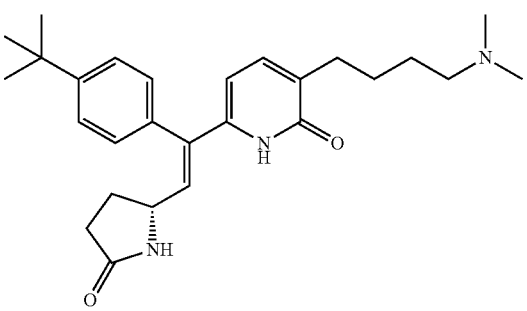
Example 4-192
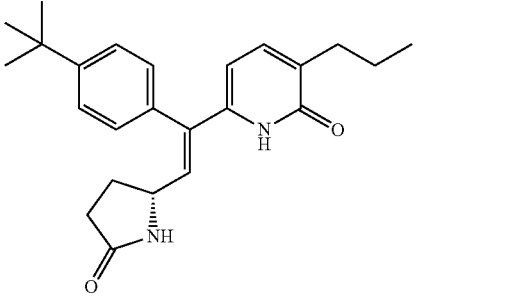
Example 4-193
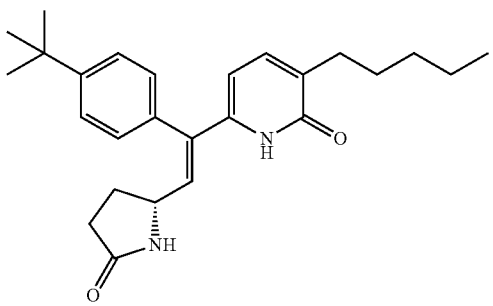
Example 4-194
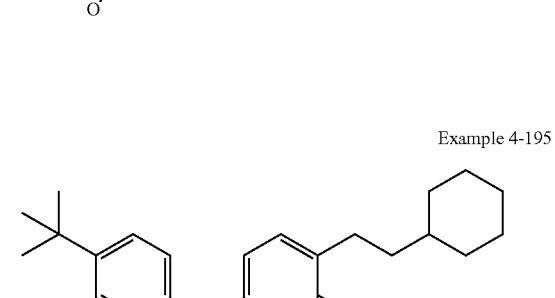
Example 4-195
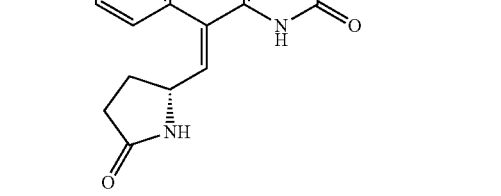
Example 4-196
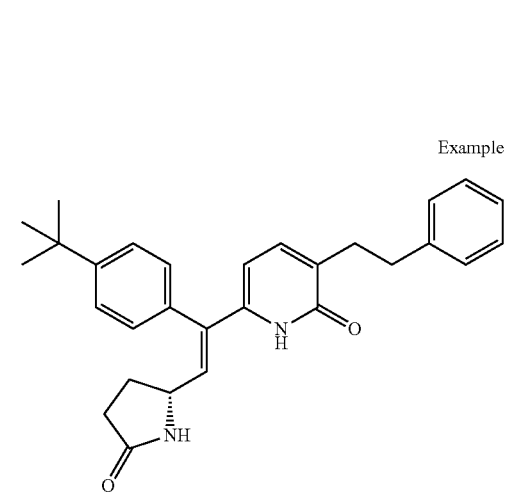

Example 4-197
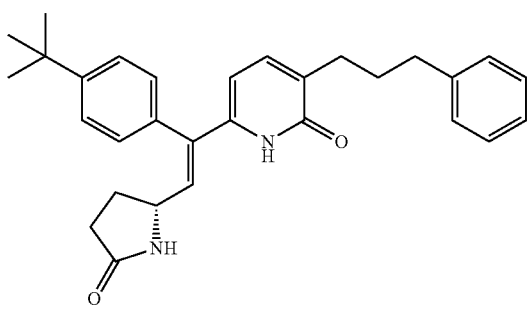
Example 4-198
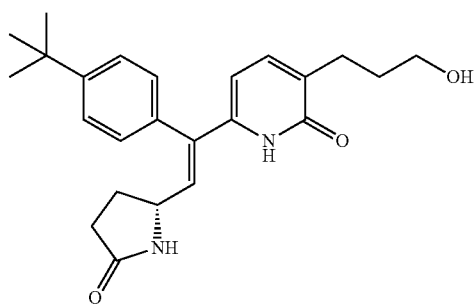
Example 4-199
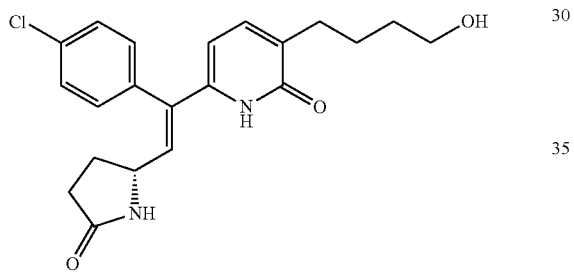
Example 4-200
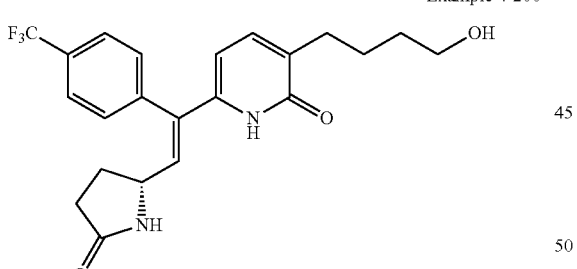
Example 4-201
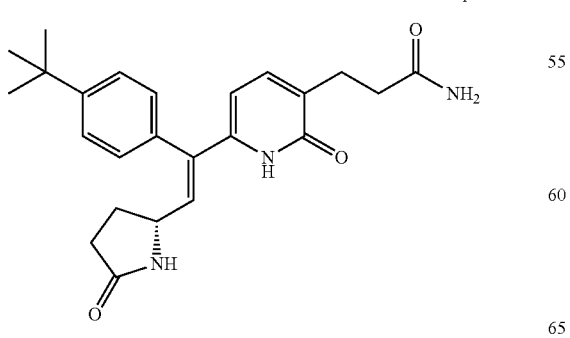
Example 4-202
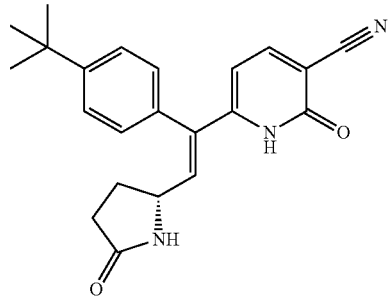
Example 4-203, 204
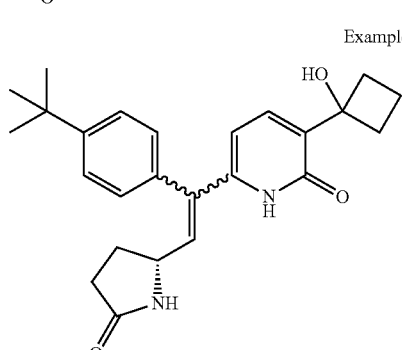
Example 4-205
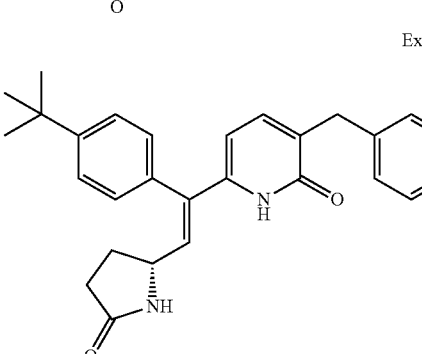
Example 4-206
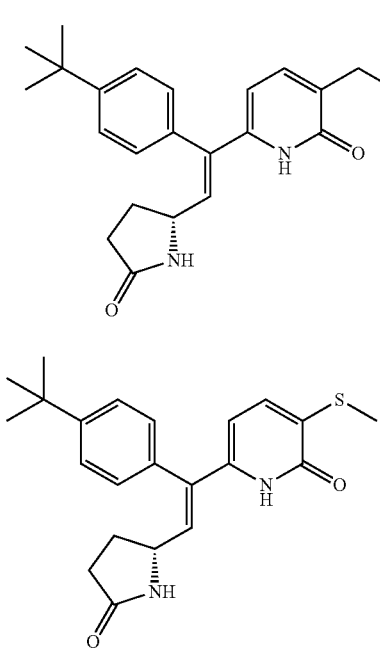
Example 4-207
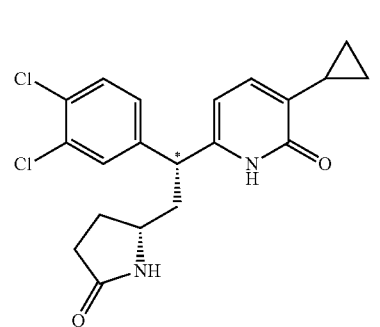

Example 4-208
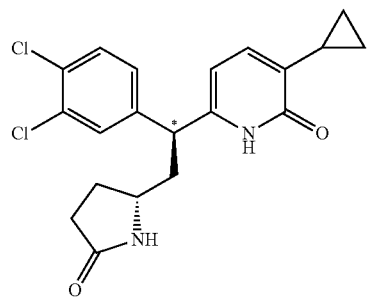
Example 4-209, 210
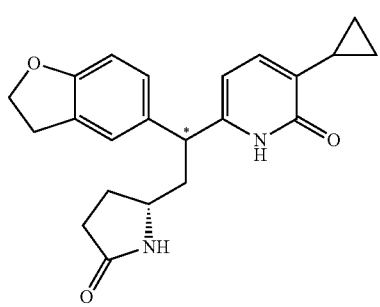
Example 4-211, 212
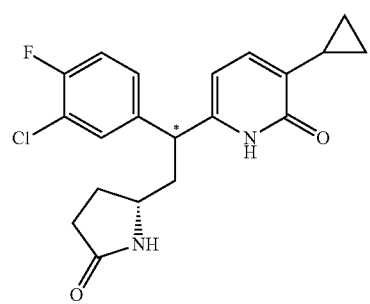
Example 4-213, 214
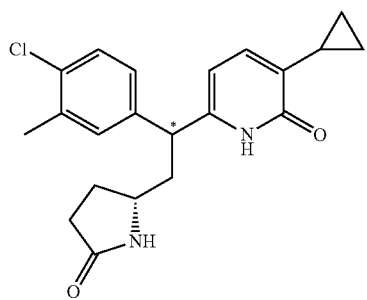
Example 4-215, 216
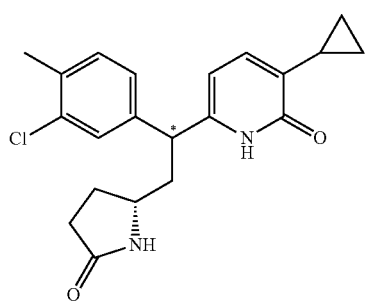
Example 4-217, 218
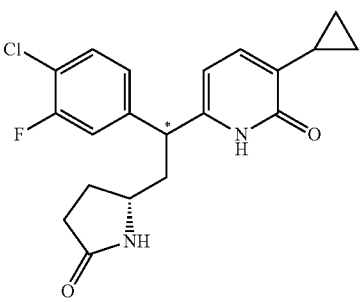
Example 4-219, 220
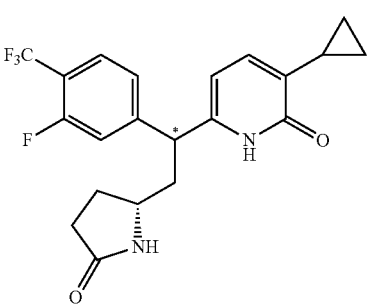
Example 4-221, 222
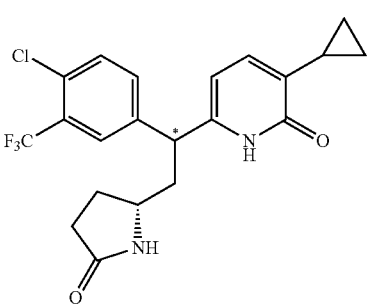
Example 4-223, 224
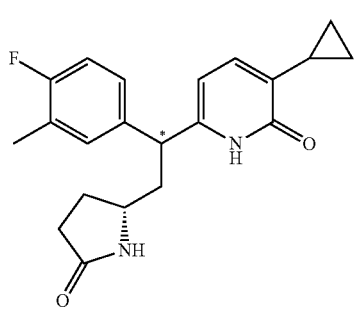
Example 4-225, 226
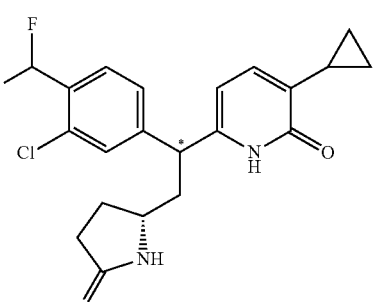

Example 4-227, 228
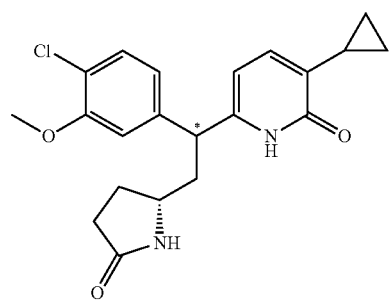
Example 4-229, 230
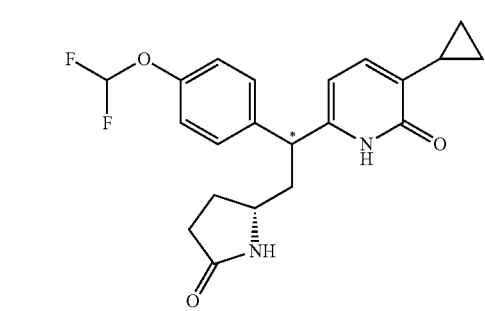
Example 4-231, 232
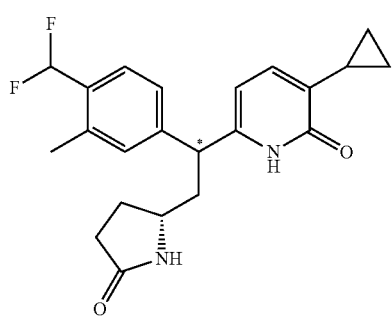
Example 4-233, 245
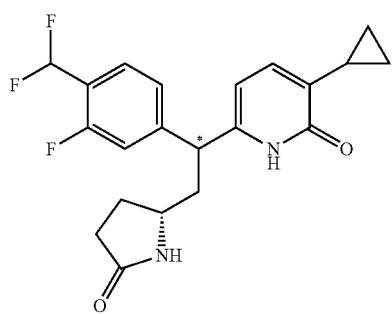
Example 4-235, 236
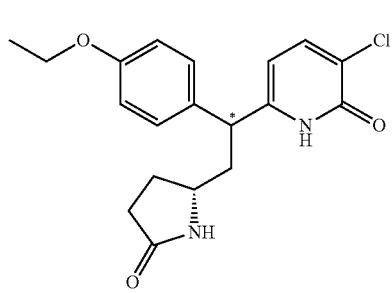
Example 4-237, 238
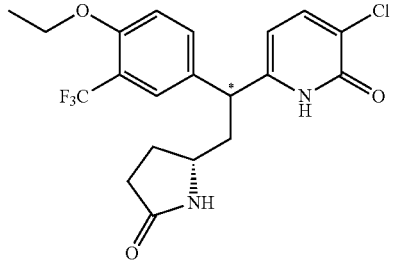
Example 4-239, 240
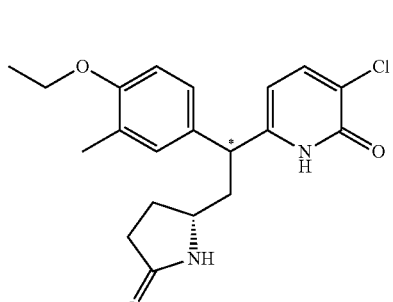
Example 4-241
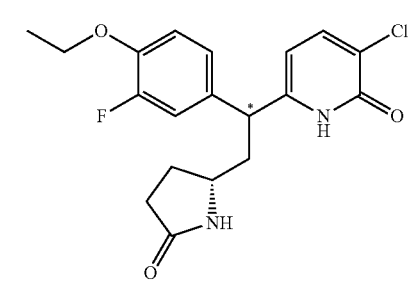
Example 4-242, 243
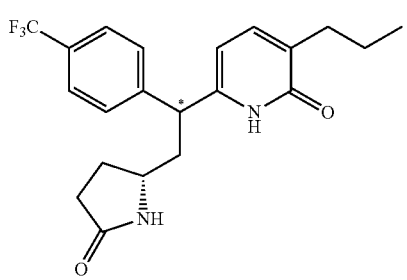
Example 4-244, 245
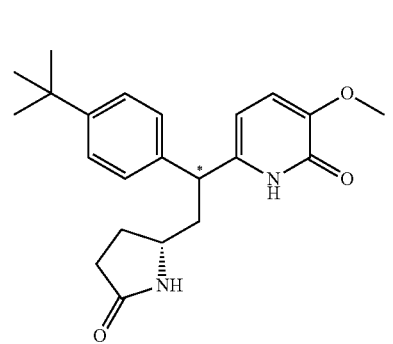

-continued

Example 4-246, 247

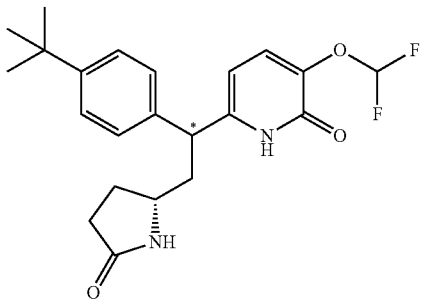

Examples 4-248 and 4-249

3-Cyclopropyl-6-{2-[(2R)-5-oxopyrrolidin-2-yl]-1-[4-(trifluoromethyl)phenyl]ethyl}pyridin-2(1H)-one (1) (5R)-5-{(E)-2-(5-Cyclopropyl-6-methoxypyridin-2-yl)-2-[4-(trifluoromethyl)phenyl]ethenyl}pyrrolidin-2-one was obtained as a pale green solid (167 mg, 70%) by performing substantially the same reaction as in Example 4-98(1) except for using 4-trifluoromethylphenylboronic acid.

(2) One diastereomer (A) of the title compound was obtained as a white solid (47 mg, 29% (two steps)) by performing substantially the same reaction as in Examples 4-69 and 4-70(2)(3) sequentially except for using (5R)-5-{(E)-2-(5-cyclopropyl-6-methoxypyridin-2-yl)-2-[4-(trifluoromethyl)phenyl]ethenyl}pyrrolidin-2-one, separating the mixture by preparative HPLC (CHIRALPAK IB (20 mm i.d.×250 mm L, Daicel Chemical Industries, LTD.), 40° C., flow rate: 10 mL/min, ethanol:hexane=40:60) and concentrating the fraction eluted with a retention time of 11 minutes. The fraction eluted with a retention time of 23 minutes was concentrated to give the other diastereomer (B) of the title compound as a white solid (39 mg, 24% (two steps)).
Diastereomer (A);
$^1$H NMR (300 MHz, CDCl$_3$) δ ppm 0.55-0.72 (m, 2H), 0.90-1.05 (m, 2H), 1.64-1.80 (m, 1H), 1.95-2.40 (m, 6H), 3.40-3.55 (m, 1H), 4.05-4.20 (m, 1H), 6.00 (d, J=7.0 Hz, 1H), 6.92 (d, J=7.0 Hz, 1H), 7.45-7.70 (m, 5H), 12.30-12.70 (m, 1H).
MS(+): 391 [M+H]$^+$.
MS(−): 389 [M−H]$^−$.
Diastereomer (B);
$^1$H NMR (300 MHz, CDCl$_3$) δ ppm 0.55-0.65 (m, 2H), 0.95-1.10 (m, 2H), 1.70-1.85 (m, 1H), 2.14-2.40 (m, 6H), 3.53-3.65 (brs, 1H), 4.15-4.25 (m, 1H), 5.99 (d, J=7.4 Hz, 1H), 6.96 (d, J=7.0 Hz, 1H), 7.45 (d, J=8.2 Hz, 2H), 7.58 (d, J=8.2 Hz, 2H), 7.85 (s, 1H), 13.20-13.38 (brs, 1H).
MS(+): 391 [M+H]$^+$.
MS(−): 389 [M−H]$^−$.

Examples 4-250 and 4-251

6-{1-(3-Chloro-4-hydroxyphenyl)-2-[(2R)-5-oxopyrrolidin-2-yl]ethyl}-3-cyclopropylpyridin-2(1H)-one (1) (5R)-5-[2-(4-{[tert-Butyl(dimethyl)silyl]oxy}-3-chlorophenyl)-2-(5-cyclopropyl-6-methoxypyridin-2-yl)ethenyl]pyrrolidin-2-one (EZ mixture) (173 mg, 58%) was obtained by performing substantially the same reaction as in Example 4-2(1) except for using (4-{[tert-butyl(dimethylsilyl]oxy}-3-chlorophenyl)(5-cyclopropyl-6-methoxypyridin-2-yl)methanone obtained in Reference Example 1-55.

(2) One diastereomer (A) of the title compound was obtained as a white solid (42 mg, 33% (two steps)) by performing substantially the same reaction as in Examples 4-69 and 4-70(2)(3) sequentially except for using (5R)-5-[2-(4-{[tert-butyl(dimethyl)silyl]oxy}-3-chlorophenyl)-2-(5-cyclopropyl-6-methoxypyridin-2-yl)ethenyl]pyrrolidin-2-one (EZ mixture), separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 18 minutes. The fraction eluted with a retention time of 54 minutes was concentrated to give the other diastereomer (B) of the title compound as a white solid (30 mg, 23% (two steps)).
Diastereomer (A);
$^1$H NMR (300 MHz, METHANOL-d4) δ ppm 0.46-0.70 (m, 2H), 0.76-1.00 (m, 2H), 1.60-1.85 (m, 1H), 1.90-2.42 (m, 6H), 3.40-3.60 (m, 1H), 3.75-3.95 (m, 1H), 6.20-6.35 (m, 1H), 6.75-6.93 (m, 1H), 6.93-7.15 (m, 2H), 7.22-7.35 (m, 1H).
MS(+): 373 [M+H]$^+$.
MS(−): 371 [M−H]$^−$.
Diastereomer (B);
$^1$H NMR (300 MHz, METHANOL-d4) δ ppm 0.45-0.70 (m, 2H), 0.77-0.95 (m, 2H), 1.70-1.89 (m, 1H), 1.89-2.05 (m, 1H), 2.05-2.40 (m, 5H), 3.40-3.55 (m, 1H), 3.80-3.92 (m, 1H), 6.25 (d, J=7.1 Hz, 1H), 6.86 (d, J=8.6 Hz, 1H), 7.00-7.12 (m, 2H), 7.26 (s, 1H).
MS(+): 373 [M+H]$^+$.
MS(−): 371 [M−H]$^−$.

Examples 4-252 and 4-253

6-{1-(4-Chlorophenyl)-2-[(2R)-5-oxopyrrolidin-2-yl]ethyl}-3-cyclopropylpyridin-2(1H)-one (1) (5R)-5-[(E)-2-(4-Chlorophenyl)-2-(5-cyclopropyl-6-methoxypyridin-2-yl)ethenyl]pyrrolidin-2-one was obtained as a pale yellow amorphous (219 mg, 100%) by performing substantially the same reaction as in Examples 4-248 and 4-249(1) except for using 4-chlorophenylboronic acid.

(2) One diastereomer (A) of the title compound was obtained as a white solid (17 mg, 15% (two steps)) by performing substantially the same reaction as in Examples 4-69 and 4-70(2)(3) sequentially except for using (5R)-5-[(E)-2-(4-chlorophenyl)-2-(5-cyclopropyl-6-methoxypyridin-2-yl)ethenyl]pyrrolidin-2-one, separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of five minutes. The fraction eluted with a retention time of 43 minutes was concentrated to give the other diastereomer (B) of the title compound as a white solid (14 mg, 13% (two steps)).
Diastereomer (A);
$^1$H NMR (300 MHz, CDCl$_3$) δ ppm 0.55-0.66 (m, 2H), 0.92-0.96 (m, 2H), 1.60-1.80 (m, 1H), 2.04-2.41 (m, 6H), 3.43-3.52 (m, 1H), 4.00-4.04 (m, 1H), 5.96 (d, J=7.4 Hz, 1H), 6.91 (d, J=7.4 Hz, 1H), 7.26-7.33 (m, 4H), 7.36-7.48 (brs, 1H), 12.10-12.50 (brs, 1H).
MS(+): 357 [M+H]$^+$.
MS(−): 355 [M−H]$^−$.
Diastereomer (B);
$^1$H NMR (300 MHz, CDCl$_3$) δ ppm 0.59-0.61 (m, 2H), 0.98-1.01 (m, 2H), 1.68-1.76 (m, 1H), 2.11-2.39 (m, 6H), 3.55-3.59 (m, 1H), 4.08-4.11 (m, 1H), 5.96 (d, J=7.4 Hz, 1H), 6.94 (d, J=7.4 Hz, 1H), 7.24-7.31 (m, 4H), 7.72-7.84 (brs, 1H), 13.00-13.40 (brs, 1H).
MS(+): 357 [M+H]$^+$.
MS(−): 355 [M−H]$^-$.

Examples 4-254 and 4-255

6-{1-[3-Chloro-4-(trifluoromethyl)phenyl]-2-[(2R)-5-oxopyrrolidin-2-yl]ethyl}-3-cyclopropylpyridin-2(1H)-one (1) (5R)-5-[(E)-2-[3-Chloro-4-(trifluoromethyl)phenyl]-2-(5-cyclopropyl-6-methoxypyridin-2-yl)ethenyl]pyrrolidin-2-one (154 mg, 40%) was obtained by performing substantially the same reaction as in Examples 4-248 and 4-249 (1) except for using 3-chloro-4-(trifluoromethyl)phenylboronic acid.

(2) One diastereomer (A) of the title compound was obtained as a white solid (45 mg, 30% (two steps)) by performing substantially the same reaction as in Examples 4-69 and 4-70(2)(3) sequentially except for using (5R)-5-[(E)-2-[3-Chloro-4-(trifluoromethyl)phenyl]-2-(5-cyclopropyl-6-methoxypyridin-2-yl)ethenyl]pyrrolidin-2-one, separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 14 minutes. The fraction eluted with a retention time of 51 minutes was concentrated to give the other diastereomer (B) of the title compound as a white solid (51 mg, 34% (two steps)).
Diastereomer (A);
$^1$H NMR (300 MHz, CDCl$_3$) δ ppm 0.50-0.70 (m, 2H), 0.80-1.00 (m, 2H), 1.60-1.82 (m, 1H), 2.00-2.45 (m, 6H), 3.35-3.55 (m, 1H), 4.00-4.20 (m, 1H), 6.06 (d, J=7.4 Hz, 1H), 6.93 (d, J=6.8 Hz, 1H), 7.46 (d, J=8.3 Hz, 1H), 7.55-7.64 (m, 2H), 7.85-8.01 (brs, 1H), 12.40-13.05 (brs, 1H).
Diastereomer (B);
$^1$H NMR (300 MHz, CDCl$_3$) δ ppm 0.50-0.75 (m, 2H), 0.85-1.10 (m, 2H), 1.70-1.90 (m, 1H), 2.00-2.65 (m, 6H), 3.45-3.65 (m, 1H), 4.07-4.25 (m, 1H), 6.09 (d, J=7.1 Hz, 1H), 6.97 (d, J=7.1 Hz, 1H), 7.37 (d, J=8.0 Hz, 1H), 7.52 (s, 1H), 7.61 (d, J=8.3 Hz, 1H), 8.23 (s, 1H), 12.76-13.60 (brs, 1H).

Example 4-256

3-Chloro-6-{(E)-1-(4-methylphenyl)-2-[(2R)-5-oxopyrrolidin-2-yl]ethenyl}pyridin-2(1H)-one (1) (5R)-5-[2-(5-Chloro-6-methoxypyridin-2-yl)-2-(4-methylphenyl)ethenyl]pyrrolidin-2-one (EZ mixture) (287 mg, 73%) was obtained by performing substantially the same reaction as in Example 4-2(1) except for using (5-chloro-6-methoxypyridin-2-yl)(4-methylphenyl)methanone obtained in Reference Example 1-91.

(2) The title compound was obtained as a white solid (33 mg, 33%) by performing substantially the same reaction as in Example 1-1(2) except for using (5R)-5-[2-(5-chloro-6-methoxypyridin-2-yl)-2-(4-methylphenyl)ethenyl]pyrrolidin-2-one (EZ mixture).
$^1$H NMR (300 MHz, CDCl$_3$) δ ppm 2.11-2.52 (m, 4H), 2.41 (s, 3H), 4.14-4.30 (m, 1H), 5.86 (d, J=7.6 Hz, 1H), 6.32 (s, 1H), 6.43 (d, J=9.2 Hz, 1H), 7.07 (d, J=7.9 Hz, 2H), 7.25 (d, J=7.6 Hz, 2H), 7.59 (d, J=7.6 Hz, 1H), 12.22-12.32 (brs, 1H).
MS(+): 329 [M+H]$^+$.
MS(−): 327 [M−H]$^-$.

Example 4-257

3-Chloro-6-{(E)-1-(3-chloro-4-ethylphenyl)-2-[(2R)-5-oxopyrrolidin-2-yl]ethenyl}pyridin-2(1H)-one (1) (5R)-5-[2-(3-Chloro-4-ethylphenyl)-2-(5-chloro-6-methoxypyridin-2-yl)ethenyl]pyrrolidin-2-one (EZ mixture) was obtained as a colorless amorphous (394 mg, 81%) by performing substantially the same reaction as in Example 4-256(1) except for using (3-chloro-4-ethylphenyl)(5-chloro-6-methoxypyridin-2-yl)methanone obtained in Reference Example 1-90. (5R)-5-[(E)-2-(3-Chloro-4-ethylphenyl)-2-(5-chloro-6-methoxypyridin-2-yl)ethenyl]pyrrolidin-2-one (72 mg, 15%) was also obtained.

(2) The title compound was obtained as a colorless solid (39 mg, 56%) by performing substantially the same reaction as in Example 1-1(2) except for using (5R)-5-[(E)-2-(3-chloro-4-ethylphenyl)-2-(5-chloro-6-methoxypyridin-2-yl)ethenyl]pyrrolidin-2-one.
$^1$H NMR (300 MHz, CDCl$_3$) δ ppm 1.29 (t, J=7.4 Hz, 3H), 2.10-2.55 (m, 4H), 2.81 (q, J=7.5 Hz, 2H), 4.10-4.30 (m, 1H), 5.74-5.86 (m, 1H), 6.28-6.60 (m, 2H), 7.04 (d, J=6.8 Hz, 1H), 7.11-7.59 (m, 3H), 12.25-12.8 (brs, 1H).
MS(+): 377 [M+H]$^+$.
MS(−): 375 [M−H]$^-$.

Example 4-258

6-{(E)-1-[3-Chloro-4-(propan-2-yloxy)phenyl]-2-[(2R)-5-oxopyrrolidin-2-yl]ethenyl}-3-cyclopropylpyridin-2(1H)-one The title compound was obtained as a white solid (65 mg, 21% (two steps)) by performing substantially the same reaction as in Example 4-256 except for using [3-chloro-4-(propan-2-yloxy)phenyl](5-cyclopropyl-6-methoxypyridin-2-yl)methanone obtained in Reference Example 1-92.
$^1$H NMR (300 MHz, CDCl$_3$) δ ppm 0.41-0.65 (m, 2H), 0.85-1.04 (m, 2H), 1.42 (d, J=6.3 Hz, 6H), 1.98-2.45 (m, 5H), 4.08-4.22 (m, 1H), 4.50-4.68 (m, 1H), 5.60-5.72 (m, 1H), 6.59 (d, J=8.9 Hz, 1H), 6.80 (d, J=7.4 Hz, 1H), 6.88-7.02 (m, 2H), 7.08-7.14 (m, 1H), 7.30-7.40 (brs, 1H), 12.20-12.75 (brs, 1H).
MS(+): 413 [M+H]$^+$.
MS(−): 411 [M−H]$^-$.

Example 4-259

6-{(E)-2-[(2R)-5-Oxopyrrolidin-2-yl]-1-[4-(trifluoromethyl)phenyl]ethenyl}-3-(trifluoromethyl)pyridin-2(1H)-one The title compound was obtained as a colorless solid (70 mg, 29% (two steps)) by performing substantially the same reaction as in Example 4-256 except for using [6-methoxy-5-(trifluoromethyl)pyridin-2-yl][4-(trifluoromethyl)phenyl]methanone obtained in Reference Example 1-93.
$^1$H NMR (300 MHz, CDCl$_3$) δ ppm 2.12-2.60 (m, 4H), 4.00-4.20 (m, 1H), 5.75 (d, J=7.4 Hz, 1H), 6.75 (d, J=8.6 Hz, 1H), 7.40 (d, J=7.4 Hz, 2H), 7.51 (s, 1H), 7.66 (d, J=7.1 Hz, 1H), 7.74 (d, J=8.0 Hz, 2H), 12.60-13.10 (brs, 1H).
MS(+): 417 [M+H]$^+$.
MS(−): 415 [M−H]$^-$.

Example 4-260

6-{(E)-1-(3-Chloro-4-methoxyphenyl)-2-[(2R)-5-oxopyrrolidin-2-yl]ethenyl}-3-cyclopropylpyridin-2(1H)-one The title compound was obtained as a white solid (25 mg, 17% (two steps)) by performing substantially the same reaction as in Example 4-256 except for using (3-chloro-4-methoxyphenyl)(5-cyclopropyl-6-methoxypyridin-2-yl)methanone obtained in Reference Example 1-94.

$^1$H NMR (300 MHz, CDCl$_3$) δ ppm 0.44-0.67 (m, 2H), 0.88-1.05 (m, 2H), 2.00-2.45 (m, 5H), 3.94 (s, 3H), 4.10-4.23 (m, 1H), 5.65-5.75 (m, 1H), 6.53 (d, J=8.9 Hz, 1H), 6.82 (d, J=7.1 Hz, 1H), 6.95 (d, J=8.6 Hz, 1H), 7.04 (dd, J=8.3, 2.1 Hz, 1H), 6.90-7.10 (brs, 1H), 7.14 (d, J=1.5 Hz, 1H), 11.95-12.55 (brs, 1H).

MS(+): 385 [M+H]$^+$.
MS(−): 383 [M−H]$^−$.

Example 4-261

3-Chloro-6-{(E)-2-[(2R)-5-oxopyrrolidin-2-yl]-1-[3-(trifluoromethyl)phenyl]ethenyl}pyridin-2(1H)-one (1) (5R)-5-{(E)-2-(5-Chloro-6-methoxypyridin-2-yl)-2-[3-(trifluoromethyl)phenyl]ethenyl}pyrrolidin-2-one was obtained as a colorless amorphous (134 mg, 75%) by performing substantially the same reaction as in Example 4-146 (1) except for using 3-(trifluoromethyl)phenylboronic acid.

(2) The title compound was obtained as a colorless solid (57 mg, 46%) by performing substantially the same reaction as in Example 1-1(2) except for using (5R)-5-{(E)-2-(5-chloro-6-methoxypyridin-2-yl)-2-[3-(trifluoromethyl)phenyl]ethenyl}pyrrolidin-2-one.

$^1$H NMR (300 MHz, CDCl$_3$) δ ppm 2.20-2.60 (m, 4H), 4.05-4.18 (m, 1H), 5.69 (d, J=7.7 Hz, 1H), 6.63 (d, J=9.5 Hz, 1H), 6.75-6.95 (brs, 1H), 7.37-7.55 (m, 3H), 7.62 (t, J=7.1 Hz, 1H), 7.70 (d, J=7.7 Hz, 1H), 12.82-13.31 (brs, 1H).

MS(+): 383 [M+H]$^+$.
MS(−): 381 [M−H]$^−$.

The compounds of Examples 4-262 to 4-264 were synthesized by performing substantially the same reaction as in Example 4-261 except for using corresponding boronic acids or boronate esters (2-fluoro-4-(trifluoromethyl)phenylboronic acid, 6-(5,5-dimethyl-1,3,2-dioxaborinan-2-yl)-2,2-dimethyl-3,4-dihydro-2H-chromene (Reference Example 5-12) and 2-[4-(3-methoxypropyl)phenyl]-4,4,5,5-tetramethyl-1,3,2-dioxaborolane (Reference Example 5-28)) in place of 3-(trifluoromethyl)phenylboronic acid, respectively.

Example 4-262

3-Chloro-6-{(E)-1-[2-fluoro-4-(trifluoromethyl)phenyl]-2-[(2R)-5-oxopyrrolidin-2-yl]ethenyl}pyridin-2(1H)-one The title compound was obtained as a white solid (23 mg, 13% (two steps)) using calcium carbonate in place of cesium carbonate.

$^1$H NMR (300 MHz, CDCl$_3$) δ ppm 2.20-2.40 (m, 3H), 2.40-2.60 (m, 1H), 3.98-4.12 (m, 1H), 5.66 (d, J=7.5 Hz, 1H), 6.82 (d, J=9.3 Hz, 1H), 7.40-7.50 (m, 3H), 7.54 (d, J=7.8 Hz, 1H), 7.50-7.70 (brs, 1H), 13.15-13.50 (brs, 1H).

MS(+): 401 [M+H]$^+$.
MS(−): 399 [M−H]$^−$.

Example 4-263

3-Chloro-6-{(E)-1-(2,2-dimethyl-3,4-dihydro-2H-chromen-6-yl)-2-[(2R)-5-oxopyrrolidin-2-yl]ethenyl}pyridin-2(1H)-one The title compound was obtained as a white solid (53 mg, 30% (two steps)).

$^1$H NMR (300 MHz, CDCl$_3$) δ ppm 1.38 (s, 6H), 1.84 (t, J=6.9 Hz, 2H), 2.04-2.18 (m, 1H), 2.27-2.48 (m, 3H), 2.78 (t, J=6.6 Hz, 2H), 4.23-4.31 (m, 1H), 5.96-6.02 (brs, 1H), 6.02 (d, J=7.6 Hz, 1H), 6.25 (d, J=8.7 Hz, 1H), 6.80-6.91 (m, 3H), 7.52 (d, J=7.6 Hz, 1H), 11.00-11.20 (brs, 1H).

MS(+): 399 [M+H]$^+$.
MS(−): 397 [M−H]$^−$.

Example 4-264

3-Chloro-6-{(E)-1-[4-(3-methoxypropyl)phenyl]-2-[(2R)-5-oxopyrrolidin-2-yl]ethenyl}pyridin-2(1H)-one The title compound was obtained as a white solid (31 mg, 60% (two steps)).

$^1$H NMR (300 MHz, CDCl$_3$) δ ppm 1.86-2.05 (m, 2H), 2.05-2.56 (m, 4H), 2.74 (t, J=8.1 Hz, 2H), 3.37 (s, 3H), 3.43 (t, J=6.5 Hz, 2H), 4.12-4.29 (m, 1H), 5.88 (d, J=7.4 Hz, 1H), 6.18 (s, 1H), 6.40 (d, J=9.4 Hz, 1H), 7.08 (d, J=8.2 Hz, 2H), 7.26 (d, J=7.8 Hz, 2H), 7.49 (d, J=7.8 Hz, 1H), 11.66-12.09 (brs, 1H).

MS(+): 387 [M+H]$^+$.
MS(−): 385 [M−H]$^−$.

Example 4-265

3-Cyclopropyl-6-{(E)-1-[3-methyl-4-(trifluoromethyl)phenyl]-2-[(2R)-5-oxopyrrolidin-2-yl]ethenyl}pyridin-2(1H)-one (1) (5R)-5-{(E)-2-(5-Cyclopropyl-6-methoxypyridin-2-yl)-2-[3-methyl-4-(trifluoromethyl)phenyl]ethenyl}pyrrolidin-2-one was obtained as a colorless solid (61 mg, 45%) by performing substantially the same reaction as in Example 4-98(1) except for using 5,5-dimethyl-2-[3-methyl-4-(trifluoromethyl)phenyl]-1,3,2-dioxaborinane obtained in Reference Example 5-11.

(2) The title compound was obtained as a colorless solid (30 mg, 51%) by performing substantially the same reaction as in Example 1-1(2) except for using (5R)-5-{(E)-2-(5-cyclopropyl-6-methoxypyridin-2-yl)-2-[3-methyl-4-(trifluoromethyl)phenyl]ethenyl}pyrrolidin-2-one.

$^1$H NMR (300 MHz, CDCl$_3$) δ ppm 0.45-0.75 (m, 2H), 0.80-1.10 (m, 2H), 2.00-2.50 (m, 5H), 2.51 (s, 3H), 4.00-4.20 (m, 1H), 5.65 (d, J=7.4 Hz, 1H), 6.55 (d, J=9.5 Hz, 1H), 6.65 (s, 1H), 6.81 (d, J=7.4 Hz, 1H), 7.05-7.18 (m, 2H), 7.65 (d, J=8.6 Hz, 1H), 11.60-12.40 (brs, 1H).

MS(+): 403 [M+H]$^+$.
MS(−): 401 [M−H]$^−$.

The compounds of Examples 4-266 to 4-276 were synthesized by performing substantially the same reaction as in Example 4-265 except for using, in place of 5,5-dimethyl-2-[3-methyl-4-(trifluoromethyl)phenyl]-1,3,2-dioxaborinane, corresponding boronic acids or boronate esters (4-chloro-2-fluorophenylboronic acid, 2-fluoro-4-(trifluoromethyl)phenylboronic acid, 2-(4-cyclopropylphenyl)-5,5-dimethyl-1,3, 2-dioxaborinane (Reference Example 5-13), 2-[3-chloro-4-(cyclopropyloxy)phenyl]-5,5-dimethyl-1,3,2-dioxaborinane (Reference Example 5-14), 2-[3-chloro-4-(2,2,2-trifluoroethoxy)phenyl]-5,5-dimethyl-1,3,2-dioxaborinane (Reference Example 5-15), 2-(3-chloro-4-ethylphenyl)-5,5-dimethyl-1,3,2-dioxaborinane (Reference Example 5-17), 4,4,5,5-tetramethyl-2-[4-(2,2,2-trifluoroethyl)phenyl]-1,3,2-dioxaborolane (Reference Example 5-27), 2-[4-(difluoromethyl)phenyl]-4,4,5,5-tetramethyl-1,3,2-dioxaborolane (Reference Example 5-29), 5-chloro-2-fluoro-4-methoxyphenylboronic acid, 3-fluoro-4-isopropoxyphenylboronic acid and 4-isopropoxyphenylboronic acid), respectively.

Example 4-266

6-{(E)-1-(4-Chloro-2-fluorophenyl)-2-[(2R)-5-oxopyrrolidin-2-yl]ethenyl}-3-cyclopropylpyridin-2(1H)-one The title compound was obtained as a white solid (40 mg, 33% (two steps)).
$^1$H NMR (300 MHz, CDCl$_3$) δ ppm 0.45-0.70 (m, 2H), 0.80-1.10 (m, 2H), 1.75-2.50 (m, 5H), 3.95-4.15 (m, 1H), 5.61 (d, J=7.4 Hz, 1H), 6.65-7.00 (m, 3H), 7.05-7.25 (m, 3H), 12.20-13.10 (brs, 1H).
MS(+): 373 [M+H]$^+$.
MS(−): 371 [M−H]$^-$.

Example 4-267

3-Cyclopropyl-6-{(E)-1-[2-fluoro-4-(trifluoromethyl)phenyl]-2-[(2R)-5-oxopyrrolidin-2-yl]ethenyl}pyridin-2(1H)-one The title compound was obtained as a white solid (24 mg, 19% (two steps)).
$^1$H NMR (300 MHz, CDCl$_3$) δ ppm 0.50-0.70 (m, 2H), 0.90-1.00 (m, 2H), 2.02-2.50 (m, 5H), 3.95-4.09 (m, 1H), 5.61 (d, J=7.5 Hz, 1H), 6.32-6.40 (brs, 1H), 6.80 (d, J=9.3 Hz, 1H), 6.81 (d, J=6.9 Hz, 1H), 7.34 (dd, J=7.2, 7.2 Hz, 1H), 7.47 (d, J=9.0 Hz, 1H), 7.50 (d, J=7.8 Hz, 1H), 12.20-12.50 (brs, 1H).
MS(+): 407 [M+H]$^+$.
MS(−): 405 [M−H]$^-$.

Example 4-268

3-Cyclopropyl-6-{(E)-1-(4-cyclopropylphenyl)-2-[(2R)-5-oxopyrrolidin-2-yl]ethenyl}pyridin-2(1H)-one The title compound was obtained as a white solid (33 mg, 11% (two steps)).
$^1$H NMR (300 MHz, CDCl$_3$) δ ppm 0.52-0.67 (m, 2H), 0.70-0.79 (m, 2H), 0.93-1.08 (m, 4H), 1.87-2.16 (m, 3H), 2.21-2.45 (m, 3H), 4.12-4.23 (m, 1H), 5.82 (d, J=7.0 Hz, 1H), 6.09-6.12 (brs, 1H), 6.34 (d, J=9.0 Hz, 1H), 6.83 (d, J=7.4 Hz, 1H), 7.03 (d, J=8.2 Hz, 2H), 7.10 (d, J=8.2 Hz, 2H), 10.96-11.11 (brs, 1H).
MS(+): 361 [M+H]$^+$.
MS(−): 359 [M−H]$^-$.

Example 4-269

6-{(E)-1-[3-Chloro-4-(cyclopropyloxy)phenyl]-2-[(2R)-5-oxopyrrolidin-2-yl]ethenyl}-3-cyclopropylpyridin-2(1H)-one The title compound was obtained as a white solid (111 mg, 75% (two steps)).
$^1$H NMR (300 MHz, CDCl$_3$) δ ppm 0.55-0.75 (m, 2H), 0.81-0.94 (m, 4H), 0.95-1.10 (m, 2H), 2.00-2.20 (m, 2H), 2.25-2.50 (m, 3H), 3.78-3.90 (m, 1H), 4.15-4.27 (m, 1H), 5.87 (d, J=7.4 Hz, 1H), 5.91-5.96 (brs, 1H), 6.29 (d, J=9.2 Hz, 1H), 6.87 (d, J=6.8 Hz, 1H), 7.00-7.13 (m, 1H), 7.16 (d, J=3.3 Hz, 1H), 7.35 (d, J=8.3 Hz, 1H), 10.40-10.78 (brs, 1H).
MS(+): 411 [M+H]$^+$.
MS(−): 409 [M−H]$^-$.

Example 4-270

6-{(E)-1-[3-Chloro-4-(2,2,2-trifluoroethoxy)phenyl]-2-[(2R)-5-oxopyrrolidin-2-yl]ethenyl}-3-cyclopropylpyridin-2(1H)-one The title compound was obtained as a white solid (97 mg, 58% (two steps)).
$^1$H NMR (300 MHz, CDCl$_3$) δ ppm 0.50-0.77 (m, 2H), 0.91-1.02 (m, 2H), 2.00-2.20 (m, 2H), 2.21-2.50 (m, 3H), 4.08-4.22 (m, 1H), 4.40-4.55 (m, 2H), 5.73 (d, J=7.4 Hz, 1H), 6.37-6.51 (brs, 1H), 6.48 (d, J=8.9 Hz, 1H), 6.85 (d, J=7.4 Hz, 1H), 6.95-7.11 (m, 2H), 7.20-7.30 (m, 1H), 11.55-12.00 (brs, 1H).
MS(+): 453 [M+H]$^+$.
MS(−): 451 [M−H]$^-$.

Example 4-271

6-{(E)-1-(3-Chloro-4-ethylphenyl)-2-[(2R)-5-oxopyrrolidin-2-yl]ethenyl}-3-cyclopropylpyridin-2(1H)-one The title compound was obtained as a white solid (67 mg, 45% (two steps)).
$^1$H NMR (300 MHz, CDCl$_3$) δ ppm 0.52-0.59 (m, 2H), 0.95-0.98 (m, 2H), 1.28 (t, J=7.4 Hz, 3H), 2.08-2.17 (m, 2H), 2.24-2.42 (m, 3H), 2.79 (q, J=7.4 Hz, 2H), 4.09-4.18 (m, 1H), 5.69 (d, J=7.4 Hz, 1H), 6.58 (d, J=7.7 Hz, 1H), 6.82 (d, J=7.4 Hz, 1H), 6.84-6.99 (brs, 1H), 7.00 (d, J=7.7 Hz, 1H), 7.12 (s, 1H), 7.27 (d, J=7.7 Hz, 1H), 11.90-12.50 (brs, 1H).
MS(+): 383 [M+H]$^+$.
MS(−): 381 [M−H]$^-$.

Example 4-272

3-Cyclopropyl-6-{(E)-2-[(2R)-5-oxopyrrolidin-2-yl]-1-[4-(2,2,2-trifluoroethyl)phenyl]ethenyl}pyridin-2(1H)-one The title compound was obtained as a white solid (39 mg, 47% (two steps)).
$^1$H NMR (300 MHz, CDCl$_3$) δ ppm 0.50-0.70 (m, 2H), 0.90-1.05 (m, 2H), 2.05-2.20 (m, 2H), 2.20-2.46 (m, 3H), 3.43 (q, J=10.7 Hz, 2H), 4.08-4.22 (m, 1H), 5.64-5.76 (m, 1H), 6.50-6.63 (m, 1H), 6.63-6.97 (brs, 1H), 6.82 (d, J=7.5 Hz, 1H), 7.18 (d, J=8.4 Hz, 2H), 7.36 (d, J=7.8 Hz, 2H), 12.00-12.40 (brs, 1H).
MS(+): 403 [M+H]$^+$.
MS(−): 401 [M−H]$^-$.

Example 4-273

3-Cyclopropyl-6-{(E)-1-[4-(difluoromethyl)phenyl]-2-[(2R)-5-oxopyrrolidin-2-yl]ethenyl}pyridin-2(1H)-one The title compound was obtained as a white solid (15 mg, 10% (two steps)).

¹H NMR (300 MHz, CDCl₃) δ ppm 0.50-0.67 (m, 2H), 0.93-1.04 (m, 2H), 2.06-2.47 (m, 5H), 4.05-4.28 (m, 1H), 5.64 (d, J=7.4 Hz, 1H), 6.62 (d, J=9.0 Hz, 1H), 6.71 (t, J=55.5 Hz, 1H), 6.82 (d, J=9.0 Hz, 1H), 6.75-6.90 (brs, 1H), 7.31 (d, J=9.0 Hz, 2H), 7.58 (d, J=7.8 Hz, 2H), 12.10-12.50 (brs, 1H).
MS(+): 371 [M+H]⁺.
MS(−): 369 [M−H]⁻.

Example 4-274

6-{(E)-1-(5-Chloro-2-fluoro-4-methoxyphenyl)-2-[(2R)-5-oxopyrrolidin-2-yl]ethenyl}-3-cyclopropylpyridin-2(1H)-one The title compound was obtained as a white solid (34 mg, 24% (two steps)).
¹H NMR (300 MHz, CDCl₃) δ ppm 0.54-0.61 (m, 2H), 0.94-1.00 (m, 2H), 2.00-2.18 (m, 2H), 2.20-2.42 (m, 3H), 3.96 (s, 3H), 4.03-4.15 (m, 1H), 5.67 (d, J=7.4 Hz, 1H), 6.74-6.80 (m, 4H), 7.09 (d, J=7.4 Hz, 1H), 12.20-12.70 (brs, 1H).
MS(+): 403 [M+H]⁺.

Example 4-275

3-Cyclopropyl-6-{(E)-1-[3-fluoro-4-(propan-2-yloxy)phenyl]-2-[(2R)-5-oxopyrrolidin-2-yl]ethenyl}pyridin-2(1H)-one The title compound was obtained as a pale yellow solid (36 mg, 33% (two steps)).
¹H NMR (300 MHz, CDCl₃) δ ppm 0.50-0.70 (m, 2H), 0.90-1.10 (m, 2H), 1.41 (d, J=5.7 Hz, 6H), 1.91-2.20 (m, 2H), 2.20-2.50 (m, 3H), 4.12-4.28 (m, 1H), 4.60 (sep, J=6.1 Hz, 1H), 5.81 (d, J=7.1 Hz, 1H), 6.29 (s, 1H), 6.36 (d, J=8.9 Hz, 1H), 6.85 (d, J=7.1 Hz, 2H), 6.85-6.95 (m, 1H), 7.00 (dd, J=8.3, 8.0 Hz, 1H), 11.13-11.58 (brs, 1H).
MS(+): 397 [M+H]⁺.
MS(−): 395 [M−H]⁻.

Example 4-276

3-Cyclopropyl-6-{(E)-2-[(2R)-5-oxopyrrolidin-2-yl]-1-[4-(propan-2-yloxy)phenyl]ethenyl}pyridin-2(1H)-one The title compound was obtained as a white solid (17 mg, 25% (two steps)).
¹H NMR (300 MHz, CDCl₃) δ ppm 0.50-0.65 (m, 2H), 0.90-1.20 (m, 2H), 1.37 (d, J=6.0 Hz, 6H), 2.00-2.20 (m, 2H), 2.20-2.50 (m, 3H), 4.15-4.30 (m, 1H), 4.58 (sep, J=6.0 Hz, 1H), 5.83 (d, J=7.5 Hz, 1H), 6.25-6.40 (m, 1H), 6.25-6.50 (brs, 1H), 6.84 (d, J=7.2 Hz, 1H), 6.90 (d, J=8.7 Hz, 2H), 7.05 (d, J=8.4 Hz, 2H), 11.00-11.60 (brs, 1H).
MS(+): 379 [M+H]⁺.

Example 4-277

3-Chloro-6-{(E)-1-[4-(hydroxymethyl)phenyl]-2-[(2R)-5-oxopyrrolidin-2-yl]ethenyl}pyridin-2(1H)-one (1) (5R)-5-{(E)-2-(5-Chloro-6-methoxypyridin-2-yl)-2-[4-(hydroxymethyl)phenyl]ethenyl}pyrrolidin-2-one was obtained as a colorless amorphous (142 mg, 88%) by performing substantially the same reaction as in Example 4-261 (1) except for using 4-(hydroxymethyl)phenylboronic acid.

(2) Chlorotrimethylsilane (0.123 mL) and potassium iodide (263 mg) were sequentially added to a solution of (5R)-5-{(E)-2-(5-chloro-6-methoxypyridin-2-yl)-2-[4-(hydroxymethyl)phenyl]ethenyl}pyrrolidin-2-one (142 mg) in acetonitrile (1.5 mL) at room temperature, after which the mixture was stirred at 60° C. for two hours. Water was added to the reaction solution, followed by extraction with ethyl acetate. The organic layer was washed with water and brine, dried over anhydrous magnesium sulfate and filtered, after which the solvent was evaporated under reduced pressure. The residue was purified by silica gel chromatography (methanol:ethyl acetate=1:10) to give the title compound as a colorless solid (19 mg, 14%).
¹H NMR (300 MHz, DMSO-d6) δ ppm 1.75-2.00 (m, 1H), 2.00-2.30 (m, 3H), 3.82-3.97 (m, 1H), 4.53 (d, J=5.1 Hz, 2H), 5.23 (t, J=5.7 Hz, 1H), 5.40-5.70 (m, 1H), 6.45 (d, J=8.6 Hz, 1H), 7.18 (d, J=8.3 Hz, 2H), 7.37 (d, J=8.3 Hz, 2H), 7.60 (d, J=7.7 Hz, 1H), 7.78 (s, 1H), 11.90-12.25 (brs, 1H).
MS(+): 345 [M+H]⁺.
MS(−): 343 [M−H]⁻.

Example 4-278

6-{(E)-1-[3-Chloro-4-(cyclopentyloxy)phenyl]-2-[(2R)-5-oxopyrrolidin-2-yl]ethenyl}-3-cyclopropylpyridin-2(1H)-one The title compound was obtained as a colorless solid (50 mg, 77% (two steps)) by performing substantially the same reaction as in Example 4-277 except for using (5R)-5-[(Z)-2-bromo-2-(5-cyclopropyl-6-methoxypyridin-2-yl)ethenyl]pyrrolidin-2-one obtained in Reference Example 4-24 and 2-[3-chloro-4-(cyclopentyloxy)phenyl]-5,5-dimethyl-1,3,2-dioxaborinane obtained in Reference Example 5-31.
¹H NMR (300 MHz, CDCl₃) δ ppm 0.45-0.73 (m, 2H), 0.90-1.15 (m, 2H), 1.50-1.80 (m, 2H), 1.80-2.20 (m, 8H), 2.20-2.50 (m, 3H), 4.10-4.30 (m, 1H), 4.75-4.95 (m, 1H), 5.80 (d, J=7.8 Hz, 1H), 6.32 (s, 1H), 6.37 (d, J=9.0 Hz, 1H), 6.85 (d, J=7.5 Hz, 1H), 6.94 (d, J=8.4 Hz, 1H), 6.99 (dd, J=8.3, 2.0 Hz, 1H), 7.15 (d, J=1.8 Hz, 1H), 11.20-11.70 (brs, 1H).
MS(+): 439 [M+H]⁺.
MS(−): 437 [M−H]⁻.

The compounds of Examples 4-279 to 4-288 were synthesized by performing substantially the same reaction as in Example 4-278 except for using, in place of 2-[3-chloro-4-(cyclopentyloxy)phenyl]-5,5-dimethyl-1,3,2-dioxaborinane, corresponding boronic acids or boronate esters (4-propoxyphenylboronic acid, 3-chloro-4-propoxyphenylboronic acid, 2-[3-chloro-4-(difluoromethoxy)phenyl]-4,4,5,5-tetramethyl-1,3,2-dioxaborolane (Reference Example 5-32), 2,3-difluoro-4-ethoxybenzeneboronic acid, 2-[4-(cyclopentyloxy)phenyl]-5,5-dimethyl-1,3,2-dioxaborinane (Reference Example 5-33), (4-ethoxy-3-fluoro)phenylboronic acid, 4-cyanophenylboronic acid, (2-chloro-4-ethoxy)phenylboronic acid, 4,4,5,5-tetramethyl-2-[4-(2,2,2-trifluoroethoxy)phenyl]-1,3,2-dioxaborolane (Reference Example 5-36) and 3-cyano-4-fluorophenylboronic acid), respectively.

Example 4-279

3-Cyclopropyl-6-[(E)-2-[(2R)-5-oxopyrrolidin-2-yl]-1-(4-propoxyphenyl)ethenyl]pyridin-2(1H)-one The title compound was obtained as a white solid (19 mg, 33% (two steps)).

¹H NMR (300 MHz, CDCl₃) δ ppm 0.55-0.70 (m, 2H), 0.92-1.03 (m, 2H), 1.08 (t, J=7.4 Hz, 3H), 1.80-1.93 (m, 2H), 1.95-2.19 (m, 2H), 2.23-2.50 (m, 3H), 3.90-4.04 (m, 2H), 4.18-4.30 (m, 1H), 5.55-5.69 (m, 1H), 5.95-6.02 (m, 1H), 6.09-6.19 (m, 1H), 6.87 (d, J=7.1 Hz, 1H), 6.90-7.00 (m, 2H), 7.06 (d, J=8.6 Hz, 2H), 9.10-9.70 (brs, 1H).
MS(+): 379 [M+H]⁺.
MS(−): 377 [M−H]⁻.

Example 4-280

6-{(E)-1-(3-Chloro-4-propoxyphenyl)-2-[(2R)-5-oxopyrrolidin-2-yl]ethenyl}-3-cyclopropylpyridin-2(1H)-one The title compound was obtained as a white solid (44 mg, 44% (two steps)).
¹H NMR (300 MHz, CDCl₃) δ ppm 0.52-0.75 (m, 2H), 0.92-1.07 (m, 2H), 1.08-1.20 (m, 3H), 1.84-1.99 (m, 2H), 2.00-2.20 (m, 2H), 2.21-2.50 (m, 3H), 4.00-4.11 (m, 2H), 4.13-4.30 (m, 1H), 5.79-5.90 (m, 1H), 6.00-6.12 (brs, 1H), 6.29-6.32 (m, 1H), 6.80-6.91 (m, 1H), 6.92-7.08 (m, 2H), 7.11-7.22 (m, 1H), 10.58-11.18 (brs, 1H).
MS(+): 413 [M+H]⁺.
MS(−): 411 [M−H]⁻.

Example 4-281

6-{(E)-1-[3-Chloro-4-(difluoromethoxy)phenyl]-2-[(2R)-5-oxopyrrolidin-2-yl]ethenyl}-3-cyclopropylpyridin-2(1H)-one The title compound was obtained as a white solid (53 mg, 71% (two steps)).
¹H NMR (300 MHz, CDCl₃) δ ppm 0.50-0.68 (m, 2H), 0.90-1.05 (m, 2H), 2.00-2.50 (m, 5H), 4.06-4.20 (m, 1H), 5.64 (d, J=7.2 Hz, 1H), 6.61 (t, J=72.3 Hz, 1H), 6.58-6.68 (m, 1H), 6.83 (d, J=7.2 Hz, 1H), 7.08-7.16 (m, 1H), 7.26-7.30 (m, 2H), 7.30-7.50 (brs, 1H), 12.30-12.65 (brs, 1H).
MS(+): 421 [M+H]⁺.
MS(−): 419 [M−H]⁻.

Example 4-282

3-Cyclopropyl-6-{(E)-1-(4-ethoxy-2,3-difluorophenyl)-2-[(2R)-5-oxopyrrolidin-2-yl]ethenyl}pyridin-2(1H)-one The title compound was obtained as a colorless solid (22 mg, 29% (two steps)).
¹H NMR (300 MHz, CDCl₃) δ ppm 0.51-0.71 (m, 2H), 0.90-1.10 (m, 2H), 1.51 (t, J=6.8 Hz, 3H), 2.00-2.21 (m, 2H), 2.21-2.50 (m, 3H), 4.00-4.28 (m, 1H), 4.18 (q, J=7.0 Hz, 2H), 5.74 (d, J=7.4 Hz, 1H), 6.08 (s, 1H), 6.64 (d, J=8.9 Hz, 1H), 6.74-6.88 (m, 3H), 11.50-12.10 (brs, 1H).
MS(+): 401 [M+H]⁺.
MS(−): 399 [M−H]⁻.

Example 4-283

6-{(E)-1-[4-(Cyclopentyloxy)phenyl]-2-[(2R)-5-oxopyrrolidin-2-yl]ethenyl}-3-cyclopropylpyridin-2(1H)-one The title compound was obtained as a colorless solid (30 mg, 30% (two steps)).
¹H NMR (300 MHz, CDCl₃) δ ppm 0.41-0.75 (m, 2H), 0.81-1.10 (m, 2H), 1.50-2.53 (m, 13H), 4.10-4.37 (m, 1H), 4.68-4.90 (m, 1H), 5.78 (d, J=7.5 Hz, 1H), 6.40 (d, J=9.0 Hz, 1H), 6.71 (s, 1H), 6.82 (d, J=7.8 Hz, 1H), 6.88 (d, J=8.1 Hz, 2H), 7.05 (d, J=8.1 Hz, 2H), 11.62-12.09 (brs, 1H).
MS(+): 405 [M+H]⁺.
MS(−): 403 [M−H]⁻.

Example 4-284

3-Cyclopropyl-6-{(E)-1-(4-ethoxy-3-fluorophenyl)-2-[(2R)-5-oxopyrrolidin-2-yl]ethenyl}pyridin-2(1H)-one The title compound was obtained as a white solid (25 mg, 35% (two steps)).
¹H NMR (300 MHz, CDCl₃) δ ppm 0.48-0.65 (m, 2H), 0.90-1.05 (m, 2H), 1.49 (t, J=6.9 Hz, 3H), 2.00-2.18 (m, 2H), 2.20-2.45 (m, 3H), 4.10-4.25 (m, 3H), 5.71 (d, J=7.2 Hz, 1H), 6.48-6.56 (m, 1H), 6.82 (d, J=7.2 Hz, 1H), 6.84-7.12 (m, 4H), 12.10-12.45 (brs, 1H).
MS(+): 383 [M+H]⁺.
MS(−): 381 [M−H]⁻.

Example 4-285

4-{(E)-1-(5-Cyclopropyl-6-oxo-1,6-dihydropyridin-2-yl)-2-[(2R)-5-oxopyrrolidin-2-yl]ethenyl}benzonitrile The title compound was obtained as a white solid (23 mg, 28% (two steps)).
¹H NMR (300 MHz, CDCl₃) δ ppm 0.50-0.67 (m, 2H), 0.90-1.05 (m, 2H), 2.00-2.50 (m, 5H), 4.00-4.15 (m, 1H), 5.55 (d, J=7.2 Hz, 1H), 6.64 (d, J=9.3 Hz, 1H), 6.90 (d, J=6.9 Hz, 1H), 7.37 (d, J=7.8 Hz, 2H), 7.35-7.55 (brs, 1H), 7.73 (d, J=8.7 Hz, 2H), 12.35-12.80 (brs, 1H).
MS(+): 346 [M+H]⁺.
MS(−): 344 [M−H]⁻.

Example 4-286

6-{(E)-1-(2-Chloro-4-ethoxyphenyl)-2-[(2R)-5-oxopyrrolidin-2-yl]ethenyl}-3-cyclopropylpyridin-2(1H)-one The title compound was obtained as a pale yellow solid (26 mg, 41% (two steps)).
¹H NMR (300 MHz, CDCl₃) δ ppm 0.50-0.65 (m, 2H), 0.90-1.00 (m, 2H), 1.45 (t, J=6.9 Hz, 3H), 1.95-2.50 (m, 5H), 4.06 (q, J=7.1 Hz, 2H), 3.90-4.15 (m, 1H), 5.61 (d, J=13.8 Hz, 1H), 6.68-6.95 (m, 4H), 6.95-7.10 (m, 2H), 11.20-12.08 (brs, 1H).
MS(+): 399 [M+H]⁺.
MS(−): 397 [M−H]⁻.

Example 4-287

3-Cyclopropyl-6-{(E)-1-[4-(2-fluoroethoxy)phenyl]-2-[(2R)-5-oxopyrrolidin-2-yl]ethenyl}pyridin-2(1H)-one The title compound was obtained as a white solid (18 mg, 17% (two steps)).
¹H NMR (300 MHz, CDCl₃) δ ppm 0.52-0.72 (m, 2H), 0.92-1.09 (m, 2H), 2.00-2.19 (m, 2H), 2.22-2.50 (m, 3H), 4.11-4.24 (m, 1H), 4.34-4.49 (m, 2H), 5.76-6.11 (m, 2H), 6.25-6.39 (m, 1H), 6.86 (d, J=7.4 Hz, 1H), 7.01 (d, J=8.3 Hz, 2H), 7.14 (d, J=8.0 Hz, 2H), 10.60-11.00 (brs, 1H).
MS(+): 419 [M+H]$^+$.
MS(−): 417 [M−H]$^-$.

Example 4-288

5-{(E)-1-(5-Cyclopropyl-6-oxo-1,6-dihydropyridin-2-yl)-2-[(2R)-5-oxopyrrolidin-2-yl]ethenyl}-2-fluorobenzonitrile The title compound was obtained as a pale orange solid (80 mg, 56% (two steps)).
$^1$H NMR (300 MHz, CDCl$_3$) δ ppm 0.50-0.73 (m, 2H), 0.91-1.10 (m, 2H), 2.07-2.53 (m, 5H), 4.00-4.12 (m, 1H), 5.58 (d, J=7.4 Hz, 1H), 6.58 (d, J=9.5 Hz, 1H), 6.83 (d, J=7.1 Hz, 1H), 6.88-7.08 (brs, 1H), 7.27-7.37 (m, 1H), 7.40-7.53 (m, 2H), 12.00-12.34 (brs, 1H).
MS(+): 364 [M+H]$^+$.
MS(−): 362 [M−H]$^-$.

Example 4-289

6-{(E)-1-[3-Chloro-4-(cyclopropylsulfonyl)phenyl]-2-[(2R)-5-oxopyrrolidin-2-yl]ethenyl}-3-cyclopropylpyridin-2(1H)-one (1) n-Butyllithium (1.6 M solution in hexane, 9.2 mL) was added dropwise to a solution of 4-bromo-2-chloro-1-(cyclopropylsulfonyl)benzene obtained in Reference Example 5-30 (1.45 g) and triisopropyl borate (5.54 g) in tetrahydrofuran (15 mL) under cooling at an external temperature of −78° C. in a nitrogen atmosphere, after which the mixture was stirred at the same temperature for three hours. 1 M hydrochloric acid (10 mL) was added and the reaction solution, still basic, was extracted with chloroform. The aqueous layer was made acidic with 1 M hydrochloric acid (10 mL), followed by extraction with chloroform. The solvent was evaporated from the organic layer under reduced pressure to give a crude product of 3-chloro-4-(cyclopropylsulfonyl)phenylboronic acid (1.02 g).

(2) The title compound was obtained as a white solid (50 mg, 48% (two steps)) by performing substantially the same reaction as in Example 4-265 except for using 3-chloro-4-(cyclopropylsulfonyl)phenylboronic acid (250 mg).
$^1$H NMR (300 MHz, CDCl$_3$) δ ppm 0.48-0.71 (m, 2H), 0.89-1.07 (m, 2H), 1.09-1.21 (m, 2H), 1.32-1.48 (m, 2H), 2.05-2.57 (m, 5H), 3.00-3.16 (m, 1H), 4.01-4.18 (m, 1H), 5.61 (d, J=7.3 Hz, 1H), 6.67 (d, J=9.2 Hz, 1H), 6.84 (d, J=7.3 Hz, 1H), 7.19 (s, 1H), 7.30 (dd, J=8.3, 1.7 Hz, 1H), 7.42 (d, J=1.7 Hz, 1H), 8.08 (d, J=8.3 Hz, 1H), 12.13-12.65 (brs, 1H).
MS(+): 459 [M+H]$^+$.
MS(−): 457 [M−H]$^-$.

Example 4-290

3-Cyclopropyl-6-{(E)-1-[4-(cyclopropylsulfonyl)phenyl]-2-[(2R)-5-oxopyrrolidin-2-yl]ethenyl}pyridin-2(1H)-one The title compound was obtained as a white solid (150 mg, 60% (two steps)) by performing substantially the same reaction as in Example 4-289(2) except for using 4-(cyclopropylsulfonyl)phenylboronic acid.
$^1$H NMR (300 MHz, CDCl$_3$) δ ppm 0.48-0.69 (m, 2H), 0.87-1.06 (m, 2H), 1.06-1.19 (m, 2H), 1.35-1.51 (m, 2H), 2.03-2.64 (m, 6H), 4.00-4.16 (m, 1H), 5.58 (d, J=7.6 Hz, 1H), 6.67 (d, J=9.2 Hz, 1H), 6.81 (d, J=7.3 Hz, 1H), 7.33-7.49 (m, 3H), 7.96 (d, J=7.9 Hz, 2H), 12.35-12.84 (brs, 1H).
MS(+): 425 [M+H]$^+$.
MS(−): 423 [M−H]$^-$.

Example 4-291

6-{(E)-1-[4-(Benzylsulfonyl)phenyl]-2-[(2R)-5-oxopyrrolidin-2-yl]ethenyl}-3-cyclopropylpyridin-2(1H)-one The title compound was obtained as a white solid (15 mg, 6% (two steps)) by performing substantially the same reaction as in Example 4-289 except for using 1-(benzylsulfonyl)-4-bromobenzene.
$^1$H NMR (300 MHz, DMSO-d$_6$) δ ppm 0.57-0.66 (m, 2H), 0.80-0.89 (m, 2H), 1.77-1.93 (m, 1H), 1.95-2.30 (m, 4H), 3.69-3.79 (m, 1H), 4.71 (s, 2H), 5.23-5.39 (brs, 1H), 6.53 (d, J=9.0 Hz, 1H), 6.83-6.93 (m, 1H), 7.12 (d, J=7.4 Hz, 2H), 7.21-7.34 (m, 3H), 7.40 (d, J=7.8 Hz, 2H), 7.71 (d, J=7.4 Hz, 2H), 7.80 (s, 1H), 11.38-11.58 (brs, 1H).
MS(+): 475 [M+H]$^+$.
MS(−): 473 [M−H]$^-$.

Example 4-292

4-{(E)-1-(5-Cyclopropyl-6-oxo-1,6-dihydropyridin-2-yl)-2-[(2R)-5-oxopyrrolidin-2-yl]ethenyl}-N,N-dimethylbenzenesulfonamide The title compound was obtained as a pale yellow solid (51 mg, 39% (two steps)) by performing substantially the same reaction as in Example 4-289(2) except for using 4-(N,N-dimethylsulfamoyl)phenylboronic acid.
$^1$H NMR (300 MHz, CDCl$_3$) δ ppm 0.53-0.63 (m, 2H), 0.95-0.98 (m, 2H), 2.07-2.48 (m, 5H), 2.77 (s, 6H), 4.03-4.13 (m, 1H), 5.56 (d, J=7.4 Hz, 1H), 6.67 (d, J=8.9 Hz, 1H), 6.81 (d, J=7.4 Hz, 1H), 7.39-7.46 (m, 3H), 7.84 (d, J=8.6 Hz, 2H), 12.46-12.73 (brs, 1H).
MS(+): 428 [M+H]$^+$.
MS(−): 426 [M−H]$^-$.

Example 4-293

6-{(E)-1-[4-(Benzylsulfonyl)-3-chlorophenyl]-2-[(2R)-5-oxopyrrolidin-2-yl]ethenyl}-3-cyclopropylpyridin-2(1H)-one The title compound was obtained as a white solid (120 mg, 40% (two steps)) by performing substantially the same reaction as in Example 4-289 except for using 1-(benzylsulfonyl)-4-bromo-2-chlorobenzene.
$^1$H NMR (300 MHz, CDCl$_3$) δ ppm 0.53-0.68 (m, 2H), 0.96-1.05 (m, 2H), 2.06-2.28 (m, 3H), 2.30-2.50 (m, 2H), 3.88-3.98 (m, 1H), 4.69 (s, 2H), 5.46 (d, J=7.3 Hz, 1H), 6.68 (d, J=9.2 Hz, 1H), 6.81 (d, J=7.3 Hz, 1H), 7.12 (dd, J=8.1, 1.5 Hz, 1H), 7.17 (s, 1H), 7.24-7.32 (m, 5H), 7.39 (d, J=1.3 Hz, 1H), 7.80 (d, J=7.9 Hz, 1H), 12.43-12.60 (brs, 1H).
MS(+): 509 [M+H]$^+$.
MS(−): 507 [M−H]$^-$.

Examples 4-294 and 4-295

3-Cyclopropyl-6-{1-(4-methylphenyl)-2-[(2R)-5-oxopyrrolidin-2-yl]ethyl}pyridin-2(1H)-one (1) (5R)-5-[2-(5-Cyclopropyl-6-methoxypyridin-2-yl)-2-(4-methylphenyl)ethenyl]pyrrolidin-2-one (EZ mixture)

(332 mg, 91%) was obtained by performing substantially the same reaction as in Example 4-2(1) except for using (5-cyclopropyl-6-methoxypyridin-2-yl)(4-methylphenyl)methanone obtained in Reference Example 1-58.

(2) 3-Cyclopropyl-6-{(Z)-1-(4-methylphenyl)-2-[(2R)-5-oxopyrrolidin-2-yl]ethenyl}pyridin-2(1H)-one was obtained as a white solid (140 mg, 44%) by performing substantially the same reaction as in Example 1-1(2) except for using (5R)-5-[2-(5-cyclopropyl-6-methoxypyridin-2-yl)-2-(4-methylphenyl)ethenyl]pyrrolidin-2-one (EZ mixture). 3-Cyclopropyl-6-{(E)-1-(4-methylphenyl)-2-[(2R)-5-oxopyrrolidin-2-yl]ethenyl}pyridin-2(1H)-one was also obtained as a white solid (78 mg, 24%).

(3) One diastereomer (A) of the title compound was obtained as a white solid (55 mg, 46%) by performing substantially the same reaction as in Examples 4-69 and 4-70(2) except for using 3-cyclopropyl-6-{(Z)-1-(4-methylphenyl)-2-[(2R)-5-oxopyrrolidin-2-yl]ethenyl}pyridin-2(1H)-one, separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 14 minutes. The fraction eluted with a retention time of 37 minutes was concentrated to give the other diastereomer (B) of the title compound as a white solid (38 mg, 32%).

Diastereomer (A);
$^1$H NMR (300 MHz, CDCl$_3$) δ ppm 0.51-0.72 (m, 2H), 0.85-1.05 (m, 2H), 1.62-1.83 (m, 1H), 1.90-2.50 (m, 6H), 2.32 (s, 3H), 3.43-3.60 (m, 1H), 3.99 (dd, J=9.6, 5.6 Hz, 1H), 5.94 (d, J=7.3 Hz, 1H), 6.90 (d, J=6.9 Hz, 1H), 7.13 (d, J=8.3 Hz, 2H), 7.24 (d, J=8.3 Hz, 2H), 7.37 (s, 1H), 11.87-12.21 (brs, 1H).
MS(+): 337 [M+H]$^+$.
MS(−): 335 [M−H]$^−$.

Diastereomer (B);
$^1$H NMR (300 MHz, CDCl$_3$) δ ppm 0.52-0.67 (m, 2H), 0.92-1.17 (m, 2H), 1.48-1.93 (m, 1H), 2.10-2.45 (m, 6H), 2.33 (s, 3H), 3.52-3.66 (m, 1H), 3.98-4.14 (m, 1H), 5.99 (d, J=7.3 Hz, 1H), 6.94 (d, J=7.3 Hz, 1H), 7.14 (d, J=8.3 Hz, 2H), 7.20 (d, J=8.3 Hz, 2H), 7.49 (s, 1H), 12.57-13.13 (brs, 1H).
MS(+): 337 [M+H]$^+$.
MS(−): 335 [M−H]$^−$.

Examples 4-296 and 4-297

3-Chloro-6-{1-[3-chloro-4-(propan-2-yloxy)phenyl]-2-[(2R)-5-oxopyrrolidin-2-yl]ethyl}pyridin-2(1H)-one One diastereomer (A) of the title compound was obtained as a white amorphous (18 mg, 6% (three steps)) by performing substantially the same reaction as in Examples 4-294 and 4-295 except for using (5-chloro-6-methoxypyridin-2-yl)[3-chloro-4-(propan-2-yloxy)phenyl]methanone obtained in Reference Example 1-30, separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 17 minutes. The fraction eluted with a retention time of 35 minutes was concentrated to give the other diastereomer (B) of the title compound as a white amorphous (19 mg, 6% (three steps)).

Diastereomer (A);
$^1$H NMR (300 MHz, CDCl$_3$) δ ppm 1.36 (d, J=5.7 Hz, 6H), 1.60-1.83 (m, 1H), 2.05-2.50 (m, 5H), 3.40-3.60 (m, 1H), 3.90-4.10 (m, 1H), 4.40-4.60 (m, 1H), 6.03 (d, J=7.5 Hz, 1H), 6.89 (d, J=8.4 Hz, 1H), 7.15-7.20 (m, 1H), 7.35 (d, J=2.4 Hz, 1H), 7.51 (d, J=7.5 Hz, 1H), 7.70-7.90 (brs, 1H), 12.30-12.80 (brs, 1H).
MS(+): 409 [M+H]$^+$.
MS(−): 407 [M−H]$^−$.

Diastereomer (B);
$^1$H NMR (300 MHz, CDCl$_3$) δ ppm 1.25-1.45 (m, 6H), 1.70-2.02 (m, 1H), 2.15-2.55 (m, 5H), 3.55-3.75 (m, 1H), 3.90-4.10 (m, 1H), 4.40-4.65 (m, 1H), 6.06 (d, J=7.8 Hz, 1H), 6.89 (d, J=8.9 Hz, 1H), 7.05-7.20 (m, 1H), 7.32 (d, J=2.4 Hz, 1H), 7.53 (d, J=7.5 Hz, 1H), 7.80-8.05 (brs, 1H), 12.90-13.30 (brs, 1H).
MS(+): 409 [M+H]$^+$.
MS(−): 407 [M−H]$^−$.

Examples 4-298 and 4-299

3-Cyclopropyl-6-{1-[4-(cyclopropylsulfonyl)-3-methylphenyl]-2-[(2R)-5-oxopyrrolidin-2-yl]ethyl}pyridin-2(1H)-one (1) 3-Cyclopropyl-6-{(Z)-1-[4-(cyclopropylsulfanyl)-3-methylphenyl]-2-[(2R)-5-oxopyrrolidin-2-yl]ethenyl}pyridin-2(1H)-one (95 mg, 19% (two steps)) was obtained by performing substantially the same reaction as in Example 4-2 except for using (5-cyclopropyl-6-methoxypyridin-2-yl)[4-(cyclopropylsulfanyl)-3-methylphenyl]methanone obtained in Reference Example 1-57.

(2) 3-Cyclopropyl-6-{(Z)-1-[4-(cyclopropylsulfonyl)-3-methylphenyl]-2-[(2R)-5-oxopyrrolidin-2-yl]ethenyl}pyridin-2(1H)-one was obtained as a colorless amorphous (65 mg, 63%) by performing substantially the same reaction as in Example 1-2 except for using 3-cyclopropyl-6-{(Z)-1-[4-(cyclopropylsulfanyl)-3-methylphenyl]-2-[(2R)-5-oxopyrrolidin-2-yl]ethenyl}pyridin-2(1H)-one.

(3) One diastereomer (A) of the title compound was obtained as a white solid (18 mg, 28%) by performing substantially the same reaction as in Examples 4-294 and 4-295 (3) except for using 3-cyclopropyl-6-{(Z)-1-[4-(cyclopropylsulfanyl)-3-methylphenyl]-2-[(2R)-5-oxopyrrolidin-2-yl]ethenyl}pyridin-2(1H)-one, separating the mixture by preparative HPLC (CHIRALPAK IB (20 mm i.d.×250 mm L, Daicel Chemical Industries, LTD.), 40° C., flow rate: 10 mL/min, ethanol:hexane=40:60) and concentrating the fraction eluted with a retention time of 20 minutes. The fraction eluted with a retention time of 35 minutes was concentrated to give the other diastereomer (B) of the title compound as a white solid (18 mg, 27%).

Diastereomer (A);
$^1$H NMR (300 MHz, CDCl$_3$) δ ppm 0.54-0.72 (m, 2H), 0.92-1.10 (m, 4H), 1.28-1.41 (m, 2H), 1.53-1.84 (m, 1H), 2.01-2.16 (m, 1H), 2.16-2.47 (m, 5H), 2.47-2.63 (m, 1H), 2.71 (s, 3H), 3.38-3.56 (m, 1H), 3.97-4.14 (m, 1H), 6.04 (d, J=6.9 Hz, 1H), 6.95 (d, J=7.3 Hz, 1H), 7.32-7.42 (m, 2H), 7.88 (d, J=8.3 Hz, 1H), 11.70-12.28 (brs, 1H).
MS(+): 441 [M+H]$^+$.
MS(−): 439 [M−H]$^−$.

Diastereomer (B);
$^1$H NMR (300 MHz, CDCl$_3$) δ ppm 0.49-0.71 (m, 2H), 0.92-1.15 (m, 4H), 1.29-1.38 (m, 2H), 1.69-1.89 (m, 1H), 2.06-2.48 (m, 6H), 2.48-2.62 (m, 1H), 2.73 (s, 3H), 3.49-3.68 (m, 1H), 4.03-4.21 (m, 1H), 6.03 (d, J=7.3 Hz, 1H), 6.98 (d, J=6.6 Hz, 1H), 7.18-7.36 (m, 2H), 7.78 (s, 1H), 7.99 (d, J=7.9 Hz, 1H).
MS(+): 441 [M+H]$^+$.
MS(−): 439 [M−H]$^−$.

Examples 4-300 and 4-301

6-{1-[3-Chloro-4-(2,2,2-trifluoroethoxy)phenyl]-2-[(2R)-5-oxopyrrolidin-2-yl]ethyl}-3-cyclopropylpyridin-2(1H)-one One diastereomer (A) of the title compound was obtained as a white amorphous (1 mg, 2%) by performing substantially the same reaction as in Examples 4-294 and 4-295(3) except for using 6-{(E)-1-[3-chloro-4-(2,2,2-trifluoroethoxy)phenyl]-2-[(2R)-5-oxopyrrolidin-2-yl]ethenyl}-3-cyclopropylpyridin-2(1H)-one obtained in Example 4-270, separating the mixture by preparative HPLC (CHIRALPAK IB (20 mm i.d.×250 mm L, Daicel Chemical Industries, LTD.), 40° C., flow rate: 10 mL/min, ethanol:hexane=25:75) and concentrating the fraction eluted with a retention time of 21 minutes. The fraction eluted with a retention time of 63 minutes was concentrated to give the other diastereomer (B) of the title compound as a white amorphous (3 mg, 5%).

Diastereomer (A);
$^1$H NMR (300 MHz, CDCl$_3$) δ ppm 0.57-0.72 (m, 2H), 0.91-1.03 (m, 2H), 1.67-1.82 (m, 1H), 2.01-2.45 (m, 6H), 3.40-3.59 (m, 1H), 3.89-4.00 (m, 1H), 4.30-4.48 (m, 2H), 6.00 (d, J=6.6 Hz, 1H), 6.85-7.00 (m, 3H), 7.15-7.33 (m, 1H), 7.41 (s, 1H), 11.40-12.00 (brs, 1H).
MS(+): 455 [M+H]$^+$.
MS(−): 453 [M−H]$^−$.

Diastereomer (B);
$^1$H NMR (300 MHz, CDCl$_3$) δ ppm 0.55-0.70 (m, 2H), 0.95-1.11 (m, 2H), 1.70-1.88 (m, 1H), 2.09-2.45 (m, 6H), 3.50-3.65 (m, 1H), 4.00-4.13 (m, 1H), 4.30-4.47 (m, 2H), 6.00 (d, J=7.1 Hz, 1H), 6.94 (d, J=8.3 Hz, 1H), 6.97 (d, J=7.1 Hz, 1H), 7.20 (dd, J=8.6, 2.1 Hz, 1H), 7.39 (d, J=2.1 Hz, 1H), 7.60-7.74 (brs, 1H), 12.68-13.39 (brs, 1H).
MS(+): 455 [M+H]$^+$.
MS(−): 453 [M−H]$^−$.

Examples 4-302 and 4-303

3-Cyclopropyl-6-{1-(4-ethylphenyl)-2-[(2R)-5-oxopyrrolidin-2-yl]ethyl}pyridin-2(1H)-one One diastereomer (A) of the title compound was obtained as a white solid (25 mg, 22%) by performing substantially the same reaction as in Examples 4-294 and 4-295(3) except for using 3-cyclopropyl-6-{(E)-1-(4-ethylphenyl)-2-[(2R)-5-oxopyrrolidin-2-yl]ethenyl}pyridin-2(1H)-one obtained in Example 4-5, separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 13 minutes. The fraction eluted with a retention time of 34 minutes was concentrated to give the other diastereomer (B) of the title compound as a white solid (31 mg, 27%).

Diastereomer (A);
$^1$H NMR (300 MHz, CDCl$_3$) δ ppm 0.50-0.70 (m, 2H), 0.84-1.03 (m, 2H), 1.22 (td, J=7.6, 0.7 Hz, 3H), 1.52-1.82 (m, 1H), 2.01-2.42 (m, 6H), 2.62 (q, J=7.6 Hz, 2H), 3.43-3.56 (m, 1H), 3.94 (dd, J=9.2, 6.6 Hz, 1H), 5.97 (d, J=7.3 Hz, 1H), 6.91 (d, J=7.3 Hz, 1H), 6.95-7.06 (m, 1H), 7.12-7.28 (m, 4H), 11.05-11.58 (brs, 1H).
MS(+): 351 [M+H]$^+$.
MS(−): 349 [M−H]$^−$.

Diastereomer (B);
$^1$H NMR (300 MHz, CDCl$_3$) δ ppm 0.51-0.66 (m, 2H), 0.90-1.06 (m, 2H), 1.22 (t, J=7.6 Hz, 3H), 1.69-1.88 (m, 1H), 2.09-2.41 (m, 6H), 2.62 (q, J=7.6 Hz, 2H), 3.50-3.64 (m, 1H), 4.04 (dd, J=8.6, 8.6 Hz, 1H), 6.00 (d, J=7.3 Hz, 1H), 6.94 (d, J=7.3 Hz, 1H), 7.08-7.28 (m, 4H), 7.32-7.50 (m, 1H).
MS(+): 351 [M+H]$^+$.
MS(−): 349 [M−H]$^−$.

Examples 4-304 and 4-305

3-Chloro-6-{1-[3-chloro-4-(cyclopropylsulfonyl)phenyl]-2-[(2R)-5-oxopyrrolidin-2-yl]ethyl}pyridin-2(1H)-one One diastereomer (A) of the title compound was obtained as a white solid (19 mg, 12%) by performing substantially the same reaction as in Examples 4-294 and 4-295(3) except for using 3-chloro-6-{(E)-1-[3-chloro-4-(cyclopropylsulfonyl)phenyl]-2-[(2R)-5-oxopyrrolidin-2-yl]ethenyl}pyridin-2(1H)-one obtained in Example 4-59, separating the mixture by preparative HPLC (CHIRALPAK IB (20 mm i.d.×250 mm L, Daicel Chemical Industries, LTD.), 40° C., flow rate: 10 mL/min, ethanol:hexane=40:60) and concentrating the fraction eluted with a retention time of 23 minutes. The fraction eluted with a retention time of 30 minutes was concentrated to give the other diastereomer (B) of the title compound as a white solid (21 mg, 13%).

Diastereomer (A);
$^1$H NMR (300 MHz, CDCl$_3$) δ ppm 1.00-1.20 (m, 2H), 1.20-1.44 (m, 2H), 1.61-1.92 (m, 1H), 2.11-2.63 (m, 5H), 2.92-3.08 (m, 1H), 3.47-3.62 (m, 1H), 4.03-4.18 (m, 1H), 6.13 (d, J=7.8 Hz, 1H), 7.43-7.70 (m, 4H), 7.99 (d, J=8.2 Hz, 1H), 12.24-12.90 (brs, 1H).
MS(+): 455 [M+H]$^+$.
MS(−): 453 [M−H]$^−$.

Diastereomer (B);
$^1$H NMR (300 MHz, CDCl$_3$) δ ppm 0.97-1.13 (m, 2H), 1.19-1.39 (m, 2H), 1.80-2.00 (m, 1H), 2.08-2.22 (m, 1H), 2.22-2.71 (m, 4H), 2.92-3.06 (m, 1H), 3.79-3.92 (m, 1H), 4.10-4.21 (m, 1H), 6.19 (d, J=7.4 Hz, 1H), 7.41 (d, J=8.2 Hz, 1H), 7.52 (s, 1H), 7.59 (d, J=7.8 Hz, 1H), 7.95 (d, J=8.2 Hz, 1H), 8.31 (s, 1H), 12.85-13.51 (brs, 1H).
MS(+): 455 [M+H]$^+$.
MS(−): 453 [M−H]$^−$.

Examples 4-306 and 4-307

3-Cyclopropyl-6-{1-[4-(cyclopropylsulfonyl)phenyl]-2-[(2R)-5-oxopyrrolidin-2-yl]ethyl}pyridin-2(1H)-one One diastereomer (A) of the title compound was obtained as a white solid (37 mg, 31%) by performing substantially the same reaction as in Examples 4-294 and 4-295(3) except for using 6-{(E)-1-[4-(cyclopropylsulfonyl)phenyl]-2-[(2R)-5-oxopyrrolidin-2-yl]ethenyl}-3-cyclopropylpyridin-2(1H)-one obtained in Example 4-290, separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 47 minutes. The fraction eluted with a retention time of 77 minutes was concentrated to give the other diastereomer (B) of the title compound as a white solid (65 mg, 55%).

Diastereomer (A);
$^1$H NMR (300 MHz, CDCl$_3$) δ ppm 0.56-0.77 (m, 2H), 0.90-1.18 (m, 4H), 1.27-1.47 (m, 2H) 1.60-1.90 (m, 1H), 2.02-2.57 (m, 7H), 3.38-3.60 (m, 1H), 4.07-4.22 (m, 1H), 6.05 (d, J=7.4 Hz, 1H), 6.95 (d, J=7.0 Hz, 1H), 7.36 (s, 1H), 7.58 (d, J=8.6 Hz, 2H), 7.83 (d, J=8.6 Hz, 2H), 12.00-12.50 (brs, 1H).
MS(+): 427 [M+H]⁺.
MS(−): 425 [M−H]⁻.
Diastereomer (B);
$^1$H NMR (300 MHz, CDCl$_3$) δ ppm 0.55-0.69 (m, 2H), 0.94-1.11 (m, 4H), 1.39-1.50 (m, 2H), 1.70-1.89 (m, 1H), 2.09-2.51 (m, 7H), 3.53-3.68 (m, 1H), 4.17-4.29 (m, 1H), 6.03 (d, J=7.4 Hz, 1H), 6.98 (d, J=7.4 Hz, 1H), 7.52 (d, J=8.2 Hz, 2H), 7.85 (d, J=7.0 Hz, 2H), 7.90 (s, 1H), 12.95-13.50 (brs, 1H).
MS(+): 427 [M+H]⁺.
MS(−): 425 [M−H]⁻.

Examples 4-308 and 4-309

3-Chloro-6-{1-(4-ethylphenyl)-2-[(2R)-5-oxopyrrolidin-2-yl]ethyl}pyridin-2(1H)-one (1) (5R)-5-[2-(5-Chloro-6-methoxypyridin-2-yl)-2-(4-ethylphenyl)ethenyl]pyrrolidin-2-one (EZ mixture) was obtained as a colorless amorphous (460 mg, 89%) by performing substantially the same reaction as in Example 4-2(1) except for using (5-chloro-6-methoxypyridin-2-yl)(4-ethylphenyl)methanone obtained in Reference Example 1-9.

(2) One diastereomer (A) of the title compound was obtained as a white amorphous (168 mg, 38% (two steps)) by performing substantially the same reaction as in Examples 4-69 and 4-70(2)(3) sequentially except for using (5R)-5-[2-(5-chloro-6-methoxypyridin-2-yl)-2-(4-ethylphenyl)ethenyl]pyrrolidin-2-one (EZ mixture), separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 14 minutes. The fraction eluted with a retention time of 24 minutes was concentrated to give the other diastereomer (B) of the title compound as a white amorphous (124 mg, 28% (two steps)).
Diastereomer (A);
$^1$H NMR (300 MHz, CDCl$_3$) δ ppm 1.23 (t, J=7.8 Hz, 3H), 1.65-1.85 (m, 1H), 2.10-2.55 (m, 5H), 2.64 (q, J=7.8 Hz, 2H), 3.45-3.65 (m, 1H), 3.85-4.10 (m, 1H), 6.02 (d, J=7.2 Hz, 1H), 7.05-7.40 (m, 5H), 7.50 (d, J=7.8 Hz, 1H), 11.50-11.80 (brs, 1H).
MS(+): 345 [M+H]⁺.
MS(−): 343 [M−H]⁻.
Diastereomer (B);
$^1$H NMR (300 MHz, CDCl$_3$) δ ppm 1.22 (t, J=7.5 Hz, 3H), 1.80-2.05 (m, 1H), 2.15-2.55 (m, 5H), 2.63 (q, J=7.5 Hz, 2H), 3.57-3.75 (m, 1H), 3.95-4.15 (m, 1H), 6.04 (d, J=7.8 Hz, 1H), 7.05-7.35 (m, 4H), 7.52 (d, J=7.5 Hz, 1H), 7.53-7.70 (m, 1H), 12.00-13.05 (brs, 1H).
MS(+): 345 [M+H]⁺.
MS(−): 343 [M−H]⁻.

The compounds of Examples 4-310 to 4-325 were synthesized by performing substantially the same reaction as in Examples 4-308 and 4-309 except for using, in place of (5-chloro-6-methoxypyridin-2-yl)(4-ethylphenyl)methanone, corresponding ketones ((5-chloro-6-methoxypyridin-2-yl)(3-chloro-4-methylphenyl)methanone (Reference Example 1-16), (5-chloro-6-methoxypyridin-2-yl)(4-propylphenyl)methanone (Reference Example 1-18), (4-tert-butylphenyl)[6-methoxy-5-(trifluoromethyl)pyridin-2-yl]methanone (Reference Example 1-82), (5-chloro-6-methoxypyridin-2-yl)(4-cyclopropylphenyl)methanone (Reference Example 1-87), (5-chloro-6-methoxypyridin-2-yl)(4-methylphenyl)methanone (Reference Example 1-91), [3-chloro-4-(propan-2-yl)phenyl](5-cyclopropyl-6-methoxypyridin-2-yl)methanone (Reference Example 1-84), [3-chloro-4-(propan-2-yloxy)phenyl](5-cyclopropyl-6-methoxypyridin-2-yl)methanone (Reference Example 1-92) and (3-chloro-4-ethylphenyl)(5-chloro-6-methoxypyridin-2-yl)methanone (Reference Example 1-90)), respectively.

Examples 4-310 and 4-311

3-Chloro-6-{1-(3-chloro-4-methylphenyl)-2-[(2R)-5-oxopyrrolidin-2-yl]ethyl}pyridin-2(1H)-one One diastereomer (A) of the title compound was obtained as a white amorphous (180 mg, 36% (three steps)) by separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 15 minutes. The fraction eluted with a retention time of 28 minutes was concentrated to give the other diastereomer (B) of the title compound as a white amorphous (141 mg, 29% (three steps)).
Diastereomer (A);
$^1$H NMR (300 MHz, CDCl$_3$) δ ppm 1.65-1.83 (m, 1H), 2.10-2.50 (m, 5H), 2.35 (s, 3H), 3.41-3.61 (m, 1H), 3.90-4.05 (m, 1H), 6.01 (d, J=7.8 Hz, 1H), 7.10-7.40 (m, 4H), 7.51 (d, J=7.8 Hz, 1H), 11.90-12.25 (brs, 1H).
MS(+): 365 [M+H]⁺.
MS(−): 363 [M−H]⁻.
Diastereomer (B);
$^1$H NMR (300 MHz, CDCl$_3$) δ ppm 1.80-2.00 (m, 1H), 2.10-2.60 (m, 5H), 2.34 (s, 3H), 3.60-3.80 (m, 1H), 3.95-4.10 (m, 1H), 6.01 (d, J=7.5 Hz, 1H), 7.05-7.35 (m, 3H), 7.54 (d, J=7.8 Hz, 1H), 7.71-7.95 (brs, 1H), 12.90-13.30 (brs, 1H).
MS(+): 365 [M+H]⁺.
MS(−): 363 [M−H]⁻.

Examples 4-312 and 4-313

3-Chloro-6-[2-[(2R)-5-oxopyrrolidin-2-yl]-1-(4-propylphenyl)ethyl]pyridin-2(1H)-one One diastereomer (A) of the title compound was obtained as a white amorphous (85 mg, 23% (three steps)) by separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 14 minutes. The fraction eluted with a retention time of 26 minutes was concentrated to give the other diastereomer (B) of the title compound as a white amorphous (71 mg, 19% (three steps)).
Diastereomer (A);
$^1$H NMR (300 MHz, CDCl$_3$) δ ppm 0.92 (t, J=7.5 Hz, 3H), 1.50-1.80 (m, 3H), 2.10-2.46 (m, 5H), 2.53 (t, J=7.5 Hz, 2H), 3.40-3.58 (m, 1H), 3.95-4.11 (m, 1H), 6.05 (d, J=7.5 Hz, 1H), 7.12 (d, J=8.1 Hz, 2H), 7.27 (d, J=8.4 Hz, 2H), 7.48 (d, J=7.5 Hz, 1H), 7.95-8.10 (brs, 1H), 12.30-12.95 (brs, 1H).
Diastereomer (B);
$^1$H NMR (300 MHz, CDCl$_3$) δ ppm 0.93 (t, J=7.4 Hz, 3H), 1.48-1.75 (m, 2H), 1.85-2.70 (m, 6H), 2.55 (t, J=7.5 Hz, 2H), 3.50-3.75 (m, 1H), 3.95-4.16 (m, 1H), 6.03 (d, J=7.5 Hz, 1H), 7.14 (d, J=7.5 Hz, 2H), 7.23 (d, J=7.5 Hz, 2H), 7.50 (d, J=7.8 Hz, 1H), 7.80-8.05 (brs, 1H), 12.90-13.40 (brs, 1H).
MS(+): 359 [M+H]⁺.
MS(−): 357 [M−H]⁻.

Examples 4-314 and 4-315

6-{1-(4-tert-Butylphenyl)-2-[(2R)-5-oxopyrrolidin-2-yl]ethyl}-3-(trifluoromethyl)pyridin-2(1H)-one One diastereomer (A) of the title compound was obtained as a colorless solid (108 mg, 26% (three steps)) by separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 10 minutes. The fraction eluted with a retention time of 14 minutes was concentrated to give the other diastereomer (B) of the title compound as a colorless solid (104 mg, 24% (three steps)).

Diastereomer (A);

$^1$H NMR (300 MHz, CDCl$_3$) δ ppm 1.28 (s, 9H), 1.61-1.79 (m, 1H), 2.12-2.51 (m, 5H), 3.45-3.58 (m, 1H), 4.04-4.14 (m, 1H), 6.15 (d, J=7.7 Hz, 1H), 7.25-7.40 (m, 4H), 7.69 (d, J=7.4 Hz, 1H), 7.70-7.89 (brs, 1H), 12.85-13.00 (brs, 1H).

MS(+): 407 [M+H]$^+$.

MS(−): 405 [M−H]$^−$.

Diastereomer (B);

$^1$H NMR (300 MHz, CDCl$_3$) δ ppm 1.29 (s, 9H), 1.80-1.97 (m, 1H), 2.16-2.51 (m, 5H), 3.47-3.62 (m, 1H), 4.05-4.17 (m, 1H), 6.29 (d, J=7.2 Hz, 1H), 7.29 (d, J=8.4 Hz, 2H), 7.35 (d, J=8.7 Hz, 2H), 7.74 (d, J=7.5 Hz, 1H), 7.67-7.85 (brs, 1H), 13.02-13.40 (brs, 1H).

MS(+): 407 [M+H]$^+$.

MS(−): 405 [M−H]$^−$.

Examples 4-316 and 4-317

3-Chloro-6-{1-(4-cyclopropylphenyl)-2-[(2R)-5-oxopyrrolidin-2-yl]ethyl}pyridin-2(1H)-one One diastereomer (A) of the title compound was obtained as a colorless solid (62 mg, 14% (three steps)) by separating the mixture by preparative HPLC (Inertsil ODS-3 (20 mm i.d.×250 mm L, GL Sciences Inc.), 40° C., flow rate: 10 mL/min, acetonitrile:water=37:63) and concentrating the fraction eluted with a retention time of 28 minutes. The fraction eluted with a retention time of 31 minutes was concentrated to give the other diastereomer (B) of the title compound as a colorless solid (33 mg, 8% (three steps)).

Diastereomer (A);

$^1$H NMR (300 MHz, CDCl$_3$) δ ppm 0.63-0.70 (m, 2H), 0.91-1.00 (m, 2H), 1.80-1.99 (m, 2H), 2.14-2.51 (m, 5H), 3.60-3.72 (m, 1H), 4.02 (t, J=7.2 Hz, 1H), 6.02 (d, J=7.8 Hz, 1H), 7.03 (d, J=8.4 Hz, 2H), 7.19 (d, J=8.4 Hz, 2H), 7.41-7.53 (brs, 1H), 7.51 (d, J=7.5 Hz, 1H), 12.73-12.90 (brs, 1H).

MS(+): 357 [M+H]$^+$.

MS(−): 355 [M−H]$^−$.

Diastereomer (B);

$^1$H NMR (300 MHz, CDCl$_3$) δ ppm 0.63-0.70 (m, 2H), 0.92-1.00 (m, 2H), 1.61-1.78 (m, 1H), 1.80-1.92 (m, 1H), 2.11-2.50 (m, 5H), 3.44-3.57 (m, 1H), 3.96 (dd, J=9.5, 5.9 Hz, 1H), 6.00 (d, J=7.5 Hz, 1H), 7.05 (d, J=8.4 Hz, 2H), 7.22 (d, J=8.1 Hz, 2H), 7.25-7.31 (brs, 1H), 7.49 (d, J=7.5 Hz, 1H), 11.87-12.50 (brs, 1H).

MS(+): 357 [M+H]$^+$.

MS(−): 355 [M−H]$^−$.

Examples 4-318 and 4-319

3-Chloro-6-{1-(4-methylphenyl)-2-[(2R)-5-oxopyrrolidin-2-yl]ethyl}pyridin-2(1H)-one One diastereomer (A) of the title compound was obtained as a white solid (70 mg, 29% (three steps)) by separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 15 minutes. The fraction eluted with a retention time of 27 minutes was concentrated to give the other diastereomer (B) of the title compound as a white solid (68 mg, 28% (three steps)).

Diastereomer (A);

$^1$H NMR (300 MHz, CDCl$_3$) δ ppm 1.64-1.80 (m, 1H), 1.95-2.55 (m, 5H), 2.32 (s, 3H), 3.44-3.59 (m, 1H), 4.07 (dd, J=8.9, 6.3 Hz, 1H), 6.01 (d, J=7.6 Hz, 1H), 7.15 (d, J=8.3 Hz, 2H), 7.25 (d, J=9.2 Hz, 2H), 7.49 (d, J=7.6 Hz, 1H), 7.60 (s, 1H), 12.15-12.55 (brs, 1H).

MS(+): 331 [M+H]$^+$.

MS(−): 329 [M−H]$^−$.

Diastereomer (B);

$^1$H NMR (300 MHz, CDCl$_3$) δ ppm 1.86-2.03 (m, 1H), 2.08-2.55 (m, 5H), 2.33 (s, 3H), 3.56-3.73 (m, 1H), 4.05 (dd, J=7.6, 7.6 Hz, 1H), 6.01 (d, J=7.6 Hz, 1H), 7.15 (d, J=7.9 Hz, 1H), 7.21 (d, J=8.3 Hz, 2H), 7.50 (d, J=7.6 Hz, 2H), 7.70 (s, 1H), 12.95-13.24 (brs, 1H).

MS(+): 331 [M+H]$^+$.

MS(−): 329 [M−H]$^−$.

Examples 4-320 and 4-321

6-{1-[3-Chloro-4-(propan-2-yl)phenyl]-2-[(2R)-5-oxopyrrolidin-2-yl]ethyl}-3-cyclopropylpyridin-2(1H)-one One diastereomer (A) of the title compound was obtained as a colorless amorphous (9 mg, 7% (three steps)) by separating the mixture by preparative HPLC (CHIRALPAK IB (20 mm i.d.×250 mm L, Daicel Chemical Industries, LTD.), 40° C., flow rate: 10 mL/min, ethanol:hexane=20:80) and concentrating the fraction eluted with a retention time of 19 minutes. The fraction separated with ethanol:hexane=35:65 and eluted with a retention time of 42 minutes was concentrated to give the other diastereomer (B) of the title compound as a colorless amorphous (5 mg, 4% (three steps)).

Diastereomer (A);

$^1$H NMR (300 MHz, CDCl$_3$) δ ppm 0.54-0.70 (m, 2H), 0.86-1.05 (m, 2H), 1.21 (d, J=6.8 Hz, 6H), 1.64-1.91 (m, 1H), 2.05-2.44 (m, 6H), 3.25-3.43 (m, 1H), 3.43-3.57 (m, 1H), 3.90-4.01 (m, 1H), 5.97 (d, J=7.4 Hz, 1H), 6.91 (d, J=7.1 Hz, 1H), 7.17-7.40 (m, 4H), 11.90-12.18 (brs, 1H).

MS(+): 399 [M+H]$^+$.

MS(−): 397 [M−H]$^−$.

Diastereomer (B);

$^1$H NMR (300 MHz, CDCl$_3$) δ ppm 0.51-0.67 (m, 2H), 0.94-1.09 (m, 2H), 1.22 (d, J=7.1 Hz, 6H), 1.70-1.90 (m, 1H), 2.09-2.45 (m, 6H), 3.27-3.44 (m, 1H), 3.50-3.65 (m, 1H), 4.05 (dd, J=9.8, 5.4 Hz, 1H), 6.01 (d, J=7.4 Hz, 1H), 6.96 (d, J=7.4 Hz, 1H), 7.15-7.33 (m, 3H), 7.71-7.80 (brs, 1H), 13.00-13.21 (brs, 1H).

MS(+): 399 [M+H]$^+$.

MS(−): 397 [M−H]$^−$.

Examples 4-322 and 4-323

6-{1-[3-Chloro-4-(propan-2-yloxy)phenyl]-2-[(2R)-5-oxopyrrolidin-2-yl]ethyl}-3-cyclopropylpyridin-2(1H)-one One diastereomer (A) of the title compound was obtained as a white solid (71 mg, 4% (three steps)) by separating the mixture by preparative HPLC (CHIRALPAK IB (20 mm i.d.×250 mm L, Daicel Chemical Industries, LTD.), 40° C., flow rate: 10 mL/min, ethanol:hexane=30:70, 50:50 from 17 min) and concentrating the fraction eluted with a retention time of 35 minutes. The fraction separated with ethanol:hexane=15:85 and eluted with a retention time of 33 minutes was concentrated to give the other diastereomer (B) of the title compound as a white solid (34 mg, 2% (three steps)).

Diastereomer (A);
$^1$H NMR (300 MHz, CDCl$_3$) δ ppm 0.52-0.76 (m, 2H), 0.91-1.12 (m, 2H), 1.36 (d, J=6.3 Hz, 6H), 1.63-1.82 (m, 1H), 2.05-2.50 (m, 6H), 3.44-3.62 (m, 1H), 3.95 (dd, J=9.6, 5.6 Hz, 1H), 4.44-4.66 (m, 1H), 5.96 (d, J=7.3 Hz, 1H), 6.88 (d, J=8.6 Hz, 1H), 6.91 (d, J=6.9 Hz, 1H), 7.20 (d, J=8.3 Hz, 1H), 7.36 (s, 1H), 7.40 (s, 1H), 12.00-12.30 (brs, 1H).

Diastereomer (B);
$^1$H NMR (300 MHz, CDCl$_3$) δ ppm 0.50-0.79 (m, 2H), 0.95-1.17 (m, 2H), 1.37 (d, J=5.9 Hz, 6H), 1.69-1.97 (m, 1H), 2.10-2.68 (m, 6H), 3.49-3.69 (m, 1H), 3.92-4.16 (m, 1H), 4.42-4.68 (m, 1H), 5.99 (d, J=7.3 Hz, 1H), 6.88 (d, J=8.6 Hz, 1H), 6.96 (d, J=7.3 Hz, 1H), 7.14 (dd, J=8.3, 2.0 Hz, 1H), 7.33 (d, J=2.0 Hz, 1H), 7.77 (s, 1H), 12.81-13.50 (brs, 1H).

MS(+): 415 [M+H]$^+$.
MS(−): 413 [M−H]$^−$.

Examples 4-324 and 4-325

3-Chloro-6-{1-(3-chloro-4-ethylphenyl)-2-[(2R)-5-oxopyrrolidin-2-yl]ethyl}pyridin-2(1H)-one One diastereomer (A) of the title compound was obtained as a colorless amorphous (32 mg, 11% (three steps)) by separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 15 minutes. The fraction eluted with a retention time of 34 minutes was concentrated to give the other diastereomer (B) of the title compound as a colorless amorphous (20 mg, 6% (three steps)).

Diastereomer (A);
$^1$H NMR (300 MHz, CDCl$_3$) δ ppm 1.14-1.35 (m, 3H), 1.64-1.84 (m, 1H), 1.92-2.51 (m, 5H), 2.72 (q, J=7.5 Hz, 2H), 3.44-3.65 (m, 1H), 3.93-4.12 (m, 1H), 6.03 (d, J=7.5 Hz, 1H), 7.13-7.30 (m, 2H), 7.34 (s, 1H), 7.51 (d, J=7.5 Hz, 1H), 7.72 (s, 1H), 12.18-12.71 (brs, 1H).

MS(+): 379 [M+H]$^+$.
MS(−): 377 [M−H]$^−$.

Diastereomer (B);
$^1$H NMR (300 MHz, CDCl$_3$) δ ppm 1.21 (t, J=7.4 Hz, 3H), 1.80-2.05 (m, 1H), 2.05-2.57 (m, 5H), 2.71 (q, J=7.4 Hz, 2H), 3.55-3.79 (m, 1H), 3.90-4.15 (m, 1H), 6.07 (d, J=7.5 Hz, 1H), 7.10-7.25 (m, 2H), 7.30 (s, 1H), 7.53 (d, J=7.5 Hz, 1H), 7.93 (s, 1H), 12.85-13.32 (brs, 1H).

MS(+): 379 [M+H]$^+$.
MS(−): 377 [M−H]$^−$.

Examples 4-326 and 4-327

6-{1-(3-Chloro-4-methoxyphenyl)-2-[(2R)-5-oxopyrrolidin-2-yl]ethyl}-3-cyclopropylpyridin-2(1H)-one (1) A crude product of (5R)-5-[(E)-2-(3-chloro-4-methoxyphenyl)-2-(5-cyclopropyl-6-methoxypyridin-2-yl)ethenyl]pyrrolidin-2-one (323 mg) was obtained by performing substantially the same reaction as in Example 4-265(1) except for using 2-(3-chloro-4-methoxyphenyl)-5,5-dimethyl-1,3,2-dioxaborinane obtained in Reference Example 5-34.

(2) One diastereomer (A) of the title compound was obtained as a white solid (49 mg, 21% (three steps)) by performing substantially the same reaction as in Examples 4-69 and 4-70(2)(3) sequentially except for using (5R)-5-[(E)-2-(3-chloro-4-methoxyphenyl)-2-(5-cyclopropyl-6-methoxypyridin-2-yl)ethenyl]pyrrolidin-2-one (323 mg), separating the mixture by preparative HPLC (CHIRALPAK IB (20 mm i.d.×250 mm L, Daicel Chemical Industries, LTD.), 40° C., flow rate: 10 mL/min, ethanol:hexane=30:70, 60:40 from 20 min, 30:70 from 35 min) and concentrating the fraction eluted with a retention time of 19 minutes. The fraction eluted with a retention time of 41 minutes was concentrated to give the other diastereomer (B) of the title compound as a white solid (39 mg, 17% (three steps)).

Diastereomer (A);
$^1$H NMR (300 MHz, CDCl$_3$) δ ppm 0.50-0.70 (m, 2H), 0.85-1.00 (m, 2H), 1.60-1.80 (m, 1H), 2.00-2.45 (m, 6H), 3.40-3.55 (m, 1H), 3.85 (s, 3H), 3.90-4.06 (m, 1H), 6.00 (d, J=7.4 Hz, 1H), 6.85 (d, J=8.6 Hz, 1H), 6.92 (d, J=7.4 Hz, 1H), 7.21-7.31 (m, 1H), 7.38 (d, J=2.1 Hz, 1H), 7.82-7.93 (brs, 1H), 12.10-12.67 (brs, 1H).

MS(+): 387 [M+H]$^+$.
MS(−): 385 [M−H]$^−$.

Diastereomer (B);
$^1$H NMR (300 MHz, CDCl$_3$) δ ppm 0.53-0.70 (m, 2H), 0.90-1.10 (m, 2H), 1.70-1.88 (m, 1H), 2.05-2.45 (m, 6H), 3.50-3.65 (m, 1H), 3.87 (s, 3H), 3.99-4.12 (m, 1H), 6.00 (d, J=6.8 Hz, 1H), 6.86 (d, J=8.3 Hz, 1H), 6.95 (d, J=7.4 Hz, 1H), 7.19 (dd, J=8.5, 2.5 Hz, 1H), 7.34 (d, J=2.1 Hz, 1H), 7.85-8.00 (brs, 1H), 12.90-13.45 (brs, 1H).

MS(+): 387 [M+H]$^+$.
MS(−): 385 [M−H]$^−$.

The compounds of Examples 4-328 to 4-353 were synthesized by performing substantially the same reaction as in Examples 4-326 and 4-327 except for using, in place of 2-(3-chloro-4-methoxyphenyl)-5,5-dimethyl-1,3,2-dioxaborinane, corresponding boronic acids or boronate esters (4-ethoxyphenylboronic acid, 5,5-dimethyl-2-[3-methyl-4-(trifluoromethyl)phenyl]-1,3,2-dioxaborinane (Reference Example 5-11), 2-fluoro-4-(trifluoromethyl)phenylboronic acid, 4-chloro-2-fluorophenylboronic acid, 2-(3-chloro-4-ethylphenyl)-5,5-dimethyl-1,3,2-dioxaborinane (Reference Example 5-17), 2-[4-(3-methoxypropyl)phenyl]-5,5-dimethyl-1,3,2-dioxaborinane (Reference Example 5-28), 2-[4-(difluoromethyl)phenyl]-4,4,5,5-tetramethyl-1,3,2-dioxaborolane (Reference Example 5-29), 3-chloro-4-(cyclopropylsulfonyl)phenylboronic acid (Example 4-289(1)), 2-[3-chloro-4-(cyclopropyloxy)phenyl]-5,5-dimethyl-1,3,2-dioxaborinane (Reference Example 5-14), 5-chloro-2-fluoro-4-methoxyphenylboronic acid, 4-isopropoxyphenylboronic acid, 3-fluoro-4-isopropoxyphenylboronic acid and 4-propoxyphenylboronic acid), respectively.

Examples 4-328 and 4-329

3-Cyclopropyl-6-{1-(4-ethoxyphenyl)-2-[(2R)-5-oxopyrrolidin-2-yl]ethyl}pyridin-2(1H)-one One diastereomer (A) of the title compound was obtained as a colorless amorphous (25 mg, 16% (three steps)) by separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 16 minutes. The fraction eluted with a retention time of 36 minutes was concentrated to give the other diastereomer (B) of the title compound as a colorless amorphous (22 mg, 13% (three steps)).

Diastereomer (A);
$^1$H NMR (300 MHz, CDCl$_3$) δ ppm 0.47-0.70 (m, 2H), 0.80-1.02 (m, 2H), 1.39 (t, J=6.8 Hz, 3H), 1.58-1.82 (m, 1H), 1.90-2.45 (m, 6H), 3.38-3.59 (m, 1H), 3.99 (q, J=6.8 Hz, 2H), 3.90-4.05 (m, 1H), 5.95 (d, J=7.1 Hz, 1H), 6.83 (d, J=9.2 Hz, 2H), 6.90 (d, J=7.4 Hz, 1H), 7.24 (d, J=8.0 Hz, 2H), 7.46 (s, 1H), 11.80-12.25 (brs, 1H).
MS(+): 367 [M+H]$^+$.
MS(−): 365 [M−H]$^−$.

Diastereomer (B);
$^1$H NMR (300 MHz, CDCl$_3$) δ ppm 0.42-0.68 (m, 2H), 0.80-1.07 (m, 2H), 1.40 (t, J=7.0 Hz, 3H), 1.65-1.97 (m, 1H), 2.05-2.42 (m, 6H), 3.45-3.70 (m, 1H), 4.00 (q, J=7.0 Hz, 2H), 3.85-4.12 (m, 1H), 5.97 (d, J=7.0 Hz, 1H), 6.83 (d, J=7.4 Hz, 2H), 6.93 (d, J=8.6 Hz, 1H), 7.22 (d, J=8.6 Hz, 2H), 7.71 (s, 1H), 12.81-13.29 (brs, 1H).
MS(+): 367 [M+H]$^+$.
MS(−): 365 [M−H]$^−$.

Examples 4-330 and 4-331

3-Cyclopropyl-6-{1-[3-methyl-4-(trifluoromethyl)phenyl]-2-[(2R)-5-oxopyrrolidin-2-yl]ethyl}pyridin-2(1H)-one One diastereomer (A) of the title compound was obtained as a colorless amorphous (38 mg, 11% (three steps)) by separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 12 minutes. The fraction eluted with a retention time of 33 minutes was concentrated to give the other diastereomer (B) of the title compound as a colorless amorphous (38 mg, 11% (three steps)).

Diastereomer (A);
$^1$H NMR (300 MHz, CDCl$_3$) δ ppm 0.52-0.78 (m, 2H), 0.85-1.08 (m, 2H), 1.60-2.60 (m, 7H), 2.44 (s, 3H), 3.40-3.60 (m, 1H), 4.00-4.20 (m, 1H), 5.99 (d, J=7.4 Hz, 1H), 6.92 (d, J=7.1 Hz, 1H), 7.29 (s, 1H), 7.30 (d, J=6.6 Hz, 1H), 7.27-7.58 (brs, 1H), 7.54 (d, J=8.3 Hz, 1H), 11.95-12.74 (brs, 1H).
MS(+): 405 [M+H]$^+$.
MS(−): 403 [M−H]$^−$.

Diastereomer (B);
$^1$H NMR (300 MHz, CDCl$_3$) δ ppm 0.50-0.70 (m, 2H), 0.90-1.10 (m, 2H), 1.68-1.19 (m, 1H), 2.10-2.48 (m, 6H), 2.46 (s, 3H), 3.50-3.70 (m, 1H), 4.05-4.20 (m, 1H), 6.00 (d, J=7.4 Hz, 1H), 6.97 (d, J=6.8 Hz, 1H), 7.23 (s, 1H), 7.24 (d, J=9.2 Hz, 1H), 7.56 (d, J=7.7 Hz, 1H), 7.80 (s, 1H), 11.94-13.38 (brs, 1H).
MS(+): 405 [M+H]$^+$.
MS(−): 403 [M−H]$^−$.

Examples 4-332 and 4-333

3-Cyclopropyl-6-{1-[2-fluoro-4-(trifluoromethyl)phenyl]-2-[(2R)-5-oxopyrrolidin-2-yl]ethyl}pyridin-2(1H)-one One diastereomer (A) of the title compound was obtained as a white solid (27 mg, 9% (three steps)) by separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 12 minutes. The fraction eluted with a retention time of 30 minutes was concentrated to give the other diastereomer (B) of the title compound as a white solid (18 mg, 6% (three steps)).

Diastereomer (A);
$^1$H NMR (300 MHz, CDCl$_3$) δ ppm 0.57-0.68 (m, 2H), 0.90-1.00 (m, 2H), 1.70-1.85 (m, 1H), 2.00-2.15 (m, 1H), 2.15-2.40 (m, 4H), 2.40-2.57 (m, 1H), 3.50-3.60 (m, 1H), 4.32-4.42 (m, 1H), 6.03 (d, J=7.2 Hz, 1H), 6.92 (d, J=7.2 Hz, 1H), 6.99-7.10 (brs, 1H), 7.30 (d, J=10.5 Hz, 1H), 7.39 (d, J=8.1 Hz, 1H), 7.65 (dd, J=7.7, 7.7 Hz, 1H), 12.40-12.85 (brs, 1H).
MS(+): 409 [M+H]$^+$.
MS(−): 407 [M−H]$^−$.

Diastereomer (B);
$^1$H NMR (300 MHz, CDCl$_3$) δ ppm 0.50-0.70 (m, 2H), 0.90-1.10 (m, 2H), 1.70-1.90 (m, 1H), 2.10-2.50 (m, 6H), 3.50-3.70 (m, 1H), 4.35-4.50 (m, 1H), 6.02 (d, J=6.0 Hz, 1H), 6.95 (d, J=6.0 Hz, 1H), 7.29 (d, J=12.0 Hz, 1H), 7.43 (d, J=9.0 Hz, 1H), 7.62 (dd, J=7.5, 7.5 Hz, 1H), 8.15-8.25 (brs, 1H), 13.15-13.50 (brs, 1H).

Examples 4-334 and 4-335

6-{1-(4-Chloro-2-fluorophenyl)-2-[(2R)-5-oxopyrrolidin-2-yl]ethyl}-3-cyclopropylpyridin-2(1H)-one One diastereomer (A) of the title compound was obtained as a white solid (44 mg, 22% (three steps)) by separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 15 minutes. The fraction eluted with a retention time of 36 minutes was concentrated to give the other diastereomer (B) of the title compound as a white solid (30 mg, 15% (three steps)).

Diastereomer (A);
$^1$H NMR (300 MHz, CDCl$_3$) δ ppm 0.50-0.70 (m, 2H), 0.80-1.05 (m, 2H), 1.65-1.85 (m, 1H), 2.00-2.60 (m, 6H), 3.40-3.60 (m, 1H), 4.20-4.40 (m, 1H), 6.00 (d, J=7.1 Hz, 1H), 6.91 (d, J=7.1 Hz, 1H), 6.98-7.15 (m, 2H), 7.28-7.40 (brs, 1H), 7.40-7.50 (m, 1H), 12.30-13.00 (brs, 1H).
MS(+): 375 [M+H]$^+$.
MS(−): 373 [M−H]$^−$.

Diastereomer (B);
$^1$H NMR (300 MHz, CDCl$_3$) δ ppm 0.50-0.70 (m, 2H), 0.80-1.10 (m, 2H), 1.65-1.85 (m, 1H), 2.05-2.50 (m, 6H), 3.50-3.67 (m, 1H), 4.25-4.42 (m, 1H), 5.98 (d, J=7.4 Hz, 1H), 6.93 (d, J=6.8 Hz, 1H), 7.05 (dd, J=9.8, 2.1 Hz, 1H), 7.09-7.19 (m, 1H), 7.30-7.47 (m, 1H), 8.05-8.20 (brs, 1H), 12.95-13.60 (brs, 1H).
MS(+): 375 [M+H]$^+$.
MS(−): 373 [M−H]$^−$.

Examples 4-336 and 4-337

6-{1-(3-Chloro-4-ethylphenyl)-2-[(2R)-5-oxopyrrolidin-2-yl]ethyl}-3-cyclopropylpyridin-2(1H)-one One diastereomer (A) of the title compound was obtained as a colorless solid (41 mg, 11% (three steps)) by separating the mixture by preparative HPLC (CHIRALPAK IB (20 mm i.d.×250 mm L, Daicel Chemical Industries, LTD.), 40° C., flow rate: 10 mL/min, ethanol:hexane=40:60) and concentrating the fraction eluted with a retention time of 11 minutes. The fraction eluted with a retention time of 34 minutes was concentrated to give the other diastereomer (B) of the title compound as a colorless solid (18 mg, 5% (three steps)).

Diastereomer (A);
$^1$H NMR (300 MHz, CDCl$_3$) δ ppm 0.59-0.63 (m, 2H), 0.91-0.97 (m, 2H), 1.20 (t, J=7.4 Hz, 3H), 1.69-1.77 (m, 1H), 2.07-2.37 (m, 6H), 2.71 (q, J=7.6 Hz, 2H), 3.48-3.54 (m, 1H), 3.96-4.01 (m, 1H), 5.98 (d, J=7.4 Hz, 1H), 6.92 (d, J=6.8 Hz, 1H), 7.16-7.23 (m, 2H), 7.35 (d, J=1.5 Hz, 1H), 7.40-7.48 (brs, 1H), 12.05-12.35 (brs, 1H).
MS(+): 385 [M+H]$^+$.
MS(−): 383 [M−H]$^-$.

Diastereomer (B);
$^1$H NMR (300 MHz, CDCl$_3$) δ ppm 0.57-0.63 (m, 2H), 0.99-1.05 (m, 2H), 1.21 (t, J=7.6 Hz, 3H), 1.75-1.81 (m, 1H), 2.17-2.39 (m, 6H), 2.72 (q, J=7.6 Hz, 2H), 3.56-3.61 (m, 1H), 4.02-4.06 (m, 1H), 6.00 (d, J=7.4 Hz, 1H), 6.96 (d, J=7.4 Hz, 1H), 7.16-7.30 (m, 3H), 7.60-7.70 (brs, 1H), 12.85-13.20 (brs, 1H).
MS(+): 385 [M+H]$^+$.
MS(−): 383 [M−H]$^-$.

Examples 4-338 and 4-339

3-Chloro-6-{1-[4-(3-methoxypropyl)phenyl]-2-[(2R)-5-oxopyrrolidin-2-yl]ethyl}pyridin-2(1H)-one One diastereomer (A) of the title compound was obtained as a white solid (6 mg, 11% (three steps)) by separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 19 minutes. The fraction eluted with a retention time of 33 minutes was concentrated to give the other diastereomer (B) of the title compound as a white solid (7 mg, 12% (three steps)).

Diastereomer (A);
$^1$H NMR (300 MHz, CDCl$_3$) δ ppm 1.63-1.80 (m, 1H), 1.80-1.93 (m, 2H), 2.11-2.50 (m, 5H), 2.75 (t, J=7.4 Hz, 2H), 3.34 (s, 3H), 3.38 (t, J=6.1 Hz, 2H), 3.44-3.58 (m, 1H), 3.94 (dd, J=9.4, 5.3 Hz, 1H), 6.03 (d, J=7.8 Hz, 1H), 7.03 (s, 1H), 7.14-7.25 (m, 4H), 7.50 (d, J=7.4 Hz, 1H), 11.28-11.60 (brs, 1H).
MS(+): 389 [M+H]$^+$.
MS(−): 387 [M−H]$^-$.

Diastereomer (B);
$^1$H NMR (300 MHz, CDCl$_3$) δ ppm 1.77-1.98 (m, 3H), 2.13-2.50 (m, 5H), 2.66 (t, J=7.4 Hz, 2H), 3.34 (s, 3H), 3.37 (t, J=6.1 Hz, 2H), 3.60-3.75 (m, 1H), 4.02 (dd, J=7.0, 7.0 Hz, 1H), 6.07 (d, J=7.4 Hz, 1H), 7.13-7.24 (m, 4H), 7.32 (s, 1H), 7.52 (d, J=7.8 Hz, 1H), 12.32-12.57 (brs, 1H).
MS(+): 389 [M+H]$^+$.
MS(−): 387 [M−H]$^-$.

Examples 4-340 and 4-341

3-Cyclopropyl-6-[1-[4-(difluoromethyl)phenyl]-2-(5-oxopyrrolidin-2-yl)ethyl]pyridin-2(1H)-one One diastereomer (A) of the title compound was obtained as a white solid (32 mg, 11% (three steps)) by separating the mixture by preparative HPLC (CHIRALPAK IB (20 mm i.d.×250 mm L, Daicel Chemical Industries, LTD.), 40° C., flow rate: 10 mL/min, ethanol:hexane=40:60) and concentrating the fraction eluted with a retention time of 15 minutes. The fraction eluted with a retention time of 30 minutes was concentrated to give the other diastereomer (B) of the title compound as a white solid (24 mg, 7% (three steps)).

Diastereomer (A);
$^1$H NMR (300 MHz, CDCl$_3$) δ ppm 0.60-0.70 (m, 2H), 0.92-1.00 (m, 2H), 1.65-1.85 (m, 1H), 2.05-2.48 (m, 6H), 3.43-3.56 (m, 1H), 4.06-4.17 (m, 1H), 5.99 (d, J=7.4 Hz, 1H), 6.60 (t, J=56.4 Hz, 1H), 6.92 (d, J=7.4 Hz, 1H), 7.40-7.55 (m, 5H), 12.20-12.60 (brs, 1H).
MS(+): 373 [M+H]$^+$.
MS(−): 371 [M−H]$^-$.

Diastereomer (B);
$^1$H NMR (300 MHz, CDCl$_3$) δ ppm 0.59-0.61 (m, 2H), 0.99-1.01 (m, 2H), 1.75-1.80 (m, 2H), 2.14-2.40 (m, 5H), 3.54-3.67 (m, 1H), 4.12-4.24 (m, 1H), 6.00 (d, J=7.4 Hz, 1H), 6.61 (d, J=56.4 Hz, 1H), 6.95 (d, J=7.4 Hz, 1H), 7.42-7.46 (m, 4H), 7.88-7.98 (brs, 1H), 13.10-13.50 (brs, 1H).
MS(+): 373 [M+H]$^+$.
MS(−): 371 [M−H]$^-$.

Examples 4-342 and 4-343

6-{1-[3-Chloro-4-(cyclopropylsulfonyl)phenyl]-2-[(2R)-5-oxopyrrolidin-2-yl]ethyl}-3-cyclopropylpyridin-2(1H)-one One diastereomer (A) of the title compound was obtained as a white solid (17 mg, 7% (three steps)) by separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 45 minutes. The fraction eluted with a retention time of 84 minutes was concentrated to give the other diastereomer (B) of the title compound as a white solid (19 mg, 8% (three steps)).

Diastereomer (A);
$^1$H NMR (300 MHz, CDCl$_3$) δ ppm 0.57-0.74 (m, 2H), 0.92-1.18 (m, 4H), 1.23-1.42 (m, 2H), 1.49-1.87 (m, 1H), 2.00-2.48 (m, 6H), 2.92-3.07 (m, 1H), 3.42-3.56 (m, 1H), 4.11 (dd, J=8.9, 6.3 Hz, 1H), 6.08 (d, J=7.3 Hz, 1H), 6.98 (d, J=7.3 Hz, 1H), 7.31-7.44 (m, 1H), 7.49 (dd J=7.9, 1.3 Hz, 1H), 7.66 (d, J=1.3 Hz, 1H), 7.96 (d, J=7.9 Hz, 1H), 12.13-12.71 (brs, 1H).
MS(+): 461 [M+H]$^+$.
MS(−): 459 [M−H]$^-$.

Diastereomer (B);
$^1$H NMR (300 MHz, CDCl$_3$) δ ppm 0.55-0.70 (m, 2H), 0.96-1.16 (m, 4H), 1.29-1.39 (m, 2H), 1.72-1.88 (m, 1H), 2.07-2.49 (m, 6H), 2.94-3.07 (m, 1H), 3.53-3.67 (m, 1H), 4.18 (dd, J=10.6, 4.3 Hz, 1H), 6.05 (d, J=7.3 Hz, 1H), 7.00 (d, J=6.9 Hz, 1H), 7.42 (d, J=8.3 Hz, 1H), 7.55 (s, 1H), 7.86 (s, 1H), 7.97 (d, J=8.3 Hz, 1H), 13.04-13.48 (brs, 1H).
MS(+): 461 [M+H]$^+$.
MS(−): 459 [M−H]$^-$.

Examples 4-344 and 4-345

6-{1-[3-Chloro-4-(cyclopropyloxy)phenyl]-2-[(2R)-5-oxopyrrolidin-2-yl]ethyl}-3-cyclopropylpyridin-2(1H)-one One diastereomer (A) of the title compound was obtained as a white solid (45 mg, 24% (three steps)) by separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 18 minutes. The fraction eluted with a retention time of 58 minutes was concentrated to give the other diastereomer (B) of the title compound as a white solid (44 mg, 23% (three steps)).
Diastereomer (A);
$^1$H NMR (300 MHz, CDCl$_3$) δ ppm 0.45-0.70 (m, 2H), 0.70-0.88 (m, 4H), 0.88-1.05 (m, 2H), 1.60-1.83 (m, 1H), 2.00-2.70 (m, 6H), 3.35-3.60 (m, 1H), 3.65-3.83 (m, 1H), 3.90-4.10 (m, 1H), 6.00 (d, J=7.4 Hz, 1H), 6.92 (d, J=7.4 Hz, 1H), 7.10-7.31 (m, 2H), 7.36 (d, J=2.1 Hz, 1H), 7.65-7.90 (brs, 1H), 12.00-12.63 (brs, 1H).
MS(+): 413 [M+H]$^+$.
MS(−): 411 [M−H]$^−$.
Diastereomer (B);
$^1$H NMR (300 MHz, CDCl$_3$) δ ppm 0.50-0.69 (m, 2H), 0.69-0.90 (m, 4H), 0.90-1.10 (m, 2H), 1.68-1.88 (m, 1H), 2.00-2.45 (m, 6H), 3.50-3.65 (m, 1H), 3.70-3.82 (m, 1H), 3.95-4.12 (m, 1H), 6.02 (d, J=7.4 Hz, 1H), 6.95 (d, J=7.1 Hz, 1H), 7.10-7.25 (m, 2H), 7.32 (d, J=1.8 Hz, 1H), 7.90-8.05 (brs, 1H), 12.65-13.50 (brs, 1H).
MS(+): 413 [M+H]$^+$.
MS(−): 411 [M−H]$^−$.

Examples 4-346 and 4-347

6-{1-(5-Chloro-2-fluoro-4-methoxyphenyl)-2-[(2R)-5-oxopyrrolidin-2-yl]ethyl}-3-cyclopropylpyridin-2(1H)-one One diastereomer (A) of the title compound was obtained as a white solid (31 mg, 13% (three steps)) by separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 17 minutes. The fraction eluted with a retention time of 51 minutes was concentrated to give the other diastereomer (B) of the title compound as a white solid (18 mg, 8% (three steps)).
Diastereomer (A);
$^1$H NMR (300 MHz, CDCl$_3$) δ ppm 0.59-0.63 (m, 2H), 0.93-0.97 (m, 2H), 1.72-1.79 (m, 1H), 2.04-2.42 (m, 6H), 3.51-3.53 (m, 1H), 3.86 (s, 3H), 4.15-4.28 (m, 1H), 5.99 (d, J=7.4 Hz, 1H), 6.65 (d, J=11.5 Hz, 1H), 6.91 (d, J=7.0 Hz, 1H), 7.00-7.25 (brs, 1H), 7.46 (d, J=8.6 Hz, 1H), 12.20-12.60 (brs, 1H).
MS(+): 405 [M+H]$^+$.
MS(−): 403 [M−H]$^−$.
Diastereomer (B);
$^1$H NMR (300 MHz, CDCl$_3$) δ ppm 0.50-0.65 (m, 2H), 0.95-1.10 (m, 2H), 1.80-1.90 (m, 1H), 2.05-2.40 (m, 6H), 3.50-3.70 (m, 1H), 3.86 (s, 3H), 4.20-4.35 (m, 1H), 5.98 (d, J=7.2 Hz, 1H), 6.64 (d, J=11.4 Hz, 1H), 6.94 (d, J=7.5 Hz, 1H), 7.42 (d, J=7.8 Hz, 1H), 7.90-8.05 (brs, 1H), 13.10-13.35 (brs, 1H).
MS(+): 405 [M+H]$^+$.
MS(−): 403 [M−H]$^−$.

Examples 4-348 and 4-349

3-Cyclopropyl-6-{2-[(2R)-5-oxopyrrolidin-2-yl]-1-[4-(propan-2-yloxy)phenyl]ethyl}pyridin-2(1H)-one One diastereomer (A) of the title compound was obtained as a colorless amorphous (36 mg, 17% (three steps)) by separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 18 minutes. The fraction eluted with a retention time of 31 minutes was concentrated to give the other diastereomer (B) of the title compound as a colorless amorphous (23 mg, 11% (three steps)).
Diastereomer (A);
$^1$H NMR (300 MHz, CDCl$_3$) δ ppm 0.52-0.65 (m, 2H), 0.88-1.00 (m, 2H), 1.31 (d, J=6.3 Hz, 6H), 1.62-1.80 (m, 1H), 2.08-2.42 (m, 6H), 3.42-3.56 (m, 1H), 3.94-4.05 (m, 1H), 4.50 (septet, 1H), 5.97 (d, J=7.2 Hz, 1H), 6.75-6.85 (m, 2H), 6.91 (d, J=6.9 Hz, 1H), 7.25 (d, J=9.3 Hz, 2H), 7.60-7.85 (m, 1H), 11.90-12.40 (brs, 1H).
MS(+): 381 [M+H]$^+$.
MS(−): 379 [M−H]$^−$.
Diastereomer (B);
$^1$H NMR (300 MHz, CDCl$_3$) δ ppm 0.47-0.75 (m, 2H), 0.85-1.10 (m, 2H), 1.34 (d, J=5.7 Hz, 6H), 1.58-1.85 (m, 1H), 1.85-2.50 (m, 6H), 3.40-3.64 (m, 1H), 3.85-4.10 (m, 1H), 4.92 (septet, J=5.9 Hz, 1H), 5.98 (d, J=7.2 Hz, 1H), 6.84-7.00 (m, 2H), 7.06 (d, J=8.7 Hz, 1H), 7.11 (dd, J=11.9, 2.0 Hz, 1H), 7.57 (s, 1H), 11.90-12.48 (brs, 1H).
MS(+): 381 [M+H]$^+$.

Examples 4-350 and 4-351

3-Cyclopropyl-6-{1-[3-fluoro-4-(propan-2-yloxy)phenyl]-2-[(2R)-5-oxopyrrolidin-2-yl]ethyl}pyridin-2(1H)-one One diastereomer (A) of the title compound was obtained as a colorless amorphous (24 mg, 7% (three steps)) by separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 15 minutes. The fraction eluted with a retention time of 45 minutes was concentrated to give the other diastereomer (B) of the title compound as a colorless amorphous (17 mg, 5% (three steps)).
Diastereomer (A);
$^1$H NMR (300 MHz, CDCl$_3$) δ ppm 0.47-0.75 (m, 2H), 0.85-1.10 (m, 2H), 1.34 (d, J=5.7 Hz, 6H), 1.58-1.85 (m, 1H), 1.85-2.50 (m, 6H), 3.40-3.64 (m, 1H), 3.85-4.10 (m, 1H), 4.92 (septet, J=5.9 Hz, 1H), 5.98 (d, J=7.2 Hz, 1H), 6.84-7.00 (m, 2H), 7.06 (d, J=8.7 Hz, 1H), 7.11 (dd, J=11.9, 2.0 Hz, 1H), 7.57 (s, 1H), 11.90-12.48 (brs, 1H).
MS(+): 399 [M+H]$^+$.
MS(−): 397 [M−H]$^−$.
Diastereomer (B);
$^1$H NMR (300 MHz, CDCl$_3$) δ ppm 0.50-0.75 (m, 2H), 0.90-1.15 (m, 2H), 1.34 (d, J=6.0 Hz, 6H), 1.65-2.00 (m, 1H), 2.00-2.50 (m, 6H), 3.40-3.75 (m, 1H), 3.96-4.20 (m, 1H), 4.40-4.65 (m, 1H), 6.01 (d, J=7.2 Hz, 1H), 6.80-7.22 (m, 4H), 7.88 (s, 1H), 12.96-13.46 (brs, 1H).
MS(+): 399 [M+H]$^+$.
MS(−): 397 [M−H]$^−$.

Examples 4-352 and 4-353

3-Cyclopropyl-6-[2-[(2R)-5-oxopyrrolidin-2-yl]-1-(4-propoxyphenyl)ethyl]pyridin-2(1H)-one One diastereomer (A) of the title compound was obtained as a white amorphous (31 mg, 20% (three steps)) by separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 14 minutes. The fraction eluted with a retention time of 33 minutes was concentrated to give the other diastereomer (B) of the title compound as a white amorphous (38 mg, 25% (three steps)).

Diastereomer (A);
$^1$H NMR (300 MHz, CDCl$_3$) δ ppm 0.50-0.72 (m, 2H), 0.85-1.12 (m, 5H), 1.62-1.90 (m, 3H), 2.02-2.44 (m, 6H), 3.40-3.59 (m, 1H), 3.80-4.07 (m, 3H), 5.96 (d, J=7.1 Hz, 1H), 6.86 (d, J=8.6 Hz, 2H), 6.91 (d, J=7.1 Hz, 1H), 7.25 (d, J=8.9 Hz, 2H), 7.30-7.43 (m, 1H), 11.17-12.55 (brs, 1H).
MS(+): 381 [M+H]$^+$.
MS(−): 379 [M−H]$^−$.

Diastereomer (B);
$^1$H NMR (300 MHz, CDCl$_3$) δ ppm 0.50-0.70 (m, 2H), 0.90-1.10 (m, 5H), 1.69-1.90 (m, 3H), 2.19-2.42 (m, 6H), 3.50-3.69 (m, 1H), 3.90 (t, J=6.8 Hz, 2H), 4.00-4.14 (m, 1H), 5.99 (d, J=7.1 Hz, 1H), 6.86 (d, J=8.6 Hz, 2H), 6.94 (d, J=6.8 Hz, 1H), 7.23 (d, J=8.6 Hz, 2H), 7.72 (s, 1H), 12.10-13.77 (brs, 1H).
MS(+): 381 [M+H]$^+$.
MS(−): 379 [M−H]$^−$.

Examples 4-354 and 4-355

3-Cyclopropyl-6-{1-(4-ethoxy-3-fluorophenyl)-2-[(2R)-5-oxopyrrolidin-2-yl]ethyl}pyridin-2(1H)-one (1) (5R)-5-[(E)-2-(5-Cyclopropyl-6-methoxypyridin-2-yl)-2-(4-ethoxy-3-fluorophenyl)ethenyl]pyrrolidin-2-one was obtained as a white solid (289 mg, 98%) except for performing substantially the same reaction as in Example 4-265(1) except for using (4-ethoxy-3-fluoro)phenylboronic acid.

(2) A crude product of (5R)-5-[2-(5-cyclopropyl-6-methoxypyridin-2-yl)-2-(4-ethoxy-3-fluorophenyl)ethyl]pyrrolidin-2-one (222 mg) was obtained by performing substantially the same reaction as in Examples 4-69 and 4-70(2) except for using (5R)-5-[(E)-2-(5-cyclopropyl-6-methoxypyridin-2-yl)-2-(4-ethoxy-3-fluorophenyl)ethenyl]pyrrolidin-2-one (221 mg).

(3) Chlorotrimethylsilane (0.17 mL) and potassium iodide (370 mg) were added to a solution of (5R)-5-[2-(5-cyclopropyl-6-methoxypyridin-2-yl)-2-(4-ethoxy-3-fluorophenyl)ethyl]pyrrolidin-2-one (222 mg) in acetonitrile (4.4 mL) at room temperature, and then the mixture was stirred at 50° C. for one hour. Water was added to the reaction solution, followed by extraction with ethyl acetate. The organic layer was washed with water and brine, dried over anhydrous magnesium sulfate and filtered, after which the solvent was evaporated under reduced pressure. One diastereomer (A) of the title compound was obtained as a white solid (71 mg, 33% (two steps)) by separating the residue by preparative HPLC (CHIRALPAK IB (20 mm i.d.×250 mm L, Daicel Chemical Industries, LTD.), 40° C., flow rate: 10 mL/min, ethanol: hexane=40:60) and concentrating the fraction eluted with a retention time of 13 minutes. The fraction eluted with a retention time of 28 minutes was concentrated to give the other diastereomer (B) of the title compound as a white solid (71 mg, 33% (two steps)).

Diastereomer (A);
$^1$H NMR (300 MHz, CDCl$_3$) δ ppm 0.50-0.70 (m, 2H), 0.85-1.05 (m, 2H), 1.42 (t, J=6.9 Hz, 3H), 1.60-1.80 (m, 1H), 2.05-2.55 (m, 6H), 3.42-3.55 (m, 1H), 3.95-4.10 (m, 3H), 5.99 (d, J=7.2 Hz, 1H), 6.82-6.95 (m, 2H), 7.04-7.18 (m, 2H), 7.76-7.89 (m, 1H), 12.15-12.60 (brs, 1H).
MS(+): 385 [M+H]$^+$.
MS(−): 383 [M−H]$^−$.

Diastereomer (B);
$^1$H NMR (300 MHz, CDCl$_3$) δ ppm 0.56-0.66 (m, 2H), 0.90-1.05 (m, 2H), 1.43 (t, J=6.9 Hz, 3H), 1.57-1.85 (m, 1H), 2.00-2.45 (m, 6H), 3.50-3.65 (m, 1H), 4.05-4.15 (m, 3H), 6.01 (d, J=6.9 Hz, 1H), 6.85-7.15 (m, 4H), 7.87-8.00 (m, 1H), 13.15-13.40 (brs, 1H).
MS(+): 385 [M+H]$^+$.
MS(−): 383 [M−H]$^−$.

Examples 4-356 and 4-357

6-{1-[3-Chloro-4-(difluoromethoxy)phenyl]-2-[(2R)-5-oxopyrrolidin-2-yl]ethyl}-3-cyclopropylpyridin-2(1H)-one One diastereomer (A) of the title compound was obtained as a white solid (40 mg, 17% (three steps)) by performing the same reaction as in Examples 4-354 and 4-355 except for using 2-[3-chloro-4-(difluoromethoxy)phenyl]-4,4,5,5-tetramethyl-1,3,2-dioxaborolane obtained in Reference Example 5-32, separating the mixture by preparative HPLC (CHIRALPAK IB (20 mm i.d.×250 mm L, Daicel Chemical Industries, LTD.), 40° C., flow rate: 10 mL/min, ethanol: hexane=20:80, 40:60 from 30 min) and concentrating the fraction eluted with a retention time of 25 minutes. The fraction eluted with a retention time of 48 minutes was concentrated to give the other diastereomer (B) of the title compound as a white solid (13 mg, 6% (three steps)).

Diastereomer (A);
$^1$H NMR (300 MHz, CDCl$_3$) δ ppm 0.46-0.78 (m, 2H), 0.82-1.16 (m, 2H), 1.55-1.87 (m, 1H), 1.89-2.78 (m, 6H), 3.39-3.61 (m, 1H), 3.99-4.19 (m, 1H), 6.05 (d, J=7.3 Hz, 1H), 6.49 (t, J=73.3 Hz, 1H), 6.94 (d, J=7.3 Hz, 1H), 7.16 (d, J=8.6 Hz, 1H), 7.35 (dd, J=8.6, 1.7 Hz, 1H), 7.54 (d, J=1.7 Hz, 1H), 7.85-8.02 (m, 1H), 12.35-12.85 (brs, 1H).
MS(+): 423 [M+H]$^+$.
MS(−): 421 [M−H]$^−$.

Diastereomer (B);
$^1$H NMR (300 MHz, CDCl$_3$) δ ppm 0.53-0.69 (m, 2H), 0.90-1.13 (m, 2H), 1.50-1.92 (m, 1H), 2.05-2.45 (m, 6H), 3.51-3.66 (m, 1H), 4.06-4.17 (m, 1H), 6.02 (d, J=7.3 Hz, 1H), 6.51 (t, J=73.3 Hz, 1H), 6.98 (d, J=7.3 Hz, 1H), 7.16-7.25 (m, 2H), 7.44 (d, J=2.0 Hz, 1H), 7.83-8.00 (m, 1H), 13.15-13.50 (brs, 1H).
MS(+): 423 [M+H]$^+$.
MS(−): 421 [M−H]$^−$.

Example 4-358

6-{1-(4-tert-Butylphenyl)-2-[(2R)-5-oxopyrrolidin-2-yl]ethyl}-3-cyclopropylpyridin-2(1H)-one (1) tert-Butyl (2R)-2-[(Z)-2-(4-tert-butylphenyl)-2-(5-cyclopropyl-6-methoxypyridin-2-yl)ethenyl]-5-oxopyrrolidine-1-carboxylate was obtained as a crude product (126 mg) by performing substantially the same reaction as in Example 4-80(2) except for using (5R)-5-[(Z)-2-(4-tert-butylphenyl)-2-(5-cyclopropyl-6-methoxypyridin-2-yl)ethenyl]pyrrolidin-2-one obtained in Example 4-83(1) (93 mg).

(2) One diastereomer of the title compound was obtained as a white amorphous (32 mg, 34% (two steps)) by performing substantially the same reaction as in Examples 4-69 and 4-70 (2)(3) sequentially except for using tert-butyl (2R)-2-[(Z)-2-(4-tert-butylphenyl)-2-(5-cyclopropyl-6-methoxypyridin-2-yl)ethenyl]-5-oxopyrrolidine-1-carboxylate (125 mg), separating the mixture by preparative HPLC (CHIRALPAK IB (20 mm i.d.×250 mm L, Daicel Chemical Industries, LTD.), 40° C., flow rate: 10 mL/min, ethanol:hexane=10:90) and concentrating the fraction eluted with a retention time of 44 minutes.

$^1$H NMR (300 MHz, CDCl$_3$) δ ppm 0.50-0.66 (m, 2H), 0.85-1.00 (m, 2H), 1.28 (s, 9H), 1.62-1.80 (m, 1H), 2.04-2.40 (m, 6H), 3.42-3.55 (m, 1H), 3.96-4.08 (m, 1H), 5.99 (d, J=7.5 Hz, 1H), 6.91 (d, J=7.2 Hz, 1H), 7.20-7.36 (m, 4H), 7.60-7.75 (brs, 1H), 11.85-12.30 (brs, 1H).

MS(+): 379 [M+H]$^+$.

MS(−): 377 [M−H]$^-$.

The structures of Examples 4-248 to 4-358 are shown below.

[Hyo 17-1]

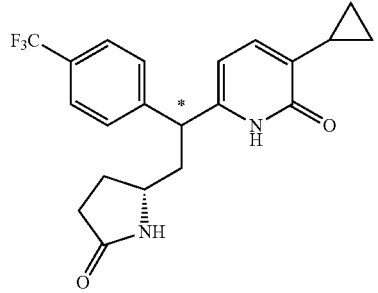

Example 4-248, 249

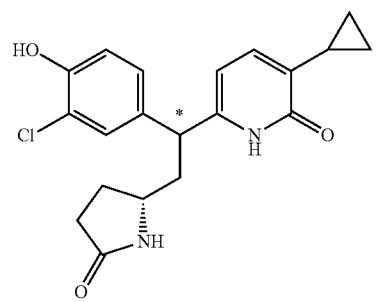

Example 4-250, 251

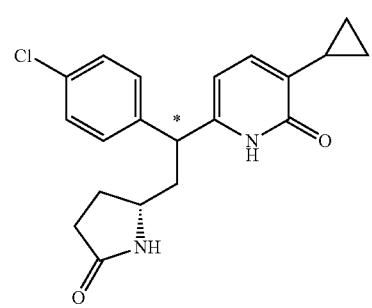

Example 4-252, 253

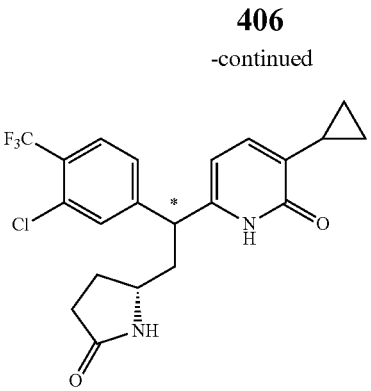

Example 4-254, 255

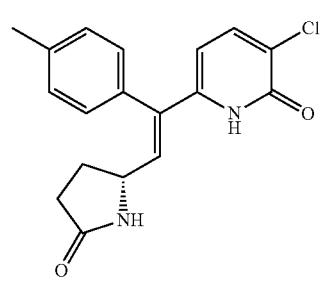

Example 4-256

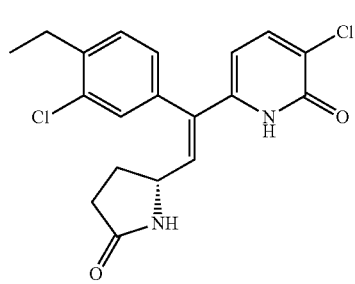

Example 4-257

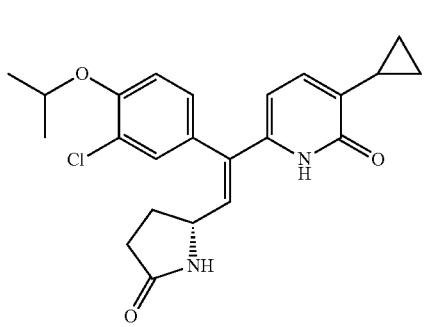

Example 4-258

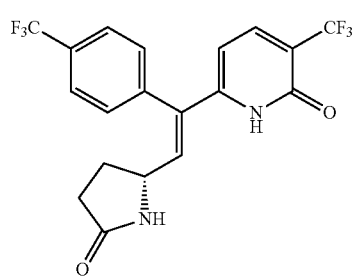

Example 4-259

Example 4-260
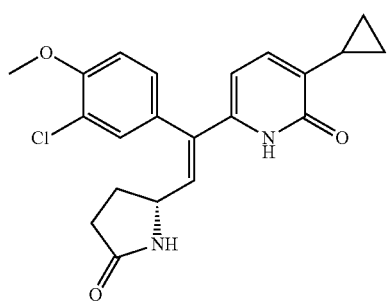
Example 4-261
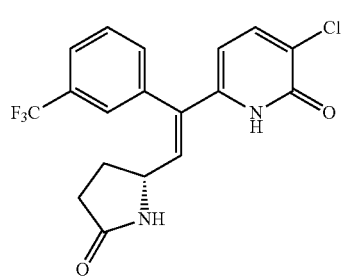
Example 4-262
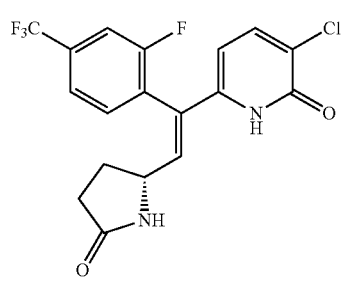
Example 4-263
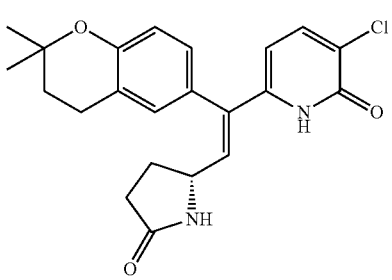
[Hyo 17-2]
Example 4-264
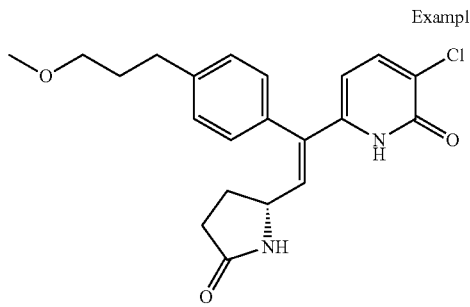
Example 4-265
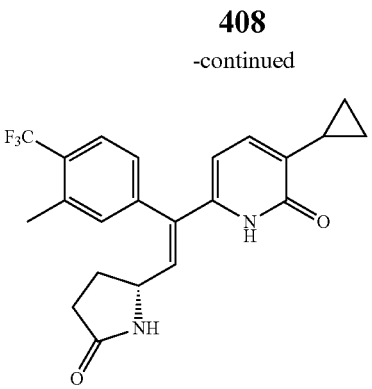
Example 4-266
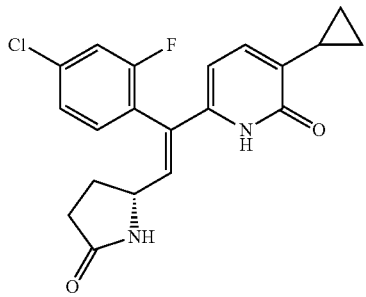
Example 4-267
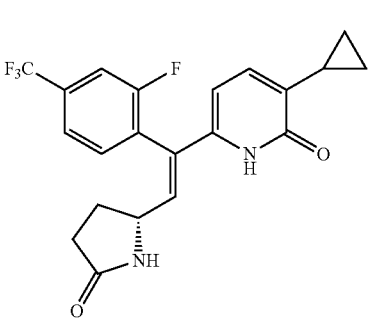
Example 4-268
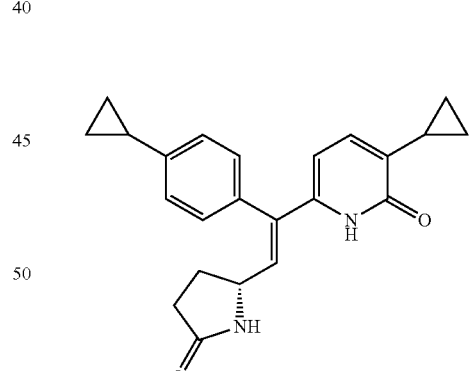
Example 4-269
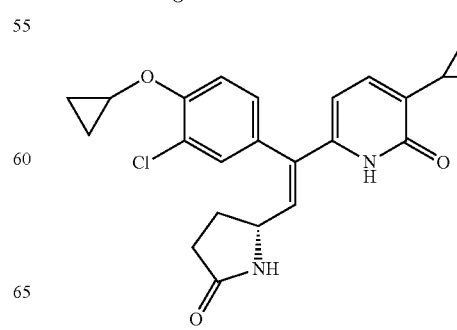

Example 4-270
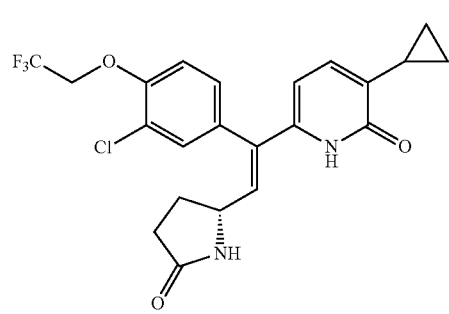
Example 4-271
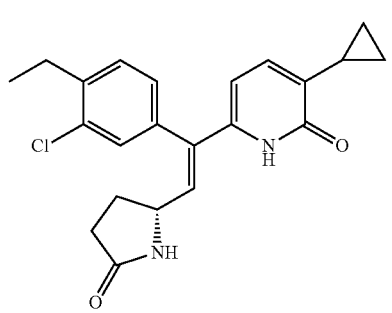
Example 4-272
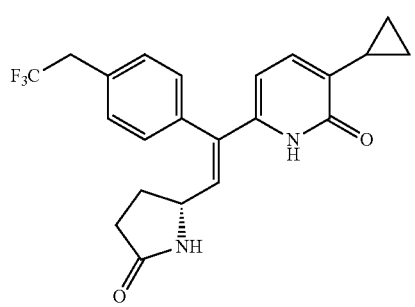
Example 4-273
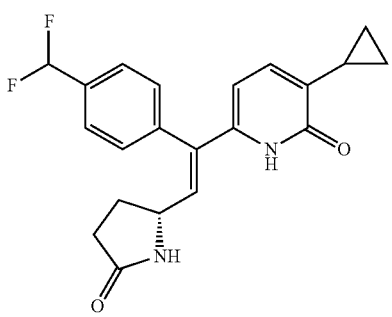
Example 4-274
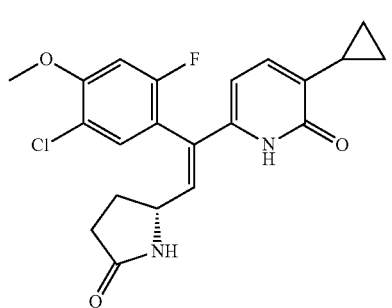
Example 4-275
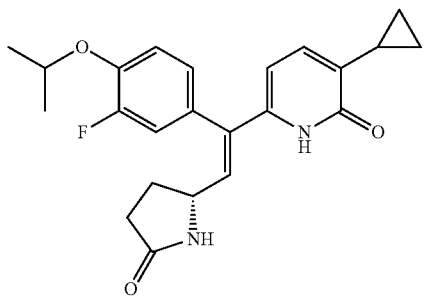
[Hyo 17-3]
Example 4-276
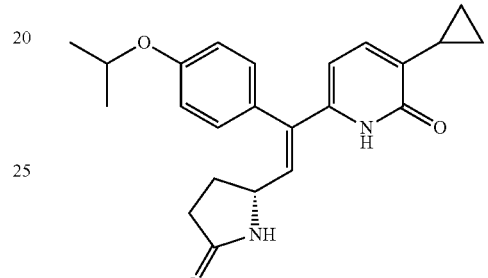
Example 4-277
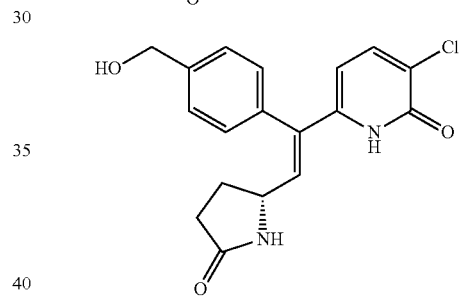
Example 4-278
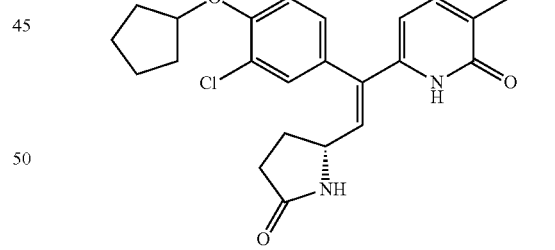
Example 4-279
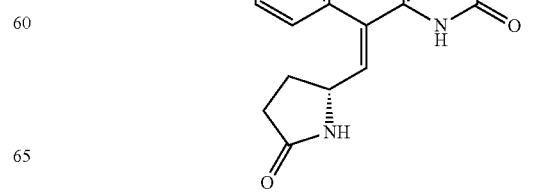

Example 4-280
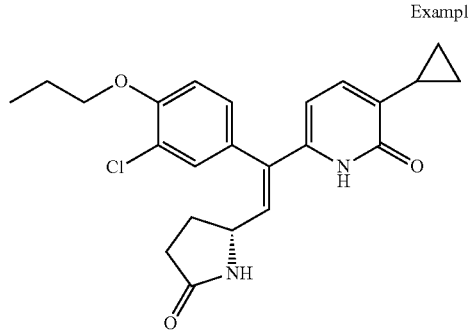
Example 4-281
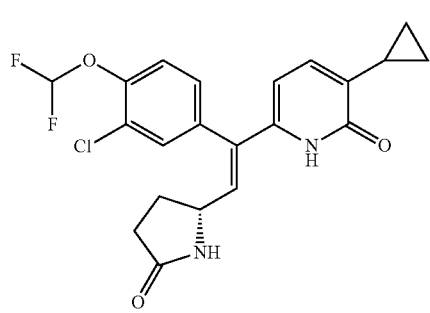
Example 4-282
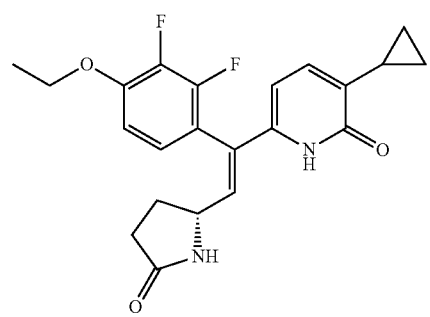
Example 4-283
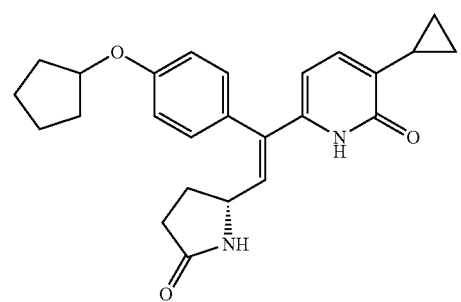
Example 4-284
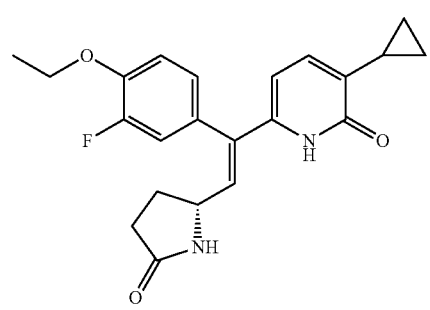
Example 4-285
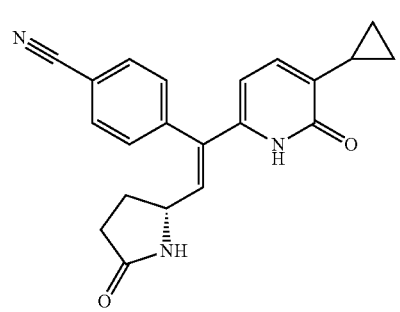
Example 4-286
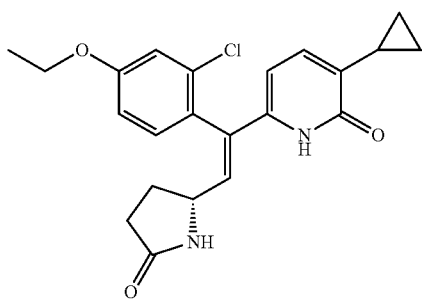
Example 4-287
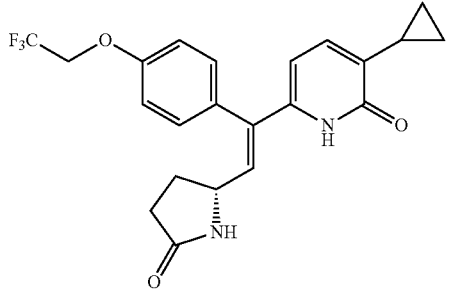
[Hyo 17-4]
Example 4-288
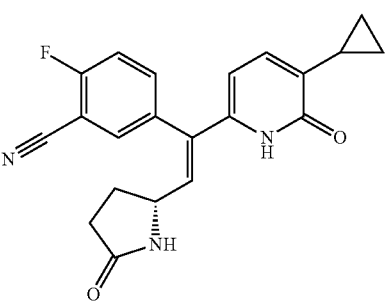
Example 4-289
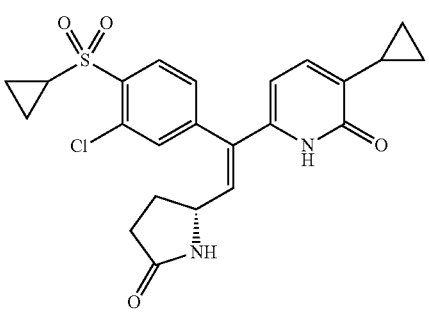

Example 4-290
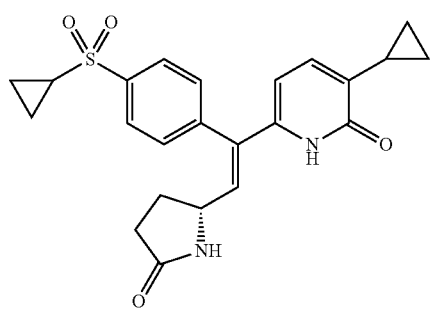
Example 4-291
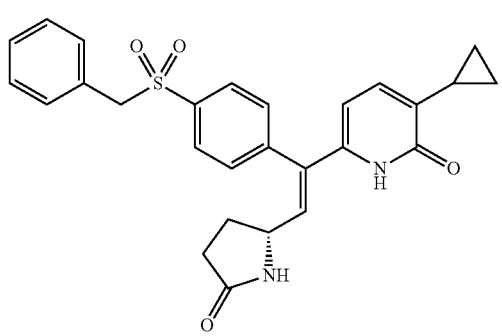
Example 4-292
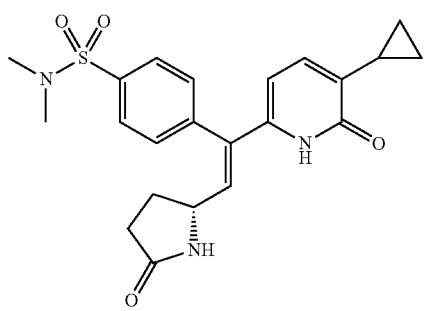
Example 4-293
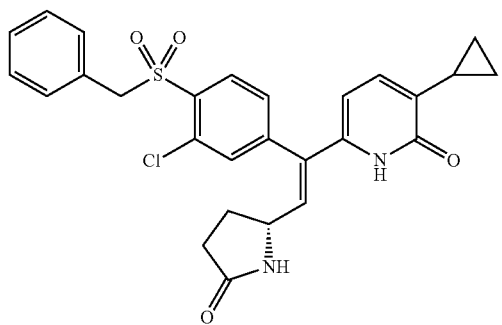
Example 4-294, 295
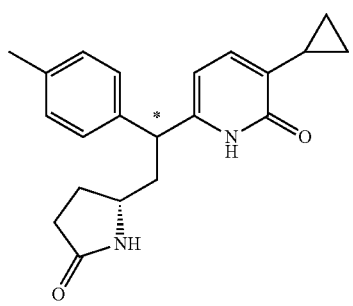
Example 4-296, 297
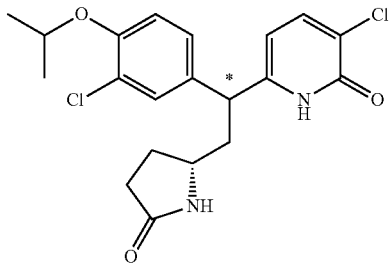
Example 4-298, 299
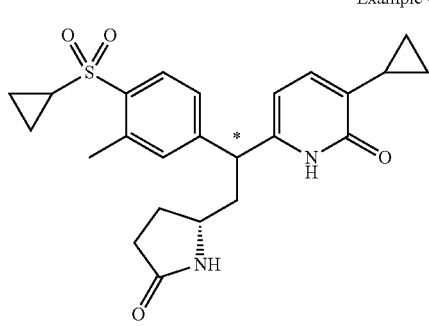
Example 4-300, 301
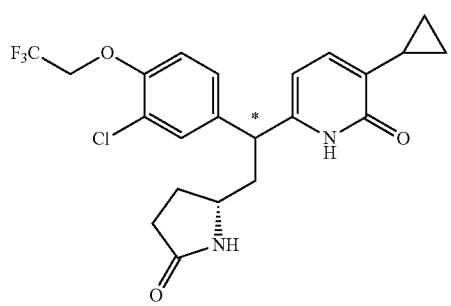
Example 4-302, 303
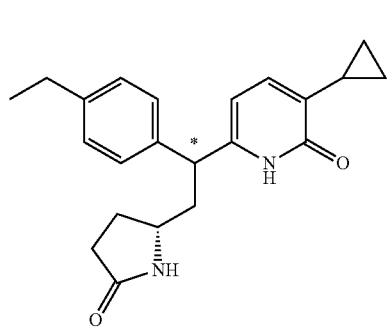
Example 4-304, 305
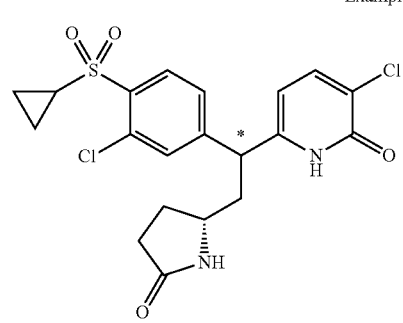

[Hyo 17-5]
Example 4-306, 307
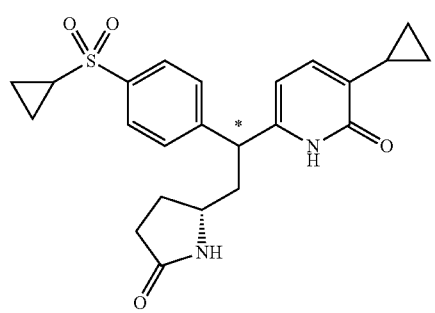
Example 4-308, 309
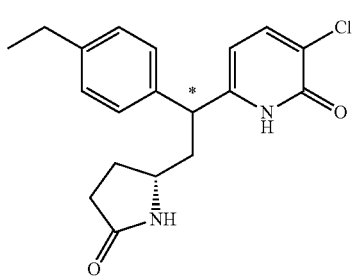
Example 4-310, 311
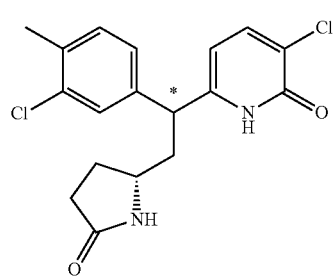
Example 4-312, 313
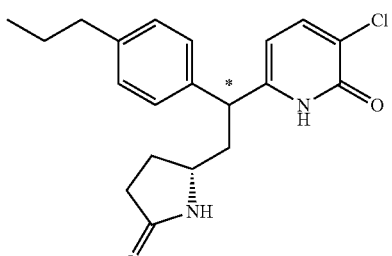
Example 4-314, 315
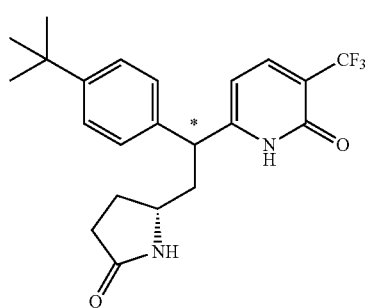
Example 4-316, 317B
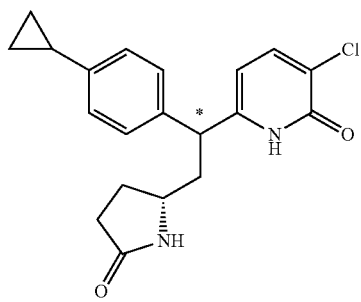
Example 4-318, 319
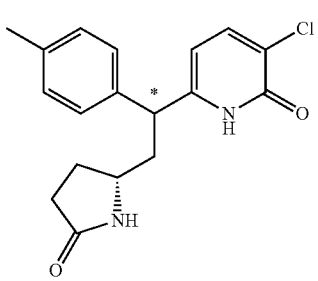
Example 4-320, 321
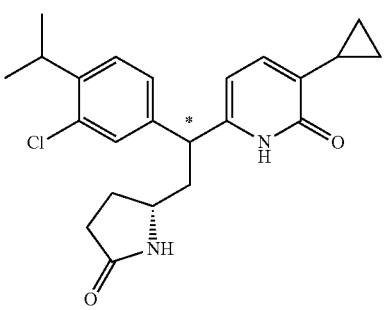
Example 4-322, 323
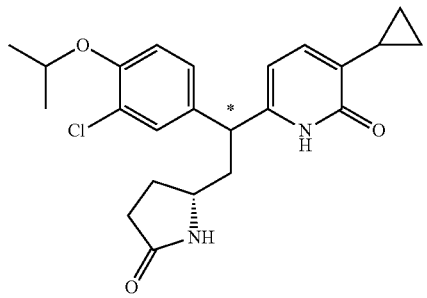
Example 4-324, 325
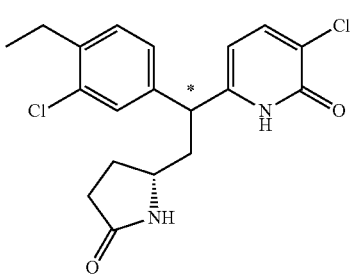

Example 4-326, 327
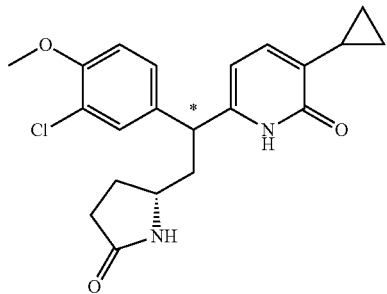
Example 4-328, 329
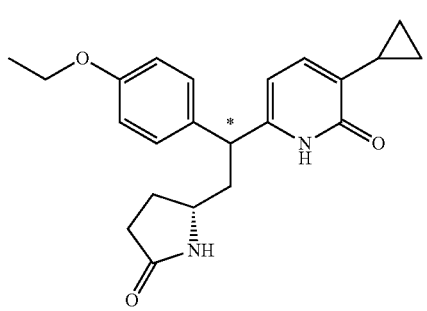
[Hyo 17-6]
Example 4-330, 331
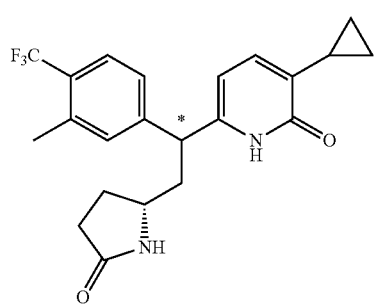
Example 4-332, 333
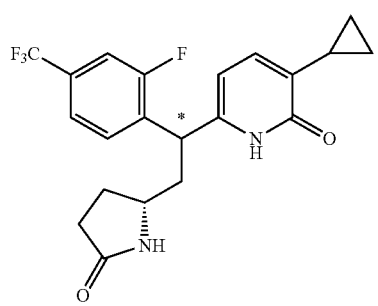
Example 4-334, 335
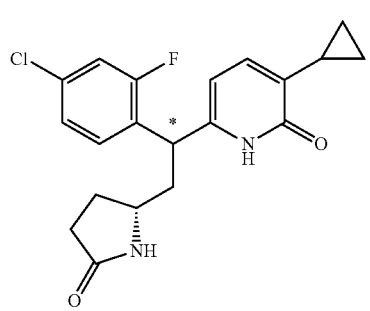
Example 4-336, 337
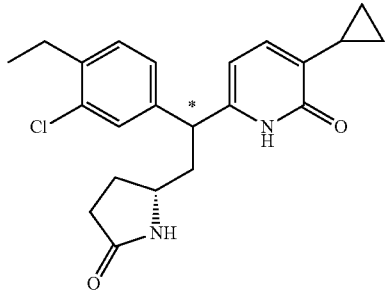
Example 4-338, 339
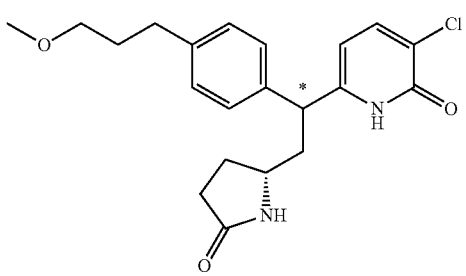
Example 4-340, 341
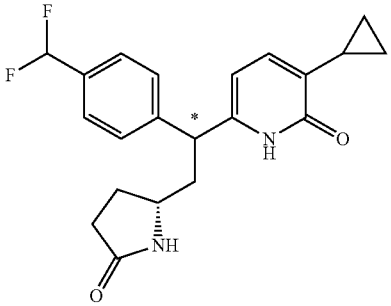
Example 4-342, 343
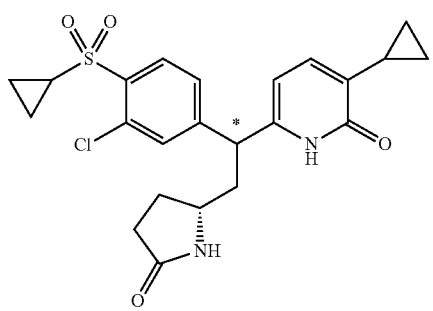
Example 4-344, 345
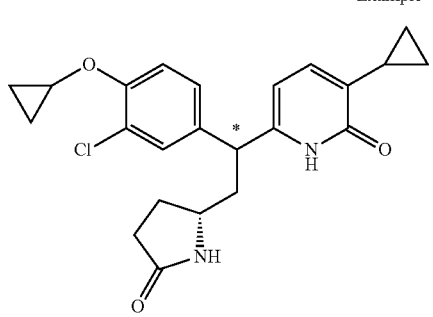

-continued

Example 4-346, 347
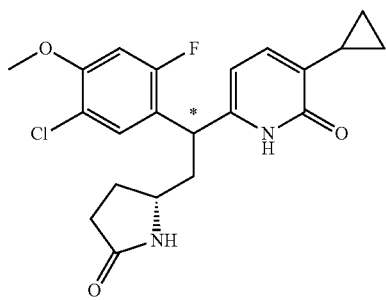

Example 4-348, 349
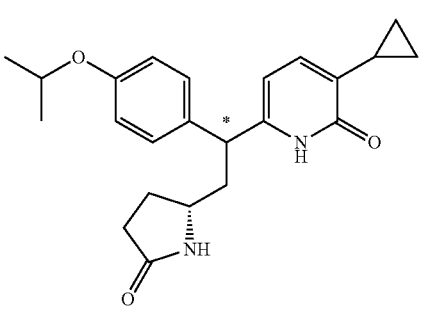

Example 4-350, 351
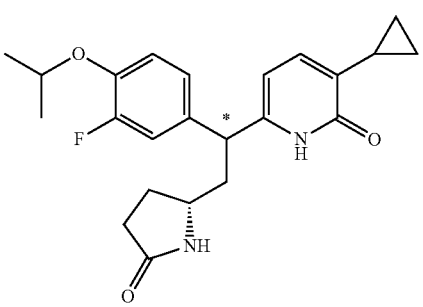

Example 4-352, 353
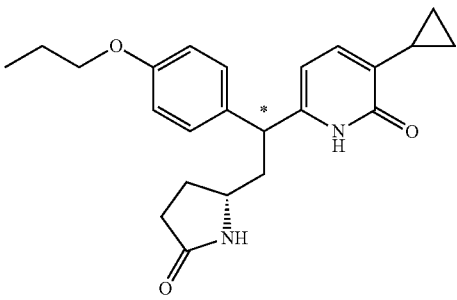

[Hyo 17-7]

Example 4-354, 355
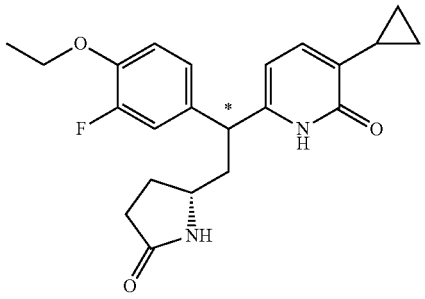

-continued

Example 4-356, 357
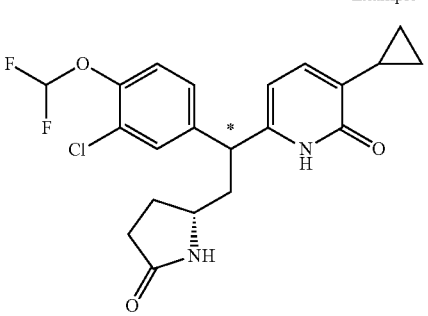

Example 4-358
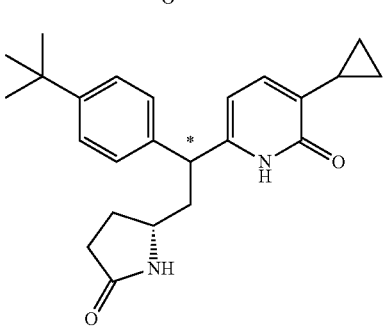

Example 4-359

6-{(E)-1-(4-Chlorophenyl)-2-[(2R)-5-oxopyrrolidin-2-yl]ethenyl}-3-(1H-pyrazol-4-yl)pyridin-2(1H)-one (1) tert-Butyl 4-(4,4,5,5-tetramethyl-1,3,2-dioxaborolan-2-yl)-1H-pyrazole-1-carboxylate (216 mg), tris(dibenzylideneacetone)dipalladium(0) (33.7 mg), tri(2-furyl)phosphine (51.5 mg) and cesium carbonate (239 mg) were added to a solution of (5R)-5-[(E)-2-(5-bromo-6-methoxypyridin-2-yl)-2-(4-chlorophenyl)ethenyl]-1-(2,4-dimethoxybenzyl)pyrrolidin-2-one obtained in Reference Example 4-43 (200 mg) in 1,4-dioxane (3 mL)-water (1 mL), and the mixture was stirred at an external temperature for 80° C. for three hours. The reaction solution was left to cool, diluted with ethyl acetate and filtered through celite. The filtrate was washed with brine and dried over sodium sulfate. After filtration, the solvent was evaporated under reduced pressure. The residue was purified by silica gel column chromatography (hexane:ethyl acetate=9:1→7:3) to give (5R)-5-{(E)-2-(4-chlorophenyl)-2-[6-methoxy-5-(1H-pyrazol-4-yl)pyridin-2-yl]ethenyl}-1-(2,4-dimethoxybenzyl)pyrrolidin-2-one as a colorless oil (125 mg, 63%).

(2) 48% hydrobromic acid (1.25 mL) was added to a solution of (5R)-5-{(E)-2-(4-chlorophenyl)-2-[6-methoxy-5-(1H-pyrazol-4-yl)pyridin-2-yl]ethenyl}-1-(2,4-dimethoxybenzyl)pyrrolidin-2-one (63 mg) in 1,4-dioxane (1.25 mL), and the mixture was stirred at 65° C. for 30 minutes. Water was added to the reaction solution, followed by extraction with ethyl acetate. The organic layer was washed with brine and dried over anhydrous magnesium sulfate, after which the solvent was evaporated under reduced pressure. The resulting residue was purified by silica gel column chromatography (chloroform:methanol=10:0→9:1) to give 6-{(E)-1-(4-chlorophenyl)-2-[(2R)-1-(2,4-dimethoxybenzyl)-5-oxopyrrolidin-2-yl]ethenyl}-3-(1H-pyrazol-4-yl)pyridin-2(1H)-one as a yellow amorphous (100 mg, 81%).

(3) Anisole (0.5 mL) was added to a solution of 6-{(E)-1-(4-chlorophenyl)-2-[(2R)-1-(2,4-dimethoxybenzyl)-5-oxopyrrolidin-2-yl]ethenyl}-3-(1H-pyrazol-4-yl)pyridin-2 (1H)-one (100 mg) in trifluoroacetic acid (1 mL), and the mixture was stirred at 70° C. for five hours. The solvent was evaporated under reduced pressure. The residue was purified by silica gel column chromatography (chloroform:methanol=1:0→9:1) and recrystallized from ethyl acetate-hexane to give the title compound as a pale yellow powder (51.2 mg).

$^1$H NMR (300 MHz, METHANOL-d4) δ ppm 1.91-2.12 (m, 1H), 2.19-2.47 (m, 3H), 4.08-4.26 (m, 1H), 5.96 (d, J=7.3 Hz, 1H), 6.37 (d, J=9.2 Hz, 1H), 7.26 (d, J=8.2 Hz, 2H), 7.49 (d, J=8.2 Hz, 2H), 7.79 (d, J=7.5 Hz, 1H), 7.99-8.50 (m, 2H).

MS(+): 381 [M+H]$^+$.

Example 4-360

6-{(E)-2-[(2R)-5-Oxopyrrolidin-2-yl]-1-[4-(trifluoromethyl)phenyl]ethenyl}-3-(1H-pyrazol-4-yl)pyridin-2(1H)-one The title compound was obtained as a pale yellow powder (22.6 mg, 14% (three steps)) by performing substantially the same reaction as in Example 4-359(1)-(3) except for using (5R)-5-{(E)-2-(5-bromo-6-methoxypyridin-2-yl)-2-[4-(trifluoromethyl)phenyl]ethenyl}-1-(2,4-dimethoxybenzyl)pyrrolidin-2-one obtained in Reference Example 4-44 in place of (5R)-5-[(E)-2-(5-bromo-6-methoxypyridin-2-yl)-2-(4-chlorophenyl)ethenyl]-1-(2,4-dimethoxybenzyl)pyrrolidin-2-one.

$^1$H NMR (300 MHz, CDCl$_3$) δ ppm 1.93-2.12 (m, 1H), 2.21-2.48 (m, 3H), 4.06-4.20 (m, 1H), 5.91 (d, J=7.9 Hz, 1H), 6.44 (d, J=9.8 Hz, 1H), 7.49 (d, J=8.7 Hz, 2H), 7.74-7.84 (m, 3H), 7.97-8.16 (m, 1H), 8.26-8.46 (m, 1H).

MS(+): 415 [M+H]$^+$.

Example 4-361

6-{(E)-1-(4-tert-Butylphenyl)-2-[(2R)-5-oxopyrrolidin-2-yl]ethenyl}-3-(1H-pyrazol-4-yl)pyridin-2(1H)-one The title compound was obtained as a light orange amorphous (37 mg, 40% (two steps)) by performing substantially the same reaction as in Example 4-359(1)(2) except for using (5R)-5-[(E)-2-(5-bromo-6-methoxypyridin-2-yl)-2-(4-tert-butylphenyl)ethenyl]pyrrolidin-2-one obtained in Reference Example 4-42(2) in place of (5R)-5-[(E)-2-(5-bromo-6-methoxypyridin-2-yl)-2-(4-chlorophenyl)ethenyl]-1-(2,4-dimethoxybenzyl)pyrrolidin-2-one.

$^1$H NMR (600 MHz, DMSO-d6) δ ppm 1.30 (s, 9H), 1.81-1.92 (m, 1H), 2.02-2.12 (m, 2H), 2.14-2.23 (m, 1H), 3.87-3.93 (m, 1H), 5.53-5.65 (m, 1H), 6.40 (d, J=9.6 Hz, 1H), 7.16 (d, J=8.3 Hz, 2H), 7.43 (d, J=8.3 Hz, 2H), 7.67 (d, J=7.3 Hz, 1H), 7.73-7.76 (brs, 1H), 7.93-8.42 (m, 2H), 11.48-11.61 (brs, 1H), 12.72-12.93 (brs, 1H).

MS(+): 403 [M+H]$^+$.

The structures of Examples 4-359 to 4-361 are shown below.

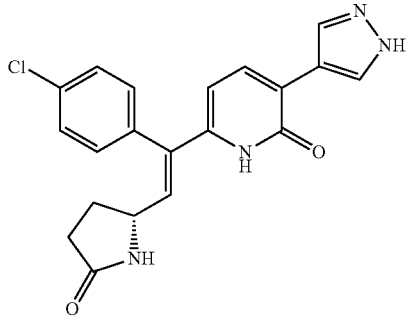

Example 4-359

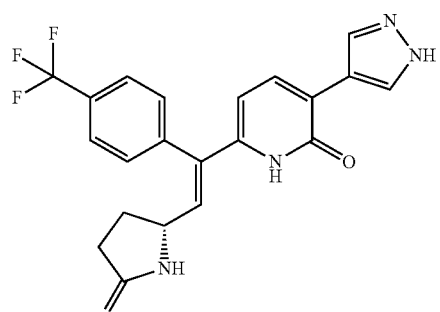

Example 4-360

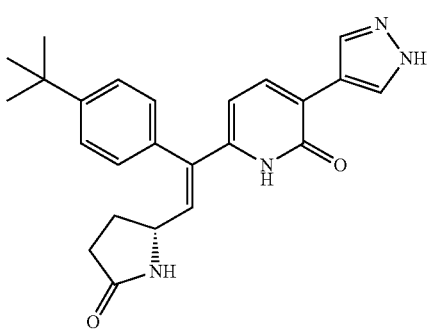

Example 4-361

The compounds of Examples 4-362 to 4-369 were synthesized by performing substantially the same reaction as in Example 4-98 except for using, in place of 4-chlorophenylboronic acid, corresponding boronic acids or boronate esters ([4-(azetidin-1-ylsulfonyl)phenyl]boronic acid, [4-(cyclopropylsulfamoyl)phenyl]boronic acid, [4-(propan-2-ylsulfamoyl)phenyl]boronic acid, {4-[(2-hydroxyethyl)sulfamoyl]phenyl}boronic acid, 2-(4-chloro-3-ethoxyphenyl)-4,4,5,5-tetramethyl-1,3,2-dioxaborolane, 4,4,5,5-tetramethyl-2-{4-[(trifluoromethyl)sulfonyl]phenyl}-1,3,2-dioxaborolane, 2-chloro-4-(4,4,5,5-tetramethyl-1,3,2-dioxaborolan-2-yl) benzenesulfonamide and 2-fluoro-4-(4,4,5,5-tetramethyl-1,3,2-dioxaborolan-2-yl)benzenesulfonamide), respectively.

Example 4-362

6-{(E)-1-[4-(Azetidin-1-ylsulfonyl)phenyl]-2-[(2R)-5-oxopyrrolidin-2-yl]ethenyl}-3-cyclopropylpyridin-2(1H)-one The title compound was obtained as a colorless powder (52 mg, 33% (two steps)).

$^1$H NMR (600 MHz, CDCl$_3$) δ ppm 0.54-0.65 (m, 2H), 0.93-1.03 (m, 2H), 2.06-2.15 (m, 4H), 2.23-2.34 (m, 2H), 2.37-2.44 (m, 1H), 3.21 (dquin, J=13.5, 6.7 Hz, 2H), 3.45 (t, J=6.4 Hz, 2H), 4.09 (dd, J=6.4, 1.5 Hz, 1H), 5.65 (d, J=7.4 Hz, 1H), 5.69-5.74 (m, 1H), 6.58 (d, J=9.1 Hz, 1H), 6.81 (d, J=7.0 Hz, 1H), 7.37 (d, J=8.3 Hz, 2H), 7.93 (d, J=8.3 Hz, 2H).
MS(−): 438 [M−H]⁻.

Example 4-363

N-Cyclopropyl-4-{(E)-1-(5-cyclopropyl-6-oxo-1,6-dihydropyridin-2-yl)-2-[(2R)-5-oxopyrrolidin-2-yl]ethenyl}benzenesulfonamide The title compound was obtained as a colorless powder (45 mg, 53% (two steps)).
¹H NMR (500 MHz, METHANOL-d4) δ ppm 0.47-0.66 (m, 6H), 0.89-0.98 (m, 2H), 1.96-2.09 (m, 2H), 2.18-2.46 (m, 4H), 4.08-4.18 (m, 1H), 5.79 (d, J=7.6 Hz, 1H), 6.38 (d, J=9.6 Hz, 1H), 6.98-7.04 (m, 1H), 7.42-7.49 (m, 2H), 7.91-8.00 (m, 2H).
MS(+): 440 [M+H]⁺.

Example 4-364

4-{(E)-1-(5-Cyclopropyl-6-oxo-1,6-dihydropyridin-2-yl)-2-[(2R)-5-oxopyrrolidin-2-yl]ethenyl}-N-(propan-2-yl)benzenesulfonamide The title compound was obtained as a colorless powder (55 mg, 67% (two steps)).
¹H NMR (500 MHz, METHANOL-d4) δ ppm 0.58-0.68 (m, 2H), 0.89-0.96 (m, 2H), 1.06 (dd, J=6.5, 1.5 Hz, 6H), 1.96-2.08 (m, 2H), 2.21-2.45 (m, 3H), 3.38-3.48 (m, 1H), 4.02-4.18 (m, 1H), 5.76 (d, J=7.3 Hz, 1H), 6.37 (d, J=9.6 Hz, 1H), 7.00 (d, J=7.3 Hz, 1H), 7.38-7.47 (m, 2H), 7.89-7.99 (m, 2H).
MS(+): 442 [M+H]⁺.

Example 4-365

4-{(E)-1-(5-Cyclopropyl-6-oxo-1,6-dihydropyridin-2-yl)-2-[(2R)-5-oxopyrrolidin-2-yl]ethenyl}-N-(2-hydroxyethyl)benzenesulfonamide The title compound was obtained as a colorless powder (52 mg, 33% (two steps)).
¹H NMR (600 MHz, DMSO-d6) δ ppm 0.56-0.60 (m, 2H), 0.81-0.86 (m, 2H), 1.82-2.24 (m, 5H), 2.84 (t, J=6.4 Hz, 2H), 3.37-3.42 (m, 2H), 3.79-3.85 (m, 1H), 4.70-4.74 (m, 1H), 6.49 (d, J=9.5 Hz, 1H), 6.83-6.88 (m, 1H), 7.43 (d, J=8.3 Hz, 2H), 7.83 (d, J=8.7 Hz, 2H),
MS(−): 442 μM-K.

Example 4-366

6-{(E)-1-(4-Chloro-3-ethoxyphenyl)-2-[(2R)-5-oxopyrrolidin-2-yl]ethenyl}-3-cyclopropylpyridin-2(1H)-one The title compound was obtained as a colorless powder (40 mg, 25% (two steps)).
¹H NMR (300 MHz, CDCl₃) δ ppm 0.43-0.74 (m, 2H), 0.88-1.17 (m, 2H), 1.41-1.52 (m, 3H), 1.96-2.48 (m, 5H), 3.97-4.32 (m, 3H), 5.63-5.87 (m, 1H), 6.37-6.59 (m, 2H), 6.65-6.77 (m, 2H), 6.78-6.89 (m, 1H), 7.33-7.49 (m, 1H), 11.65-12.04 (brs, 1H).
MS(+): 399 [M+H]⁺.

Example 4-367

3-Cyclopropyl-6-[(E)-2-[(2R)-5-oxopyrrolidin-2-yl]-1-{4-[(trifluoromethyl)sulfonyl]phenyl}ethenyl]pyridin-2(1H)-one The title compound was obtained as a colorless amorphous (29 mg, 25% (two steps)).
¹H NMR (600 MHz, METHANOL-d4) δ ppm 0.60-0.67 (m, 2H), 0.92-0.97 (m, 2H), 1.97-2.10 (m, 2H), 2.25-2.46 (m, 3H), 4.05-4.15 (m, 1H), 5.81 (d, J=7.4 Hz, 1H), 6.44 (d, J=9.5 Hz, 1H), 7.04 (d, J=7.4 Hz, 1H), 7.63-7.70 (m, 2H), 8.13-8.21 (m, 2H).
MS(+): 453 [M+H]⁺.

Example 4-368

2-Chloro-4-{(E)-1-(5-cyclopropyl-6-oxo-1,6-dihydropyridin-2-yl)-2-[(2R)-5-oxopyrrolidin-2-yl]ethenyl}benzenesulfonamide The title compound was obtained as a colorless powder (32 mg, 21% (two steps)).
¹H NMR (600 MHz, DMSO-d6) δ ppm 0.59 (td, J=5.6, 3.7 Hz, 2H), 0.83-0.86 (m, 2H), 1.82-1.88 (m, 1H), 1.95-2.01 (m, 1H), 2.03-2.15 (m, 2H), 2.17-2.23 (m, 1H), 3.81 (dt, J=9.7, 6.5 Hz, 1H), 5.39-5.57 (m, 1H), 6.51 (d, J=9.5 Hz, 1H), 6.87 (d, J=6.6 Hz, 1H), 7.36 (dd, J=7.8, 1.7 Hz, 1H), 7.53 (d, J=1.7 Hz, 1H), 7.82 (s, 1H), 8.00 (d, J=8.3 Hz, 1H).
MS(−): 432 [M−H]⁻.

Example 4-369

4-{(E)-1-(5-Cyclopropyl-6-oxo-1,6-dihydropyridin-2-yl)-2-[(2R)-5-oxopyrrolidin-2-yl]ethenyl}-2-fluorobenzenesulfonamide The title compound was obtained as a colorless powder (28 mg, 19% (two steps)).
¹H NMR (600 MHz, DMSO-d6) δ ppm 0.57-0.61 (m, 2H), 0.83-0.86 (m, 2H), 1.81-1.90 (m, 1H), 1.98 (tt, J=8.5, 5.3 Hz, 1H), 2.04-2.15 (m, 2H), 2.16-2.24 (m, 1H), 3.83 (dt, J=9.5, 6.6 Hz, 1H), 5.36-5.54 (m, 1H), 6.50 (d, J=9.5 Hz, 1H), 6.82-6.89 (m, 1H), 7.20 (dd, J=7.8, 1.2 Hz, 1H), 7.36 (d, J=10.7 Hz, 1H), 7.78-7.84 (m, 2H).
MS(−): 416 [M−H]⁻.

Examples 4-370 and 4-371

6-{1-[3-Chloro-4-(trifluoromethoxy)phenyl]-2-[(2R)-5-oxopyrrolidin-2-yl]ethyl}-3-cyclopropylpyridin-2(1H)-one An (R,S) mixture of the title compound was obtained by performing substantially the same reaction as in Examples 4-207 and 4-208 except for using [3-chloro-4-(trifluoromethoxy)phenyl]boronic acid obtained in Reference Example 5-2 in place of 3,4-dichlorophenylboronic acid. The mixture was separated by CHIRALPAK IB (40° C., flow rate: 10 mL/min, ethanol:hexane=50:50) to give one diastereomer (A) of the title compound as a colorless amorphous (75 mg, 43% (three steps)) and the other diastereomer (B) of the title compound as a colorless amorphous (19 mg, 11% (three steps)).

Diastereomer (A);
¹H NMR (600 MHz, CDCl₃) δ ppm 0.60-0.67 (m, 2H), 0.95-0.99 (m, 2H), 1.71-1.79 (m, 1H), 2.08-2.14 (m, 1H), 2.16-2.40 (m, 5H), 3.48-3.54 (m, 1H), 3.99-4.04 (m, 1H), 6.00 (d, J=7.0 Hz, 1H), 6.94 (d, J=7.0 Hz, 1H), 7.13 (brs., 1H), 7.25-7.29 (m, 1H), 7.32-7.35 (m, 1H), 7.54 (d, J=2.1 Hz, 1H), 12.23-12.35 (m, 1H).
MS(+): 441 [M+H]⁺.
CHIRALPAK IB 4.6×250 mm 5 μm (DAICEL), hexane:ethanol=50:50 v/v, 40° C., 1.0 mL/min, 210 nm, Rt=4.461 min.

Diastereomer (B);
¹H NMR (600 MHz, CDCl₃) δ ppm 0.58-0.66 (m, 2H), 0.98-1.07 (m, 2H), 1.75-1.83 (m, 1H), 2.12-2.18 (m, 1H), 2.21-2.41 (m, 5H), 3.55-3.61 (m, 1H), 4.09-4.14 (m, 1H), 6.01 (d, J=7.0 Hz, 1H), 6.99 (d, J=7.4 Hz, 1H), 7.25-7.28 (m, 2H), 7.46 (d, J=1.7 Hz, 1H), 7.81 (brs, 1H), 13.26-13.36 (m, 1H).
MS(+): 441 [M+H]⁺.
CHIRALPAK IB 4.6×250 mm 5 μm (DAICEL), hexane:ethanol=50:50 v/v, 40° C., 1.0 mL/min, 210 nm, Rt=9.686 min.

Examples 4-372 and 4-373

6-{1-(4-Chlorophenyl)-2-[(2R)-5-oxopyrrolidin-2-yl]ethyl}-3-(1H-pyrazol-4-yl)pyridin-2(1H)-one (1) (5R)-5-{(E)-2-(4-Chlorophenyl)-2-[6-methoxy-5-(1H-pyrazol-4-yl)pyridin-2-yl]ethenyl}pyrrolidin-2-one was obtained as a yellow oil (218 mg) by performing substantially the same reaction as in Example 4-359(3) except for using (5R)-5-{(E)-2-(4-chlorophenyl)-2-[6-methoxy-5-(1H-pyrazol-4-yl)pyridin-2-yl]ethenyl}-1-(2,4-dimethoxybenzyl)pyrrolidin-2-one obtained in Example 4-359(1).

(2) 10% palladium-activated carbon (60 mg) and acetic acid (2 mL) were added to a solution of (5R)-5-{(E)-2-(4-chlorophenyl)-2-[6-methoxy-5-(1H-pyrazol-4-yl)pyridin-2-yl]ethenyl}pyrrolidin-2-one (122 mg) in methanol (3 mL) in a hydrogen gas stream, and the mixture was stirred at room temperature for 20 hours. The reaction solution was filtered through celite, and then the solvent was evaporated under reduced pressure. Saturated aqueous sodium bicarbonate was added to the residue, followed by extraction with chloroform. The solvent was evaporated from the organic layer under reduced pressure to give a crude product of (5R)-5-{2-(4-chlorophenyl)-2-[6-methoxy-5-(1H-pyrazol-4-yl)pyridin-2-yl]ethenyl}pyrrolidin-2-one as a yellow oil (77 mg).

(3) An (R,S) mixture of the title compound (43 mg) was obtained by performing substantially the same reaction as in Example 4-98(2) except for using (5R)-5-{2-(4-chlorophenyl)-2-[6-methoxy-5-(1H-pyrazol-4-yl)pyridin-2-yl]ethyl}pyrrolidin-2-one. The mixture was separated by CHIRALPAK IB (40° C., flow rate: 10 mL/min, ethanol:hexane=20:80) to give one diastereomer (A) of the title compound as a colorless amorphous (11 mg) and the other diastereomer (B) of the title compound as a colorless amorphous (12 mg).

Diastereomer (A);
¹H NMR (300 MHz, METHANOL-d4) δ ppm 2.25-2.41 (m, 1H), 2.65-3.01 (m, 5H), 4.06-4.17 (m, 1H), 4.53-4.63 (m, 1H), 7.02 (d, J=7.3 Hz, 1H), 7.87-7.95 (m, 4H), 8.45 (d, J=7.5 Hz, 1H), 8.61-8.95 (brs, 2H).
MS(+): 383 [M+H]⁺.
CHIRALPAK IB 4.6×250 mm 5 μm (DAICEL), hexane:ethanol=50:50 v/v, 40° C., 1.0 mL/min, 210 nm, Rt=6.944 min.

Diastereomer (B);
¹H NMR (300 MHz, METHANOL-d4) δ ppm 1.75-1.91 (m, 1H), 2.14-2.41 (m, 5H), 3.45-3.58 (m, 1H), 3.93-4.06 (m, 1H), 6.43 (d, J=7.5 Hz, 1H), 7.28-7.39 (m, 4H), 7.87 (d, J=7.3 Hz, 1H), 8.03-8.37 (brs, 2H).
MS(+): 383 [M+H]⁺.
CHIRALPAK IB 4.6×250 mm 5 μm (DAICEL), hexane:ethanol=50:50 v/v, 40° C., 1.0 mL/min, 210 nm, Rt=17.841 min.

Examples 4-374 and 4-375

6-{2-[(2R)-5-Oxopyrrolidin-2-yl]-1-[4-(trifluoromethyl)phenyl]ethyl}-3-(1H-pyrazol-4-yl)pyridin-2(1H)-one An (R,S) mixture of the title compound was obtained by performing substantially the same reaction as in Examples 4-359(1)(3) and 4-372(2)(3) sequentially except for using (5R)-5-{(E)-2-(5-bromo-6-methoxypyridin-2-yl)-2-[4-(trifluoromethyl)phenyl]ethenyl}-1-(2,4-dimethoxybenzyl)pyrrolidin-2-one obtained in Reference Example 4-44 in place of (5R)-5-[(E)-2-(5-bromo-6-methoxypyridin-2-yl)-2-(4-chlorophenyl)ethenyl]-1-(2,4-dimethoxybenzyl)pyrrolidin-2-one obtained in Reference Example 4-43. The mixture was separated by CHIRALPAK IB (40° C., flow rate: 10 mL/min, ethanol:hexane=20:80) to give one diastereomer (A) of the title compound as a colorless amorphous (15 mg) and the other diastereomer (B) of the title compound as a colorless amorphous (20 mg).

Diastereomer (A);
¹H NMR (300 MHz, METHANOL-d4) δ ppm 1.67-1.86 (m, 1H), 2.09-2.53 (m, 5H), 3.47-3.67 (m, 1H), 4.02-4.17 (m, 1H), 6.47 (d, J=7.3 Hz, 1H), 7.52-7.60 (m, 2H), 7.60-7.67 (m, 2H), 7.86 (d, J=7.3 Hz, 1H), 8.19 (s, 2H).
MS(+): 417 [M+H]⁺.
CHIRALPAK IB 4.6×250 mm 5 μm (DAICEL), hexane:ethanol=50:50 v/v, 40° C., 1.0 mL mL/min, 210 nm, Rt=6.124 min.

Diastereomer (B);
¹H NMR (300 MHz, METHANOL-d4) δ ppm 1.77-1.93 (m, 1H), 2.16-2.42 (m, 5H), 3.47-3.59 (m, 1H), 4.07-4.18 (m, 1H), 6.47 (d, J=7.5 Hz, 1H), 7.49-7.57 (m, 2H), 7.57-7.67 (m, 2H), 7.89 (d, J=7.3 Hz, 1H), 8.10-8.34 (brs, 2H).
MS(+): 417 [M+H]⁺.
CHIRALPAK IB 4.6×250 mm 5 μm (DAICEL), hexane:ethanol=50:50 v/v, 40° C., 1.0 mL/min, 210 nm, Rt=15.900 min.

Example 4-376

6-{(E)-1-[4-(Cyclopropylsulfonyl)phenyl]-2-[(2R)-5-oxopyrrolidin-2-yl]ethenyl}-3-(1H-pyrazol-4-yl)pyridin-2(1H)-one (1) (5R)-5-{(E)-2-[4-(cyclopropylsulfonyl)phenyl]-2-[6-methoxy-5-(1H-pyrazol-4-yl)pyridin-2-yl]ethenyl}pyrrolidin-2-one was obtained as a light yellow amorphous (275 mg, 43% (three steps)) by performing substantially the same reaction as in Reference Example 4-43 and Example 4-359(1)(3) except for using (5R)-5-[(E)-2-[4-(cyclopropylsulfonyl)phenyl]-2-(tributylstannyl)ethenyl]pyrrolidin-2-one obtained in Reference Example 4-45 in place of (5R)-5-[(E)-2-(4-chlorophenyl)-2-(tributylstannyl)ethenyl]-1-(2,4-dimethoxybenzyl)pyrrolidin-2-one obtained in Reference Example 4-28.

(2) The title compound was obtained as a yellow powder (32 mg, 55%) by performing substantially the same reaction as in Example 4-98(2) except for using (5R)-5-{(E)-2-[4-(cyclopropylsulfonyl)phenyl]-2-[6-methoxy-5-(1H-pyrazol-4-yl)pyridin-2-yl]ethenyl}pyrrolidin-2-one.

$^1$H NMR (600 MHz, DMSO-d6) δ ppm 1.02-1.09 (m, 2H), 1.10-1.18 (m, 2H), 1.80-1.91 (m, 1H), 2.02-2.12 (m, 2H), 2.15-2.24 (m, 1H), 2.87-2.95 (m, 1H), 3.79-3.87 (m, 1H), 5.49-5.64 (brs, 1H), 6.52 (d, J=9.5 Hz, 1H), 7.51 (d, J=8.3 Hz, 2H), 7.67 (d, J=7.0 Hz, 1H), 7.76-7.82 (m, 1H), 7.92 (d, J=8.3 Hz, 2H), 7.95-8.07 (brs, 1H), 8.22-8.39 (brs, 1H), 11.53-11.80 (brs, 1H), 12.77-12.97 (brs, 1H).

MS(+): 451 [M+H]$^+$.

Examples 4-377 and 4-378

6-{1-[4-(Cyclopropylsulfonyl)phenyl]-2-[(2R)-5-oxopyrrolidin-2-yl]ethyl}-3-(1H-pyrazol-4-yl)pyridin-2(1H)-one (1) 10% palladium-activated carbon (175 mg) and concentrated hydrochloric acid (1 mL) were added to a solution of (5R)-5-{(E)-2-[4-(cyclopropylsulfonyl)phenyl]-2-[6-methoxy-5-(1H-pyrazol-4-yl)pyridin-2-yl]ethenyl}pyrrolidin-2-one obtained in Example 4-376(1) (175 mg) in methanol (3 mL) in a hydrogen gas stream, and the mixture was stirred at room temperature for five hours. The reaction solution was filtered through celite, and then the solvent was evaporated under reduced pressure. Saturated aqueous sodium bicarbonate was added to the residue, followed by extraction with chloroform. The solvent was evaporated from the organic layer under reduced pressure to give a crude product of (5R)-5-{2-[4-(cyclopropylsulfonyl)phenyl]-2-[6-methoxy-5-(1H-pyrazol-4-yl)pyridin-2-yl]ethyl}pyrrolidin-2-one as a colorless amorphous (129 mg, 73%).

(2) An (R,S) mixture of the title compound (84 mg) was obtained by performing substantially the same reaction as in Example 4-98(2) except for using (5R)-5-{2-[4-(cyclopropylsulfonyl)phenyl]-2-[6-methoxy-5-(1H-pyrazol-4-yl)pyridin-2-yl]ethyl}pyrrolidin-2-one. The mixture was separated by CHIRALPAK IB (40° C., flow rate: 10 mL/min, ethanol:hexane=15:85) to give one diastereomer (A) of the title compound as a colorless amorphous (30 mg) and the other diastereomer (B) of the title compound as a colorless amorphous (23 mg).
Diastereomer (A);

$^1$H NMR (600 MHz, DMSO-d6) δ ppm 0.88-0.95 (m, 2H), 0.99-1.05 (m, 2H), 1.48-1.58 (m, 1H), 1.91-2.10 (m, 4H), 2.20-2.28 (m, 1H), 2.69-2.78 (m, 1H), 4.03 (t, J=7.8 Hz, 1H), 6.16-6.31 (brs, 1H), 7.59 (d, J=8.3 Hz, 2H), 7.66-7.73 (m, 2H), 7.76 (d, J=8.7 Hz, 2H), 7.83-8.27 (brs, 2H), 11.52-11.90 (brs, 1H), 12.45-12.86 (brs, 1H).

MS(+): 453 [M+H]$^+$.

CHIRALPAK IB 4.6×250 mm 5 μm (DAICEL), hexane:ethanol=30:70 v/v, 40° C., 1.0 mL/min, 210 nm, Rt=8.061 min.
Diastereomer (B);

$^1$H NMR (600 MHz, DMSO-d$_6$) δ ppm 0.93-1.01 (m, 2H), 1.04-1.11 (m, 2H), 1.58-1.69 (m, 1H), 1.99-2.17 (m, 4H), 2.26-2.34 (m, 1H), 2.76-2.83 (m, 1H), 4.10 (t, J=8.1 Hz, 1H), 6.22-6.36 (brs, 1H), 7.60 (d, J=8.3 Hz, 2H), 7.70-7.77 (m, 2H), 7.83 (d, J=8.3 Hz, 2H), 7.89-8.09 (brs, 1H), 8.12-8.35 (brs, 1H), 11.45-11.78 (brs, 1H), 12.55-12.94 (brs, 1H).

MS(+): 453 [M+H]$^+$.

CHIRALPAK IB 4.6×250 mm 5 μm (DAICEL), hexane:ethanol=30:70 v/v, 40° C., 1.0 mL/min, 210 nm, Rt=14.495 min.

Example 4-379

6-{(E)-2-[(2R)-5-Oxopyrrolidin-2-yl]-1-[4-(trifluoromethyl)phenyl]ethenyl}-1',2',3',6'-tetrahydro-3,4'-bipyridin-2(1H)-one The title compound was obtained as a pale orange powder (9 mg) by performing substantially the same reaction as in Example 4-360 except for using tert-butyl 4-(4,4,5,5-tetramethyl-1,3,2-dioxaborolan-2-yl)-3,6-dihydropyridine-1(2H)-carboxylate.

$^1$H NMR (300 MHz, CDCl$_3$) δ ppm 1.81-2.11 (m, 1H), 2.15-2.63 (m, 5H), 2.94-3.16 (m, 2H), 3.49-3.83 (m, 3H), 3.98-4.10 (m, 1H), 5.54-5.75 (m, 1H), 6.51-6.59 (m, 1H), 6.61-6.72 (m, 1H), 7.13-7.24 (m, 1H), 7.31-7.46 (m, 2H), 7.61-7.81 (m, 3H).

MS(+): 430 [M+H]$^+$.

The structures of Examples 4-362 to 4-379 are shown below.

[Hyo 19-1]

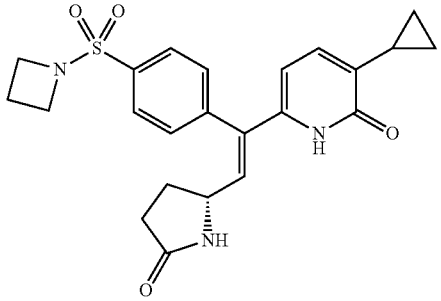

Example 4-362

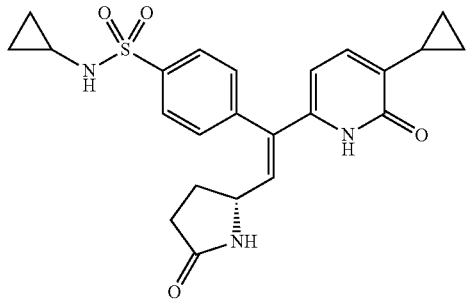

Example 4-363

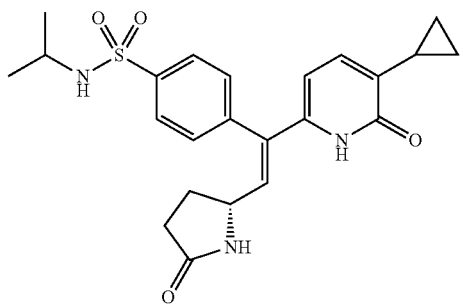

Example 4-364

Example 4-365
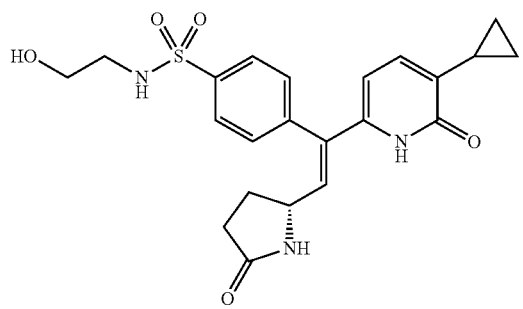
Example 4-366
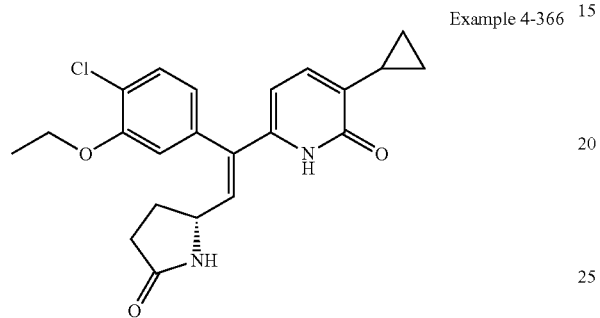
Example 4-367
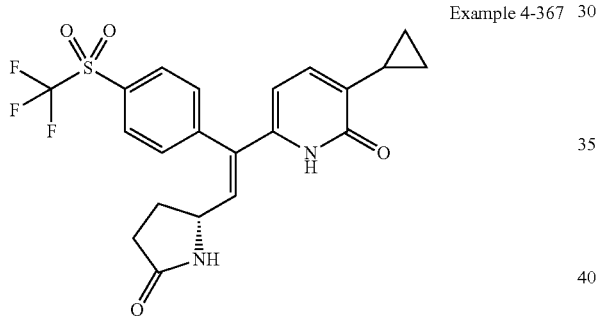
Example 4-368
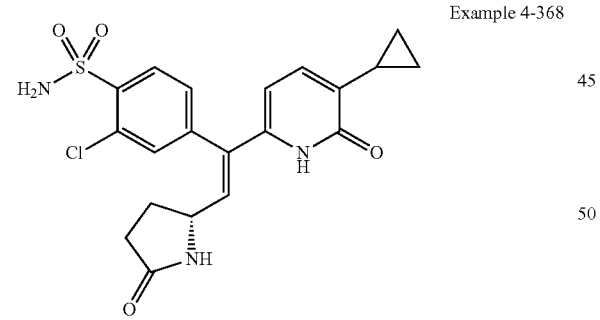
Example 4-369
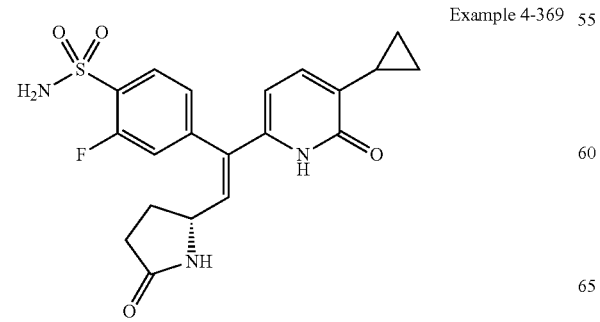
Example 4-370, 371
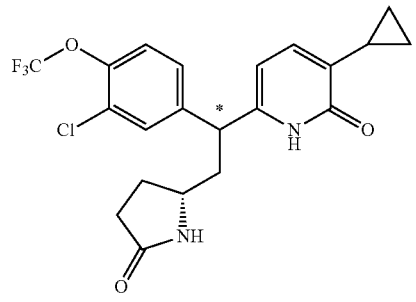
Example 4-372, 373
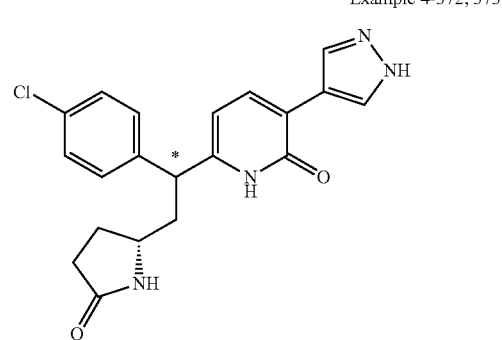
Example 4-374, 375
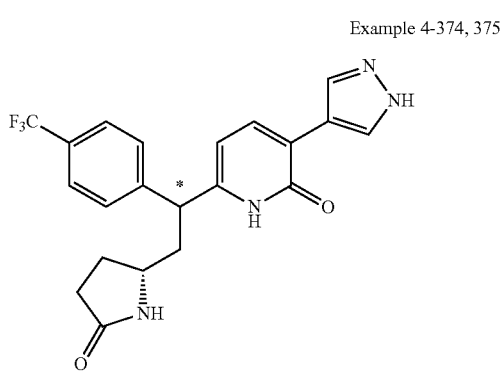
Example 4-376
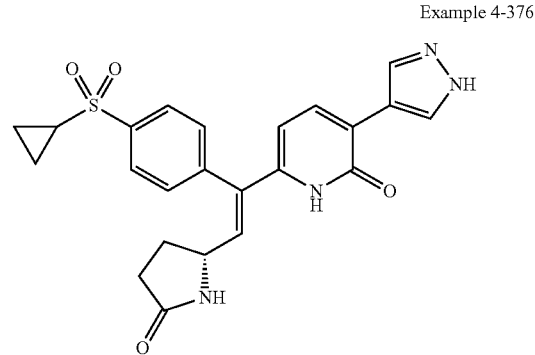

-continued

[Hyo 19-2]

Example 4-377, 378

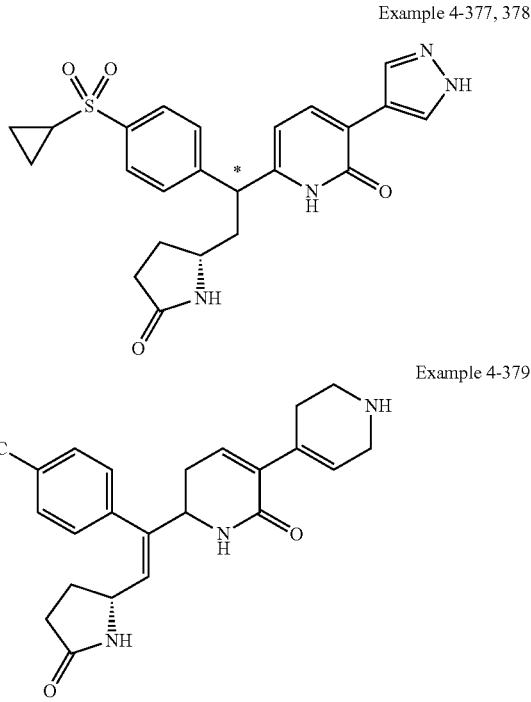

Example 4-379

Examples 4-380 and 4-381

4-{1-(5-Cyclopropyl-6-oxo-1,6-dihydropyridin-2-yl)-2-[(2R)-5-oxopyrrolidin-2-yl]ethyl}benzonitrile One diastereomer (A) of the title compound was obtained as a white solid (72 mg, 21% (three steps)) by performing the same reaction as in Examples 4-354 and 4-355 sequentially except for using 4-cyanophenylboronic acid, separating the mixture by preparative HPLC (CHIRALPAK IB (20 mm i.d.×250 mm L, Daicel Chemical Industries, LTD.), 40° C., flow rate: 10 mL/min, ethanol:hexane=30:70) and concentrating the fraction eluted with a retention time of 23 minutes. The fraction eluted with a retention time of 46 minutes was concentrated to give the other diastereomer (B) of the title compound as a white solid (28 mg, 8% (three steps)).

Diastereomer (A);
$^1$H NMR (300 MHz, CDCl$_3$) δ ppm 0.56-0.70 (m, 2H), 0.85-1.05 (m, 2H), 1.63-1.83 (m, 1H), 2.00-2.50 (m, 6H), 3.35-3.55 (m, 1H), 4.05-4.20 (m, 1H), 6.02 (d, J=7.2 Hz, 1H), 6.93 (d, J=7.5 Hz, 1H), 7.54 (d, 8.4 Hz, 2H), 7.59 (d, 8.4 Hz, 2H), 7.70-7.86 (brs, 1H), 12.30-12.90 (brs, 1H).
MS(+): 348 [M+H]$^+$.
MS(−): 346 [M−H]$^−$.

Diastereomer (B);
$^1$H NMR (300 MHz, CDCl$_3$) δ ppm 0.55-0.69 (m, 2H), 0.95-1.20 (m, 2H), 1.65-1.95 (m, 1H), 2.10-2.50 (m, 6H), 3.54-3.66 (m, 1H), 4.15-4.25 (m, 1H), 6.02 (d, J=7.5 Hz, 1H), 6.98 (d, J=7.5 Hz, 1H), 7.48 (d, J=8.1 Hz, 2H), 7.63 (d, J=8.1 Hz, 2H), 8.00-8.12 (brs, 1H), 13.15-13.55 (brs, 1H).
MS(+): 348 [M+H]$^+$.
MS(−): 346 [M−H]$^−$.

Example 4-382

3-Cyclopropyl-6-{(E)-2-[(2R)-5-oxopyrrolidin-2-yl]-1-[4-(propan-2-ylsulfonyl)phenyl]ethenyl}pyridin-2(1H)-one The title compound was obtained as a white solid (53 mg, 25% (two steps)) by performing the same reaction as in Example 4-289 except for using 4-bromo-1-(propan-2-ylsulfonyl)benzene.
$^1$H NMR (300 MHz, CDCl$_3$) δ ppm 0.51-0.66 (m, 2H), 0.92-1.02 (m, 2H), 1.36 (d, J=6.5 Hz, 6H), 2.07-2.45 (m, 5H), 3.20-3.34 (m, 1H), 4.00-4.10 (m, 1H), 5.54 (d, J=7.4 Hz, 1H), 6.69 (d, J=9.4 Hz, 1H), 6.80 (d, J=7.4 Hz, 1H), 7.44 (d, J=8.2 Hz, 2H), 7.50 (s, 1H), 7.95 (d, J=7.8 Hz, 2H), 12.56-12.77 (brs, 1H).
MS(+): 427 [M+H]$^+$.
MS(−): 425 [M−H]$^−$.

Example 4-383

4-{(E)-1-(5-Cyclopropyl-6-oxo-1,6-dihydropyridin-2-yl)-2-[(2R)-5-oxopyrrolidin-2-yl]ethenyl}-2-methylbenzonitrile The title compound was obtained as a pale yellow solid (39 mg, 54%) by performing substantially the same reaction as in Example 4-278 except for using 4-(5,5-dimethyl-1,3,2-dioxaborinan-2-yl)-2-methylbenzonitrile obtained in Reference Example 5-46.
$^1$H NMR (300 MHz, CDCl$_3$) δ ppm 0.50-0.70 (m, 2H), 0.85-1.10 (m, 2H), 2.02-2.55 (m, 5H), 2.58 (s, 3H), 4.00-4.15 (m, 1H), 5.55 (d, J=7.5 Hz, 1H), 6.63 (d, J=9.6 Hz, 1H), 6.77 (d, J=7.5 Hz, 1H), 7.17 (d, J=7.8 Hz, 1H), 7.23 (s, 1H), 7.65 (d, J=7.8 Hz, 1H), 7.70-7.80 (brs, 1H), 12.20-13.20 (brs, 1H).
MS(+): 360 [M+H]$^+$.

Example 4-384

3-Cyclopropyl-6-{(E)-1-{4-[2-(methylsulfonyl)ethyl]phenyl}-2-[(2R)-5-oxopyrrolidin-2-yl]ethenyl}pyridin-2(1H)-one The title compound was obtained as a pale brown solid (46 mg, 24% (two steps)) by performing the same reaction as in Example 4-289(2) except for using 4,4,5,5-tetramethyl-2-{4-[2-(methylsulfonyl)ethyl]phenyl}-1,3,2-dioxaborolane (see US 2006043289).
$^1$H NMR (300 MHz, DMSO-d6) δ ppm 0.58-0.61 (m, 2H), 0.81-0.86 (m, 2H), 1.86-2.24 (m, 5H), 2.93 (s, 3H), 3.02-3.08 (m, 2H), 3.45-3.57 (m, 2H), 3.83-3.88 (m, 1H), 5.31-5.48 (brs, 1H), 6.40 (d, J=9.5 Hz, 1H), 6.83 (d, J=7.1 Hz, 1H), 7.16 (d, J=8.0 Hz, 2H), 7.35 (d, J=7.7 Hz, 2H), 7.77 (s, 1H), 11.32-11.45 (brs, 1H).
MS(+): 427 [M+H]$^+$.
MS(−): 425 [M−H]$^−$.

Example 4-385

3-Cyclopropyl-6-{(E)-1-{4-[(3-hydroxypropyl)sulfonyl]phenyl}-2-[(2R)-5-oxopyrrolidin-2-yl]ethenyl}pyridin-2(1H)-one The title compound was obtained as a pale yellow solid (11 mg, 5% (two steps)) by performing as in Example 4-289 except for using {3-[(4-bromophenyl)sulfonyl]propoxy}(tert-butyl)dimethylsilane obtained in Reference Example 5-48.

$^1$H NMR (300 MHz, DMSO-d6) δ ppm 0.58-0.59 (m, 2H), 0.82-0.85 (m, 2H), 1.69-2.27 (m, 7H), 3.33-3.38 (m, 2H), 3.44 (q, J=5.7 Hz, 2H), 3.78-3.85 (m, 1H), 4.66 (t, J=5.4 Hz, 1H), 5.34-5.42 (brs, 1H), 6.50 (d, J=10.4 Hz, 1H), 6.80-6.88 (brs, 1H), 7.51 (d, J=8.3 Hz, 2H), 7.82 (s, 1H), 7.93 (d, J=8.3 Hz, 2H), 11.45-11.57 (brs, 1H).

MS(+): 443 [M+H]$^+$.
MS(−): 441 [M−H]$^−$.

Example 4-386

3-Cyclopropyl-6-{(E)-1-[3-fluoro-4-(methylsulfonyl)phenyl]-2-[(2R)-5-oxopyrrolidin-2-yl]ethenyl}pyridin-2(1H)-one The title compound was obtained as a pale yellow solid (90 mg, 38% (two steps)) by performing the same reaction as in Example 4-289(2) except for using 3-fluoro-4-(methylsulfonyl)phenylboronic acid.

$^1$H NMR (300 MHz, CDCl$_3$) δ ppm 0.51-0.71 (m, 2H), 0.92-1.10 (m, 2H), 2.00-2.54 (m, 5H), 3.31 (s, 3H), 4.00-4.13 (m, 1H), 5.63 (d, J=7.1 Hz, 1H), 6.65 (d, J=9.5 Hz, 1H), 6.84 (d, J=7.4 Hz, 1H), 7.04-7.25 (m, 3H), 7.98-8.12 (m, 1H), 12.06-12.42 (brs, 1H).

MS(+): 417 [M+H]$^+$.
MS(−): 415 [M−H]$^−$.

Example 4-387

6-{(E)-1-[3-Chloro-4-(propan-2-ylsulfonyl)phenyl]-2-[(2R)-5-oxopyrrolidin-2-yl]ethenyl}-3-cyclopropylpyridin-2(1H)-one The title compound was obtained as a white solid (36 mg, 14% (two steps)) by performing the same reaction as in Example 4-289 except for using 4-bromo-2-chloro-1-(propan-2-ylsulfonyl)benzene obtained in Reference Example 5-47.

$^1$H NMR (300 MHz, CDCl$_3$) δ ppm 0.50-0.78 (m, 2H), 0.90-1.15 (m, 2H), 1.25-1.50 (m, 6H), 2.00-2.60 (m, 5H), 3.70-3.95 (m, 1H), 3.95-4.23 (m, 1H), 5.58 (d, J=7.1 Hz, 1H), 6.66 (d, J=9.2 Hz, 1H), 6.83 (d, J=7.4 Hz, 1H), 7.20 (s, 1H), 7.32 (d, J=8.0 Hz, 1H), 7.40 (s, 1H), 8.16 (dd, J=7.9, 1.0 Hz, 1H), 12.20-12.80 (brs, 1H).

MS(+): 461 [M+H]$^+$.
MS(−): 459 [M−H]$^−$.

Example 4-388

3-Cyclopropyl-6-{(E)-1-[3-methoxy-4-(methylsulfonyl)phenyl]-2-[(2R)-5-oxopyrrolidin-2-yl]ethenyl}pyridin-2(1H)-one A 28% solution of sodium methoxide in methanol (14 μL) was added to a solution of 3-cyclopropyl-6-{(E)-1-[3-fluoro-4-(methylsulfonyl)phenyl]-2-[(2R)-5-oxopyrrolidin-2-yl]ethenyl}pyridin-2(1H)-one obtained in Example 4-386 (10 mg) in methanol (0.5 mL), after which the mixture was stirred at 70° C. for 30 minutes. The reaction solution was left to cool to room temperature. 3-Cyclopropyl-6-{(E)-1-[3-fluoro-4-(methylsulfonyl)phenyl]-2-[(2R)-5-oxopyrrolidin-2-yl]ethenyl}pyridin-2(1H)-one (50 mg), methanol (3 mL) and a 28% solution of sodium methoxide in methanol (80 μL) were then added, after which the mixture was stirred at 70° C. for two hours. The reaction solution was left to cool to room temperature and a 28% solution of sodium methoxide in methanol (1 mL) was then added, after which the mixture was stirred at 70° C. for one hour. The reaction solution was left to cool to room temperature, and water was then added to the reaction solution, followed by extraction with ethyl acetate. The organic layer was washed with water and brine, dried over anhydrous magnesium sulfate and filtered, after which the solvent was evaporated under reduced pressure. The residue was purified by NH-silica gel column chromatography (methanol:ethyl acetate=1:10) to give the title compound as a pale yellow solid (40 mg, 65%).

$^1$H NMR (300 MHz, CDCl$_3$) δ ppm 0.57-0.76 (m, 2H), 0.95-1.12 (m, 2H), 2.04-2.57 (m, 5H), 3.30 (s, 3H), 4.02 (s, 3H), 4.05-4.20 (m, 1H), 5.65-5.80 (m, 1H), 6.44-6.69 (m, 2H), 6.84 (d, J=7.4 Hz, 1H), 6.88-6.93 (m, 1H), 6.95-7.05 (m, 1H), 8.06 (d, J=8.3 Hz, 1H), 11.40-11.89 (brs, 1H).

MS(+): 429 [M+H]$^+$.
MS(−): 427 [M−H]$^−$.

Example 4-389

3-Cyclopropyl-6-{(E)-1-{4-[(cyclopropylmethyl)sulfonyl]phenyl}-2-[(2R)-5-oxopyrrolidin-2-yl]ethenyl}pyridin-2(1H)-one The title compound was obtained as a white solid (53 mg, 21% (two steps)) by performing the same reaction as in Example 4-289 except for using 1-bromo-4-[(cyclopropylmethyl)sulfonyl]benzene.

$^1$H NMR (300 MHz, CDCl$_3$) δ ppm 0.14-0.27 (m, 2H), 0.53-0.71 (m, 4H), 0.92-1.15 (m, 3H), 2.01-2.19 (m, 2H), 2.20-2.50 (m, 3H), 3.09 (d, J=6.8 Hz, 2H), 3.99-4.12 (m, 1H), 5.62 (d, J=7.4 Hz, 1H), 6.28 (s, 1H), 6.53 (d, J=8.9 Hz, 1H), 6.83 (d, J=7.4 Hz, 1H), 7.40 (d, J=8.3 Hz, 2H), 8.01 (d, J=8.6 Hz, 2H), 11.30-11.68 (brs, 1H).

MS(+): 439 [M+H]$^+$.
MS(−): 437 [M−H]$^−$.

Example 4-390

6-{(E)-1-[4-(Cyclopentylsulfonyl)phenyl]-2-[(2R)-5-oxopyrrolidin-2-yl]ethenyl}-3-cyclopropylpyridin-2(1H)-one The title compound was obtained as a white solid (29 mg, 11% (two steps)) by performing the same reaction as in Example 4-289 except for using 1-bromo-4-(cyclopentylsulfonyl)benzene.

$^1$H NMR (300 MHz, CDCl$_3$) δ ppm 0.48-0.72 (m, 2H), 0.93-1.19 (m, 2H), 1.50-2.53 (m, 13H), 3.45-3.63 (m, 1H), 3.99-4.14 (m, 1H), 5.61 (d, J=7.3 Hz, 1H), 6.58 (d, J=9.2 Hz, 1H), 6.66 (s, 1H), 6.83 (d, J=7.3 Hz, 1H), 7.40 (d, J=8.3 Hz, 2H), 7.97 (d, J=8.3 Hz, 2H), 11.77-12.22 (brs, 1H).

MS(+): 453 [M+H]$^+$.
MS(−): 451 [M−H]$^−$.

Example 4-391

6-{(E)-1-[3-Chloro-4-(cyclopentylsulfonyl)phenyl]-2-[(2R)-5-oxopyrrolidin-2-yl]ethenyl}-3-cyclopropylpyridin-2(1H)-one The title compound was obtained as a white solid (25 mg, 25% (two steps)) by performing the same reaction as in Example 4-289 except for using 4-bromo-2-chloro-1-(cyclopentylsulfonyl)benzene obtained in Reference Example 5-49.

¹H NMR (300 MHz, CDCl₃) δ ppm 0.50-0.70 (m, 2H), 0.93-1.10 (m, 2H), 1.53-2.52 (m, 13H), 3.96-4.21 (m, 2H), 5.60 (d, J=7.3 Hz, 1H), 6.64 (d, J=9.2 Hz, 1H), 6.85 (d, J=7.3 Hz, 1H), 6.97 (s, 1H), 7.31 (dd, J=8.3, 1.7 Hz, 1H), 7.40 (d, J=1.7 Hz, 1H), 8.18 (d, J=8.3 Hz, 1H), 12.17-12.53 (brs, 1H).

MS(+): 487 [M+H]⁺.
MS(−): 485 [M−H]⁻.

Example 4-392

2-Chloro-5-{(E)-1-(5-cyclopropyl-6-oxo-1,6-dihydropyridin-2-yl)-2-[(2R)-5-oxopyrrolidin-2-yl]ethenyl}benzonitrile The title compound was obtained as a yellow solid (64 mg, 34% (two steps)) by performing substantially the same reaction as in Example 4-278 except for using 2-chloro-5-(5,5-dimethyl-1,3,2-dioxaborinan-2-yl)benzonitrile obtained in Reference Example 5-50.

¹H NMR (300 MHz, CDCl₃) δ ppm 0.45-0.70 (m, 2H), 0.80-1.06 (m, 2H), 1.92-2.55 (m, 5H), 3.90-4.13 (m, 1H), 5.52 (d, J=7.4 Hz, 1H), 6.69 (d, J=9.8 Hz, 1H), 6.78 (d, J=7.1 Hz, 1H), 7.40-7.52 (m, 1H), 7.52-7.65 (m, 2H), 8.15-8.35 (brs, 1H), 12.60-13.11 (brs, 1H).

MS(+): 380 [M+H]⁺.
MS(−): 378 [M−H]⁻.

Example 4-393

3-Cyclopropyl-6-{(E)-1-[4-(difluoromethoxy)-3-methoxyphenyl]-2-[(2R)-5-oxopyrrolidin-2-yl]ethenyl}pyridin-2(1H)-one The title compound was obtained as a white solid (29 mg, 27% (two steps)) by performing substantially the same reaction as in Example 4-278 except for using 2-[4-(difluoromethoxy)-3-methoxyphenyl]-4,4,5,5-tetramethyl-1,3,2-dioxaborolane obtained in Reference Example 5-51.

¹H NMR (300 MHz, CDCl₃) δ ppm 0.53-0.65 (m, 2H), 0.88-1.40 (m, 2H), 2.05-2.50 (m, 5H), 3.88 (s, 3H), 4.10-4.24 (m, 1H), 5.69 (d, J=7.5 Hz, 1H), 6.53 (d, J=9.3 Hz, 1H), 6.61 (t, J=75.3 Hz, 1H), 6.75-6.90 (m, 3H), 7.20 (d, J=7.8 Hz, 1H), 7.32-7.53 (brs, 1H), 12.30-12.55 (brs, 1H).

MS(+): 417 [M+H]⁺.
MS(−): 415 [M−H]⁻.

Example 4-394

3-Cyclopropyl-6-{(E)-1-[4-(difluoromethoxy)-3-methylphenyl]-2-[(2R)-5-oxopyrrolidin-2-yl]ethenyl}pyridin-2(1H)-one The title compound was obtained as a white solid (64 mg, 55% (two steps)) by performing substantially the same reaction as in Example 4-278 except for using 2-[4-(difluoromethoxy)-3-methylphenyl]-4,4,5,5-tetramethyl-1,3,2-dioxaborolane obtained in Reference Example 5-52.

¹H NMR (300 MHz, CDCl₃) δ ppm 0.53-0.67 (m, 2H), 0.85-1.08 (m, 2H), 2.05-2.50 (m, 5H), 2.31 (s, 3H), 4.05-4.24 (m, 1H), 5.63-5.74 (m, 1H), 6.55 (d, J=8.4 Hz, 1H), 6.56 (t, J=74.4 Hz, 1H), 6.79 (d, J=9.0 Hz, 1H), 6.96-7.15 (m, 3H),= 7.21-7.40 (brs, 1H), 12.10-12.60 (brs, 1H).

MS(+): 401 [M+H]⁺.
MS(−): 399 [M−H]⁻.

Example 4-395

3-Cyclopropyl-6-{(E)-1-[4-(difluoromethoxy)-3-fluorophenyl]-2-[(2R)-5-oxopyrrolidin-2-yl]ethenyl}pyridin-2(1H)-one The title compound was obtained as a white solid (70 mg, 41% (two steps)) by performing substantially the same reaction as in Example 4-278 except for using 2-[4-(difluoromethoxy)-3-fluorophenyl]-4,4,5,5-tetramethyl-1,3,2-dioxaborolane obtained in Reference Example 5-53.

¹H NMR (300 MHz, CDCl₃) δ ppm 0.40-0.70 (m, 2H), 0.80-1.05 (m, 2H), 2.00-2.50 (m, 5H), 4.00-4.20 (m, 1H), 5.60 (d, J=7.4 Hz, 1H), 6.60 (t, J=73.0 Hz, 1H), 6.64 (d, J=9.5 Hz, 1H), 6.77 (d, J=7.4 Hz, 1H), 6.90-7.10 (m, 2H), 7.20-7.35 (m, 1H), 7.70-7.90 (brs, 1H), 12.43-13.00 (brs, 1H).

MS(+): 405 [M+H]⁺.
MS(−): 403 [M−H]⁻.

Example 4-396

6-{(E)-1-{3-Chloro-4-[(cyclopropylmethyl)sulfonyl]phenyl}-2-[(2R)-5-oxopyrrolidin-2-yl]ethenyl}-3-cyclopropylpyridin-2(1H)-one The title compound was obtained as a white solid (35 mg, 14% (two steps)) by performing the same reaction as in Example 4-289 except for using 4-bromo-2-chloro-1-[(cyclopropylmethyl)sulfonyl]benzene obtained in Reference Example 5-54.

¹H NMR (300 MHz, CDCl₃) δ ppm 0.22-0.34 (m, 2H), 0.51-0.73 (m, 4H), 0.95-1.12 (m, 3H), 2.07-2.53 (m, 5H), 3.41 (d, J=7.4 Hz, 2H), 4.00-4.15 (m, 1H), 5.61 (d, J=7.1 Hz, 1H), 6.64 (d, J=9.5 Hz, 1H), 6.69 (s, 1H), 6.86 (d, J=7.4 Hz, 1H), 7.34 (dd, J=8.2, 1.7 Hz, 1H), 7.41 (d, J=1.8 Hz, 1H), 8.24 (d, J=8.0 Hz, 1H), 11.95-12.30 (brs, 1H).

MS(+): 473 [M+H]⁺.
MS(−): 471 [M−H]⁻.

The structures of Examples 4-380 to 4-396 are shown below.

[Hyo 20-1]

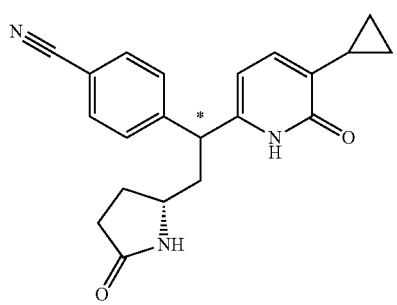

Example 4-380, 381

Example 4-382
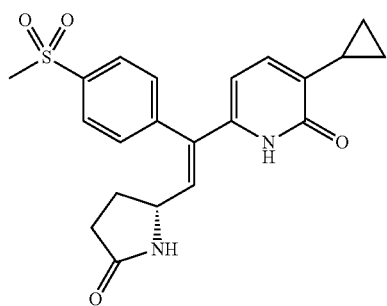
Example 4-387
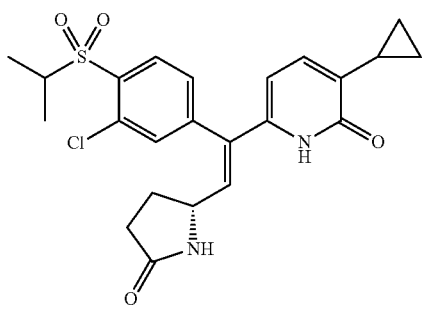
Example 4-383
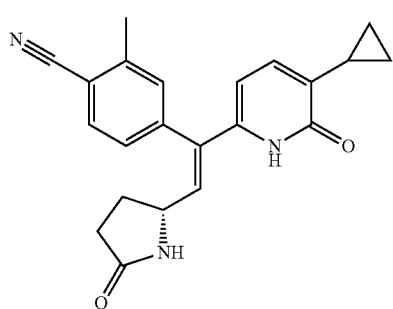
Example 4-388
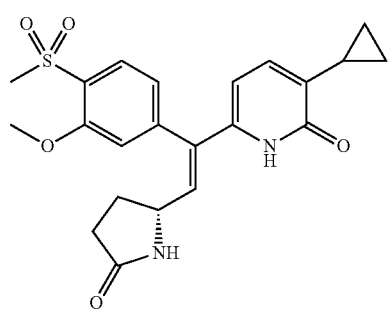
Example 4-384
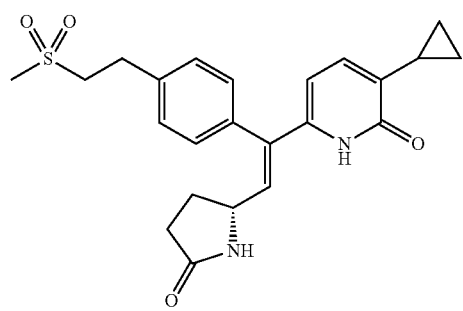
Example 4-389
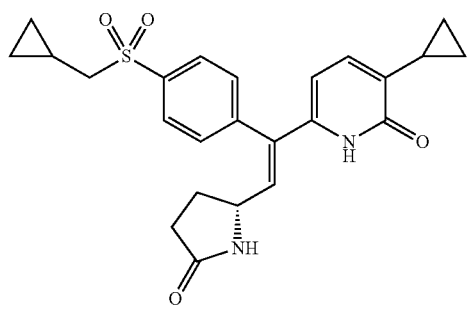
Example 4-385
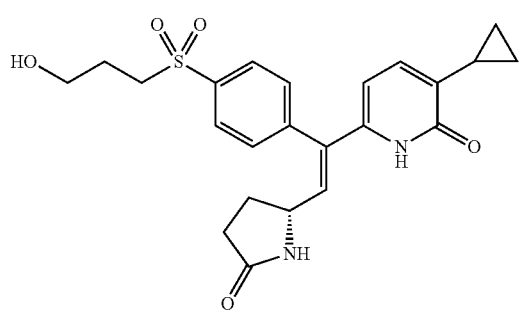
Example 4-390
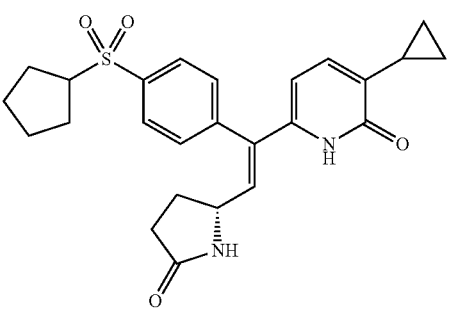
[Hyo 20-2]
Example 4-386
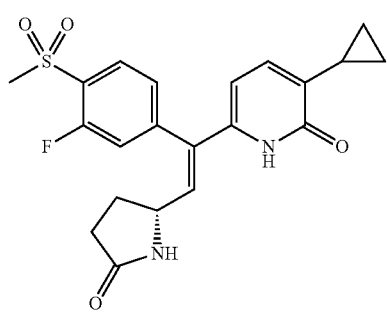
Example 4-391
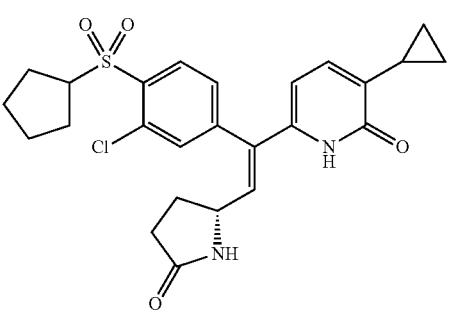

-continued

Example 4-392

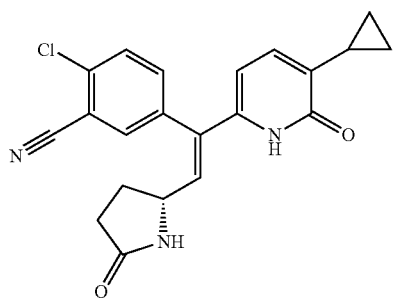

Example 4-393

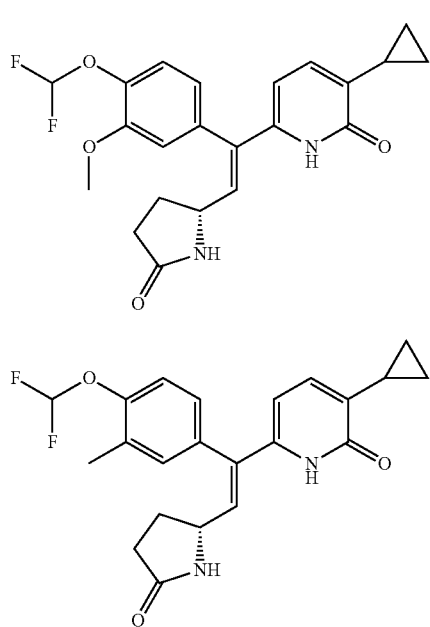

Example 4-394

Example 4-395

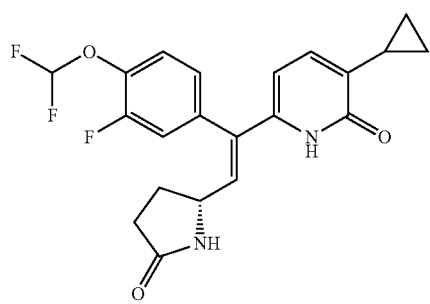

Example 4-396

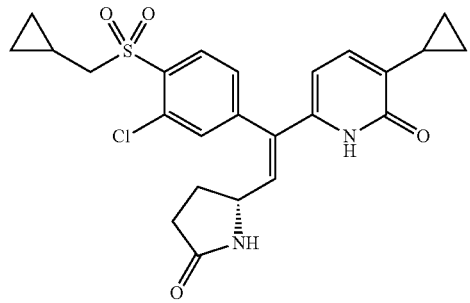

Example 5-1

(E)-6-{[3-Chloro-4-(methylsulfonyl)phenyl](cyclopentyloxyimino)methyl}-3-methylpyridin-2(1H)-one and (Z)-6-{[3-chloro-4-(methylsulfonyl)phenyl](cyclopentyloxyimino)methyl}-3-methylpyridin-2(1H)-one

[Ka 276]

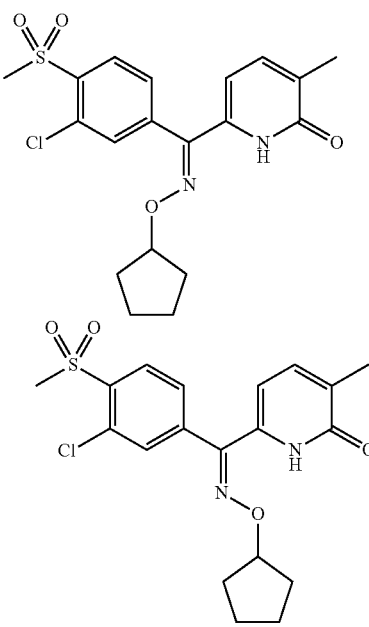

(1) 48% hydrobromic acid (7 mL) was added to a solution of [3-chloro-4-(methylsulfanyl)phenyl](6-methoxy-5-methylpyridin-2-yl)methanone obtained in Reference Example 1-40 (700 mg) in acetonitrile (7 mL) at room temperature, and the mixture was stirred at 95° C. for one hour. The reaction solution was neutralized with saturated aqueous sodium bicarbonate at room temperature and extracted with chloroform. The organic layer was dried over anhydrous magnesium sulfate and filtered. The solvent was then evaporated under reduced pressure. The resulting residue was purified by silica gel column chromatography (chloroform:methanol=50:1) to give 6-[3-chloro-4-(methylsulfanyl)benzoyl]-3-methylpyridin-2(1H)-one as a pale yellow solid (632 mg, 95%).

(2) Water (0.32 mL) and Oxone(R) (201 mg) were sequentially added to a solution of 6-[3-chloro-4-(methylsulfanyl)benzoyl]-3-methylpyridin-2(1H)-one (32 mg) in tetrahydrofuran-methanol (1:1, 1 mL) under ice-cooling, and the mixture was stirred at room temperature for one hour. Oxone (R) (201 mg) was further added at room temperature, followed by stirring for two hours. Oxone(R) (201 mg) was further added at room temperature, followed by stirring overnight. Separately, water (3 mL) and Oxone(R) (3.135 g) were sequentially added to a solution of 6-[3-chloro-4-(methylsulfanyl)benzoyl]-3-methylpyridin-2(1H)-one (300 mg) in tetrahydrofuran-methanol (1:1, 10 mL) under ice-cooling, and the mixture was stirred at room temperature overnight. Water was added to the reaction solutions. The reaction solutions were combined and extracted with chloroform. The organic layer was dried over anhydrous magnesium sulfate and filtered. The solvent was then evaporated under reduced pressure. The resulting residue was purified by silica gel column chromatography (chloroform:methanol=100:0→50:1) to give 6-[3-chloro-4-(methylsulfonyl)benzoyl]-3-methylpyridin-2(1H)-one (258 mg, 70%) as a pale yellow amorphous.

(3) O-cyclopentylhydroxylamine (0.3 mL) was added to a solution of 6-[3-chloro-4-(methylsulfonyl)benzoyl]-3-methylpyridin-2(1H)-one (220 mg) in n-butanol (2 mL) at room temperature, and the mixture was stirred under microwave irradiation at 200° C. for two hours. O-cyclopentylhydroxylamine (0.3 mL) was further added at room temperature, and the mixture was stirred under microwave irradiation at 200° C. for three hours. Water was added to the reaction solution, followed by extraction with chloroform. The organic layer was dried over anhydrous magnesium sulfate and filtered. The solvent was then evaporated under reduced pressure. The resulting residue was purified by silica gel column chromatography (hexane:ethyl acetate=3:1→1:1) and further purified by silica gel column chromatography (chloroform:ethyl acetate=50:1→25:1). The resulting less polar product was powdered with an ethyl acetate/hexane solution, and filtration operation gave (E)-6-{[3-chloro-4-(methylsulfonyl)phenyl](cyclopentyloxyimino)methyl}-3-methylpyridin-2(1H)-one as a white solid (95 mg, 34%). The more polar product was powdered with an ethyl acetate/hexane solution, and filtration operation gave (Z)-6-{[3-chloro-4-(methylsulfonyl)phenyl](cyclopentyloxyimino)methyl}-3-methylpyridin-2(1H)-one as a white solid (36 mg, 13%).

(E)-6-{[3-Chloro-4-(methylsulfonyl)phenyl] (cyclopentyloxyimino)methyl}-3-methylpyridin-2(1H)-one $^1$H NMR (300 MHz, CDCl$_3$) δ ppm 1.51-1.66 (m, 4H), 1.70-1.90 (m, 4H), 2.18 (s, 3H), 3.34 (s, 3H), 4.78-4.87 (m, 1H), 5.72 (d, J=7.0 Hz, 1H), 7.14 (d, J=7.0 Hz, 1H), 7.38 (dd, J=8.2, 1.6 Hz, 1H), 7.48 (d, J=1.6 Hz, 1H), 8.23 (d, J=8.2 Hz, 1H), 9.57-9.72 (brs, 1H).
MS(+): 409 [M+H]$^+$.

(Z)-6-{[3-Chloro-4-(methylsulfonyl)phenyl] (cyclopentyloxyimino)methyl}-3-methylpyridin-2(1H)-one $^1$H NMR (300 MHz, CDCl$_3$) δ ppm 1.52-1.83 (m, 4H), 1.84-2.08 (m, 4H), 2.18 (s, 3H), 3.29 (s, 3H), 4.83-5.00 (m, 1H), 5.95 (d, J=7.0 Hz, 1H), 7.22-7.35 (m, 1H), 7.56 (dd, J=8.2, 1.6 Hz, 1H), 7.69 (d, J=1.6 Hz, 1H), 8.16 (d, J=8.2 Hz, 1H), 10.17-10.52 (brs, 1H).
MS(+): 409 [M+H]$^+$.

Example 5-2

(E)-6-{[3-Chloro-4-(methylsulfanyl)phenyl] (cyclopentyloxyimino)methyl}-3-methylpyridin-2(1H)-one and (Z)-6-{[3-chloro-4-(methylsulfanyl)phenyl](cyclopentyloxyimino)methyl}-3-methylpyridin-2(1H)-one

[Ka 277]

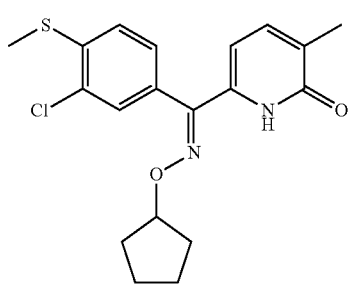

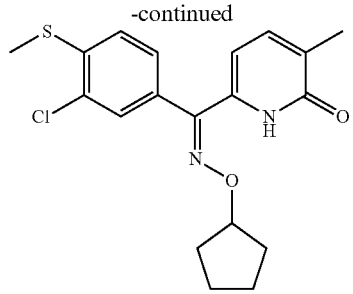

(E)-6-{[3-Chloro-4-(methylsulfanyl)phenyl] (cyclopentyloxyimino)methyl}-3-methylpyridin-2(1H)-one (45.7 mg, 17%) and (Z)-6-{[3-chloro-4-(methylsulfanyl)phenyl](cyclopentyloxyimino)methyl}-3-methylpyridin-2(1H)-one (27.4 mg, 10%) were obtained as white solids by performing substantially the same reaction as in Example 5-1(3) except for using 6-[3-chloro-4-(methylsulfanyl)benzoyl]-3-methylpyridin-2(1H)-one obtained in Example 5-1(1).

(E)-6-{[3-Chloro-4-(methylsulfanyl)phenyl] (cyclopentyloxyimino)methyl}-3-methylpyridin-2(1H)-one $^1$H NMR (300 MHz, CDCl$_3$) δ ppm 1.50-1.70 (m, 4H), 1.70-1.89 (m, 4H), 2.17 (d, J=0.8 Hz, 3H), 2.52 (s, 3H), 4.78 (quintet, J=4.1 Hz, 1H), 5.84 (d, J=7.0 Hz, 1H), 7.14 (dd, J=7.0, 1.2 Hz, 1H), 7.16-7.22 (m, 2H), 7.24-7.29 (m, 1H), 9.61-9.78 (brs, 1H).
MS(+): 377 [M+H]$^+$.

(Z)-6-{[3-Chloro-4-(methylsulfanyl)phenyl[(cyclopentyloxyimino)methyl]-3-methylpyridin-2(1H)-one $^1$H NMR (300 MHz, CDCl$_3$) δ ppm 1.54-1.79 (m, 4H), 1.79-2.08 (m, 4H), 2.18 (d, J=0.8 Hz, 3H), 2.50 (s, 3H), 4.80-4.92 (m, 1H), 6.01 (d, J=7.0 Hz, 1H), 7.14 (d, J=8.2 Hz, 1H), 7.23 (dd, J=7.0, 0.8 Hz, 1H), 7.33 (dd, J=8.2, 2.0 Hz, 1H), 7.48 (d, J=2.0 Hz, 1H), 10.05-10.17 (brs, 1H).
MS(+): 377 [M+H]$^+$.

Example 5-3

(E)-6-{(Cyclopentyloxyimino)[4-(methylsulfonyl)phenyl]methyl}-3-methylpyridin-2(1H)-one

[Ka 278]

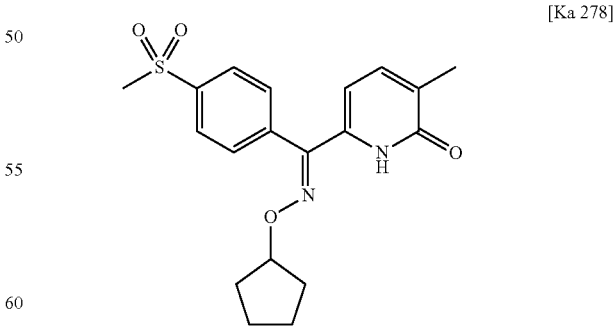

The title compound was obtained as a white solid (67.5 mg, 39% (three steps)) by performing substantially the same reaction as in Example 5-1 except for using (6-methoxy-5-methylpyridin-2-yl)[4-(methylsulfanyl)phenyl]methanone obtained in Reference Example 1-36.

¹H NMR (300 MHz, CDCl₃) δ ppm 1.45-1.90 (m, 8H), 2.17 (d, J=0.8 Hz, 3H), 3.14 (s, 3H), 4.75-4.90 (m, 1H), 5.71 (d, J=7.0 Hz, 1H), 7.13 (dd, J=7.0, 1.2 Hz, 1H), 7.46-7.52 (m, 2H), 8.00-8.07 (m, 2H), 9.60-9.90 (brs, 1H).
MS(+): 375 [M+H]⁺.

Example 6-1

6-[(1E)-1-(4-tert-Butylphenyl)-3-hydroxyprop-1-en-1-yl]-3-chloropyridin-2(1H)-one

[Ka 279]

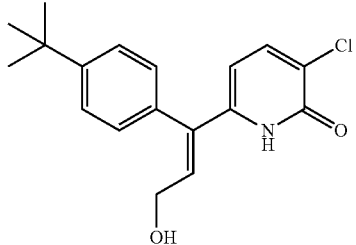

The title compound was obtained as a colorless powder (5 mg, 26%) by performing substantially the same reaction as in Example 1-1(2) except for using (2E)-3-(4-tert-butylphenyl)-3-(5-chloro-6-methoxypyridin-2-yl)prop-2-en-1-ol obtained in Reference Example 4-4.
¹H NMR (300 MHz, CDCl₃) δ ppm 1.35 (s, 9H), 4.29 (d, J=6.7 Hz, 2H), 6.12 (d, J=7.6 Hz, 1H), 6.48 (t, J=6.1 Hz, 1H), 7.08 (d, J=8.6 Hz, 2H), 7.42 (d, J=8.4 Hz, 2H), 7.54 (d, J=7.8 Hz, 1H).
MS(+): 318 [M+H]⁺.

Example 6-2

6-[(1E)-1-(4-tert-Butylphenyl)-3-(2-oxo-1,3-oxazolidin-3-yl)prop-1-en-1-yl]-3-chloropyridin-2(1H)-one

[Ka 280]

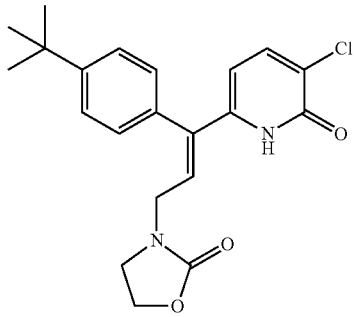

(1) A suspension of sodium hydride (purity: 60%, 60 mg) in tetrahydrofuran (1.0 mL) was added to a solution of 2-oxazolidinone (153 mg) in tetrahydrofuran (1.0 mL) under ice-cooling, and the mixture was stirred at room temperature for 30 minutes. 6-[(1E)-3-Bromo-1-(4-tert-butylphenyl)prop-1-en-1-yl]-3-chloro-2-methoxypyridine obtained in Reference Example 4-5 (303 mg) was added thereto, and the mixture was stirred at room temperature for 20 hours. Water was added to the reaction solution, followed by extraction with ethyl acetate. The organic layer was washed with brine and dried over sodium sulfate. After filtration, the solvent was evaporated under reduced pressure. The residue was purified by silica gel column chromatography (hexane:ethyl acetate=9:1→3:2) to give 3-[(2E)-3-(4-tert-butylphenyl)-3-(5-chloro-6-methoxypyridin-2-yl)prop-2-en-1-yl]-1,3-oxazolidin-2-one as a light brown powder (298 mg, 98%).

(2) The title compound was obtained as a colorless powder (148 mg, 52%) by performing substantially the same reaction as in Example 1-1(2) except for using 3-[(2E)-3-(4-tert-butylphenyl)-3-(5-chloro-6-methoxypyridin-2-yl)prop-2-en-1-yl]-1,3-oxazolidin-2-one.
¹H NMR (300 MHz, CDCl₃) δ ppm 1.36 (s, 9H), 3.56-3.66 (m, 2H), 3.99 (d, J=6.5 Hz, 2H), 4.27-4.36 (m, 2H), 6.03 (d, J=7.6 Hz, 1H), 6.43 (t, J=6.4 Hz, 1H), 7.11 (d, J=8.1 Hz, 2H), 7.46 (d, J=8.2 Hz, 2H), 7.51 (d, J=7.5 Hz, 1H), 10.36-10.67 (brs, 1H).
MS(+): 387 [M+H]⁺.

Example 6-3

6-[(1E)-1-(4-tert-Butylphenyl)-3-(2-oxopyrrolidin-1-yl)prop-1-en-1-yl]-3-chloropyridin-2(1H)-one

[Ka 281]

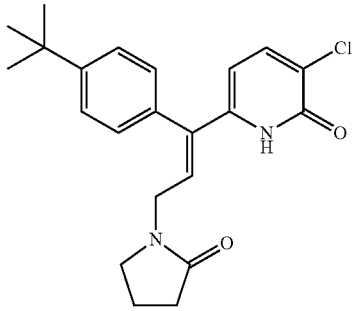

The title compound was obtained as a colorless powder (3 mg, 21%) by performing substantially the same reaction as in Example 6-2 except for using 2-pyrrolidinone in place of 2-oxazolidinone.
¹H NMR (300 MHz, CDCl₃) δ ppm 1.36 (s, 9H), 1.91-2.08 (m, 2H), 2.36 (t, J=8.2 Hz, 2H), 3.40 (t, J=7.1 Hz, 2H), 4.01 (d, J=6.5 Hz, 2H), 5.98 (d, J=7.6 Hz, 1H), 6.38 (t, J=6.5 Hz, 1H), 7.12 (d, J=8.4 Hz, 2H), 7.44 (d, J=8.4 Hz, 2H), 7.49 (d, J=7.6 Hz, 1H), 10.57-10.70 (m, 1H).
MS(+): 385 [M+H]⁺.

Example 6-4

6-[(1E)-1-(4-tert-Butylphenyl)-3-(2-oxopiperidin-1-yl)prop-1-en-1-yl]-3-chloropyridin-2(1H)-one

[Ka 282]

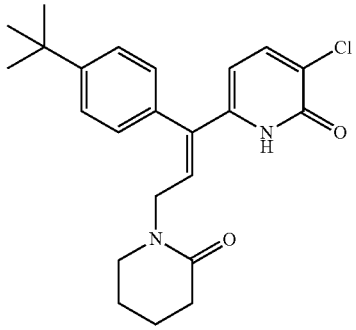

The title compound was obtained as a colorless powder (6 mg, 24%) by performing substantially the same reaction as in Example 6-2 except for using 2-piperidinone in place of 2-oxazolidinone.

¹H NMR (300 MHz, CDCl₃) δ ppm 1.36 (s, 9H), 1.73-1.81 (m, 4H), 2.33-2.44 (m, 2H), 3.10-3.19 (m, 2H), 4.07 (d, J=6.5 Hz, 2H), 6.13 (d, J=7.8 Hz, 1H), 6.24 (t, J=6.5 Hz, 1H), 7.11 (d, J=8.6 Hz, 2H), 7.45 (d, J=8.6 Hz, 2H), 7.50 (d, J=7.6 Hz, 1H).
MS(+): 399 [M+H]⁺.

Example 6-5

6-[(1E)-1-(4-tert-Butylphenyl)-3-(morpholin-4-yl)prop-1-en-1-yl]-3-chloropyridin-2(1H)-one

[Ka 283]

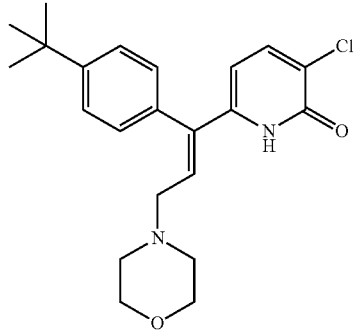

The title compound was obtained as a colorless powder (54 mg, 69%) by performing substantially the same reaction as in Example 6-2 except for using morpholine in place of 2-oxazolidinone.
¹H NMR (300 MHz, CDCl₃) δ ppm 1.36 (s, 9H), 2.35-2.55 (m, 4H), 3.06 (d, J=6.5 Hz, 2H), 3.63-3.82 (m, 4H), 6.14 (d, J=7.6 Hz, 1H), 6.41 (t, J=6.6 Hz, 1H), 7.07 (d, J=8.4 Hz, 2H), 7.44 (d, J=8.6 Hz, 2H), 7.51 (d, J=7.6 Hz, 1H), 9.02-9.30 (brs, 1H).
MS(+): 387 [M+H]⁺.

Example 6-6

1-[(2E)-3-(4-tert-Butylphenyl)-3-(5-chloro-6-oxo-1,6-dihydropyridin-2-yl)prop-2-en-1-yl]azepan-2-one

[Ka 284]

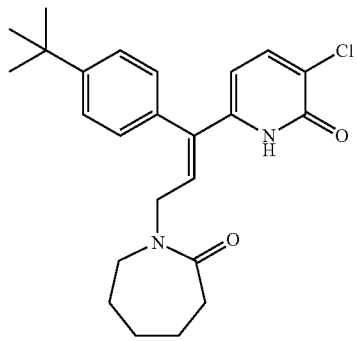

The title compound was obtained as a colorless powder (4 mg, 16%) by performing substantially the same reaction as in Example 6-2 except for using ε-caprolactam in place of 2-oxazolidinone.
¹H NMR (300 MHz, CDCl₃) δ ppm 1.36 (s, 9H), 1.59-1.80 (m, 6H), 2.49-2.58 (m, 2H), 3.17-3.26 (m, 2H), 4.08 (d, J=6.7 Hz, 2H), 6.14 (d, J=7.8 Hz, 1H), 6.22 (t, J=6.6 Hz, 1H), 7.10 (d, J=8.2 Hz, 2H), 7.46 (d, J=8.1 Hz, 2H), 7.51 (d, J=7.6 Hz, 1H).
MS(+): 413 [M+H]⁺.

Example 6-7

6-[(1E)-1-(4-tert-Butylphenyl)-3-(1,1-dioxido-1,2-thiazolidin-2-yl)prop-1-en-1-yl]-3-chloropyridin-2(1H)-one

[Ka 285]

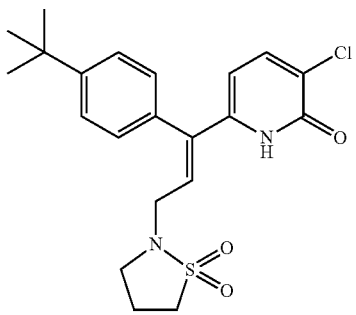

The title compound was obtained as a colorless powder (27 mg, 30%) by performing substantially the same reaction as in Example 6-2 except for using 1,1-dioxido-1-isothiazolidine in place of 2-oxazolidinone.
¹H NMR (300 MHz, CDCl₃) δ ppm 1.36 (s, 9H), 2.28-2.41 (m, 2H), 3.11-3.20 (m, 2H), 3.26 (t, J=6.8 Hz, 2H), 3.75 (d, J=6.7 Hz, 2H), 6.11 (d, J=7.8 Hz, 1H), 6.43 (t, J=6.7 Hz, 1H), 7.09 (d, J=8.6 Hz, 2H), 7.45 (d, J=8.6 Hz, 2H), 7.52 (d, J=7.6 Hz, 1H).
MS(+): 421 [M+H]⁺.

Example 6-8

6-[(1E)-1-(4-tert-Butylphenyl)-3-(pyrrolidin-1-yl)prop-1-en-1-yl]-3-chloropyridin-2(1H)-one

[Ka 286]

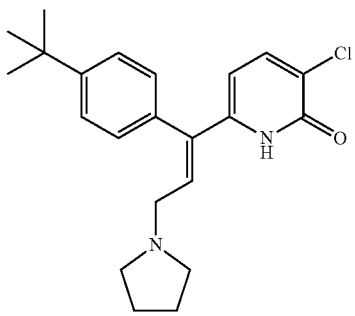

The title compound was obtained as a colorless powder (57 mg, 63%) by performing substantially the same reaction as in Example 6-2 except for using pyrrolidine in place of 2-oxazolidinone.
¹H NMR (300 MHz, CDCl₃) δ ppm 1.36 (s, 9H), 1.75-1.85 (m, 4H), 2.48-2.63 (m, 4H), 3.22 (d, J=6.7 Hz, 2H), 6.15-6.21 (m, 1H), 6.47 (t, J=6.7 Hz, 1H), 7.08 (d, J=8.4 Hz, 2H), 7.43 (d, J=8.4 Hz, 2H), 7.52 (d, J=8.1 Hz, 1H).
MS(+): 371 [M+H]⁺.

Example 6-9

1-[(2E)-3-(4-tert-Butylphenyl)-3-(5-chloro-6-oxo-1,6-dihydropyridin-2-yl)prop-2-en-1-yl]pyrrolidine-2,5-dione

[Ka 287]

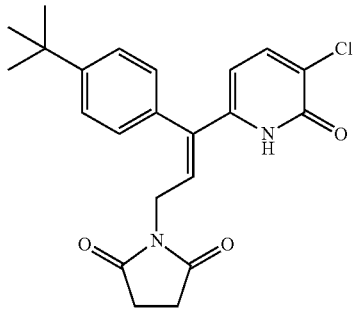

The title compound was obtained as a colorless powder (50 mg, 52%) by performing substantially the same reaction as in Example 6-2 except for using succinimide in place of 2-oxazolidinone.

$^1$H NMR (300 MHz, CDCl$_3$) δ ppm 1.36 (s, 9H), 2.68 (s, 4H), 4.22 (d, J=6.2 Hz, 2H), 6.08-6.17 (m, 2H), 7.19 (d, J=8.6 Hz, 2H), 7.44-7.54 (m, 3H).
MS(+): 399 [M+H]$^+$.

Example 6-10

6-[(1E)-1-(4-tert-Butylphenyl)-3-phenoxyprop-1-en-1-yl]-3-chloropyridin-2(1H)-one

[Ka 288]

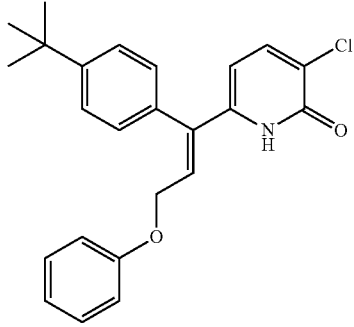

(1) N,N,N',N'-Tetramethylazodicarbodiimide (104 mg) was added to a solution of (2E)-3-(4-tert-butylphenyl)-3-(5-chloro-6-methoxypyridin-2-yl)prop-2-en-1-ol obtained in Reference Example 4-4 (199 mg), phenol (63 mg) and tributylphosphine (189 mg) in tetrahydrofuran (4 mL) under ice-cooling, and the mixture was stirred at room temperature for 20 hours. The solvent was evaporated from the reaction solution under reduced pressure. The residue was purified by silica gel column chromatography (hexane:ethyl acetate=19:1) to give 6-[(1E)-1-(4-tert-butylphenyl)-3-phenoxyprop-1-en-1-yl]-3-chloro-2-methoxypyridine as a yellow oil (212 mg, 87%).

(2) The title compound was obtained as a colorless powder (3 mg, 2%) by performing substantially the same reaction as in Example 1-1(2) except for using 6-[(1E)-1-(4-tert-butylphenyl)-3-phenoxyprop-1-en-1-yl]-3-chloro-2-methoxypyridine.

$^1$H NMR (300 MHz, CDCl$_3$) δ ppm 1.36 (s, 9H), 4.59 (d, J=6.4 Hz, 2H), 6.24 (d, J=7.6 Hz, 1H), 6.48 (t, J=6.3 Hz, 1H), 6.79-6.85 (m, 2H), 6.96 (t, J=7.2 Hz, 1H), 7.13 (d, J=8.4 Hz, 2H), 7.20-7.33 (m, 2H), 7.46 (d, J=8.4 Hz, 2H), 7.54 (d, J=7.6 Hz, 1H).
MS(+): 394 [M+H]$^+$.

Example 6-11

6-[(1E)-1-(4-tert-Butylphenyl)-3-(2-oxopyridin-1(2H)-yl)prop-1-en-1-yl]-3-chloropyridin-2(1H)-one

[Ka 289]

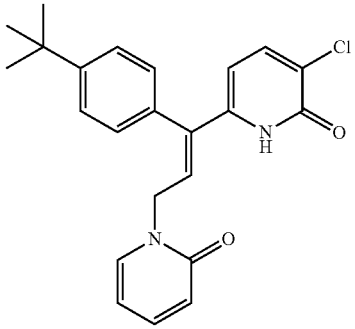

The title compound was obtained as a colorless powder (103 mg, 59%) by performing substantially the same reaction as in Example 6-10 except for using 2-hydroxypyridine in place of phenol.

$^1$H NMR (300 MHz, CDCl$_3$) δ ppm 1.37 (s, 9H), 4.61 (d, J=6.5 Hz, 2H), 6.15 (d, J=7.2 Hz, 2H), 6.44 (t, J=6.7 Hz, 1H), 6.59 (d, J=9.8 Hz, 1H), 7.03-7.07 (m, 1H), 7.17 (d, J=8.2 Hz, 2H), 7.30-7.36 (m, 1H), 7.48-7.52 (m, 3H).
MS(+): 395 [M+H]$^+$.

Example 6-12

6-[(1E)-1-(4-tert-Butylphenyl)-4-(1,1-dioxide-1,2-thiazolidin-2-yl)but-1-en-1-yl]-3-chloropyridin-2(1H)-one

[Ka 290]

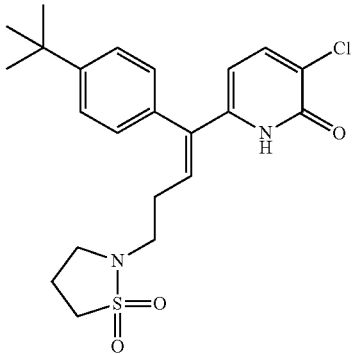

The title compound was obtained as a colorless powder (2 mg, 2%) by performing substantially the same reaction as in Example 6-10 except for using (3E)-4-(4-tert-butylphenyl)-4-(5-chloro-6-methoxypyridin-2-yl)but-3-en-1-ol obtained in Reference Example 4-10 in place of (2E)-3-(4-tert-butylphenyl)-3-(5-chloro-6-methoxypyridin-2-yl)prop-2-en-1-ol and using 1,1-dioxide-1-isothiazolidine in place of phenol.

$^1$H NMR (300 MHz, CDCl$_3$) δ ppm 1.35 (s, 9H), 2.27-2.34 (m, 2H), 2.40-2.45 (m, 2H), 3.10 (t, J=6.7 Hz, 2H), 3.12-3.17

(m, 4H), 6.13 (d, J=7.8 Hz, 1H), 6.30 (t, J=7.3 Hz, 1H), 7.08 (d, J=8.7 Hz, 2H), 7.42 (d, J=8.3 Hz, 2H), 7.49 (d, J=7.8 Hz, 1H), 9.05-9.16 (brs, 1H).

MS(+): 435 [M+H]⁺.

Example 6-13

1-[(3E)-4-(4-tert-Butylphenyl)-4-(5-chloro-6-oxo-1,6-dihydropyridin-2-yl)but-3-en-1-yl]pyrrolidine-2,5-dione

[Ka 291]

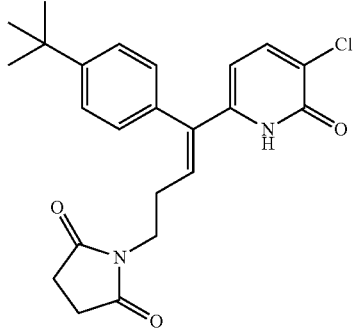

The title compound was obtained as a colorless powder (102 mg, 59%) by performing substantially the same reaction as in Example 6-10 except for using (3E)-4-(4-tert-butylphenyl)-4-(5-chloro-6-methoxypyridin-2-yl)but-3-en-1-ol obtained in Reference Example 4-10 in place of (2E)-3-(4-tert-butylphenyl)-3-(5-chloro-6-methoxypyridin-2-yl)prop-2-en-1-ol and using succinimide in place of phenol.

¹H NMR (300 MHz, CDCl₃) δ ppm 1.35 (s, 9H), 2.42-2.52 (m, 2H), 2.64 (s, 4H), 3.62 (t, J=6.6 Hz, 2H), 6.15 (d, J=7.6 Hz, 1H), 6.21 (t, J=7.5 Hz, 1H), 7.02 (d, J=8.4 Hz, 2H), 7.41 (d, J=8.6 Hz, 2H), 7.51 (d, J=7.6 Hz, 1H).

MS(+): 413 [M+H]⁺.

Example 6-14

6-[(E)-1-(4-tert-Butylphenyl)-2-(2-oxopyrrolidin-1-yl)ethenyl]-3-chloropyridin-2(1H)-one

[Ka 292]

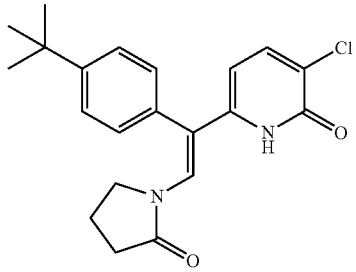

(1) A solution of 6-[(E)-2-bromo-1-(4-tert-butylphenyl)ethenyl]-3-chloro-2-methoxypyridine obtained in Reference Example 4-7 (109 mg), 2-pyrrolidone (73 mg), tris(dibenzylideneacetone)dipalladium(0) (11 mg), rac-2,2'-bis(diphenylphosphino)-1,1'-binaphthyl (22 mg) and cesium carbonate (329 mg) in toluene (3 mL) was stirred at an external temperature of 130° C. for four hours in a nitrogen atmosphere. Water was added to the reaction solution, followed by extraction with ethyl acetate. The organic layer was washed with brine and dried over sodium sulfate. After filtration, the solvent was evaporated under reduced pressure. The residue was purified by silica gel column chromatography (hexane:ethyl acetate=9:1→1:1) to give 1-[(E)-2-(4-tert-butylphenyl)-2-(5-chloro-6-methoxypyridin-2-yl)ethenyl]pyrrolidin-2-one as a yellow powder (82 mg, 75%).

(2) The title compound was obtained as a colorless powder (11 mg, 15%) by performing substantially the same reaction as in Example 1-1(2) except for using 1-[(E)-2-(4-tert-butylphenyl)-2-(5-chloro-6-methoxypyridin-2-yl)ethenyl]pyrrolidin-2-one.

¹H NMR (300 MHz, CDCl₃) δ ppm 1.36 (s, 9H), 1.85-1.98 (m, 2H), 2.44 (t, J=8.1 Hz, 2H), 2.95 (t, J=7.3 Hz, 2H), 6.20 (d, J=7.6 Hz, 1H), 7.13 (d, J=8.6 Hz, 2H), 7.43 (d, J=8.6 Hz, 2H), 7.51 (d, J=7.8 Hz, 1H), 7.56 (s, 1H).

MS(+): 371 [M+H]⁺.

Example 6-15

6-[(1E)-1-(4-tert-Butylphenyl)-3-oxo-3-(pyrrolidin-1-yl)prop-1-en-1-yl]-3-chloropyridin-2(1H)-one

[Ka 293]

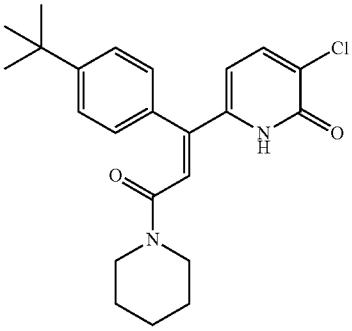

(1) 1-Ethyl-3-(3-dimethylaminopropyl)carbodiimide hydrochloride (80 mg) and 1-hydroxybenzotriazole (61 mg) were added to a solution of (2E)-3-(4-tert-butylphenyl)-3-(5-chloro-6-methoxypyridin-2-yl)prop-2-enoic acid obtained in Reference Example 4-6 (137 mg) in N,N-dimethylformamide (2 mL), and the mixture was stirred for 15 minutes. Thereafter, piperidine (50 mg) was added and the mixture was stirred at room temperature for 15 hours. The reaction solution was diluted with ethyl acetate. This was sequentially washed with saturated aqueous sodium bicarbonate, water and brine and dried over sodium sulfate. After filtration, the solvent was evaporated under reduced pressure. The residue was purified by silica gel column chromatography (hexane:ethyl acetate=4:1→1:1) to give (2E)-3-(4-tert-butylphenyl)-3-(5-chloro-6-methoxypyridin-2-yl)-1-(pyrrolidin-1-yl)prop-2-en-1-one as a colorless oil (63 mg, 40%).

(2) The title compound was obtained as a colorless powder (23 mg, 38%) by performing substantially the same reaction as in Example 1-1(2) except for using (2E)-3-(4-tert-butylphenyl)-3-(5-chloro-6-methoxypyridin-2-yl)-1-(pyrrolidin-1-yl)prop-2-en-1-one.

¹H NMR (300 MHz, CDCl₃) δ ppm 1.33 (s, 9H), 1.67-1.76 (m, 4H), 3.23-3.31 (m, 2H), 3.34-3.42 (m, 2H), 6.17 (d, J=7.6 Hz, 1H), 6.62 (s, 1H), 7.23 (d, J=8.6 Hz, 2H), 7.36-7.42 (m, 2H), 7.55 (d, J=7.6 Hz, 1H).

MS(+): 385 [M+H]⁺.

Example 6-16

6-[(1E)-1-(4-tert-Butylphenyl)-3-(3-methyl-2-oxoimidazolidin-1-yl)prop-1-en-1-yl]-3-chloropyridin-2(1H)-one (1) 1-Methyl-2-imidazolidinone (80 mg) and potassium carbonate (135 mg) were added to a solution of 6-[(1E)-3- bromo-1-(4-tert-butylphenyl)prop-1-en-1-yl]-3-chloro-2-methoxypyridine (123 mg) in acetonitrile (2 mL), and the mixture was stirred at room temperature for 3.5 days. The reaction solution was poured into water, followed by extraction with ethyl acetate. The organic layer was washed with brine, dried over sodium sulfate and filtered, after which the solvent was evaporated under reduced pressure. The residue was purified by silica gel column chromatography (hexane:ethyl acetate=4:1→0:10) to give 1-[(2E)-3-(4-tert-butylphenyl)-3-(5-chloro-6-methoxypyridin-2-yl)prop-2-en-1-yl]-3-methylimidazolidin-2-one as a yellow oil (13 mg, 10%).

(2) The title compound was obtained as a green powder (3 mg, 22%) by performing substantially the same reaction as in Example 1-1(2) except for using 1-[(2E)-3-(4-tert-butylphenyl)-3-(5-chloro-6-methoxypyridin-2-yl)prop-2-en-1-yl]-3-methylimidazolidin-2-one.

$^1$H NMR (600 MHz, CDCl$_3$) δ ppm 1.38 (s, 9H), 2.81 (s, 3H), 3.23-3.34 (m, 4H), 3.91 (d, J=6.9 Hz, 2H), 6.12 (d, J=7.3 Hz, 1H), 6.31 (t, J=6.6 Hz, 1H), 7.13 (d, J=8.3 Hz, 2H), 7.46 (d, J=8.3 Hz, 2H), 7.52 (d, J=7.8 Hz, 1H), 9.33-9.53 (brs, 1H).
MS(+): 400 [M+H]$^+$.

Example 6-17

2-[(2E)-3-(4-tert-Butylphenyl)-3-(5-chloro-6-oxo-1,6-dihydropyridin-2-yl)prop-2-en-1-yl]-2,3-dihydro-1H-isoindol-1-one (1) 2-[(2E)-3-(4-tert-Butylphenyl)-3-(5-chloro-6-oxo-1,6-dihydropyridin-2-yl)prop-2-en-1-yl]-1H-isoindole-1,3(2H)-dione was obtained as a gray powder (184 mg, 69% (two steps)) by performing substantially the same reaction as in Examples 1-94(1) and 1-1(2) sequentially except for using (2E)-3-(4-tert-butylphenyl)-3-(5-chloro-6-methoxypyridin-2-yl)prop-2-en-1-ol obtained in Reference Example 4-4 in place of (3E)-4-(5-cyclopropyl-6-methoxypyridin-2-yl)-4-[4-(methylsulfanyl)phenyl]but-3-en-1-ol obtained in Example 1-92(2).

(2) Sodium borohydride (52 mg) was added to a suspension of 2-[(2E)-3-(4-tert-butylphenyl)-3-(5-chloro-6-oxo-1,6-dihydropyridin-2-yl)prop-2-en-1-yl]-1H-isoindole-1,3(2H)-dione (50 mg) in methanol (2 mL) under ice-cooling, and the mixture was stirred at room temperature for one hour. Water was added to the reaction solution, followed by extraction with chloroform. The organic layer was dried over sodium sulfate and filtered. The solvent was then evaporated under reduced pressure. A solution of the resulting residue in trifluoroacetic acid (2 mL) was stirred under ice-cooling, during which sodium borohydride (50 mg) was added thereto. The mixture was stirred at room temperature for one hour. The reaction solution was ice-cooled, adjusted to a pH of 12 or more with a 1 M sodium hydroxide solution and then extracted with chloroform. The organic layer was dried over sodium sulfate and filtered. The solvent was then evaporated under reduced pressure. The residue was purified by silica gel column chromatography (chloroform:methanol=10:0→9:1) and then powdered with ethyl acetate. The precipitated crystals were collected by filtration and dried to give the title compound as a colorless powder (11 mg, 23%).

$^1$H NMR (300 MHz, CDCl$_3$) δ ppm 1.36 (s, 9H), 4.34 (d, J=6.5 Hz, 2H), 4.38 (s, 2H), 6.11 (d, J=7.1 Hz, 1H), 6.43 (t, J=6.5 Hz, 1H), 7.18 (d, J=8.4 Hz, 2H), 7.40-7.58 (m, 6H), 7.84 (d, J=6.8 Hz, 1H).
MS(+): 433 [M+H]$^+$.

Example 6-18

1-[(2E)-3-(4-tert-Butylphenyl)-3-(5-chloro-6-oxo-1,6-dihydropyridin-2-yl)prop-2-en-1-yl]azocan-2-one The title compound was obtained as a light gray powder (3 mg, 2% (two steps)) by performing substantially the same reaction as in Example 6-16 except for using azocan-2-one in place of 1-methyl-2-imidazolidinone.

$^1$H NMR (300 MHz, CDCl$_3$) δ ppm 1.36 (s, 9H), 1.41-1.54 (m, 6H), 1.74-1.88 (m, 2H), 2.46-2.54 (m, 2H), 3.33-3.42 (m, 2H), 4.03 (d, J=6.5 Hz, 2H), 6.13 (d, J=7.6 Hz, 1H), 6.29 (t, J=6.5 Hz, 1H), 7.11 (d, J=8.4 Hz, 2H), 7.45 (d, J=8.4 Hz, 2H), 7.51 (d, J=7.6 Hz, 1H).
MS(+): 427 [M+H]$^+$.

Example 6-19

6-[(1E)-1-(4-tert-Butylphenyl)-3-(1-methyl-2-oxopyrrolidin-3-yl)prop-1-en-1-yl]-3-chloropyridin-2(1H)-one (1) A solution of N-methylpyrrolidone (0.7 mL) in tetrahydrofuran (3 mL) was stirred at −78° C. in a nitrogen atmosphere, during which a lithium diisopropylamide solution (2.2 M, 0.5 mL) was added dropwise thereto. The mixture was stirred at the same temperature for 30 minutes. A solution of 6-[(1E)-3-bromo-1-(4-tert-butylphenyl)prop-1-en-1-yl]-3-chloro-2-methoxypyridine (182 mg) in tetrahydrofuran (2 mL) was slowly added dropwise thereto, and the mixture was stirred at −78° C. for one hour. Water was added to the reaction solution, which was then warmed to room temperature and extracted with ethyl acetate. The organic layer was washed with brine, dried over sodium sulfate and filtered, after which the solvent was evaporated under reduced pressure. The residue was purified by silica gel column chromatography (hexane:ethyl acetate=1:1→0:10) to give 3-[(2E)-3-(4-tert-butylphenyl)-3-(5-chloro-6-methoxypyridin-2-yl)prop-2-en-1-yl]-1-methylpyrrolidin-2-one as a colorless oil (176 mg, 93%).

(2) The title compound was obtained as a colorless powder (112 mg, 66%) by performing substantially the same reaction as in Example 1-1(2) except for using 3-[(2E)-3-(4-tert-butylphenyl)-3-(5-chloro-6-methoxypyridin-2-yl)prop-2-en-1-yl]-1-methylpyrrolidin-2-one.

$^1$H NMR (300 MHz, CDCl$_3$) δ ppm 1.35 (s, 9H), 1.52-1.70 (m, 1H), 2.19-2.36 (m, 2H), 2.55-2.75 (m, 2H), 2.83 (s, 3H), 3.18-3.36 (m, 2H), 5.96-6.04 (m, 1H), 6.39-6.50 (m, 1H), 7.08 (d, J=8.4 Hz, 2H), 7.41 (d, J=8.2 Hz, 2H), 7.47 (d, J=7.6 Hz, 1H).
MS(+): 399 [M+H]$^+$.

Example 6-20

3-Chloro-6-[(1E)-1-[4-(cyclopropylsulfonyl)phenyl]-3-(2-oxopyrrolidin-1-yl)prop-1-en-1-yl]pyridin-2(1H)-one The title compound was obtained as a colorless powder (8 mg, 5% (three steps)) by performing substantially the same reaction as in Examples 6-3 and 1-2 sequentially except for using 6-{(1E)-3-bromo-1-[4-(cyclopropylsulfanyl)phenyl]prop-1-en-1-yl}-3-chloro-2-methoxypyridine obtained in Reference Example 4-12 in place of 6-[(1E)-3-bromo-1-(4-tert-butylphenyl)prop-1-en-1-yl]-3-chloro-2-methoxypyridine obtained in Reference Example 4-5.

¹H NMR (600 MHz, CDCl₃) δ ppm 1.08-1.19 (m, 2H), 1.38-1.47 (m, 2H), 1.98-2.10 (m, 2H), 2.33-2.43 (m, 2H), 2.51-2.58 (m, 1H), 3.45 (t, J=7.1 Hz, 2H), 3.97 (d, J=6.4 Hz, 2H), 5.82 (d, J=7.3 Hz, 1H), 6.54 (t, J=6.6 Hz, 1H), 7.48 (d, J=8.3 Hz, 2H), 7.51 (d, J=7.8 Hz, 1H), 8.01 (d, J=8.3 Hz, 2H), 10.78-11.02 (brs, 1H).
MS(+): 433 [M+H]⁺.

Example 6-21

3-Chloro-6-[(1E)-1-[4-(cyclopropylsulfonyl)phenyl]-3-(2-oxo-1,3-oxazolidin-3-yl)prop-1-en-1-yl]pyridin-2(1H)-one The title compound was obtained as a colorless powder (61 mg, 37% (three steps)) by performing substantially the same reaction as in Examples 6-2 and 1-2 sequentially except for using 6-{(1E)-3-bromo-1-[4-(cyclopropylsulfanyl)phenyl]prop-1-en-1-yl}-3-chloro-2-methoxypyridine obtained in Reference Example 4-12 in place of 6-[(1E)-3-bromo-1-(4-tert-butylphenyl)prop-1-en-1-yl]-3-chloro-2-methoxypyridine obtained in Reference Example 4-5.
¹H NMR (300 MHz, CDCl₃) δ ppm 1.08-1.17 (m, 2H), 1.39-1.47 (m, 2H), 2.48-2.60 (m, 1H), 3.74 (dd, J=8.7, 7.3 Hz, 2H), 3.97 (d, J=6.4 Hz, 2H), 4.33 (dd, J=8.9, 7.1 Hz, 2H), 5.74 (d, J=7.6 Hz, 1H), 6.77 (t, J=6.6 Hz, 1H), 7.40-7.54 (m, 3H), 8.01 (d, J=8.2 Hz, 2H).
MS(+): 435 [M+H]⁺.

Example 6-22

3-Chloro-6-{(1E)-3-(2-oxo-1,3-oxazolidin-3-yl)-1-[4-(propan-2-yl)phenyl]prop-1-en-1-yl}pyridin-2(1H)-one (1) 6-[(1Z)-3-Bromo-1-iodoprop-1-en-1-yl]-3-chloro-2-methoxypyridine was obtained as a red oil (2.3 g, 100%) by performing substantially the same reaction as in Reference Example 4-5 except for using (2Z)-3-(5-chloro-6-methoxypyridin-2-yl)-3-iodoprop-2-en-1-ol obtained in Reference Example 4-3.
(2) 3-[(2Z)-3-Bromo-3-(5-chloro-6-methoxypyridin-2-yl)prop-2-en-1-yl]-1,3-oxazolidin-2-one was obtained as a light brown oil (225 mg, 18%) by performing substantially the same reaction as in Example 6-2(1) except for using 6-[(1Z)-3-bromo-1-iodoprop-1-en-1-yl]-3-chloro-2-methoxypyridine.
(3) The title compound was obtained as a colorless powder (32 mg, 25% (two steps)) by performing substantially the same reaction as in Example 4-98(1)(2) except for using 4-isopropylphenylboronic acid and 3-[(2Z)-3-bromo-3-(5-chloro-6-methoxypyridin-2-yl)prop-2-en-1-yl]-1,3-oxazolidin-2-one in a nitrogen atmosphere.
¹H NMR (300 MHz, CDCl₃) δ ppm 1.29 (d, J=7.0 Hz, 6H), 2.96 (quin, J=7.2 Hz, 1H), 3.62 (s, 2H), 3.99 (d, J=6.5 Hz, 2H), 4.26-4.36 (m, 2H), 5.93-6.02 (m, 1H), 6.41-6.51 (m, 1H), 7.11 (d, J=8.1 Hz, 2H), 7.30 (d, J=8.4 Hz, 2H), 7.50 (d, J=7.6 Hz, 1H).
MS(+): 373 [M+H]⁺.

Example 6-23

6-[(1E)-1-(4-tert-Butylphenyl)-3-(5-oxo-2,5-dihydro-1,2,4-oxadiazol-3-yl)prop-1-en-1-yl]-3-chloropyridin-2(1H)-one (1) A solution of (3E)-4-(4-tert-butylphenyl)-4-(5-chloro-6-methoxypyridin-2-yl)but-3-enenitrile obtained in Reference Example 4-13 (101 mg) in isopropanol (3 mL) was stirred at 105° C., during which a 50% hydroxylamine solution (0.1 mL) was added dropwise thereto. The mixture was stirred at the same temperature for two hours. The reaction solution was left to cool and then the solvent was evaporated under reduced pressure. Carbonyldiimidazole (72 mg) was added to a solution of the residue in 1,4-dioxane (3 mL), and the mixture was stirred at 120° C. for 30 minutes. Carbonyldiimidazole (55 mg) was further added and the mixture was stirred at 140° C. for 30 minutes. The reaction solution was left to cool and then water was added, followed by extraction with ethyl acetate. The organic layer was washed with brine, dried over sodium sulfate and filtered, after which the solvent was evaporated under reduced pressure. The residue was purified by silica gel column chromatography (chloroform:methanol=10:0→9:1) to give 3-[(2E)-3-(4-tert-butylphenyl)-3-(5-chloro-6-methoxypyridin-2-yl)prop-2-en-1-yl]-1,2,4-oxadiazol-5(2H)-one as an orange oil (73 mg, 62%).
(2) The title compound was obtained as a colorless powder (1 mg, 2%) by performing substantially the same reaction as in Example 1-1(2) except for using 3-[(2E)-3-(4-tert-butylphenyl)-3-(5-chloro-6-methoxypyridin-2-yl)prop-2-en-1-yl]-1,2,4-oxadiazol-5(2H)-one.
¹H NMR (300 MHz, CDCl₃) δ ppm 1.36 (s, 9H), 3.62 (d, J=6.8 Hz, 2H), 6.05 (d, J=7.9 Hz, 1H), 6.52 (t, J=7.0 Hz, 1H), 7.14 (d, J=8.5 Hz, 2H), 7.46 (d, J=8.5 Hz, 2H), 7.63 (d, J=7.8 Hz, 1H).
MS(+): 386 [M+H]⁺.

Example 6-24

6-[(1E)-1-(4-tert-Butylphenyl)-4-hydroxybut-1-en-1-yl]-3-chloropyridin-2(1H)-one The title compound was obtained as a colorless powder (33 mg, 34%) by performing substantially the same reaction as in Example 1-1(2) except for using (3E)-4-(4-tert-butylphenyl)-4-(5-chloro-6-methoxypyridin-2-yl)but-3-en-1-ol obtained in Reference Example 4-10.
¹H NMR (300 MHz, CDCl₃) δ ppm 1.36 (s, 9H), 2.39-2.51 (m, 2H), 2.94-3.08 (m, 1H), 3.74-3.86 (m, 2H), 5.95 (d, J=7.6 Hz, 1H), 6.57 (t, J=7.1 Hz, 1H), 7.13 (d, J=8.2 Hz, 2H), 7.41 (d, J=8.2 Hz, 2H), 7.50 (d, J=7.6 Hz, 1H), 11.39-11.66 (brs, 1H).
MS(+): 332 [M+H]⁺.

Example 6-25

6-[(1E)-1-(4-tert-Butylphenyl)-4-(pyrrolidin-1-yl)but-1-en-1-yl]-3-chloropyridin-2(1H)-one The title compound was obtained as a light brown powder (13 mg, 14% (two steps)) by performing substantially the same reaction as in Reference Example 4-5 and Example 6-2 sequentially except for using pyrrolidine in place of NaH and 2-oxazolidinone and using (3E)-4-(4-tert-butylphenyl)-4-(5-chloro-6-methoxypyridin-2-yl)but-3-en-1-ol obtained in Reference Example 4-10.
¹H NMR (300 MHz, CDCl₃) δ ppm 1.36 (s, 9H), 1.87-1.98 (m, 4H), 2.48-2.62 (m, 2H), 2.75-3.07 (m, 6H), 5.93 (d, J=7.6 Hz, 1H), 6.54 (t, J=7.0 Hz, 1H), 7.12 (d, J=8.5 Hz, 2H), 7.39-7.52 (m, 3H).
MS(+): 385 [M+H]⁺.

Example 6-26

6-[(1E)-1-(4-tert-Butylphenyl)-4-phenoxybut-1-en-1-yl]-3-chloropyridin-2(1H)-one

The title compound was obtained as a pale yellow powder (4 mg, 2% (two steps)) by performing substantially the same reaction as in Example 6-17(1) except for using phenol in place of isoindoline-1,3-dione and using (3E)-4-(4-tert-butylphenyl)-4-(5-chloro-6-methoxypyridin-2-yl)but-3-en-1-ol obtained in Reference Example 4-10.

$^1$H NMR (300 MHz, CDCl$_3$) δ ppm 1.36 (s, 9H), 2.56-2.67 (m, 2H), 4.03 (t, J=6.3 Hz, 2H), 6.16 (d, J=7.6 Hz, 1H), 6.44 (t, J=7.6 Hz, 1H), 6.85-6.90 (m, 2H), 6.96 (t, J=6.8 Hz, 1H), 7.13 (d, J=8.5 Hz, 2H), 7.27-7.32 (m, 2H), 7.44 (d, J=8.5 Hz, 2H), 7.51 (d, J=7.6 Hz, 1H).
MS(+): 408 [M+H]$^+$.

Example 6-27

6-[(1E)-1-(4-tert-Butylphenyl)-4-(2-oxopyrrolidin-1-yl)but-1-en-1-yl]-3-chloropyridin-2(1H)-one

The title compound was obtained as a colorless powder (15 mg, 31% (three steps)) by performing substantially the same reaction as in Example 6-17(1)(2) except for using succinimide in place of isoindoline-1,3-dione and using (3E)-4-(4-tert-butylphenyl)-4-(5-chloro-6-methoxypyridin-2-yl)but-3-en-1-ol obtained in Reference Example 4-10.

$^1$H NMR (300 MHz, CDCl$_3$) δ ppm 1.35 (s, 9H), 1.85-2.01 (m, 2H), 2.31-2.45 (m, 4H), 3.07-3.16 (m, 2H), 3.34-3.43 (m, 2H), 6.14 (d, J=7.6 Hz, 1H), 6.24 (t, J=7.5 Hz, 1H), 7.06 (d, J=8.5 Hz, 2H), 7.43 (d, J=8.5 Hz, 2H), 7.50 (d, J=7.6 Hz, 1H).
MS(+): 399 [M+H]$^+$.

Example 6-28

6-[(1E)-1-(4-tert-Butylphenyl)-3-phenylprop-1-en-1-yl]-3-chloropyridin-2(1H)-one

The title compound was obtained as a colorless powder (17 mg, 18% (two steps)) by performing substantially the same reaction as in Example 4-98 except for using phenylboronic acid and 6-[(1E)-3-bromo-1-(4-tert-butylphenyl)prop-1-en-1-yl]-3-chloro-2-methoxypyridine obtained in Reference Example 4-5.

$^1$H NMR (300 MHz, CDCl$_3$) δ ppm 1.37 (s, 9H), 3.47 (d, J=7.6 Hz, 2H), 6.16 (d, J=7.6 Hz, 1H), 6.44 (t, J=7.6 Hz, 1H), 7.11-7.22 (m, 4H), 7.28-7.34 (m, 3H), 7.43-7.53 (m, 3H).
MS(+): 378 [M+H]$^+$.

Examples 6-29 and 6-30

6-[1-(4-tert-Butylphenyl)-3-(2-oxo-1,3-oxazolidin-3-yl)propyl]-3-chloropyridin-2(1H)-one

An (R,S) mixture of the title compound was obtained as a colorless amorphous (46 mg) by performing substantially the same reaction as in Examples 4-209 and 4-210(1)(2)(3) except for using 4-isopropylphenylboronic acid and 3-[(2Z)-3-bromo-3-(5-chloro-6-methoxypyridin-2-yl)prop-2-en-1-yl]-1,3-oxazolidin-2-one obtained in Example 6-22(2). This was separated by chiral HPLC (CHIRALCEL OD-H, 40° C., flow rate: 8 mL/min, ethanol:hexane=34:66, 210 nm) to give one enantiomer (A) of the title compound as a colorless amorphous (18 mg, 33%, Rt=11.5 min) and the other enantiomer (B) of the title compound as a colorless amorphous (18 mg, 33%, Rt=14.5 min).

Diastereomer (A)
$^1$H NMR (300 MHz, CDCl$_3$) δ ppm 1.30 (s, 9H), 2.22-2.40 (m, 2H), 3.17-3.41 (m, 2H), 3.47-3.59 (m, 2H), 3.81-3.90 (m, 1H), 4.19-4.30 (m, 2H), 6.16 (d, J=7.8 Hz, 1H), 7.21 (d, J=8.5 Hz, 2H), 7.36 (d, J=8.4 Hz, 2H), 7.53 (d, J=7.5 Hz, 1H).
MS(+): 389 [M+H]$^+$.

Diastereomer (B)
$^1$H NMR (300 MHz, CDCl$_3$) δ ppm 1.30 (s, 9H), 2.26-2.41 (m, 2H), 3.18-3.40 (m, 2H), 3.48-3.59 (m, 2H), 3.82-3.90 (m, 1H), 4.17-4.33 (m, 2H), 6.16 (d, J=7.5 Hz, 1H), 7.22 (d, J=8.4 Hz, 2H), 7.32-7.39 (m, 2H), 7.53 (d, J=7.5 Hz, 1H).
MS(+): 389 [M+H]$^+$.

Example 6-31

3-[(2E)-3-(4-tert-Butylphenyl)-3-(5-chloro-6-oxo-1,6-dihydropyridin-2-yl)prop-2-en-1-yl]-1-methylpyrimidine-2,4(1H, 3H)-dione

The title compound was obtained as a white solid (18 mg, 43% (two steps)) by performing substantially the same reaction as in Example 6-2 except for using 1-methyluracil.

$^1$H NMR (300 MHz, CDCl$_3$) δ ppm 1.36 (s, 9H), 3.39 (s, 3H), 4.64 (d, J=5.9 Hz, 2H), 5.73 (d, J=7.9 Hz, 1H), 6.07-6.15 (m, 2H), 7.13 (d, J=7.9 Hz, 1H), 7.20-7.28 (m, 2H), 7.42-7.51 (m, 3H), 8.76-8.93 (brs, 1H).
MS(+): 426 [M+H]$^+$.
MS(−): 424 [M−H]$^−$.

Example 6-32

1-[(2E)-3-(4-tert-Butylphenyl)-3-(5-chloro-6-oxo-1,6-dihydropyridin-2-yl)prop-2-en-1-yl]pyrimidin-2(1H)-one

The title compound was obtained as a white solid (42 mg, 42% (two steps)) by performing substantially the same reaction as in Example 6-2 except for using 2(1H)-pyrimidinone.

$^1$H NMR (300 MHz, CDCl$_3$) δ ppm 1.36 (s, 9H), 4.66 (d, J=6.3 Hz, 2H), 5.95 (d, J=7.9 Hz, 1H), 6.29 (dd, J=6.3, 4.0 Hz, 1H), 6.68 (t, J=6.3 Hz, 1H), 7.18 (d, J=7.9 Hz, 2H), 7.42-7.54 (m, 3H), 7.78 (dd, J=6.6, 3.0 Hz, 1H), 8.51-8.62 (m, 1H), 11.46-11.95 (brs, 1H).
MS(+): 396 [M+H]$^+$.
MS(−): 394 [M−H]$^−$.

Example 6-33

2-[(2E)-3-(4-tert-Butylphenyl)-3-(5-chloro-6-oxo-1,6-dihydropyridin-2-yl)prop-2-en-1-yl]pyridazin-3(2H)-one

The title compound was obtained as a white solid (25 mg, 62% (two steps)) by performing substantially the same reaction as in Example 6-2 except for using 3(2H)-pyridazinone and using potassium carbonate in place of sodium hydride.

$^1$H NMR (300 MHz, CDCl$_3$) δ ppm 1.36 (s, 9H), 4.85 (d, J=6.6 Hz, 2H), 6.14 (d, J=7.6 Hz, 1H), 6.43 (t, J=6.3 Hz, 1H), 6.94 (d, J=9.6 Hz, 1H), 7.14-7.28 (m, 3H), 7.42-7.54 (m, 3H), 7.74-7.82 (m, 1H), 8.93-9.50 (brs, 1H).
MS(+): 396 [M+H]$^+$.
MS(−): 394 [M−H]$^−$.

Example 6-34

3-[(2E)-3-(4-tert-Butylphenyl)-3-(5-chloro-6-oxo-1,6-dihydropyridin-2-yl)prop-2-en-1-yl]pyrimidin-4(3H)-one The title compound was obtained as a white solid (32 mg, 40% (two steps)) by performing substantially the same reaction as in Example 6-2 except for using 4(3H)-pyrimidinone and using potassium carbonate in place of sodium hydride.

$^1$H NMR (300 MHz, CDCl$_3$) δ ppm 1.37 (s, 9H), 4.59 (d, J=6.6 Hz, 2H), 6.05 (d, J=7.7 Hz, 1H), 6.45 (d, J=6.3 Hz, 1H), 6.56 (t, J=6.3 Hz, 1H), 7.17 (d, J=8.3 Hz, 2H), 7.45-7.55 (m, 3H), 7.87 (d, J=6.6 Hz, 1H), 7.92 (s, 1H), 10.06-10.42 (brs, 1H).

MS(+): 396 [M+H]$^+$.
MS(−): 394 [M−H]$^−$.

Example 6-35

N-[(2E)-3-(4-tert-Butylphenyl)-3-(5-chloro-6-oxo-1,6-dihydropyridin-2-yl)prop-2-en-1-yl]acetamide (1) 6-[(1E)-3-Bromo-1-(4-tert-butylphenyl)prop-1-en-1-yl]-3-chloro-2-methoxypyridine obtained in Reference Example 4-5 at room temperature (79 mg) was added to a solution of potassium phthalimide (45 mg) in N,N-dimethylformamide (1 mL) under ice-cooling, and the mixture was stirred at the same temperature for 30 minutes. Water was added to the reaction solution, followed by extraction with chloroform. The organic layer was dried over anhydrous magnesium sulfate and filtered, after which the solvent was evaporated under reduced pressure. The residue was purified by silica gel column chromatography (hexane:ethyl acetate=5:1) to give 2-[(2E)-3-(4-tert-butylphenyl)-3-(5-chloro-6-methoxypyridin-2-yl)prop-2-en-1-yl]-1H-isoindole-1,3(2H)-dione as a white solid (98 mg, quant.).

(2) Hydrazine monohydrate (13 μL) was added to a solution of 2-[(2E)-3-(4-tert-butylphenyl)-3-(5-chloro-6-methoxypyridin-2-yl)prop-2-en-1-yl]-1H-isoindole-1,3(2H)-dione (98 mg) in ethanol. Thereafter, the mixture was stirred with heating under reflux for three hours and then stirred at room temperature overnight. Brine was added to the reaction solution, followed by extraction with chloroform. The organic layer was dried over anhydrous magnesium sulfate and filtered, after which the solvent was evaporated under reduced pressure to give a crude product of (2E)-3-(4-tert-butylphenyl)-3-(5-chloro-6-methoxypyridin-2-yl)prop-2-en-1-amine.

(3) Acetic anhydride (21 μL) was added to a solution of (2E)-3-(4-tert-butylphenyl)-3-(5-chloro-6-methoxypyridin-2-yl)prop-2-en-1-amine in pyridine (1 mL), and the mixture was stirred at room temperature for 1.5 hours. 1 M hydrochloric acid was added to the reaction solution, followed by extraction with chloroform. The organic layer was dried over magnesium sulfate and filtered, after which the solvent was evaporated under reduced pressure. The residue was purified by silica gel column chromatography (hexane:ethyl acetate=3:1→1:1) to give N-[(2E)-3-(4-tert-butylphenyl)-3-(5-chloro-6-methoxypyridin-2-yl)prop-2-en-1-yl]acetamide as a pale yellow amorphous (50 mg, 67% (two steps)).

(4) The title compound was obtained as a white solid (12 mg, 25%) by performing substantially the same reaction as in Example 1-1(2) except for using N-[(2E)-3-(4-tert-butylphenyl)-3-(5-chloro-6-methoxypyridin-2-yl)prop-2-en-1-yl]acetamide.

$^1$H NMR (300 MHz, CDCl$_3$) δ ppm 1.35 (s, 9H), 2.01 (s, 3H), 4.07 (d, J=5.3 Hz, 2H), 5.97 (d, J=7.9 Hz, 1H), 6.14-6.32 (brs, 1H), 6.46 (t, J=6.3 Hz, 1H), 7.12 (d, J=8.3 Hz, 2H), 7.42 (d, J=7.9 Hz, 2H), 7.52 (d, J=7.6 Hz, 1H), 11.85-12.12 (brs, 1H).

MS(+): 359 [M+H]$^+$.
MS(−): 357[M−H H]$^−$.

Example 6-36

6-[(1E)-1-(4-tert-Butylphenyl)-3-(4-methyl-5-oxo-4,5-dihydro-1H-pyrazol-4-yl)prop-1-en-1-yl]-3-chloropyridin-2(1H)-one (1) 4-[(2E)-3-(4-tert-Butylphenyl)-3-(5-chloro-6-methoxypyridin-2-yl)prop-2-en-1-yl]-4-methyl-2,4-dihydro-3H-pyrazol-3-one was obtained as a pale yellow solid (66 mg, 39%) by performing substantially the same reaction as in Example 6-2(1) except for using 4-methyl-2-pyrazolin-5-one and using potassium carbonate in place of sodium hydride. A mixture of 6-{(1E)-1-(4-tert-butylphenyl)-3-[(4-methyl-1H-pyrazol-5-yl)oxy]prop-1-en-1-yl}-3-chloro-2-methoxypyridine and 2-[(2E)-3-(4-tert-butylphenyl)-3-(5-chloro-6-methoxypyridin-2-yl)prop-2-en-1-yl]-4-methyl-1,2-dihydro-3H-pyrazol-3-one (90 mg, 54%) was also obtained.

(2) The title compound was obtained as a white solid (29 mg, 75%) by performing substantially the same reaction as in Example 1-1(2) except for using 4-[(2E)-3-(4-tert-butylphenyl)-3-(5-chloro-6-methoxypyridin-2-yl)prop-2-en-1-yl]-4-methyl-2,4-dihydro-3H-pyrazol-3-one.

$^1$H NMR (300 MHz, CDCl$_3$) δ ppm 1.27 (s, 3H), 1.37 (s, 9H), 2.42-2.60 (m, 2H), 5.86 (d, J=7.9 Hz, 1H), 6.24 (t, J=8.3 Hz, 1H), 7.04-7.10 (m, 2H), 7.29 (s, 1H), 7.41-7.49 (m, 3H), 9.67 (s, 1H), 11.60-11.80 (brs, 1H).

MS(+): 398 [M+H]$^+$.
MS(−): 396 [M−H]$^−$.

Example 6-37

6-[(1E)-1-(4-tert-Butylphenyl)-3-(4-methyl-5-oxo-2,5-dihydro-1H-pyrazol-1-yl)prop-1-en-1-yl]-3-chloropyridin-2(1H)-one The title compound was obtained as a white solid (17 mg, 10% (two steps: yield from 6-[(1E)-3-bromo-1-(4-tert-butylphenyl)prop-1-en-1-yl]-3-chloro-2-methoxypyridine)) by performing substantially the same reaction as in Example 1-1(2) except for using a mixture of 6-{(1E)-1-(4-tert-butylphenyl)-3-[(4-methyl-1H-pyrazol-5-yl)oxy]prop-1-en-1-yl}-3-chloro-2-methoxypyridine and 2-[(2E)-3-(4-tert-butylphenyl)-3-(5-chloro-6-methoxypyridin-2-yl)prop-2-en-1-yl]-4-methyl-1,2-dihydro-3H-pyrazol-3-one obtained in Example 6-36(1).

$^1$H NMR (300 MHz, CDCl$_3$) δ ppm 1.35 (s, 9H), 1.92 (d, J=0.7 Hz, 3H), 4.53 (d, J=6.7 Hz, 2H), 6.08 (d, J=7.7 Hz, 1H), 6.37 (t, J=6.7 Hz, 1H), 6.88 (s, 1H), 7.15 (d, J=8.7 Hz, 2H), 7.41-7.49 (m, 3H).

MS(+): 398 [M+H]$^+$.
MS(−): 396 [M−H]$^−$.

The structures of Examples 6-16 to 6-37 are shown below.

[Hyo 21-1]
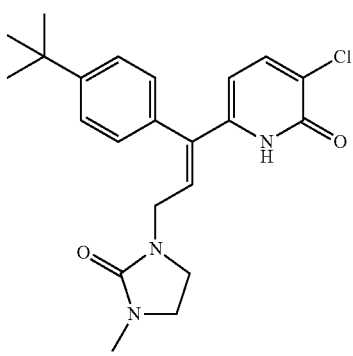
Example 6-16
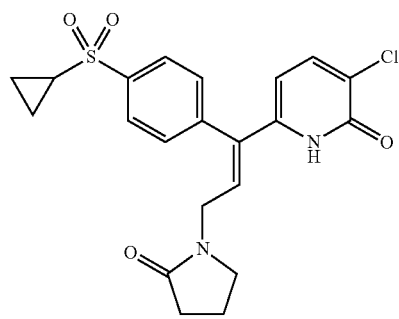
Example 6-20
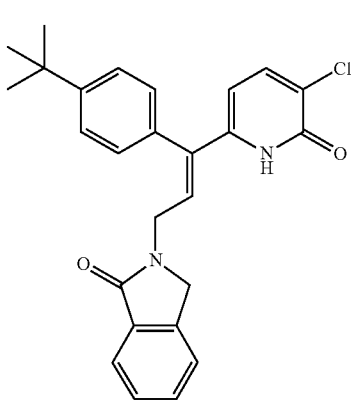
Example 6-17
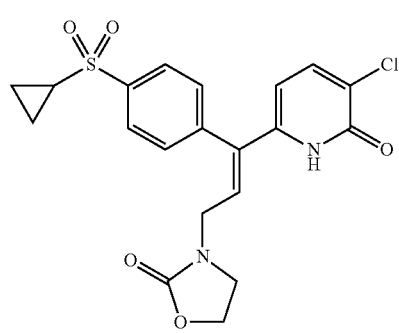
Example 6-21
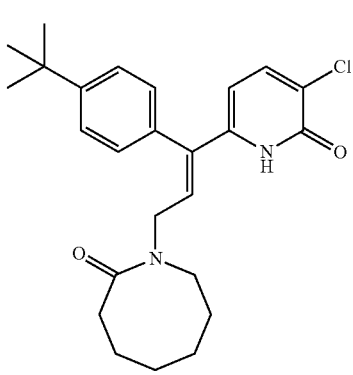
Example 6-18
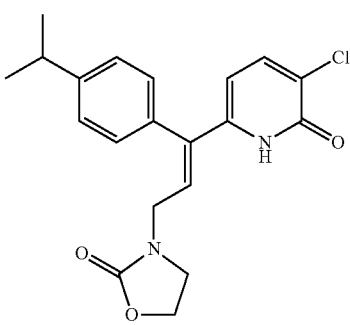
Example 6-22
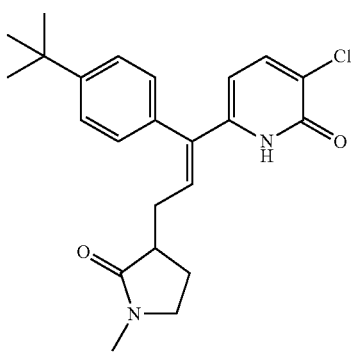
Example 6-19
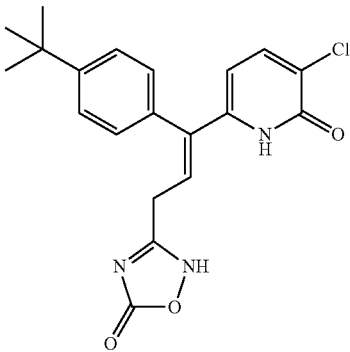
Example 6-23
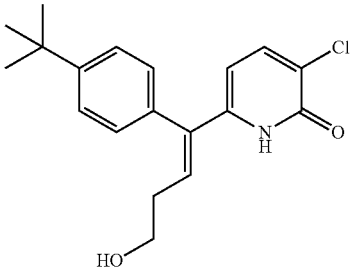
Example 6-24

Example 6-25
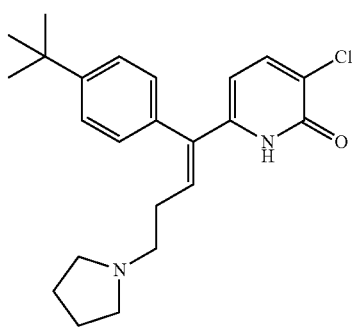
[Hyo 21-2]
Example 6-26
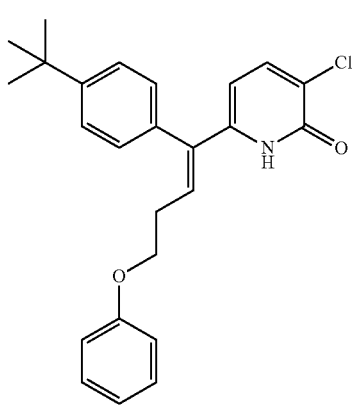
Example 6-27
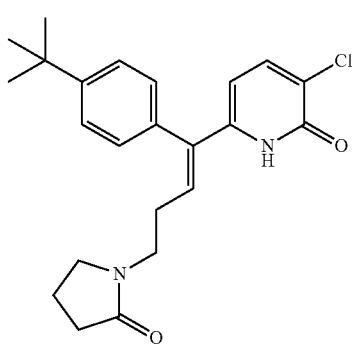
Example 6-28
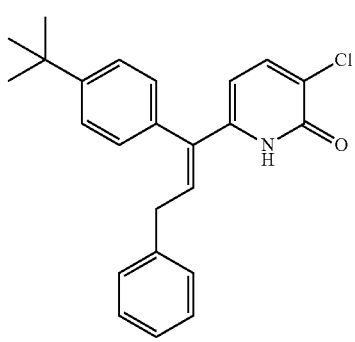
Example 6-29, 30
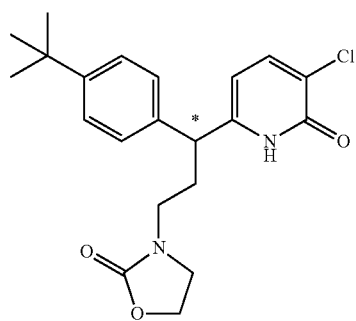
Example 6-31
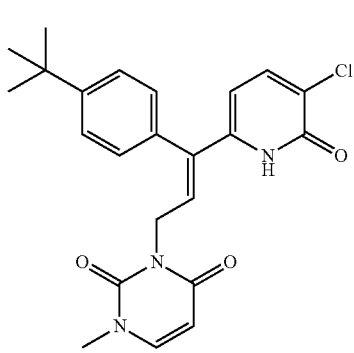
Example 6-32
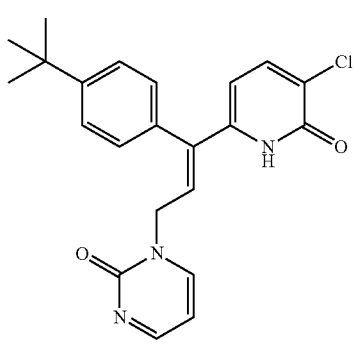
Example 6-33
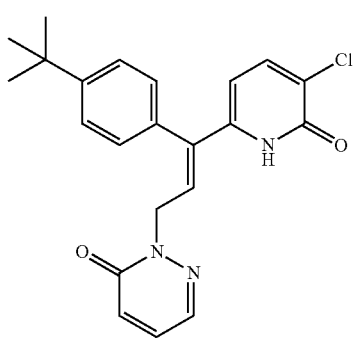

-continued

Example 6-34

Example 6-35

Example 6-36

[Hyo 21-3]

Example 6-37

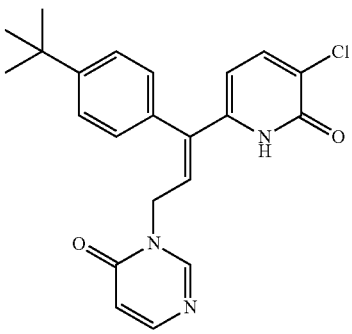

Example 7-1

6-{(Cyclopentyloxy)[4-(cyclopropylsulfanyl)phenyl]methyl}-3-(trifluoromethyl)pyridin-2(1H)-one (1) 48% hydrobromic acid (2 mL) was added to a solution of [4-(cyclopropylsulfanyl)phenyl][6-methoxy-5-(trifluoromethyl)pyridin-2-yl]methanone obtained in Reference Example 1-68 (400 mg) in 1,4-dioxane (4 mL), and the mixture was stirred at 65° C. for one hour. Water was added to the reaction solution, followed by extraction with ethyl acetate. The organic layer was dried over anhydrous magnesium sulfate, after which the solvent was evaporated under reduced pressure. The residue was purified by silica gel column chromatography (hexane:ethyl acetate=1:1→1:5) to give 6-{[4-(cyclopropylsulfanyl)phenyl]carbonyl}-3-(trifluoromethyl)pyridin-2(1H)-one (210 mg, 55%).

(2) Sodium triacetoxyborohydride (125 mg) was added to a solution of 6-{[4-(cyclopropylsulfanyl)phenyl]carbonyl}-3-(trifluoromethyl)pyridin-2(1H)-one (110 mg) in chloroform (3 mL), and the mixture was stirred at room temperature overnight. An ammonium chloride solution was added to the reaction solution, followed by extraction with chloroform. The organic layer was dried over anhydrous magnesium sulfate. The solvent was evaporated under reduced pressure. The residue was purified by silica gel column chromatography (ethyl acetate only) to give 6-{[4-(cyclopropylsulfanyl)phenyl](hydroxy)methyl}-3-(trifluoromethyl)pyridin-2(1H)-one (40 mg, 36%).

(3) Methanesulfonic acid (250 μL) was added to a solution of 6-{[4-(cyclopropylsulfanyl)phenyl](hydroxy)methyl}-3-(trifluoromethyl)pyridin-2(1H)-one (40 mg) in cyclopentanol (500 μL), and the mixture was stirred at 100° C. for six hours. Water was added to the reaction solution, followed by extraction with ethyl acetate. The organic layer was dried over magnesium sulfate, after which the solvent was evaporated under reduced pressure. The residue was purified by preparative HPLC (Waters Sunfire 19×150 mm 5 μm, rate: 20 mL/min, eluent: A=acetonitrile, B=0.1% trifluoroacetic acid solution, gradient: 10 to 90%) to give the title compound as a colorless amorphous (25 mg, 52%).

$^1$H NMR (600 MHz, CDCl$_3$) δ ppm 0.65-0.72 (m, 2H), 1.04-1.12 (m, 2H), 1.46-1.62 (m, 2H), 1.65-1.83 (m, 6H), 2.14-2.20 (m, 1H), 3.94-4.03 (m, 1H), 5.23 (s, 1H), 6.03 (d, J=7.3 Hz, 1H), 7.25 (d, J=8.7 Hz, 2H), 7.36 (d, J=8.3 Hz, 2H), 7.69 (d, J=7.3 Hz, 1H), 10.36 (brs, 1H).

MS(+): 410 [M+H]$^+$.

Example 7-2

6-{(Cyclopentyloxy)[4-(cyclopropylsulfonyl)phenyl]methyl}-3-(trifluoromethyl)pyridin-2(1H)-one 3-Chloroperbenzoic acid (31 mg) was added to a solution of 6-{(cyclopentyloxy)[4-(cyclopropylsulfanyl)phenyl]methyl}-3-(trifluoromethyl)pyridin-2(1H)-one (25 mg) in chloroform (1 mL), and the mixture was stirred at room temperature overnight. A sodium thiosulfate solution and aqueous sodium bicarbonate were added to the reaction solution, followed by extraction with ethyl acetate. The organic layer was dried over anhydrous magnesium sulfate, after which the solvent was evaporated under reduced pressure. The residue was purified by preparative HPLC (Waters Sunfire 19×150 mm 5 μm, rate: 20 mL/min, eluent: A=acetonitrile, B=0.1% trifluoroacetic acid solution, gradient: 10 to 90%) to give the title compound as a colorless amorphous (7 mg, 26%).

$^1$H NMR (600 MHz, CDCl$_3$) δ ppm 0.84-0.91 (m, 1H), 1.01-1.09 (m, 2H), 1.24-1.32 (m, 1H), 1.34-1.39 (m, 2H), 1.68-1.81 (m, 6H), 2.41-2.50 (m, 1H), 3.97-4.04 (m, 1H), 5.36 (s, 1H), 6.12-6.22 (m, 1H), 7.57-7.63 (m, 2H), 7.72-7.77 (m, 1H), 7.88-7.94 (m, 2H).

MS(+): 442 [M+H]$^+$.

Example 7-3

3-Cyclopropyl-6-[[4-(cyclopropylsulfonyl)phenyl](2,4-difluorophenoxy)methyl]pyridin-2(1H)-one (1) 48% hydrobromic acid (3 mL) was added to a solution of 5-cyclopropyl-6-methoxypyridine-2-carbaldehyde obtained in Reference Example 1-51(6) (437 mg) in 1,4-dioxane (6 mL), and the mixture was stirred at 65° C. for two hours. The reaction solution was poured into water, followed by extraction with chloroform/methanol (2:1). The organic layer was dried over anhydrous magnesium sulfate and filtered. The filtrate was concentrated under reduced pressure. The resulting residue was purified by silica gel column chromatography (hexane:ethyl acetate=75:25→0:100) to give 5-cyclopropyl-6-oxo-1,6-dihydropyridine-2-carbaldehyde as a yellow powder (278 mg, 69%).

(2) p-Methoxybenzyl chloride (329 mg) was added to a solution of 5-cyclopropyl-6-oxo-1,6-dihydropyridine-2-carbaldehyde (228 mg) in chloroform (10 mL), after which the reaction tube was covered with aluminum foil to provide shading conditions. Silver carbonate (771 mg) was added and the mixture was stirred at room temperature for three hours. The insoluble matter was filtered off and then the filtrate was concentrated under reduced pressure. The resulting residue was purified by silica gel column chromatography (hexane:ethyl acetate=92:8→34:66) to give 5-cyclopropyl-6-[(4-methoxybenzyl)oxy]pyridine-2-carbaldehyde as a colorless oil (417 mg, 86%).

(3) A solution of (4-bromophenyl)(cyclopropyl)sulfane (440 mg) in tetrahydrofuran (10 mL) was cooled to −78° C., and n-butyllithium (2.6 M, 0.74 mL) was slowly added dropwise, followed by stirring for 30 minutes. A solution of 5-cyclopropyl-6-[(4-methoxy benzyl)oxy]pyridine-2-carbaldehyde (417 mg) in tetrahydrofuran (5 mL) was slowly added dropwise, and the mixture was stirred at −78° C. for 4.5 hours. The reaction solution was stirred in an ice bath and a saturated ammonium chloride solution was added, followed by extraction with chloroform. The organic layer was dried over anhydrous magnesium sulfate and filtered. The filtrate was concentrated under reduced pressure. The resulting residue was purified by silica gel column chromatography (hexane:ethyl acetate=95:5→62:38) to give {5-cyclopropyl-6-[(4-methoxybenzyl)oxy]pyridin-2-yl}[4-(cyclopropylsulfanyl)phenyl]methanol as a yellow oil (469 mg, 73%).

(4) A solution of {5-cyclopropyl-6-[(4-methoxybenzyl)oxy]pyridin-2-yl}[4-(cyclopropylsulfanyl)phenyl]methanol (469 mg) in chloroform (15 mL) was stirred in an ice bath, and m-chloroperbenzoic acid (560 mg) was added as powder. The mixture was returned to room temperature and stirred for 3.5 hours. The reaction solution was stirred again in an ice bath, and sodium thiosulfate and a potassium carbonate solution were added, followed by extraction with chloroform. The organic layer was dried over anhydrous magnesium sulfate and filtered. The filtrate was concentrated under reduced pressure. The resulting residue was purified by silica gel column chromatography (hexane:ethyl acetate=92:8→34:66) to give {5-cyclopropyl-6-[(4-methoxybenzyl)oxy]pyridin-2-yl}[4-(cyclopropylsulfonyl)phenyl]methanol as a light yellow oil (403 mg, 80%).

(5) 2,4-Difluorophenol (219 mg), tributylphosphine (340 mg) and N,N,N',N'-tetramethylazodicarboxyamide (289 mg) were sequentially added to a solution of {5-cyclopropyl-6-[(4-methoxybenzyl)oxy]pyridin-2-yl}[4-(cyclopropylsulfonyl)phenyl]methanol (390 mg) in tetrahydrofuran (12 mL). After replacement with nitrogen, the mixture was stirred under reflux at an external temperature of 86° C. for six hours, returned to room temperature and stirred overnight. The reaction solution was poured into water and a potassium carbonate solution was added, followed by extraction with chloroform. The organic layer was dried over anhydrous magnesium sulfate and filtered. The filtrate was concentrated under reduced pressure. The resulting residue was purified by silica gel column chromatography (hexane:ethyl acetate=92: 8→34:66) to give 3-cyclopropyl-6-{[4-(cyclopropylsulfonyl)phenyl](2,4-difluorophenoxy)methyl}-2-[(4-methoxybenzyl)oxy]pyridine as a yellow gum (373 mg, 77%).

(6) Trifluoroacetic acid (50 mg) was added to a solution of 3-cyclopropyl-6-{[4-(cyclopropylsulfonyl)phenyl](2,4-difluorophenoxy)methyl}-2-[(4-methoxybenzyl)oxy]pyridine (90 mg) in chloroform (5 mL), and the mixture was stirred at room temperature for two hours. The reaction solution was concentrated under reduced pressure. The resulting residue was purified by silica gel column chromatography (hexane:ethyl acetate=88:12→0:100) to give the title compound as a yellow powder (53 mg, 74%).

$^1$H NMR (600 MHz, CDCl$_3$) δ ppm 0.61-0.67 (m, 2H), 0.91-0.96 (m, 2H), 1.03-1.08 (m, 2H), 1.34-1.38 (m, 2H), 2.02-2.08 (m, 1H), 2.42-2.48 (m, 1H), 6.04 (s, 1H), 6.15 (d, J=6.9 Hz, 1H), 6.70 (t, J=7.8 Hz, 1H), 6.86 (ddd, J=11.0, 8.3, 2.8 Hz, 1H), 6.90-6.96 (m, 2H), 7.71 (d, J=8.3 Hz, 2H), 7.90 (d, J=8.3 Hz, 2H).

MS(+): 458 [M+H]$^+$.

Example 7-4

6-[(4-tert-Butylphenyl)(cyclopentylsulfanyl)methyl]-3-chloropyridin-2(1H)-one (1) (4-tert-Butylphenyl)(5-chloro-6-methoxypyridin-2-yl)methanol was obtained as a colorless solid (1.26 g, 76%) by performing substantially the same reaction as in Reference Example 1-1(2) except for using 1-bromo-4-tert-butylbenzene.

(2) Cyclopentylmethanol (0.039 mL) and palladium chloride (6.0 mg) were added to a solution of (4-tert-butylphenyl)(5-chloro-6-methoxypyridin-2-yl)methanol (110 mg) in 1,2-dichloroethane (2 mL) at room temperature, after which the mixture was stirred at 80° C. for six hours and then stirred at room temperature for two days. Water was added to the reaction solution, followed by extraction with ethyl acetate. The organic layer was washed with water and brine, dried over anhydrous magnesium sulfate and filtered, after which the solvent was evaporated under reduced pressure. The residue was purified by silica gel column chromatography (hexane:ethyl acetate=20:1) to give 6-[(4-tert-butylphenyl)(cyclopentylmethoxy)methyl]-3-chloro-2-methoxypyridine as a pale red oil (112 mg, 86%).

(3) Aluminum chloride (66 mg) was added to a solution of 6-[(4-tert-butylphenyl)(cyclopentylmethoxy)methyl]-3-chloro-2-methoxypyridine (64 mg) in cyclopentanethiol (1 mL) under ice-cooling, and then the mixture was stirred at 40° C. for two hours. Water was added to the reaction solution, followed by extraction with ethyl acetate. The organic layer was washed with water and brine, dried over anhydrous magnesium sulfate and filtered, after which the solvent was evaporated under reduced pressure. The residue was purified by preparative TLC (hexane:ethyl acetate=1:10) to give the title compound as a pale yellow solid (15 mg, 25%).

$^1$H NMR (300 MHz, CDCl$_3$) δ ppm 1.22 (s, 9H), 1.35-2.00 (m, 8H), 2.75-3.00 (m, 1H), 4.92 (s, 1H), 6.16 (d, J=7.2 Hz, 1H), 7.14-7.24 (m, 2H), 7.27 (d, J=8.1 Hz, 2H), 7.44 (dd, J=7.7, 2.6 Hz, 1H), 10.04-11.03 (brs, 1H).

MS(+): 376 [M+H]$^+$.
MS(−): 374 [M−H]$^-$.

Example 7-5

6-[(4-tert-Butylphenyl)(cyclopentylamino)methyl]-3-chloropyridin-2(1H)-one (1) Sulfuryl chloride (0.37 mL) was added to a solution of (4-tert-butylphenyl)(5-chloro-6-methoxypyridin-2-yl)

methanol obtained in Example 7-4(1) (200 mg) and triethylamine (0.27 mL) in cyclohexane (4 mL) at room temperature, and then the mixture was stirred at the same temperature for 17 hours. After completion of the reaction, the solvent was evaporated under reduced pressure. The residue was purified by silica gel column chromatography (hexane:ethyl acetate=20:1) to give 6-[(4-tert-butylphenyl)(chloro)methyl]-3-chloro-2-methoxypyridine as a colorless oil (203 mg, 96%).

(2) Cyclohexylamine (0.30 mL) and sodium bicarbonate (259 mg) were sequentially added to a solution of 6-[(4-tert-butylphenyl)(chloro)methyl]-3-chloro-2-methoxypyridine (200 mg) in acetonitrile (4 mL) at room temperature, and then the mixture was heated under reflux for six hours. Water was added to the reaction solution, followed by extraction with ethyl acetate. The organic layer was washed with water and brine, dried over anhydrous magnesium sulfate and filtered, after which the solvent was evaporated under reduced pressure. The residue was purified by silica gel column chromatography (hexane:ethyl acetate=1:50→1:10) to give N-[(4-tert-butylphenyl)(5-chloro-6-methoxypyridin-2-yl)methyl]cyclopentanamine as a pale yellow amorphous (201 mg, 87%).

(3) The title compound was obtained as a colorless amorphous (25 mg, 13%) by performing substantially the same reaction as in Example 4-277(2) except for using N-[(4-tert-butylphenyl)(5-chloro-6-methoxypyridin-2-yl)methyl]cyclopentanamine.

$^1$H NMR (300 MHz, CDCl$_3$) δ ppm 1.30 (s, 9H), 1.10-2.10 (m, 9H), 3.02 (quint, J=6.6 Hz, 1H), 4.66 (s, 1H), 5.95 (dd, J=7.2, 0.6 Hz, 1H), 7.17 (d, J=8.1 Hz, 2H), 7.35 (d, J=8.4 Hz, 2H), 7.46 (d, J=7.5 Hz, 1H), 9.57-11.43 (brs, 1H).

MS(+): 359 [M+H]$^+$.

MS(−): 357 [M−H]$^-$.

The structures of Examples 7-1 to 7-5 are shown below.

Example 7-1

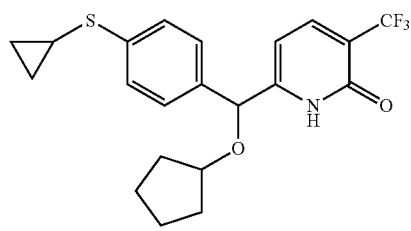

Example 7-2

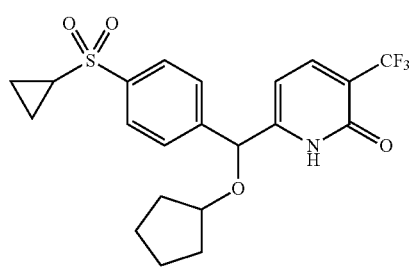

-continued

Example 7-3

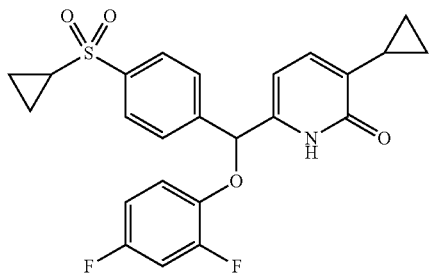

Example 7-4

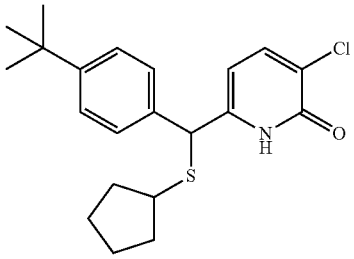

Example 7-5

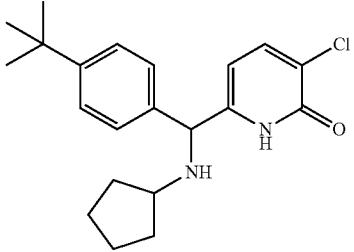

The GK activating effect of the compounds of the present invention can be evaluated according to a known technique such as the method described in Test Example, for example.

The GK activating effect of the compounds of the present invention was measured using the method described in the following Test Example.

Test Example 1

GK Activation Test

The GK activation test for the test compounds was performed by the method of Irwin A. Rose et al. (J. Biol. Chem. 1964 January; 239:12-7) with partial modifications.

The enzyme source used in this assay, human liver GK, was expressed in *E. coli* as a fusion protein with GST (glutathione S-transferase) added to the amino terminus and was purified using Glutathione Sepharose 4B (Amersham Biosciences).

The test was carried out using flat-bottom 96-well plates (Sumitomo Bakelite Co., Ltd.). A solution of the test compound in dimethyl sulfoxide (DMSO) and DMSO as a control were added to each well of the plates at a final DMSO concentration of 1%. 25 mM Hepes-KOH (pH=7.1), 25 mM KCl, 2 mM MgCl$_2$, 2 mM ATP, 4 mM $^{14}$C-labeled glucose (Muromachi Yakuhin) and 1 mM DTT (dithiothreitol) were further added at the indicated final concentrations, respectively. Finally, human liver GK was added at 0.24 microgram per well and the reaction was started. The reaction was carried out at room temperature.

After 20 minutes, AG1-X4 resin (BioRad) suspended in 25 mM Hepes-KOH (pH=7.1) was added and the reaction product, labeled glucose 6-phosphate, was allowed to bind thereto. The whole volume was transferred to MultiScreen plates (Millipore) and the resin was washed with water. Thereafter, the labeled glucose 6-phosphate binding to the resin was eluted with a 0.5 M NaCl solution. The labeling activity of the eluted labeled glucose 6-phosphate was measured as an index of GK activity.

The GK activity maximally activated by the test compound was described as maximum activation ability, and the test compound concentration needed to activate 50% of that ability was described as $EC_{50}$.

The results are shown below.

| Example No. | $EC_{50}$ |
|---|---|
| [Hyo 23-1] | |
| 1-1 | B |
| 1-2 | B |
| 1-3 | A |
| 1-4 | A |
| 1-5 | A |
| 1-6 | A |
| 1-7 | A |
| 1-8 | B |
| 1-9 | A |
| 1-10 | A |
| 1-11 | A |
| 1-12 | A |
| 1-13 | A |
| 1-14 | A |
| 1-15 | A |
| 1-16 | A |
| 1-17 | A |
| 1-18 | A |
| 1-19 | A |
| 1-20 | A |
| 1-21 | A |
| 1-22 | A |
| 1-23 | A |
| 1-24 | A |
| 1-25 | B |
| 1-26 | A |
| 1-27 | A |
| 1-28 | B |
| 1-29 | A |
| 1-30 | A |
| 1-31 | B |
| 1-32 | B |
| 1-33 | B |
| 1-34 | B |
| 1-35 | B |
| 1-36 | A |
| 1-37 | A |
| 1-38 | B |
| 1-39 | B |
| 1-40 | B |
| 1-41 | B |
| 1-42 | B |
| 1-43 | C |
| 1-44 | B |
| 1-45 | B |
| 1-46 | B |
| 1-47 | A |
| 1-48 | B |
| 1-49 | B |
| 1-50 | B |
| 1-51 | B |
| 1-52 | B |
| 1-53 | B |
| 1-54 | B |
| 1-55 | B |
| 1-56 | B |
| 1-57 | B |
| 1-58 | A |
| 1-59 | A |
| 1-60 | A |
| 1-61 | A |
| 1-62 | A |
| 1-63 | B |
| 1-64 | A |
| 1-65 | A |
| 1-66 | B |
| 1-67 | A |
| 1-68 | B |
| 1-69 | A |
| 1-70 | A |
| 1-71 | A |
| 1-72 | A |
| 1-73 | A |
| 1-74 | B |
| 1-75 | A |
| 1-76 | A |
| 1-77 | A |
| 1-78 | A |
| 1-79 | A |
| 1-80 | A |
| 1-81 | B |
| 1-82 | A |
| 1-83 | B |
| 1-84 | B |
| 1-85 | A |
| 1-86 | B |
| 1-87 | B |
| 1-88 | B |
| 1-89 | B |
| 1-90 | A |
| 1-91 | B |
| 1-92 | C |
| 1-93 | C |
| 1-94 | C |
| 1-95 | C |
| 1-96 | B |
| [Hyo 23-2] | |
| 1-97 | B |
| 1-98 | C |
| 1-99 | B |
| 1-100 | C |
| 1-101 | C |
| 1-102 | B |
| 1-103 | A |
| 1-104 | A |
| 1-105 | B |
| 1-106 | B |
| 1-107 | A |
| 1-108 | A |
| 1-109 | B |
| 1-110 | B |
| 1-111 | C |
| 1-112 | C |
| 1-113 | C |
| 2-1 | B |
| 2-2 | B |
| 2-3 | A |
| 2-4 | B |
| 2-5 | B |
| 2-6 | B |
| 2-7 | B |
| 2-8 | B |
| 2-9 | B |
| 2-10 | B |
| 2-11 | B |
| 2-12 | B |
| 2-13 | B |
| 2-14 | B |
| 2-15 | A |
| 2-16 | B |
| 2-17 | B |
| 2-18 | C |
| 2-19 | C |
| 2-20 | B |
| 2-21 | C |
| 2-22 | B |
| 2-23 | C |
| 2-24 | C |

| Example No. | EC$_{50}$ |
|---|---|
| 2-25 | B |
| 3-1 | B |
| 3-2 | B |
| 3-3 | B |
| 3-4 | C |
| 4-1 | A |
| 4-2 | B |
| 4-3 | B |
| 4-4 | A |
| 4-5 | A |
| 4-6 | A |
| 4-7 | B |
| 4-8 | B |
| 4-9 | B |
| 4-10 | A |
| 4-11 | A |
| 4-12 | A |
| 4-13 | A |
| 4-14 | B |
| 4-15 | A |
| 4-16 | B |
| 4-17 | A |
| 4-18 | A |
| 4-19 | B |
| 4-20 | A |
| 4-21 | A |
| 4-22 | A |
| 4-23 | B |
| 4-24 | B |
| 4-25 | B |
| 4-26 | B |
| 4-27 | A |
| 4-28 | B |
| 4-29 | B |
| 4-30 | B |
| 4-31 | C |
| 4-32 | A |
| 4-33 | A |
| 4-34 | B |
| 4-35 | B |
| 4-36 | C |
| 4-37 | A |
| 4-38 | A |
| 4-39 | A |
| 4-40 | B |
| 4-41 | B |
| 4-42 | C |
| 4-43 | C |
| 4-44 | B |
| 4-45 | A |
| 4-47 | B |
| 4-48 | B |
| 4-49 | B |
| 4-50 | B |
| 4-51 | B |
| 4-52 | B |
| 4-53 | A |
| 4-54 | A |

[Hyo 23-3]

| Example No. | EC$_{50}$ |
|---|---|
| 4-55 | A |
| 4-56 | B |
| 4-57 | A |
| 4-58 | B |
| 4-59 | A |
| 4-60 | A |
| 4-61 | B |
| 4-62 | A |
| 4-63 | B |
| 4-64 | A |
| 4-65 | B |
| 4-67 | A |
| 4-68 | A |
| 4-69 | C |
| 4-70 | B |
| 4-71 | A |
| 4-72 | A |
| 4-73 | B |
| 4-74 | A |
| 4-75 | C |
| 4-76 | C |
| 4-77 | C |
| 4-78 | A |
| 4-79 | B |
| 4-80 | A |
| 4-81 | A |
| 4-82 | C |
| 4-83 | A |
| 4-84 | A |
| 4-85 | B |
| 4-86 | A |
| 4-87 | A |
| 4-88 | B |
| 4-89 | C |
| 4-90 | B |
| 4-92 | A |
| 4-93 | C |
| 4-96 | A |
| 4-97 | C |
| 4-98 | A |
| 4-99 | A |
| 4-100 | B |
| 4-101 | A |
| 4-102 | A |
| 4-103 | A |
| 4-104 | B |
| 4-105 | A |
| 4-106 | A |
| 4-107 | A |
| 4-108 | B |
| 4-109 | B |
| 4-110 | B |
| 4-111 | A |
| 4-112 | B |
| 4-113 | B |
| 4-114 | A |
| 4-115 | A |
| 4-116 | A |
| 4-117 | B |
| 4-118 | C |
| 4-119 | B |
| 4-120 | B |
| 4-121 | C |
| 4-122 | A |
| 4-123 | A |
| 4-124 | A |
| 4-125 | A |
| 4-126 | A |
| 4-127 | A |
| 4-128 | A |
| 4-129 | B |
| 4-130 | B |
| 4-131 | A |
| 4-132 | A |
| 4-133 | A |
| 4-134 | A |
| 4-135 | A |
| 4-136 | A |
| 4-137 | A |
| 4-138 | A |
| 4-139 | A |
| 4-140 | A |
| 4-141 | A |
| 4-142 | B |
| 4-143 | A |
| 4-144 | C |
| 4-145 | A |
| 4-146 | A |
| 4-147 | A |
| 4-148 | B |
| 4-149 | B |
| 4-150 | C |
| 4-151 | B |
| 4-152 | A |

| Example No. | EC$_{50}$ |
|---|---|
| 4-153 | C |
| 4-154 | B |
| 4-155 | B |
| 4-156 | C |
| 4-157 | C |
| [Hyo 23-4] | |
| 4-158 | C |
| 4-159 | C |
| 4-160 | C |
| 4-161 | C |
| 4-162 | A |
| 4-163 | C |
| 4-165 | A |
| 4-166 | B |
| 4-167 | B |
| 4-168 | B |
| 4-169 | C |
| 4-170 | C |
| 4-171 | C |
| 4-172 | B |
| 4-173 | B |
| 4-174 | A |
| 4-175 | B |
| 4-176 | A |
| 4-177 | A |
| 4-178 | A |
| 4-179 | A |
| 4-180 | A |
| 4-181 | B |
| 4-182 | B |
| 4-183 | A |
| 4-184 | A |
| 4-185 | A |
| 4-186 | B |
| 4-187 | B |
| 4-188 | B |
| 4-189 | B |
| 4-190 | A |
| 4-191 | B |
| 4-192 | A |
| 4-193 | A |
| 4-194 | A |
| 4-195 | A |
| 4-196 | A |
| 4-197 | B |
| 4-198 | A |
| 4-199 | B |
| 4-200 | B |
| 4-201 | B |
| 4-202 | B |
| 4-203 | C |
| 4-204 | C |
| 4-205 | A |
| 4-206 | A |
| 4-207 | A |
| 4-208 | C |
| 4-209 | B |
| 4-211 | B |
| 4-213 | B |
| 4-214 | C |
| 4-215 | A |
| 4-216 | C |
| 4-217 | B |
| 4-219 | B |
| 4-221 | B |
| 4-222 | C |
| 4-223 | B |
| 4-224 | C |
| 4-225 | A |
| 4-226 | C |
| 4-227 | B |
| 4-229 | B |
| 4-230 | C |
| 4-231 | A |
| 4-232 | C |
| 4-233 | B |
| 4-234 | C |
| 4-235 | C |
| 4-237 | B |
| 4-239 | B |
| 4-240 | C |
| 4-241 | C |
| 4-242 | B |
| 4-243 | C |
| 4-244 | B |
| 4-245 | C |
| 4-246 | B |
| 4-247 | C |
| 4-248 | B |
| 4-249 | C |
| 4-250 | B |
| 4-251 | C |
| 4-252 | B |
| 4-254 | A |
| 4-255 | C |
| 4-256 | B |
| 4-257 | A |
| 4-258 | A |
| 4-259 | B |
| 4-260 | A |
| 4-261 | C |
| 4-262 | B |
| 4-263 | B |
| 4-264 | B |
| 4-265 | A |
| [Hyo 23-5] | |
| 4-266 | A |
| 4-267 | A |
| 4-268 | A |
| 4-269 | A |
| 4-270 | A |
| 4-271 | A |
| 4-272 | A |
| 4-273 | A |
| 4-274 | A |
| 4-275 | A |
| 4-276 | A |
| 4-277 | C |
| 4-279 | A |
| 4-280 | A |
| 4-281 | A |
| 4-282 | A |
| 4-283 | A |
| 4-284 | A |
| 4-285 | B |
| 4-286 | A |
| 4-287 | A |
| 4-288 | C |
| 4-289 | A |
| 4-290 | A |
| 4-291 | A |
| 4-292 | A |
| 4-293 | A |
| 4-294 | B |
| 4-296 | B |
| 4-297 | C |
| 4-298 | A |
| 4-299 | C |
| 4-302 | A |
| 4-303 | C |
| 4-304 | A |
| 4-305 | C |
| 4-306 | A |
| 4-307 | C |
| 4-308 | B |
| 4-309 | C |
| 4-310 | B |
| 4-311 | C |
| 4-312 | B |
| 4-314 | B |
| 4-315 | C |
| 4-316 | C |

| Example No. | EC₅₀ |
|---|---|
| 4-317 | B |
| 4-318 | C |
| 4-320 | A |
| 4-321 | B |
| 4-322 | A |
| 4-323 | C |
| 4-324 | B |
| 4-325 | C |
| 4-326 | A |
| 4-327 | C |
| 4-328 | B |
| 4-330 | B |
| 4-331 | C |
| 4-332 | B |
| 4-333 | C |
| 4-334 | B |
| 4-335 | C |
| 4-336 | A |
| 4-337 | B |
| 4-338 | B |
| 4-340 | B |
| 4-341 | C |
| 4-342 | A |
| 4-343 | C |
| 4-344 | A |
| 4-345 | C |
| 4-346 | A |
| 4-347 | C |
| 4-348 | B |
| 4-350 | A |
| 4-352 | B |
| 4-354 | B |
| 4-356 | A |
| 4-357 | C |
| 4-358 | A |
| 4-359 | A |
| 4-360 | A |
| 4-361 | A |
| 5-1 E | C |
| 5-1 Z | B |
| 5-2 E | B |
| 5-2 Z | B |
| 5-3 | C |
| 6-1 | C |
| 6-2 | A |
| 6-3 | A |
| 6-4 | B |
| 6-5 | C |
| 6-6 | B |
| 6-7 | B |
| 6-9 | B |
| 6-10 | B |
| 6-11 | B |

[Hyo 23-6]

| Example No. | EC₅₀ |
|---|---|
| 6-12 | B |
| 6-13 | B |
| 6-14 | B |
| 6-15 | C |
| 6-16 | A |
| 6-18 | C |
| 6-19 | B |
| 6-20 | B |
| 6-21 | B |
| 6-22 | B |
| 6-23 | C |
| 6-24 | C |
| 6-27 | B |
| 6-28 | B |
| 6-29 | B |
| 6-31 | B |
| 6-32 | C |
| 6-33 | B |
| 6-34 | B |
| 6-35 | C |
| 6-37 | B |
| 7-2 | C |
| 7-3 | A |
| 7-4 | B |
| 7-5 | C |

GK EC₅₀
10 nM to 500 nM = A
500 nM to 3000 nM = B
3000 nM to 10000 nM = C

Formulation Examples of the compounds of the present invention will be shown below.

Formulation Example 1

Granules containing the following ingredients are prepared.

| Ingredient | | |
|---|---|---|
| | Compound represented by the formula [1] | 10 mg |
| | Lactose | 700 mg |
| | Corn starch | 274 mg |
| | HPC-L | 16 mg |
| | | 1000 mg |

The compound represented by the formula [1] and lactose are allowed to pass through a 60-mesh sieve. Corn starch is allowed to pass through a 120-mesh sieve. These ingredients are mixed in a V-shaped mixer. A low-viscosity hydroxypropylcellulose (HPC-L) solution is added to the mixed powder. The mixture is kneaded, granulated (extrusion granulation, pore size: 0.5 to 1 mm) and then dried. The resulting dry granules are sieved through a vibrating sieve (12/60 mesh) to provide granules.

Formulation Example 2

Encapsulation powder containing the following ingredients is prepared.

| Ingredient | | |
|---|---|---|
| | Compound represented by the formula [1] | 10 mg |
| | Lactose | 79 mg |
| | Corn starch | 10 mg |
| | Magnesium stearate | 1 mg |
| | | 100 mg |

The compound represented by the formula [1] and lactose are allowed to pass through a 60-mesh sieve. Corn starch is allowed to pass through a 120-mesh sieve. These ingredients and magnesium stearate are mixed in a V-shaped mixer. A No. 5 hard gelatin capsule is filled with 100 mg of the 10% powder.

Formulation Example 3

Encapsulation granules containing the following ingredients are prepared.

| Ingredient | | |
|---|---|---|
| | Compound represented by the formula [1] | 15 mg |
| | Lactose | 90 mg |
| | Corn starch | 42 mg |
| | HPC-L | 3 mg |
| | | 150 mg |

The compound represented by the formula [1] and lactose are allowed to pass through a 60-mesh sieve. Corn starch is allowed to pass through a 120-mesh sieve. These ingredients are mixed in a V-shaped mixer. A low-viscosity hydroxypropylcellulose (HPC-L) solution is added to the mixed powder. The mixture is kneaded, granulated and then dried. The resulting dry granules are sieved and size-regulated through a vibrating sieve (12/60 mesh) and a No. 4 hard gelatin capsule is filled with 150 mg of the resulting granules.

Formulation Example 4

A tablet containing the following ingredients is prepared.

| Ingredient | Compound represented by the formula [1] | 10 mg |
|---|---|---|
| | Lactose | 90 mg |
| | Microcrystalline cellulose | 30 mg |
| | Magnesium stearate | 5 mg |
| | CMC-Na | 15 mg |
| | | 150 mg |

The compound represented by the formula [1], lactose, microcrystalline cellulose and CMC—Na (sodium carboxymethylcellulose) are allowed to pass through a 60-mesh sieve and mixed. Magnesium stearate is added to the mixed powder to provide a mixed powder for formulation. The mixed powder is directly compressed to provide 150 mg of a tablet.

Formulation Example 5

An intravenous formulation is prepared as follows.

| Compound represented by the formula [1] | 100 mg |
|---|---|
| Saturated fatty acid glyceride | 1000 ml |

Typically, the solution having the above ingredients is intravenously administered to a patient at a rate of 1 ml per minute.

INDUSTRIAL APPLICABILITY

The compounds of the present invention have an excellent GK activating effect and can provide therapeutic and prophylactic agents not only for diabetes but also for diabetes-related diseases such as obesity and hyperlipidemia or chronic diabetic complications such as retinopathy, nephropathy and arteriosclerosis.

The invention claimed is:
1. A 2-pyridone compound represented by the formula [1]:

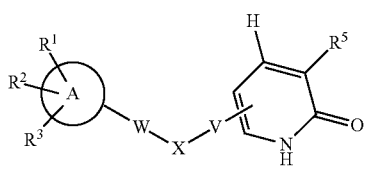

[1]

wherein in the formula [1],
the ring represented by A represents a benzene ring;
$R^1$ represents $R^A-Z^A-$,
wherein $-Z^A-$ represents a single bond or represents any of the following formulas [2]:

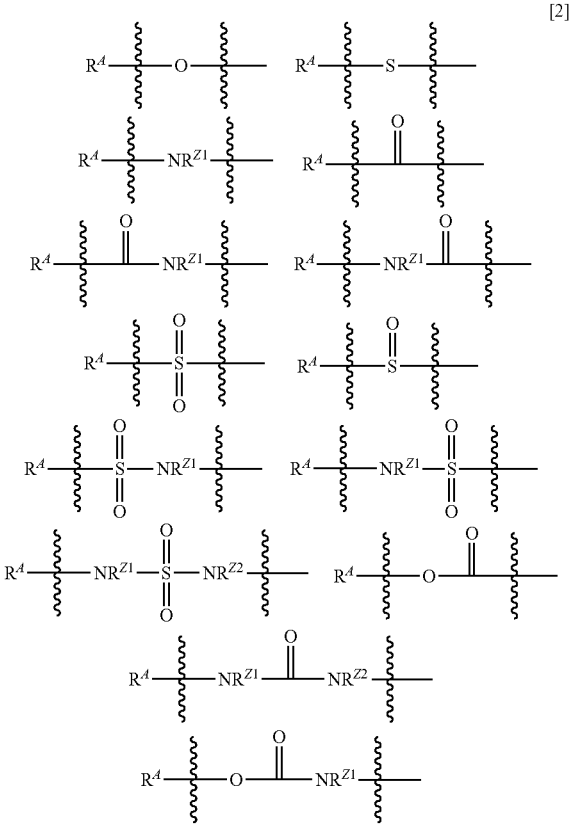

[2]

when $-Z^A-$ represents any of the formulas [2],
$R^A$ represents a lower alkyl group, a lower cycloalkyl group or a phenyl group (wherein the lower alkyl group, lower cycloalkyl group or phenyl group is unsubstituted or substituted with 1 to 3 groups which may be the same or different and selected from the following Substituent Group A1), or when $-Z^A-$ represents a single bond,
$R^A$ represents a lower alkyl group, a lower cycloalkyl group or a phenyl group (wherein the lower alkyl group, lower cycloalkyl group or phenyl group is unsubstituted or substituted with 1 to 3 groups which may be the same or different and selected from the following Substituent Group A1), a hydrogen atom, a cyano group, a halogen atom, a hydroxy group, an amino group, a carbamoyl group, a sulfamoyl group or a ureido group, $R^{Z1}$ and $R^{Z2}$ are the same or different and each represent a hydrogen atom or a lower alkyl group;
X represents any of the structures represented by the formulas [3] shown below:

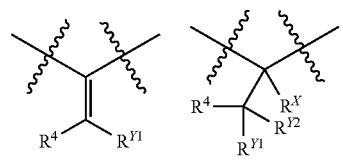

[3]

$R^X$ represents a hydrogen atom,
$R^{Y1}$ and $R^{Y2}$ each represent a hydrogen atom;
$R^4$ represents $R^B-Z^B-$, wherein —$Z^B$— represents a single bond, and
$R^B$ represents an oxopyrrolidinyl group,
Substituent Group A1 represents a halogen atom, a lower cycloalkyl group, a phenyl group, a hydroxy group, a lower alkoxy group, a mono-lower alkylamino group, a di-lower alkylamino group or a lower alkylsulfonyl group;
$R^2$ and $R^3$ are the same or different and each represent a hydrogen atom, a halogen atom, a cyano group, a carbamoyl group, a lower alkyl group, a lower alkylsulfonyl group, a lower cycloalkyl group, a lower alkoxy group, a lower cycloalkoxy group (wherein the lower alkyl group, lower alkylsulfonyl group, lower cycloalkyl group, lower alkoxy group or lower cycloalkoxy group is unsubstituted or substituted with 1 to 3 halogen atoms) or a hydroxy group,
or the adjacent $R^1$ and $R^2$ together form a naphthalene ring together with the benzene ring;
$R^5$ represents a halogen atom, a carbamoyl group, a lower alkanoyl group, an amino group, a di-lower alkylamino group, a lower alkyl group, a lower cycloalkyl group, a lower alkoxy group, a lower cycloalkoxy group, a phenyl group or a phenoxy group (wherein the lower alkyl group, lower cycloalkyl group, lower alkoxy group, lower cycloalkoxy group, phenyl group or phenoxy group is unsubstituted or substituted with 1 to 3 groups which may be the same or different and selected from the following Substituent Group A3),
Substituent Group A3 represents a halogen atom, a hydroxy group, a lower alkyl group (wherein the lower alkyl group is unsubstituted or substituted with 1 to 3 halogen atoms), a lower cycloalkyl group, a phenyl group, a di-lower alkylamino group or a carbamoyl group;
V represents a single bond, and
W represents a single bond,
a tautomer or stereoisomer of the compound, or a pharmaceutically acceptable salt thereof.

2. The 2-pyridone compound according to claim 1 represented by the formula [1]:

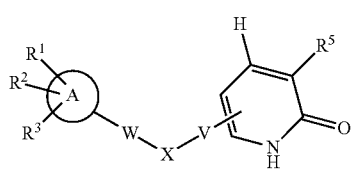

[1]

wherein in the formula [1],
the ring represented by A represents a benzene ring;
$R^1$ represents $R^A$—$Z^A$—,
wherein —$Z^A$— represents a single bond or represents any of the following formulas [2]:

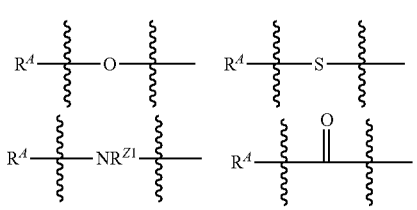

[2]

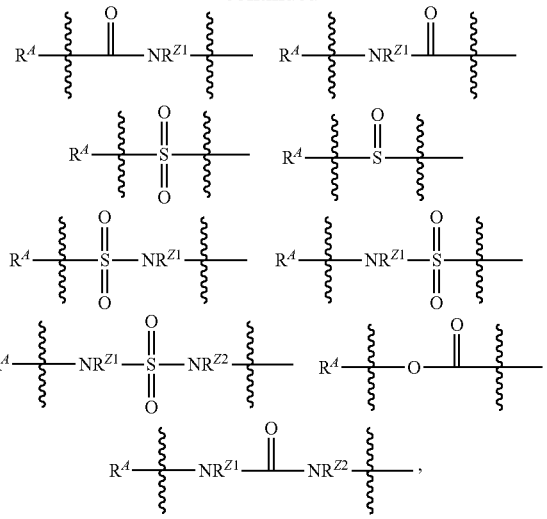

when —$Z^A$— represents any of the formulas [2],
$R^A$ represents a lower alkyl group, a lower cycloalkyl group or a phenyl group (wherein the lower alkyl group, lower cycloalkyl group or phenyl group is unsubstituted or substituted with 1 to 3 groups which may be the same or different and selected from the following Substituent Group A1), or
when —$Z^A$— represents a single bond,
$R^A$ represents a lower alkyl group, a lower cycloalkyl group or a phenyl group (wherein the lower alkyl group, lower cycloalkyl group or phenyl group is unsubstituted or substituted with 1 to 3 groups which may be the same or different and selected from the following Substituent Group A1), a hydrogen atom, a cyano group, a halogen atom, a hydroxy group, an amino group, a carbamoyl group, a sulfamoyl group or a ureido group,
$R^{Z1}$ and $R^{Z2}$ are the same or different and each represent a hydrogen atom or a lower alkyl group;
X represents any of the structures represented by the formulas [3] shown below:

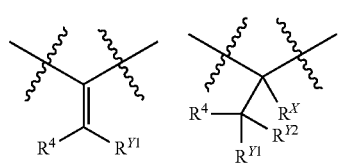

[3]

$R^X$ represents a hydrogen atom,
$R^{Y1}$ and $R^{Y2}$ each represent a hydrogen atom;
$R^4$ represents $R^B$—$Z^B$—,
wherein —$Z^B$— represents a single bond, and
$R^B$ represents an oxopyrrolidinyl group,
Substituent Group A1 represents a halogen atom, a lower cycloalkyl group, a phenyl group, a hydroxy group, a lower alkoxy group, a mono-lower alkylamino group, a di-lower alkylamino group or a lower alkylsulfonyl group;
$R^2$ and $R^3$ are the same or different and each represent a hydrogen atom, a halogen atom, a lower alkyl group, a lower cycloalkyl group, a lower alkoxy group or a lower cycloalkoxy group (wherein the lower alkyl group, lower cycloalkyl group, lower alkoxy group or lower cycloalkoxy group is unsubstituted or substituted with 1 to 3 halogen atoms),
or the adjacent $R^1$ and $R^2$ together form a naphthalene ring together with the benzene ring;
$R^5$ represents a halogen atom, a lower alkyl group, a lower cycloalkyl group, a lower alkoxy group, a lower cycloalkoxy group or a phenyl group (wherein the lower alkyl group, lower cycloalkyl group, lower alkoxy group, lower cycloalkoxy group or phenyl group is unsubstituted or substituted with 1 to 3 groups which may be the same or different and selected from the following Substituent Group A3),
Substituent Group A3 represents a halogen atom, a hydroxy group, a lower alkyl group (wherein the lower alkyl group is unsubstituted or substituted with 1 to 3 halogen atoms), a lower cycloalkyl group, a phenyl group or a di-lower alkylamino group;
V represents a single bond, and
W represents a single bond,
a tautomer or stereoisomer of the compound, or a pharmaceutically acceptable salt thereof.

3. The 2-pyridone compound according to claim 1 represented by the formula [5]:

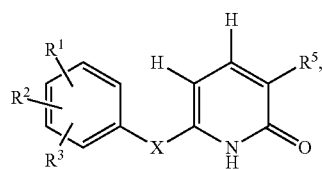

[5]

a tautomer or stereoisomer of the compound, or a pharmaceutically acceptable salt thereof.

4. The 2-pyridone compound according to claim 3 represented by the formula [6]:

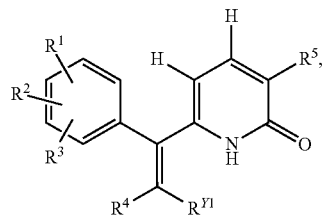

[6]

a tautomer or stereoisomer of the compound, or a pharmaceutically acceptable salt thereof.

5. The 2-pyridone compound according to claim 4 represented by the formula [7]:

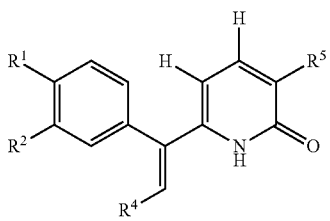

[7]

wherein in the formula [7],
$R^4$ represents $R^B$—$Z^B$—,
wherein —$Z^B$— represents a single bond, and
$R^B$ represents an oxopyrrolidinyl group,
a tautomer or stereoisomer of the compound, or a pharmaceutically acceptable salt thereof.

6. The 2-pyridone compound according to claim 5, wherein
$R^1$ represents $R^A$—$Z^A$—,
wherein —$Z^A$— represents a single bond or represents any of the following formulas [9]:

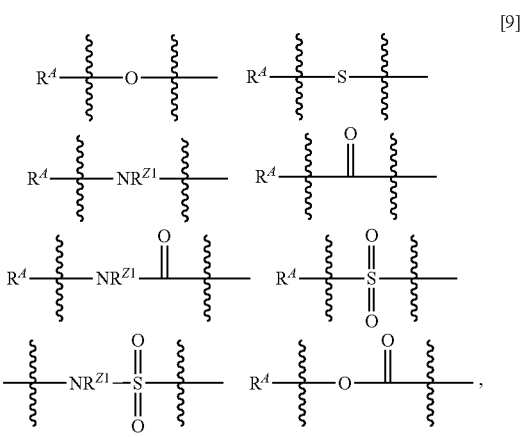

[9]

when —$Z^A$— represents any of the formulas [9],
$R^A$ represents a lower alkyl group (wherein the lower alkyl group is unsubstituted or substituted with 1 to 3 groups which may be the same or different and selected from the group consisting of a halogen atom, a hydroxy group, a mono-lower alkylamino group and a di-lower alkylamino group) or a lower cycloalkyl group,
$R^{Z1}$ represents a hydrogen atom or a lower alkyl group, or
when —$Z^A$— represents a single bond,
$R^A$ represents a hydrogen atom or a lower alkyl group (wherein the lower alkyl group is unsubstituted or substituted with 1 to 3 groups which may be the same or different and selected from the group consisting of a halogen atom, a hydroxy group and a lower alkoxy group);
$R^2$ represents a hydrogen atom, a halogen atom, a lower alkyl group (wherein the lower alkyl group is unsubstituted or substituted with 1 to 3 halogen atoms) or a lower alkoxy group;
$R^4$ represents $R^B$—$Z^B$—,
wherein —$Z^B$— represents a single bond, and
$R^B$ represents an oxopyrrolidinyl group, and
$R^5$ represents a halogen atom, a lower alkyl group (wherein the lower alkyl group is unsubstituted or substituted with 1 to 3 groups which may be the same or different and selected from the group consisting of a halogen atom and a hydroxy group), a lower cycloalkyl group or a phenyl group,
a tautomer or stereoisomer of the compound, or a pharmaceutically acceptable salt thereof.

7. The 2-pyridone compound according to claim 4 represented by the formula [10]:

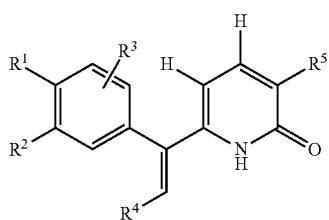
[10]

wherein in the formula [10],
$R^4$ represents $R^B$—$Z^B$—,
wherein —$Z^B$— represents a single bond, and
$R^B$ represents an oxopyrrolidinyl group,
a tautomer or stereoisomer of the compound, or a pharmaceutically acceptable salt thereof.

8. The 2-pyridone compound according to claim 7, wherein $R^1$ represents $R^A$—$Z^A$—,
wherein —$Z^A$— represents a single bond or represents any of the following formulas [9]:

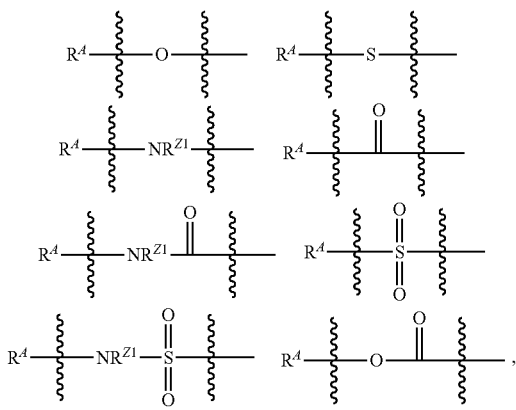
[9]

when —$Z^A$— represents any of the formulas [9],
$R^A$ represents a lower alkyl group (wherein the lower alkyl group is unsubstituted or substituted with 1 to 3 groups which may be the same or different and selected from the group consisting of a halogen atom, a hydroxy group, a mono-lower alkylamino group and a di-lower alkylamino group) or a lower cycloalkyl group,
$R^{Z1}$ represents a hydrogen atom or a lower alkyl group, or
when —$Z^A$— represents a single bond,
$R^A$ represents a hydrogen atom, a halogen atom, a lower alkyl group (wherein the lower alkyl group is unsubstituted or substituted with 1 to 3 groups which may be the same or different and selected from the group consisting of a halogen atom, a hydroxy group and a lower alkoxy group), a lower cycloalkyl group or a phenyl group;
$R^2$ represents a hydrogen atom, a halogen atom, a lower alkyl group (wherein the lower alkyl group is unsubstituted or substituted with 1 to 3 halogen atoms) or a lower alkoxy group (wherein the lower alkoxy group is unsubstituted or substituted with 1 to 3 halogen atoms);
$R^3$ represents a hydrogen atom, a halogen atom, a lower alkyl group (wherein the lower alkyl group is unsubstituted or substituted with 1 to 3 halogen atoms) or a lower alkoxy group;
$R^4$ represents $R^B$—$Z^B$—,
wherein —$Z^B$— represents a single bond, and
$R^B$ represents an oxopyrrolidinyl group, and
$R^5$ represents a halogen atom, a lower alkyl group (wherein the lower alkyl group is unsubstituted or substituted with 1 to 3 groups which may be the same or different and selected from the group consisting of a halogen atom and a hydroxy group), a lower cycloalkyl group (wherein the lower cycloalkyl group is unsubstituted or substituted with one hydroxy group), a lower alkoxy group (wherein the lower alkoxy group is unsubstituted or substituted with 1 to 3 halogen atoms) or a phenyl group,
a tautomer or stereoisomer of the compound, or a pharmaceutically acceptable salt thereof.

9. The 2-pyridone compound according to claim 8, wherein $R^1$ represents $R^A$—$Z^A$—,
wherein —$Z^A$— represents a single bond or represents any of the following formulas [11]:

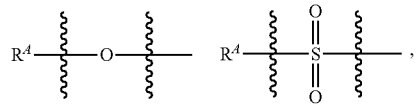
[11]

when —$Z^A$— represents any of the formulas [11],
$R^A$ represents a lower alkyl group (wherein the lower alkyl group is unsubstituted or substituted with 1 to 3 halogen atoms) or a lower cycloalkyl group, or
when —$Z^A$— represents a single bond,
$R^A$ represents a lower alkyl group (wherein the lower alkyl group is unsubstituted or substituted with 1 to 3 halogen atoms) or a halogen atom;
$R^2$ represents a hydrogen atom, a lower alkyl group (wherein the lower alkyl group is unsubstituted or substituted with 1 to 3 halogen atoms), a halogen atom or a lower alkoxy group;
$R^3$ represents a hydrogen atom or a halogen atom, and
$R^5$ represents a chlorine atom or a cyclopropyl group,
a tautomer or stereoisomer of the compound, or a pharmaceutically acceptable salt thereof.

10. The 2-pyridone compound according to claim 6 or 9, wherein
$R^B$ is a group represented by the formula [12]:

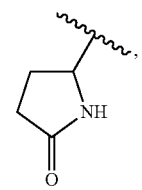
[12]

a tautomer or stereoisomer of the compound, or a pharmaceutically acceptable salt thereof.

11. A 2-pyridone compound selected from the group consisting of:
6-{(E)-1-(3-chloro-4-ethoxyphenyl)-2-[(2R)-5-oxopyrrolidin-2-yl]ethenyl}-3-cyclopropylpyridin-2(1H)-one,
6-{(E)-1-(4-chlorophenyl)-2-[(2R)-5-oxopyrrolidin-2-yl]ethenyl}-3-cyclopropylpyridin-2(1H)-one,
6-{(E)-1-[3-chloro-4-(trifluoromethyl)phenyl]-2-[(2R)-5-oxopyrrolidin-2-yl]ethenyl}-3-cyclopropylpyridin-2(1H)-one, 6-{(E)-1-(4-chloro-3-methylphenyl)-2-[(2R)-5-oxopyrrolidin-2-yl]ethenyl}-3-cyclopropylpyridin-2(1H)-one,
6-{(E)-1-(4-chloro-3-fluorophenyl)-2-[(2R)-5-oxopyrrolidin-2-yl]ethenyl}-3-cyclopropylpyridin-2(1H)-one,
3-cyclopropyl-6-{(E)-1-(4-fluoro-3-methylphenyl)-2-[(2R)-5-oxopyrrolidin-2-yl]ethenyl}pyridin-2(1H)-one,
3-cyclopropyl-6-{(E)-1-[3-fluoro-4-(trifluoromethyl)phenyl]-2-[(2R)-5-oxopyrrolidin-2-yl]ethenyl}pyridin-2(1H)-one,
3-cyclopropyl-6-{(E)-1-[4-fluoro-3-(trifluoromethyl)phenyl]-2-[(2R)-5-oxopyrrolidin-2-yl]ethenyl}pyridin-2(1H)-one,
6-{(E)-1-(4-chloro-3-methoxyphenyl)-2-[(2R)-5-oxopyrrolidin-2-yl]ethenyl}-3-cyclopropylpyridin-2(1H)-one,
3-cyclopropyl-6-{(E)-1-[4-(difluoromethyl)-3-fluorophenyl]-2-[(2R)-5-oxopyrrolidin-2-yl]ethenyl}pyridin-2(1H)-one,
3-cyclopropyl-6-{(E)-1-[4-methoxy-3-(trifluoromethyl)phenyl]-2-[(2R)-5-oxopyrrolidin-2-yl]ethenyl}pyridin-2(1H)-one,
3-cyclopropyl-6-{(E)-1-[3-methyl-4-(trifluoromethyl)phenyl]-2-[(2R)-5-oxopyrrolidin-2-yl]ethenyl}pyridin-2(1H)-one,
6-{(E)-1-(4-chloro-2-fluorophenyl)-2-[(2R)-5-oxopyrrolidin-2-yl]ethenyl}-3-cyclopropylpyridin-2(1H)-one,
3-cyclopropyl-6-{(E)-1-[2-fluoro-4-(trifluoromethyl)phenyl]-2-[(2R)-5-oxopyrrolidin-2-yl]ethenyl}pyridin-2(1H)-one,
6-{(E)-1-[3-chloro-4-(cyclopropyloxy)phenyl]-2-[(2R)-5-oxopyrrolidin-2-yl]ethenyl}-3-cyclopropylpyridin-2(1H)-one,
6-{(E)-1-[3-chloro-4-(2,2,2-trifluoroethoxy)phenyl]-2-[(2R)-5-oxopyrrolidin-2-yl]ethenyl}-3-cyclopropylpyridin-2(1H)-one,
6-{(E)-1-(5-chloro-2-fluoro-4-methoxyphenyl)-2-[(2R)-5-oxopyrrolidin-2-yl]ethenyl}-3-cyclopropylpyridin-2(1H)-one,
6-{(E)-1-[3-chloro-4-(difluoromethoxy)phenyl]-2-[(2R)-5-oxopyrrolidin-2-yl]ethenyl}-3-cyclopropylpyridin-2(1H)-one,
3-cyclopropyl-6-{(E)-1-(4-ethoxy-2,3-difluorophenyl)-2-[(2R)-5-oxopyrrolidin-2-yl]ethenyl}pyridin-2(1H)-one,
3-cyclopropyl-6-{(E)-1-[4-(cyclopropylsulfonyl)phenyl]-2-[(2R)-5-oxopyrrolidin-2-yl]ethenyl}pyridin-2(1H)-one,
6-{(E)-1-(2-chloro-4-ethoxyphenyl)-2-[(2R)-5-oxopyrrolidin-2-yl]ethenyl}-3-cyclopropylpyridin-2(1H)-one,
3-cyclopropyl-6-[(E)-2-[(2R)-5-oxopyrrolidin-2-yl]-1-{4-[(trifluoromethyl)sulfonyl]phenyl}ethenyl]pyridin-2(1H)-one,
3-chloro-6-{(E)-1-[4-(cyclopropylsulfonyl)phenyl]-2-[(2R)-5-oxopyrrolidin-2-yl]ethenyl}pyridin-2(1H)-one,
3-chloro-6-{(E)-1-[3-chloro-4-(ethylsulfonyl)phenyl]-2-[(2R)-5-oxopyrrolidin-2-yl]ethenyl}pyridin-2(1H)-one,
3-chloro-6-{(E)-1-[4-(cyclopentylsulfonyl)phenyl]-2-[(2R)-5-oxopyrrolidin-2-yl]ethenyl}pyridin-2(1H)-one,
3-cyclopropyl-6-{(E)-1-[4-(methylsulfonyl)phenyl]-2-[(2R)-5-oxopyrrolidin-2-yl]ethenyl}pyridin-2(1H)-one,
6-{(E)-1-[3-chloro-4-(cyclopropylsulfonyl)phenyl]-2-[(2R)-5-oxopyrrolidin-2-yl]ethenyl}-3-cyclopropylpyridin-2(1H)-one,
3-cyclopropyl-6-{(E)-1-[4-(cyclopropylsulfonyl)-3-methylphenyl]-2-[(2R)-5-oxopyrrolidin-2-yl]ethenyl}pyridin-2(1H)-one,
3-chloro-6-{(E)-1-[4-(cyclopropylsulfonyl)-3-methylphenyl]-2-[(2R)-5-oxopyrrolidin-2-yl]ethenyl}pyridin-2(1H)-one, and
3-chloro-6-{(E)-1-[3-chloro-4-(cyclopropylsulfonyl)phenyl]-2-[(2R)-5-oxopyrrolidin-2-yl]ethenyl}pyridin-2(1H)-one,
a tautomer or stereoisomer of the compound, or a pharmaceutically acceptable salt thereof.

12. The 2-pyridone compound according to claim 3 represented by the formula [13]:

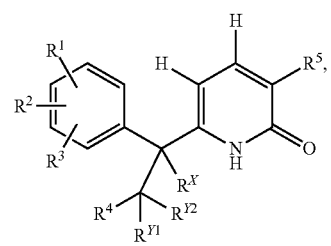

[13]

a tautomer or stereoisomer of the compound, or a pharmaceutically acceptable salt thereof.

13. The 2-pyridone compound according to claim 12 represented by the formula [14]:

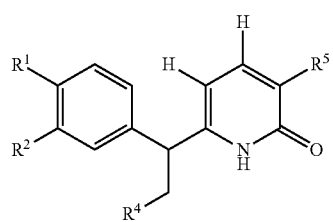

[14]

wherein in the formula [14],
$R^4$ represents $R^B-Z^B-$,
wherein $-Z^B-$ represents a single bond, and
$R^B$ represents an oxopyrrolidinyl group,
a tautomer or stereoisomer of the compound, or a pharmaceutically acceptable salt thereof.

14. The 2-pyridone compound according to claim 13, wherein
$R^1$ represents $R^A-Z^A-$,
wherein $-Z^A-$ represents a single bond or represents any of the following formulas [9]:

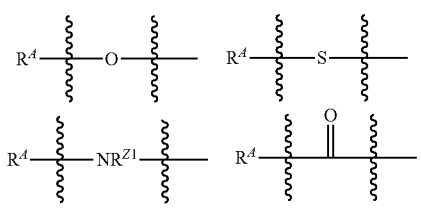

[9]

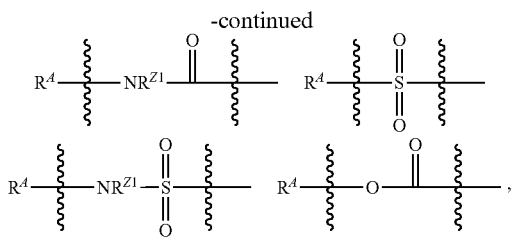

when —$Z^A$— represents any of the formulas [9],
$R^A$ represents a lower alkyl group (wherein the lower alkyl group is unsubstituted or substituted with 1 to 3 groups which may be the same or different and selected from the group consisting of a halogen atom, a mono-lower alkylamino group and a di-lower alkylamino group) or a lower cycloalkyl group,
$R^{Z1}$ represents a hydrogen atom or a lower alkyl group, or
when —$Z^A$— represents a single bond,
$R^A$ represents a hydrogen atom or a lower alkyl group (wherein the lower alkyl group is unsubstituted or substituted with 1 to 3 groups which may be the same or different and selected from the group consisting of a halogen atom, and a lower alkoxy group);
$R^2$ represents a hydrogen atom, a halogen atom, a lower alkyl group (wherein the lower alkyl group is unsubstituted or substituted with 1 to 3 halogen atoms) or a lower alkoxy group;
$R^4$ represents $R^B$—$Z^B$—,
wherein —$Z^B$— represents a single bond, and
$R^B$ represents an oxopyrrolidinyl group, and
$R^5$ represents a halogen atom, a lower alkyl group (wherein the lower alkyl group is unsubstituted or substituted with 1 to 3 groups which may be the same or different and selected from the group consisting of a halogen atom and a hydroxy group), a lower cycloalkyl group or a phenyl group,
a tautomer or stereoisomer of the compound, or a pharmaceutically acceptable salt thereof.

15. The 2-pyridone compound according to claim 12 represented by the formula [15]:

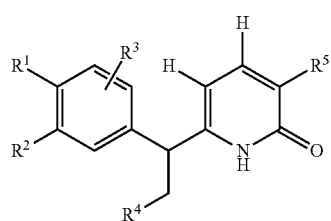

wherein in the formula [15],
$R^4$ represents $R^B$—$Z^B$—,
wherein —$Z^B$— represents a single bond, and
$R^B$ represents an oxopyrrolidinyl group,
a tautomer or stereoisomer of the compound, or a pharmaceutically acceptable salt thereof.

16. The 2-pyridone compound according to claim 15, wherein
$R^1$ represents $R^A$—$Z^A$—,
wherein —$Z^A$— represents a single bond or represents any of the following formulas [9]:

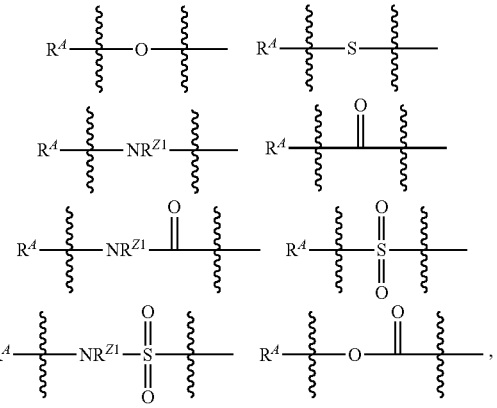

when —$Z^A$— represents any of the formulas [9],
$R^A$ represents a lower alkyl group (wherein the lower alkyl group is unsubstituted or substituted with 1 to 3 groups which may be the same or different and selected from the group consisting of a halogen atom, a hydroxy group, a mono-lower alkylamino group and a di-lower alkylamino group) or a lower cycloalkyl group,
$R^{Z1}$ represents a hydrogen atom or a lower alkyl group, or
when —$Z^A$— represents a single bond,
$R^A$ represents a hydrogen atom, a halogen atom, a lower alkyl group (wherein the lower alkyl group is unsubstituted or substituted with 1 to 3 groups which may be the same or different and selected from the group consisting of a halogen atom, a hydroxy group, and a lower alkoxy group), a lower cycloalkyl group or a phenyl group;
$R^2$ represents a hydrogen atom, a halogen atom, a lower alkyl group (wherein the lower alkyl group is unsubstituted or substituted with 1 to 3 halogen atoms) or a lower alkoxy group (wherein the lower alkoxy group is unsubstituted or substituted with 1 to 3 halogen atoms);
$R^3$ represents a hydrogen atom, a halogen atom, a lower alkyl group (wherein the lower alkyl group is unsubstituted or substituted with 1 to 3 halogen atoms) or a lower alkoxy group;
$R^4$ represents $R^B$—$Z^B$—,
wherein —$Z^B$— represents a single bond, and
$R^B$ represents an oxopyrrolidinyl group, and
$R^5$ represents a halogen atom, a lower alkyl group (wherein the lower alkyl group is unsubstituted or substituted with 1 to 3 groups which may be the same or different and selected from the group consisting of a halogen atom and a hydroxy group), a lower cycloalkyl group (wherein the lower cycloalkyl group is unsubstituted or substituted with one hydroxy group), a lower alkoxy group (wherein the lower alkoxy group is unsubstituted or substituted with 1 to 3 halogen atoms) or a phenyl group,
a tautomer or stereoisomer of the compound, or a pharmaceutically acceptable salt thereof.

17. The 2-pyridone compound according to claim 16, wherein
$R^1$ represents $R^A$—$Z^A$—,
wherein —$Z^A$— represents a single bond or represents any of the following formulas [11]:

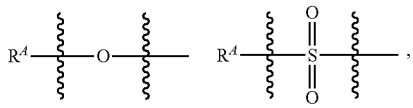

when —$Z^A$— represents any of the formulas [11],
$R^A$ represents a lower alkyl group (wherein the lower alkyl group is unsubstituted or substituted with 1 to 3 halogen atoms) or a lower cycloalkyl group, or
when —$Z^A$— represents a single bond,
$R^A$ represents a lower alkyl group (wherein the lower alkyl group is unsubstituted or substituted with 1 to 3 halogen atoms) or a halogen atom;
$R^2$ represents a hydrogen atom, a lower alkyl group (wherein the lower alkyl group is unsubstituted or substituted with 1 to 3 halogen atoms), a halogen atom or a lower alkoxy group;
$R^3$ represents a hydrogen atom or a halogen atom, and
$R^5$ represents a chlorine atom or a cyclopropyl group,
a tautomer or stereoisomer of the compound, or a pharmaceutically acceptable salt thereof.

18. The 2-pyridone compound according to claim 14 or 17, wherein
$R^B$ is a group represented by the formula [12]:

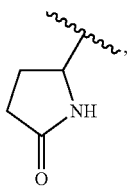

a tautomer or stereoisomer of the compound, or a pharmaceutically acceptable salt thereof.

19. A 2-pyridone compound selected from the group consisting of:
6-{1-(4-chloro-3-methylphenyl)-2-[(2R)-5-oxopyrrolidin-2-yl]ethyl}-3-cyclopropylpyridin-2(1H)-one,
6-{1-[4-chloro-3-(trifluoromethyl)phenyl]-2-[(2R)-5-oxopyrrolidin-2-yl]ethyl}-3-cyclopropylpyridin-2(1H)-one,
3-cyclopropyl-6-{1-[4-(difluoromethyl)-3-methylphenyl]-2-[(2R)-5-oxopyrrolidin-2-yl]ethyl}pyridin-2(1H)-one,
3-cyclopropyl-6-{1-[4-(difluoromethyl)-3-fluorophenyl]-2-[(2R)-5-oxopyrrolidin-2-yl]ethyl}pyridin-2(1H)-one,
6-{1-[3-chloro-4-(trifluoromethyl)phenyl]-2-[(2R)-5-oxopyrrolidin-2-yl]ethyl}-3-cyclopropylpyridin-2(1H)-one,
6-{1-[3-chloro-4-(propan-2-yloxy)phenyl]-2-[(2R)-5-oxopyrrolidin-2-yl]ethyl}-3-cyclopropylpyridin-2(1H)-one,
3-cyclopropyl-6-{1-[3-methyl-4-(trifluoromethyl)phenyl]-2-[(2R)-5-oxopyrrolidin-2-yl]ethyl}pyridin-2(1H)-one,
6-{1-[3-chloro-4-(cyclopropyloxy)phenyl]-2-[(2R)-5-oxopyrrolidin-2-yl]ethyl}-3-cyclopropylpyridin-2(1H)-one,
6-{1-(5-chloro-2-fluoro-4-methoxyphenyl)-2-[(2R)-5-oxopyrrolidin-2-yl]ethyl}-3-cyclopropylpyridin-2(1H)-one,
6-{1-[3-chloro-4-(difluoromethoxy)phenyl]-2-[(2R)-5-oxopyrrolidin-2-yl]ethyl}-3-cyclopropylpyridin-2(1H)-one,
3-cyclopropyl-6-{1-[4-(cyclopropylsulfonyl)-3-methylphenyl]-2-[(2R)-5-oxopyrrolidin-2-yl]ethyl}pyridin-2(1H)-one,
3-chloro-6-{1-[3-chloro-4-(cyclopropylsulfonyl)phenyl]-2-[(2R)-5-oxopyrrolidin-2-yl]ethyl}pyridin-2(1H)-one and
6-{1-[3-chloro-4-(cyclopropylsulfonyl)phenyl]-2-[(2R)-5-oxopyrrolidin-2-yl]ethyl}-3-cyclopropylpyridin-2(1H)-one,
a tautomer or stereoisomer of the compound, or a pharmaceutically acceptable salt thereof.

20. A pharmaceutical composition comprising, as an active ingredient, the 2-pyridone compound according to claim 1, a tautomer or stereoisomer of the compound, or a pharmaceutically acceptable salt thereof, and a pharmaceutically acceptable carrier or diluent.

21. A method for activating glucokinase comprising administering an effective amount of the compound according to claim 1 to a subject in need thereof.

22. A method for treating diabetes or obesity comprising administering an effective amount of the compound according to claim 1 to a subject in need thereof.

23. The 2-pyridone compound according to claim 18,
wherein $R^1$ represents $R^A$—$Z^A$—, wherein —$Z^A$— is a single bond, and $R^A$ is a $C_{1-2}$ alkyl group which is unsubstituted or substituted with 1 to 3 fluorine atoms;
$R^2$ is a hydrogen atom;
$R^3$ is a hydrogen atom, and
$R^5$ is a cyclopropyl group,
a tautomer or stereoisomer of the compound, or a pharmaceutically acceptable salt thereof.

* * * * *

UNITED STATES PATENT AND TRADEMARK OFFICE
CERTIFICATE OF CORRECTION

PATENT NO.       : 8,822,503 B2
APPLICATION NO.  : 13/081201
DATED            : September 2, 2014
INVENTOR(S)      : Takanori Kawaguchi et al.

It is certified that error appears in the above-identified patent and that said Letters Patent is hereby corrected as shown below:

In the Specification

At column 247, lines 14-24, Example 4-3, please amend as follows:

[Ka 225]

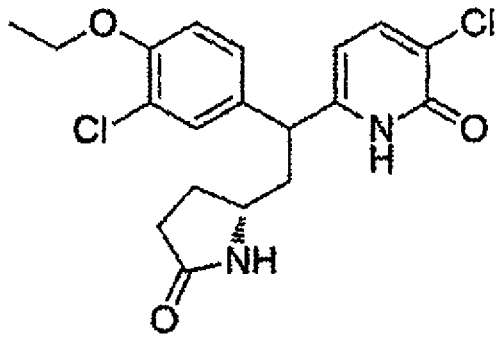

At column 262, lines 45-60, Example 4-39, please amend as follows:

[Ka 226]

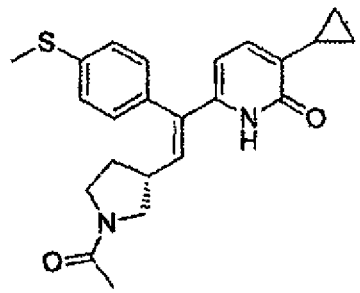

Signed and Sealed this
Twenty-third Day of December, 2014

Michelle K. Lee
*Deputy Director of the United States Patent and Trademark Office*

CERTIFICATE OF CORRECTION (continued)
U.S. Pat. No. 8,822,503 B2

At column 263, lines 6-20, Example 4-40, please amend as follows:

[Ka 227]

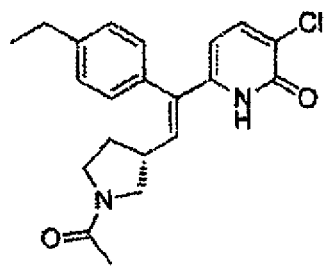

At column 263, lines 44-55, Example 4-41, please amend as follows:

[Ka 228]

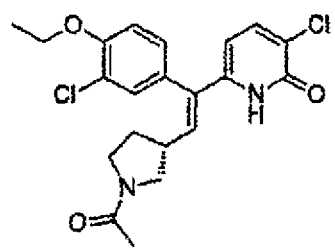

At column 371, lines 42-54, please amend as follows:

Example 4-233, 234

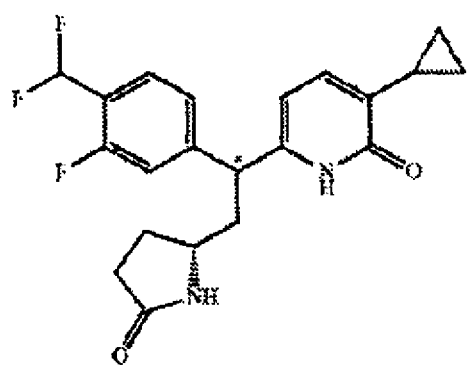

CERTIFICATE OF CORRECTION (continued)
U.S. Pat. No. 8,822,503 B2

At column 431, lines 17-29, Example 4-379, please amend as follows:

Example 4-379

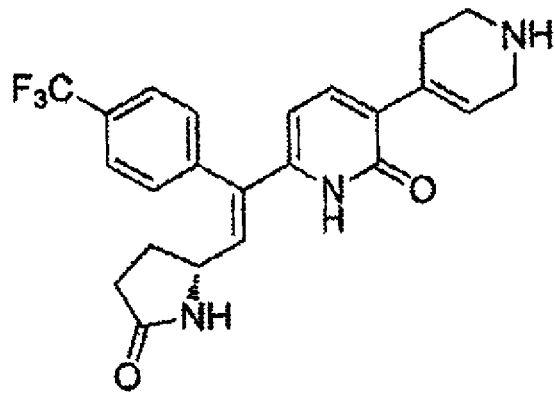

At column 437, lines 1-14, Example 4-382, please amend as follows:

Example 4-382

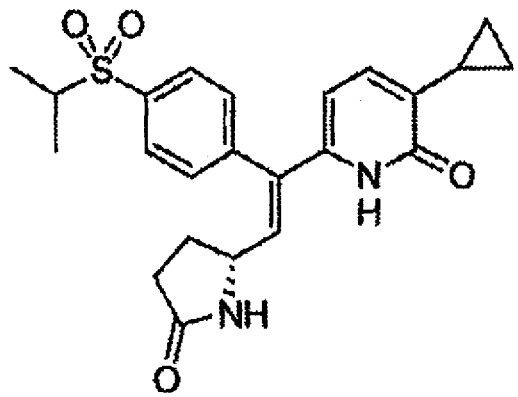

At column 450, lines 18-31, Example 6-15, please amend as follows:

[Ka 293]

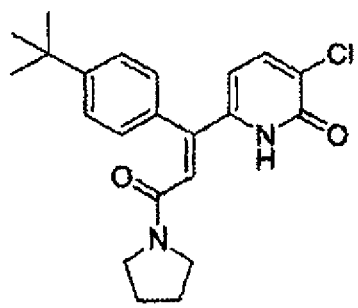

CERTIFICATE OF CORRECTION (continued)　　　　　　　　　　　　　　　　Page 4 of 4
U.S. Pat. No. 8,822,503 B2

In the Claims

At column 478, lines 30-34, please delete the formula as follows:

"  "